US010010556B2

(12) United States Patent
Quinn et al.

(10) Patent No.: US 10,010,556 B2
(45) Date of Patent: *Jul. 3, 2018

(54) BICYCLIC BROMODOMAIN INHIBITORS

(71) Applicant: ZENITH EPIGENETICS LTD., Calgary (CA)

(72) Inventors: John Frederick Quinn, Albany, NY (US); Bryan Cordell Duffy, Glenmont, NY (US); Shuang Liu, Schenectady, NY (US); Ruifang Wang, Schenectady, NY (US); May Xiaowu Jiang, Guilderland, NY (US); Gregory Scott Martin, Colonie, NY (US); Gregory Steven Wagner, Foster City, CA (US); Peter Ronald Young, San Francisco, CA (US)

(73) Assignee: Zenith Epigenetics Ltd., Calgary, AB (CA)

( * ) Notice: Subject to any disclaimer, the term of this patent is extended or adjusted under 35 U.S.C. 154(b) by 0 days.

This patent is subject to a terminal disclaimer.

(21) Appl. No.: 15/486,256

(22) Filed: Apr. 12, 2017

(65) Prior Publication Data

US 2017/0216301 A1    Aug. 3, 2017

Related U.S. Application Data

(60) Division of application No. 14/977,508, filed on Dec. 21, 2015, now Pat. No. 9,663,520, which is a continuation of application No. PCT/US2014/043423, filed on Jun. 20, 2014.

(60) Provisional application No. 61/837,841, filed on Jun. 21, 2013.

(51) Int. Cl.

| A61K 31/5377 | (2006.01) |
| A61K 31/52 | (2006.01) |
| A61K 31/437 | (2006.01) |
| A61K 31/423 | (2006.01) |
| A61K 31/422 | (2006.01) |
| A61K 31/498 | (2006.01) |
| A61K 31/517 | (2006.01) |
| A61K 31/4985 | (2006.01) |
| A61K 31/496 | (2006.01) |
| A61K 31/4184 | (2006.01) |
| A61K 31/4545 | (2006.01) |
| A61K 45/06 | (2006.01) |

(52) U.S. Cl.
CPC ...... *A61K 31/5377* (2013.01); *A61K 31/4184* (2013.01); *A61K 31/422* (2013.01); *A61K 31/423* (2013.01); *A61K 31/437* (2013.01); *A61K 31/4545* (2013.01); *A61K 31/496* (2013.01); *A61K 31/498* (2013.01); *A61K 31/4985* (2013.01); *A61K 31/517* (2013.01); *A61K 31/52* (2013.01); *A61K 45/06* (2013.01)

(58) Field of Classification Search
CPC .............. A61K 31/5377; A61K 31/498; A61K 31/4184; A61K 31/496; A61K 31/4985; A61K 45/06; A61K 31/4545; A61K 31/422; A61K 31/423; A61K 31/437; A61K 31/52; A61K 31/517
See application file for complete search history.

(56) References Cited

U.S. PATENT DOCUMENTS

| 4,748,163 | A | 5/1988 | Schmidt et al. |
| 5,565,469 | A | 10/1996 | Mihm et al. |
| 6,380,235 | B1 | 4/2002 | Zhang et al. |
| 8,053,440 | B2 | 11/2011 | Hansen |
| 8,093,273 | B2 | 1/2012 | Wong et al. |
| 8,691,747 | B2 | 4/2014 | Kruidenier et al. |
| 8,697,725 | B2 | 4/2014 | Demont et al. |
| 8,735,586 | B2 | 5/2014 | Alonso et al. |
| 8,993,554 | B2 | 3/2015 | Amans et al. |
| 9,029,395 | B2 | 5/2015 | Amans et al. |
| 9,067,936 | B2 | 6/2015 | Demont et al. |
| 9,073,878 | B2 | 7/2015 | Fairfax et al. |
| 9,102,677 | B2 | 8/2015 | Bailey et al. |
| 9,125,915 | B2 | 9/2015 | Miyoshi et al. |
| 9,271,978 | B2 | 3/2016 | Liu et al. |
| 9,278,940 | B2 | 3/2016 | Fairfax et al. |
| 9,315,487 | B2 | 4/2016 | Amans et al. |
| 9,321,765 | B2 | 4/2016 | Gong |
| 9,388,161 | B2 | 7/2016 | Bair et al. |
| 9,393,232 | B2 | 7/2016 | Ren et al. |
| 9,422,281 | B2 | 8/2016 | Bair et al. |
| 9,458,156 | B2 | 10/2016 | Norris et al. |

(Continued)

FOREIGN PATENT DOCUMENTS

| CA | 2113361 A1 | 3/1993 |
| CA | 2195107 A1 | 2/1996 |

(Continued)

OTHER PUBLICATIONS

International Search Report and Written Opinion issued in International Application No. PCT/IB2016/001874; dated Apr. 25, 2016.
Aiello, R.J., et al., "Monocyte chemoattractant protein-1 accelerates atherosclerosis in apolipoprotein E-deficient mice" *Arterioscler Thromb. Vasc. Biol.* 19(6): 1518-25 (1999).
Alexandraki, K. et al., "Inflammatory process in type 2 diabetes: The role of cytokines" *Ann N Y Acad Sci*, 2006. 1084:89-117.
Ambinter, "2(1H)-Pyridone, 1-[(4-chlorophenyl)methyl]-5-(1,3,4-oxadiazol-2-yl)-" Chemical Abstracts Record No. 1209999-95-0 [online], entered into STN Registry File Mar. 15, 2010.
Antonelli, A. et al., "Serum levels of proinflammatory cytokines interleukin-1beta, interleukin-6, and tumor necrosis factor alpha in mixed cryoglobulinemia" *Arthritis Rheum*, 2009. 60(12):3841-7.
Aricha, R. et al., "Blocking of IL-6 suppresses experimental autoimmune myasthenia gravis" *J Autoimmun*, 2011. 36(2):135-41.
Arif, M. et al., "Protein lysine acetylation in cellular function and its role in cancer manifestation" *Biochim Biophys Acta*, 2010. 1799(10-12):702-16.
Ash, Z. and P. Emery, "The role of tocilizumab in the management of rheumatoid arthritis" *Expert Opin Biol Ther*, 2012. 12(9): 1277-89.
Bandukwala, H.S. et al., "Selective inhibition of CD4+ T-cell cytokine production and autoimmunity by BET protein and c-Myc inhibitors" *Proc Natl Acad Sci USA*, 2012. 109(36):14532-7.
Bandyopadhyay, K. et al., "Spermidinyl-CoA-based HAT inhibitors block DNA repair and provide cancer-specific chemo- and radiosensitization" *Cell Cycle*, 2009. 8(17):2779-86. (Author's manuscript, 19 pages).

(Continued)

*Primary Examiner* — John M Mauro

(74) *Attorney, Agent, or Firm* — Finnegan, Henderson, Farabow, Garrett & Dunner, LLP

(57) ABSTRACT

The invention relates to substituted bicyclic compounds, which are useful for inhibition of BET protein function by binding to bromodomains, pharmaceutical compositions comprising these compounds, and use of the compounds and compositions in therapy.

54 Claims, No Drawings

(56) References Cited

U.S. PATENT DOCUMENTS

| | | | |
|---|---|---|---|
| 9,598,367 B2 | 3/2017 | Liu et al. | |
| 9,636,328 B2 | 5/2017 | Liu et al. | |
| 9,662,311 B2 | 5/2017 | Liu et al. | |
| 9,663,520 B2 | 5/2017 | Quinn et al. | |
| 9,718,847 B2 * | 8/2017 | Zhang | C07D 471/04 |
| 9,765,039 B2 | 9/2017 | Fairfax et al. | |
| 9,855,271 B2 | 1/2018 | Quinn et al. | |
| 9,861,637 B2 | 1/2018 | Liu et al. | |
| 2002/0019395 A1 | 2/2002 | Zhu et al. | |
| 2003/0036545 A1 | 2/2003 | Castelhano et al. | |
| 2004/0044203 A1 | 3/2004 | Wittman et al. | |
| 2004/0166137 A1 | 8/2004 | Lackey | |
| 2005/0014812 A1 | 1/2005 | Hayashida et al. | |
| 2005/0176775 A1 | 8/2005 | Devadas et al. | |
| 2005/0176858 A1 | 8/2005 | Nohara et al. | |
| 2007/0134161 A1 | 6/2007 | Brown | |
| 2007/0213323 A1 | 9/2007 | Imogai et al. | |
| 2007/0275984 A1 | 11/2007 | Imogai et al. | |
| 2008/0015196 A1 | 1/2008 | Doller et al. | |
| 2008/0188467 A1 | 8/2008 | Wong et al. | |
| 2009/0312353 A1 | 12/2009 | Messersmith et al. | |
| 2010/0063104 A1 | 3/2010 | Nakai et al. | |
| 2010/0234354 A1 | 9/2010 | Dorsch et al. | |
| 2010/0267714 A1 | 10/2010 | Jorgensen et al. | |
| 2011/0070297 A1 | 3/2011 | Cao et al. | |
| 2011/0136819 A1 | 6/2011 | Dorsch et al. | |
| 2011/0136834 A1 | 8/2011 | Critchley et al. | |
| 2011/0257181 A1 | 10/2011 | Stieber et al. | |
| 2012/0004261 A1 | 1/2012 | Jorgensen et al. | |
| 2012/0028912 A1 | 2/2012 | Zhou et al. | |
| 2012/0157428 A1 | 6/2012 | Albrecht et al. | |
| 2012/0208798 A1 | 8/2012 | Demont et al. | |
| 2012/0208800 A1 | 8/2012 | Chung et al. | |
| 2012/0208814 A1 | 8/2012 | Demont et al. | |
| 2012/0220573 A1 | 8/2012 | Gosmini et al. | |
| 2013/0085133 A1 | 4/2013 | Severson et al. | |
| 2013/0143880 A1 | 6/2013 | Dudkin et al. | |
| 2013/0261109 A1 | 10/2013 | Miyoshi et al. | |
| 2013/0281396 A1 | 10/2013 | McLure et al. | |
| 2013/0281397 A1 | 10/2013 | McLure et al. | |
| 2013/0281398 A1 | 10/2013 | McLure et al. | |
| 2013/0281399 A1 | 10/2013 | McLure et al. | |
| 2014/0031336 A1 | 1/2014 | Amans et al. | |
| 2014/0045834 A1 | 2/2014 | Demont et al. | |
| 2014/0140956 A1 | 5/2014 | Fairfax et al. | |
| 2014/0162971 A1 | 6/2014 | Wang et al. | |
| 2014/0171462 A1 | 6/2014 | Demont et al. | |
| 2014/0256700 A1 | 9/2014 | Poss et al. | |
| 2014/0256705 A1 | 9/2014 | Hasvold et al. | |
| 2014/0256706 A1 | 9/2014 | Wang et al. | |
| 2014/0256710 A1 | 9/2014 | Liu et al. | |
| 2014/0275030 A1 | 9/2014 | Combs et al. | |
| 2014/0275079 A1 | 9/2014 | Hasvold et al. | |
| 2014/0296246 A1 | 10/2014 | Aktoudianakis et al. | |
| 2014/0303121 A1 | 10/2014 | Zhang et al. | |
| 2014/0336190 A1 | 11/2014 | Aktoudianakis et al. | |
| 2014/0349990 A1 | 11/2014 | Blank et al. | |
| 2015/0011540 A1 | 1/2015 | Combs et al. | |
| 2015/0246919 A1 | 9/2015 | Engelhardt et al. | |
| 2016/0137613 A1 | 5/2016 | Hansen | |
| 2016/0159801 A1 | 6/2016 | Quinn et al. | |
| 2016/0184273 A1 | 6/2016 | Liu et al. | |
| 2016/0193218 A1 | 7/2016 | Quinn et al. | |
| 2017/0143731 A1 | 5/2017 | Liu et al. | |
| 2017/0182029 A1 | 6/2017 | Liu et al. | |
| 2017/0216257 A1 | 8/2017 | Liu et al. | |
| 2017/0320866 A1 | 11/2017 | Jiang et al. | |
| 2017/0360756 A1 | 12/2017 | Brown et al. | |
| 2017/0360760 A1 | 12/2017 | Kharenko et al. | |
| 2017/0360765 A1 | 12/2017 | Jiang et al. | |

FOREIGN PATENT DOCUMENTS

| | | |
|---|---|---|
| CA | 2440211 A1 | 9/2002 |
| CA | 2818187 A1 | 6/2012 |
| CA | 2911408 A1 | 11/2014 |
| CA | 2915561 A1 | 1/2015 |
| CA | 2915838 A1 | 1/2015 |
| CN | 1113235 A | 12/1995 |
| CN | 1636977 A | 7/2005 |
| CN | 1263757 C | 7/2006 |
| CN | 1934092 A | 3/2007 |
| CN | 101061098 A | 10/2007 |
| CN | 101220077 A | 7/2008 |
| CN | 101384593 A | 3/2009 |
| CN | 101636386 A | 1/2010 |
| CN | 101983198 A | 3/2011 |
| CN | 102186833 A | 9/2011 |
| CN | 102731409 A | 10/2012 |
| CN | 105102453 A | 11/2015 |
| EP | 0 385 850 A2 | 9/1990 |
| EP | 0 556 789 A2 | 8/1993 |
| EP | 0 566 020 A1 | 10/1993 |
| EP | 0 195 947 B1 | 4/1996 |
| EP | 1 944 311 A1 | 7/2008 |
| EP | 2 196 465 A1 | 6/2010 |
| EP | 2 390 250 A2 | 11/2011 |
| EP | 2 792 355 A1 | 10/2014 |
| JP | 2000-072675 A | 3/2000 |
| JP | 2003-523353 A | 8/2003 |
| JP | 2004-519512 A | 7/2004 |
| JP | 2007-530477 A | 11/2007 |
| JP | 2008-513414 A | 5/2008 |
| JP | 2009-532424 A | 9/2009 |
| JP | 2010-513224 A | 4/2010 |
| JP | 2010-532768 A | 10/2010 |
| JP | 2010-540590 A | 12/2010 |
| JP | 2012-513418 A | 6/2012 |
| KR | 10-1165996 B1 | 10/2011 |
| KR | 10-1242572 B1 | 4/2012 |
| WO | WO 96/33194 A1 | 10/1996 |
| WO | WO 00/34248 A1 | 6/2000 |
| WO | WO 00/66564 A1 | 11/2000 |
| WO | WO 01/55132 A1 | 8/2001 |
| WO | WO 02/057267 A1 | 7/2002 |
| WO | WO 02/067675 A2 | 9/2002 |
| WO | WO 02/076976 A2 | 10/2002 |
| WO | WO 02/078708 A1 | 10/2002 |
| WO | WO 2004/024897 A2 | 3/2004 |
| WO | WO 2004/078733 A1 | 9/2004 |
| WO | WO 2004/098494 A2 | 11/2004 |
| WO | WO 2005/013950 A2 | 2/2005 |
| WO | WO 2005/075432 A1 | 8/2005 |
| WO | WO 2005/080380 A1 | 9/2005 |
| WO | WO 2005/090317 A1 | 9/2005 |
| WO | WO 2005/117876 A1 | 12/2005 |
| WO | WO 2006/030032 A1 | 3/2006 |
| WO | WO 2006/038734 A1 | 4/2006 |
| WO | WO 2006/119400 A2 | 11/2006 |
| WO | WO 2007/016525 A2 | 2/2007 |
| WO | WO 2007/040208 A1 | 4/2007 |
| WO | WO 2007/063012 A1 | 6/2007 |
| WO | WO 2007/093901 A1 | 8/2007 |
| WO | WO 2007/113232 A1 | 10/2007 |
| WO | WO 2008/054599 A2 | 5/2008 |
| WO | WO 2008/072784 A1 | 6/2008 |
| WO | WO 2009/006959 A1 | 1/2009 |
| WO | WO 2009/024221 A1 | 2/2009 |
| WO | WO 2009/043883 A1 | 4/2009 |
| WO | WO 2009/054790 A1 | 4/2009 |
| WO | WO 2009/099801 A1 | 8/2009 |
| WO | WO 2009/158258 A1 | 12/2009 |
| WO | WO 2010/021693 A2 | 2/2010 |
| WO | WO 2010/068483 A2 | 6/2010 |
| WO | WO 2010/072296 A1 | 7/2010 |
| WO | WO 2010/077275 A1 | 7/2010 |
| WO | WO 2010/097368 A1 | 9/2010 |
| WO | WO 2010/104851 A1 | 9/2010 |
| WO | WO 2010/106436 A2 | 9/2010 |
| WO | WO 2010/123975 A1 | 10/2010 |
| WO | WO 2010/0127976 A1 | 11/2010 |
| WO | WO 2011/054843 A1 | 5/2011 |
| WO | WO 2011/054846 A1 | 5/2011 |
| WO | WO 2011/143669 A2 | 11/2011 |

(56) References Cited

FOREIGN PATENT DOCUMENTS

| WO | WO 2011/156626 A1 | 12/2011 |
|---|---|---|
| WO | WO 2011/159926 A1 | 12/2011 |
| WO | WO 2012/003576 A1 | 1/2012 |
| WO | WO 2012/009258 A2 | 1/2012 |
| WO | WO 2012/021382 A1 | 2/2012 |
| WO | WO 2012/040499 A2 | 3/2012 |
| WO | WO 2012/075456 A1 | 6/2012 |
| WO | WO 2012/143413 A1 | 10/2012 |
| WO | WO 2012/174487 A2 | 12/2012 |
| WO | WO 2013/024104 A1 | 2/2013 |
| WO | WO 2013/027168 A1 | 2/2013 |
| WO | WO 2013/064900 A1 | 5/2013 |
| WO | WO 2013/082429 A1 | 6/2013 |
| WO | WO 2013/156869 A1 | 10/2013 |
| WO | WO 2013/158952 A1 | 10/2013 |
| WO | WO 2013/184878 A1 | 12/2013 |
| WO | WO 2013/186229 A1 | 12/2013 |
| WO | WO 2014/031928 A2 | 2/2014 |
| WO | WO 2014/043246 A1 | 3/2014 |
| WO | WO 2014/078257 A1 | 5/2014 |
| WO | WO 2014/095775 A1 | 6/2014 |
| WO | WO 2014/128070 A1 | 8/2014 |
| WO | WO 2014/128111 A1 | 8/2014 |
| WO | WO 2014/128655 A1 | 8/2014 |
| WO | WO 2014/134267 A1 | 9/2014 |
| WO | WO 2014/140076 A1 | 9/2014 |
| WO | WO 2014/140077 A1 | 9/2014 |
| WO | WO 2014/152029 A2 | 9/2014 |
| WO | WO 2014/154760 A1 | 10/2014 |
| WO | WO 2014/154762 A1 | 10/2014 |
| WO | WO 2014/159837 A1 | 10/2014 |
| WO | WO 2014/160873 A1 | 10/2014 |
| WO | WO 2014/165143 A1 | 10/2014 |
| WO | WO 2014/170350 A1 | 10/2014 |
| WO | WO 2014/173241 A1 | 10/2014 |
| WO | WO 2014/182929 A1 | 11/2014 |
| WO | WO 2014/202578 A1 | 12/2014 |
| WO | WO 2015/002754 A2 | 1/2015 |
| WO | WO 2015/004533 A2 | 1/2015 |
| WO | WO 2015/004534 A2 | 1/2015 |
| WO | WO 2015/011084 A1 | 1/2015 |
| WO | WO 2015/013635 A2 | 1/2015 |
| WO | WO 2015/015318 A2 | 2/2015 |
| WO | WO 2015/086507 A1 | 6/2015 |
| WO | WO 2016/087936 A1 | 6/2016 |
| WO | WO 2016/087942 A1 | 6/2016 |
| WO | WO 2016/092375 A1 | 6/2016 |
| WO | WO 2016/097863 A1 | 6/2016 |
| WO | WO 2016/097870 A1 | 6/2016 |

OTHER PUBLICATIONS

Banerjee, C. et al., "BET bromodomain inhibition as a novel strategy for reactivation of HIV-1" *J Leukoc Biol*, 2012. 92(6):1147-54.
Baron, P. et al., "Production of IL-6 by human myoblasts stimulated with Abeta: relevance in the pathogenesis of IBM" *Neurology*, 2001. 57(9):1561-5.
Bartholomeeusen, K. et al., "BET bromodomain inhibition activates transcription via a transient release of P-TEFb from 7SK snRNP" JBC In Press, 2012. M112.410746, 16 pages. Final publication in: *J Biol Chem*, 287:36609-16.
Bassiouny, D.A. and O. Shaker, "Role of interleukin-17 in the pathogenesis of vitiligo" *Clin Exp Dermatol*, 2011. 36(3):292-7.
Bayraktaroolu, T. et al., "Serum levels of tumor necrosis factor-alpha, interleukin-6 and interleukin-8 are not increased in dyspeptic patients with Helicobacter pylori-associated gastritis" *Mediators Inflamm*, 2004. 13(1):25-8.
Belanger, D.B. et al., "Discovery of imidazo[1,2-a]pyrazine-based Aurora kinase inhibitors" *Bioorg. Med. Chem. Lett.*, 20:5170-5174 (2010).
Belkina, A.C. and G.V. Denis, "BET domain co-regulators in obesity, inflammation and cancer" *Nat Rev Cancer*, 2012. 12(7):465-77.

Bellan, C. et al., "CDK9/CYCLIN T1 expression during normal lymphoid differentiation and malignant transformation" *J. Pathol.*, 2004. 203(4):946-52.
Belli, F. et al., "Cytokines assay in peripheral blood and bronchoalveolar lavage in the diagnosis and staging of pulmonary granulomatous diseases" *Int J Immunopathol Pharmacol*, 2000. 13(2):61-67.
Berkovits, B.D. et al., "The testis-specific double bromodomain-containing protein BRDT forms a complex with multiple spliceosome components and is required for mRNA splicing and 3'-UTR truncation in round spermatids" *Nucleic Acids Res*, 2012. 40(15):7162-75.
Besnard, A.G. et al., "Inflammasome-IL-1-Th17 response in allergic lung inflammation" *J Mol Cell Biol*, 2012. 4(1):3-10.
Boring, L. et al., "Decreased lesion formation in CCR2-/- mice reveals a role for chemokines in the initiation of atherosclerosis" *Nature*, 1998. 394(6696):894-7.
Bradley, D.T. and S.E. Kountakis, "Role of interleukins and transforming growth factor-beta in chronic rhinosinusitis and nasal polyposis" *Laryngoscope*, 2005. 115(4):684-6.
Brennan, P., "Isoxazole inhibitors of Bromodomains" presented at the *RSC Advances in Synthesis and Medicinal Chemistry Conference*, BioPark, Welwyn Garden City, UK, May 1, 2012 (46 pages).
Brodmerkel, C.M. et al., "Discovery and pharmacological characterization of a novel rodent-active CCR2 antagonist, INCB3344" *J Immunol*, 2005. 175(8):5370-8.
Brühl, H. et al., "Dual role of CCR2 during initiation and progression of collagen-induced arthritis: evidence for regulatory activity of CCR2+ T cells" *J Immunol*, 2004. 172(2);890-8.
Cannon, J.G., "Analog Design" in *Burger's Medicinal Chemistry and Drug Discovery. 5th Ed., vol. 1: Principles and Practice.* Manfred E. Wolff (ed.), John Wiley & Sons, Inc., New York, NY, 1995; Chapter 19, pp. 783-802.
Chaidos, A. et al., "Inhibition of bromodomain and extraterminal proteins (BET) as a potential therapeutic approach in haematological malignancies; emerging preclinical and clinical evidence" *Ther Adv Hematol*, 6(3):128-141 (2015).
ChemDiv, Inc. In Chemical Abstracts Record No. 1340694-11-8, Entered into the Registry File Nov. 4, 2011.
Chemical Abstracts Service, 'Registry' File, RN 1348662-08-5; STN Database [online]. Entry Date: Dec. 4, 2011 (1 page).
Chemical Abstracts Service, 'Registry' File, RN 1349387-93-4; STN Database [online]. Entry Date: Dec. 6, 2011 (1 page).
Chen, L. et al., "IL-17RA aptamer-mediated repression of IL-6 inhibits synovium inflammation in a murine model of osteoarthritis" *Osteoarthritis Cartilage*, 2011. 19(6):711-8.
Chevrel, G. et al., "Interleukin-17 increases the effects of IL-1 beta on muscle cells: arguments for the role of T cells in the pathogenesis of myositis" *J Neuroimmunol*, 2003. 137(1-2):125-33.
Chung, C.W. et al., "Bromodomains: a new target class for small molecule drug discovery" *Drug Discovery Today: Therapeutic Strategies* 9(2-3):e111-e120 (2012).
Chung, C.W. et al., "Discovery and characterization of small molecule inhibitors of the BET family bromodomains" *J Med Chem*, 2011. 54(11):3827-38.
Chung, C.W., "Small Molecule Bromodomain Inhibitors: Extending the Druggable Genome" *Progr. Med. Chem.*, 51:1-55 (2012).
Cid, J.M. et al., "Discovery of 1,5-Disubstituted Pyridones: A New Class of Positive Allosteric Modulators of the Metabotropic Glutamate 2 Receptor" *ACS Chem. Neurosci.* 1:786-795 (2010).
clinical trials.gov, "A Study to Investigate the Safety, Pharmacokinetics, Pharmacodynamics, and Clinical Activity of GSK525762 in Subjects With NUT Midline Carcinoma (NMC) and Other Cancers" GlaxoSmithKline, Identifier NCT01587703, verified Dec. 2016 [online], Retrieved from: https://clinicaltrials.gov/ct2/show/NCT01587703, on Dec. 28, 2016 (6 pages).
Costello, J.F. et al., "Cyclin-dependent kinase 6 (CDK6) amplification in human gliomas identified using two-dimensional separation of genomic DNA" *Cancer Res*, 1997. 57(7):1250-4.
D'Auria, L. et al., "Cytokines and bullous pemphigoid" *Eur Cytokine Netw*, 1999. 10(2):123-34.
Dawson, J. et al., "Targeting monocyte chemoattractant protein-1 signalling in disease" *Expert Opin Ther Targets*, 2003. 7(1):35-48.

(56) References Cited

OTHER PUBLICATIONS

Dawson, M.A. et al., "Inhibition of BET Recruitment to Chromatin as an Effective Treatment for MLL-fusion Leukaemia" *Nature*, 2011, 478:529-533.
De Falco, G. et al., "Cdk9 regulates neural differentiation and its expression correlates with the differentiation grade of neuroblastoma and PNET tumors" *Cancer Biol Ther*, 2005. 4(3):277-81.
De Lemos, J.A. et al., "Association between plasma levels of monocyte chemoattractant protein-1 and long-term clinical outcomes in patients with acute coronary syndromes" *Circulation*, 2003. 107(5):690-5.
De Paiva, C.S. et al., "IL-17 disrupts corneal barrier following desiccating stress" *Mucosal Immunol*, 2009. 2(3):243-53.
Degoma, E.M. and D.J. Rader, "Novel HDL-directed pharmacotherapeutic strategies" *Nat Rev Cardiol*, 2011, 8(5):266-77.
Delmore, J.E. et al., "BET bromodomain inhibition as a therapeutic strategy to target c-Myc" *Cell*, 2011. 146(6):904-17.
Deng, J. et al., "Th17 and Th1 T-cell responses in giant cell arteritis" *Circulation*, 2010. 121(7):906-15.
Denis, G.V. et al., "An emerging role for bromodomain-containing proteins in chromatin regulation and transcriptional control of adipogenesis" *FEBS Lett*, 2010. 584(15):3260-8. (Author manuscript, 21 pages).
Denis, G.V., "Bromodomain coactivators in cancer, obesity, type 2 diabetes, and inflammation" *Discov Med*, 2010. 10(55):489-99.
Deo, R. et al., "Association among plasma levels of monocyte chemoattractant protein-1, traditional cardiovascular risk factors, and subclinical atherosclerosis" *J Am Coll Cardiol*, 2004. 44(9): p. 1812-8.
Dias, P.M. and G. Banerjee, "The Role of Th17/IL-17 on Eosinophilic Inflammation" *J Autoimmun*, 2012. Article in Press: http://dx.doi.org/10.1016/j.jaut.2012.07.004, 12 pages.
Elliott, D.A. et al., "Apolipoproteins in the brain: implications for neurological and psychiatric disorders" *Clin Lipidol*, 2010. 51(4):555-573. (Author manuscript, 28 pages).
El-Osta, H.E. and R. Kurzrock, "Castleman's disease: from basic mechanisms to molecular therapeutics" *Oncologist*. 2011. 16(4):497-511.
European Patent Application No. 13864406.7, by Zenith Epigenetics Corp.: Extended European Search Report, including Search Opinion, dated Mar. 30, 2016 (6 pages).
European Patent Application No. 14820520.6, by Zenith Epigenetics Corp.: Extended European Search Report, including Search Opinion, dated Feb. 8, 2017 (9 pages).
European Patent Application No. 14822480.1, by Zenith Epigenetics Corp.: Extended European Search Report, including Search Opinion, dated Jan. 4, 2017 (10 pages).
European Patent Application No. 14822511.3, by Zenith Epigenetics Corp.: Extended European Search Report, including Search Opinion, dated Jan. 2, 2017 (7 pages).
European Patent Application No. 14832298.5, by Zenith Epigenetics Corp.: Extended European Search Report, including Search Opinion, dated Nov. 11, 2016 (6 pages).
European Patent No. EP 0 385 850 A2: Machine English translation; retrieved from ProQuest Dialog, on Aug. 15, 2016; 68 pages.
European Patent No. EP 0 556 789 A2: Machine English translation; retrieved from ProQuest Dialog, on Aug. 15, 2016, 59 pages.
Fife, B.T. et al., "CC chemokine receptor 2 is critical for induction of experimental autoimmune encephalomyelitis" *J Exp Med*, 2000. 192(8):899-905.
Figueroa-Vega, N. et al., "Increased circulating pro-inflammatory cytokines and Th17 lymphocytes in Hashimoto's thyroiditis" *J Clin Endocrinol Metab*, 2010. 95(2):953-62.
Filippakopoulos, P. and S. Knapp, "Targeting bromodomains: epigenetic, readers of lysine acetylation" *Nature Reviews*, 13:337-356 (2014).
Filippakopoulos, P. et al., "Selective inhibition of BET Bromodomains", *Nature*, 2010, 468:1067-1073.

Fish, P.V. et al., "Identification of a chemical probe for bromo and extra C-terminal bromodomain inhibition through optimization of a fragment-derived hit" *J. Med. Chem*. 55:9831-9837 (2012).
Freireich, E.J. et al., "Quantitative comparison of toxicity of anticancer agents in mouse, rat, hamster, dog, monkey, and man" *Cancer Chemother Rep*, 50(4):219-244 (1966).
French, C.A., "NUT midline carcinoma" *Cancer Genet Cytogenet*, 2010. 203(1):16-20. (Author manuscript, 9 pages).
Fujioka, A. et al., "The analysis of mRNA expression of cytokines from skin lesions in Churg-Strauss syndrome" *J Dermatol*, 1998. 25(3):171-7.
Fujishima, S. et al., "Involvement of IL-17F via the induction of IL-6 in psoriasis" *Arch Dermatol Res*2010. 302(7):499-505.
Gagnon, D. et al., "Proteasomal degradation of the papillomavirus E2 protein is inhibited by overexpression of bromodomain-containing protein 4" *J Virol*, 2009. 83(9):4127-39.
Gaucher, J. et al., "Bromodomain-dependent stage-specific male genome programming by Brdt" *EMBO J*, 2012. 31(19)3809-20.
Gharbi et al., "Exploring the specificity of the PI3k family inhibitor LY294002" *Biochem. J*. 404:15-21 (2007).
Gloddek, B. et al., "Pharmacological influence on inner ear endothelial cells in relation to the pathogenesis of sensorineural hearing loss" *Adv Otorhinolaryngol*, 2002. 59:75-83.
Gong, J-H. et al., "An antagonist of monocyte chemoattractant protein 1 (MCP-1) inhibits arthritis in the MRL-lpr mouse model" *J Exp Med*. 1997. 186(1):131-7.
Gong, J-H. et al., "Post-onset inhibition of murine arthritis using combined chemokine antagonist therapy" *Rheumatology*, 2004. 43(1):39-42.
González-Serrano, M.E. et al., "Increased Pro-inflammatory Cytokine Production After Lipopolysaccharide Stimulation in Patients with X-linked Agammaglobulinemia" *J Clin Immunol*, 2012. 32(5):967-74.
Gosling, J. et al., "MCP-1 deficiency reduces susceptibility to atherosclerosis in mice that overexpress human apolipoprotein B" *J Clin Invest*, 1999. 103(6)773-8.
Graber, J.J. et al., "Interleukin-17 in transverse myelitis and multiple sclerosis" *J Neuroimmunol*, 2008. 196(1-2):124-32.
Greenwald, R.J. et al., "E mμ-BRD2 transgenic mice develop B-cell lymphoma and leukemia" *Blood*, 2004. 103(4):1475-84.
Grunwald, C. et al., "Expression of multiple epigenetically regulated cancer/germline genes in nonsmall cell lung cancer" *Int J Cancer*, 2006. 118(10):2522-8.
Gu, L. et al., "Absence of monocyte chemoattractant protein-1 reduces atherosclerosis in low density lipoprotein receptor-deficient mice" *Mol Cell*. 1998. 2(2):275-81.
Gu, Y. et al., "Interleukin (IL-)-17 promotes macrophages to produce IL-8, IL-6 and tumour necrosis factor-alpha in aplastic anaemia" *Br J Haematol*, 2008. 142(1):109-14.
Hankovszky, H.O. et al., "Synthesis and reaction of orthofluoronitroaryl nitroxides. Novel versatile synthons and reagents for spin-labelling studies" *Can J Chem*, 67:1392-1400 (1989).
Harada, K. et al., "Periductal interleukin-17 production in association with biliary innate immunity contributes to the pathogenesis of cholangiopathy in primary biliary cirrhosis" *Clin Exp Immunol*. 2009. 157(2):261-70.
Haruta, H. et al., "Blockade of interleukin-6 signaling suppresses not only TH17 but also interphotoreceptor retinoid binding protein-specific Th1 by promoting regulatory T cells in experimental autoimmune uveoretinitis" *Invest Ophthalmol Vis Sci*, 2011. 52(6):3264-71.
Hay et al., "The design and synthesis of 5- and 6-isoxazolylbenzimidazoles as selective inhibitors of the BET bromodomains" *Med. Chem. Commun*. 4:140-144 (2013).
Hay, D.A. et al., "Discovery and Optimization of Small-Molecule Ligands for the CBP/p300 Bromodomains" *J. Am. Chem. Soc*. 136:9308-9319 (2014).
Hewings et al., "3,5-Dimethylisoxazoles Act As Acetyl-lysine-mimetic Bromadomain Ligands" *J. Med. Chem*. 54:6761-6770 (2011).
Hewings et al., "3,5-Dimethylisoxazoles inhibit the bromodomain-histone protein-protein interaction" *243rd National Spring Meeting of the American-Chemical-Society (Symposium on Ionic Liquids—*

(56) References Cited

OTHER PUBLICATIONS

*Science and Applications*), San Diego, CA. General Poster Session, Mar. 28, 2012, Poster 326 Abstract [online]. Retrieved from: http://acselb-529643017.us-west-2.elb.amazonaws.com/chem/243nm/program/view.php?pub_num=326&par=MEDI.
Hewings et al., "Optimization of 3,5-Dimethylisoxazole Derivatives as Potent Bromodomain Ligands" *J. Med. Chem.* 56:3217-3227 (2013).
Hewings et al., "Progress in the development and application of small molecule inhibitors of bromodomain-acetyl-lysine interactions" *J. Med. Chem.* 55:9393-9413 (2012).
Hintermann, S. et al., "Identification of a series of highly potent activators of the Nurr 1 signaling pathway" *Bioorg Med Chem Lett*, 17:193-196 (2007).
Hohki, S. et al., "Blockade of interleukin-6 signaling suppresses experimental autoimmune uveoretinitis by the inhibition of inflammatory Th17 responses" *Exp Eye Res*, 2010. 91(2):162-70.
Hölttä, V. et al., "IL-23/IL-17 immunity as a hallmark of Crohn's disease" *Inflamm Bowel Dis*, 2008. 14(9):1175-84.
Hoshino, I. and H. Matsubara, "Recent advances in histone deacetylase targeted cancer therapy" *Surg Today*, 2010. 40(9):809-15.
Huang, D. et al., "Absence of monocyte chemoattractant protein 1 in mice leads to decreased local macrophage recruitment and antigen-specific T helper cell type 1 immune response in experimental autoimmune encephalomyelitis" *J Exp Med*, 2001. 193(6):713-26.
Içöz, S. et al., "Enhanced IL-6 production in aquaporin-4 antibody positive neuromyelitis optica patients" *Int J Neurosci*, 2010. 120(1):71-5.
International Search Report and Written Opinion Issued in International Application No. PCT/IB2013/000968; dated Sep. 13, 2013.
International Search Report and Written Opinion issued in International Application No. PCT/IB2013/001026; dated Sep. 30, 2013.
International Search Report and Written Opinion issued in International Application No. PCT/IB2013/001232; dated Sep. 6, 2013.
International Search Report and Written Opinion issued in International Application No. PCT/IB2013/003122; dated Jul. 9, 2014.
International Search Report and Written Opinion issued in International Application No. PCT/IB2013/003126; dated Jun. 26, 2014.
International Search Report and Written Opinion issued in International Application No. PCT/IB2013/003202; dated Jul. 17, 2014.
International Search Report and Written Opinion issued in International Application No. PCT/IB2014/002238; dated Apr. 23, 2015.
International Search Report and Written Opinion issued in International Application No. PCT/IB2014/002240; dated Mar. 10, 2015.
International Search Report and Written Opinion issued in International Application No. PCT/IB2014/002510; dated Apr. 15, 2015.
International Search Report and Written Opinion issued in International Application No. PCT/IB2015/002429; dated Apr. 13, 2016.
International Search Report and Written Opinion issued in International Application No. PCT/IB2015/002462; dated Apr. 13, 2016.
International Search Report and Written Opinion issued in International Application No. PCT/IB2015/002479; dated Apr. 21, 2016.
International Search Report and Written Opinion issued in International Application No. PCT/IB2015/002490; dated Apr. 1, 2016.
International Search Report and Written Opinion issued in International Application No. PCT/IB2015/002522; dated Apr. 13, 2016.
International Search Report and Written Opinion issued in International Application No. PCT/US2014/043423; dated Jan. 12, 2005.
Ishizu, T. et al., "CSF cytokine and chemokine profiles in acute disseminated encephalomyelitis" *J Neuroimmunol*, 2006. 175(1-2):52-58.
Ito, V. et al., "Pathogenic significance of interleukin-6 in a patient with antiglomerular basement membrane antibody-induced glomerulonephritis with multinucleated giant cells" *Am J Kidney Dis*, 1995. 26(1):72-9.
Jadidi-Niaragh, F. and A. Mirshafiey, "Th17 cell, the new player of neuroinflammatory process in multiple sclerosis" *Scand J Immunol*, 2011. 74(1):1-13.
Jahagirdar, R, et al., "An Orally Bioavailable Small Molecule RVX-297 Significantly Decreases Disease in a Mouse Model of Multiple Sclerosis" (Poster Presentation). World Congress of Inflammation, Paris, France, 2011, 1 page.
Jen, H-Y. et al., "Increased serum interleukin-17 and peripheral Th17 cells in children with acute Henoch-Schonlein purpura" *Pediatr Allergy Immunol*, 2011. 22(8):862-8.
Jia, S., et al., "The T helper type 17/regulatory T cell imbalance in patients with acute Kawasaki disease" *Clin Exp Immunol*, 2010. 162(1):131-7.
Johnson, R.B. et al., "'Interleukin-11 and IL-17 and the pathogenesis of periodontal disease" *J Periodontol*, 2004. 75(1):37-43.
Kahawita, I.P. and D.N. Lockwood, "Towards understanding the pathology of erythema nodosum leprosum" *Trans R Soc Trop Med Hyg*, 2008. 102(4):329-37.
Kallen, K.J. et al., "New developments in IL-6 dependent biology and therapy: where do we stand and what are the options?" *Expert Opin Investig Drugs*, 1999. 8(9):1327-49.
Kaplanski, G. et al., "Jarisch-Herxheimer reaction complicating the treatment of chronic Q fever endocarditis: elevated TNFalpha and IL-6 serum levels" *J Infect*, 1998. 37(1):83-4.
Kappel, L.W. et al., "IL-17 contributes to CD4-mediated graft-versus-host disease" *Blood*, 2009. 113(4):945-52.
Katsifis, G.E. et al., "Systemic and local interleukin-17 and linked cytokines associated with Sjogren's syndrome immunopathogenesis" *Am J Pathol*, 2009. 175(3):1167-77.
Kawai, M. et al., "Sustained response to tocilizumab, anti-interleukin-6 receptor antibody, in two patients with refractory relapsing polychondritis" *Rheumatology*, 2009. 48(3):318-9.
Kawakami, T. et al., "Reduction of interleukin-6, interleukin-8, and anti-phosphatidylserine-prothrombin complex antibody by granulocyte and monocyte adsorption apheresis in a patient with pyoderma gangrenosum and ulcerative colitis" *Am J Gastroenterol*, 2009. 104(9):2363-4.
Kawakami, T. et al., "Serum levels of interleukin-6 in patients with cutaneous polyarteritis nodosa" *Acta Derm Venereol*, 2012. 92(3):322-3.
Kelly, P.N. and A. Strasser, "The role of Bcl-2 and its pro-survival relatives in tumourigenesis and cancer therapy" *Cell Death Differ*, 2011. 18(9):1414-24.
Kim, S.E. et al., "Increased serum interleukin-17 in Graves' ophthalmopathy" *Graefes Arch Clin Exp Ophthalmol*, 2012. 250(10):1521-6.
Kimura, A. and T. Kishimoto, "IL-6: regulator of Treg/Th17 balance" *Eur J Immunol*, 2010. 40(7):1830-5.
Koch, A.E. et al., "Enhanced production of monocyte chemoattractant protein-1 in rheumatoid arthritis" *J Clin Invest*, 1992. 90(3):772-9.
Kyburz, D. and M. Corr, "Th17 cells generated in the absence of TGF-beta induce experimental allergic encephalitis upon adoptive transfer" *Expert Rev Clin Immunol*, 2011. 7(3).283-5.
Lahdenperä, A.I. et al., "Up-regulation of small intestinal interleukin-17 immunity in untreated coeliac disease but not in potential coeliac disease or in type 1 diabetes" *Clin Exp Immunol*, 2012.167(2):226-34.
Lamale, L.M. et al., "Interleukin-6, histamine, and methylhistamine as diagnostic markers for interstitial cystitis" *Urology*, 2006. 68(4):702-6.
Lamotte, Y. et al., "Identification of a novel series of BET family Bromodomain inhibitors: binding mode and profile of I-BET151 (GSK1210151A)" Bioorganic & Medicinal Chemistry Letters, 2012. Accepted manuscript, doi: 10.1016/j.bmcl.2012.02.041. Final publication as: Seal, J. et al., "Identification of a novel series of BET family bromadomain inhibitors: binding mode and profile of I-BET151 (GSK1210151A)" *Bioorg Med Chem Lett*, 2012. 22(8):2968-72.
Latifi, S.Q., et al., "Persistent elevation of serum interleukin-6 in intraabdominal sepsis identifies those with prolonged length of stay" *J Pediatr Surg*, 2004. 39(10):1548-52.
Lee, D.K. et al., "Androgen receptor interacts with the positive elongation factor P-TEFb and enhances the efficiency of transcriptional elongation" *J Biol Chem*, 2001. 276(13):9978-84.

(56) References Cited

OTHER PUBLICATIONS

Li, Z., et al., "The BET bromodomain inhibitor JQ1 activates HIV latency through antagonizing Brd4 inhibition of Tat-transactivation" *Nucleic Acids Res Advance Access*, 2012. DOI.10.1093/nar/gks976, 11 pages.
Lin, F.J. et al., "Imbalance of regulatory T cells to Th17 cells in IgA nephropathy" *Scand J Clin Lab Invest*, 2012. 72(3)221-9.
Linhares, U.C. et al., "The Ex Vivo Production of IL-6 and IL-21 by CD4(+) T Cells is Directly Associated with Neurological Disability in Neuromyelitis Optica Patients" *J Clin Immunol*, 2012, DOI 10.1007/s10875-012-9780-2, 11 pages.
Lopez-Robles, E. et al., "TNFalpha and IL-6 are mediators in the blistering process of pemphigus" *Int J Dermatol*, 2001. 40(3):185-8.
Lu, M.O. and J. Zhu, "The role of cytokines in Guillain-Barre syndrome" *J Neurol*, 2011. 258(4):533-48.
Ma, D. et al., "Profile of Th17 cytokines (IL-17, TGF-beta, IL-6) and Th1 cytokine (IFN-gamma) in patients with immune thrombocytopenic purpura" *Ann Hematol*, 2008. 87(11):899-904.
Mahad, D.J. and R.M. Ransohoff, "The role of MCP-1 (CCL2) and CCR2 in multiple sclerosis and experimental autoimmune encephalomyelitis (EAE)" *Semin Immunol*, 2003. 15(1):23-32.
Matzuk, M.M. et al., "Small-Molecule Inhibition of BRDT for Male Contraception" *Cell*, 2012. 150(4):673-684, with supplemental pp. S1-S8.
McKeown, M. et al., "Biased Multicomponent Reactions to Develop Novel Bromodomain Inhibitors" *J Med Chem*, 57:9019-9027 (2014).
McKinley, L. et al., "TH17 cells mediate steroid-resistant airway inflammation and airway hyperresponsiveness in mice" *J Immunol*, 2008. 181(6):4089-97.
McMahon, G. "VEGF Receptor Signaling in Tumor Angiogenesis" *The Oncologist*; 5(Suppl 1):3-10 (2000).
Medina-Franco, J.L. et al., "Pyridin-2(1H)-ones: A Promising Class of HIV-f1 Non-nucleoside Reverse Transcriptase Inhibitors" *ChemMedChem*, 2:1141-1147 (2007).
Mendrzyk, F. et al., "Genomic and protein expression profiling identifies CDK6 as novel independent prognostic marker in medulloblastoma" *J Clin Oncol*, 2005. 23(34):8853-62.
Mertz, Jennifer A., "Targeting MYC Dependence in Cancer by Inhibiting BET Bromodomains", *PNAS*, 2011, 108(40):16669-16674.
Min, C.K. et al., "Cutaneous leucoclastic vasculitis (LV) following bortezomib therapy in a myeloma patient; association with proinflammatory cytokines" *Eur J Haematol*, 2006. 76(3):265-8.
Mirguet, O. et al., "From ApoA1 upregulation to BET family bromodomain inhibition: discovery of I-BET151" *Bioorg Med Chem Lett*, Article in Press, 2012. doi: 10.1016/j.bmcl.2012.01.125, 5 pages. Final publication in vol. 22, No. 8, pp. 2963-2967.
Mitsuyama, K. et al., "STAT3 activation via interleukin 6 trans-signalling contributes to Ileitis in SAMP1/Yit mice" *Gut*, 2006. 55(9):1263-9.
Miyazaki, et al. "Intravenous Injection of Rabbit Apolipoprotein A-I Inhibits the Progression of Atherosclerosis in Cholesterol-Fed Rabbits" *Arterioscler. Thromb. Vasc. Biol.* 15: 1882-1888 (1995).
Mok, M.Y. et al., "The relation of interleukin 17 (IL-17) and IL-23 to Th1/Th2 cytokines and disease activity in systemic lupus erythematosus" *J Rheumatol*, 2010. 37(10):2046-52.
Morin, R.D. et al., "Frequent mutation of histone-modifying genes in non-Hodgkin lymphoma" *Nature*, 2011, 476(7360):298-303. (Author manuscript, 17 pages.).
Mudter, J. and M.F. Neurath, "IL-6 signaling in inflammatory bowel disease: pathophysiological role and clinical relevance" *Inflamm Bowel Dis*. 2007. 13(8):1016-23.
Muller Kobold, A.C. et al., "In vitro up-regulation of E-selectin and induction of interteukin-6 in endothelial cells by autoantibodies in Wegener's granulomatosis and microscopic polyanglitis" *Clin Exp Rheumatol*, 1999. 17(4):433-40.
Muller, S. et al., "Bromodomains as therapeutic targets" *Expert Rev Mol Med*, 2011. 13: e29, 21 pages.

Nakahama, H. et al., "Distinct responses of interleukin-6 and other laboratory parameters to treatment in a patient with Wegener's granulomatosis" *Intern Med*, 1993. 32(2):189-92.
Narayana, B.L. et al., "Synthesis of New 2-Substituted Pyrido[2,3-d]pyrimidine-4(1H)-ones and Their Antibacterial Activity" *Eur. J. Med. Chem.* 44(3):1369-1376 (2009).
Nelken, N.A. et al., "Monocyte chemoattractant protein-1 in human atheromatous plaques" *J Clin Invest*, 1991. 88(4):1121-7.
Ni, J. et al., "Involvement of Interleukin-17A in Pancreatic Damage in Rat Experimental Acute Necrotizing Pancreatitis" *Inflammation*, 2012. [online] DOI: 10.1007/s10753-012-9519-5, published Sep. 19, 2012 (13 pages).
Nicodeme et al., "Suppression of inflammation by a synthetic histone mimic" *Nature* 468:1119-1123 (2010).
Niu, J. and P.E. Kolattukudy, "Role of MCP-1 in cardiovascular disease: molecular mechanisms and clinical implications" *Clin Sci*. 2009. 117(3):95-109.
Ooi, J.D. et al, "Review: T helper 17 cells: their role in glomerulonephritis" *Nephrology*, 2010. 15(5):513-21.
Ortiz-Lucas, M. et al., "Irritable bowel syndrome immune hypothesis. Part two: the role of cytokines" *Rev Esp Enferm Dig*, 2010. 102(12):711-7.
Ott, C.J. et al., "BET bromodomain inhibition targets both c-Myc and IL7R in high-risk acute lymphoblastic leukemia" *Blood*, 2012. 120(14):2843-52.
Pakrashi, S.C. "4-Quinazolinones. II. Self-condensation of anthranilamide" *J Org Chem*, 36(5):642-645 (1971).
Palermo, R.D. et al., RNA polymerase II stalling promotes nucleosome occlusion and pTEFb recruitment to drive immortalization by Epstein-Barr virus. *PLoS Pathog*, 2011. 7(10): e1002334, 15 pages.
Paquet, P. and G.E. Plerard, "Interleukin-6 and the skin" *Int Arch Allergy Immunol*, 1996. 109(4):308-17.
Peserico, A. and C. Simone, "Physical and functional HAT/HDAC interplay regulates protein acetylation balance" *J Biomed Biotechnol*, 2011. 371832, 10 pages.
Pinedo, H.M. and D.J. Slamon, "Translational Research: The Role of VEGF in Tumor Angiogenesis" *The Oncologist*, 5(Suppl. 1):1-2 (2000).
Poreba, E. et al., "Epigenetic mechanisms in virus-induced tumorigenesis" *Clin Epigenetics*, 2011. 2(2):233-47.
Prabakaran, K, et al., "Iridium bromide catalysed, ultrasound-assisted, region-selective synthesis of ethyl-5-(trifluoromethyl)-1-(3-substituted-isoquinolin-l-yl)-1H-pyrazole-4-carboxylates", *Res. Chem. Intermed.*, 38:429-441 (2012).
Prinjha, R.K. et al., "Place your BETs: the therapeutic potential of bromodomains" *Trends Pharmacol Sci*, 2012. 33(3):146-53.
Radstake, T.R. et al., "The pronounced Th17 profile in systemic sclerosis (SSc) together with intracellular expression of TGFbeta and IFNgamma distinguishes SSc phenotypes" *PLoS One*, 2009. 4(6):e5903. 9 pages.
Ramsay, R.G. and T.J. Gonda, "MYB function in normal and cancer cells" *Nat Rev Cancer*, 2008. 8(7):523-34.
Raychaudhuri, S.P. et al., "IL-17 receptor and its functional significance in psoriatic arthritis" *Mol Cell Biochem*. 2012. 359(1-2):419-29.
Rhodus, N.L. et al., "Proinflammatory cytokine levels in saliva before and after treatment of (erosive) oral lichen planus with dexamethasone" *Oral Dis*, 2006. 12(2):112-6.
Rodriguez, R.M. et al., "Aberrant epigenetic regulation of bromodomain BRD4 in human colon cancer" *J Mol Med*, 2012. 90(5):587-95.
Roger, V.L. et al., "Heart disease and stroke statistics—2012 update: a report from the American Heart Association" *Circulation*, 2012. 125(1):3-e220.
Ruden, M. and N Puri, "Novel anticancer therapeutics targeting telomerase" *Cancer Treat Rev*, 2012. Article in Press: http://dx.doi.org/10.1016/j.ctrv.2012.06.007, 13 pages.
Rudloff, U. and Y. Samuels, "TYRO3-mediated regulation of MITF: a novel target in melanoma?" *Pigment Cell Melanoma Res*, 2010. 23(1):9-11.

(56) References Cited

OTHER PUBLICATIONS

Sanchez, R. and M.M. Zhou, "The role of human bromodomains in chromatin biology and gene transcription" *Curr Opin Drug Discov Devel*, 2009. 12(5): 659-65. (Author manuscript, 12 pages.).

Scanlan, M.J. et al., "Expression of cancer-testis antigens in lung cancer: definition of bromodomain testis-specific gene (BRDT) as a new CT gene, CT9" *Cancer Lett*, 2000, 150(2):155-64.

Seal, J. et al., "Identification of a novel series of BET family bromodomain inhibitors: Binding mode and profile of I-BET1. 5I(GSK1 21051A)" *Bioorg. Med. Chem. Lett.*, 22:2968-2972 (2012).

Segura, M.F. et al., "BRD4 Is a novel therapeutic target in melanoma" Poster Presentation, AACR 103rd Annual Meeting, Mar. 31-Apr. 4, 2012 in Chicago, IL. *Cancer Research*, 2012. 72(8), Supplement 1. Abstract 2185.

Shang, E. et al., "The first bromodomain of Brdt, a testis-specific member of the BET sub-family of double-bromodomain-containing proteins, is essential for male germ cell differentiation" *Development*, 2007. 134(19):3507-15.

Shibuya, M. et al., "Successful treatment with tocilizumab in a case of Cogan's syndrome complicated with aortitis" *Mod Rheumatol*. 2012, online: DOI 10.1007/s10165-012-0691-0, 5 pages.

Simmons, E.M. et al., "Plasma cytokine levels predict mortality in patients with acute renal failure" *Kidney Int*, 2004, 65(4):1357-65.

Simone, C. and A. Giordano, "Abrogation of signal-dependent activation of the cdk9/cyclin T2a complex in human RD rhabdomyosarcoma cells" *Cell Death Differ*, 2007. 14(1):192-5

Soltesz, P. et al., "Immunological features of primary anti-phospholipid syndrome in connection with endothelial dysfunction" *Rheumatology*, 2008. 47(11):1628-34.

Stenman, G. et al., "New tricks from an old oncogene: gene fusion and copy number alterations of MYB in human cancer" *Cell Cycle*, 2010. 9(15):2986-95.

Sun, Y. et al., "MMP-9 and IL-6 are potential biomarkers for disease activity in Takayasu's arteritis" *Int J Cardiol*. 2012. 156(2):236-8.

Tang, X. et al., "Assessment of Brd4 inhibition in idiopathic pulmonary fibrosis lung fibrobalsts and in vivo models of lung fibrosis" *Am. J. Pathol.*, 183(2):470-479 (2013).

Taylan, A. et al., "Evaluation of the T helper 17 axis in ankylosing spondylitis" *Rheumatol Int*, 2012. 32(8):2511-5.

Tong, W.G. et al., "Phase I and pharmacologic study of SNS-032, a potent and selective Cdk2, 7, and 9 inhibitor, in patients with advanced chronic lymphocytic leukemia and multiple myeloma" *J Clin Oncol*, 2010. 28(18):3015-22.

Traves, S.L. and L.E. Donnelly, "Th17 cells in airway diseases" *Curr. Mol. Med.*, 2008. 8(5):416-26.

Uchida, T. et al., "Antitumor effect of bcl-2 antisense phosphorothioate oligodeoxynucleotides on human renal-cell carcinoma cells in vitro and in mice" *Mol Urol*, 2001. 5(2):71-8.

Urano, W. et al., "The inflammatory process in the mechanism of decreased serum uric acid concentrations during acute gouty arthritis" *J Rheumatol*. 2002. 29(9):1950-3.

Utsunomiya, I. et al., "Preparation of Alkyl-Substituted Indoles in the Benzene Portion. Part 13. Enantiospecific Synthesis of Mitosene Analogues Related to FFR 900482 and FR 66979" *Chem Pharm Bull*, 43(1):37-48.

Velisek, L. et al., "GABAergic neuron deficit as an idiopathic generalized epilepsy mechanism: the role of BRD2 haploinsufficiency in juvenile myoclonic epilepsy" *PLoS One*, 2011. 6(8): e23656, 8 pages.

Vernarecci, S. et al., "Tuning acetylated chromatin with HAT inhibitors: a novel tool for therapy" *Epigenetics*, 2010. 5(2): p. 105-11.

Vidal, B. et al., "Discovery and Characterization of 4'-(2-Furyl)-N-pyridin-3-yl-4,5'-bipyrimidin-2'-amine (LAS38096), a Potent, Selective, and Efficacious $A_{26}$ Adenosine Receptor Antagonist" *J. Med. Chem.* 50:2732-2736 (2007).

Vidler, L.R. et al., "Discovery of Novel Small-Molecule Inhibitors of BRD4 Using Structure-Based Virtual Screening" *J Med Chem*, 56:8073-8088 (2013).

Vippagunta, S.R. et al., "Crystalline solids" *Adv Drug Del Rev*, 2001. 48:3-26.

Vita, M. and M. Henriksson, "The Myc oncoprotein as a therapeutic target for human cancer" *Semin Cancer Biol*. 2006. 18(4):316-30.

Voitenko et al., "Esters of o-(4-oxo-3,4-dihydro-2-quinazolinyl)benzoic acid and 5,11-dihydroisoindoio[2,1-a]quinazolinone-5 derivatives as β-cyclodextrin modifiers" *Dopovidi Natsional'noi Akademii Nauk Uraini(Reports of the National Academy of Sciences of Ukraine*), 8:132-138 (2005) English abstract on p. 132.

Wang, F. et al., "Brd2 disruption in mice causes severe obesity without Type 2 diabetes" *Biochem J*, 2010. 425(1): p. 71-83, with supplemental online material, 2 pages.

Wang, G. et al., "Increased cyclin-dependent kinase 6 expression in bladder cancer" *Oncol Lett*, 2012. 4(1): p. 43-46.

Wang, S. and P.M. Fischer, "Cyclin-dependent kinase 9: a key transcriptional regulator and potential drug target in oncology, virology and cardiology" *Trends Pharmacol Sci*, 2008. 29(6):302-13.

Watson, J.D., "Curing "incurable" cancer" *Cancer Discov*, 2011. 1(6):477-80.

Wu, S.Y. and C.M. Chiang, "The double bromodomain-containing chromatin adaptor Brd4 and transcriptional regulation" *J Biol Chem*, 2007. 282(18):13141-5.

Xing, W. et al., "Discovery of novel 2,6-disubstituted pyridazinone derivatives as acetylcholinesterase inhibitors" *Eur. J. Med. Chem*. 63:95-103 (2013).

Xu, L. et al., "Critical role of Th17 cells in development of autoimmune hemolytic anemia" *Exp Hematol*, 2012. Article In Press: http://dx.doi.org/10.1016/j.exphem.2012.08.008, 15 pages.

Yamaguchi, M. et al., "Novel Antiasthmatic Agents with Dual Activities of Thromboxane $A_2$ Synthetase Inhibition and Bronchodilation. 2. 4-(3-Pyridyl)-1(2H)-phthalazinones" *J. Med. Chem.*, 36:4061-4068 (1993).

Yamashita, T. et al., "IL-6-mediated Th17 differentiation through RORγt is essential for the initiation of experimental autoimmune myocarditis" *Cardiovasc Res*, 2011. 91(4):640-8.

Yoshii, T. et al., "Local levels of interleukin-1beta, -4, -6 and tumor necrosis factor alpha in an experimental model of murine osteomyelitis due to Staphylococcus aureus" *Cytokine*, 2002. 19(2):59-65.

Yoshimura, T. et al., "Involvement of Th17 cells and the effect of anti-IL-6 therapy in autoimmune uveitis" *Rheumatology*, 48(4):347-354 (2009).

You, J. et al., "Kaposi's sarcoma-associated herpesvirus latency-associated nuclear antigen interacts with bromodomain protein Brd4 on host mitotic chromosomes" *J Virol*, 2006. 80(18):8909-19.

Yu et al., "Discovery of Highly Potent and Selective α4β2-Nicotinic Acetylcholine Receptor (nAChR) Partial Agonists Containing an Isoxazolylpyridine Ether Scaffold that Demonstrate Antidepressant-like Activity" *J Med Chem*, 55:9997-10009 (2012).

Yu et al., "Toll-Like Receptor 7 Agonists: Chemical Feature Based Pharmacophore Identification and Molecular Docking Studies" *PLoS ONE* 8(3):e56514. doi:10.1371/journal.pone.0056514 (2013).

Zhang, G. et al., "Down-regulation of NF-kappaB Transcriptional Activity in HIVassociated Kidney Disease by BRD4 Inhibition" *JBC Papers in Press*, 2012. M112.359505 with supplement, 38 pages. Final publication in: *J Biol Chem*, 287(34):28840-51.

Zhang, W.S. et al., "Bromodomain-Containing-Protein 4 (BRD4) Regulates RNA Polymerase II Serine 2 Phosphorylation In Human CD4+ T Cells" JBC Papers in Press. 2012. M112.413047, 30 pages. Final publication in: *J Biol Chem*, 287:43137-55.

Zhao, L. et al., "Interleukin-17 contributes to the pathogenesis of autoimmune hepatitis through inducing hepatic interleukin-6 expression" *PLoS One*, 2011. 6(4):e18909, 8 pages.

Zhou, M. et al., "Bromodomain protein Brd4 regulates human immunodeficiency virus transcription through phosphorylation of CDK9 at threonine 29" *J Virol*. 2009. 83(2):1036-44.

Zhu, J. et al., "Reactivation of Latent HIV-1 by Inhibition of BRD4" *Cell Rep*, 2012. 2:1-10, with supplemental pp. S1-S7.

Zuber, J. et al., "RNAi screen identifies Brd4 as a therapeutic target in acute myeloid leukaemia" *Nature*, 2011. 478(7370):524-8.

(56) References Cited

OTHER PUBLICATIONS

Gottschalk, S. et al., "An Epstein-Barr virus deletion mutant associated with fatal lymphoproliferative disease unresponsive to therapy with virus-specific CTLs" *Blood*, 2001. 97:835-843.

He, A. and J.J.L. Miranda, "JQ1 reduces Epstein-Barr virus-associated lymphoproliferative disease in mice without sustained oncogene repression" *Leukemia & Lymphoma*, 2017. DOI: 10.1080/10428194.2017.1372578 [online], Retrieved Oct. 31, 2017 (5 pages).

McLaughlin-Drubin, M.E. and K. Munger, "Viruses Associated with Human Cancer" *Biochim Biophys Acta*, 2008. 1782(3):127-150. NIH Public Access Author Manuscript; available in PMC Mar. 1, 2009 (50 pages).

Patton, J.T. et al., "Silvestrol Modulates Direct Anti-Tumor Activity Against Epstein-Barr Virus (EBV)-Associated Lymphomas While Sparing Innate and Antigen Specific Adaptive Immunity" *Blood*, 2011. 118:Abstract 104 (2 pages).

Chemical Abstracts Service, 'Registry' File, RN 1209999-95-0; STN Database [online]. Entry Date: Mar. 15. 2010 (1 page).

Feng, Q. et al., "An epigenomic approach to therapy for tamoxifen-resistant breast cancer" *Cell Research*, 24:809-819 (2014).

Whelligan, D.K. et al. "Aminopyrazine inhibitors binding to an unusual inactive conformation of the mitotic kinase Nek2: SAR and structural characterization" *J Med Chem*. 53(21):7682-7698 (2010).

Yamaguchi, M. et al., "Novel Antiasthmatic Agents with Dual Activities of Thromboxane $A_2$ Synthetase Inhibition and Bronchodilation. 1. 2-[2-(1-Imidazolyl)alkyl]-1(2H)-phthalazinones" *J. Med. Chem.*, 36:4052-4060 (1993).

\* cited by examiner

BICYCLIC BROMODOMAIN INHIBITORS

CROSS-REFERENCE TO RELATED PATENT APPLICATIONS

This application is a divisional of U.S. application Ser. No. 14/977,508, filed Dec. 21, 2015 (issued as U.S. Pat. No. 9,663,520), which is a continuation of International Patent Application No. PCT/US2014/043423, filed Jun. 20, 2014, which claims the benefit of priority to U.S. Provisional Application No. 61/837,841, filed Jun. 21, 2013, each of which is incorporated herein by reference in its entirety.

This application claims priority from U.S. Provisional Patent Application No. 61/837,841, filed Jun. 21, 2013, which is hereby incorporated by reference in its entirety.

The invention provides novel compounds, pharmaceutical compositions containing such compounds, and their use in prevention and treatment of diseases and conditions associated with bromodomain and extra terminal domain (BET) proteins. Post-translational modifications (PTMs) of histones are involved in regulation of gene expression and chromatin organization in eukaryotic cells. Histone acetylation at specific lysine residues is a PTM that is regulated by histone acetylases (HATs) and deacetylases (HDACs). Peserico, A. and C. Simone, "Physical and functional HAT/HDAC interplay regulates protein acetylation balance," *J Biomed Biotechnol*, 2011:371832 (2011). Small molecule inhibitors of HDACs and HATs are being investigated as cancer therapy. Hoshino, I. and H. Matsubara, "Recent advances in histone deacetylase targeted cancer therapy" *Surg Today* 40(9):809-15 (2010); Vernarecci, S., F. Tosi, and P. Filetici, "Tuning acetylated chromatin with HAT inhibitors: a novel tool for therapy" *Epigenetics* 5(2):105-11 (2010); Bandyopadhyay, K., et al., "Spermidinyl-CoA-based HAT inhibitors block DNA repair and provide cancer-specific chemo- and radiosensitization," *Cell Cycle* 8(17): 2779-88 (2009); Arif, M., et al., "Protein lysine acetylation in cellular function and its role in cancer manifestation," *Biochim BiophysActa* 1799(10-12):702-16 (2010). Histone acetylation controls gene expression by recruiting protein complexes that bind directly to acetylated lysine via bromodomains. Sanchez, R. and M. M. Zhou, "The role of human bromodomains in chromatin biology and gene transcription," *Curr Opin Drug Discov Devel* 12(5):659-65 (2009). One such family, the bromodomain and extra terminal domain (BET) proteins, comprises Brd2, Brd3, Brd4, and BrdT, each of which contains two bromodomains in tandem that can independently bind to acetylated lysines, as reviewed in Wu, S. Y. and C. M. Chiang, "The double bromodomain-containing chromatin adaptor Brd4 and transcriptional regulation," *J Biol Chem* 282(18):13141-5 (2007).

Interfering with BET protein interactions via bromodomain inhibition results in modulation of transcriptional programs that are often associated with diseases characterized by dysregulation of cell cycle control, inflammatory cytokine expression, viral transcription, hematopoietic differentiation, insulin transcription, and adipogenesis. Belkina, A. C. and G. V. Denis, "BET domain co-regulators in obesity, inflammation and cancer," *Nat Rev Cancer* 12(7): 465-77 (2012). BET inhibitors are believed to be useful in the treatment of diseases or conditions related to systemic or tissue inflammation, inflammatory responses to infection or hypoxia, cellular activation and proliferation, lipid metabolism, fibrosis, and the prevention and treatment of viral infections. Belkina, A. C. and G. V. Denis, "BET domain co-regulators in obesity, inflammation and cancer," *Nat Rev Cancer* 12(7):465-77 (2012); Prinjha, R. K., J. Witherington, and K. Lee, "Place your BETs: the therapeutic potential of bromodomains," *Trends Pharmacol Sci* 33(3):146-53 (2012).

Autoimmune diseases, which are often chronic and debilitating, are a result of a dysregulated immune response, which leads the body to attack its own cells, tissues, and organs. Pro-inflammatory cytokines including IL-1β, TNF-α, IL-6, MCP-1, and IL-17 are overexpressed in autoimmune disease. IL-17 expression defines the T cell subset known as Th17 cells, which are differentiated, in part, by IL-6, and drive many of the pathogenic consequences of autoimmune disease. Thus, the IL-6/Th17 axis represents an important, potentially druggable target in autoimmune disease therapy. Kimura, A. and T. Kishimoto, "IL-6: regulator of Treg/Th17 balance," *Eur J Immunol* 40(7):1830-5 (2010). BET inhibitors are expected to have anti-inflammatory and immunomodulatory properties. Belkina, A. C. and G. V. Denis, "BET domain co-regulators in obesity, inflammation and cancer," *Nat Rev Cancer* 12(7):465-77 (2012); Prinjha, R. K., J. Witherington, and K. Lee, "Place your BETs: the therapeutic potential of bromodomains," *Trends Pharmacol Sci* 33(3):146-53 (2012). BET inhibitors have been shown to have a broad spectrum of anti-inflammatory effects in vitro including the ability to decrease expression of pro-inflammatory cytokines such as IL-1β, MCP-1, TNF-α, and IL-6 in activated immune cells. Mirguet, O., et al., "From ApoA1 upregulation to BET family bromodomain inhibition: discovery of I-BET151," *Bioorg Med Chem Lett* 22(8):2963-7 (2012); Nicodeme, E., et al., "Suppression of inflammation by a synthetic histone mimic," *Nature* 468(7327):1119-23 (2010); Seal, J., et al., "Identification of a novel series of BET family bromodomain inhibitors: binding mode and profile of I-BET151 (GSK1210151A)," *Bioorg Med Chem Lett* 22(8):2968-72 (2012). The mechanism for these anti-inflammatory effects may involve BET inhibitor disruption of Brd4 co-activation of NF-κB-regulated pro-inflammatory cytokines and/or displacement of BET proteins from cytokine promoters, including IL-6. Nicodeme, E., et al., "Suppression of inflammation by a synthetic histone mimic," *Nature* 468(7327):1119-23 (2010); Zhang, G., et al., "Down-regulation of NF-kappaB Transcriptional Activity in HIVassociated Kidney Disease by BRD4 Inhibition," *J Biol Chem*, 287(34):8840-51 (2012); Zhou, M., et al., "Bromodomain protein Brd4 regulates human immunodeficiency virus transcription through phosphorylation of CDK9 at threonine 29," *J Virol* 83(2):1036-44 (2009). In addition, because Brd4 is involved in T-cell lineage differentiation, BET inhibitors may be useful in inflammatory disorders characterized by specific programs of T cell differentiation. Zhang, W. S., et al., "Bromodomain-Containing-Protein 4 (BRD4) Regulates RNA Polymerase II Serine 2 Phosphorylation in Human CD4+ T Cells," *J Biol Chem* (2012).

The anti-inflammatory and immunomodulatory effects of BET inhibition have also been confirmed in vivo. A BET inhibitor prevented endotoxin- or bacterial sepsis-induced death and cecal ligation puncture-induced death in mice, suggesting utility for BET inhibitors in sepsis and acute inflammatory disorders. Nicodeme, E., et al., "Suppression of inflammation by a synthetic histone mimic," *Nature* 468(7327):1119-23 (2010). A BET inhibitor has been shown to ameliorate inflammation and kidney injury in HIV-1 transgenic mice, an animal model for HIV-associated nephropathy, in part through inhibition of Brd4 interaction with NF-κB. Zhang, G., et al., "Down-regulation of NF-kappaB Transcriptional Activity in HIVassociated Kidney Disease by BRD4 Inhibition," *J Biol Chem*, 287(34):8840-51 (2012).

The utility of BET inhibition in autoimmune disease was demonstrated in a mouse model of multiple sclerosis, where BET inhibition resulted in abrogation of clinical signs of disease, in part, through inhibition of IL-6 and IL-17. R. Jahagirdar, S. M. et al., "An Orally Bioavailable Small Molecule RVX-297 Significantly Decreases Disease in a Mouse Model of Multiple Sclerosis," *World Congress of Inflammation*, Paris, France (2011). These results were supported in a similar mouse model where it was shown that treatment with a BET inhibitor inhibited T cell differentiation into pro-autoimmune Th1 and Th17 subsets in vitro, and further abrogated disease induction by pro-inflammatory Th1 cells. Bandukwala, H. S., et al., "Selective inhibition of CD4+ T-cell cytokine production and autoimmunity by BET protein and c-Myc inhibitors," *Proc Natl Acad Sci USA*, 109(36):14532-7 (2012).

BET inhibitors may be useful in the treatment of a variety of chronic autoimmune inflammatory conditions. Thus, one aspect of the invention provides compounds, compositions, and methods for treating autoimmune and/or inflammatory diseases by administering one or more compounds of the invention or pharmaceutical compositions comprising one or more of those compounds. Examples of autoimmune and inflammatory diseases, disorders, and syndromes that may be treated using the compounds and methods of the invention include but are not limited to, inflammatory pelvic disease, urethritis, skin sunburn, sinusitis, pneumonitis, encephalitis, meningitis, myocarditis, nephritis (Zhang, G., et al., "Down-regulation of NF-kappaB Transcriptional Activity in HIVassociated Kidney Disease by BRD4 Inhibition," *J Biol Chem*, 287(34):8840-51 (2012)), osteomyelitis, myositis, hepatitis, gastritis, enteritis, dermatitis, gingivitis, appendicitis, pancreatitis, cholecystitis, agammaglobulinemia, psoriasis, allergy, Crohn's disease, irritable bowel syndrome, ulcerative colitis (Prinjha, R. K., J. Witherington, and K. Lee, "Place your BETs: the therapeutic potential of bromodomains," *Trends Pharmacol Sci* 33(3):146-53 (2012)), Sjogren's disease, tissue graft rejection, hyperacute rejection of transplanted organs, asthma, allergic rhinitis, chronic obstructive pulmonary disease (COPD), autoimmune polyglandular disease (also known as autoimmune polyglandular syndrome), autoimmune alopecia, pernicious anemia, glomerulonephritis, dermatomyositis, multiple sclerosis (Bandukwala, H. S., et al., "Selective inhibition of CD4+ T-cell cytokine production and autoimmunity by BET protein and c-Myc inhibitors," *Proc Natl Acad Sci USA*, 109(36):14532-7 (2012)), scleroderma, vasculitis, autoimmune hemolytic and thrombocytopenic states, Goodpasture's syndrome, atherosclerosis, Addison's disease, Parkinson's disease, Alzheimer's disease, Type I diabetes (Belkina, A. C. and G. V. Denis, "BET domain co-regulators in obesity, inflammation and cancer," *Nat Rev Cancer* 12(7):465-77 (2012)), septic shock (Zhang, G., et al., "Down-regulation of NF-kappaB Transcriptional Activity in HIVassociated Kidney Disease by BRD4 Inhibition," *J Biol Chem*, 287(34):8840-51 (2012)), systemic lupus erythematosus (SLE) (Prinjha, R. K., J. Witherington, and K. Lee, "Place your BETs: the therapeutic potential of bromodomains," *Trends Pharmacol Sci* 33(3):146-53 (2012)), rheumatoid arthritis (Denis, G. V., "Bromodomain coactivators in cancer, obesity, type 2 diabetes, and inflammation," *Discov Med* 10(55):489-99 (2010)), psoriatic arthritis, juvenile arthritis, osteoarthritis, chronic idiopathic thrombocytopenic purpura, Waldenstrom macroglobulinemia, myasthenia gravis, Hashimoto's thyroiditis, atopic dermatitis, degenerative joint disease, vitiligo, autoimmune hypopituitarism, Guillain-Barre syndrome, Behcet's disease, uveitis, dry eye disease, scleroderma, mycosis fungoides, and Graves' disease.

BET inhibitors may be useful in the treatment of a wide variety of acute inflammatory conditions. Thus, one aspect of the invention provides compounds, compositions, and methods for treating inflammatory conditions including but not limited to, acute gout, giant cell arteritis, nephritis including lupus nephritis, vasculitis with organ involvement, such as glomerulonephritis, vasculitis, including giant cell arteritis, Wegener's granulomatosis, polyarteritis nodosa, Behcet's disease, Kawasaki disease, and Takayasu's arteritis.

BET inhibitors may be useful in the prevention and treatment of diseases or conditions that involve inflammatory responses to infections with bacteria, viruses, fungi, parasites, and their toxins, such as, but not limited to sepsis, sepsis syndrome, septic shock (Nicodeme, E., et al., "Suppression of inflammation by a synthetic histone mimic," *Nature* 468(7327):1119-23 (2010)), systemic inflammatory response syndrome (SIRS), multi-organ dysfunction syndrome, toxic shock syndrome, acute lung injury, adult respiratory distress syndrome (ARDS), acute renal failure, fulminant hepatitis, burns, post-surgical syndromes, sarcoidosis, Herxheimer reactions, encephalitis, myelitis, meningitis, malaria, and SIRS associated with viral infections, such as influenza, herpes zoster, herpes simplex, and coronavirus. Belkina, A. C. and G. V. Denis, "BET domain co-regulators in obesity, inflammation and cancer," *Nat Rev Cancer* 12(7):465-77 (2012). Thus, one aspect of the invention provides compounds, compositions, and methods for treating these inflammatory responses to infections with bacteria, viruses, fungi, parasites, and their toxins described herein.

Cancer is a group of diseases caused by dysregulated cell proliferation. Therapeutic approaches aim to decrease the numbers of cancer cells by inhibiting cell replication or by inducing cancer cell differentiation or death, but there is still significant unmet medical need for more efficacious therapeutic agents. Cancer cells accumulate genetic and epigenetic changes that alter cell growth and metabolism, promoting cell proliferation and increasing resistance to programmed cell death, or apoptosis. Some of these changes include inactivation of tumor suppressor genes, activation of oncogenes, and modifications of the regulation of chromatin structure, including deregulation of histone PTMs. Watson, J. D., "Curing 'incurable' cancer," *Cancer Discov* 1(6):477-80 (2011); Morin, R. D., et al., "Frequent mutation of histone-modifying genes in non-Hodgkin lymphoma" *Nature* 476(7360):298-303 (2011).

One aspect of the invention provides compounds, compositions, and methods for treating human cancer, including, but not limited to, cancers that result from aberrant translocation or overexpression of BET proteins (e.g., NUT midline carcinoma (NMC) (French, C. A., "NUT midline carcinoma," *Cancer Genet Cytogenet* 203(1):16-20 (2010) and B-cell lymphoma (Greenwald, R. J., et al., "E mu-BRD2 transgenic mice develop B-cell lymphoma and leukemia," *Blood* 103(4):1475-84 (2004)). NMC tumor cell growth is driven by a translocation of the Brd4 or Brd3 gene to the nutlin 1 gene. Filippakopoulos, P., et al., "Selective inhibition of BET bromodomains," *Nature* 468(7327):1067-73 (2010). BET inhibition has demonstrated potent antitumor activity in murine xenograft models of NMC, a rare but lethal form of cancer. The present disclosure also provides a method for treating human cancers, including, but not limited to, cancers dependent on a member of the myc family of oncoproteins including c-myc, MYCN, and L-myc. Vita, M. and M. Henriksson, "The Myc oncoprotein as a therapeutic target for human cancer," *Semin Cancer Biol* 16(4): 318-30 (2006). These cancers include Burkitt's lymphoma, acute myelogenous leukemia, multiple myeloma, and aggressive human medulloblastoma. Vita, M. and M. Henriksson, "The Myc oncoprotein as a therapeutic target for human cancer," *Semin Cancer Biol* 16(4):318-30 (2006). Cancers in which c-myc is overexpressed may be particularly susceptible to BET protein inhibition; it has been shown that treatment of tumors that have activation of c-myc with a BET inhibitor resulted in tumor regression through inactivation of c-myc transcription. Dawson, M. A., et al., Inhibition of BET recruitment to chromatin as an effective treatment for MLL-fusion leukaemia. Nature, 2011. 478 (7370): p. 529-33; Delmore, J. E., et al., "BET bromodomain inhibition as a therapeutic strategy to target c-Myc," *Cell* 146(6):904-17 (2010); Mertz, J. A., et al., "Targeting MYC dependence in cancer by inhibiting BET bromodomains," *Proc Natl Acad Sci USA* 108(40):16669-74 (2011); Ott, C. J., et al., "BET bromodomain inhibition targets both c-Myc and IL7R in high risk acute lymphoblastic leukemia," *Blood* 120(14):2843-52 (2012); Zuber, J., et al., "RNAi screen identifies Brd4 as a therapeutic target in acute myeloid leukaemia," *Nature* 478(7370):524-8 (2011).

Embodiments of the invention include methods for treating human cancers that rely on BET proteins and pTEFb (Cdk9/CyclinT) to regulate oncogenes (Wang, S. and P. M. Fischer, "Cyclin-dependent kinase 9: a key transcriptional regulator and potential drug target in oncology, virology and cardiology," *Trends Pharmacol Sci* 29(6):302-13 (2008)), and cancers that can be treated by inducing apoptosis or senescence by inhibiting Bcl2, cyclin-dependent kinase 6 (CDK6) (Dawson, M. A., et al., "Inhibition of BET recruitment to chromatin as an effective treatment for MLL-fusion leukaemia," *Nature* 478(7370):529-33 (2011)), or human telomerase reverse transcriptase (hTERT). Delmore, J. E., et al., "BET bromodomain inhibition as a therapeutic strategy to target c-Myc," *Cell* 146(6):904-17 (2010); Ruden, M. and N. Puri, "Novel anticancer therapeutics targeting telomerase," *Cancer Treat Rev* (2012).

BET inhibitors may be useful in the treatment of cancers including, but not limited to, adrenal cancer, acinic cell carcinoma, acoustic neuroma, acral lentiginous melanoma, acrospiroma, acute eosinophilic leukemia, acute erythroid leukemia, acute lymphoblastic leukemia, acute megakaryoblastic leukemia, acute monocytic leukemia, acute myeloid leukemia (Dawson, M. A., et al., "Inhibition of BET recruitment to chromatin as an effective treatment for MLL-fusion leukaemia," *Nature* 478(7370):529-33 (2011); Mertz, J. A., et al., "Targeting MYC dependence in cancer by inhibiting BET bromodomains," *Proc Natl Acad Sci USA* 108(40): 16669-74 (2011); Zuber, J., et al., "RNAi screen identifies Brd4 as a therapeutic target in acute myeloid leukaemia," *Nature* 478(7370):524-8 (2011)), adenocarcinoma, adenoid cystic carcinoma, adenoma, adenomatoid odontogenic tumor, adenosquamous carcinoma, adipose tissue neoplasm, adrenocortical carcinoma, adult T-cell leukemia/lymphoma, aggressive NK-cell leukemia, AIDS-related lymphoma, alveolar rhabdomyosarcoma, alveolar soft part sarcoma, ameloblastic fibroma, anaplastic large cell lymphoma, anaplastic thyroid cancer, angioimmunoblastic T-cell lymphoma, angiomyolipoma, angiosarcoma, astrocytoma, atypical teratoid rhabdoid tumor, B-cell acute lymphoblastic leukemia (Ott, C. J., et al., "BET bromodomain inhibition targets both c-Myc and IL7R in highrisk acute lymphoblastic leukemia," *Blood* 120(14):2843-52 (2012)), B-cell chronic lymphocytic leukemia, B-cell prolymphocytic leukemia, B-cell lymphoma (Greenwald, R. J., et al., "E mu-BRD2 transgenic mice develop B-cell lymphoma and leukemia,". *Blood* 103(4):1475-84 (2004)), basal cell carcinoma, biliary tract cancer, bladder cancer, blastoma, bone cancer, Brenner tumor, Brown tumor, Burkitt's lymphoma (Mertz, J. A., et al., "Targeting MYC dependence in cancer by inhibiting BET bromodomains," *Proc Natl Acad Sci USA* 108(40):16669-74 (2011)), breast cancer, brain cancer, carcinoma, carcinoma in situ, carcinosarcoma, cartilage tumor, cementoma, myeloid sarcoma, chondroma, chordoma, choriocarcinoma, choroid plexus papilloma, clear-cell sarcoma of the kidney, craniopharyngioma, cutaneous T-cell lymphoma, cervical cancer, colorectal cancer, Degos disease, desmoplastic small round cell tumor, diffuse large B-cell lymphoma, dysembryoplastic neuroepithelial tumor, dysgerminoma, embryonal carcinoma, endocrine gland neoplasm, endodermal sinus tumor, enteropathy-associated T-cell lymphoma, esophageal cancer, fetus in fetu, fibroma, fibrosarcoma, follicular lymphoma, follicular thyroid cancer, ganglioneuroma, gastrointestinal cancer, germ cell tumor, gestational choriocarcinoma, giant cell fibroblastoma, giant cell tumor of the bone, glial tumor, glioblastoma multiforme, glioma, gliomatosis cerebri, glucagonoma, gonadoblastoma, granulosa cell tumor, gynandroblastoma, gallbladder cancer, gastric cancer, hairy cell leukemia, hemangioblastoma, head and neck cancer, hemangiopericytoma, hematological malignancy, hepatoblastoma, hepatosplenic T-cell lymphoma, Hodgkin's lymphoma, non-Hodgkin's lymphoma, invasive lobular carcinoma, intestinal cancer, kidney cancer, laryngeal cancer, lentigo maligna, lethal midline carcinoma, leukemia, Leydig cell tumor, liposarcoma, lung cancer, lymphangioma, lymphangiosarcoma, lymphoepithelioma, lymphoma, acute lymphocytic leukemia, acute myelogenous leukemia (Mertz, J. A., et al., "Targeting MYC dependence in cancer by inhibiting BET bromodomains," *Proc Natl Acad Sci USA* 108(40):16669-74 (2011)), chronic lymphocytic leukemia, liver cancer, small cell lung cancer, non-small cell lung cancer, MALT lymphoma, malignant fibrous histiocytoma, malignant peripheral nerve sheath tumor, malignant triton tumor, mantle cell lymphoma, marginal zone B-cell lymphoma, mast cell leukemia, mediastinal germ cell tumor, medullary carcinoma of the breast, medullary thyroid cancer, medulloblastoma, melanoma (Miguel F. Segura, et al, "BRD4 is a novel therapeutic target in melanoma," *Cancer Research.* 72(8): Supplement 1 (2012)), meningioma, Merkel cell cancer, mesothelioma, metastatic urothelial carcinoma, mixed Mullerian tumor, mixed lineage leukemia (Dawson, M. A., et al., "Inhibition of BET recruitment to chromatin as an effective treatment for MLL-fusion leukaemia," *Nature* 478(7370): 529-33 (2011)), mucinous tumor, multiple myeloma (Delmore, J. E., et al., "BET bromodomain inhibition as a therapeutic strategy to target c-Myc," *Cell* 146(6):904-17 (2010)), muscle tissue neoplasm, mycosis fungoides, myxoid liposarcoma, myxoma, myxosarcoma, nasopharyngeal carcinoma, neurinoma, neuroblastoma, neurofibroma, neuroma, nodular melanoma, NUT-midline carcinoma (Filippakopoulos, P., et al., "Selective inhibition of BET bromodomains," *Nature* 468(7327):1067-73 (2010)), ocular cancer, oligoastrocytoma, oligodendroglioma, oncocytoma, optic nerve sheath meningioma, optic nerve tumor, oral cancer, osteosarcoma, ovarian cancer, Pancoast tumor, papillary thyroid cancer, paraganglioma, pinealoblastoma, pineocytoma, pituicytoma, pituitary adenoma, pituitary tumor, plasmacytoma, polyembryoma, precursor T-lymphoblastic lymphoma, primary central nervous system lymphoma, primary effusion lymphoma, primary peritoneal cancer, prostate cancer, pancreatic cancer, pharyngeal cancer, pseudomyxoma peritonei, renal cell carcinoma, renal medullary carcinoma, retinoblastoma, rhabdomyoma, rhabdomyosarcoma, Richter's transformation, rectal cancer, sarcoma, Schwannomatosis, seminoma, Sertoli cell tumor, sex cord-gonadal stromal tumor, signet ring cell carcinoma, skin cancer, small blue round cell tumors, small cell carcinoma, soft tissue sarcoma, somatostatinoma, soot wart, spinal tumor, splenic marginal zone lymphoma, squamous cell carcinoma, synovial sarcoma, Sezary's disease, small intestine cancer, squamous carcinoma, stomach cancer, testicular cancer, thecoma, thyroid cancer, transitional cell carcinoma, throat cancer, urachal cancer, urogenital cancer, urothelial carcinoma, uveal melanoma, uterine cancer, verrucous carcinoma, visual pathway glioma, vulvar cancer, vaginal cancer, Waldenstrom's macroglobulinemia, Warthin's tumor, and Wilms' tumor. Thus, one aspect of the inventions provides compounds, compositions, and methods for treating such cancers.

BET inhibitors may be useful in the treatment of benign proliferative and fibrotic disorders, including benign soft tissue tumors, bone tumors, brain and spinal tumors, eyelid and orbital tumors, granuloma, lipoma, meningioma, multiple endocrine neoplasia, nasal polyps, pituitary tumors, prolactinoma, pseudotumor cerebri, seborrheic keratoses, stomach polyps, thyroid nodules, cystic neoplasms of the pancreas, hemangiomas, vocal cord nodules, polyps, and cysts, Castleman disease, chronic pilonidal disease, dermatofibroma, pilar cyst, pyogenic granuloma, juvenile polyposis syndrome, idiopathic pulmonary fibrosis, renal fibrosis, post-operative stricture, keloid formation, scleroderma, and cardiac fibrosis. See e.g., Tang, X et al., "Assessment of Brd4 Inhibition in Idiopathic Pulmonary Fibrosis Lung Fibroblasts and in Vivo Models of Lung Fibrosis,". Am J Pathology in press (2013). Thus, one aspect of the invention provides compounds, compositions, and methods for treating such benign proliferative and fibrotic disorders.

Cardiovascular disease (CVD) is the leading cause of mortality and morbidity in the United States. Roger, V. L., et al., "Heart disease and stroke statistics—2012 update: a report from the American Heart Association," *Circulation* 125(1):e2-e220 (2012). Atherosclerosis, an underlying cause of CVD, is a multifactorial disease characterized by dyslipidemia and inflammation. BET inhibitors are expected to be efficacious in atherosclerosis and associated conditions because of aforementioned anti-inflammatory effects as well as ability to increase transcription of ApoA-I, the major constituent of HDL. Mirguet, O., et al., "From ApoA1 upregulation to BET family bromodomain inhibition: discovery of I-BET151," *Bioorg Med Chem Lett* 22(8):2963-7 (2012); Chung, C. W., et al., "Discovery and characterization of small molecule inhibitors of the BET family bromodomains," *J Med Chem* 54(11):3827-38 (2011). Accordingly, one aspect of the invention provides compounds, compositions, and methods for treating cardiovascular disease, including but not limited to atherosclerosis.

Up-regulation of ApoA-I is considered to be a useful strategy in treatment of atherosclerosis and CVD. Degoma, E. M. and D. J. Rader, "Novel HDL-directed pharmacotherapeutic strategies," *Nat Rev Cardiol* 8(5):266-77 (2011) BET inhibitors have been shown to increase ApoA-I transcription and protein expression. Mirguet, O., et al., "From ApoA1 upregulation to BET family bromodomain inhibition: discovery of I-BET151," *Bioorg Med Chem Lett* 22(8):2963-7 (2012); Chung, C. W., et al., "Discovery and characterization of small molecule inhibitors of the BET family bromodomains," *J Med Chem* 54(11):3827-38 (2011). It has also been shown that BET inhibitors bind directly to BET proteins and inhibit their binding to acetylated histones at the ApoA-1 promoter, suggesting the presence of a BET protein repression complex on the ApoA-1 promoter, which can be functionally disrupted by BET inhibitors. It follows that, BET inhibitors may be useful in the treatment of disorders of lipid metabolism via the regulation of ApoA-I and HDL such as hypercholesterolemia, dyslipidemia, atherosclerosis (Degoma, E. M. and D. J. Rader, "Novel HDL-directed pharmacotherapeutic strategies," *Nat Rev Cardiol* 8(5):266-77 (2011)), and Alzheimer's disease and other neurological disorders. Elliott, D. A., et al., "Apolipoproteins in the brain: implications for neurological and psychiatric disorders," *Clin Lipidol* 51(4):555-573 (2010). Thus, one aspect of the invention provides compounds, compositions, and methods for treating cardiovascular disorders by upregulation of ApoA-1.

BET inhibitors may be useful in the prevention and treatment of conditions associated with ischemia-reperfusion injury such as, but not limited to, myocardial infarction, stroke, acute coronary syndromes (Prinjha, R. K., J. Witherington, and K. Lee, "Place your BETs: the therapeutic potential of bromodomains," *Trends Pharmacol Sci* 33(3): 146-53 (2012)), renal reperfusion injury, organ transplantation, coronary artery bypass grafting, cardio-pulmonary bypass procedures, hypertension, pulmonary, renal, hepatic, gastro-intestinal, or peripheral limb embolism. Accordingly, one aspect of the invention provides compounds, compositions, and methods for prevention and treatment of conditions described herein that are associated with ischemia-reperfusion injury.

Obesity-associated inflammation is a hallmark of type II diabetes, insulin resistance, and other metabolic disorders. Belkina, A. C. and G. V. Denis, "BET domain co-regulators in obesity, inflammation and cancer," *Nat Rev Cancer* 12(7): 465-77 (2012); Denis, G. V., "Bromodomain coactivators in cancer, obesity, type 2 diabetes, and inflammation," *Discov Med* 10(55):489-99 (2010). Consistent with the ability of BET inhibitors to inhibit inflammation, gene disruption of Brd2 in mice ablates inflammation and protects animals from obesity-induced insulin resistance. Wang, F., et al., "Brd2 disruption in mice causes severe obesity without Type 2 diabetes," *Biochem J* 425(1):71-83 (2010). It has been shown that Brd2 interacts with PPARγ and opposes its transcriptional function. Knockdown of Brd2 in vitro promotes transcription of PPARγ-regulated networks, including those controlling adipogenesis. Denis, G. V., et al, "An emerging role for bromodomain-containing proteins in chromatin regulation and transcriptional control of adipogenesis," *FEBS Lett* 584(15):3260-8 (2010). In addition Brd2 is highly expressed in pancreatic β-cells and regulates proliferation and insulin transcription. Wang, F., et al., "Brd2 disruption in mice causes severe obesity without Type 2 diabetes," *Biochem J* 425(1):71-83 (2010). Taken together, the combined effects of BET inhibitors on inflammation and metabolism decrease insulin resistance and may be useful in the treatment of pre-diabetic and type II diabetic individuals as well as patients with other metabolic complications. Belkina, A. C. and G. V. Denis, "BET domain co-regulators in obesity, inflammation and cancer," *Nat Rev Cancer* 12(7): 465-77 (2012). Accordingly, one aspect of the invention provides compounds, compositions, and methods for treatment and prevention of metabolic disorders, including but not limited to obesity-associated inflammation, type II diabetes, and insulin resistance.

Host-encoded BET proteins have been shown to be important for transcriptional activation and repression of viral promoters. Brd4 interacts with the E2 protein of human papilloma virus (HPV) to enable E2 mediated transcription of E2-target genes. Gagnon, D., et al., "Proteasomal degradation of the papillomavirus E2 protein is inhibited by overexpression of bromodomain-containing protein 4," *J Virol* 83(9):4127-39 (2009). Similarly, Brd2, Brd3, and Brd4 all bind to latent nuclear antigen 1 (LANA1), encoded by Kaposi's sarcoma-associated herpes virus (KSHV), promoting LANA1-dependent proliferation of KSHV-infected cells. You, J., et al., "Kaposi's sarcoma-associated herpesvirus latency-associated nuclear antigen interacts with bromodomain protein Brd4 on host mitotic chromosomes," *J Virol* 80(18):8909-19 (2006). A BET inhibitor has been shown to inhibit the Brd4-mediated recruitment of the transcription elongation complex pTEFb to the Epstein-Barr virus (EBV) viral C promoter, suggesting therapeutic value for EBV-associated malignancies. Palermo, R. D., et al., "RNA polymerase II stalling promotes nucleosome occlusion and pTEFb recruitment to drive immortalization by Epstein-Barr virus," *PLoS Pathog* 7(10):e1002334 (2011). Also, a BET inhibitor reactivated HIV in models of latent T cell infection and latent monocyte infection, potentially allowing for viral eradication by complementary anti-retroviral therapy. Zhu, J., et al., "Reactivation of Latent HIV-1 by Inhibition of BRD4," *Cell Rep* (2012); Banerjee, C., et al., "BET bromodomain inhibition as a novel strategy for reactivation of HIV-1," *J Leukoc Biol* (2012); Bartholomeeusen, K., et al., "BET bromodomain inhibition activates transcription via a transient release of P-TEFb from 7SK snRNP," *J Biol Chem* (2012); Li, Z., et al., "The BET bromodomain inhibitor JQ1 activates HIV latency through antagonizing Brd4 inhibition of Tat-transactivation," *Nucleic Acids Res* (2012).

BET inhibitors may be useful in the prevention and treatment of episome-based DNA viruses including, but not limited to, human papillomavirus, herpes virus, Epstein-Barr virus, human immunodeficiency virus (Belkina, A. C. and G. V. Denis, "BET domain co-regulators in obesity, inflammation and cancer," *Nat Rev Cancer* 12(7):465-77 (2012)), adenovirus, poxvirus, hepatitis B virus, and hepatitis C virus. Thus, the invention also provides compounds, compositions, and methods for treatment and prevention of episome-based DNA virus infections described herein.

Some central nervous system (CNS) diseases are characterized by disorders in epigenetic processes. Brd2 haploinsufficiency has been linked to neuronal deficits and epilepsy. Velisek, L., et al., "GABAergic neuron deficit as an idiopathic generalized epilepsy mechanism: the role of BRD2 haploinsufficiency in juvenile myoclonic epilepsy," *PLoS One* 6(8): e23656 (2011) SNPs in various bromodomain-containing proteins have also been linked to mental disorders including schizophrenia and bipolar disorders. Prinjha, R. K., J. Witherington, and K. Lee, "Place your BETs: the therapeutic potential of bromodomains," *Trends Pharmacol Sci* 33(3):146-53 (2012). In addition, the ability of BET inhibitors to increase ApoA-I transcription may make BET inhibitors useful in Alzheimer's disease therapy considering the suggested relationship between increased ApoA-I and Alzheimer's disease and other neurological disorders. Elliott, D. A., et al., "Apolipoproteins in the brain: implications for neurological and psychiatric disorders," *Clin Lipidol* 51(4):555-573 (2010). Accordingly, one aspect of the invention provides compounds, compositions, and methods for treating such CNS diseases and disorders.

BRDT is the testis-specific member of the BET protein family which is essential for chromatin remodeling during spermatogenesis. Gaucher, J., et al., "Bromodomain-dependent stage-specific male genome programming by Brdt," *EMBO J* 31(19):3809-20 (2012); Shang, E., et al., "The first bromodomain of Brdt, a testis-specific member of the BET sub-family of double-bromodomain-containing proteins, is essential for male germ cell differentiation," *Development* 134(19):3507-15 (2007). Genetic depletion of BRDT or inhibition of BRDT interaction with acetylated histones by a BET inhibitor resulted in a contraceptive effect in mice, which was reversible when small molecule BET inhibitors were used. Matzuk, M. M., et al., "Small-Molecule Inhibition of BRDT for Male Contraception," *Cell* 150(4): 673-684 (2012); Berkovits, B. D., et al., "The testis-specific double bromodomain-containing protein BRDT forms a complex with multiple spliceosome components and is required for mRNA splicing and 3'-UTR truncation in round spermatids," *Nucleic Acids Res* 40(15):7162-75 (2012). These data suggest potential utility of BET inhibitors as a novel and efficacious approach to male contraception. Thus, another aspect of the invention provides compounds, compositions, and methods for male contraception.

Monocyte chemotactic protein-1 (MCP-1, CCL2) plays an important role in cardiovascular disease. Niu, J. and P. E. Kolattukudy, "Role of MCP-1 in cardiovascular disease: molecular mechanisms and clinical implications," *Clin Sci (Lond)* 117(3):95-109 (2009). MCP-1, by its chemotactic activity, regulates recruitment of monocytes from the arterial lumen to the subendothelial space, where they develop into macrophage foam cells, and initiate the formation of fatty streaks which can develop into atherosclerotic plaque. Dawson, J., et al., "Targeting monocyte chemoattractant protein-1 signalling in disease," *Expert Opin Ther Targets* 7(1):35-48 (2003). The critical role of MCP-1 (and its cognate receptor CCR2) in the development of atherosclerosis has been examined in various transgenic and knockout mouse models on a hyperlipidemic background. Boring, L., et al., "Decreased lesion formation in CCR2-/- mice reveals a role for chemokines in the initiation of atherosclerosis," *Nature* 394(6696):894-7 (1998); Gosling, J., et al., "MCP-1 deficiency reduces susceptibility to atherosclerosis in mice that overexpress human apolipoprotein B," *J Clin Invest* 103(6):773-8 (1999); Gu, L., et al., "Absence of monocyte chemoattractant protein-1 reduces atherosclerosis in low density lipoprotein receptor-deficient mice," *Mol Cell* 2(2): 275-81 (1998); Aiello, R. J., et al., "Monocyte chemoattractant protein-1 accelerates atherosclerosis in apolipoprotein E-deficient mice," *Arterioscler Thromb Vasc Biol* 19(6): 1518-25 (1999). These reports demonstrate that abrogation of MCP-1 signaling results in decreased macrophage infiltration to the arterial wall and decreased atherosclerotic lesion development.

The association between MCP-1 and cardiovascular disease in humans is well-established. Niu, J. and P. E. Kolattukudy, "Role of MCP-1 in cardiovascular disease: molecular mechanisms and clinical implications," *Clin Sci (Lond)* 117(3):95-109 (2009). MCP-1 and its receptor are overexpressed by endothelial cells, smooth muscle cells, and infiltrating monocytes/macrophages in human atherosclerotic plaque. Nelken, N. A., et al., "Monocyte chemoattractant protein-1 in human atheromatous plaques," *Clin Invest* 88(4):1121-7 (1991). Moreover, elevated circulating levels of MCP-1 are positively correlated with most cardiovascular risk factors, measures of coronary atherosclerosis burden, and the incidence of coronary heart disease (CHD). Deo, R., et al., "Association among plasma levels of monocyte chemoattractant protein-1, traditional cardiovascular risk factors, and subclinical atherosclerosis," *J Am Coil Cardiol* 44(9):1812-8 (2004). CHD patients with among the highest levels of MCP-1 are those with acute coronary syndrome (ACS). de Lemos, J. A., et al., "Association between plasma levels of monocyte chemoattractant protein-1 and long-term clinical outcomes in patients with acute coronary syndromes," *Circulation* 107(5):690-5 (2003). In addition to playing a role in the underlying inflammation associated with CHD, MCP-1 has been shown to be involved in plaque rupture, ischemic/reperfusion injury, restenosis, and heart transplant rejection. Niu, J. and P. E. Kolattukudy, "Role of MCP-1 in cardiovascular disease: molecular mechanisms and clinical implications," *Clin Sci (Lond)* 117(3):95-109 (2009).

MCP-1 also promotes tissue inflammation associated with autoimmune diseases including rheumatoid arthritis (RA) and multiple sclerosis (MS). MCP-1 plays a role in the infiltration of macrophages and lymphocytes into the joint in RA, and is overexpressed in the synovial fluid of RA patients. Koch, A. E., et al., "Enhanced production of monocyte chemoattractant protein-1 in rheumatoid arthritis," *J Clin Invest* 90(3):772-9 (1992). Blockade of MCP-1 and MCP-1 signaling in animal models of RA have also shown the importance of MCP-1 to macrophage accumulation and proinflammatory cytokine expression associated with RA. Brodmerkel, C. M., et al., "Discovery and pharmacological characterization of a novel rodent-active CCR2 antagonist, INCB3344," *J Immunol* 175(8):5370-8 (2005); Bruhl, H., et al., "Dual role of CCR2 during initiation and progression of collagen-induced arthritis: evidence for regulatory activity of CCR2+ T cells," *J Immunol* 172(2):890-8 (2004); Gong, J. H., et al., "An antagonist of monocyte chemoattractant protein 1 (MCP-1) inhibits arthritis in the MRL-lpr mouse model," *J Exp Med* 186(1):131-7 (1997); 65. Gong, J. H., et al., "Post-onset inhibition of murine arthritis using combined chemokine antagonist therapy," *Rheumatology* (Oxford 43(1): 39-42 (2004).

Overexpression of MCP-1, in the brain, cerebrospinal fluid (CSF), and blood, has also been associated with chronic and acute MS in humans. Mahad, D. J. and R. M. Ransohoff, "The role of MCP-1 (CCL2) and CCR2 in multiple sclerosis and experimental autoimmune encephalomyelitis (EAE)," *Semin Immunol* 15(1):23-32 (2003). MCP-1 is overexpressed by a variety of cell types in the brain during disease progression and contributes to the infiltration of macrophages and lymphocytes which mediate the tissue damage associated with MS. Genetic depletion of MCP-1 or CCR2 in the experimental autoimmune encephalomyelitis (EAE) mouse model, a model resembling human MS, results in resistance to disease, primarily because of decreased macrophage infiltration to the CNS. Fife, B. T., et al., "CC chemokine receptor 2 is critical for induction of experimental autoimmune encephalomyelitis," *J Exp Med* 192(6):899-905 (2000); Huang, D. R., et al., "Absence of monocyte chemoattractant protein 1 in mice leads to decreased local macrophage recruitment and antigen-specific T helper cell type 1 immune response in experimental autoimmune encephalomyelitis," *J Exp Med* 193(6):713-26 (2001).

Preclinical data have suggested that small- and large-molecule inhibitors of MCP-1 and CCR2 have potential as therapeutic agents in inflammatory and autoimmune indications. Thus, one aspect of the invention provides compounds, compositions, and methods for treating cardiovascular, inflammatory, and autoimmune conditions associated with MCP-1 and CCR2.

Accordingly, the invention provides compounds that are useful for inhibition of BET protein function by binding to bromodomains, pharmaceutical compositions comprising one or more of those compounds, and use of these compounds or compositions in the treatment and prevention of diseases and conditions, including, but not limited to, cancer, autoimmune, and cardiovascular diseases. The compounds of the invention are defined by Formula Ia or Formula IIa:

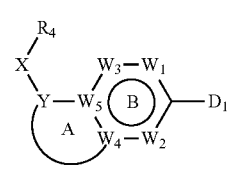

Formula Ia

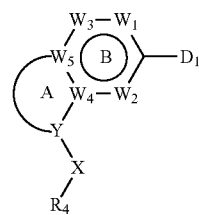

Formula IIa or are stereoisomers, tautomers, pharmaceutically acceptable salts, or hydrates thereof, wherein:

A is selected from 5- or 6-membered monocyclic heterocycles fused to ring B;

with the proviso that A cannot be substituted or unsubstituted

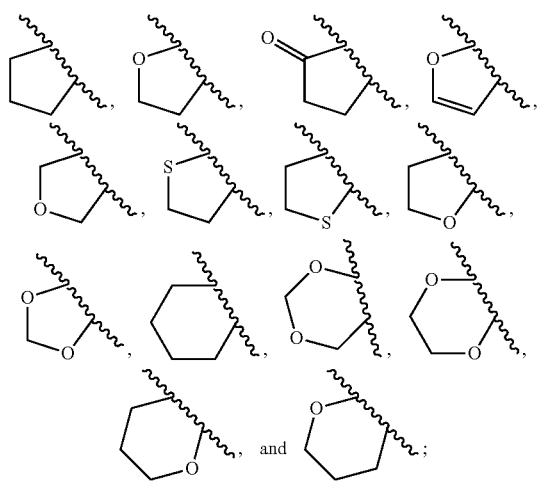

B is a six-membered aromatic carbocycle or heterocycle;
Y is selected from N, C, and CH;
$W_1$ is selected from N and $CR_1$;
$W_2$ is selected from N and $CR_2$;
$W_3$ is selected from N and $CR_3$;
$W_4$ and $W_5$ are independently selected from N, CH, and C or alternatively, $W_4$ and $W_5$ are both C (see, e.g., Formula Ib and Formula IIb below);
$W_1$, $W_2$, and $W_3$ may be the same or different from each other;
$R_1$ and $R_2$ are independently selected from hydrogen, deuterium, alkyl, —OH, —NH$_2$, -thioalkyl, alkoxy, ketone, ester, carboxylic acid, urea, carbamate, amino, amide, halogen, carbocycle, heterocycle, sulfone, sulfoxide, sulfide, sulfonamide, and —CN;

$R_3$ is selected from hydrogen, —$NH_2$, —CN, —$N_3$, halogen, and deuterium; or alternatively, $R_3$ is selected from —$NO_2$, —OMe, —OEt, —NHC(O)Me, $NHSO_2Me$, cylcoamino, cycloamido, —OH, —$SO_2Me$, —$SO_2Et$, —$CH_2NH_2$, —C(O)$NH_2$, and —C(O)OMe;

X is selected from —$CH_2$—, —$CH_2CH_2$—, —$CH_2CH_2CH_2$—, —$CH_2CH_2O$—, —$CH_2CH_2NH$—, —$CH_2CH_2S$—, —C(O)—, —C(O)$CH_2$—, —C(O)$CH_2CH_2$—, —$CH_2C(O)$—, —$CH_2CH_2C(O)$—, —C(O)NH—, —C(O)O—, —C(O)S—, —C(O)$NHCH_2$—, —C(O)$OCH_2$—, —C(O)$SCH_2$—, where one or more hydrogen may independently be replaced with deuterium, halogen, —$CF_3$, ketone, and where S may be oxidized to sulfoxide or sulfone; or alternatively, X may be selected from —NH—, —CH(OH)—, —CH($CH_3$)—, and hydroxyl methyl, where one or more hydrogen may independently be replaced with deuterium, halogen, —$CF_3$, ketone, and where S may be oxidized to sulfoxide or sulfone;

$R_4$ is selected from 4-7 membered carbocycles and heterocycles; or alternatively, $R_4$ is a 3 membered carbocycle or heterocycle;

$D_1$ is selected from 5-membered monocyclic carbocycles and heterocycles; or alternatively, $D_1$ is a monocyclic heterocycle, where $D_1$ is attached to the B ring via a carbon atom that is part of a double bond;

with the proviso that if $R_3$ is hydrogen and A is a 5-membered ring, then $D_1$ cannot be

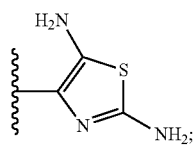

and with the proviso that if $D_1$ is

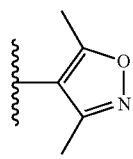 [SMILES: *c1c(C)noc1C]

and $R_2$ and $R_3$ are hydrogen and $R_1$ is —OMe, then the A-B bicyclic ring is not;

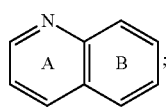

and with the proviso that if $D_1$ is

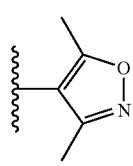 [SMILES: *c1c(C)noc1C]

and each of $R_1$, $R_2$, $R_3$, are hydrogen, then the A-B bicyclic ring is not

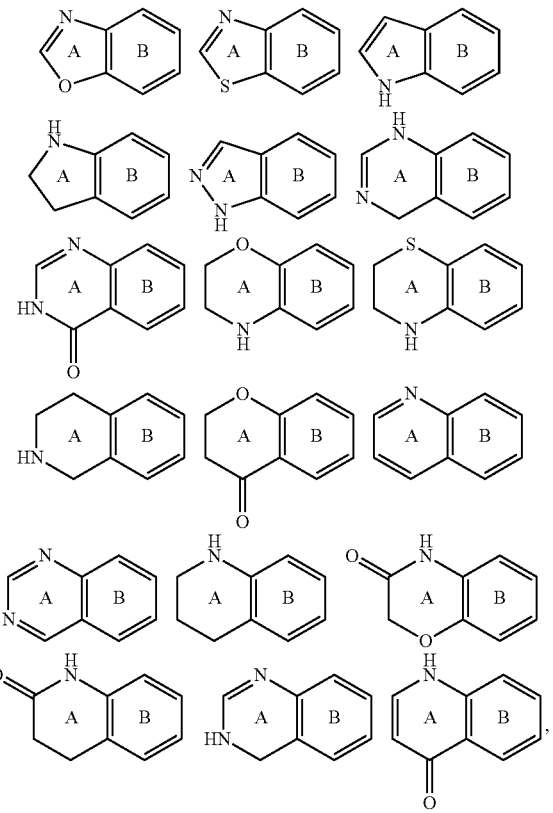

unless the B ring is substituted;

and with the proviso that if each of $R_1$, $R_2$, $R_3$ are hydrogen, then the A-B bicyclic ring is not

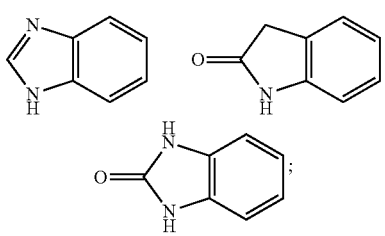

and with the proviso that if each of $R_1$, $R_2$, $R_3$ are hydrogen, then the A-B bicyclic ring is not

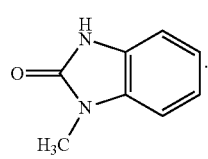

In certain embodiments A is a five membered ring. In some embodiments Y is N or C. In some embodiments, $R_1$ and $R_2$ are independently selected from hydrogen, deuterium, alkyl, —OH, —$NH_2$, -thioalkyl, alkoxy, ketone, ester, carboxylic acid, urea, carbamate, amino, amide, halogen, sulfone, sulfoxide, sulfide, sulfonamide, and —CN. In some embodiments, the compound of Formula Ia is a compound of Formula Ib, i.e., wherein $W_4$ and $W_5$ of Formula I are both C.

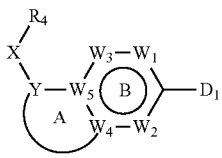

Formula Ia

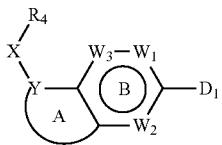

Formula Ib

In some embodiments, the compound of Formula IIa is a compound of Formula IIb, i.e., wherein $W_4$ and $W_5$ of Formula I are both C.

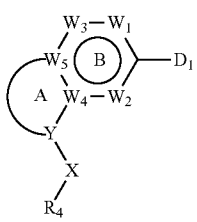

Formula IIa

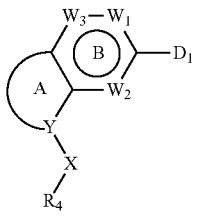

Formula IIb

In another aspect of the invention, a pharmaceutical composition comprising a compound of Formula Ia, Formula Ib, Formula IIa, and/or Formula IIb, or stereoisomer, tautomer, pharmaceutically acceptable salt, or hydrate thereof and one or more pharmaceutically acceptable carriers, diluents or excipients is provided.

In yet another aspect of the invention there is provided a compound of Formula Ia, Formula Ib, Formula IIa, and/or Formula IIb, or a stereoisomer, tautomer, pharmaceutically acceptable salt, or hydrate thereof, or a pharmaceutical composition comprising such compound, for use in therapy, in particular in the treatment of diseases or conditions for which a bromodomain inhibitor is indicated.

In yet another aspect of the invention there is provided a compound of Formula Ia, Formula Ib, Formula IIa, and/or Formula IIb, or a stereoisomer, tautomer, pharmaceutically acceptable salt, or hydrate thereof in the manufacture of a medicament for the treatment of diseases or conditions for which a bromodomain inhibitor is indicated.

Definitions

As used in the present specification, the following words, phrases and symbols are generally intended to have the meanings as set forth below, except to the extent that the context in which they are used indicates otherwise. The following abbreviations and terms have the indicated meanings throughout.

As used herein, "cardiovascular disease" refers to diseases, disorders and conditions of the heart and circulatory system that are mediated by BET inhibition. Exemplary cardiovascular diseases, including cholesterol- or lipid-related disorders, include, but are not limited to, acute coronary syndrome, angina, arteriosclerosis, atherosclerosis, carotid atherosclerosis, cerebrovascular disease, cerebral infarction, congestive heart failure, congenital heart disease, coronary heart disease, coronary artery disease, coronary plaque stabilization, dyslipidemias, dyslipoproteinemias, endothelium dysfunctions, familial hypercholesterolemia, familial combined hyperlipidemia, hypoalphalipoproteinemia, hypertriglyceridemia, hyperbetalipoproteinemia, hypercholesterolemia, hypertension, hyperlipidemia, intermittent claudication, ischemia, ischemia reperfusion injury, ischemic heart diseases, cardiac ischemia, metabolic syndrome, multi-infarct dementia, myocardial infarction, obesity, peripheral vascular disease, reperfusion injury, restenosis, renal artery atherosclerosis, rheumatic heart disease, stroke, thrombotic disorder, transitory ischemic attacks, and lipoprotein abnormalities associated with Alzheimer's disease, obesity, diabetes mellitus, syndrome X, impotence, multiple sclerosis, Parkinson's disease, and inflammatory diseases.

As used herein, "inflammatory diseases" refers to diseases, disorders, and conditions that are mediated by BET inhibition. Exemplary inflammatory diseases, include, but are not limited to, arthritis, asthma, dermatitis, psoriasis, cystic fibrosis, post transplantation late and chronic solid organ rejection, multiple sclerosis, systemic lupus erythematosus, inflammatory bowel diseases, autoimmune diabetes, diabetic retinopathy, diabetic nephropathy, diabetic vasculopathy, ocular inflammation, uveitis, rhinitis, ischemia-reperfusion injury, post-angioplasty restenosis, chronic obstructive pulmonary disease (COPD), glomerulonephritis, Graves disease, gastrointestinal allergies, conjunctivitis, atherosclerosis, coronary artery disease, angina, and small artery disease.

As used herein, "cancer" refers to diseases, disorders, and conditions that are mediated by BET inhibition. Exemplary cancers, include, but are not limited to, chronic lymphocytic leukemia and multiple myeloma, follicular lymphoma, diffuse large B cell lymphoma with germinal center phenotype, Burkitt's lymphoma, Hodgkin's lymphoma, follicular lymphomas and activated, anaplastic large cell lymphoma, neuroblastoma and primary neuroectodermal tumor, rhabdomyosarcoma, prostate cancer, breast cancer, NMC (NUT-midline carcinoma), acute myeloid leukemia (AML), acute B lymphoblastic leukemia (B-ALL), Burkitt's Lymphoma, B-cell lymphoma, melanoma, mixed lineage leukemia, multiple myeloma, pro-myelocytic leukemia (PML), non-Hodgkin's lymphoma, neuroblastoma, medulloblastoma, lung carcinoma (NSCLC, SCLC), and colon carcinoma.

"Subject" refers to an animal, such as a mammal, that has been or will be the object of treatment, observation, or experiment. The methods described herein may be useful for both human therapy and veterinary applications. In one embodiment, the subject is a human.

As used herein, "treatment" or "treating" refers to an amelioration of a disease or disorder, or at least one discernible symptom thereof. In another embodiment, "treatment" or "treating" refers to an amelioration of at least one measurable physical parameter, not necessarily discernible by the patient. In yet another embodiment, "treatment" or "treating" refers to inhibiting the progression of a disease or disorder, either physically, e.g., stabilization of a discernible symptom, physiologically, e.g., stabilization of a physical parameter, or both. In yet another embodiment, "treatment" or "treating" refers to delaying the onset of a disease or disorder. For example, treating a cholesterol disorder may comprise decreasing blood cholesterol levels.

As used herein, "prevention" or "preventing" refers to a reduction of the risk of acquiring a given disease or disorder.

A dash ("-") that is not between two letters or symbols is used to indicate a point of attachment for a substituent. For example, —CONH$_2$ is attached through the carbon atom.

By "optional" or "optionally" is meant that the subsequently described event or circumstance may or may not occur, and that the description includes instances where the event or circumstance occurs and instances in which is does not. For example, "optionally substituted aryl" encompasses both "aryl" and "substituted aryl" as defined below. It will be understood by those skilled in the art, with respect to any group containing one or more substituents, that such groups are not intended to introduce any substitution or substitution patterns that are sterically impractical, synthetically non-feasible and/or inherently unstable.

As used herein, the term "hydrate" refers to a crystal form with either a stoichiometric or non-stoichiometric amount of water is incorporated into the crystal structure.

The term "alkenyl" as used herein refers to an unsaturated straight or branched hydrocarbon having at least one carbon-carbon double bond, such as a straight or branched group of 2-8 carbon atoms, referred to herein as $(C_2-C_8)$alkenyl. Exemplary alkenyl groups include, but are not limited to, vinyl, allyl, butenyl, pentenyl, hexenyl, butadienyl, pentadienyl, hexadienyl, 2-ethylhexenyl, 2-propyl-2-butenyl, and 4-(2-methyl-3-butene)-pentenyl.

The term "alkoxy" as used herein refers to an alkyl group attached to an oxygen (—O-alkyl-). "Alkoxy" groups also include an alkenyl group attached to an oxygen ("alkenyloxy") or an alkynyl group attached to an oxygen ("alkynyloxy") groups. Exemplary alkoxy groups include, but are not limited to, groups with an alkyl, alkenyl or alkynyl group of 1-8 carbon atoms, referred to herein as $(C_1-C_8)$alkoxy. Exemplary alkoxy groups include, but are not limited to methoxy and ethoxy.

The term "alkyl" as used herein refers to a saturated straight or branched hydrocarbon, such as a straight or branched group of 1-8 carbon atoms, referred to herein as $(C_1-C_8)$alkyl. Exemplary alkyl groups include, but are not limited to, methyl, ethyl, propyl, isopropyl, 2-methyl-1-propyl, 2-methyl-2-propyl, 2-methyl-1-butyl, 3-methyl-1-butyl, 2-methyl-3-butyl, 2,2-dimethyl-1-propyl, 2-methyl-1-pentyl, 3-methyl-1-pentyl, 4-methyl-1-pentyl, 2-methyl-2-pentyl, 3-methyl-2-pentyl, 4-methyl-2-pentyl, 2,2-dimethyl-1-butyl, 3,3-dimethyl-1-butyl, 2-ethyl-1-butyl, butyl, isobutyl, t-butyl, pentyl, isopentyl, neopentyl, hexyl, heptyl, and octyl.

The term "alkynyl" as used herein refers to an unsaturated straight or branched hydrocarbon having at least one carbon-carbon triple bond, such as a straight or branched group of 2-8 carbon atoms, referred to herein as $(C_2-C_8)$alkynyl. Exemplary alkynyl groups include, but are not limited to, ethynyl, propynyl, butynyl, pentynyl, hexynyl, methylpropynyl, 4-methyl-1-butynyl, 4-propyl-2-pentynyl, and 4-butyl-2-hexynyl.

The term "amide" as used herein refers to the form —NR$_a$C(O)(R$_b$)— or —C(O)NR$_b$R$_c$, wherein R$_a$, R$_b$ and R$_c$ are each independently selected from alkyl, alkenyl, alkynyl, aryl, arylalkyl, cycloalkyl, haloalkyl, heteroaryl, heterocyclyl, and hydrogen. The amide can be attached to another group through the carbon, the nitrogen, R$_b$, or R$_c$. The amide also may be cyclic, for example R$_b$ and R$_c$, may be joined to form a 3- to 8-membered ring, such as 5- or 6-membered ring. The term "amide" encompasses groups such as sulfonamide, urea, ureido, carbamate, carbamic acid, and cyclic versions thereof. The term "amide" also encompasses an amide group attached to a carboxy group, e.g., -amide-COOH or salts such as -amide-COONa, an amino group attached to a carboxy group (e.g., -amino-COOH or salts such as -amino-COONa).

The term "amine" or "amino" as used herein refers to the form —NR$_d$R$_e$ or —N(R$_d$)R$_e$—, where R$_d$ and R$_e$ are independently selected from alkyl, alkenyl, alkynyl, aryl, arylalkyl, carbamate, cycloalkyl, haloalkyl, heteroaryl, heterocycle, and hydrogen. The amino can be attached to the parent molecular group through the nitrogen. The amino also may be cyclic, for example any two of R$_d$ and R$_e$ may be joined together or with the N to form a 3- to 12-membered ring (e.g., morpholino or piperidinyl). The term amino also includes the corresponding quaternary ammonium salt of any amino group. Exemplary amino groups include alkylamino groups, wherein at least one of R$_d$ or R$_e$ is an alkyl group. In some embodiments Rd and Re each may be optionally substituted with hydroxyl, halogen, alkoxy, ester, or amino.

The term "aryl" as used herein refers to a mono-, bi-, or other multi-carbocyclic, aromatic ring system. The aryl group can optionally be fused to one or more rings selected from aryls, cycloalkyls, and heterocyclyls. The aryl groups of this present disclosure can be substituted with groups selected from alkoxy, aryloxy, alkyl, alkenyl, alkynyl, amide, amino, aryl, arylalkyl, carbamate, carboxy, cyano, cycloalkyl, ester, ether, formyl, halogen, haloalkyl, heteroaryl, heterocyclyl, hydroxyl, ketone, nitro, phosphate, sulfide, sulfinyl, sulfonyl, sulfonic acid, sulfonamide, and thioketone. Exemplary aryl groups include, but are not limited to, phenyl, tolyl, anthracenyl, fluorenyl, indenyl, azulenyl, and naphthyl, as well as benzo-fused carbocyclic moieties such as 5,6,7,8-tetrahydronaphthyl. Exemplary aryl groups also include, but are not limited to a monocyclic aromatic ring system, wherein the ring comprises 6 carbon atoms, referred to herein as "$(C_6)$aryl."

The term "arylalkyl" as used herein refers to an alkyl group having at least one aryl substituent (e.g., -aryl-alkyl-). Exemplary arylalkyl groups include, but are not limited to, arylalkyls having a monocyclic aromatic ring system, wherein the ring comprises 6 carbon atoms, referred to herein as "$(C_6)$arylalkyl."

The term "carbamate" as used herein refers to the form —R$_g$OC(O)N(R$_h$)—, —R$_g$OC(O)N(R$_h$)R$_i$—, or —OC(O)NR$_h$R$_i$, wherein R$_g$, R$_h$ and R$_i$ are each independently selected from alkyl, alkenyl, alkynyl, aryl, arylalkyl, cycloalkyl, haloalkyl, heteroaryl, heterocyclyl, and hydrogen. Exemplary carbamates include, but are not limited to, arylcarbamates or heteroaryl carbamates (e.g., wherein at least one of R$_g$, R$_h$ and R$_i$ are independently selected from aryl or heteroaryl, such as pyridine, pyridazine, pyrimidine, and pyrazine).

The term "carbocycle" as used herein refers to an aryl or cycloalkyl group.

The term "carboxy" as used herein refers to —COOH or its corresponding carboxylate salts (e.g., —COONa). The term carboxy also includes "carboxycarbonyl," e.g. a carboxy group attached to a carbonyl group, e.g., —C(O)—COOH or salts, such as —C(O)—COONa.

The term "cyano" as used herein refers to —CN.

The term "cycloalkoxy" as used herein refers to a cycloalkyl group attached to an oxygen.

The term "cycloalkyl" as used herein refers to a saturated or unsaturated cyclic, bicyclic, or bridged bicyclic hydrocarbon group of 3-12 carbons, or 3-8 carbons, referred to herein as "($C_3$-$C_8$)cycloalkyl," derived from a cycloalkane. Exemplary cycloalkyl groups include, but are not limited to, cyclohexanes, cyclohexenes, cyclopentanes, and cyclopentenes. Cycloalkyl groups may be substituted with alkoxy, aryloxy, alkyl, alkenyl, alkynyl, amide, amino, aryl, arylalkyl, carbamate, carboxy, cyano, cycloalkyl, ester, ether, formyl, halogen, haloalkyl, heteroaryl, heterocyclyl, hydroxyl, ketone, nitro, phosphate, sulfide, sulfinyl, sulfonyl, sulfonic acid, sulfonamide and thioketone. Cycloalkyl groups can be fused to other cycloalkyl saturated or unsaturated, aryl, or heterocyclyl groups.

The term "dicarboxylic acid" as used herein refers to a group containing at least two carboxylic acid groups such as saturated and unsaturated hydrocarbon dicarboxylic acids and salts thereof. Exemplary dicarboxylic acids include alkyl dicarboxylic acids. Dicarboxylic acids may be substituted with alkoxy, aryloxy, alkyl, alkenyl, alkynyl, amide, amino, aryl, arylalkyl, carbamate, carboxy, cyano, cycloalkyl, ester, ether, formyl, halogen, haloalkyl, heteroaryl, heterocyclyl, hydrogen, hydroxyl, ketone, nitro, phosphate, sulfide, sulfinyl, sulfonyl, sulfonic acid, sulfonamide and thioketone. Dicarboxylic acids include, but are not limited to succinic acid, glutaric acid, adipic acid, suberic acid, sebacic acid, azelaic acid, maleic acid, phthalic acid, aspartic acid, glutamic acid, malonic acid, fumaric acid, (+)/(−)-malic acid, (+)/(−) tartaric acid, isophthalic acid, and terephthalic acid. Dicarboxylic acids further include carboxylic acid derivatives thereof, such as anhydrides, imides, hydrazides (for example, succinic anhydride and succinimide).

The term "ester" refers to the structure —C(O)O—, —C(O)O—$R_j$—, —$R_k$C(O)O—$R_j$—, or —$R_k$C(O)O—, where O is not bound to hydrogen, and $R_j$ and $R_k$ can independently be selected from alkoxy, aryloxy, alkyl, alkenyl, alkynyl, amide, amino, aryl, arylalkyl, cycloalkyl, ether, haloalkyl, heteroaryl, and heterocyclyl. $R_k$ can be a hydrogen, but $R_j$ cannot be hydrogen. The ester may be cyclic, for example the carbon atom and $R_j$, the oxygen atom and $R_k$, or $R_j$ and $R_k$ may be joined to form a 3- to 12-membered ring. Exemplary esters include, but are not limited to, alkyl esters wherein at least one of Rj or Rk is alkyl, such as —O—C(O)-alkyl, —C(O)—O-alkyl-, and -alkyl-C(O)—O-alkyl-. Exemplary esters also include aryl or heteoraryl esters, e.g. wherein at least one of Rj or Rk is a heteroaryl group such as pyridine, pyridazine, pyrimidine and pyrazine, such as a nicotinate ester. Exemplary esters also include reverse esters having the structure —$R_k$C(O)O—, where the oxygen is bound to the parent molecule. Exemplary reverse esters include succinate, D-argininate, L-argininate, L-lysinate and D-lysinate. Esters also include carboxylic acid anhydrides and acid halides.

The terms "halo" or "halogen" as used herein refer to F, Cl, Br, or I.

The term "haloalkyl" as used herein refers to an alkyl group substituted with one or more halogen atoms. "Haloalkyls" also encompass alkenyl or alkynyl groups substituted with one or more halogen atoms.

The term "heteroaryl" as used herein refers to a mono-, bi-, or multi-cyclic, aromatic ring system containing one or more heteroatoms, for example 1-3 heteroatoms, such as nitrogen, oxygen, and sulfur. Heteroaryls can be substituted with one or more substituents including alkoxy, aryloxy, alkyl, alkenyl, alkynyl, amide, amino, aryl, arylalkyl, carbamate, carboxy, cyano, cycloalkyl, ester, ether, formyl, halogen, haloalkyl, heteroaryl, heterocyclyl, hydroxyl, ketone, nitro, phosphate, sulfide, sulfinyl, sulfonyl, sulfonic acid, sulfonamide and thioketone. Heteroaryls can also be fused to non-aromatic rings. Illustrative examples of heteroaryl groups include, but are not limited to, pyridinyl, pyridazinyl, pyrimidyl, pyrazyl, triazinyl, pyrrolyl, pyrazolyl, imidazolyl, (1,2,3)- and (1,2,4)-triazolyl, pyrazinyl, pyrimidilyl, tetrazolyl, furyl, thienyl, isoxazolyl, thiazolyl, furyl, phenyl, isoxazolyl, and oxazolyl. Exemplary heteroaryl groups include, but are not limited to, a monocyclic aromatic ring, wherein the ring comprises 2-5 carbon atoms and 1-3 heteroatoms, referred to herein as "($C_2$-$C_5$)heteroaryl."

The terms "heterocycle," "heterocyclyl," or "heterocyclic" as used herein refer to a saturated or unsaturated 3-, 4-, 5-, 6- or 7-membered ring containing one, two, or three heteroatoms independently selected from nitrogen, oxygen, and sulfur. Heterocycles can be aromatic (heteroaryls) or non-aromatic. Heterocycles can be substituted with one or more substituents including alkoxy, aryloxy, alkyl, alkenyl, alkynyl, amide, amino, aryl, arylalkyl, carbamate, carboxy, cyano, cycloalkyl, ester, ether, formyl, halogen, haloalkyl, heteroaryl, heterocyclyl, hydroxyl, ketone, nitro, phosphate, sulfide, sulfinyl, sulfonyl, sulfonic acid, sulfonamide and thioketone. Heterocycles also include bicyclic, tricyclic, and tetracyclic groups in which any of the above heterocyclic rings is fused to one or two rings independently selected from aryls, cycloalkyls, and heterocycles. Exemplary heterocycles include acridinyl, benzimidazolyl, benzofuryl, benzothiazolyl, benzothienyl, benzoxazolyl, biotinyl, cinnolinyl, dihydrofuryl, dihydroindolyl, dihydropyranyl, dihydrothienyl, dithiazolyl, furyl, homopiperidinyl, imidazolidinyl, imidazolinyl, imidazolyl, indolyl, isoquinolyl, isothiazolidinyl, isothiazolyl, isoxazolidinyl, isoxazolyl, morpholinyl, oxadiazolyl, oxazolidinyl, oxazolyl, piperazinyl, piperidinyl, pyranyl, pyrazolidinyl, pyrazinyl, pyrazolyl, pyrazolinyl, pyridazinyl, pyridyl, pyrimidinyl, pyrimidyl, pyrrolidinyl, pyrrolidin-2-onyl, pyrrolinyl, pyrrolyl, quinolinyl, quinoxaloyl, tetrahydrofuryl, tetrahydroisoquinolyl, tetrahydropyranyl, tetrahydroquinolyl, tetrazolyl, thiadiazolyl, thiazolidinyl, thiazolyl, thienyl, thiomorpholinyl, thiopyranyl, and triazolyl.

The terms "hydroxy" and "hydroxyl" as used herein refer to —OH.

The term "hydroxyalkyl" as used herein refers to a hydroxy attached to an alkyl group.

The term "hydroxyaryl" as used herein refers to a hydroxy attached to an aryl group.

The term "ketone" as used herein refers to the structure —C(O)—Rn (such as acetyl, —C(O)CH$_3$) or —$R_n$—C(O)—$R_o$— The ketone can be attached to another group through $R_n$ or $R_o$. $R_n$ or $R_o$ can be alkyl, alkenyl, alkynyl, cycloalkyl, heterocyclyl or aryl, or $R_n$ or $R_o$ can be joined to form a 3- to 12-membered ring.

The term "monoester" as used herein refers to an analogue of a dicarboxylic acid wherein one of the carboxylic acids is functionalized as an ester and the other carboxylic acid is a free carboxylic acid or salt of a carboxylic acid. Examples of monoesters include, but are not limited to, to monoesters of succinic acid, glutaric acid, adipic acid, suberic acid, sebacic acid, azelaic acid, oxalic and maleic acid.

The term "phenyl" as used herein refers to a 6-membered carbocyclic aromatic ring. The phenyl group can also be fused to a cyclohexane or cyclopentane ring. Phenyl can be substituted with one or more substituents including alkoxy, aryloxy, alkyl, alkenyl, alkynyl, amide, amino, aryl, arylalkyl, carbamate, carboxy, cyano, cycloalkyl, ester, ether, formyl, halogen, haloalkyl, heteroaryl, heterocyclyl, hydroxyl, ketone, phosphate, sulfide, sulfinyl, sulfonyl, sulfonic acid, sulfonamide and thioketone.

The term "thioalkyl" as used herein refers to an alkyl group attached to a sulfur (—S-alkyl-).

"Alkyl," "alkenyl," "alkynyl", "alkoxy", "amino" and "amide" groups can be optionally substituted with or interrupted by or branched with at least one group selected from alkoxy, aryloxy, alkyl, alkenyl, alkynyl, amide, amino, aryl, arylalkyl, carbamate, carbonyl, carboxy, cyano, cycloalkyl, ester, ether, formyl, halogen, haloalkyl, heteroaryl, heterocyclyl, hydroxyl, ketone, phosphate, sulfide, sulfinyl, sulfonyl, sulfonic acid, sulfonamide, thioketone, ureido and N. The substituents may be branched to form a substituted or unsubstituted heterocycle or cycloalkyl.

As used herein, a suitable substitution on an optionally substituted substituent refers to a group that does not nullify the synthetic or pharmaceutical utility of the compounds of the present disclosure or the intermediates useful for preparing them. Examples of suitable substitutions include, but are not limited to: $C_{1-8}$ alkyl, alkenyl or alkynyl; $C_{1-6}$ aryl, $C_{2-5}$ heteroaryl; $C_{37}$ cycloalkyl; $C_{1-8}$ alkoxy; $C_6$ aryloxy; —CN; —OH; oxo; halo, carboxy; amino, such as —NH($C_{1-8}$ alkyl), —N($C_{1-8}$ alkyl)$_2$, —NH(($C_6$)aryl), or —N(($C_6$)aryl)$_2$; formyl; ketones, such as —CO($C_{1-8}$ alkyl), —CO(($C_6$ aryl) esters, such as —CO$_2$($C_{1-8}$ alkyl) and —CO$_2$ ($C_6$ aryl). One of skill in art can readily choose a suitable substitution based on the stability and pharmacological and synthetic activity of the compound of the present disclosure.

The term "pharmaceutically acceptable carrier" as used herein refers to any and all solvents, dispersion media, coatings, isotonic and absorption delaying agents, and the like, that are compatible with pharmaceutical administration. The use of such media and agents for pharmaceutically active substances is well known in the art. The compositions may also contain other active compounds providing supplemental, additional, or enhanced therapeutic functions.

The term "pharmaceutically acceptable composition" as used herein refers to a composition comprising at least one compound as disclosed herein formulated together with one or more pharmaceutically acceptable carriers.

The term "pharmaceutically acceptable prodrugs" as used herein represents those prodrugs of the compounds of the present disclosure that are, within the scope of sound medical judgment, suitable for use in contact with the tissues of humans and lower animals without undue toxicity, irritation, allergic response, commensurate with a reasonable benefit/risk ratio, and effective for their intended use, as well as the zwitterionic forms, where possible, of the compounds of the present disclosure. A discussion is provided in Higuchi et al., "Prodrugs as Novel Delivery Systems," *ACS Symposium Series*, Vol. 14, and in Roche, E. B., ed. *Bioreversible Carriers in Drug Design*, American Pharmaceutical Association and Pergamon Press, 1987, both of which are incorporated herein by reference.

The term "pharmaceutically acceptable salt(s)" refers to salts of acidic or basic groups that may be present in compounds used in the present compositions. Compounds included in the present compositions that are basic in nature are capable of forming a wide variety of salts with various inorganic and organic acids. The acids that may be used to prepare pharmaceutically acceptable acid addition salts of such basic compounds are those that form non-toxic acid addition salts, i.e., salts containing pharmacologically acceptable anions, including but not limited to sulfate, citrate, matate, acetate, oxalate, chloride, bromide, iodide, nitrate, sulfate, bisulfate, phosphate, acid phosphate, isonicotinate, acetate, lactate, salicylate, citrate, tartrate, oleate, tannate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate and pamoate (i.e., 1,1'-methylene-bis-(2-hydroxy-3-naphthoate)) salts. Compounds included in the present compositions that include an amino moiety may form pharmaceutically acceptable salts with various amino acids, in addition to the acids mentioned above. Compounds included in the present compositions, that are acidic in nature are capable of forming base salts with various pharmacologically acceptable cations. Examples of such salts include alkali metal or alkaline earth metal salts and, particularly, calcium, magnesium, sodium, lithium, zinc, potassium, and iron salts.

The compounds of the disclosure may contain one or more chiral centers and/or double bonds and, therefore, exist as stereoisomers, such as geometric isomers, enantiomers or diastereomers. The term "stereoisomers" when used herein consist of all geometric isomers, enantiomers or diastereomers. These compounds may be designated by the symbols "R" or "S," depending on the configuration of substituents around the stereogenic carbon atom. The present disclosure encompasses various stereoisomers of these compounds and mixtures thereof. Stereoisomers include enantiomers and diastereomers. Mixtures of enantiomers or diastereomers may be designated "(±)" in nomenclature, but the skilled artisan will recognize that a structure may denote a chiral center implicitly.

Individual stereoisomers of compounds of the present disclosure can be prepared synthetically from commercially available starting materials that contain asymmetric or stereogenic centers, or by preparation of racemic mixtures followed by resolution methods well known to those of ordinary skill in the art. These methods of resolution are exemplified by (1) attachment of a mixture of enantiomers to a chiral auxiliary, separation of the resulting mixture of diastereomers by recrystallization or chromatography and liberation of the optically pure product from the auxiliary, (2) salt formation employing an optically active resolving agent, or (3) direct separation of the mixture of optical enantiomers on chiral chromatographic columns. Stereoisomeric mixtures can also be resolved into their component stereoisomers by well-known methods, such as chiral-phase gas chromatography, chiral-phase high performance liquid chromatography, crystallizing the compound as a chiral salt complex, or crystallizing the compound in a chiral solvent. Stereoisomers can also be obtained from stereomerically-pure intermediates, reagents, and catalysts by well-known asymmetric synthetic methods.

Geometric isomers can also exist in the compounds of the present disclosure. The present disclosure encompasses the various geometric isomers and mixtures thereof resulting from the arrangement of substituents around a carbon-carbon double bond or arrangement of substituents around a carbocyclic ring. Substituents around a carbon-carbon double bond are designated as being in the "Z" or "E" configuration wherein the terms "Z" and "E" are used in accordance with IUPAC standards. Unless otherwise specified, structures depicting double bonds encompass both the E and Z isomers.

Substituents around a carbon-carbon double bond alternatively can be referred to as "cis" or "trans," where "cis"

represents substituents on the same side of the double bond and "trans" represents substituents on opposite sides of the double bond. The arrangements of substituents around a carbocyclic ring are designated as "cis" or "trans." The term "cis" represents substituents on the same side of the plane of the ring and the term "trans" represents substituents on opposite sides of the plane of the ring. Mixtures of compounds wherein the substituents are disposed on both the same and opposite sides of plane of the ring are designated "cis/trans."

The compounds disclosed herein may exist as tautomers and both tautomeric forms are intended to be encompassed by the scope of the present disclosure, even though only one tautomeric structure is depicted.

Exemplary Embodiments of the Invention

The invention provides compounds and pharmaceutical composition comprising one or more of those compounds wherein the structure of the compound is defined by Formula Ia, Formula Ib, Formula IIa, and/or Formula IIb:

Formula Ia
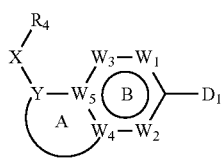

Formula Ib
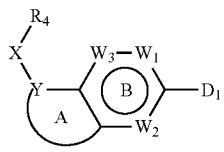

Formula IIa
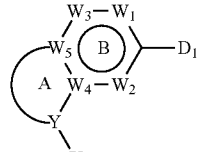

Formula IIb
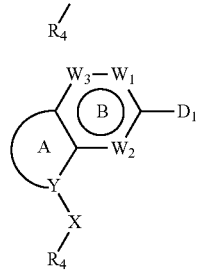

or is a stereoisomer, tautomer, pharmaceutically acceptable salt, or hydrate thereof,
wherein:

A is selected from optionally substituted 5- or -6 membered monocyclic heterocycles fused to ring B,
with the proviso that A cannot be substituted or unsubstituted

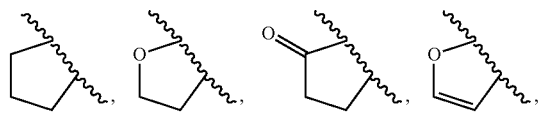

-continued

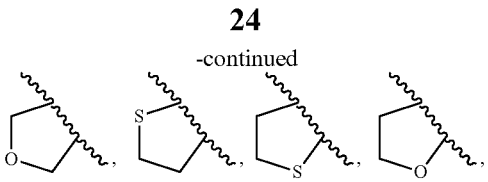

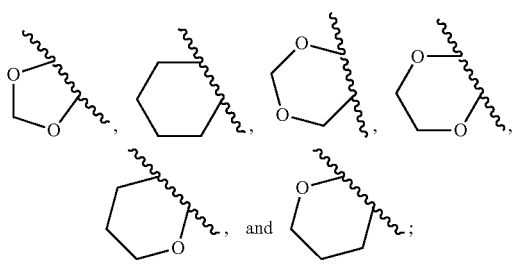

B is a six-membered aromatic carbocycle or heterocycle;
Y is selected from N and C;
$W_1$ is selected from N and $CR_1$;
$W_2$ is selected from N and $CR_2$;
$W_3$ is selected from N and $CR_3$;
$W_4$ and $W_5$, if present, are independently selected from N, CH, and C;
$W_1$, $W_2$, and $W_3$ may be the same or different from each other;
X is selected from —NH—, —CH$_2$—, —CH$_2$CH$_2$—, —CH$_2$CH$_2$CH$_2$—, —CH$_2$CH$_2$O—, —CH$_2$CH$_2$NH—, —CH$_2$CH$_2$S—, —C(O)—, —C(O)CH$_2$—, —C(O)CH$_2$CH$_2$—, —CH$_2$C(O)—, —CH$_2$CH$_2$C(O)—, —C(O)NH—, —C(O)O—, —C(O)S—, —C(O)NHCH$_2$—, —C(O)OCH$_2$—, —C(O)SCH$_2$—, —CH(OH)—, and —CH(CH$_3$)— where one or more hydrogen may independently be replaced with deuterium, hydroxymethyl, halogen, —CF$_3$, ketone, and where S may be oxidized to sulfoxide or sulfone;
$R_4$ is selected from 3-7 membered carbocycles and heterocycles;
$D_1$ is selected from 5-membered monocyclic heterocycles, where $D_1$ is attached to the B ring via a carbon atom that is part of a doublebond within the $D_1$ ring.
$R_1$ and $R_2$ are independently selected from hydrogen, deuterium, alkyl, —OH, —NH$_2$, -thioalkyl, alkoxy, ketone, ester, carboxylic acid, urea, carbamate, amino, amide, halogen, sulfone, sulfoxide, sulfide, sulfonamide, and —CN;
$R_3$ is selected from hydrogen, —NH$_2$, —CN, —N$_3$, halogen, deuterium, —NO$_2$, —OMe, —OEt, —NHC(O)Me, NHSO$_2$Me, cylcoamino, cycloamido, —OH, —SO$_2$Me, —SO$_2$Et, —CH$_2$NH$_2$, —C(O)NH$_2$, and —C(O)OMe;
with the proviso that if $R_3$ is hydrogen and A is a 5-membered ring, then $D_1$ cannot be

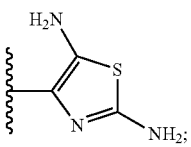

and with the proviso that if $D_1$ is

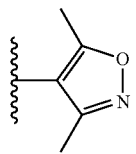 [SMILES: *c1c(C)noc1C]

and $R_2$ and $R_3$ are hydrogen and $R_1$ is —OMe, then the A-B bicyclic ring is not

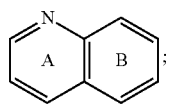

and with the proviso that if $D_1$ is

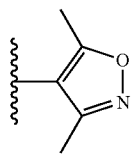 [SMILES: *c1c(C)noc1C]

and each of $R_1$, $R_2$, $R_3$, are hydrogen, then the A-B bicyclic ring is not

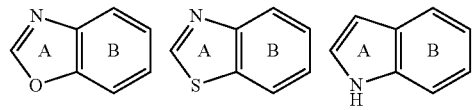

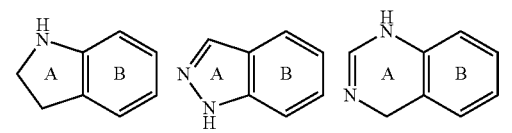

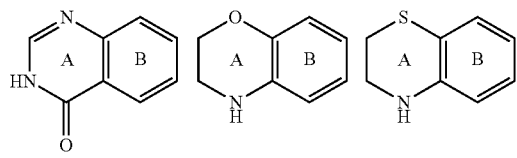

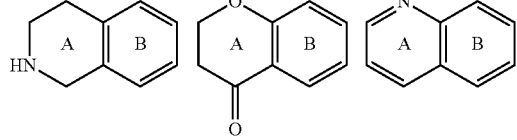

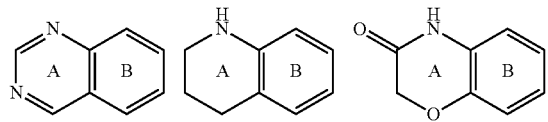

-continued

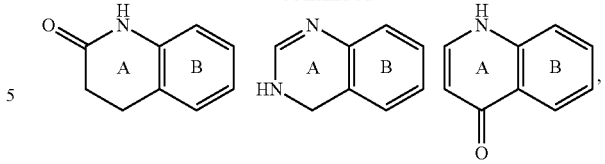

unless the B ring is substituted;
and with the proviso that if each of $R_1$, $R_2$, $R_3$ are hydrogen, then the A-B bicyclic ring is not

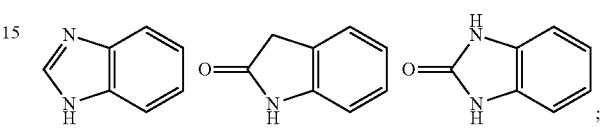

and with the proviso that if each of $R_1$, $R_2$, $R_3$ are hydrogen, then the A-B bicyclic ring is not

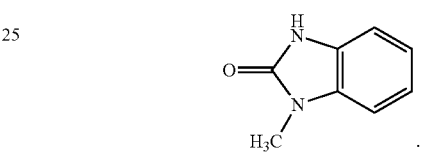

In some embodiments, the A ring a compound of any one of Formula Ia, Ib, IIa, or IIb or stereoisomer, tautomer, pharmaceutically acceptable salt, or hydrate thereof is optionally substituted with Z, wherein Z is selected from hydrogen, deuterium, —NH$_2$, amino (such as —NH(C$_1$-C$_5$), —N(C$_1$-C$_5$)$_2$, —NHPh, —NHBn, —NHpyridyl, —NHheterocycle(C$_4$-C$_6$), —NHcarbocycle(C$_4$-C$_6$)), alkyl(C$_1$-C$_6$), thioalkyl(C$_1$-C$_6$), alkenyl(C$_1$-C$_6$), and alkoxy(C$_1$-C$_6$). In some embodiments, Z is selected from
-Me, —CF$_3$, -Et, CH$_3$CH$_2$O—, CF$_3$CH$_2$—, —SMe, —SOMe, —SO$_2$Me, —CN,

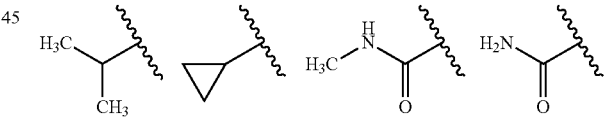

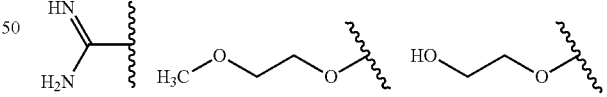

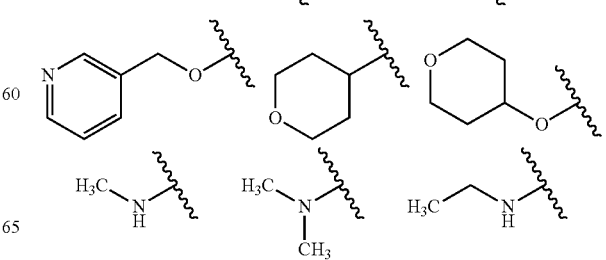

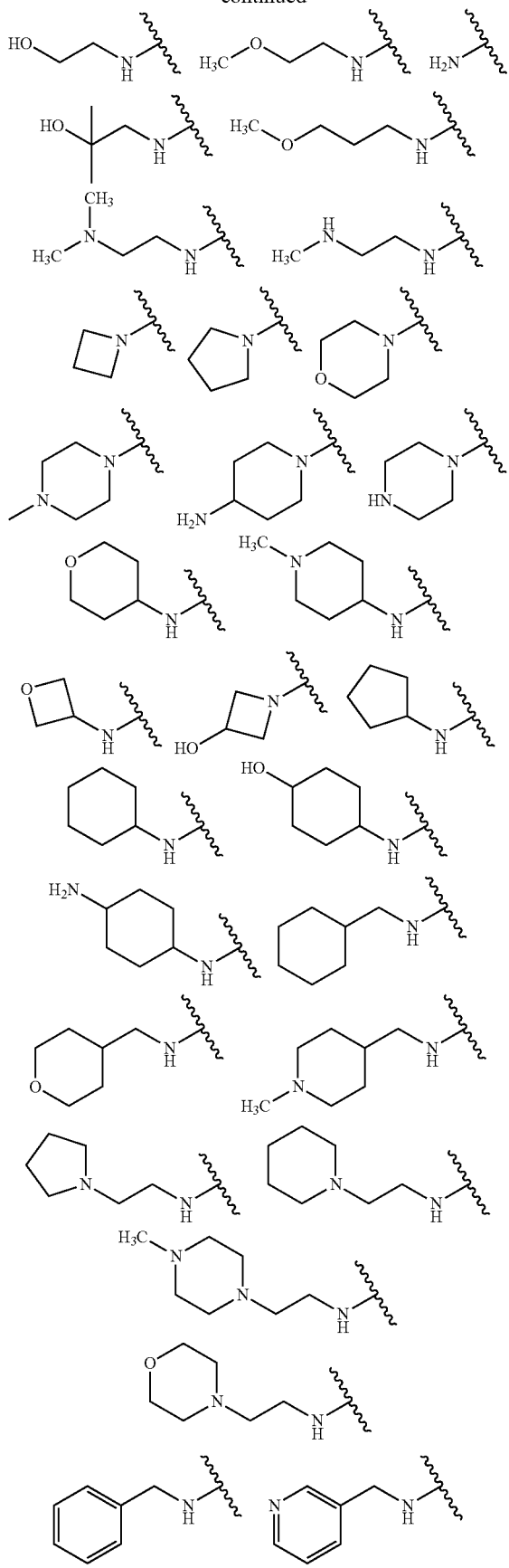
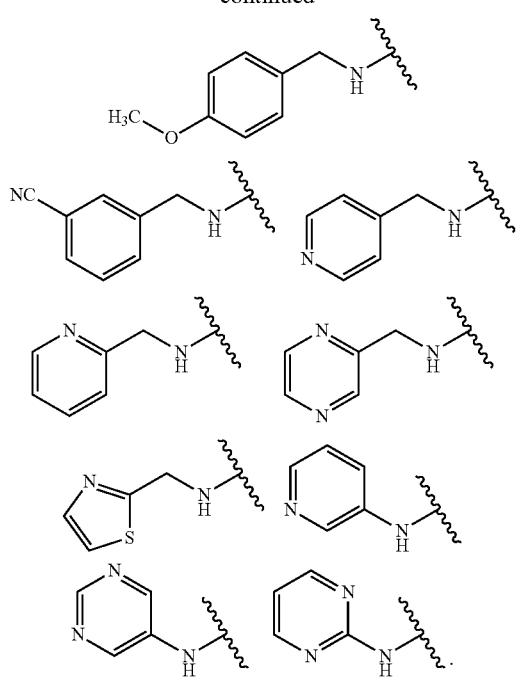
In some embodiments, compounds of any one of Formula Ia, Ib, IIa, or IIb or stereoisomer, tautomer, pharmaceutically acceptable salt, or hydrate thereof, are selected from
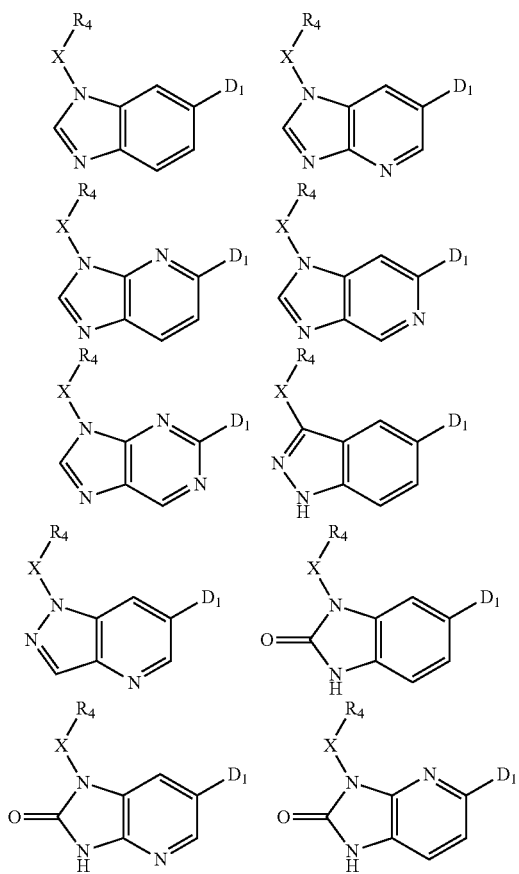

-continued

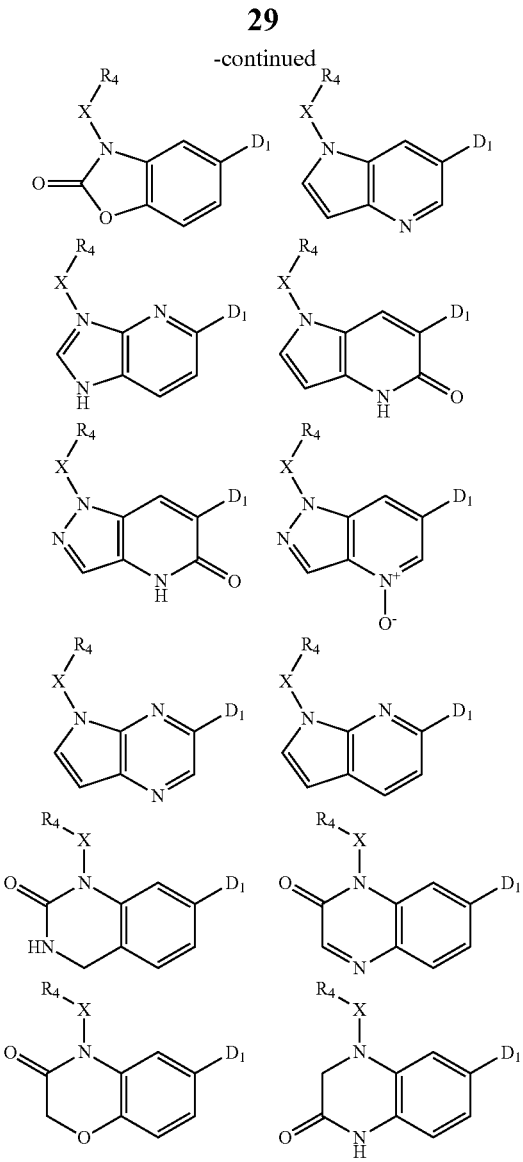

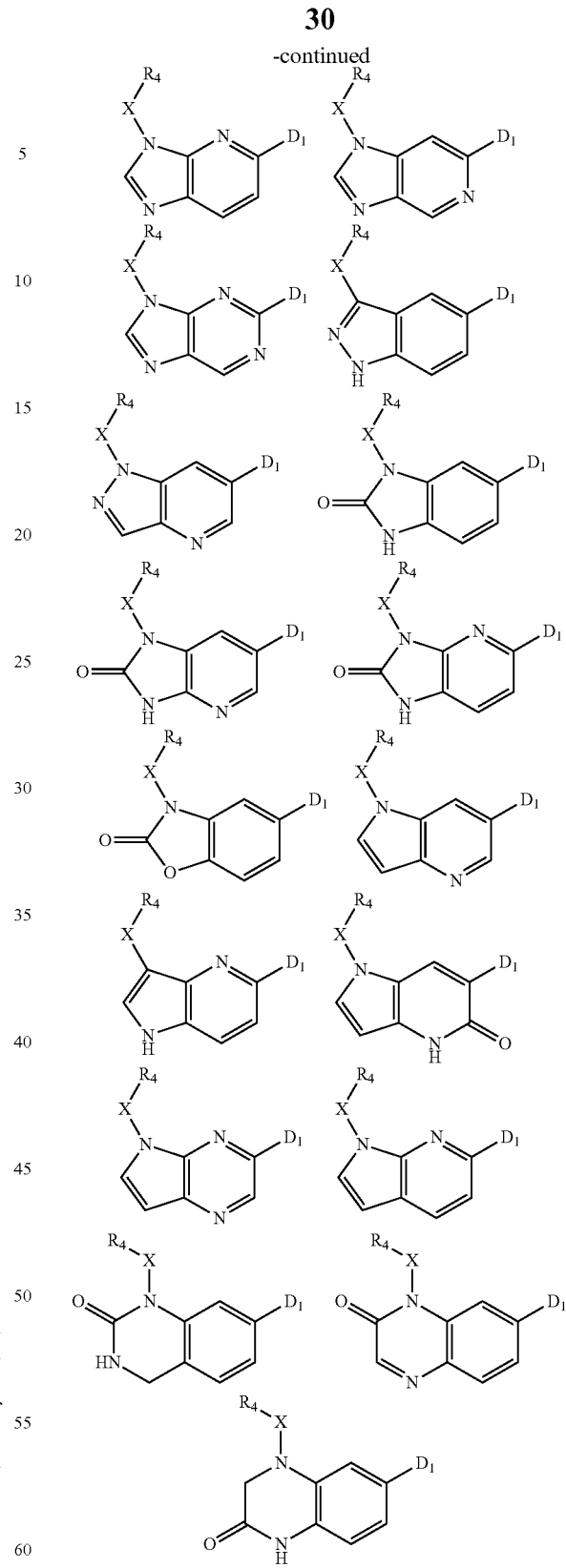

which may be optionally substituted with groups independently selected from hydrogen, deuterium, —NH$_2$, amino (such as NH(C$_1$-C$_5$), carbocycle (C$_1$-C$_5$)$_2$, —NHPh, —NHBn, —NHpyridyl, —NHheterocycle(C$_4$-C$_6$), —NHcarbocycle(C$_4$-C$_6$)), heterocycle(C$_4$-C$_6$), carbocycle (C$_4$-C$_6$), halogen, —CN, —OH, —CF$_3$, alkyl(C$_1$-C$_6$), thioalkyl(C$_1$-C$_6$), alkenyl(C$_1$-C$_6$), and alkoxy(C$_1$-C$_6$); wherein X, R$_4$, and D$_1$ are as defined for any embodiment disclosed herein.

In some embodiments, the compounds of any one of Formula Ia, Ib, IIa, or IIb or stereoisomer, tautomer, pharmaceutically acceptable salt, or hydrate thereof, are selected from

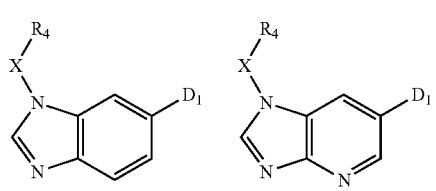

which may be optionally substituted with groups independently selected from hydrogen, deuterium, —NH$_2$, amino (such as —NH(C$_1$-C$_5$), —N(C$_1$-C$_5$)$_2$, —NHPh, —NHBn, —NHpyridyl, —NHheterocycle(C$_4$-C$_6$), —NHcarbocycle (C$_4$-C$_6$), heterocycle(C$_4$-C$_6$), carbocycle(C$_4$-C$_6$), halogen, —CN, —OH, —CF$_3$, alkyl(C$_1$-C$_6$), thioalkyl(C$_1$-C$_6$), alkenyl(C$_1$-C$_6$), and alkoxy(C$_1$-C$_6$); wherein X, R$_4$, and D$_1$ are as defined for any embodiment disclosed herein.

In some embodiments, the compounds of any one of Formula Ia, Ib, IIa, or IIb or stereoisomer, tautomer, pharmaceutically acceptable salt, or hydrate thereof, are selected from

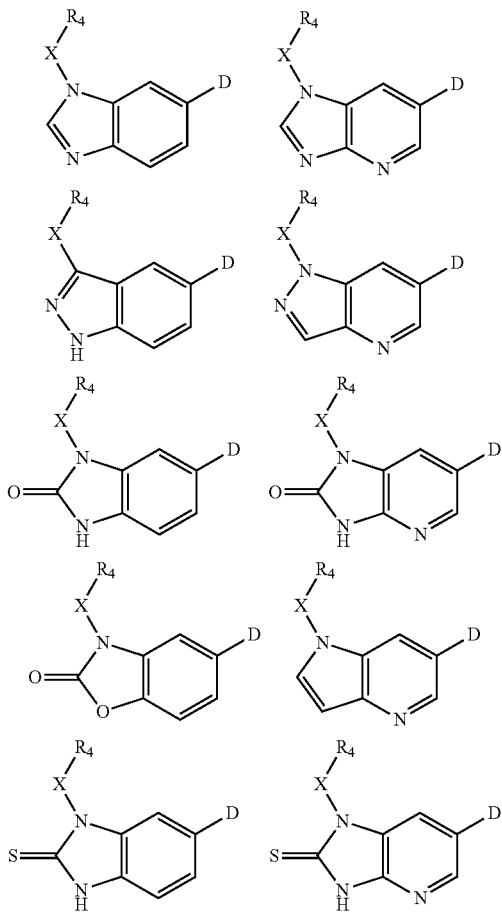

which may be optionally substituted with groups independently selected from hydrogen, deuterium, —NH$_2$, amino (such as —NH(C$_1$-C$_5$), —N(C$_1$-C$_5$)$_2$, —NHPh, —NHBn, —NHpyridyl, —NHheterocycle(C$_4$-C$_6$), —NHcarbocycle (C$_4$-C$_6$)), heterocycle(C$_4$-C$_6$), carbocycle(C$_4$-C$_6$), halogen, —CN, —OH, —CF$_3$, alkyl(C$_1$-C$_6$), thioalkyl(C$_1$-C$_6$), alkenyl(C$_1$-C$_6$), and alkoxy(C$_1$-C$_6$); wherein X, R$_4$, and D$_1$ are as defined for any embodiment disclosed herein.

In some embodiments, compounds of any one of Formula Ia, Ib, IIa, or IIb or stereoisomer, tautomer, pharmaceutically acceptable salt, or hydrate thereof, are selected from

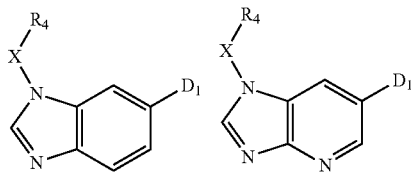

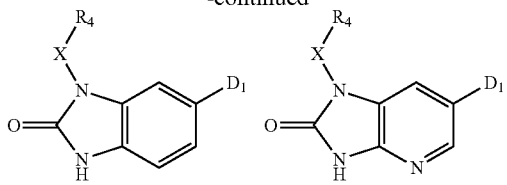

-continued which may be optionally substituted with groups independently selected from hydrogen, deuterium, —NH$_2$, amino (such as —NH(C$_1$-C$_5$), —N(C$_1$-C$_5$)$_2$, —NHPh, —NHBn, —NHpyridyl, —NHheterocycle(C$_4$-C$_6$), —NHcarbocycle (C$_4$-C$_6$)), heterocycle(C$_4$-C$_6$), carbocycle(C$_4$-C$_6$), halogen, —CN, —OH, —CF$_3$, alkyl(C$_1$-C$_6$), thioalkyl(C$_1$-C$_6$), alkenyl(C$_1$-C$_6$), and alkoxy(C$_1$-C$_6$); wherein the definition of X, R$_4$, and D$_1$ are as defined for any embodiment disclosed herein.

In some embodiments, compounds of any one of Formula Ia, Ib, IIa, or IIb or stereoisomer, tautomer, pharmaceutically acceptable salt, or hydrate thereof, is selected from

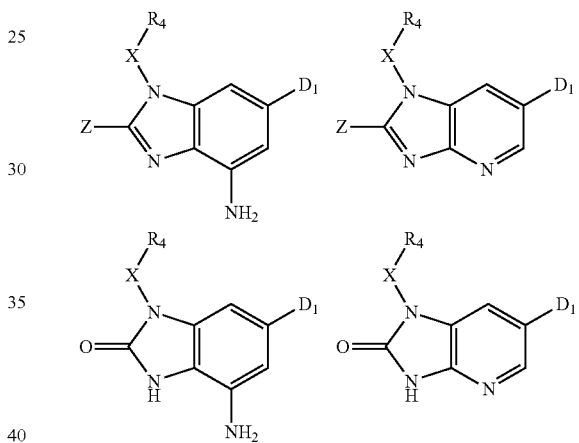

wherein Z is selected from hydrogen, deuterium, —NH$_2$, amino (such as —NH(C$_1$-C$_5$), —N(C$_1$-C$_5$)$_2$, —NHPh, —NHBn, —NHpyridyl, —NHheterocycle(C$_4$-C$_6$), —NHcarbocycle(C$_4$-C$_6$)), alkyl(C$_1$-C$_6$), thioalkyl(C$_1$-C$_6$), alkenyl(C$_1$-C$_6$), and alkoxy(C$_1$-C$_6$); carboxyl;

D$_1$ is

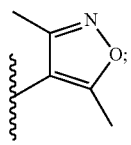 [SMILES: *c1c(C)noc1C]

X is selected from —CH$_2$— and —CH(CH$_3$)—; and

R$_4$ is a phenyl ring optionally substituted with groups independently substituted with one or more groups independently selected from deuterium, alkyl(C$_1$-C$_4$), alkoxy(C$_1$-C$_4$), halogen, —CF$_3$, CN, and -thioalkyl(C$_1$-C$_4$), wherein each alkyl, alkoxy, and thioalkyl may be optionally substituted with F, Cl, or Br.

In certain embodiments, R$_4$ is a phenyl ring is optionally substituted with one or more alkyl(C$_1$-C$_4$) selected from methyl, ethyl, propyl, isopropyl, and butyl; alkoxy(C$_1$-C$_4$), selected from methoxy, ethoxy, and isopropoxy; halogen selected from F and Cl; and thioalkyl($C_1$-$C_4$) selected from —SMe, —SEt, —SPr, and -Sbu.

In some embodiments, the A-B bicyclic ring in the compound of any one of Formula Ia, Ib, IIa, or IIb or stereoisomer, tautomer, pharmaceutically acceptable salt, or hydrate thereof, is selected from

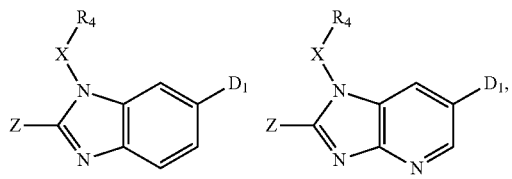

wherein Z is selected from hydrogen, deuterium, —$NH_2$, amino (such as —NH($C_1$-$C_5$), —N($C_1$-$C_5$)$_2$, —NHPh, —NHBn, —NHpyridyl, —NHheterocycle($C_4$-$C_6$), —NHcarbocycle($C_4$-$C_6$)), alkyl($C_1$-$C_6$), thioalkyl($C_1$-$C_6$), alkenyl($C_1$-$C_6$), and alkoxy($C_1$-$C_6$).

In some embodiments, the A-B bicyclic ring in the compound of any one of Formula Ia, Formula Ib, Formula Ia, and Formula IIb or stereoisomer, tautomer, pharmaceutically acceptable salt, or hydrate thereof, is selected from

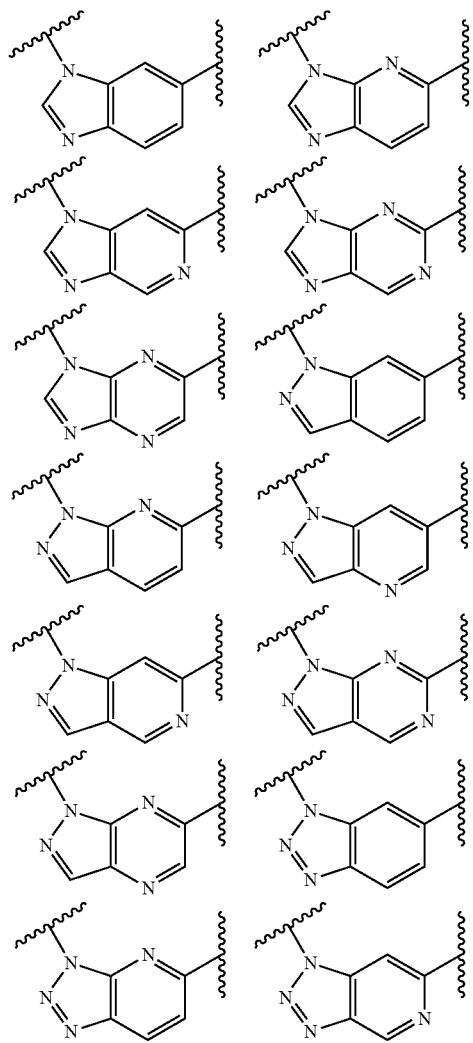

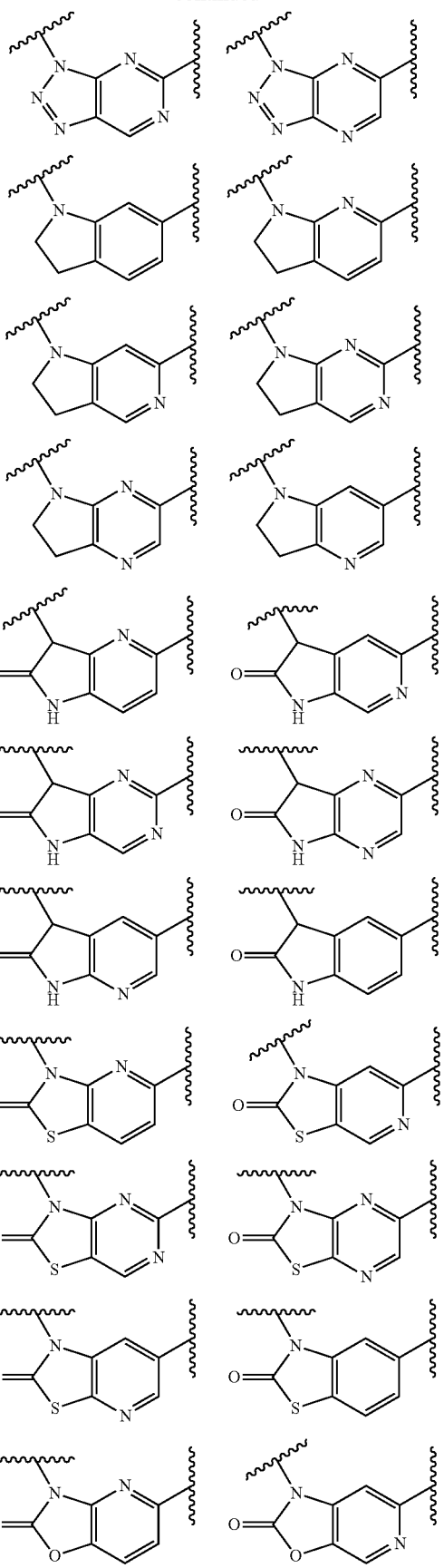

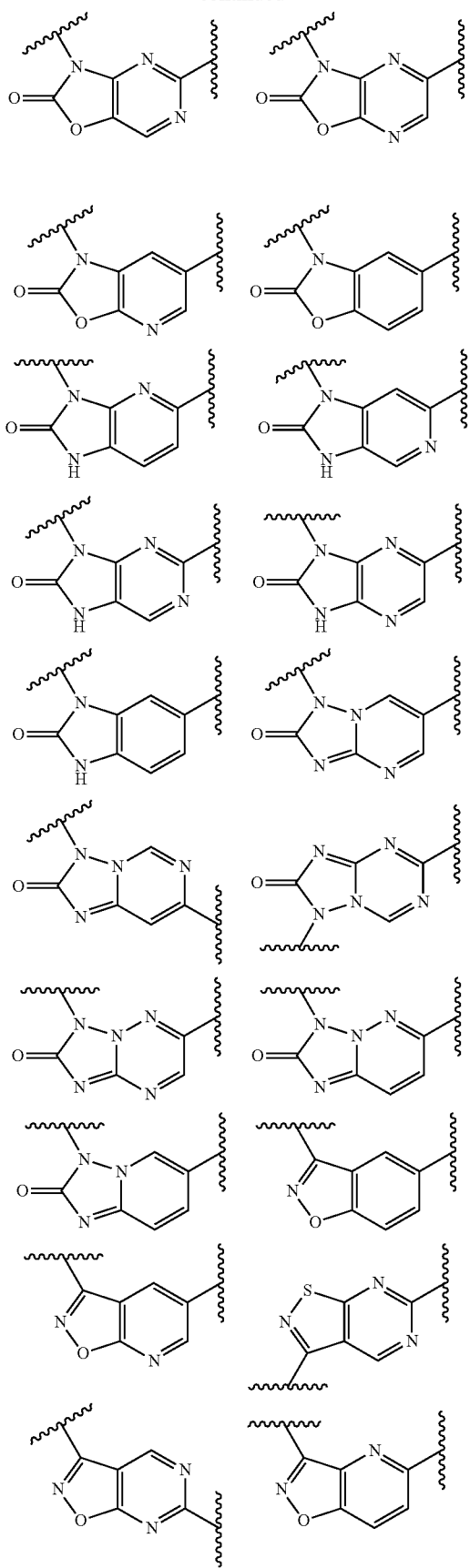
In some embodiments, the A-B bicyclic ring in the compound of any one of Formula Ia, Formula Ib, Formula IIa, and Formula IIb or stereoisomer, tautomer, pharmaceutically acceptable salt, or hydrate thereof, is selected from, but not limited to
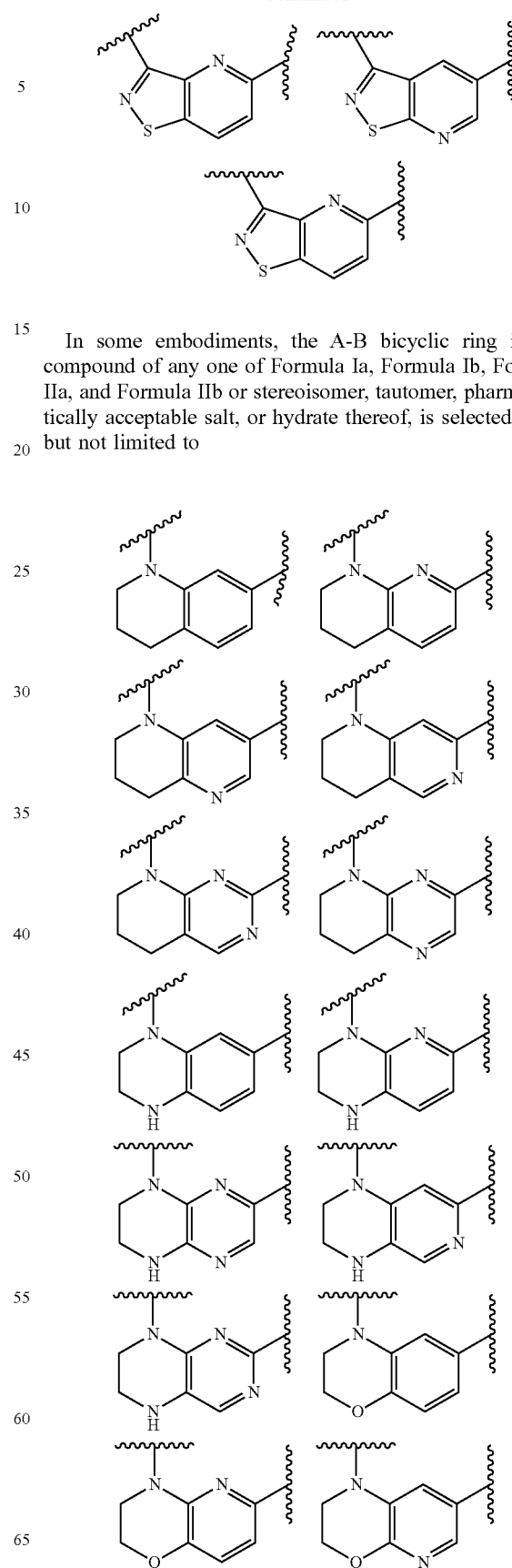

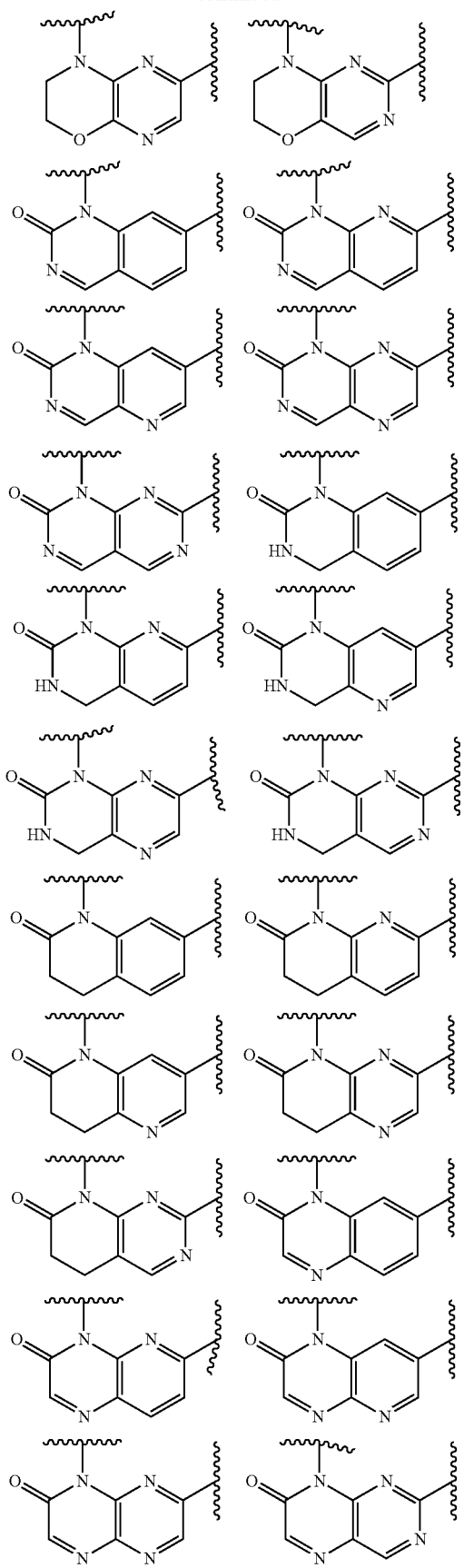
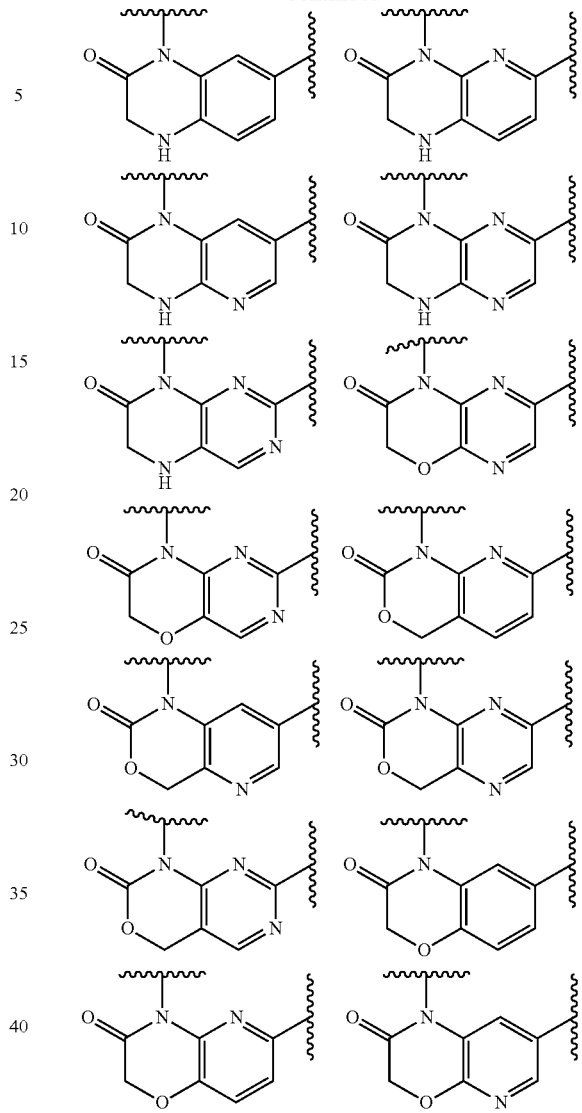

which may be optionally substituted with groups independently selected from hydrogen, deuterium, —NH$_2$, amino (such as —NH(C$_1$-C$_5$), —N(C$_1$-C$_5$)$_2$, —NHPh, —NHBn, —NHpyridyl, —NHheterocycle(C$_4$-C$_7$), —NHcarbocycle (C$_4$-C$_7$)), heterocycle(C$_4$-C$_7$), carbocycle(C$_4$-C$_7$), halogen, —CN, —OH, —CF$_3$, sulfone, sulfoxide, alkyl(C$_1$-C$_6$), thioalkyl(C$_1$-C$_6$), Alkenyl(C$_1$-C$_6$), alkoxy(C$_1$-C$_6$), ketone(C$_1$-C$_6$), ester, urea, carboxylic acid, carbamate, amide(C$_1$-C$_6$), oxo, and thio-oxo.

In some embodiments of any of Formula Ia, Formula Ib, Formula IIa, and Formula IIb, or stereoisomer, tautomer, pharmaceutically acceptable salt, or hydrate thereof, the A-B bicyclic ring, is selected from

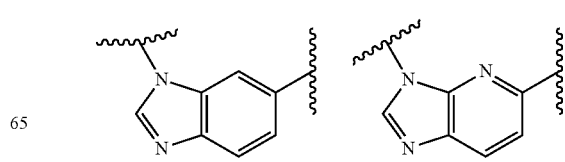

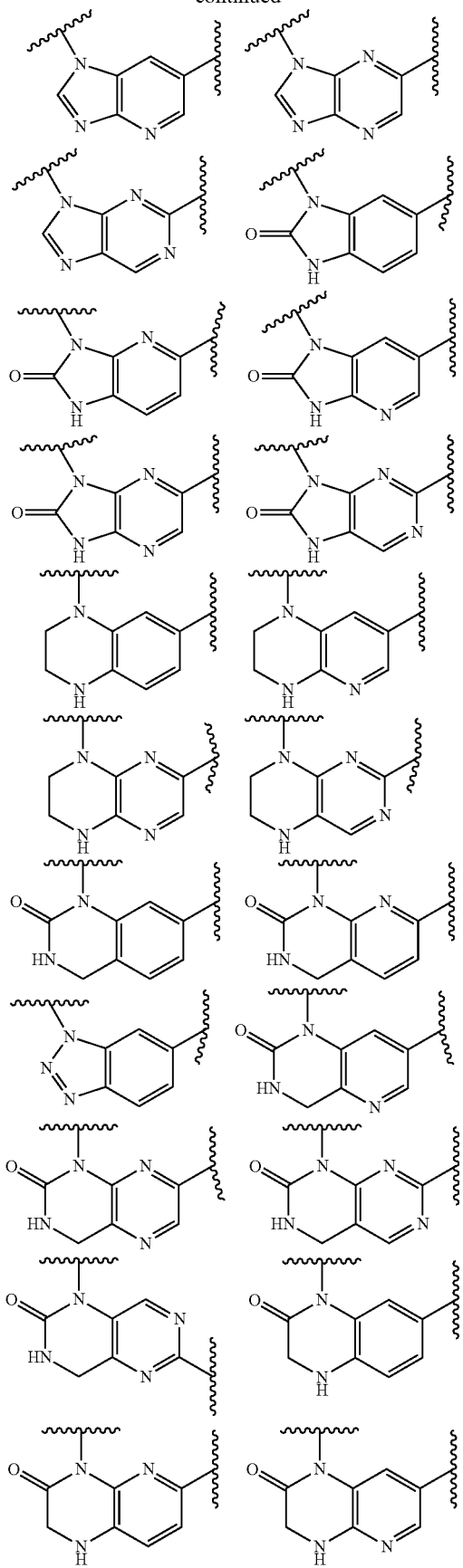
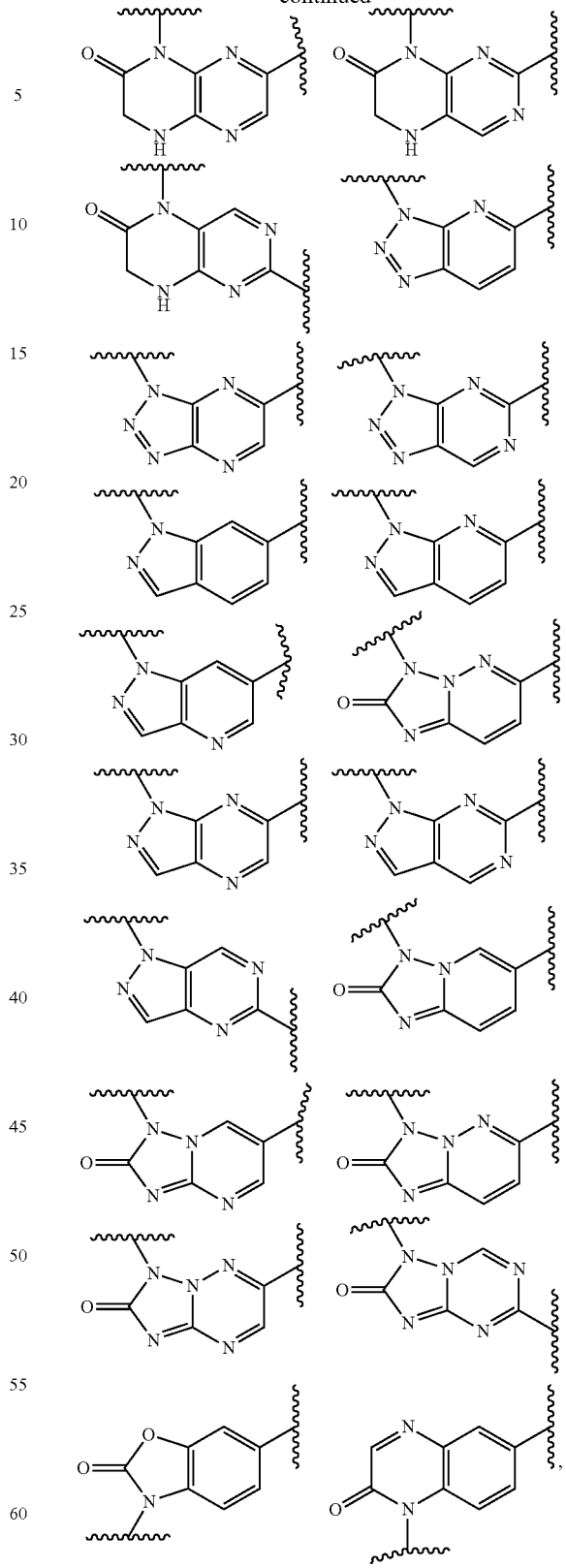
which may be optionally substituted with groups independently selected from hydrogen, deuterium, —NH$_2$, amino (such as —NH(C$_1$-C$_5$), —N(C$_1$-C$_5$)$_2$, —NHPh, —NHBn, —NHpyridyl, —NHheterocycle(C$_4$-C$_7$),—NHcarbocycle ($C_4$-$C_7$)), heterocycle($C_4$-$C_7$), carbocycle($C_4$-$C_7$), halogen, —CN, —OH, —$CF_3$, sulfone, sulfoxide, alkyl($C_1$-$C_6$), thioalkyl($C_1$-$C_6$), Alkenyl($C_1$-$C_6$), alkoxy($C_1$-$C_6$), ketone($C_1$-$C_6$), ester, urea, carboxylic acid, carbamate, amide($C_1$-$C_6$), oxo, and thio-oxo.

In some embodiments, the A-B bicyclic ring in the compound of any one of Formula Ia, Formula Ib, Formula Ia, and Formula IIb or stereoisomer, tautomer, pharmaceutically acceptable salt, or hydrate thereof, is selected from

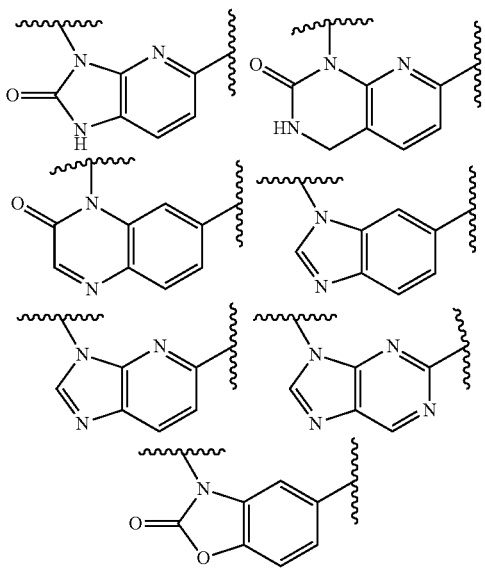

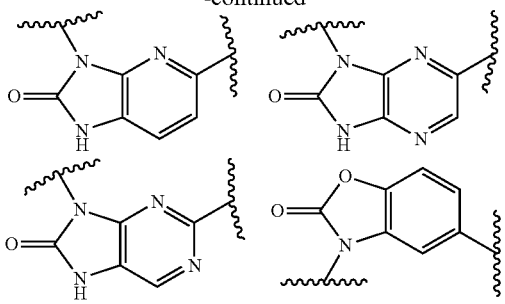

which may be optionally substituted with groups independently selected from hydrogen, deuterium, —$NH_2$, amino (such as —NH($C_1$-$C_5$), —N($C_1$-$C_5$)$_2$, —NHPh, —NHBn, —NHpyridyl, —NHheterocycle($C_4$-$C_7$), —NHcarbocycle ($C_4$-$C_7$)), heterocycle($C_4$-$C_7$), carbocycle($C_4$-$C_7$), halogen, —CN, —OH, —$CF_3$, sulfone, sulfoxide, sulfonamide, alkyl ($C_1$-$C_6$), thioalkyl($C_1$-$C_6$), alkenyl($C_1$-$C_6$), alkoxy($C_1$-$C_6$), ketone($C_1$-$C_6$), ester, urea, carboxylic acid, carbamate, amide($C_1$-$C_6$), oxo, and thio-oxo.

In some embodiments, the A-B bicyclic ring in the compound of any one of Formula Ia, Formula Ib, Formula IIa, and Formula IIb or stereoisomer, tautomer, pharmaceutically acceptable salt, or hydrate thereof, is selected from

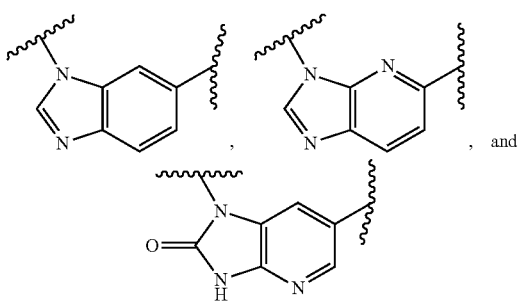

which may be optionally substituted with groups independently selected from hydrogen, deuterium, —$NH_2$, amino (such as —NH($C_1$-$C_5$), —N($C_1$-$C_5$)$_2$, —NHPh, —NHBn, —NHpyridyl, —NHheterocycle($C_4$-$C_7$), —NHcarbocycle ($C_4$-$C_7$)), heterocycle($C_4$-$C_7$), carbocycle($C_4$-$C_7$), halogen, —CN, —OH, —$CF_3$, sulfone, sulfoxide, alkyl($C_1$-$C_6$), thioalkyl($C_1$-$C_6$), Alkenyl($C_1$-$C_6$), alkoxy($C_1$-$C_6$), ketone($C_1$-$C_6$), ester, urea, carboxylic acid, carbamate, amide($C_1$-$C_6$), oxo, and thio-oxo.

In some embodiments, the A-B bicyclic ring in the compound of any one of Formula Ia, Formula Ib, Formula IIa, and Formula IIb or stereoisomer, tautomer, pharmaceutically acceptable salt, or hydrate thereof, is selected from

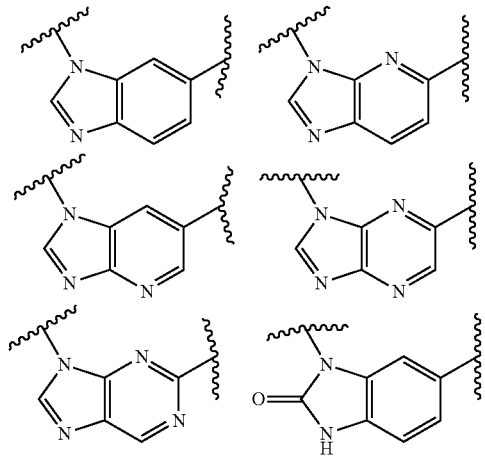

which may be optionally substituted with groups independently selected from hydrogen, deuterium, —$NH_2$, amino (such as —NH($C_1$-$C_5$), —N($C_1$-$C_5$)$_2$, —NHPh, —NHBn, —NHpyridyl, —NHheterocycle($C_4$-$C_7$), —NHcarbocycle ($C_4$-$C_7$)), heterocycle($C_4$-$C_7$), carbocycle($C_4$-$C_7$), halogen, —CN, —OH, —$CF_3$, sulfone, sulfoxide, sulfonamide, alkyl ($C_1$-$C_6$), thioalkyl($C_1$-$C_6$), alkenyl($C_1$-$C_6$), alkoxy($C_1$-$C_6$), ketone($C_1$-$C_6$), ester, urea, carboxylic acid, carbamate, amide($C_1$-$C_6$), oxo, and thio-oxo.

In some embodiments, the A ring in the compound of any one of Formula Ia, Formula Ib, Formula IIa, and Formula IIb or stereoisomer, tautomer, pharmaceutically acceptable salt, or hydrate thereof, is selected from 5-membered heterocycles fused to the B ring.

In some embodiments, Y in the compound of any one of Formula Ia, Formula Ib, Formula IIa, and Formula IIb or stereoisomer, tautomer, pharmaceutically acceptable salt, or hydrate thereof, is nitrogen.

In some embodiments, $D_1$ in the compound of any one of Formula I, Formula Ia, or Formula II or stereoisomer, tautomer, pharmaceutically acceptable salt, or hydrate thereof, is selected from an 5-membered monocyclic heterocycle, such as, but not limited to:

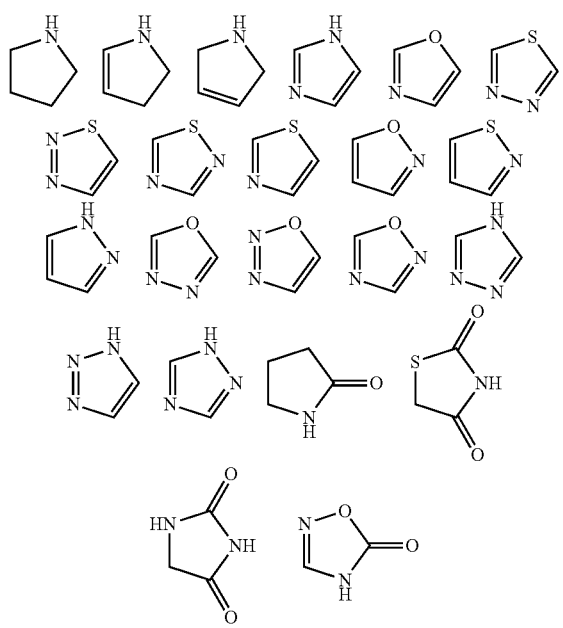

which is optionally substituted with hydrogen, deuterium, alkyl($C_1$-$C_4$)(such as methyl, ethyl, propyl, isopropyl, butyl), alkoxy($C_1$-$C_4$) (such as methoxy, ethoxy, isopropoxy), amino (such as —$NH_2$, —NHMe, —NHEt, —NHiPr, —NHBu —$NMe_2$, NMeEt, —$NEt_2$, —NEtBu, —NHC(O)NHalkyl), halogen (such as F, Cl), amide (such as —NHC(O)Me, —NHC(O)Et, —C(O)NHMe, —C(O)$NEt_2$, —C(O)NiPr), —$CF_3$, CN, —$N_3$, ketone ($C_1$-$C_4$) (such as acetyl, —C(O)Et, —C(O)Pr), —S(O)Alkyl($C_1$-$C_4$) (such as —S(O)Me, —S(O)Et), —$SO_2$alkyl($C_1$-$C_4$) (such as —$SO_2$Me, —$SO_2$Et, —$SO_2$Pr), -thioalkyl($C_1$-$C_4$) (such as —SMe, —SEt, —SPr, —SBu), —COOH, and/or ester (such as —C(O)OMe, —C(O)OEt, —C(O)OBu), each of which may be optionally substituted with hydrogen, F, Cl, Br, —OH, —$NH_2$, —NHMe, —OMe, —SMe, oxo, and/or thio-oxo.

In some embodiments, $D_1$ in the compound of any one of Formula Ia, Ib, IIa, or IIb or stereoisomer, tautomer, pharmaceutically acceptable salt, or hydrate thereof, is a monocyclic heterocycle optionally substituted with hydrogen, deuterium, alkyl($C_1$-$C_4$)(such as methyl, ethyl, propyl, isopropyl, butyl), alkoxy($C_1$-$C_4$) (such as methoxy, ethoxy, isopropoxy), amino (such as —$NH_2$, —NHMe, —NHEt, —NHiPr, —NHBu —$NMe_2$, NMeEt, —$NEt_2$, —NEtBu, —NHC(O)NHalkyl), halogen (such as F, Cl), amide (such as —NHC(O)Me, —NHC(O)Et, —C(O)NHMe, —C(O)$NEt_2$, —C(O)NiPr), —$CF_3$, CN, —$N_3$, ketone ($C_1$-$C_4$) (such as acetyl, —C(O)Et, —C(O)Pr), —S(O)Alkyl($C_1$-$C_4$) (such as —S(O)Me, —S(O)Et), —$SO_2$alkyl($C_1$-$C_4$) (such as —$SO_2$Me, —$SO_2$Et, —$SO_2$Pr), -thioalkyl($C_1$-$C_4$) (such as —SMe, —SEt, —SPr, —SBu), —COOH, and/or ester (such as —C(O)OMe, —C(O)OEt, —C(O)OBu), each of which may be optionally substituted with hydrogen, F, Cl, Br, —OH, —$NH_2$, —NHMe, —OMe, —SMe, oxo, and/or thio-oxo.

In some embodiments, $D_1$ in the compound of any one of Formula Ia, Formula Ib, Formula IIa, and Formula IIb or stereoisomer, tautomer, pharmaceutically acceptable salt, or hydrate thereof, is selected from a 5-membered monocyclic heterocycle containing one oxygen and one or two nitrogens, where the heterocycle is connected to the rest of the molecule via a carbon-carbon bond, and which is optionally substituted with hydrogen, deuterium, alkyl($C_1$-$C_4$)(such as methyl, ethyl, propyl, isopropyl, butyl), alkoxy($C_1$-$C_4$) (such as methoxy, ethoxy, isopropoxy), amino (such as —$NH_2$, —NHMe, —NHEt, —NHiPr, —NHBu —$NMe_2$, NMeEt, —$NEt_2$, —NEtBu, —NHC(O)NHalkyl), halogen (such as F, Cl), amide (such as —NHC(O)Me, —NHC(O)Et, —C(O)NHMe, —C(O)$NEt_2$, —C(O)NiPr), —$CF_3$, CN, —$N_3$, ketone ($C_1$-$C_4$) (such as acetyl, —C(O)Et, —C(O)Pr), —S(O)Alkyl($C_1$-$C_4$) (such as —S(O)Me, —S(O)Et), —$SO_2$alkyl($C_1$-$C_4$) (such as —$SO_2$Me, —$SO_2$Et, —$SO_2$Pr), -thioalkyl($C_1$-$C_4$) (such as —SMe, —SEt, —SPr, —SBu), —COOH, and/or ester (such as —C(O)OMe, —C(O)OEt, —C(O)OBu), each of which may be optionally substituted with hydrogen, F, Cl, Br, —OH, —$NH_2$, —NHMe, —OMe, —SMe, oxo, and/or thio-oxo.

In some embodiments, $D_1$ in the compound of any one of Formula Ia, Formula Ib, Formula IIa, and Formula IIb or stereoisomer, tautomer, pharmaceutically acceptable salt, or hydrate thereof, is an isoxazole optionally substituted with hydrogen, deuterium, alkyl($C_1$-$C_4$)(such as methyl, ethyl, propyl, isopropyl, butyl), alkoxy($C_1$-$C_4$) (such as methoxy, ethoxy, isopropoxy), amino (such as —$NH_2$, —NHMe, —NHEt, —NHiPr, —NHBu —$NMe_2$, NMeEt, —$NEt_2$, —NEtBu, —NHC(O)NHalkyl), halogen (such as F, Cl), amide (such as —NHC(O)Me, —NHC(O)Et, —C(O)NHMe, —C(O)$NEt_2$, —C(O)NiPr), —$CF_3$, CN, —$N_3$, ketone ($C_1$-$C_4$) (such as acetyl, —C(O)Et, —C(O)Pr), —S(O)Alkyl($C_1$-$C_4$) (such as —S(O)Me, —S(O)Et), —$SO_2$alkyl($C_1$-$C_4$) (such as —$SO_2$Me, —$SO_2$Et, —$SO_2$Pr), -thioalkyl($C_1$-$C_4$) (such as —SMe, —SEt, —SPr, —SBu), —COOH, and/or ester (such as —C(O)OMe, —C(O)OEt, —C(O)OBu), each of which may be optionally substituted with hydrogen, F, Cl, Br, —OH, —$NH_2$, —NHMe, —OMe, —SMe, oxo, and/or thio-oxo.

In some embodiments, $D_1$ in the compound of any one of Formula Ia, Formula Ib, Formula IIa, and Formula IIb or stereoisomer, tautomer, pharmaceutically acceptable salt, or hydrate thereof, is selected from an 5-membered monocyclic heterocycle, which is optionally substituted with hydrogen, deuterium, Alkyl(C1-C4), (such as methyl, ethyl, propyl), each of which may be optionally substituted with hydrogen, —OH, —F, and —NH2.

In some embodiments, $D_1$ in the compound of any one of Formula Ia, Formula Ib, Formula IIa, and Formula IIb or stereoisomer, tautomer, pharmaceutically acceptable salt, or hydrate thereof, is selected from a 5-membered monocyclic heterocycle containing one oxygen and one or two nitrogens, where the heterocycle is connected to the rest of the molecule via a carbon-carbon bond, and which is optionally substituted with hydrogen, deuterium, Alkyl($C_1$-$C_4$), (such as methyl, ethyl, propyl), each of which may be optionally substituted with hydrogen, —OH, —F, and —$NH_2$.

In some embodiments, $D_1$ in the compound of any one of Formula Ia, Formula Ib, Formula IIa, and Formula IIb or stereoisomer, tautomer, pharmaceutically acceptable salt, or hydrate thereof, is an isoxazole or pyrazole optionally substituted with hydrogen, deuterium, Alkyl($C_1$-$C_4$), (such as methyl, ethyl, propyl), each of which may be optionally substituted with hydrogen, —OH, —F, and —$NH_2$.

In some embodiments, $D_1$ in the compound of any one of Formula Ia, Formula Ib, Formula IIa, and Formula IIb or stereoisomer, tautomer, pharmaceutically acceptable salt, or hydrate thereof is In some embodiments, $D_1$ in the compound of any one of Formula Ia, Formula Ib, Formula IIa, and Formula IIb or stereoisomer, tautomer, pharmaceutically acceptable salt, or hydrate thereof is In some embodiments, $D_1$ in the compound of Formula Ia, Formula Ib, Formula IIa, and Formula IIb or stereoisomer, tautomer, pharmaceutically acceptable salt, or hydrate thereof is

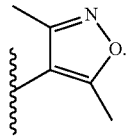

In some embodiments, $W_1$ in the compound of any one of Formula Ia, Formula Ib, Formula IIa, and Formula IIb or stereoisomer, tautomer, pharmaceutically acceptable salt, or hydrate thereof is $CR_1$.

In some embodiments, $W_2$ in the compound of any one of Formula Ia, Formula Ib, Formula IIa, and Formula IIb or stereoisomer, tautomer, pharmaceutically acceptable salt, or hydrate thereof is $CR_2$.

In some embodiments, at least one of $W_1$ and $W_2$ in the compound of any one of Formula Ia, Formula Ib, Formula IIa, and Formula IIb or stereoisomer, tautomer, pharmaceutically acceptable salt, or hydrate thereof, is nitrogen.

In some embodiments, $W_1$ in the compound of any one of Formula Ia, Formula Ib, Formula IIa, and Formula IIb or stereoisomer, tautomer, pharmaceutically acceptable salt, or hydrate thereof, is CH.

In some embodiments, $W_2$ in the compound of any one of Formula Ia, Formula Ib, Formula IIa, and Formula IIb or stereoisomer, tautomer, pharmaceutically acceptable salt, or hydrate thereof, is $CR_2$, where $R_2$ is selected from hydrogen, deuterium, —OH, —$NH_2$, methyl, halogen, and —CN.

In some embodiments, $W_2$ in the compound of any one of Formula Ia, Formula Ib, Formula IIa, and Formula IIb or stereoisomer, tautomer, pharmaceutically acceptable salt, or hydrate thereof, is CH.

In some embodiments, $W_4$ and $W_5$ in the compound of any one of Formula Ia, Formula Ib, Formula IIa, and Formula IIb or stereoisomer, tautomer, pharmaceutically acceptable salt, or hydrate thereof are carbon.

In some embodiments, at least one of $W_4$ and $W_5$ in the compound of any one of Formula Ia, Formula Ib, Formula IIa, and Formula IIb or stereoisomer, tautomer, pharmaceutically acceptable salt, or hydrate thereof, is nitrogen.

In some embodiments, $W_3$ in the compound of any one of Formula Ia, Formula Ib, Formula IIa, and Formula IIb or stereoisomer, tautomer, pharmaceutically acceptable salt, or hydrate thereof, is nitrogen.

In some embodiments, $W_3$ in the compound of any one of Formula Ia, Formula Ib, Formula IIa, and Formula IIb or stereoisomer, tautomer, pharmaceutically acceptable salt, or hydrate thereof is $CR_3$, where $R_3$ is selected from hydrogen, —$NH_2$, and halogen.

In some embodiments, $R_3$ in the compound of any one of Formula Ia, Formula Ib, Formula IIa, and Formula IIb or stereoisomer, tautomer, pharmaceutically acceptable salt, or hydrate thereof is selected from hydrogen and —$NH_2$.

In some embodiments, $R_3$ in the compound of any one of Formula Ia, Formula Ib, Formula IIa, and Formula IIb or stereoisomer, tautomer, pharmaceutically acceptable salt, or hydrate thereof, is —$NH_2$.

In some embodiments, X in the compound of any one of Formula I, Formula Ia, or Formula II or stereoisomer, tautomer, pharmaceutically acceptable salt, or hydrate thereof, is selected from —$CH_2$—, —$CH_2CH_2$—, —$CH_2CH_2CH_2$—, —$CH_2CH_2O$—, —$CH_2CH_2NH$—, —$CH_2CH_2S$—, —C(O)—, —C(O)NH—, —C(O)O—, —C(O)S—, where one or more hydrogen may independently be replaced with deuterium, halogen, and where S may be oxidized to sulfoxide or sulfone.

In some embodiments, X in the compound of any one of Formula I, Formula Ia, or Formula II or stereoisomer, tautomer, pharmaceutically acceptable salt, or hydrate thereof, is selected from —$CH_2$— and —C(O)—.

In some embodiments, X is selected from —$CH_2$—, —$CH(CH_3)$—, —CH(OH)—, —NH—, $CH_2CH_2$—, where one or more hydrogen may independently be replaced with deuterium or halogen.

In some embodiments, X is selected from —$CH_2$—, $CH(CH_3)$—, and —NH—, where one or more hydrogen may independently be replaced with deuterium or halogen.

In some embodiments, X is selected from —$CH_2$—, —$CH(CH_3)$—, where one or more hydrogen may independently be replaced with deuterium or halogen.

In some embodiments, X in the compound of any one of Formula Ia, Formula Ib, Formula IIa, and Formula IIb or stereoisomer, tautomer, pharmaceutically acceptable salt, or hydrate thereof, is —$CH_2$—.

In some embodiments, $R_1$ in the compound of any one of Formula Ia, Formula Ib, Formula IIa, and Formula IIb or stereoisomer, tautomer, pharmaceutically acceptable salt, or hydrate thereof, is selected from hydrogen, deuterium, alkyl, —OH, —$NH_2$, -thioalkyl, alkoxy, ketone, ester, carboxylic acid, urea, carbamate, amino, amide, halogen, carbocycle, heterocycle, sulfone, sulfoxide, sulfide, sulfonamide, and —CN.

In some embodiments, $R_2$ in the compound of any one of Formula Ia, Formula Ib, Formula IIa, and Formula IIb or stereoisomer, tautomer, pharmaceutically acceptable salt, or hydrate thereof, is selected from hydrogen, deuterium, alkyl, —OH, —$NH_2$, -thioalkyl, alkoxy, ketone, ester, carboxylic acid, urea, carbamate, amino, amide, halogen, carbocycle, heterocycle, sulfone, sulfoxide, sulfide, sulfonamide, and —CN.

In some embodiments, $R_1$ and $R_2$ in the compound of any one of Formula I, Formula Ia, or stereoisomer, tautomer, pharmaceutically acceptable salt, or hydrate thereof are independently selected from hydrogen, deuterium, alkyl, —$NH_2$, -thioalkyl, alkoxy, amino, amide, halogen, carbocycle, heterocycle, and —CN.

In some embodiments, $R_1$ and $R_2$ in the compound of any one of Formula Ia, Formula Ib, Formula IIa, and Formula IIb or stereoisomer, tautomer, pharmaceutically acceptable salt, or hydrate thereof, are independently selected from hydrogen, deuterium, alkyl($C_1$-$C_6$), —$NH_2$, -thioalkyl($C_1$-$C_6$), alkoxy($C_1$-$C_6$), amino, and amide.

In some embodiments, $R_1$ and $R_2$ are hydrogen.

In some embodiments, at least one of $R_1$, $R_2$, and $R_3$ in the compound of any one of Formula Ia, Formula Ib, Formula IIa, and Formula IIb or stereoisomer, tautomer, pharmaceutically acceptable salt, or hydrate thereof, is not hydrogen.

In some embodiments, $R_4$ in the compound of any one of Formula Ia, Formula Ib, Formula IIa, and Formula IIb or stereoisomer, tautomer, pharmaceutically acceptable salt, or hydrate thereof, is selected from 5-6 membered carbocycles and heterocycles.

In some embodiments, $R_4$ in the compound of any one of Formula Ia, Formula Ib, Formula IIa, and Formula IIb or stereoisomer, tautomer, pharmaceutically acceptable salt, or hydrate thereof, is selected from 5-6 membered heterocycles.

In some embodiments, $R_4$ in the compound of any one of Formula Ia, Formula Ib, Formula IIa, and Formula IIb or stereoisomer, tautomer, pharmaceutically acceptable salt, or hydrate thereof, is selected from 5-6 membered heterocycles containing 1 or 2 nitrogens, such as unsubstituted and substituted pyrimidyl rings, which are optionally substituted with groups independently selected from hydrogen, deuterium, alkyl($C_1$-$C_4$)(such as methyl, ethyl, propyl, isopropyl, butyl), alkoxy($C_1$-$C_4$) (such as methoxy, ethoxy, isopropoxy), amino (such as —$NH_2$, —NHMe, —NHEt, —NHiPr, —NHBu —$NMe_2$, NMeEt, —$NEt_2$, —NEtBu, —NHC(O)NHalkyl), halogen (such as F, Cl), amide (such as —NHC(O)Me, —NHC(O)Et, —C(O)NHMe, —C(O)$NEt_2$, —C(O)NiPr), —$CF_3$, CN, —$N_3$, ketone ($C_1$-$C_4$) (such as acetyl, —C(O)Et, —C(O)Pr), —S(O)Alkyl($C_1$-$C_4$) (such as —S(O)Me, —S(O)Et), —$SO_2$alkyl($C_1$-$C_4$) (such as —$SO_2$Me, —$SO_2$Et, —$SO_2$Pr), -thioalkyl($C_1$-$C_4$) (such as —SMe, —SEt, —SPr, —SBu), carboxyl (such as —COOH), and/or ester (such as —C(O)OMe, —C(O)OEt, —C(O)OBu), each of which may be optionally substituted with hydrogen, F, Cl, Br, —OH, —$NH_2$, —NHMe, —OMe, —SMe, oxo, and/or thio-oxo.

In some embodiments, $R_4$ in the compound of any one of Formula Ia, Formula Ib, Formula IIa, and Formula IIb or stereoisomer, tautomer, pharmaceutically acceptable salt, or hydrate thereof, is selected from 6-membered heterocycles containing at least one nitrogen, such as unsubstituted and substituted pyridyl rings, which are optionally substituted with groups independently selected from hydrogen, deuterium, alkyl($C_1$-$C_4$)(such as methyl, ethyl, propyl, isopropyl, butyl), alkoxy($C_1$-$C_4$) (such as methoxy, ethoxy, isopropoxy), amino (such as —$NH_2$, —NHMe, —NHEt, —NHiPr, —NHBu —$NMe_2$, NMeEt, —$NEt_2$, —NEtBu, —NHC(O)NHalkyl), halogen (such as F, Cl), amide (such as —NHC(O)Me, —NHC(O)Et, —C(O)NHMe, —C(O)$NEt_2$, —C(O)NiPr), —$CF_3$, CN, —$N_3$, ketone ($C_1$-$C_4$) (such as acetyl, —C(O)Et, —C(O)Pr), —S(O)Alkyl($C_1$-$C_4$) (such as —S(O)Me, —S(O)Et), —$SO_2$alkyl($C_1$-$C_4$) (such as —$SO_2$Me, —$SO_2$Et, —$SO_2$Pr), -thioalkyl($C_1$-$C_4$) (such as —SMe, —SEt, —SPr, —SBu), carboxyl (such as —COOH), and/or ester (such as —C(O)OMe, —C(O)OEt, —C(O)OBu), each of which may be optionally substituted with hydrogen, F, Cl, Br, —OH, —$NH_2$, —NHMe, —OMe, —SMe, oxo, and/or thio-oxo.

In some embodiments, $R_4$ in the compound of any one of Formula I, Formula Ia, or Formula II or stereoisomer, tautomer, pharmaceutically acceptable salt, or hydrate thereof, is selected from

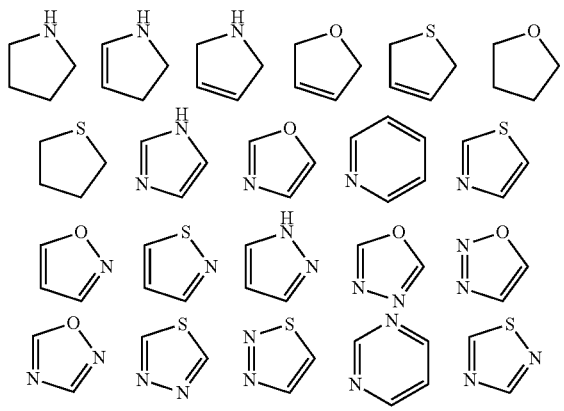

-continued

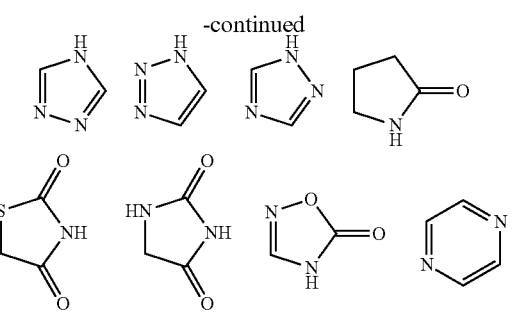

In some embodiments, $R_4$ in the compound of any one of Formula Ia, Formula Ib, Formula IIa, and Formula IIb or stereoisomer, tautomer, pharmaceutically acceptable salt, or hydrate thereof, is an isoxazole or pyrazole optionally substituted with groups independently selected from hydrogen, deuterium, alkyl($C_1$-$C_4$)(such as methyl, ethyl, propyl, isopropyl, butyl), alkoxy($C_1$-$C_4$) (such as methoxy, ethoxy, isopropoxy), amino (such as —$NH_2$, —NHMe, —NHEt, —NHiPr, —NHBu —$NMe_2$, NMeEt, —$NEt_2$, —NEtBu, —NHC(O)NHalkyl), halogen (such as F, Cl), amide (such as —NHC(O)Me, —NHC(O)Et, —C(O)NHMe, —C(O)$NEt_2$, —C(O)NiPr), —$CF_3$, CN, —$N_3$, ketone ($C_1$-$C_4$) (such as acetyl, —C(O)Et, —C(O)Pr), —S(O)Alkyl($C_1$-$C_4$) (such as —S(O)Me, —S(O)Et), —$SO_2$alkyl($C_1$-$C_4$) (such as —$SO_2$Me, —$SO_2$Et, —$SO_2$Pr), -thioalkyl($C_1$-$C_4$) (such as —SMe, —SEt, —SPr, —SBu), carboxyl (such as —COOH), and/or ester (such as —C(O)OMe, —C(O)OEt, —C(O)OBu), each of which may be optionally substituted with hydrogen, F, Cl, Br, —OH, —$NH_2$, —NHMe, —OMe, —SMe, oxo, and/or thio-oxo.

In some embodiments, $R_4$ in the compound of any one of Formula Ia, Formula Ib, Formula IIa, and Formula IIb or stereoisomer, tautomer, pharmaceutically acceptable salt, or hydrate thereof, is selected from a 5-membered heterocycle containing one or two nitrogens.

In some embodiments, $R_4$ in the compound of any one of Formula Ia, Formula Ib, Formula IIa, and Formula IIb or stereoisomer, tautomer, pharmaceutically acceptable salt, or hydrate thereof, is selected from 5-6 membered carbocycles, such as a phenyl ring optionally substituted with groups independently selected from hydrogen, deuterium, alkyl($C_1$-$C_4$)(such as methyl, ethyl, propyl, isopropyl, butyl), alkoxy($C_1$-$C_4$) (such as methoxy, ethoxy, isopropoxy), amino (such as —$NH_2$, —NHMe, —NHEt, —NHiPr, —NHBu —$NMe_2$, NMeEt, —$NEt_2$, —NEtBu, —NHC(O)NHalkyl), halogen (such as F, Cl), amide (such as —NHC(O)Me, —NHC(O)Et, —C(O)NHMe, —C(O)$NEt_2$, —C(O)NiPr), —$CF_3$, CN, —$N_3$, ketone ($C_1$-$C_4$) (such as acetyl, —C(O)Et, —C(O)Pr), —S(O)Alkyl($C_1$-$C_4$) (such as —S(O)Me, —S(O)Et), —$SO_2$alkyl($C_1$-$C_4$) (such as —$SO_2$Me, —$SO_2$Et, —$SO_2$Pr), -thioalkyl($C_1$-$C_4$) (such as —SMe, —SEt, —SPr, —SBu), carboxyl (such as —COOH), and/or ester (such as —C(O)OMe, —C(O)OEt, —C(O)OBu), each of which may be optionally substituted with hydrogen, F, Cl, Br, —OH, —$NH_2$, —NHMe, —OMe, —SMe, oxo, and/or thio-oxo.

In some embodiments, $R_4$ in the compound of any one of Formula Ia, Formula Ib, Formula IIa, and Formula IIb or stereoisomer, tautomer, pharmaceutically acceptable salt, or hydrate thereof, is a phenyl ring optionally substituted with groups independently selected from hydrogen, deuterium, alkyl($C_1$-$C_4$)(such as methyl, ethyl, propyl, isopropyl, butyl), alkoxy($C_1$-$C_4$) (such as methoxy, ethoxy, isopropoxy), amino (such as —$NH_2$, —NHMe, —NHEt, —NHiPr, —NHBu —NMe$_2$, NMeEt, —NEt$_2$, —NEtBu, —NHC(O)NHalkyl), halogen (such as F, Cl), amide (such as —NHC(O)Me, —NHC(O)Et, —C(O)NHMe, —C(O)NEt$_2$, —C(O)NiPr), —CF$_3$, CN, —N$_3$, ketone (C$_1$-C$_4$) (such as acetyl, —C(O)Et, —C(O)Pr), —S(O)Alkyl(C$_1$-C$_4$) (such as —S(O)Me, —S(O)Et), —SO$_2$alkyl(C$_1$-C$_4$) (such as —SO$_2$Me, —SO$_2$Et, —SO$_2$Pr), -thioalkyl(C$_1$-C$_4$) (such as —SMe, —SEt, —SPr, —SBu), carboxyl (such as —COOH), and/or ester (such as —C(O)OMe, —C(O)OEt, —C(O)OBu), each of which may be optionally substituted with hydrogen, F, Cl, Br, —OH, —NH$_2$, —NHMe, —OMe, —SMe, oxo, and/or thio-oxo.

In some embodiments, R$_4$ in the compound of any one of Formula Ia, Formula Ib, Formula IIa, and Formula IIb or stereoisomer, tautomer, pharmaceutically acceptable salt, or hydrate thereof, is selected from an aryl optionally substituted with groups independently selected from hydrogen, deuterium, alkyl(C$_1$-C$_4$)(such as methyl, ethyl, propyl, isopropyl, butyl), alkoxy(C$_1$-C$_4$) (such as methoxy, ethoxy, isopropoxy), amino (such as —NH$_2$, —NHMe, —NHEt, —NHiPr, —NHBu —NMe$_2$, NMeEt, —NEt$_2$, —NEtBu, —NHC(O)NHalkyl), halogen (such as F, Cl), amide (such as —NHC(O)Me, —NHC(O)Et, —C(O)NHMe, —C(O)NEt$_2$, —C(O)NiPr), —CF$_3$, CN, —N$_3$, ketone (C$_1$-C$_4$) (such as acetyl, —C(O)Et, —C(O)Pr), —S(O)Alkyl(C$_1$-C$_4$) (such as —S(O)Me, —S(O)Et), —SO$_2$alkyl(C$_1$-C$_4$) (such as —SO$_2$Me, —SO$_2$Et, —SO$_2$Pr), -thioalkyl(C$_1$-C$_4$) (such as —SMe, —SEt, —SPr, —SBu), carboxyl (such as —COOH), and/or ester (such as —C(O)OMe, —C(O)OEt, —C(O)OBu), each of which may be optionally substituted with hydrogen, F, Cl, Br, —OH, —NH$_2$, —NHMe, —OMe, —SMe, oxo, and/or thio-oxo.

In some embodiments, in the compound of any one of Formula Ia, Formula Ib, Formula IIa, and Formula IIb or stereoisomer, tautomer, pharmaceutically acceptable salt, or hydrate thereof, —X—R$_4$ is selected from —CH$_2$Aryl.

In some embodiments, R$_4$ in the compound of any one of Formula Ia, Formula Ib, Formula IIa, and Formula IIb or stereoisomer, tautomer, pharmaceutically acceptable salt, or hydrate thereof, is selected from a pyridyl optionally substituted with groups independently selected from hydrogen, deuterium, alkyl(C$_1$-C$_4$)(such as methyl, ethyl, propyl, isopropyl, butyl), alkoxy(C$_1$-C$_4$) (such as methoxy, ethoxy, isopropoxy), amino (such as —NH$_2$, —NHMe, —NHEt, —NHiPr, —NHBu —NMe$_2$, NMeEt, —NEt$_2$, —NEtBu, —NHC(O)NHalkyl), halogen (such as F, Cl), amide (such as —NHC(O)Me, —NHC(O)Et, —C(O)NHMe, —C(O)NEt$_2$, —C(O)NiPr), —CF$_3$, CN, —N$_3$, ketone (C$_1$-C$_4$) (such as acetyl, —C(O)Et, —C(O)Pr), —S(O)Alkyl(C$_1$-C$_4$) (such as —S(O)Me, —S(O)Et), —SO$_2$alkyl(C$_1$-C$_4$) (such as —SO$_2$Me, —SO$_2$Et, —SO$_2$Pr), -thioalkyl(C$_1$-C$_4$) (such as —SMe, —SEt, —SPr, —SBu), carboxyl (such as —COOH), and/or ester (such as —C(O)OMe, —C(O)OEt, —C(O)OBu), each of which may be optionally substituted with hydrogen, F, Cl, Br, —OH, —NH$_2$, —NHMe, —OMe, —SMe, oxo, and/or thio-oxo.

In some embodiments, R$_4$ in the compound of any one of Formula Ia, Formula Ib, Formula IIa, and Formula IIb or stereoisomer, tautomer, pharmaceutically acceptable salt, or hydrate thereof, is optionally substituted with groups independently selected from hydrogen, deuterium, alkyl(C$_1$-C$_4$) (such as methyl, ethyl, propyl, isopropyl, butyl), alkoxy(C$_1$-C$_4$) (such as methoxy, ethoxy, isopropoxy), amino (such as —NH$_2$, —NHMe, —NHEt, —NHiPr, —NHBu —NMe$_2$, NMeEt, —NEt$_2$, —NEtBu, —NHC(O)NHalkyl), halogen (such as F, Cl), amide (such as —NHC(O)Me, —NHC(O)Et, —C(O)NHMe, —C(O)NEt$_2$, —C(O)NiPr), —CF$_3$, CN, —N$_3$, ketone (C$_1$-C$_4$) (such as acetyl, —C(O)Et, —C(O)Pr), —S(O)Alkyl(C$_1$-C$_4$) (such as —S(O)Me, —S(O)Et), —SO$_2$alkyl(C$_1$-C$_4$) (such as —SO$_2$Me, —SO$_2$Et, —SO$_2$Pr), -thioalkyl(C$_1$-C$_4$) (such as —SMe, —SEt, —SPr, —SBu), carboxyl (such as —COOH), and/or ester (such as —C(O)OMe, —C(O)OEt, —C(O)OBu), each of which may be optionally substituted with hydrogen, F, Cl, Br, —OH, —NH$_2$, —NHMe, —OMe, —SMe, oxo, and/or thio-oxo.

In some embodiments, R$_4$ in the compound of any one of Formula Ia, Formula Ib, Formula IIa, and Formula IIb or stereoisomer, tautomer, pharmaceutically acceptable salt, or hydrate thereof, is selected from 5-6 membered carbocycles.

In some embodiments, R$_4$ in the compound of any one of Formula Ia, Formula Ib, Formula IIa, and Formula IIb or stereoisomer, tautomer, pharmaceutically acceptable salt, or hydrate thereof, is selected from a small cycloalkyl(C$_3$-C$_6$) and phenyl ring optionally substituted with one or more groups independently selected from deuterium, alkyl(C$_1$-C$_4$) (such as methyl, ethyl, propyl, isopropyl, and butyl), alkoxy (C$_1$-C$_4$) (such as methoxy, ethoxy, and isopropoxy), halogen (such as F and Cl), —CF$_3$, CN, and -thioalkyl(C$_1$-C$_4$) (such as, e.g., —SMe, —SEt, —SPr, and -Sbu), wherein each alkyl, alkoxy, and thioalkyl may be optionally substituted with F, Cl, or Br.

In some embodiments, R$_4$ in the compound of any one of Formula Ia, Formula Ib, Formula IIa, and Formula IIb or stereoisomer, tautomer, pharmaceutically acceptable salt, or hydrate thereof, is a phenyl ring optionally substituted with one or more groups independently selected from deuterium, alkyl(C$_1$-C$_4$) (such as methyl, ethyl, propyl, isopropyl, and butyl), alkoxy(C$_1$-C$_4$) (such as methoxy, ethoxy, and isopropoxy), halogen (such as F and Cl), —CF$_3$, CN, and -thioalkyl(C$_1$-C$_4$) (such as, e.g., —SMe, —SEt, —SPr, and -Sbu), wherein each alkyl, alkoxy, and thioalkyl may be optionally substituted with F, Cl, or Br.

In some embodiments, R$_4$ in the compound of any one of Formula Ia, Formula Ib, Formula IIa, and Formula IIb or stereoisomer, tautomer, pharmaceutically acceptable salt, or hydrate thereof, is an aryl optionally substituted with one or more groups independently selected from deuterium, alkyl (C$_1$-C$_4$) (such as methyl, ethyl, propyl, isopropyl, and butyl), alkoxy(C$_1$-C$_4$) (such as methoxy, ethoxy, and isopropoxy), halogen (such as F and Cl), —CF$_3$, CN, and -thioalkyl(C$_1$-C$_4$) (such as, e.g., —SMe, —SEt, —SPr, and -Sbu), wherein each alkyl, alkoxy, and thioalkyl may be optionally substituted with F, Cl, or Br.

In some embodiments, in the compound of any one of Formula Ia, Formula Ib, Formula IIa, and Formula IIb or stereoisomer, tautomer, pharmaceutically acceptable salt, or hydrate thereof, the A-B bicyclic ring, is selected from

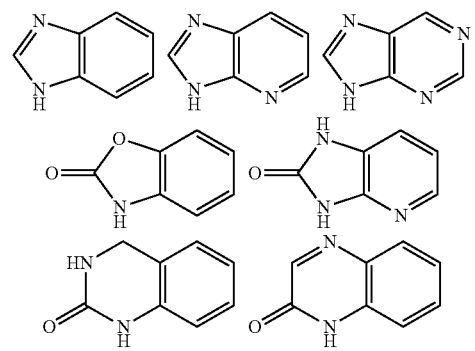

which may be optionally substituted with groups independently selected from hydrogen, deuterium, —NH$_2$, amino (such as —NH(C$_1$-C$_5$), —N(C$_1$-C$_5$)$_2$, —NHPh, —NHBn, —NHpyridyl, —NHheterocycle(C$_4$-C$_7$), —NHcarbocycle (C$_4$-C$_7$)), heterocycle(C$_4$-C$_7$), carbocycle(C$_4$-C$_7$), halogen, —CN, —OH, —CF$_3$, sulfone, sulfoxide, alkyl(C$_1$-C$_6$), thioalkyl(C$_1$-C$_6$), Alkenyl(C$_1$-C$_6$), alkoxy(C$_1$-C$_6$), ketone(C$_1$-C$_6$), ester, urea, carboxylic acid, carbamate, amide(C$_1$-C$_6$), oxo, and thio-oxo;

D$_1$ is

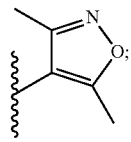 [SMILES: *c1c(C)noc1C]

X is selected from —CH$_2$— and —C(O)—;

R$_4$ is a phenyl ring optionally substituted with groups independently selected from hydrogen, deuterium, alkyl(C$_1$-C$_4$)(such as methyl, ethyl, propyl, isopropyl, butyl), alkoxy (C$_1$-C$_4$) (such as methoxy, ethoxy, isopropoxy), amino (such as —NH$_2$, —NHMe, —NHEt, —NHiPr, —NHBu —NMe$_2$, NMeEt, —NEt$_2$, —NEtBu, —NHC(O)NHalkyl), halogen (such as F, Cl), amide (such as —NHC(O)Me, —NHC(O)Et, —C(O)NHMe, —C(O)NEt$_2$, —C(O)NiPr), —CF$_3$, CN, —N$_3$, ketone (C$_1$-C$_4$) (such as acetyl, —C(O)Et, —C(O)Pr), —S(O)Alkyl(C$_1$-C$_4$) (such as —S(O)Me, —S(O)Et), —SO$_2$alkyl(C$_1$-C$_4$) (such as —SO$_2$Me, —SO$_2$Et, —SO$_2$Pr), -thioalkyl(C$_1$-C$_4$) (such as —SMe, —SEt, —SPr, —SBu), carboxyl (such as —COOH), and/or ester (such as —C(O)OMe, —C(O)OEt, —C(O)OBu), each of which may be optionally substituted with hydrogen, F, Cl, Br, —OH, —NH$_2$, —NHMe, —OMe, —SMe, oxo, and/or thio-oxo.

In some embodiments, in the compound of any one of Formula Ia, Formula Ib, Formula IIa, and Formula IIb or stereoisomer, tautomer, pharmaceutically acceptable salt, or hydrate thereof, the A-B bicyclic ring, is selected from

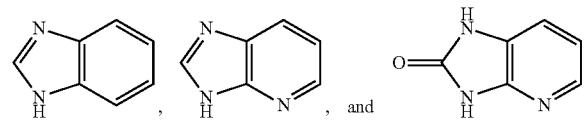

which may be optionally substituted with groups independently selected from hydrogen, deuterium, —NH$_2$, amino (such as —NH(C$_1$-C$_5$), —N(C$_1$-C$_5$)$_2$, —NHPh, —NHBn, —NHpyridyl, —NHheterocycle(C$_4$-C$_7$), —NHcarbocycle (C$_4$-C$_7$)), heterocycle(C$_4$-C$_7$), carbocycle(C$_4$-C$_7$), halogen, —CN, —OH, —CF$_3$, sulfone, sulfoxide, sulfonamide, alkyl (C$_1$-C$_6$), thioalkyl(C$_1$-C$_6$), alkenyl(C$_1$-C$_6$), alkoxy(C$_1$-C$_6$), ketone(C$_1$-C$_6$), ester, urea, carboxylic acid, carbamate, amide(C$_1$-C$_6$), oxo, and thio-oxo.

D$_1$ is

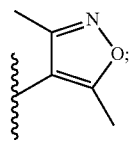

X is selected from —CH$_2$—, —CH(CH$_3$)—, —CH(OH)—, and —NH—;

R$_4$ is a phenyl ring optionally substituted with groups independently selected from hydrogen, deuterium, alkyl(C$_1$-C$_4$)(such as methyl, ethyl, propyl, isopropyl, butyl), alkoxy (C$_1$-C$_4$) (such as methoxy, ethoxy, isopropoxy), amino (such as —NH$_2$, —NHMe, —NHEt, —NHiPr, —NHBu —NMe$_2$, NMeEt, —NEt$_2$, —NEtBu, —NHC(O)NHalkyl), halogen (such as F, Cl), amide (such as —NHC(O)Me, —NHC(O)Et, —C(O)NHMe, —C(O)NEt$_2$, —C(O)NiPr), —CF$_3$, CN, —N$_3$, ketone (C$_1$-C$_4$) (such as acetyl, —C(O)Et, —C(O)Pr), —S(O)Alkyl(C$_1$-C$_4$) (such as —S(O)Me, —S(O)Et), —SO$_2$alkyl(C$_1$-C$_4$) (such as —SO$_2$Me, —SO$_2$Et, —SO$_2$Pr), -thioalkyl(C$_1$-C$_4$) (such as —SMe, —SEt, —SPr, —SBu), carboxyl (such as —COOH), and/or ester (such as —C(O)OMe, —C(O)OEt, —C(O)OBu), each of which may be optionally substituted with hydrogen, F, Cl, Br, —OH, —NH$_2$, —NHMe, —OMe, —SMe, oxo, and/or thio-oxo.

In some embodiments, —X—R$_4$ in the compound of any one of Formula Ia, Formula Ib, Formula IIa, and Formula IIb or stereoisomer, tautomer, pharmaceutically acceptable salt, or hydrate thereof, is —CH$_2$Aryl.

In some embodiments, in the compound of any one of Formula Ia, Formula Ib, Formula IIa, and Formula IIb or stereoisomer, tautomer, pharmaceutically acceptable salt, or hydrate thereof, the A-B bicyclic ring is selected from

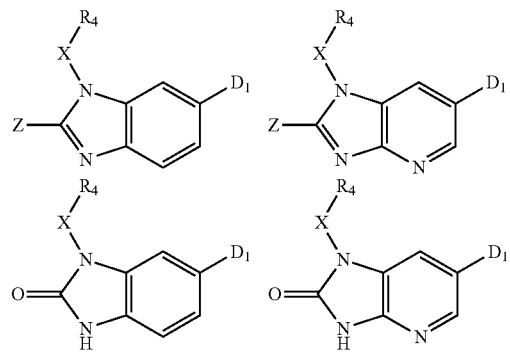

wherein Z is selected from hydrogen, deuterium, —NH$_2$, amino (such as —NH(C$_1$-C$_5$), —N(C$_1$-C$_5$)$_2$, —NHPh, —NHBn, —NHpyridyl, —NHheterocycle(C$_4$-C$_6$), —NHcarbocycle(C$_4$-C$_6$)), alkyl(C$_1$-C$_6$), thioalkyl(C$_1$-C$_6$), alkenyl(C$_1$-C$_6$), and alkoxy(C$_1$-C$_6$), carboxyl;

D$_1$ is

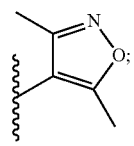

and

X is selected from —CH$_2$— and —CH(CH$_3$)—; and

R$_4$ is a phenyl ring optionally substituted with groups independently selected with one or more groups independently selected from deuterium, alkyl(C$_1$-C$_4$), alkoxy(C$_1$-C$_4$), halogen, —CF$_3$, CN, and -thioalkyl(C$_1$-C$_4$), wherein each alkyl, alkoxy, and thioalkyl may be optionally substituted with F, Cl, or Br.

In some embodiments, in the compound of any one of Formula Ia, Formula Ib, Formula IIa, and Formula IIb or stereoisomer, tautomer, pharmaceutically acceptable salt, or hydrate thereof, the A-B bicyclic ring is selected from

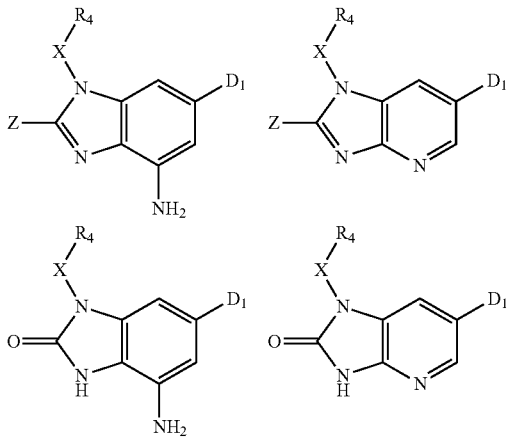

wherein Z is selected from hydrogen, deuterium, —NH$_2$, amino (such as —NH(C$_1$-C$_5$), —N(C$_1$-C$_5$)$_2$, —NHPh, —NHBn, —NHpyridyl, —NHheterocycle(C$_4$-C$_6$), —NHcarbocycle(C$_4$-C$_6$)), alkyl(C$_1$-C$_6$), thioalkyl(C$_1$-C$_6$), alkenyl(C$_1$-C$_6$), and alkoxy(C$_1$-C$_6$); carboxyl;

D$_1$ is

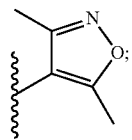

X is selected from —CH$_2$— and —CH(CH$_3$)—; and

R$_4$ is a phenyl ring optionally substituted with one or more groups independently selected from deuterium, alkyl(C$_1$-C$_4$) (such as methyl, ethyl, propyl, isopropyl, and butyl), alkoxy (C$_1$-C$_4$) (such as methoxy, ethoxy, and isopropoxy), halogen (such as F and Cl), —CF$_3$, CN, and -thioalkyl(C$_1$-C$_4$) (such as, e.g., —SMe, —SEt, —SPr, and -Sbu), wherein each alkyl, alkoxy, and thioalkyl may be optionally substituted with F, Cl, or Br.

In certain embodiments of the invention, the compound of Formula I, Formula Ia, or Formula II is selected from:
9-Benzyl-2-(3,5-dimethylisoxazol-4-yl)-9H-purin-6-amine;
3-Benzyl-5-(3,5-dimethylisoxazol-4-yl)-1H-imidazo[4,5-b]pyridin-2(3H)-one;
1-Benzyl-5-(3,5-dimethylisoxazol-4-yl)-1H-imidazo[4,5-b]pyridin-2(3H)-one;
4-(3-Benzyl-3H-imidazo[4,5-b]pyridin-6-yl)-3,5-dimethylisoxazole;
4-(1-Benzyl-1H-imidazo[4,5-b]pyridin-6-yl)-3,5-dimethylisoxazole;
3-Benzyl-5-(3,5-dimethylisoxazol-4-yl)benzo[d]oxazol-2(3H)-one;
1-Benzyl-6-(3,5-dimethylisoxazol-4-yl)-1H-benzo[d]imidazol-4-amine;
1-Benzyl-5-(3,5-dimethylisoxazol-4-yl)-1H-benzo[d]imidazol-7-amine;
N,1-Dibenzyl-6-(3,5-dimethylisoxazol-4-yl)-1H-benzo[d]imidazol-4-amine;
1-Benzyl-6-(3,5-dimethylisoxazol-4-yl)-1H-imidazo[4,5-b]pyridin-2(3H)-one;
1-Benzyl-7-(3,5-dimethylisoxazol-4-yl)quinoxalin-2(1H)-one; and
1-Benzyl-7-(3,5-dimethylisoxazol-4-yl)-3,4-dihydroquinazolin-2(1H)-one.

In certain embodiments of the invention, the compound of Formula I, Formula Ia, or Formula II is selected from:
9-benzyl-2-(3,5-dimethylisoxazol-4-yl)-9H-purin-6-amine;
3-benzyl-5-(3,5-dimethylisoxazol-4-yl)-1H-imidazo[4,5-b]pyridin-2(3H)-one;
1-benzyl-5-(3,5-dimethylisoxazol-4-yl)-1H-imidazo[4,5-b]pyridin-2(3H)-one;
4-(3-benzyl-3H-imidazo[4,5-b]pyridin-6-yl)-3,5-dimethylisoxazole;
4-(1-benzyl-1H-imidazo[4,5-b]pyridin-6-yl)-3,5-dimethylisoxazole;
3-benzyl-5-(3,5-dimethylisoxazol-4-yl)benzo[d]oxazol-2(3H)-one;
1-benzyl-6-(3,5-dimethyl isoxazol-4-yl)-1H-benzo[d]imidazol-4-amine;
1-benzyl-5-(3,5-dimethyl isoxazol-4-yl)-1H-benzo[d]imidazol-7-amine;
N,1-dibenzyl-6-(3,5-dimethylisoxazol-4-yl)-1H-benzo[d]imidazol-4-amine;
1-benzyl-6-(3,5-dimethylisoxazol-4-yl)-1H-imidazo[4,5-b]pyridin-2(3H)-one;
1-benzyl-7-(3,5-dimethylisoxazol-4-yl)quinoxalin-2(1H)-one;
1-benzyl-7-(3,5-dimethylisoxazol-4-yl)-3,4-dihydroquinazolin-2(1H)-one;
4-(1-benzyl-2-methyl-1H-imidazo[4,5-b]pyridin-6-yl)-3,5-dimethylisoxazole;
4-(1-(cyclopropylmethyl)-2-methyl-4-nitro-1H-benzo[d]imidazol-6-yl)-3,5-dimethyl isoxazole;
1-benzyl-6-(3,5-dimethyl isoxazol-4-yl)-4-nitro-1H-benzo[d]imidazol-2(3H)-one;
4-amino-1-benzyl-6-(3,5-dimethylisoxazol-4-yl)-1H-benzo[d]imidazol-2(3H)-one;
1-benzyl-6-(3,5-dimethylisoxazol-4-yl)-2-ethoxy-1H-benzo[d]imidazol-4-amine;
1-benzyl-6-(3,5-dimethylisoxazol-4-yl)-N-ethyl-4-nitro-1H-benzo[d]imidazol-2-amine;
1-benzyl-6-(3,5-dimethylisoxazol-4-yl)-N2-ethyl-1H-benzo[d]imidazole-2,4-diamine;
methyl 1-benzyl-6-(3,5-dimethylisoxazol-4-yl)-2-oxo-2,3-dihydro-1H-benzo[d]imidazole-4-carboxylate;
1-benzyl-6-(3,5-dimethylisoxazol-4-yl)-2-oxo-2,3-dihydro-1H-benzo[d]imidazole-4-carboxamide
4-(aminomethyl)-1-benzyl-6-(3,5-dimethylisoxazol-4-yl)-1H-benzo[d]imidazol-2(3H)-one
5-(3,5-dimethylisoxazol-4-yl)-N-phenyl-1H-pyrrolo[3,2-b]pyridin-3-amine
6-(3,5-dimethylisoxazol-4-yl)-1-(4-fluorobenzyl)-3-methyl-1H-pyrazolo[4,3-b]pyridine 4-oxide
6-(3,5-dimethylisoxazol-4-yl)-1-(4-fluorobenzyl)-3-methyl-1H-pyrazolo[4,3-b]pyridin-5(4H)-one
4-(3-benzyl-3H-imidazo[4,5-b]pyridin-5-yl)-3,5-dimethylisoxazole
6-(3,5-dimethylisoxazol-4-yl)-1-(4-fluorobenzyl)-1H-benzo[d]imidazol-4-amine
6-(3,5-dimethylisoxazol-4-yl)-1-(4-fluorobenzyl)-N-methyl-1H-benzo[d]imidazol-4-amine
6-(3,5-dimethylisoxazol-4-yl)-1-(4-fluorobenzyl)-N,N-dimethyl-1H-benzo[d]imidazol-4-amine
3,5-dimethyl-4-(1-(1-phenylethyl)-1H-imidazo[4,5-b]pyridin-6-yl)isoxazole
4-(1-benzyl-1H-imidazo[4,5-c]pyridin-6-yl)-3,5-dimethylisoxazole 1-benzyl-6-(3,5-dimethylisoxazol-4-yl)-1H-imidazo[4,5-c]pyridine 5-oxide
1-benzyl-6-(3,5-dimethylisoxazol-4-yl)-1H-imidazo[4,5-c]pyridin-4-amine
4-(1-benzyl-3-bromo-1H-pyrrolo[3,2-b]pyridin-6-yl)-3,5-dimethylisoxazole
1-benzyl-6-(3,5-dimethylisoxazol-4-yl)-1H-pyrrolo[3,2-b]pyridine-3-carbaldehyde
1-(1-benzyl-6-(3,5-dimethylisoxazol-4-yl)-1H-pyrrolo[3,2-b]pyridin-3-yl)ethanone
1-benzyl-6-(3,5-dimethylisoxazol-4-yl)-1H-pyrrolo[3,2-b]pyridin-5-yl formate
4-((6-(3,5-dimethyl isoxazol-4-yl)-2-methyl-1H-imidazo[4,5-b]pyridin-1-yl)methyl)benzamide
4-(1-benzyl-3-nitro-1H-pyrrolo[3,2-b]pyridin-6-yl)-3,5-dimethylisoxazole
3,5-dimethyl-4-(3-(4-(trifluoromethyl)benzyl)-3H-imidazo[4,5-b]pyridin-6-yl)isoxazole
3,5-dimethyl-4-(1-(4-(trifluoromethyl)benzyl)-1H-imidazo[4,5-b]pyridin-6-yl)isoxazole
4-(3-(4-chlorobenzyl)-3H-imidazo[4,5-b]pyridin-6-yl)-3,5-dimethyl isoxazole
4-(1-(4-chlorobenzyl)-1H-imidazo[4,5-b]pyridin-6-yl)-3,5-dimethyl isoxazole
4-(3-(4-fluorobenzyl)-3H-imidazo[4,5-b]pyridin-6-yl)-3,5-dimethylisoxazole
4-(1-(4-fluorobenzyl)-1H-imidazo[4,5-b]pyridin-6-yl)-3,5-dimethylisoxazole
3,5-dimethyl-4-(3-(pyridin-2-ylmethyl)-3H-imidazo[4,5-b]pyridin-6-yl)isoxazole
3,5-dimethyl-4-(1-(pyridin-2-ylmethyl)-1H-imidazo[4,5-b]pyridin-6-yl)isoxazole
4-(1-(4-fluorobenzyl)-1H-pyrrolo[3,2-b]pyridin-6-yl)-3,5-dimethyl isoxazole
4-(1-(4-fluorobenzyl)-1H-pyrrolo[2,3-b]pyridin-6-yl)-3,5-dimethyl isoxazole
4-(5-(4-fluorobenzyl)-5H-pyrrolo[2,3-b]pyrazin-3-yl)-3,5-dimethylisoxazole
4-(1-(4-fluorobenzyl)-1H-pyrazolo[4,3-b]pyridin-6-yl)-3,5-dimethylisoxazole
6-(3,5-dimethylisoxazol-4-yl)-1-(4-fluorobenzyl)-1H-pyrrolo[2,3-b]pyridin-4-amine
4-(1-(4-fluorobenzyl)-3-methyl-1H-pyrazolo[4,3-b]pyridin-6-yl)-3,5-dimethylisoxazole
1-benzyl-6-(3,5-dimethyl isoxazol-4-yl)-1H-indazol-4-amine
1-benzyl-6-(3,5-dimethylisoxazol-4-yl)-2-methyl-1H-benzo[d]imidazol-4-amine
1-benzyl-6-(3,5-dimethylisoxazol-4-yl)-1H-pyrrolo[3,2-b]pyridin-5(4H)-one
3-((5-(3,5-dimethylisoxazol-4-yl)-1H-pyrrolo[3,2-b]pyridin-3-yl)amino)benzonitrile
4-(1-(4-fluorobenzyl)-2-methyl-1H-imidazo[4,5-b]pyridin-6-yl)-3,5-dimethyl isoxazole
4-(1-benzyl-2-ethoxy-1H-imidazo[4,5-b]pyridin-6-yl)-3,5-dimethyl isoxazole
4-((6-(3,5-dimethylisoxazol-4-yl)-2-methyl-1H-imidazo[4,5-b]pyridin-1-yl)methyl)-3,5-dimethylisoxazole
4-(1-(2,4-dichlorobenzyl)-2-methyl-1H-imidazo[4,5-b]pyridin-6-yl)-3,5-dimethylisoxazole
4-(1-(4-methoxybenzyl)-2-methyl-1H-imidazo[4,5-b]pyridin-6-yl)-3,5-dimethyl isoxazole
4-(1-(cyclopropylmethyl)-2-methyl-1H-imidazo[4,5-b]pyridin-6-yl)-3,5-dimethylisoxazole
N-(1-benzyl-6-(3,5-dimethylisoxazol-4-yl)-2-methyl-1H-benzo[d]imidazol-4-yl)acetamide
N-(1-benzyl-6-(3,5-dimethylisoxazol-4-yl)-2-methyl-1H-benzo[d]imidazol-4-yl)ethanesulfonamide
4-(1-benzyl-4-methoxy-2-methyl-1H-benzo[d]imidazol-6-yl)-3,5-dimethylisoxazole
7-amino-3-benzyl-5-(3,5-dimethylisoxazol-4-yl)benzo[d]oxazol-2(3H)-one
3,5-dimethyl-4-(2-methyl-1-(pyridin-3-ylmethyl)-1H-imidazo[4,5-b]pyridin-6-yl)isoxazole
3,5-dimethyl-4-(2-methyl-1-(thiophen-2-ylmethyl)-1H-imidazo[4,5-b]pyridin-6-yl)isoxazole
4-((6-(3,5-dimethylisoxazol-4-yl)-2-methyl-1H-imidazo[4,5-b]pyridin-1-yl)methyl)benzonitrile
4-(1-benzyl-1H-pyrrolo[3,2-b]pyridin-6-yl)-3,5-dimethyl-isoxazole
1-(1-benzyl-6-(3,5-dimethylisoxazol-4-yl)-1H-pyrrolo[3,2-b]pyridin-3-yl)-N,N-dimethylmethanamine
1-benzyl-6-(3,5-dimethylisoxazol-4-yl)-1H-pyrrolo[2,3-b]pyridin-4-amine
3,5-dimethyl-4-(2-methyl-1-(pyridin-4-ylmethyl)-1H-imidazo[4,5-b]pyridin-6-yl)isoxazole
1-(cyclopropylmethyl)-6-(3,5-dimethylisoxazol-4-yl)-2-methyl-1H-benzo[d]imidazol-4-amine
3,5-dimethyl-4-(2-methyl-1-((5-methylthiophen-2-yl)methyl)-1H-imidazo[4,5-b]pyridin-6-yl)isoxazole
4-(1-((5-chlorothiophen-2-yl)methyl)-2-methyl-1H-imidazo[4,5-b]pyridin-6-yl)-3,5-dimethylisoxazole
5-((6-(3,5-dimethylisoxazol-4-yl)-2-methyl-1H-imidazo[4,5-b]pyridin-1-yl)methyl)thiophene-2-carbonitrile
6-(3,5-dimethylisoxazol-4-yl)-1-(4-fluorobenzyl)-1H-imidazo[4,5-b]pyridine 4-oxide
6-(3,5-dimethylisoxazol-4-yl)-1-(4-fluorobenzyl)-1H-imidazo[4,5-b]pyridin-5-yl acetate
1-benzyl-6-(1,4-dimethyl-1H-pyrazol-5-yl)-2-methyl-4-nitro-1H-benzo[d]imidazole
1-benzyl-6-(1,4-dimethyl-1H-pyrazol-5-yl)-2-methyl-1H-benzo[d]imidazol-4-amine
4-(1-(4-chlorobenzyl)-2-methyl-1H-imidazo[4,5-b]pyridin-6-yl)-3,5-dimethylisoxazole
4-((6-(3,5-dimethylisoxazol-4-yl)-2-methyl-1H-imidazo[4,5-b]pyridin-1-yl)methyl)phenol
1-benzyl-6-(3,5-dimethylisoxazol-4-yl)-2-methyl-1H-benzo[d]imidazole-4-carbonitrile
1-benzyl-6-(3,5-dimethylisoxazol-4-yl)-2-oxo-2,3-dihydro-1H-benzo[d]imidazole-4-carbonitrile
1-benzyl-6-(3,5-dimethylisoxazol-4-yl)-2-morpholino-1H-benzo[d]imidazol-4-amine
1-benzyl-6-(3,5-dimethylisoxazol-4-yl)-1H-pyrrolo[3,2-b]pyridine-3-carbonitrile
4-(1-benzyl-3-chloro-1H-pyrrolo[3,2-b]pyridin-6-yl)-3,5-dimethylisoxazole
4-amino-1-(4-chlorobenzyl)-6-(3,5-dimethylisoxazol-4-yl)-1H-benzo[d]imidazol-2(3H)-one
1-(4-chlorobenzyl)-6-(3,5-dimethylisoxazol-4-yl)-4-nitro-1H-benzo[d]imidazol-2(3H)-one
4-(1-benzyl-1H-pyrazolo[4,3-b]pyridin-6-yl)-3,5-dimethyl-isoxazole
4-(1-(4-chlorobenzyl)-1H-pyrazolo[4,3-b]pyridin-6-yl)-3,5-dimethylisoxazole
1-benzyl-2-methyl-6-(1-methyl-1H-pyrazol-5-yl)-1H-benzo[d]imidazol-4-amine
4-(1-(3,4-dichlorobenzyl)-2-methyl-1H-imidazo[4,5-b]pyridin-6-yl)-3,5-dimethylisoxazole
6-(3,5-dimethylisoxazol-4-yl)-2-methyl-1-(1-phenylethyl)-1H-benzo[d]imidazol-4-amine
2-(azetidin-1-yl)-1-benzyl-6-(3,5-dimethylisoxazol-4-yl)-1H-benzo[d]imidazol-4-amine 3,5-dimethyl-4-(1-(thiophen-3-ylmethyl)-1H-pyrazolo[4,3-b]pyridin-6-yl)isoxazole
N-(1-benzyl-6-(3,5-dimethylisoxazol-4-yl)-1H-pyrrolo[3,2-b]pyridin-3-yl)acetamide
1-benzyl-6-(3,5-dimethylisoxazol-4-yl)-1H-pyrrolo[3,2-b]pyridin-3-amine
1-(3,4-dichlorobenzyl)-6-(3,5-dimethylisoxazol-4-yl)-1H-imidazo[4,5-b]pyridin-2(3H)-one
1-(4-chlorobenzyl)-6-(3,5-dimethylisoxazol-4-yl)-1H-indazol-4-amine
6-(3,5-dimethylisoxazol-4-yl)-1-(4-methoxybenzyl)-4-nitro-1H-benzo[d]imidazol-2(3H)-one
4-amino-6-(3,5-dimethyl isoxazol-4-yl)-1-(4-methoxybenzyl)-1H-benzo[d]imidazol-2(3H)-one
1-(4-chlorobenzyl)-6-(3,5-dimethylisoxazol-4-yl)-1H-imidazo[4,5-b]pyridin-2(3H)-one
6-(3,5-dimethylisoxazol-4-yl)-1-(thiophen-2-ylmethyl)-1H-imidazo[4,5-b]pyridin-2(3H)-one
1-benzyl-6-(3,5-dimethylisoxazol-4-yl)-N-ethyl-1H-imidazo[4,5-b]pyridin-2-amine
3,5-dimethyl-4-(2-methyl-1-(1-phenylethyl)-1H-imidazo[4,5-b]pyridin-6-yl)isoxazole
1-benzyl-6-(3,5-dimethyl isoxazol-4-yl)-N2-(tetrahydro-2H-pyran-4-yl)-1H-benzo[d]imidazole-2,4-diamine
6-(3,5-dimethylisoxazol-4-yl)-4-nitro-1-(1-phenylethyl)-1H-benzo[d]imidazol-2(3H)-one
N-(1-benzyl-6-(3,5-dimethylisoxazol-4-yl)-2-oxo-2,3-dihydro-1H-benzo[d]imidazol-4-yl)acetamide
6-(3,5-dimethylisoxazol-4-yl)-1-(1-phenylethyl)-1H-imidazo[4,5-b]pyridin-2(3H)-one
6-(3,5-dimethylisoxazol-4-yl)-N-ethyl-1-(1-phenylethyl)-1H-imidazo[4,5-b]pyridin-2-amine
4-(1-benzyl-6-(3,5-dimethyl isoxazol-4-yl)-1H-imidazo[4,5-b]pyridin-2-yl)morpholine
4-amino-6-(3,5-dimethyl isoxazol-4-yl)-1-(1-phenylethyl)-1H-benzo[d]imidazol-2(3H)-one
4-(1-(cyclobutylmethyl)-2-methyl-4-nitro-1H-benzo[d]imidazol-6-yl)-3,5-dimethylisoxazole
4-(1-(cyclopentylmethyl)-2-methyl-4-nitro-1H-benzo[d]imidazol-6-yl)-3,5-dimethyl isoxazole
1-(cyclopropylmethyl)-6-(3,5-dimethylisoxazol-4-yl)-1H-imidazo[4,5-b]pyridin-2(3H)-one
N-(1-benzyl-6-(3,5-dimethylisoxazol-4-yl)-2-(ethylamino)-1H-benzo[d]imidazol-4-yl)acetamide
N-(1-benzyl-6-(3,5-dimethylisoxazol-4-yl)-2-ethoxy-1H-benzo[d]imidazol-4-yl)acetamide
4-(1-benzyl-4-bromo-2-methyl-1H-benzo[d]imidazol-6-yl)-3,5-dimethylisoxazole
3-benzyl-5-(3,5-dimethylisoxazol-4-yl)-1-ethyl-1H-benzo[d]imidazol-2(3H)-one
4-(2-(azetidin-1-yl)-1-benzyl-1H-imidazo[4,5-b]pyridin-6-yl)-3,5-dimethylisoxazole
1-((5-chlorothiophen-2-yl)methyl)-6-(3,5-dimethylisoxazol-4-yl)-1H-imidazo[4,5-b]pyridin-2(3H)-one
(S)-3,5-dimethyl-4-(2-methyl-4-nitro-1-(1-phenylethyl)-1H-benzo[d]imidazol-6-yl)isoxazole
(R)-3,5-dimethyl-4-(2-methyl-4-nitro-1-(1-phenylethyl)-1H-benzo[d]imidazol-6-yl)isoxazole
6-(3,5-dimethylisoxazol-4-yl)-N-ethyl-4-nitro-1-(1-phenylethyl)-1H-benzo[d]imidazol-2-amine
4-(1-benzyl-2-ethyl-1H-imidazo[4,5-b]pyridin-6-yl)-3,5-dimethyl isoxazole
4-amino-6-(3,5-dimethylisoxazol-4-yl)-1-(4-hydroxybenzyl)-1H-benzo[d]imidazol-2(3H)-one
N-(2-(azetidin-1-yl)-1-benzyl-6-(3,5-dimethyl isoxazol-4-yl)-1H-benzo[d]imidazol-4-yl)acetamide
1-(cyclopropylmethyl)-6-(3,5-dimethylisoxazol-4-yl)-N-ethyl-1H-imidazo[4,5-b]pyridin-2-amine
1-(cyclobutylmethyl)-6-(3,5-dimethyl isoxazol-4-yl)-2-methyl-1H-benzo[d]imidazol-4-amine
1-(cyclopentylmethyl)-6-(3,5-dimethyl isoxazol-4-yl)-2-methyl-1H-benzo[d]imidazol-4-amine
6-(3,5-dimethylisoxazol-4-yl)-N2-ethyl-1-(1-phenylethyl)-1H-benzo[d]imidazole-2,4-diamine
4-(1-benzyl-4-nitro-2-(pyrrolidin-1-yl)-1H-benzo[d]imidazol-6-yl)-3,5-dimethylisoxazole
4-(1-benzyl-2-(4-methyl piperazin-1-yl)-4-nitro-1H-benzo[d]imidazol-6-yl)-3,5-dimethylisoxazole
1-benzyl-6-(3,5-dimethylisoxazol-4-yl)-N-(2-methoxyethyl)-4-nitro-1H-benzo[d]imidazol-2-amine
4-(1-benzyl-2-cyclopropyl-1H-imidazo[4,5-b]pyridin-6-yl)-3,5-dimethylisoxazole
1-benzyl-6-(3,5-dimethylisoxazol-4-yl)-N2-(2-methoxyethyl)-1H-benzo[d]imidazole-2,4-diamine
1-benzyl-6-(3,5-dimethylisoxazol-4-yl)-2-(pyrrolidin-1-yl)-1H-benzo[d]imidazol-4-amine
1-benzyl-6-(3,5-dimethyl isoxazol-4-yl)-2-(4-methylpiperazin-1-yl)-1H-benzo[d]imidazol-4-amine
1-benzyl-N6-(3,5-dimethylisoxazol-4-yl)-2-methyl-1H-benzo[d]imidazole-4,6-diamine
(S)-6-(3,5-dimethylisoxazol-4-yl)-2-methyl-1-(1-phenylethyl)-1H-benzo[d]imidazol-4-amine
(R)-6-(3,5-dimethylisoxazol-4-yl)-2-methyl-1-(1-phenylethyl)-1H-benzo[d]imidazol-4-amine
1-(cyclopropylmethyl)-6-(3,5-dimethylisoxazol-4-yl)-4-nitro-1H-benzo[d]imidazol-2(3H)-one
1-benzyl-6-(3,5-dimethylisoxazol-4-yl)-N-methyl-1H-imidazo[4,5-b]pyridin-2-amine
N,1-dibenzyl-6-(3,5-dimethylisoxazol-4-yl)-4-nitro-1H-benzo[d]imidazol-2-amine
1-benzyl-6-(3,5-dimethyl isoxazol-4-yl)-4-nitro-N-(pyridin-3-ylmethyl)-1H-benzo[d]imidazol-2-amine
1-benzyl-6-(3,5-dimethylisoxazol-4-yl)-N-methyl-4-nitro-1H-benzo[d]imidazol-2-amine
1-benzyl-6-(3,5-dimethylisoxazol-4-yl)-3-methyl-4-nitro-1H-benzo[d]imidazol-2(3H)-one
1-benzyl-6-(3,5-dimethylisoxazol-4-yl)-N2-methyl-1H-benzo[d]imidazole-2,4-diamine
N2,1-dibenzyl-6-(3,5-dimethylisoxazol-4-yl)-1H-benzo[d]imidazole-2,4-diamine
N,1-dibenzyl-6-(3,5-dimethylisoxazol-4-yl)-1H-imidazo[4,5-b]pyridin-2-amine
1-benzyl-2-methyl-6-(1-methyl-1H-pyrazol-5-yl)-1H-imidazo[4,5-b]pyridine
N-(1-benzyl-2-methyl-1H-imidazo[4,5-b]pyridin-6-yl)-3,5-dimethylisoxazol-4-amine
4-benzyl-6-(3,5-dimethylisoxazol-4-yl)-3,4-dihydroquinoxalin-2(1H)-one
1-benzyl-6-(3,5-dimethylisoxazol-4-yl)-N2-(pyridin-3-ylmethyl)-1H-benzo[d]imidazole-2,4-diamine
4-(1-benzyl-4-fluoro-2-methyl-1H-benzo[d]imidazol-6-yl)-3,5-dimethyl isoxazole
1-(cyclopropylmethyl)-6-(3,5-dimethylisoxazol-4-yl)-N-ethyl-4-nitro-1H-benzo[d]imidazol-2-amine
1-(cyclopropylmethyl)-6-(3,5-dimethyl isoxazol-4-yl)-N2-ethyl-1H-benzo[d]imidazole-2,4-diamine
4-amino-1-(cyclopropylmethyl)-6-(3,5-dimethyl isoxazol-4-yl)-1H-benzo[d]imidazol-2(3H)-one
4-amino-1-benzyl-6-(3,5-dimethylisoxazol-4-yl)-3-methyl-1H-benzo[d]imidazol-2(3H)-one
1-benzyl-6-(3,5-dimethylisoxazol-4-yl)-4-fluoro-1H-benzo[d]imidazol-2(3H)-one N-(1-benzyl-6-(3,5-dimethylisoxazol-4-yl)-3-methyl-2-oxo-2,3-dihydro-1H-benzo[d]imidazol-4-yl)acetamide
4-(1-benzyl-2-(4-methyl piperazin-1-yl)-1H-imidazo[4,5-b]pyridin-6-yl)-3,5-dimethyl isoxazole
4-benzyl-6-(1-methyl-1H-pyrazol-5-yl)-3,4-dihydroquinoxalin-2 (1H)-one
1-benzyl-6-(3,5-dimethylisoxazol-4-yl)-N-(2-methoxyethyl)-1H-imidazo[4,5-b]pyridin-2-amine
4-(1-benzyl-2-methyl-4-(methylsulfonyl)-1H-benzo[d]imidazol-6-yl)-3,5-dimethylisoxazole
1-benzyl-6-(3,5-dimethyl isoxazol-4-yl)-N-(pyridin-4-ylmethyl)-1H-imidazo[4,5-b]pyridin-2-amine
1-benzyl-6-(3,5-dimethylisoxazol-4-yl)-N-(tetrahydro-2H-pyran-4-yl)-1H-imidazo[4,5-b]pyridin-2-amine
1-benzyl-6-(1-methyl-1H-pyrazol-5-yl)-1H-imidazo[4,5-b]pyridin-2(3H)-one
(S)-6-(3,5-dimethylisoxazol-4-yl)-4-nitro-1-(1-phenylethyl)-1H-benzo[d]imidazol-2(3H)-one
1-benzyl-6-(3,5-dimethylisoxazol-4-yl)-2-methyl-1H-benzo[d]imidazol-4-ol
(R)-4-benzyl-6-(3, 5-dimethylisoxazol-4-yl)-3-methyl-3,4-dihydroquinoxalin-2 (1H)-one
4-(1-benzyl-6-(1-methyl-1H-pyrazol-5-yl)-1H-imidazo[4,5-b]pyridin-2-yl)morpholine
1-benzyl-6-(1-methyl-1H-pyrazol-5-yl)-N-(tetrahydro-2H-pyran-4-yl)-1H-imidazo[4, 5-b]pyridin-2-amine
4-amino-1-benzyl-6-(3,5-dimethylisoxazol-4-yl)-1H-benzo[d]imidazole-2(3H)-thione
(S)-4-amino-6-(3,5-dimethyl isoxazol-4-yl)-1-(1-phenylethyl)-1H-benzo[d]imidazol-2(3H)-one
(R)-4-amino-6-(3,5-dimethyl isoxazol-4-yl)-1-(1-phenylethyl)-1H-benzo[d]imidazol-2(3H)-one
1-benzyl-6-(3,5-dimethylisoxazol-4-yl)-7-methyl-1H-imidazo[4,5-b]pyridin-2(3H)-one
4-(1-benzyl-2,7-dimethyl-1H-imidazo[4,5-b]pyridin-6-yl)-3,5-dimethyl isoxazole
4-(1-benzyl-6-(3,5-dimethyl isoxazol-4-yl)-2-methyl-1H-benzo[d]imidazol-4-yl)morpholine
1-(1-benzyl-6-(3,5-dimethyl isoxazol-4-yl)-2-methyl-1H-benzo[d]imidazol-4-yl)azetidin-2-one
1-benzyl-2-methyl-6-(1,3,5-trimethyl-1H-pyrazol-4-yl)-1H-benzo[d]imidazol-4-amine
1-benzyl-6-(3,5-dimethyl isoxazol-4-yl)-N-(pyridin-3-ylmethyl)-1H-imidazo[4,5-b]pyridin-2-amine
4-(4-bromo-2-methyl-1-phenethyl-1H-benzo[d]imidazol-6-yl)-3,5-dimethylisoxazole
4-(4-bromo-2-methyl-1-(3-phenylpropyl)-1H-benzo[d]imidazol-6-yl)-3,5-dimethylisoxazole
4-(7-bromo-2-methyl-1-(3-phenylpropyl)-1H-benzo[d]imidazol-5-yl)-3,5-dimethylisoxazole
4-(4-bromo-2-methyl-1-(2-phenoxyethyl)-1H-benzo[d]imidazol-6-yl)-3,5-dimethylisoxazole
4-(7-bromo-2-methyl-1-(2-phenoxyethyl)-1H-benzo[d]imidazol-5-yl)-3,5-dimethylisoxazole
4-(1-(cyclohexylmethyl)-2-methyl-1H-imidazo[4,5-b]pyridin-6-yl)-3,5-dimethylisoxazole
4-(1-(cyclopentylmethyl)-2-methyl-1H-imidazo[4,5-b]pyridin-6-yl)-3,5-dimethyl isoxazole
4-(1-(cyclobutylmethyl)-2-methyl-1H-imidazo[4,5-b]pyridin-6-yl)-3,5-dimethyl isoxazole
1-benzyl-6-(3,5-dimethyl isoxazol-4-yl)-N-(pyridin-2-ylmethyl)-1H-imidazo[4,5-b]pyridin-2-amine
4-(1-benzyl-2-(pyrrolidin-1-yl)-1H-imidazo[4,5-b]pyridin-6-yl)-3,5-dimethylisoxazole
2-((1-benzyl-6-(3,5-dimethyl isoxazol-4-yl)-1H-imidazo[4,5-b]pyridin-2-yl)amino)ethanol
1-(1-benzyl-6-(3,5-dimethyl isoxazol-4-yl)-2-methyl-1H-benzo[d]imidazol-4-yl)azetidin-3-ol
1-benzyl-3-methyl-6-(1-methyl-1H-pyrazol-5-yl)-4-nitro-1H-benzo[d]imidazol-2(3H)-one
4-amino-1-benzyl-3-methyl-6-(1-methyl-1H-pyrazol-5-yl)-1H-benzo[d]imidazol-2(3H)-one
(4-bromo-6-(3,5-dimethylisoxazol-4-yl)-2-methyl-1H-benzo[d]imidazol-1-yl) (phenyl)methanone
1-benzyl-2-methyl-6-(5-methylisoxazol-4-yl)-1H-benzo[d]imidazol-4-amine
1-(cyclopentylmethyl)-6-(3,5-dimethylisoxazol-4-yl)-1H-imidazo[4,5-b]pyridin-2(3H)-one
1-(cyclobutylmethyl)-6-(3,5-dimethylisoxazol-4-yl)-1H-imidazo[4,5-b]pyridin-2(3H)-one
N-(1-benzyl-3-methyl-6-(1-methyl-1H-pyrazol-5-yl)-2-oxo-2,3-dihydro-1H-benzo[d]imidazol-4-yl)acetamide
1-benzyl-6-(3,5-dimethylisoxazol-4-yl)-N-(4-methoxybenzyl)-1H-imidazo[4,5-b]pyridin-2-amine
1-benzyl-2-methyl-6-(1-methyl-1H-1,2,3-triazol-5-yl)-1H-imidazo[4,5-b]pyridine
4-((1-benzyl-6-(3,5-dimethyl isoxazol-4-yl)-1H-imidazo[4,5-b]pyridin-2-yl)amino)cyclohexanol
4-(1-(cyclopentylmethyl)-6-(3,5-dimethylisoxazol-4-yl)-1H-imidazo[4,5-b]pyridin-2-yl)morpholine
4-(2-(azetidin-1-yl)-1-(cyclopentylmethyl)-1H-imidazo[4,5-b]pyridin-6-yl)-3,5-dimethylisoxazole
4-(1-(cyclobutylmethyl)-6-(3,5-dimethylisoxazol-4-yl)-1H-imidazo[4,5-b]pyridin-2-yl)morpholine
4-(2-(azetidin-1-yl)-1-(cyclobutylmethyl)-1H-imidazo[4,5-b]pyridin-6-yl)-3,5-dimethylisoxazole
N1-(1-benzyl-6-(3,5-dimethylisoxazol-4-yl)-1H-imidazo[4,5-b]pyridin-2-yl)-N2,N2-dimethylethane-1,2-diamine
4-(1-benzyl-2-(piperazin-1-yl)-1H-imidazo[4,5-b]pyridin-6-yl)-3,5-dimethylisoxazole
1-benzyl-N-cyclopentyl-6-(3,5-dimethyl isoxazol-4-yl)-1H-imidazo[4,5-b]pyridin-2-amine;
1-benzyl-6-(3,5-dimethylisoxazol-4-yl)-N-(2-morpholinoethyl)-1H-imidazo[4,5-b]pyridin-2-amine;
1-benzyl-6-(3,5-dimethylisoxazol-4-yl)-1H-imidazo[4,5-b]pyridin-2-amine;
3-(((1-benzyl-6-(3,5-dimethyl isoxazol-4-yl)-1H-imidazo[4,5-b]pyridin-2-yl)amino)methyl)benzonitrile;
(R)-6-(3,5-dimethylisoxazol-4-yl)-1-(1-phenylethyl)-1H-imidazo[4,5-b]pyridin-2(3H)-one;
(S)-6-(3,5-dimethylisoxazol-4-yl)-1-(1-phenylethyl)-1H-imidazo[4,5-b]pyridin-2(3H)-one;
4-(1-benzyl-2-(tetrahydro-2H-pyran-4-yl)-1H-imidazo[4,5-b]pyridin-6-yl)-3,5-dimethylisoxazole;
1-benzyl-6-(3,5-dimethylisoxazol-4-yl)-N-methyl-1H-imidazo[4,5-b]pyridine-2-carboxamide;
1-(cyclopentylmethyl)-6-(3,5-dimethyl isoxazol-4-yl)-N-(tetrahydro-2H-pyran-4-yl)-1H-imidazo[4,5-b]pyridin-2-amine;
1-(cyclobutylmethyl)-6-(3,5-dimethylisoxazol-4-yl)-N-(tetrahydro-2H-pyran-4-yl)-1H-imidazo[4,5-b]pyridin-2-amine;
N1-(1-benzyl-6-(3,5-dimethylisoxazol-4-yl)-1H-imidazo[4,5-b]pyridin-2-yl)cyclohexane-1,4-diamine;
1-benzyl-N-(cyclohexylmethyl)-6-(3,5-dimethyl isoxazol-4-yl)-1H-imidazo[4,5-b]pyridin-2-amine;
1-benzyl-6-(3,5-dimethylisoxazol-4-yl)-N-(3-methoxypropyl)-1H-imidazo[4,5-b]pyridin-2-amine;
1-benzyl-6-(3,5-dimethyl isoxazol-4-yl)-N-(oxetan-3-yl)-1H-imidazo[4,5-b]pyridin-2-amine;
6-(3,5-dimethylisoxazol-4-yl)-1-(4-fluorobenzyl)-1H-imidazo[4,5-b]pyridin-2(3H)-one;

1-benzyl-6-(3,5-dimethylisoxazol-4-yl)-N-(pyrazin-2-ylmethyl)-1H-imidazo[4,5-b]pyridin-2-amine;
1-benzyl-6-(3,5-dimethylisoxazol-4-yl)-N-((tetrahydro-2H-pyran-4-yl)methyl)-1H-imidazo[4,5-b]pyridin-2-amine;
1-benzyl-6-(3,5-dimethylisoxazol-4-yl)-N-(2-(4-methylpiperazin-1-yl)ethyl)-1H-imidazo[4,5-b]pyridin-2-amine;
6-(3,5-dimethylisoxazol-4-yl)-1-(4-fluorobenzyl)-N-methyl-1H-imidazo[4,5-b]pyridin-2-amine;
1-(4-chlorobenzyl)-6-(3,5-dimethylisoxazol-4-yl)-N-methyl-1H-imidazo[4,5-b]pyridin-2-amine;
1-benzyl-N-cyclohexyl-6-(3,5-dimethylisoxazol-4-yl)-1H-imidazo[4,5-b]pyridin-2-amine;
1-benzyl-6-(3,5-dimethylisoxazol-4-yl)-N-(1-methylpiperidin-4-yl)-1H-imidazo[4,5-b]pyridin-2-amine;
4-(1-benzyl-2-(pyridin-3-yloxy)-1H-imidazo[4,5-b]pyridin-6-yl)-3,5-dimethylisoxazole;
1-((1-benzyl-6-(3,5-dimethylisoxazol-4-yl)-1H-imidazo[4,5-b]pyridin-2-yl)amino)-2-methylpropan-2-ol;
1-benzyl-6-(3,5-dimethylisoxazol-4-yl)-N-(2-(pyrrolidin-1-yl)ethyl)-1H-imidazo[4,5-b]pyridin-2-amine;
1-benzyl-6-(3,5-dimethylisoxazol-4-yl)-N-(2-(piperidin-1-yl)ethyl)-1H-imidazo[4,5-b]pyridin-2-amine;
(R)-6-(3,5-dimethylisoxazol-4-yl)-4-nitro-1-(1-phenylethyl)-1H-benzo[d]imidazol-2(3H)-one;
4-(1-benzyl-7-methoxy-2-(trifluoromethyl)-1H-benzo[d]imidazol-6-yl)-3,5-dimethylisoxazole;
1-benzyl-6-(3,5-dimethylisoxazol-4-yl)-N-(thiazol-2-ylmethyl)-1H-imidazo[4,5-b]pyridin-2-amine;
1-benzyl-6-(3,5-dimethylisoxazol-4-yl)-1H-benzo[d]imidazole-2-carboximidamide;
1-benzyl-6-(3,5-dimethylisoxazol-4-yl)-1H-benzo[d]imidazole-2-carboxamide;
1-benzyl-6-(3,5-dimethylisoxazol-4-yl)-N-((1-methylpiperidin-4-yl)methyl)-1H-imidazo[4,5-b]pyridin-2-amine;
1-(1-benzyl-6-(3,5-dimethylisoxazol-4-yl)-1H-imidazo[4,5-b]pyridin-2-yl)azetidin-3-ol;
4-(1-benzyl-2-(pyridin-4-yloxy)-1H-imidazo[4,5-b]pyridin-6-yl)-3,5-dimethylisoxazole;
1-benzyl-6-(3,5-dimethylisoxazol-4-yl)-N-(pyridin-3-yl)-1H-benzo[d]imidazol-2-amine; and
3-(1-benzyl-1H-benzo[d]imidazol-6-yl)-4-ethyl-1H-1,2,4-triazol-5(4H)-one;
or a stereoisomer, tautomer, salt, or hydrate thereof.

Another aspect of the invention provides a method for inhibition of BET protein function by binding to bromodomains, and their use in the treatment and prevention of diseases and conditions in a mammal (e.g., a human) comprising administering a therapeutically effective amount of a compound of Formula I, Formula Ia, and/or Formula II.

In one embodiment, because of potent effects of BET inhibitors in vitro on IL-6 and IL-17 transcription, BET inhibitor compounds of Formula I, Formula Ia, and/or Formula II may be used as therapeutics for inflammatory disorders in which IL-6 and/or IL-17 have been implicated in disease. The following autoimmune diseases are amenable to therapeutic use of BET inhibition by administration of a compound of Formula I, Formula Ia, and/or Formula II or stereoisomer, tautomer, pharmaceutically acceptable salt, or hydrate of Formula I, Formula Ia, and/or Formula II because of a prominent role of IL-6 and/or IL-17: Acute Disseminated Encephalomyelitis (Ishizu, T., et al., "CSF cytokine and chemokine profiles in acute disseminated encephalomyelitis," *J Neuroimmunol* 175(1-2): 52-8 (2006)), Agammaglobulinemia (Gonzalez-Serrano, M. E., et al., "Increased Pro-inflammatory Cytokine Production After Lipopolysaccharide Stimulation in Patients with X-linked Agammaglobulinemia," *J Clin Immunol* 32(5):967-74 (2012)), Allergic Disease (McKinley, L., et al., "TH17 cells mediate steroid-resistant airway inflammation and airway hyperresponsiveness in mice," *J Immunol* 181(6):4089-97 (2008)), Ankylosing spondylitis (Taylan, A., et al., "Evaluation of the T helper 17 axis in ankylosing spondylitis," *Rheumatol Int* 32(8):2511-5 (2012)), Anti-GBM/Anti-TBM nephritis (Ito, Y., et al., "Pathogenic significance of interleukin-6 in a patient with antiglomerular basement membrane antibody-induced glomerulonephritis with multinucleated giant cells," *Am J Kidney Dis* 26(1):72-9 (1995)), Anti-phospholipid syndrome (Soltesz, P., et al., "Immunological features of primary anti-phospholipid syndrome in connection with endothelial dysfunction," *Rheumatology* (Oxford) 47(11):1628-34 (2008)), Autoimmune aplastic anemia (Gu, Y., et al., "Interleukin (IL)-17 promotes macrophages to produce IL-8, IL-6 and tumour necrosis factor-alpha in aplastic anaemia," *Br J Haematol* 142(1):109-14 (2008)), Autoimmune hepatitis (Zhao, L., et al., "Interleukin-17 contributes to the pathogenesis of autoimmune hepatitis through inducing hepatic interleukin-6 expression," *PLoS One* 6(4):e18909 (2011)), Autoimmune inner ear disease (Gloddek, B., et al., "Pharmacological influence on inner ear endothelial cells in relation to the pathogenesis of sensorineural hearing loss," *Adv Otorhinolaryngol* 59:75-83 (2002)), Autoimmune myocarditis (Yamashita, T., et al., "IL-6-mediated Th17 differentiation through RORgammat is essential for the initiation of experimental autoimmune myocarditis," *Cardiovasc Res* 91(4):640-8 (2011)), Autoimmune pancreatitis (Ni, J., et al., "Involvement of Interleukin-17A in Pancreatic Damage in Rat Experimental Acute Necrotizing Pancreatitis," Inflammation (2012)), Autoimmune retinopathy (Hohki, S., et al., "Blockade of interleukin-6 signaling suppresses experimental autoimmune uveoretinitis by the inhibition of inflammatory Th17 responses," *Exp Eye Res* 91(2):162-70 (2010)), Autoimmune thrombocytopenic purpura (Ma, D., et al., "Profile of Th17 cytokines (IL-17, TGF-beta, IL-6) and Th1 cytokine (IFN-gamma) in patients with immune thrombocytopenic purpura," *Ann Hematol* 87(11):899-904 (2008)), Behcet's Disease (Yoshimura, T., et al., "Involvement of Th17 cells and the effect of anti-IL-6 therapy in autoimmune uveitis," *Rheumatology* (Oxford) 48(4):347-54 (2009)), Bullous pemphigoid (D'Auria, L., P. et al., "Cytokines and bullous pemphigoid," *Eur Cytokine Netw* 10(2):123-34 (1999)), Castleman's Disease (El-Osta, H. E. and R. Kurzrock, "Castleman's disease: from basic mechanisms to molecular therapeutics," *Oncologist* 16(4):497-511 (2011)), Celiac Disease (Lahdenpera, A. I., et al., "Up-regulation of small intestinal interleukin-17 immunity in untreated coeliac disease but not in potential coeliac disease or in type 1 diabetes," *Clin Exp Immunol* 167(2):226-34 (2012)), Churg-Strauss syndrome (Fujioka, A., et al., "The analysis of mRNA expression of cytokines from skin lesions in Churg-Strauss syndrome," *J Dermatol* 25(3):171-7 (1998)), Crohn's Disease (Holtta, V., et al., "IL-23/IL-17 immunity as a hallmark of Crohn's disease," *Inflamm Bowel Dis* 14(9):1175-84 (2008)), Cogan's syndrome (Shibuya, M., et al., "Successful treatment with tocilizumab in a case of Cogan's syndrome complicated with aortitis," *Mod Rheumatol* (2012)), Dry eye syndrome (De Paiva, C. S., et al., "IL-17 disrupts corneal barrier following desiccating stress," *Mucosal Immunol* 2(3):243-53 (2009)), Essential mixed cryoglobulinemia (Antonelli, A., et al., "Serum levels of proinflammatory cytokines interleukin-1beta, interleukin-6, and tumor necrosis factor alpha in mixed cryoglobulinemia," *Arthritis Rheum* 60(12):3841-7 (2009)), Dermatomyositis (Chevrel, G., et al., "Interleukin-17 increases the effects of IL-1 beta on muscle cells: arguments for the role of T cells in the pathogenesis of myositis," *J Neuroimmunol* 137(1-2):125-33 (2003)), Devic's Disease (Linhares, U. C., et al., "The Ex Vivo Production of IL-6 and IL-21 by CD4(+) T Cells is Directly Associated with Neurological Disability in Neuromyelitis Optica Patients," *J Clin Immunol* (2012)), Encephalitis (Kyburz, D. and M. Corr, "Th17 cells generated in the absence of TGF-beta induce experimental allergic encephalitis upon adoptive transfer," *Expert Rev Clin Immunol* 7(3):283-5 (2011)), Eosinophlic esophagitis (Dias, P. M. and G. Banerjee, "The Role of Th17/IL-17 on Eosinophilic Inflammation," *J Autoimmun* (2012)), Eosinophilic fasciitis (Dias, P. M. and G. Banerjee, "The Role of Th17/IL-17 on Eosinophilic Inflammation," *J Autoimmun* (2012)), Erythema nodosum (Kahawita, I. P. and D. N. Lockwood, "Towards understanding the pathology of erythema nodosum leprosum," *Trans R Soc Trop Med Hyg* 102(4):329-37 (2008)), Giant cell arteritis (Deng, J., et al., "Th17 and Th1 T-cell responses in giant cell arteritis," *Circulation* 121(7): 906-15 (2010)), Glomerulonephritis (Ooi, J. D., et al., "Review: T helper 17 cells: their role in glomerulonephritis," *Nephrology* (Carlton) 15(5):513-21 (2010)), Goodpasture's syndrome (Ito, Y., et al., "Pathogenic significance of interleukin-6 in a patient with antiglomerular basement membrane antibody-induced glomerulonephritis with multinucleated giant cells," *Am J Kidney Dis* 26(1):72-9 (1995)), Granulomatosis with Polyangiitis (Wegener's) (Nakahama, H., et al., "Distinct responses of interleukin-6 and other laboratory parameters to treatment in a patient with Wegener's granulomatosis," *Intern Med* 32(2):189-92 (1993)), Graves' Disease (Kim, S. E., et al., "Increased serum interleukin-17 in Graves' ophthalmopathy," *Graefes Arch Clin Exp Ophthalmol* 250(10):1521-6 (2012)), Guillain-Barre syndrome (Lu, M. O. and J. Zhu, "The role of cytokines in Guillain-Barre syndrome," *J Neurol* 258(4): 533-48 (2011)), Hashimoto's thyroiditis (Figueroa-Vega, N., et al., "Increased circulating pro-inflammatory cytokines and Th17 lymphocytes in Hashimoto's thyroiditis," *J Clin Endocrinol Metab* 95(2):953-62 (2009)), Hemolytic anemia (Xu, L., et al., "Critical role of Th17 cells in development of autoimmune hemolytic anemia," *Exp Hematol* (2012)), Henoch-Schonlein purpura (Jen, H. Y., et al., "Increased serum interleukin-17 and peripheral Th17 cells in children with acute Henoch-Schonlein purpura," *Pediatr Allergy Immunol* 22(8):862-8 (2011)), IgA nephropathy (Lin, F. J., et al., "Imbalance of regulatory T cells to Th17 cells in IgA nephropathy," *Scand J Clin Lab Invest* 72(3):221-9 (2012)), Inclusion body myositis (Baron, P., et al., "Production of IL-6 by human myoblasts stimulated with Abeta: relevance in the pathogenesis of IBM," *Neurology* 57(9):1561-5 (2001)), Type I diabetes (Belkina, A. C. and G. V. Denis, "BET domain co-regulators in obesity, inflammation and cancer," *Nat Rev Cancer* 12(7):465-77 (2012)), Interstitial cystitis (Lamale, L. M., et al., "Interleukin-6, histamine, and methylhistamine as diagnostic markers for interstitial cystitis," *Urology* 68(4):702-6 (2006)), Kawasaki's Disease (Jia, S., et al., "The T helper type 17/regulatory T cell imbalance in patients with acute Kawasaki disease," *Clin Exp Immunol* 162(1):131-7 (2010)), Leukocytoclastic vasculitis (Min, C. K., et al., "Cutaneous leucoclastic vasculitis (LV) following bortezomib therapy in a myeloma patient; association with pro-inflammatory cytokines," *Eur J Haematol* 76(3):265-8 (2006)), Lichen planus (Rhodus, N. L., et al., "Proinflammatory cytokine levels in saliva before and after treatment of (erosive) oral lichen planus with dexamethasone," *Oral Dis* 12(2):112-6 (2006)), Lupus (SLE) (Mok, M. Y., et al., "The relation of interleukin 17 (IL-17) and IL-23 to Th1/Th2 cytokines and disease activity in systemic lupus erythematosus," *J Rheumatol* 37(10):2046-52 (2010)), Microscopic polyangitis (Muller Kobold, A. C., et al., "In vitro up-regulation of E-selectin and induction of interleukin-6 in endothelial cells by autoantibodies in Wegener's granulomatosis and microscopic polyangiitis," *Clin Exp Rheumatol* 17(4):433-40 (1999)), Multiple sclerosis (Jadidi-Niaragh, F. and Mirshafiey A., "Th17 cell, the new player of neuroinflammatory process in multiple sclerosis," *Scand J Immunol* 74(1):1-13 (2011)), Myasthenia gravis (Aricha, R., et al., "Blocking of IL-6 suppresses experimental autoimmune myasthenia gravis," *J Autoimmun* 36(2):135-41 (2011)), myositis (Chevrel, G., et al., "Interleukin-17 increases the effects of IL-1 beta on muscle cells: arguments for the role of T cells in the pathogenesis of myositis," *J Neuroimmunol* 137(1-2):125-33 (2003)), Optic neuritis (Icoz, S., et al., "Enhanced IL-6 production in aquaporin-4 antibody positive neuromyelitis optica patients," *Int J Neurosci* 120(1):71-5 (2010)), Pemphigus (Lopez-Robles, E., et al., "TNFalpha and IL-6 are mediators in the blistering process of pemphigus," *Int J Dermatol* 40(3):185-8 (2001)), POEMS syndrome (Kallen, K. J., et al., "New developments in IL-6 dependent biology and therapy: where do we stand and what are the options?" *Expert Opin Investig Drugs* 8(9):1327-49 (1999)), Polyarteritis nodosa (Kawakami, T., et al., "Serum levels of interleukin-6 in patients with cutaneous polyarteritis nodosa," *Acta Derm Venereol* 92(3):322-3 (2012)), Primary biliary cirrhosis (Harada, K., et al., "Periductal interleukin-17 production in association with biliary innate immunity contributes to the pathogenesis of cholangiopathy in primary biliary cirrhosis," *Clin Exp Immunol* 157(2):261-70 (2009)), Psoriasis (Fujishima, S., et al., "Involvement of IL-17F via the induction of IL-6 in psoriasis," *Arch Dermatol Res* 302(7):499-505 (2010)), Psoriatic arthritis (Raychaudhuri, S. P., et al., IL-17 receptor and its functional significance in psoriatic arthritis," *Mol Cell Biochem* 359 (1-2):419-29 (2012)), Pyoderma gangrenosum (Kawakami, T., et al., "Reduction of interleukin-6, interleukin-8, and anti-phosphatidylserine-prothrombin complex antibody by granulocyte and monocyte adsorption apheresis in a patient with pyoderma gangrenosum and ulcerative colitis," *Am J Gastroenterol* 104(9):2363-4 (2009)), Relapsing polychondritis (Kawai, M., et al., "Sustained response to tocilizumab, anti-interleukin-6 receptor antibody, in two patients with refractory relapsing polychondritis," *Rheumatology (Oxford)* 48(3):318-9 (2009)), Rheumatoid arthritis (Ash, Z. and P. Emery, "The role of tocilizumab in the management of rheumatoid arthritis," *Expert Opin Biol Ther,* 12(9):1277-89 (2012)), Sarcoidosis (Belli, F., et al., "Cytokines assay in peripheral blood and bronchoalveolar lavage in the diagnosis and staging of pulmonary granulomatous diseases," *Int J Immunopathol Pharmacol* 13(2):61-67 (2000)), Scleroderma (Radstake, T. R., et al., "The pronounced Th17 profile in systemic sclerosis (SSc) together with intracellular expression of TGFbeta and IFNgamma distinguishes SSc phenotypes," *PLoS One,* 4(6): e5903 (2009)), Sjogren's syndrome (Katsifis, G. E., et al., *"Systemic and local interleukin-17 and linked cytokines associated with Sjogren's syndrome immunopathogenesis,"* Am J Pathol 175(3):1167-77 (2009)), Takayasu's arteritis (Sun, Y., et al., "MMP-9 and IL-6 are potential biomarkers for disease activity in Takayasu's arteritis," *Int J Cardiol* 156(2):236-8 (2012)), Transverse myelitis (Graber, J. J., et al., "Interleukin-17 in transverse myelitis and multiple sclerosis," *J Neuroimmunol* 196(1-2):124-32 (2008)), Ulcerative colitis (Mudter, J. and M. F. Neurath, "Il-6 signaling in inflammatory bowel disease: pathophysiological role and clinical relevance,"

Inflamm Bowel Dis 13(8):1016-23 (2007)), Uveitis (Haruta, H., et al., "Blockade of interleukin-6 signaling suppresses not only th17 but also interphotoreceptor retinoid binding protein-specific Th1 by promoting regulatory T cells in experimental autoimmune uveoretinitis," *Invest Ophthalmol Vis Sci* 52(6):3264-71 (2011)), and Vitiligo (Bassiouny, D. A. and O. Shaker, "Role of interleukin-17 in the pathogenesis of vitiligo," *Clin Exp Dermatol* 36(3):292-7 115. (2011)). Thus, the invention includes compounds of Formula I, Formula Ia, and/or Formula II, stereoisomers, tautomers, pharmaceutically acceptable salts, or hydrates thereof; pharmaceutical compositions comprising one or more of those compounds; and methods of using those compounds or compositions for treating these diseases.

Acute and chronic (non-autoimmune) inflammatory diseases characterized by increased expression of pro-inflammatory cytokines, including IL-6, MCP-1, and IL-17, would also be amenable to therapeutic BET inhibition. These include, but are not limited to, sinusitis (Bradley, D. T. and S. E. Kountakis, "Role of interleukins and transforming growth factor-beta in chronic rhinosinusitis and nasal polyposis," *Laryngoscope* 115(4):684-6 (2005)), pneumonitis (Besnard, A. G., et al., "*Inflammasome-IL-1-Th17 response in allergic lung inflammation*" *J Mol Cell Biol* 4(1):3-10 (2012)), osteomyelitis (Yoshii, T., et al., "Local levels of interleukin-1beta, -4, -6 and tumor necrosis factor alpha in an experimental model of murine osteomyelitis due to *staphylococcus aureus*," *Cytokine* 19(2):59-65 2002), gastritis (Bayraktaroglu, T., et al., "Serum levels of tumor necrosis factor-alpha, interleukin-6 and interleukin-8 are not increased in dyspeptic patients with *Helicobacter pylori*-associated gastritis," *Mediators Inflamm* 13(1):25-8 (2004)), enteritis (Mitsuyama, K., et al., "STAT3 activation via interleukin 6 trans-signalling contributes to ileitis in SAMP1/Yit mice," *Gut* 55(9):1263-9. (2006)), gingivitis (Johnson, R. B., et al., "Interleukin-11 and IL-17 and the pathogenesis of periodontal disease," *J Periodontol* 75(1):37-43 (2004)), appendicitis (Latifi, S. Q., et al., "Persistent elevation of serum interleukin-6 in intraabdominal sepsis identifies those with prolonged length of stay," *J Pediatr Surg* 39(10):1548-52 (2004)), irritable bowel syndrome (Ortiz-Lucas, M., et al., "Irritable bowel syndrome immune hypothesis. Part two: the role of cytokines," *Rev Esp Enferm Dig* 102(12):711-7 (2010)), tissue graft rejection (Kappel, L. W., et al., "IL-17 contributes to CD4-mediated graft-versus-host disease," *Blood* 113(4):945-52 (2009)), chronic obstructive pulmonary disease (COPD) (Traves, S. L. and L. E. Donnelly, "Th17 cells in airway diseases," *Curr Mol Med* 8(5):416-26 (2008)), septic shock (toxic shock syndrome, SIRS, bacterial sepsis, etc) (Nicodeme, E., et al., "Suppression of inflammation by a synthetic histone mimic," *Nature* 468(7327):1119-23 (2010)), osteoarthritis (Chen, L., et al., "IL-17RA aptamer-mediated repression of IL-6 inhibits synovium inflammation in a murine model of osteoarthritis," *Osteoarthritis Cartilage* 19(6):711-8 (2011)), acute gout (Urano, W., et al., "The inflammatory process in the mechanism of decreased serum uric acid concentrations during acute gouty arthritis," *J Rheumatol* 29(9):1950-3 (2002)), acute lung injury (Traves, S. L. and L. E. Donnelly, "Th17 cells in airway diseases," *Curr Mol Med* 8(5):416-26 (2008)), acute renal failure (Simmons, E. M., et al., "Plasma cytokine levels predict mortality in patients with acute renal failure," *Kidney Int* 65(4):1357-65 (2004)), burns (Paquet, P. and G. E. Pierard, "Interleukin-6 and the skin," *Int Arch Allergy Immunol* 109(4):308-17 (1996)), Herxheimer reaction (Kaplanski, G., et al., "Jarisch-Herxheimer reaction complicating the treatment of chronic Q fever endocarditis: elevated TNFalpha and IL-6 serum levels," *J Infect* 37(1):83-4 (1998)), and SIRS associated with viral infections (Belkina, A. C. and G. V. Denis, "BET domain co-regulators in obesity, inflammation and cancer," *Nat Rev Cancer* 12(7):465-77 (2012)). Thus, the invention includes compounds of Formula I, Formula Ia, and/or Formula II, stereoisomers, tautomers, pharmaceutically acceptable salts, or hydrates thereof; pharmaceutical compositions comprising one or more of those compounds; and methods of using those compounds or compositions for treating these diseases.

In one embodiment, BET inhibitor compounds of Formula I, Formula Ia, and/or Formula II, stereoisomers, tautomers, pharmaceutically acceptable salts, or hydrates thereof, or compositions comprising one or more of those compounds may be used for treating rheumatoid arthritis (RA) and multiple sclerosis (MS). Strong proprietary data exist for the utility of BET inhibitors in preclinical models of RA and MS. R. Jahagirdar, S. M. et al., "An Orally Bioavailable Small Molecule RVX-297 Significantly Decreases Disease in a Mouse Model of Multiple Sclerosis," *World Congress of Inflammation*, Paris, France (2011). Both RA and MS are characterized by a dysregulation of the IL-6 and IL-17 inflammatory pathways (Kimura, A. and T. Kishimoto, "IL-6: regulator of Treg/Th17 balance," *Eur J Immunol* 40(7):1830-5 (2010)) and thus would be especially sensitive to BET inhibition. In another embodiment, BET inhibitor compounds of Formula I, Formula Ia, and/or Formula II may be used for treating sepsis and associated afflictions. BET inhibition has been shown to inhibit development of sepsis, in part, by inhibiting IL-6 expression, in preclinical models in both published (Nicodeme, E., et al., "Suppression of inflammation by a synthetic histone mimic," *Nature* 468(7327):1119-23 (2010)) and proprietary data.

In one embodiment, BET inhibitor compounds of Formula I, Formula Ia, and/or Formula II, stereoisomers, tautomers, pharmaceutically acceptable salts, or hydrates thereof, or compositions comprising one or more of those compounds may be used to treat cancer. Cancers that have an overexpression, translocation, amplification, or rearrangement c-myc or other myc family oncoproteins (MYCN, L-myc) are particularly sensitive to BET inhibition. Delmore, J. E., et al., "BET bromodomain inhibition as a therapeutic strategy to target c-Myc," *Cell* 146(6):904-17 (2010); Mertz, J. A., et al., "Targeting MYC dependence in cancer by inhibiting BET bromodomains," *Proc Natl Acad Sci USA* 108(40):16669-74 (2011). These cancers include, but are not limited to, B-acute lymphocytic leukemia, Burkitt's lymphoma, Diffuse large cell lymphoma, Multiple myeloma, Primary plasma cell leukemia, Atypical carcinoid lung cancer, Bladder cancer, Breast cancer, Cervix cancer, Colon cancer, Gastric cancer, Glioblastoma, Hepatocellular carcinoma, Large cell neuroendocrine carcinoma, Medulloblastoma, Melanoma, nodular, Melanoma, superficial spreading, Neuroblastoma, esophageal squamous cell carcinoma, Osteosarcoma, Ovarian cancer, Prostate cancer, Renal clear cell carcinoma, Retinoblastoma, Rhabdomyosarcoma, and Small cell lung carcinoma. Vita, M. and M. Henriksson, "The Myc oncoprotein as a therapeutic target for human cancer," *Semin Cancer Biol* 16(4):318-30 (2006).

In one embodiment, BET inhibitor compounds of Formula I, Formula Ia, and/or Formula II, stereoisomers, tautomers, pharmaceutically acceptable salts, or hydrates thereof, or compositions comprising one or more of those compounds may be used to treat cancers that result from an aberrant regulation (overexpression, translocation, etc) of BET proteins. These include, but are not limited to, NUT midline carcinoma (Brd3 or Brd4 translocation to nutlin 1 gene) (French, C. A., "NUT midline carcinoma," *Cancer Genet Cytogenet* 203(1):16-20 (2010)), B-cell lymphoma (Brd2 overexpression) (Greenwald, R. J., et al., "E mu-BRD2 transgenic mice develop B-cell lymphoma and leukemia,". *Blood* 103(4):1475-84 (2004)), non-small cell lung cancer (BrdT overexpression) (Grunwald, C., et al., "Expression of multiple epigenetically regulated cancer/germline genes in nonsmall cell lung cancer," *Int J Cancer* 118(10):2522-8 (2006)), esophageal cancer and head and neck squamous cell carcinoma (BrdT overexpression) (Scanlan, M. J., et al., "Expression of cancer-testis antigens in lung cancer: definition of bromodomain testis-specific gene (BRDT) as a new CT gene, CT9," *Cancer Lett* 150(2):55-64 (2000)), and colon cancer (Brd4) (Rodriguez, R. M., et al., "Aberrant epigenetic regulation of bromodomain BRD4 in human colon cancer," *J Mol Med (Berl)* 90(5):587-95 (2012)).

In one embodiment, because BET inhibitors decrease Brd-dependent recruitment of pTEFb to genes involved in cell proliferation, BET inhibitor compounds of Formula I, Formula Ia, and/or Formula II, stereoisomers, tautomers, pharmaceutically acceptable salts, or hydrates thereof, or compositions comprising one or more of those compounds may be used to treat cancers that rely on pTEFb (Cdk9/cyclin T) and BET proteins to regulate oncogenes. These cancers include, but are not limited to, chronic lymphocytic leukemia and multiple myeloma (Tong, W. G., et al., "Phase I and pharmacologic study of SNS-032, a potent and selective Cdk2, 7, and 9 inhibitor, in patients with advanced chronic lymphocytic leukemia and multiple myeloma," *J Clin Oncol* 28(18):3015-22 (2010)), follicular lymphoma, diffuse large B cell lymphoma with germinal center phenotype, Burkitt's lymphoma, Hodgkin's lymphoma, follicular lymphomas and activated, anaplastic large cell lymphoma (Bellan, C., et al., "CDK9/CYCLIN T1 expression during normal lymphoid differentiation and malignant transformation," *J Pathol* 203(4):946-52 (2004)), neuroblastoma and primary neuroectodermal tumor (De Falco, G., et al., "Cdk9 regulates neural differentiation and its expression correlates with the differentiation grade of neuroblastoma and PNET tumors," *Cancer Biol Ther* 4(3):277-81 (2005)), rhabdomyosarcoma (Simone, C. and A. Giordano, "Abrogation of signal-dependent activation of the cdk9/cyclin T2a complex in human RD rhabdomyosarcoma cells," *Cell Death Differ* 14(1):192-5 (2007)), prostate cancer (Lee, D. K., et al., "Androgen receptor interacts with the positive elongation factor P-TEFb and enhances the efficiency of transcriptional elongation," *J Biol Chem* 276(13):9978-84 (2001)), and breast cancer (Bartholomeeusen, K., et al., "BET bromodomain inhibition activates transcription via a transient release of P-TEFb from 7SK snRNP," *J Biol Chem* (2012)).

In one embodiment, BET inhibitor compounds of Formula I, Formula Ia, and/or Formula II, stereoisomers, tautomers, pharmaceutically acceptable salts, or hydrates thereof, or compositions comprising one or more of those compounds may be used to treat cancers in which BET-responsive genes, such as CDK6, Bcl2, TYRO3, MYB, and hTERT are up-regulated. Dawson, M. A., et al., "Inhibition of BET recruitment to chromatin as an effective treatment for MLL-fusion leukaemia," *Nature* 478(7370):529-33 (2011); Delmore, J. E., et al., "BET bromodomain inhibition as a therapeutic strategy to target c-Myc," *Cell* 146(6):904-17 (2010). These cancers include, but are not limited to, pancreatic cancer, breast cancer, colon cancer, glioblastoma, adenoid cystic carcinoma, T-cell prolymphocytic leukemia, malignant glioma, bladder cancer, medulloblastoma, thyroid cancer, melanoma, multiple myeloma, Barret's adenocarcinoma, hepatoma, prostate cancer, pro-myelocytic leukemia, chronic lymphocytic leukemia, mantle cell lymphoma, diffuse large B-cell lymphoma, small cell lung cancer, and renal carcinoma. Ruden, M. and N. Puri, "Novel anticancer therapeutics targeting telomerase," *Cancer Treat Rev* (2012); Kelly, P. N. and A. Strasser, "The role of Bcl-2 and its pro-survival relatives in tumourigenesis and cancer therapy" *Cell Death Differ* 18(9):1414-24 (2011); Uchida, T., et al., "Antitumor effect of bcl-2 antisense phosphorothioate oligodeoxynucleotides on human renal-cell carcinoma cells in vitro and in mice," *Mol Urol* 5(2):71-8 (2001).

Published and proprietary data have shown direct effects of BET inhibition on cell proliferation in various cancers. In one embodiment, BET inhibitor compounds of Formula I, Formula Ia, and/or Formula II, stereoisomers, tautomers, pharmaceutically acceptable salts, or hydrates thereof, or compositions comprising one or more of those compounds may be used to treat cancers for which exist published and, for some, proprietary, in vivo and/or in vitro data showing a direct effect of BET inhibition on cell proliferation. These cancers include NMC (NUT-midline carcinoma), acute myeloid leukemia (AML), acute B lymphoblastic leukemia (B-ALL), Burkitt's Lymphoma, B-cell Lymphoma, Melanoma, mixed lineage leukemia, multiple myeloma, pro-myelocytic leukemia (PML), and non-Hodgkin's lymphoma. Filippakopoulos, P., et al., "Selective inhibition of BET bromodomains," *Nature* 468(7327):1067-73 (2010); Dawson, M. A., et al., "Inhibition of BET recruitment to chromatin as an effective treatment for MLL-fusion leukaemia," *Nature* 478(7370):529-33 (2011); Zuber, J., et al., "RNAi screen identifies Brd4 as a therapeutic target in acute myeloid leukaemia," *Nature* 478(7370):524-8 (2011); Miguel F. Segura, et al, "BRD4 is a novel therapeutic target in melanoma," *Cancer Research.* 72(8):Supplement 1 (2012). The compounds of the invention have a demonstrated BET inhibition effect on cell proliferation in vitro for the following cancers: Neuroblastoma, Medulloblastoma, lung carcinoma (NSCLC, SCLC), and colon carcinoma.

In one embodiment, because of potential synergy or additive effects between BET inhibitors and other cancer therapy, BET inhibitor compounds of Formula I, Formula Ia, and/or Formula II, stereoisomers, tautomers, pharmaceutically acceptable salts, or hydrates thereof, or compositions comprising one or more of those compounds may be combined with other therapies, chemotherapeutic agents, or anti-proliferative agents to treat human cancer and other proliferative disorders. The list of therapeutic agents which can be combined with BET inhibitors in cancer treatment includes, but is not limited to, ABT-737, Azacitidine (Vidaza), AZD1152 (Barasertib), AZD2281 (Olaparib), AZD6244 (Selumetinib), BEZ235, Bleomycin Sulfate, Bortezomib (Velcade), Busulfan (Myleran), Camptothecin, Cisplatin, Cyclophosphamide (Clafen), CYT387, Cytarabine (Ara-C), Dacarbazine, DAPT (GSI-IX), Decitabine, Dexamethasone, Doxorubicin (Adriamycin), Etoposide, Everolimus (RAD001), Flavopiridol (Alvocidib), Ganetespib (STA-9090), Gefitinib (Iressa), Idarubicin, Ifosfamide (Mitoxana), IFNa2a (Roferon A), Melphalan (Alkeran), Methazolastone (temozolomide), Metformin, Mitoxantrone (Novantrone), Paclitaxel, Phenformin, PKC412 (Midostaurin), PLX4032 (Vemurafenib), Pomalidomide (CC-4047), Prednisone (Deltasone), Rapamycin, Revlimid (Lenalidomide), Ruxolitinib (INCB018424), Sorafenib (Nexavar), SU11248 (Sunitinib), SU11274, Vinblastine, Vincristine (Oncovin), Vinorelbine (Navelbine), Vorinostat (SAHA), and WP1130 (Degrasyn).

In one embodiment, BET inhibitor compounds of Formula I, Formula Ia, and/or Formula II, stereoisomers, tautomers, pharmaceutically acceptable salts, or hydrates thereof, or compositions comprising one or more of those compounds may be used to treat benign proliferative and fibrotic disorders, including, but not limited to, benign soft tissue tumors, bone tumors, brain and spinal tumors, eyelid and orbital tumors, granuloma, lipoma, meningioma, multiple endocrine neoplasia, nasal polyps, pituitary tumors, prolactinoma, pseudotumor cerebri, seborrheic keratoses, stomach polyps, thyroid nodules, cystic neoplasms of the pancreas, hemangiomas, vocal cord nodules, polyps, and cysts, Castleman disease, chronic pilonidal disease, dermatofibroma, pilar cyst, pyogenic granuloma, juvenile polyposis syndrome, idiopathic pulmonary fibrosis, renal fibrosis, post-operative stricture, keloid formation, scleroderma, and cardiac fibrosis. Tang, X et al., "Assessment of Brd4 Inhibition in Idiopathic Pulmonary Fibrosis Lung Fibroblasts and in Vivo Models of Lung Fibrosis,". Am J Pathology in press (2013).

In one embodiment, because of their ability to up-regulate ApoA-1 transcription and protein expression (Mirguet, O., et al., "From ApoA1 upregulation to BET family bromodomain inhibition: discovery of I-BET151," *Bioorg Med Chem Lett* 22(8):2963-7 (2012); Chung, C. W., et al., "Discovery and characterization of small molecule inhibitors of the BET family bromodomains," *J Med Chem* 54(11):3827-38 (2011)), BET inhibitor compounds of Formula I, Formula Ia, and/or Formula II, stereoisomers, tautomers, pharmaceutically acceptable salts, or hydrates thereof, or compositions comprising one or more of those compounds may be used to treat cardiovascular diseases that are generally associated with including dyslipidemia, atherosclerosis, hypercholesterolemia, and metabolic syndrome (Belkina, A. C. and G. V. Denis, "BET domain co-regulators in obesity, inflammation and cancer," *Nat Rev Cancer* 12(7):465-77 (2012); Denis, G. V., "Bromodomain coactivators in cancer, obesity, type 2 diabetes, and inflammation," *Discov Med* 10(55):489-99 (2010)). In another embodiment, BET inhibitor compounds of Formula I, Formula Ia, and/or Formula II may be used to treat non-cardiovascular disease characterized by deficits in ApoA-1, including Alzheimer's disease. Elliott, D. A., et al., "Apolipoproteins in the brain: implications for neurological and psychiatric disorders," *Clin Lipidol* 51(4):555-573 (2010).

In one embodiment, BET inhibitor compounds of Formula I, Formula Ia, and/or Formula II, stereoisomers, tautomers, pharmaceutically acceptable salts, or hydrates thereof, or compositions comprising one or more of those compounds may be used in patients with insulin resistance and type II diabetes. Belkina, A. C. and G. V. Denis, "BET domain co-regulators in obesity, inflammation and cancer," *Nat Rev Cancer* 12(7):465-77 (2012); Denis, G. V., "Bromodomain coactivators in cancer, obesity, type 2 diabetes, and inflammation," *Discov Med* 10(55):489-99 (2010); Wang, F., et al., "Brd2 disruption in mice causes severe obesity without Type 2 diabetes," *Biochem J* 425(1):71-83 (2010); Denis, G. V., et al, "An emerging role for bromodomain-containing proteins in chromatin regulation and transcriptional control of adipogenesis," *FEBS Lett* 584(15): 3260-8 (2010). The anti-inflammatory effects of BET inhibition would have additional value in decreasing inflammation associated with diabetes and metabolic disease. Alexandraki, K., et al., "Inflammatory process in type 2 diabetes: The role of cytokines," *Ann NY Acad Sci* 1084: 89-117 (2006).

In one embodiment, because of their ability to down-regulate viral promoters, BET inhibitor compounds of Formula I, Formula Ia, and/or Formula II, stereoisomers, tautomers, pharmaceutically acceptable salts, or hydrates thereof, or compositions comprising one or more of those compounds may be used as therapeutics for cancers that are associated with viruses including Epstein-Barr Virus (EBV), hepatitis virus (HBV, HCV), Kaposi's sarcoma associated virus (KSHV), human papilloma virus (HPV), Merkel cell polyomavirus, and human cytomegalovirus (CMV). Gagnon, D., et al., "Proteasomal degradation of the papillomavirus E2 protein is inhibited by overexpression of bromodomain-containing protein 4," *J Virol* 83(9):4127-39 (2009); You, J., et al., "Kaposi's sarcoma-associated herpesvirus latency-associated nuclear antigen interacts with bromodomain protein Brd4 on host mitotic chromosomes," *J Virol* 80(18):8909-19 (2006); Palermo, R. D., et al., "RNA polymerase II stalling promotes nucleosome occlusion and pTEFb recruitment to drive immortalization by Epstein-Barr virus," *PLoS Pathog* 7(10):e1002334 (2011); Poreba, E., et al., "Epigenetic mechanisms in virus-induced tumorigenesis," *Clin Epigenetics* 2(2):233-47. 2011. In another embodiment, because of their ability to reactivate HIV-1 in models of latent T cell infection and latent monocyte infection, BET inhibitors could be used in combination with anti-retroviral therapeutics for treating HIV. Zhu, J., et al., "Reactivation of Latent HIV-1 by Inhibition of BRD4," *Cell Rep* (2012); Banerjee, C., et al., "BET bromodomain inhibition as a novel strategy for reactivation of HIV-1," *J Leukoc Biol* (2012); Bartholomeeusen, K., et al., "BET bromodomain inhibition activates transcription via a transient release of P-TEFb from 7SK snRNP," *J Biol Chem* (2012); Li, Z., et al., "The BET bromodomain inhibitor JQ1 activates HIV latency through antagonizing Brd4 inhibition of Tat-transactivation," *Nucleic Acids Res* (2012.)

In one embodiment, because of the role of epigenetic processes and bromodomain-containing proteins in neurological disorders, BET inhibitor compounds of Formula I, Formula Ia, and/or Formula II, stereoisomers, tautomers, pharmaceutically acceptable salts, or hydrates thereof, or compositions comprising one or more of those compounds may be used to treat diseases including, but not limited to, Alzheimer's disease, Parkinson's disease, Huntington disease, bipolar disorder, schizophrenia, Rubinstein-Taybi syndrome, and epilepsy. Prinjha, R. K., J. Witherington, and K. Lee, "Place your BETs: the therapeutic potential of bromodomains," *Trends Pharmacol Sci* 33(3):146-53 (2012); Muller, S., et al., "Bromodomains as therapeutic targets," *Expert Rev Mol Med* 13:e29 (2011).

In one embodiment, because of the effect of BRDT depletion or inhibition on spermatid development, BET inhibitor compounds of Formula I, Formula Ia, and/or Formula II, stereoisomers, tautomers, pharmaceutically acceptable salts, or hydrates thereof, or compositions comprising one or more of those compounds may be used as reversible, male contraceptive agents. Matzuk, M. M., et al., "Small-Molecule Inhibition of BRDT for Male Contraception," *Cell* 150(4): p. 673-684 (2012); Berkovits, B. D., et al., "The testis-specific double bromodomain-containing protein BRDT forms a complex with multiple spliceosome components and is required for mRNA splicing and 3'-UTR truncation in round spermatids," *Nucleic Acids Res* 40(15): 7162-75 (2012).

Pharmaceutical Compositions

Pharmaceutical compositions of the present disclosure comprise at least one compound of Formulae I-II, or tautomer, stereoisomer, pharmaceutically acceptable salt or hydrate thereof formulated together with one or more pharmaceutically acceptable carriers. These formulations include those suitable for oral, rectal, topical, buccal and parenteral (e.g., subcutaneous, intramuscular, intradermal, or intravenous) administration. The most suitable form of administration in any given case will depend on the degree and severity of the condition being treated and on the nature of the particular compound being used.

Formulations suitable for oral administration may be presented in discrete units, such as capsules, cachets, lozenges, or tablets, each containing a predetermined amount of a compound of the present disclosure as powder or granules; as a solution or a suspension in an aqueous or non-aqueous liquid; or as an oil-in-water or water-in-oil emulsion. As indicated, such formulations may be prepared by any suitable method of pharmacy which includes the step of bringing into association at least one compound of the present disclosure as the active compound and a carrier or excipient (which may constitute one or more accessory ingredients). The carrier must be acceptable in the sense of being compatible with the other ingredients of the formulation and must not be deleterious to the recipient. The carrier may be a solid or a liquid, or both, and may be formulated with at least one compound described herein as the active compound in a unit-dose formulation, for example, a tablet, which may contain from about 0.05% to about 95% by weight of the at least one active compound. Other pharmacologically active substances may also be present including other compounds. The formulations of the present disclosure may be prepared by any of the well-known techniques of pharmacy consisting essentially of admixing the components.

For solid compositions, conventional nontoxic solid carriers include, for example, pharmaceutical grades of mannitol, lactose, starch, magnesium stearate, sodium saccharin, talc, cellulose, glucose, sucrose, magnesium carbonate, and the like. Liquid pharmacologically administrable compositions can, for example, be prepared by, for example, dissolving or dispersing, at least one active compound of the present disclosure as described herein and optional pharmaceutical adjuvants in an excipient, such as, for example, water, saline, aqueous dextrose, glycerol, ethanol, and the like, to thereby form a solution or suspension. In general, suitable formulations may be prepared by uniformly and intimately admixing the at least one active compound of the present disclosure with a liquid or finely divided solid carrier, or both, and then, if necessary, shaping the product. For example, a tablet may be prepared by compressing or molding a powder or granules of at least one compound of the present disclosure, which may be optionally combined with one or more accessory ingredients. Compressed tablets may be prepared by compressing, in a suitable machine, at least one compound of the present disclosure in a free-flowing form, such as a powder or granules, which may be optionally mixed with a binder, lubricant, inert diluent and/or surface active/dispersing agent(s). Molded tablets may be made by molding, in a suitable machine, where the powdered form of at least one compound of the present disclosure is moistened with an inert liquid diluent.

Formulations suitable for buccal (sub-lingual) administration include lozenges comprising at least one compound of the present disclosure in a flavored base, usually sucrose and acacia or tragacanth, and pastilles comprising the at least one compound in an inert base such as gelatin and glycerin or sucrose and acacia.

Formulations of the present disclosure suitable for parenteral administration comprise sterile aqueous preparations of at least one compound of Formulae I-II or tautomers, stereoisomers, pharmaceutically acceptable salts, and hydrates thereof, which are approximately isotonic with the blood of the intended recipient. These preparations are administered intravenously, although administration may also be effected by means of subcutaneous, intramuscular, or intradermal injection. Such preparations may conveniently be prepared by admixing at least one compound described herein with water and rendering the resulting solution sterile and isotonic with the blood. Injectable compositions according to the present disclosure may contain from about 0.1 to about 5% w/w of the active compound.

Formulations suitable for rectal administration are presented as unit-dose suppositories. These may be prepared by admixing at least one compound as described herein with one or more conventional solid carriers, for example, cocoa butter, and then shaping the resulting mixture.

Formulations suitable for topical application to the skin may take the form of an ointment, cream, lotion, paste, gel, spray, aerosol, or oil. Carriers and excipients which may be used include Vaseline, lanoline, polyethylene glycols, alcohols, and combinations of two or more thereof. The active compound (i.e., at least one compound of Formulae I-IV or tautomers, stereoisomers, pharmaceutically acceptable salts, and hydrates thereof) is generally present at a concentration of from about 0.1% to about 15% w/w of the composition, for example, from about 0.5 to about 2%.

The amount of active compound administered may be dependent on the subject being treated, the subject's weight, the manner of administration and the judgment of the prescribing physician. For example, a dosing schedule may involve the daily or semi-daily administration of the encapsulated compound at a perceived dosage of about 1 µg to about 1000 mg. In another embodiment, intermittent administration, such as on a monthly or yearly basis, of a dose of the encapsulated compound may be employed. Encapsulation facilitates access to the site of action and allows the administration of the active ingredients simultaneously, in theory producing a synergistic effect. In accordance with standard dosing regimens, physicians will readily determine optimum dosages and will be able to readily modify administration to achieve such dosages.

A therapeutically effective amount of a compound or composition disclosed herein can be measured by the therapeutic effectiveness of the compound. The dosages, however, may be varied depending upon the requirements of the patient, the severity of the condition being treated, and the compound being used. In one embodiment, the therapeutically effective amount of a disclosed compound is sufficient to establish a maximal plasma concentration. Preliminary doses as, for example, determined according to animal tests, and the scaling of dosages for human administration is performed according to art-accepted practices.

Toxicity and therapeutic efficacy can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compositions that exhibit large therapeutic indices are preferable.

Data obtained from the cell culture assays or animal studies can be used in formulating a range of dosage for use in humans. Therapeutically effective dosages achieved in one animal model may be converted for use in another animal, including humans, using conversion factors known in the art (see, e.g., Freireich et al., *Cancer Chemother. Reports* 50(4):219-244 (1966) and Table I for Equivalent Surface Area Dosage Factors).

TABLE I

Equivalent Surface Area Dosage Factors:

| From: | To: | | | | |
|---|---|---|---|---|---|
| | Mouse (20 g) | Rat (150 g) | Monkey (3.5 kg) | Dog (8 kg) | Human (60 kg) |
| Mouse | 1 | ½ | ¼ | ⅙ | 1/12 |
| Rat | 2 | 1 | ½ | ¼ | 1/7 |
| Monkey | 4 | 2 | 1 | ⅗ | ⅓ |
| Dog | 6 | 4 | ⅗ | 1 | ½ |
| Human | 12 | 7 | 3 | 2 | 1 |

The dosage of such compounds lies preferably within a range of circulating concentrations that include the $ED_{50}$ with little or no toxicity. The dosage may vary within this range depending upon the dosage form employed and the route of administration utilized. Generally, a therapeutically effective amount may vary with the subject's age, condition, and gender, as well as the severity of the medical condition in the subject. The dosage may be determined by a physician and adjusted, as necessary, to suit observed effects of the treatment.

In one embodiment, a compound of Formulae I-II or a tautomer, stereoisomer, pharmaceutically acceptable salt or hydrate thereof, is administered in combination with another therapeutic agent. The other therapeutic agent can provide additive or synergistic value relative to the administration of a compound of the present disclosure alone. The therapeutic agent can be, for example, a statin; a PPAR agonist, e.g., a thiazolidinedione or fibrate; a niacin, a RVX, FXR or LXR agonist; a bile-acid reuptake inhibitor; a cholesterol absorption inhibitor; a cholesterol synthesis inhibitor; a cholesteryl ester transfer protein (CETP), an ion-exchange resin; an antioxidant; an inhibitor of AcylCoA cholesterol acyltransferase (ACAT inhibitor); a tyrophostine; a sulfonylurea-based drug; a biguanide; an alpha-glucosidase inhibitor; an apolipoprotein E regulator; a HMG-CoA reductase inhibitor, a microsomal triglyceride transfer protein; an LDL-lowing drug; an HDL-raising drug; an HDL enhancer; a regulator of the apolipoprotein A-IV and/or apolipoprotein genes; or any cardiovascular drug.

In another embodiment, a compound of Formulae I and/or Formula II or a tautomer, stereoisomer, pharmaceutically acceptable salt or hydrate thereof, is administered in combination with one or more anti-inflammatory agents. Anti-inflammatory agents can include immunosuppressants, TNF inhibitors, corticosteroids, non-steroidal anti-inflammatory drugs (NSAIDs), disease-modifying anti-rheumatic drugs (DMARDS), and the like. Exemplary anti-inflammatory agents include, for example, prednisone; methylprenisolone (Medrol®), triamcinolone, methotrexate (Rheumatrex®, Trexall®), hydroxychloroquine (Plaquenil®), sulfasalzine (Azulfidine®), leflunomide (Arava®), etanercept (Enbrel®), infliximab (Remicade®), adalimumab (Humira®), rituximab (Rituxan®), abatacept (Orencia®), interleukin-1, anakinra (Kineret™), ibuprofen, ketoprofen, fenoprofen, naproxen, aspirin, acetominophen, indomethacin, sulindac, meloxicam, piroxicam, tenoxicam, lornoxicam, ketorolac, etodolac, mefenamic acid, meclofenamic acid, flufenamic acid, tolfenamic acid, diclofenac, oxaprozin, apazone, nimesulide, nabumetone, tenidap, etanercept, tolmetin, phenylbutazone, oxyphenbutazone, diflunisal, salsalate, olsalazine, or sulfasalazine.

EXAMPLES

General Methods.

Unless otherwise noted, reagents and solvents were used as received from commercial suppliers. Proton nuclear magnetic resonance spectra were obtained on a Bruker AVANCE 300 spectrometer at 300 MHz or Bruker AVANCE 500 spectrometer at 500 MHz or a Bruker AVANCE 300 spectrometer at 300 MHz. Spectra are given in ppm (δ) and coupling constants, J values, are reported in hertz (Hz). Tetramethylsilane was used as an internal standard for $^1$H nuclear magnetic resonance. Mass spectra analyses were performed on Waters Aquity UPLC Mass Spectrometer in ESI or APCI mode when appropriate, Agilent 6130A Mass Spectrometer in ESI, APCI, or MultiMode mode when appropriate or Applied Biosystems API-150EX Spectrometer in ESI or APCI mode when appropriate. Silica gel chromatographys were in general performed on a Teledyne Isco CombiFlash® Rf 200 system or a Teledyne Isco CombiFlash® Companion system.

Abbreviations: CDI: 1,1'-carbonyldiimidazole; DMAP: N,N-dimethylaminopropylamine; EDC: 1-(3-dimethylaminopropyl)-3-ethylcarbodiimide hydrochloride; m-CPBA: 3-chloroperoxybenzoic acid; NBS: N-bromosuccinimide.

General Procedure A:

Preparation of 9-Benzyl-2-(3,5-dimethylisoxazol-4-yl)-9H-purin-6-amine (Example Compound 1)

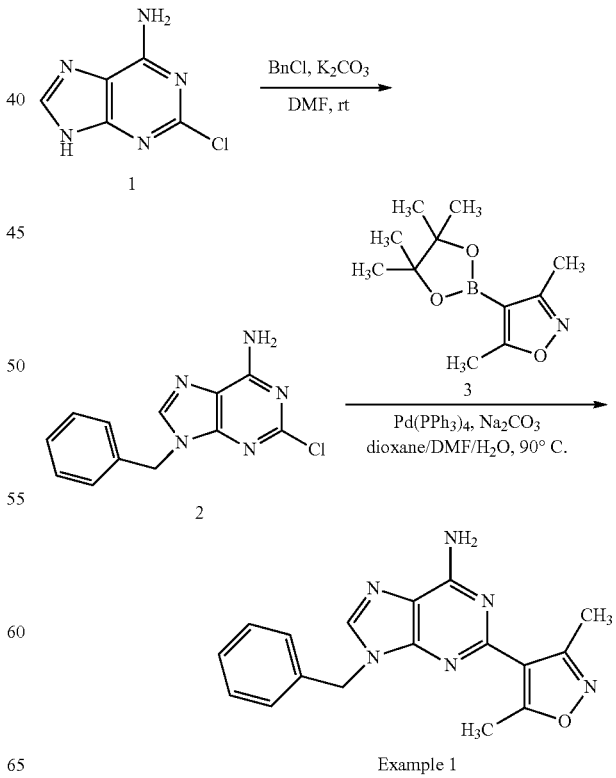

Example 1

Step 1: To a slurry of 1 (1.50 g, 8.84 mmol) in DMF (50 mL) was added potassium carbonate (3.64 g, 26.4 mmol) and benzyl chloride (1.01 mL, 8.84 mmol). The reaction was stirred at rt for 16 h. The reaction mixture was filtered, the filtrate was poured into water (100 mL) and stirred for 5 minutes. The solid was collected and dried to give 2 (1.60 g, 70%) as a yellow solid: $^1$H NMR (300 MHz, DMSO-d$_6$) δ 8.26 (s, 1H), 7.80 (br s, 2H), 7.38-7.26 (m, 5H), 5.34 (s, 2H); ESI m/z 260 [M+H]$^+$.

Step 2: To a solution of 2 (260 mg, 1.0 mmol) in 1,4-dioxane (10 mL) and DMF (4 mL) was added 3,5-dimethyl-4-(4,4,5,5-tetramethyl-1,3,2-dioxaborolan-2-yl)isoxazole (335 mg, 1.5 mmol), sodium carbonate (2.0 M in H$_2$O, 1.0 mL, 2.0 mmol) and tetrakis(triphenylphosphine)palladium(0) (116 mg, 0.1 mmol). The reaction mixture was purged with nitrogen and heated at 80° C. for 16 h. The mixture was diluted with methylene chloride (20 mL) and filtered. The filtrate was concentrated and purified by chromatography (silica gel, 0-5% methylene chloride/methanol) followed by trituration with EtOAc/hexanes to afford 9-benzyl-2-(3,5-dimethylisoxazol-4-yl)-9H-purin-6-amine (Example Compound 1) (110 mg, 34%) as a white solid: $^1$H NMR (300 MHz, DMSO-d$_6$) δ 8.29 (s, 1H), 7.36-7.28 (m, 7H), 5.38 (s, 2H), 2.73 (s, 3H), 2.51 (s, 3H); ESI m/z 321 [M+H]$^+$.

Preparation of 3-Benzyl-5-(3,5-dimethylisoxazol-4-yl)-1H-imidazo[4,5-b]pyridin-2(3H)-one (Example Compound 2)

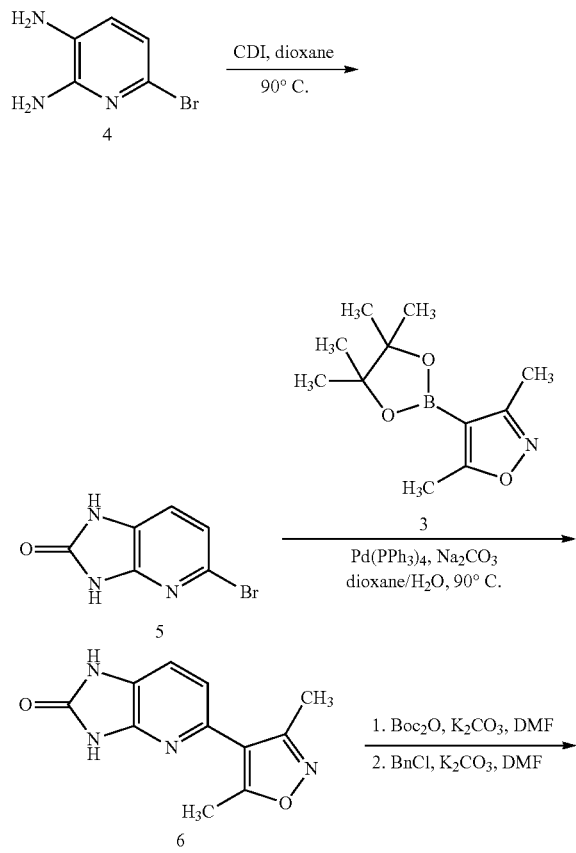

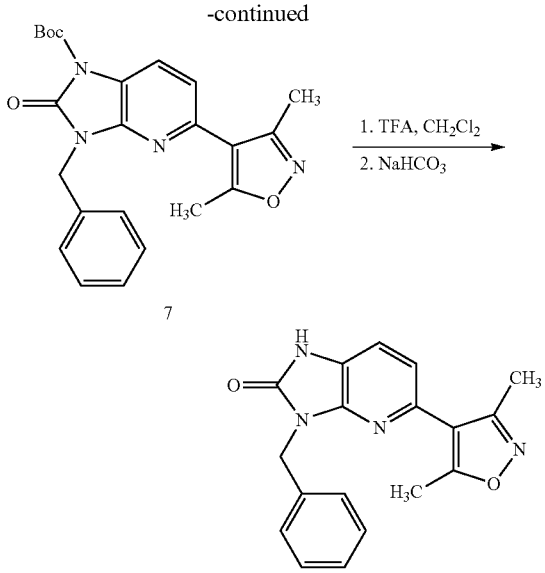

Example 2

Step 1: To a solution of 4 (500 mg, 2.66 mmol) in 1,4-dioxane (15 mL) was added CDI (517 mg, 3.19 mmol). The reaction was heated at 60° C. for 16 h. The solid was collected and dried to give 5 (340 mg, 60%) as a light purple solid: $^1$H NMR (300 MHz, DMSO-d$_6$) δ 11.58 (br s, 1H), 11.02 (br s, 1H), 7.19 (d, J=8.1 Hz, 1H), 7.13 (d, J=8.1 Hz, 1H).

Step 2: To a solution of 5 (170 mg, 0.79 mmol) in 1,4-dioxane (12 mL) and DMF (6 mL) was added 3,5-dimethyl-4-(4,4,5,5-tetramethyl-1,3,2-dioxaborolan-2-yl)isoxazole (352 mg, 1.58 mmol), sodium carbonate (2.0 M in H$_2$O, 1.19 mL, 2.37 mmol) and tetrakis(triphenylphosphine)palladium(0) (92 mg, 0.08 mmol). The reaction mixture was purged with nitrogen and heated at 80° C. for 16 h. The mixture was diluted with methylene chloride (20 mL) and filtered. The filtrate was concentrated and purified by chromatography (silica gel, 0-5% methylene chloride/methanol) to afford 6 (130 mg, 71%) as a white solid: $^1$H NMR (300 MHz, DMSO-d$_6$) δ 11.38 (br s, 1H), 10.90 (br s, 1H), 7.30 (d, J=7.8 Hz, 1H), 7.07 (d, J=8.1 Hz, 1H), 2.49 (s, 3H), 2.33 (s, 3H).

Step 3: To a solution of 6 (100 mg, 0.43 mmol) in DMF (10 mL) was added potassium carbonate (72 mg, 0.52 mmol) and di-tert-butyl dicarbonate (104 mg, 0.48 mmol). The reaction was stirred at rt for 16 h. To the reaction mixture was added potassium carbonate (72 mg, 0.52 mmol) and benzyl chloride (0.14 mL, 0.48 mmol). The reaction was stirred at rt for 16 h. The mixture was diluted with EtOAc (100 mL) and washed with brine (50 mL). The organic layer was dried over sodium sulfate, filtered and concentrated. Purification by chromatography (silica gel, 0-30% ethyl acetate/hexanes) afforded 6 (130 mg, 71%) as a colorless gum: $^1$H NMR (300 MHz, DMSO-d$_6$) δ 7.97 (d, J=8.1 Hz, 1H), 7.38-7.27 (m, 6H), 5.05 (s, 2H), 2.49 (s, 3H), 2.29 (s, 3H), 1.61 (s, 9H).

Step 4: A solution of 7 (130 mg, 0.31 mmol) in methylene chloride (4 mL) and TFA (2 mL) was stirred at rt for 2 h. The mixture was concentrated, the residue was dissolved in methylene chloride (100 mL), washed with saturated NaHCO$_3$ (50 mL×2) and brine (50 mL). The organic layer was dried over sodium sulfate, filtered and concentrated to afford 3-benzyl-5-(3,5-dimethylisoxazol-4-yl)-1H-imidazo

[4,5-b]pyridin-2(3H)-one (Example Compound 2) (81 mg, 81%) as an off-white solid: ¹H NMR (300 MHz, DMSO-d₆) δ 11.31 (s, 1H), 7.40 (d, J=7.8 Hz, 1H), 7.34-7.25 (m, 5H), 7.15 (d, J=7.8 Hz, 1H), 5.03 (s, 2H), 2.47 (s, 3H), 2.28 (s, 3H); ESI m/z 321 [M+H]⁺.

Preparation of 1-Benzyl-5-(3,5-dimethylisoxazol-4-yl)-1H-imidazo[4,5-b]pyridin-2(3H)-one (Example Compound 3)

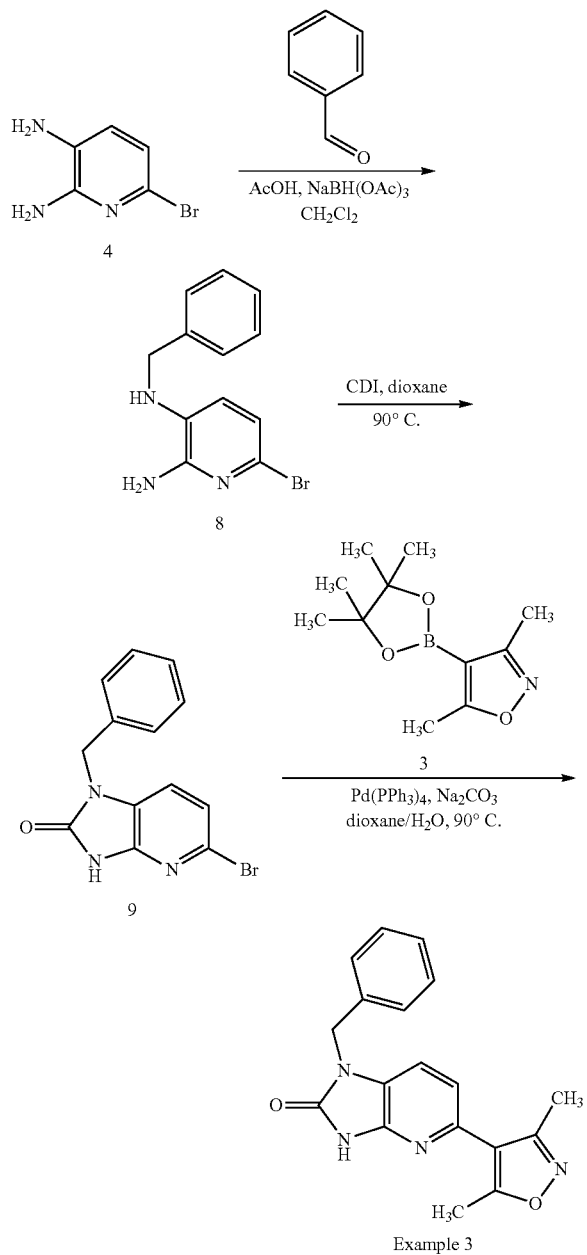

Example 3

Step 1: To a solution of 4 (500 mg, 2.66 mmol) and benzaldehyde (282 mg, 2.66 mmol) in methylene chloride (15 mL) was added acetic acid (319 mg, 5.32 mmol). The reaction was stirred at rt for 30 minutes, then NaBH(OAc)₃ (1.69 g, 7.98 mmol) was added. The reaction mixture was stirred at rt for 16 h. The mixture was diluted with methylene chloride (100 mL) and saturated aq. NaHCO₃ (50 mL) was added slowly. The organic layer was separated, dried over sodium sulfate, filtered and concentrated. The residue was triturated with methylene chloride/EtOAc to give 8 (401 mg, 54%) as a light brown solid: ¹H NMR (300 MHz, DMSO-d₆) δ 7.34-7.22 (m, 5H), 6.48 (d, J=7.8 Hz, 1H), 6.40 (d, J=7.8 Hz, 1H), 6.02 (br s, 2H), 5.54 (t, J=5.7 Hz, 1H), 4.27 (d, J=5.4 Hz, 2H).

Step 2: To a solution of 8 (400 mg, 1.44 mmol) in 1,4-dioxane (10 mL) was added CDI (514 mg, 3.17 mmol). The reaction was heated at 110° C. for 16 h. The reaction mixture was concentrated. Purification by chromatography (silica gel, 0-40% ethyl acetate/hexanes) afforded 9 (310 mg, 71%) as a white solid: ¹H NMR (300 MHz, DMSO-d₆) δ 11.96 (s, 1H), 7.35-7.27 (m, 6H), 7.19 (d, J=7.8 Hz, 1H), 5.02 (s, 2H).

Step 3: To a solution of 9 (310 mg, 1.02 mmol) in 1,4-dioxane (10 mL) was added 3,5-dimethyl-4-(4,4,5,5-tetramethyl-1,3,2-dioxaborolan-2-yl)isoxazole (341 mg, 1.53 mmol), sodium carbonate (2.0 M in H₂O, 1.02 mL, 2.04 mmol) and tetrakis(triphenylphosphine)palladium(0) (59 mg, 0.05 mmol). The reaction mixture was purged with nitrogen and heated at 80° C. for 16 h. The mixture was diluted with methylene chloride (20 mL) and filtered. The filtrate was concentrated and the residue was purified by chromatography (silica gel, 0-80% EtOAc/hexanes) and trituration with EtOAc to afford 1-benzyl-5-(3,5-dimethyl-isoxazol-4-yl)-1H-imidazo[4,5-b]pyridin-2(3H)-one (Example Compound 3) (202 mg, 62%) as a white solid: ¹H NMR (300 MHz, DMSO-d₆) δ 11.76 (s, 1H), 7.44 (d, J=7.8 Hz, 1H), 7.36-7.28 (m, 5H), 7.11 (d, J=7.8 Hz, 1H), 5.05 (s, 2H), 2.49 (s, 3H), 2.32 (s, 3H); ESI m/z 321 [M+H]⁺.

General Procedure B

Preparation of 4-(3-Benzyl-3H-imidazo[4,5-b]pyridin-6-yl)-3,5-dimethylisoxazole (Example Compound 4) and 4-(1-Benzyl-1H-imidazo[4,5-b]pyridin-6-yl)-3,5-dimethylisoxazole (Example Compound 5)

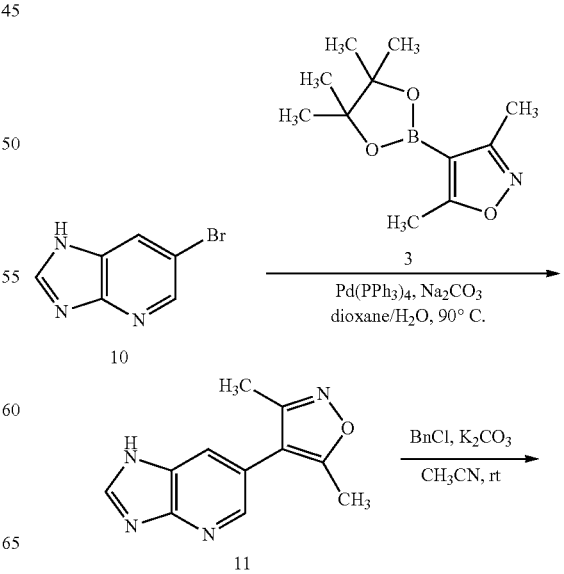

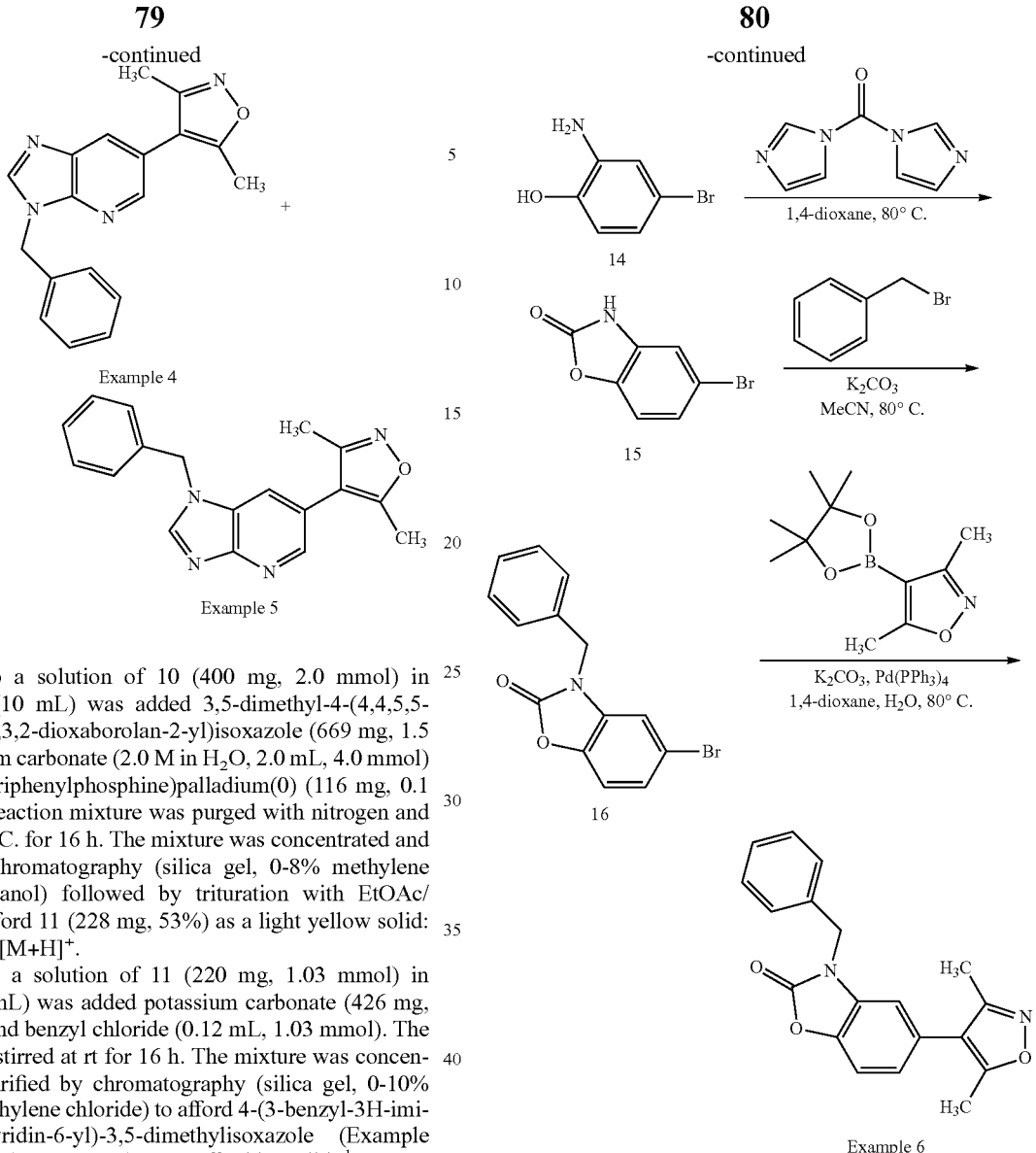

Example 4

Example 5

Step 1: To a solution of 10 (400 mg, 2.0 mmol) in 1,4-dioxane (10 mL) was added 3,5-dimethyl-4-(4,4,5,5-tetramethyl-1,3,2-dioxaborolan-2-yl)isoxazole (669 mg, 1.5 mmol), sodium carbonate (2.0 M in H$_2$O, 2.0 mL, 4.0 mmol) and tetrakis(triphenylphosphine)palladium(0) (116 mg, 0.1 mmol). The reaction mixture was purged with nitrogen and heated at 80° C. for 16 h. The mixture was concentrated and purified by chromatography (silica gel, 0-8% methylene chloride/methanol) followed by trituration with EtOAc/hexanes to afford 11 (228 mg, 53%) as a light yellow solid: ESI m/z 215 [M+H]$^+$.

Step 2: To a solution of 11 (220 mg, 1.03 mmol) in CH$_3$CN (10 mL) was added potassium carbonate (426 mg, 3.09 mmol) and benzyl chloride (0.12 mL, 1.03 mmol). The reaction was stirred at rt for 16 h. The mixture was concentrated and purified by chromatography (silica gel, 0-10% methanol/methylene chloride) to afford 4-(3-benzyl-3H-imidazo[4,5-b]pyridin-6-yl)-3,5-dimethylisoxazole (Example Compound 4) (34 mg, 11%) as an off-white solid: $^1$H NMR (300 MHz, CDCl$_3$) δ 8.34 (d, J=1.8 Hz, 1H), 8.14 (s, 1H), 7.99 (d, J=1.8 Hz, 1H), 7.40-7.31 (m, 5H), 5.52 (s, 2H), 2.44 (s, 3H), 2.30 (s, 3H); ESI m/z 305 [M+H]$^+$; 4-(1-benzyl-1H-imidazo[4,5-b]pyridin-6-yl)-3,5-dimethylisoxazole (Example Compound 5) (39 mg, 12%) as an off-white solid: $^1$H NMR (300 MHz, CDCl$_3$) δ 8.46 (d, J=1.8 Hz, 1H), 8.29 (s, 1H), 7.40-7.37 (m, 3H), 7.34 (d, J=2.1 Hz, 1H), 7.24-7.21 (m, 2H), 5.41 (s, 2H), 2.33 (s, 3H), 2.16 (s, 3H); ESI m/z 305 [M+H]$^+$.

Preparation of 3-Benzyl-5-(3,5-dimethylisoxazol-4-yl)benzo[d]oxazol-2(3H)-one (Example Compound 6)

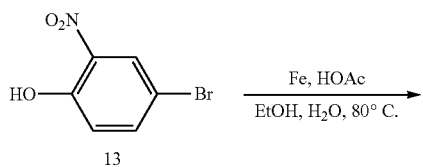

13

Example 6

Step 1: To a solution of 13 (5.00 g, 22.9 mmol) in acetic acid (50 mL), ethanol (100 mL), and water (5 mL) was added iron powder (6.42 g, 115 mmol). The reaction was heated at 80° C. for 2 h under nitrogen. The reaction mixture was cooled to room temperature, concentrated and purified by chromatography (silica gel, 0-100% hexanes/ethyl acetate) to give 14 (3.27 g, 76%) as a brown solid: $^1$H NMR (300 MHz, CDCl$_3$) δ 6.88 (d, J=2.2 Hz, 1H), 6.77 (dd, J=8.3, 2.3 Hz, 1H), 6.60 (d, J=8.3 Hz, 1H), 6.00-5.20 (br s, 3H).

Step 2: To a solution of 14 (1.50 g, 7.98 mmol) in 1,4-dioxane (100 mL) was added 1,1'-carbonyldiimidazole (1.55 g, 9.58 mmol). The reaction was heated at 80° C. for 17 h under nitrogen. The mixture was cooled to room temperature and 2N aq. HCl (40 mL) was added. The solution was diluted with ethyl acetate (200 mL) and washed with brine (2×50 mL). The organic layer was dried over sodium sulfate, filtered and concentrated. Purification by chromatography (silica gel, 0-50% ethyl acetate/hexanes) afforded 15 (1.08 g, 63%) as an orange solid: $^1$H NMR (500 MHz, DMSO-d$_6$) δ 11.81 (s, 1H), 7.27-7.25 (m, 3H).

Step 3: To a solution of 15 (150 mg, 0.701 mmol) in acetonitrile (10 mL) was added benzyl bromide (180 mg, 1.05 mmol) and potassium carbonate (193 mg, 1.40 mmol).

The reaction was heated at 80° C. for 3 h. The reaction mixture was cooled to room temperature, concentrated and purified by chromatography (silica gel, 0-50% ethyl acetate/hexanes) to afford 16 (195 mg, 92%) as an off-white solid: ¹H NMR (500 MHz, CDCl₃) δ 7.41-7.30 (m, 5H), 7.22 (dd, J=8.5, 1.7 Hz, 1H), 7.08 (d, J=8.5 Hz, 1H), 6.97 (d, J=1.6 Hz, 1H), 4.97 (s, 2H).

Step 4: To a solution of 16 (195 mg, 0.641 mmol) in 1,4-dioxane (10 mL) was added 3,5-dimethyl-4-(4,4,5,5-tetramethyl-1,3,2-dioxaborolan-2-yl)isoxazole (172 mg, 0.769 mmol), potassium carbonate (177 mg, 1.28 mmol), and tetrakis(triphenylphosphine)palladium(0) (37 mg, 0.032 mmol). The reaction mixture was purged with nitrogen and heated at 100° C. for 4 h. The reaction mixture was cooled to room temperature, concentrated and purified by chromatography (silica gel, 0-30% ethyl acetate/hexanes). It was further purified by reverse phase HPLC on Polaris column eluting with 10-90% CH₃CN in H₂O to give 3-benzyl-5-(3, 5-dimethylisoxazol-4-yl)benzo[d]oxazol-2(3H)-one (Example Compound 6) (115 mg, 56%) as an off-white solid: ¹H NMR (500 MHz, DMSO-d₆) δ 7.47-7.42 (m, 3H), 7.40-7.34 (m, 2H), 7.34-7.28 (m, 1H), 7.23 (d, J=1.6 Hz, 1H), 7.12 (dd, J=8.2 Hz, 7.7 Hz, 1H), 5.07 (s, 2H), 2.33 (s, 3H), 2.15 (s, 3H); ESI m/z 321 [M+H]⁺.

General Procedure C:

Preparation of 1-Benzyl-6-(3,5-dimethylisoxazol-4-yl)-1H-benzo[d]imidazol-4-amine (Example Compound 7), 1-Benzyl-5-(3,5-dimethylisoxazol-4-yl)-1H-benzo[d]imidazol-7-amine (Example Compound 8) and N,1-Dibenzyl-6-(3,5-dimethylisoxazol-4-yl)-1H-benzo[d]imidazol-4-amine (Example Compound 9)

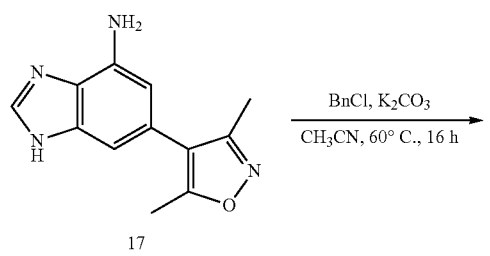

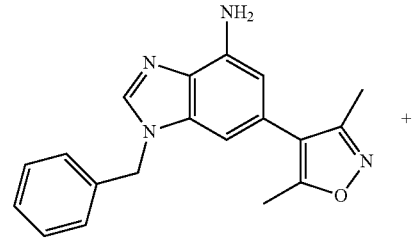

Example 7

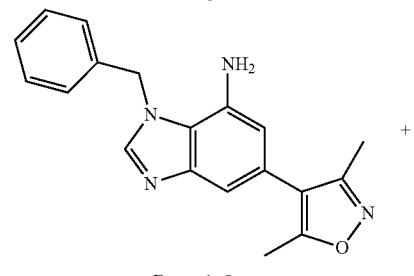

Example 8

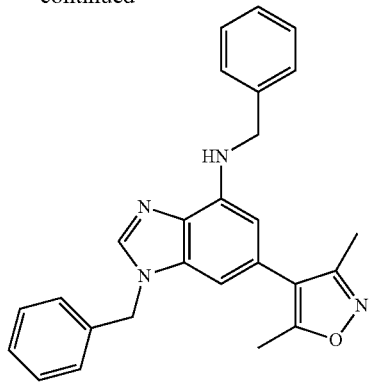

Example 9

To a solution of 6-(3,5-dimethylisoxazol-4-yl)-1H-benzo[d]imidazol-4-amine 17 (290 mg, 1.27 mmol) in CH₃CN (15 mL) was added potassium carbonate (350 mg, 2.54 mmol) and benzyl chloride (200 mg, 1.59 mmol). The reaction mixture was stirred at 60° C. for 16 h. The mixture was diluted with methylene chloride (20 mL) and filtered through a layer of Celite. The filtrate was concentrated and purified by chromatography (silica gel, 0-10% CH₃OH/CH₂Cl₂) to afford 1-benzyl-6-(3,5-dimethylisoxazol-4-yl)-1H-benzo[d]imidazol-4-amine (Example Compound 7) (109 mg, 27%) as an off-white solid: ¹H NMR (300 MHz, CDCl₃) δ 7.95 (s, 1H), 7.37-7.34 (m, 3H), 7.23-7.20 (m, 2H), 6.46 (d, J=1.2 Hz, 1H), 6.40 (d, J=1.2 Hz, 1H), 5.34 (s, 2H), 2.31 (s, 3H), 2.16 (s, 3H); ESI MS m/z 319 [M+H]⁺; 1-benzyl-5-(3,5-dimethylisoxazol-4-yl)-1H-benzo[d]imidazol-7-amine (Example Compound 8) (19 mg, 4.7%) as an off-white solid: ¹H NMR (300 MHz, CDCl₃) δ 8.15 (s, 1H), 7.43-7.40 (m, 3H), 7.23 (d, J=1.2 Hz, 1H), 7.20-7.17 (m, 2H), 6.39 (d, J=1.2 Hz, 1H), 5.69 (s, 2H), 2.40 (s, 3H), 2.27 (s, 3H); ESI MS m/z 319 [M+H]⁺; N,1-dibenzyl-6-(3,5-dimethylisoxazol-4-yl)-1H-benzo[d]imidazol-4-amine (Example Compound 9) (40 mg, 8%) as an off-white solid: ¹H NMR (300 MHz, DMSO-d₆) δ 8.27 (s, 1H), 7.40-7.18 (m, 10H), 6.62 (d, J=1.2 Hz, 1H), 6.57 (t, J=6.0 Hz, 1H), 5.97 (d, J=1.2 Hz, 1H), 5.41 (s, 2H), 4.48 (d, J=6.0 Hz, 2H), 2.12 (s, 3H), 1.94 (s, 3H); ESI MS m/z 409 [M+H]⁺.

Preparation of 1-Benzyl-6-(3,5-dimethylisoxazol-4-yl)-1H-imidazo[4,5-b]pyridin-2(3H)-one (Example Compound 10)

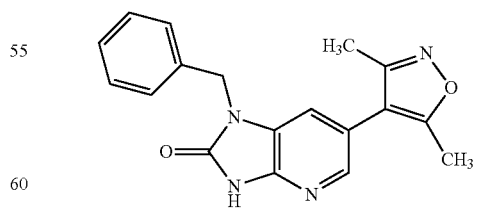

Example 10

1-Benzyl-6-(3,5-dimethylisoxazol-4-yl)-1H-imidazo[4,5-b]pyridin-2(3H)-one (Example Compound 10) was prepared by following the method for the preparation of Example 3 affording the product (158 mg, 47%) as a white solid: ¹H NMR (300 MHz, DMSO-d₆) δ 11.81 (s, 1H), 7.90 (d, J=2.1

Hz, 1H), 7.44-7.25 (m, 6H), 5.05 (s, 2H), 2.34 (s, 3H), 2.16 (s, 3H); MM m/z 321 [M+H]+.

Preparation of 1-Benzyl-7-(3,5-dimethylisoxazol-4-yl)quinoxalin-2(1H)-one (Example Compound 11)

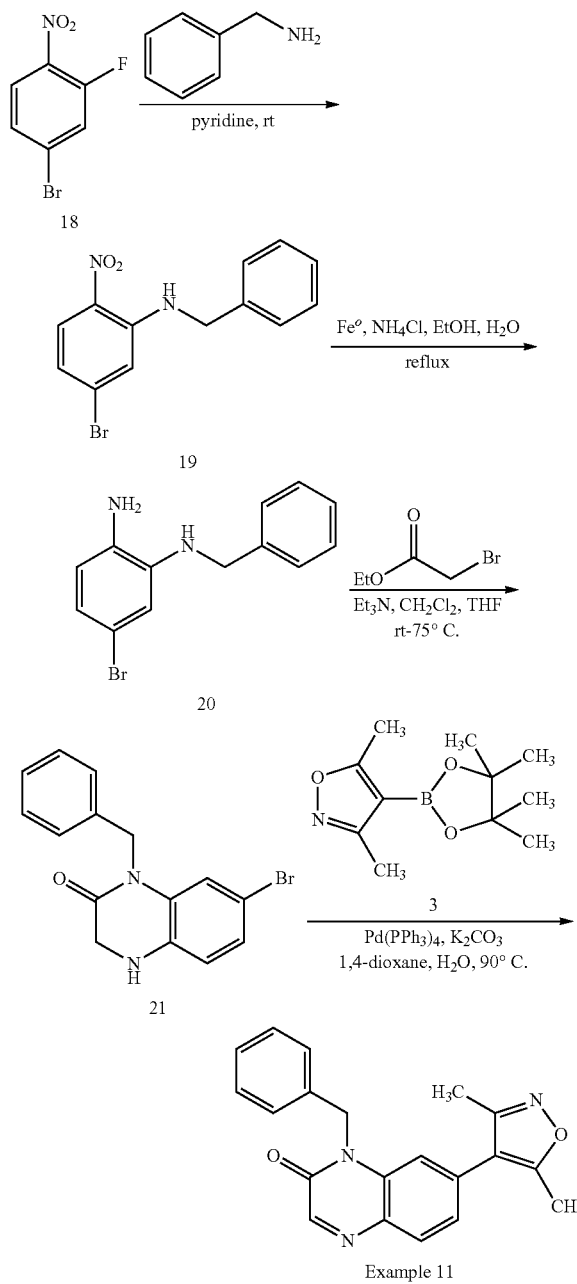

Step 1: A solution of 18 (500 mg, 2.3 mmol), benzylamine (1.2 g, 11.4 mmmol) and pyridine (5.0 mL) was stirred at room temperature for 18 hours. The solvent was removed in vacuo and the product was purified by chromatography (silica gel, 0-10% ethyl acetate/hexanes) to provide 19 (630 mg, 91%) as a yellow solid: $^1$H NMR (500 MHz, CDCl$_3$) δ 8.38 (s, 1H), 8.05 (d, J=9.1 Hz, 1H), 7.40-7.32 (m, 5H), 7.01 (d, J=1.9 Hz, 1H), 6.79 (dd, J=9.1, 1.9 Hz, 1H), 4.51 (d, J=5.5 Hz, 2H).

Step 2: A mixture of 19 (100 mg, 0.33 mmol), iron powder (127 mg, 2.28 mmol), ammonium chloride (27 mg, 0.5 mmol), water (0.5 mL) and ethanol (3 mL) was heated at reflux for 0.5 hour. The reaction mixture was cooled and filtered. The solvent was removed to provide 20 (90 mg, 100%) as an off-white solid: $^1$H NMR (300 MHz, CDCl$_3$) δ 7.40-7.29 (m, 5H), 6.81-6.77 (m, 2H), 6.61-6.58 (m, 1H), 4.27 (s, 2H), 3.41 (s, 1H); ESI m/z 278 [M+H]+.

Step 3: To a mixture of 20 (100 mg, 0.36 mmol), triethylamine (48 mg, 0.47 mmol), CH$_2$Cl$_2$ (0.5 mL) and THF (1.0 mL) was added a solution of ethyl bromoacetate (78 mg, 0.47 mmol) in THF (1.0 mL) at room temperature. The reaction mixture was stirred for 18 hours and then heated to 75° C. for 1 hour. The reaction mixture was concentrated and the product purified by chromatography (silica gel, 0-30% ethyl acetate/hexanes) to provide 21 (44 mg, 39%) as a tan solid: $^1$H NMR (500 MHz, CDCl$_3$) δ 7.38-7.29 (m, 4H), 7.24-7.22 (m, 2H), 6.98-6.93 (m, 2H), 6.55 (d, J=8.3 Hz, 1H), 5.13 (s, 2H), 4.05 (s, 2H); ESI m/z 318 [M+H]+.

Step 4: A mixture of 21 (44 mg, 0.14 mmol), 3 (47 mg, 0.21 mmol), K$_2$CO$_3$ (39 mg, 0.28 mmol), tetrakis(triphenylphosphine)palladium(0) (8 mg, 0.01 mmol), 1,4-dioxane (3 mL) and water (0.5 mL) was heated at 90° C. for 16 hours. The reaction mixture was concentrated onto silica gel and the product purified by chromatography (silica gel, 0-50% ethyl acetate/hexanes) to provide 1-benzyl-7-(3,5-dimethylisoxazol-4-yl)quinoxalin-2(1H)-one (Example Compound 11) (16 mg, 34%) as an off-white solid: $^1$H NMR (300 MHz, CDCl$_3$) δ 8.43 (s, 1H), 7.94 (d, J=8.2 Hz, 1H), 7.35-7.32 (m, 2H), 7.29-7.27 (m, 1H), 7.21-7.18 (m, 3H), 7.04 (s, 1H), 5.51 (s, 1H), 2.16 (s, 3H), 2.02 (s, 3H); ESI m/z 332 [M+H]+.

Preparation of 1-Benzyl-7-(3,5-dimethylisoxazol-4-yl)-3,4-dihydroquinazolin-2(1H)-one (Example Compound 12)

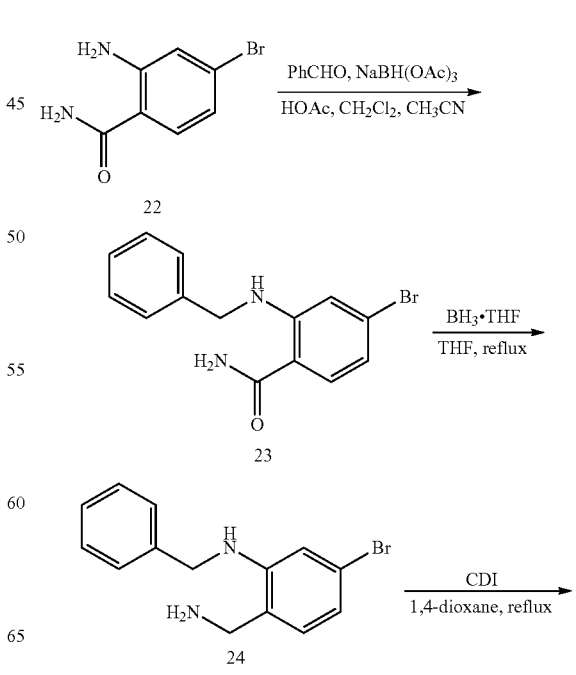

-continued

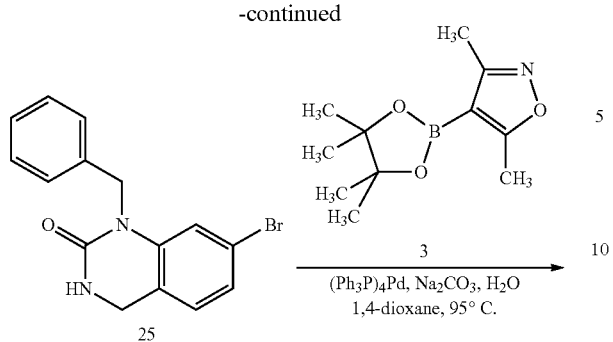

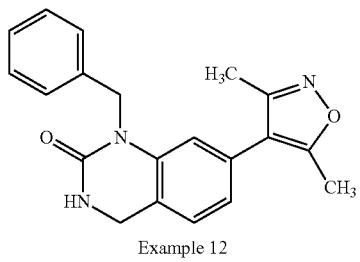

Example 12

Step 1: To a solution of 22 (1.19 g, 5.53 mmol) and benzaldehyde (594 mg, 5.60 mmol) in CH₂Cl₂ (50 mL) and CH₃CN (50 mL) was added acetic acid (0.2 mL). The mixture was stirred at rt for 1 h. NaBH(OAc)₃ (3.52 g, 16.59 mmol) was added. The mixture was stirred at rt for 8 h. The reaction was quenched with saturated aq. NaHCO₃ (50 mL) and concentrated, the residue was suspended in EtOAc (300 mL), washed with brine (100 mL). The organic layer was separated, dried over sodium sulfate, filtered and concentrated. The residue was purified by chromatography (silica gel, 0-50% EtOAc/heptane) to afford 23 (201 mg, 12%) as an off-white solid: $^1$H NMR (300 MHz, DMSO-d₆) δ 8.75 (d, J=5.7 Hz, 1H), 7.93 (br.s, 1H), 7.55 (d, J=8.4 Hz, 1H), 7.38-7.31 (m, 6H), 6.76 (d, J=1.8 Hz, 1H), 6.69 (dd, J=8.4, 1.8 Hz, 1H), 4.39 (d, J=6.0 Hz, 2H).

Step 2: To a solution of 23 (518 mg, 1.70 mmol) in THF (20 mL) was added BH₃*THF (1.0 M in THF, 8.50 mL, 8.50 mmol). The mixture was heated to reflux for 16 h. MeOH (40 mL) was added slowly followed by 2 N HCl (40 mL). The mixture was heated to reflux for 3 h. NH₄OH (60 mL) was added, the mixture was extracted with EtOAc (200 mL×3). The organic layer was separated, dried over sodium sulfate, filtered and concentrated. The residue was purified by chromatography (silica gel, 0-10% MeOH/methylene chloride) to afford 24 (372 mg, 75%) as an colorless gum: $^1$H NMR (300 MHz, DMSO-d₆) δ 7.32-7.21 (m, 5H), 6.98 (d, J=7.8 Hz, 1H), 6.87 (t, J=6.0 Hz, 1H), 6.65 (dd, J=8.1, 2.1 Hz, 1H), 6.53 (d, J=2.1 Hz, 1H), 4.33 (d, J=5.7 Hz, 2H), 3.71 (s, 2H), 1.92 (br.s, 2H).

Step 3: Using the procedure used for Example Compound 3 step 2 starting with compound 24 (362 mg, 1.24 mmol) afforded 25 (325 mg, 85%) as a yellow solid: $^1$H NMR (300 MHz, DMSO-d₆) δ 7.33-7.31 (m, 3H), 7.25-7.23 (m, 3H), 7.09 (d, J=1.8 Hz, 2H), 6.86 (s, 1H), 5.05 (s, 2H), 4.35 (d, J=1.5 Hz, 2H).

Step 4: Using the procedure used for Example Compound 3 step 3 starting with compound 25 (317 mg, 1.00 mmol) afforded Example Compound 12 (199 mg, 60%) as a white solid: $^1$H NMR (500 MHz, DMSO-d₆) δ 7.34-7.21 (m, 7H), 6.90 (dd, J=7.5, 1.0 Hz, 1H), 6.58 (d, J=1.0 Hz, 1H), 5.09 (s, 2H), 4.43 (s, 2H), 2.06 (s, 3H), 1.89 (s, 3H); MM m/z 334 [M+H]⁺.

General Procedure D:

Preparation of 4-(1-benzyl-2-methyl-1H-imidazo[4,5-b]pyridin-6-yl)-3,5-dimethylisoxazol (Example Compound 13)

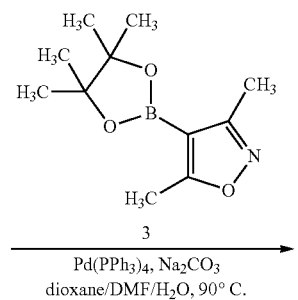

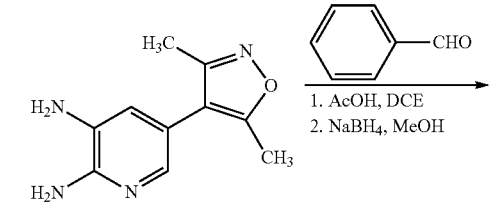

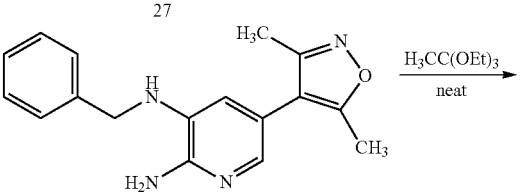

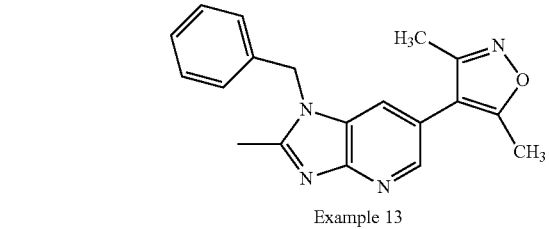

Example 13

Step 1: To a mixture of 26 (1.00 g, 5.32 mmol) and 3 (1.78 g, 7.98 mmol) in 1,4-dioxane (35 mL) and water (7.5 mL) was added potassium carbonate (1.47 g, 10.6 mmol) and tetrakis(triphenylphosphine)palladium(0) (307 mg, 0.27 mmol). The reaction was stirred and heated at 90° C. for 16 h. The reaction mixture was diluted with methanol (20 mL) and silica gel (15 g) was added. The slurry was concentrated to dryness and the resulting powder was loaded onto silica gel and eluted with 0-90% ethyl acetate in hexanes. The clean product was concentrated to give 27 (939 mg, 70%) as a yellow-green solid: $^1$H NMR (500 MHz, CDCl₃) δ 7.45 (t, J=2.0 Hz, 1H), 6.78 (t, J=2.0 Hz, 1H), 2.37 (s, 3H), 2.22 (s, 3H).

Step 2: To a solution of 27 (300 mg, 1.47 mmol) in 1,2-dichloroethane (15 mL) was added benzaldehyde (156 mg, 1.47 mmol) and glacial acetic acid (200 µL) at room temperature. After stirring for 17 h, CH₂Cl₂ (20 mL) then saturated aq. NaHCO₃ (20 mL, slowly) was added. The organic layer was separated and dried over Na₂SO₄. The suspension was filtered and concentrated. The material was purified by chromatography (silica gel, 0-60% ethyl acetate in hexanes) to afford a yellow solid which was dissolved in methanol (10 mL), sodium borohydride (52 mg, 1.35 mmol) was added at room temperature. After stirring for 1 h, additional sodium borohydride (156 mg, 3.40 mmol) was added and the reaction stirred 1 h. A 2N aq. HCl solution was added to the mixture until pH 4 (2 mL) then a saturated NaHCO$_3$ solution was added to basify to pH 8 (2 mL). Water was added (10 mL) and the solution was extracted with ethyl acetate (3×100 mL). The ethyl acetate extracts were combined, dried over Na$_2$SO$_4$, filtered and concentrated to afford 28 (401 mg, 93%) as a white solid: $^1$H NMR (500 MHz, CDCl$_3$) δ 7.48 (s, 1H), 7.37-7.26 (m, 5H), 6.58 (s, 1H), 4.38 (s, 2H), 4.33 (br s, 2H), 3.77 (br s, 1H), 2.24 (s, 3H), 2.08 (s, 3H).

Step 3: To 28 (350 mg, 1.19 mmol) was added triethylorthoacetate (3.0 mL, 16.4 mmol) and sulfamic acid (1 mg). The mixture was heated to 100° C. for 1 h. The mixture was diluted with methanol (20 mL) and adsorbed onto silica gel (10 g). The material was purified by chromatography (silica gel, 0-60% ethyl acetate in hexanes then 0-5% methanol in CH$_2$Cl$_2$) to afford 4-(1-benzyl-2-methyl-1H-imidazo[4,5-b]pyridin-6-yl)-3,5-dimethylisoxazole (Example Compound 13, 169 mg, 45%) as a white solid: $^1$H NMR (500 MHz, CD$_3$OD) δ 8.32 (d, J=1.0 Hz, 1H), 7.78 (d, J=1.0 Hz, 1H), 7.36-7.29 (m, 3H), 7.20-7.17 (m, 2H), 5.56 (s, 2H), 2.69 (s, 3H), 2.36 (s, 3H), 2.18 (s, 3H); ESI m/z 319 [M+H]$^+$.

General Procedure E:

Preparation of 1-(4-chlorobenzyl)-6-(3,5-dimethylisoxazol-4-yl)-4-nitro-1H-benzo[d]imidazol-2(3H)-one (Example Compound 91) and 4-Amino-1-(4-chlorobenzyl)-6-(3,5-dimethylisoxazol-4-yl)-1H-benzo[d]imidazol-2(3H)-one (Example Compound 90)

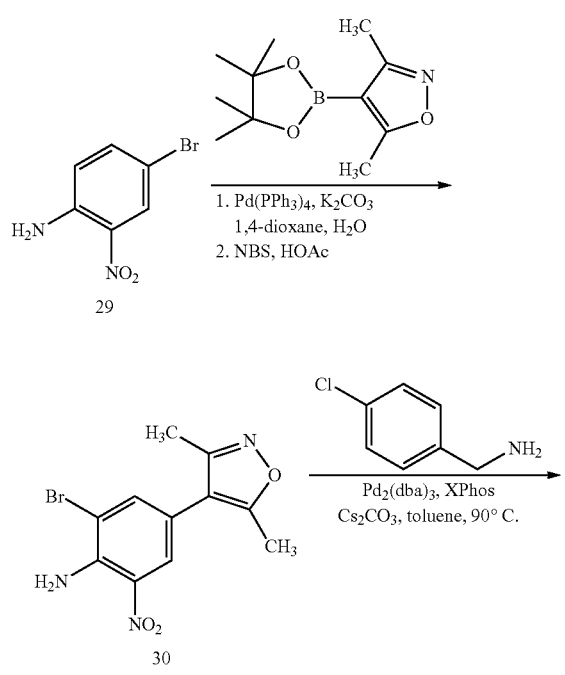

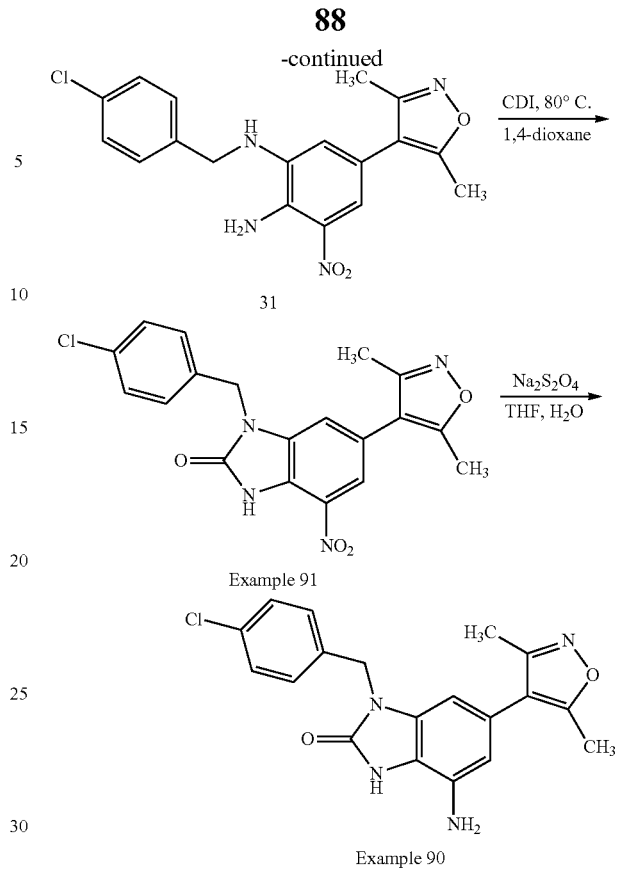

Example 91

Example 90

Step 1: To a solution of 29 (1.00 g, 4.61 mmol) in 1,4-dioxane (40 mL) and water (4 mL) was added 3,5-dimethyl-4-(4,4,5,5-tetramethyl-1,3,2-dioxaborolan-2-yl)isoxazole (1.23 g, 5.53 mmol), potassium carbonate (1.27 g, 9.22 mmol), and tetrakis(triphenylphosphine)palladium(0) (266 mg, 0.231 mmol). The reaction mixture was purged with nitrogen and heated at 90° C. overnight. The reaction mixture was cooled to room temperature, concentrated and purified by chromatography (silica gel, 0-30% ethyl acetate/hexanes) to give a yellow solid which was dissolved in acetic acid (15 mL), N-bromosuccinimide (753 mg, 4.23 mmol) was added at 0° C. The reaction was warmed to room temperature and stirred overnight. The mixture was concentrated in vacuo. The residue was suspended in hot MeOH, cooled to room temperature and basified with 10% aq. NaHCO$_3$. The mixture was diluted with water and filtered. The filter cake was washed with water and dried in vacuo to afford 30 (1.10 g, 87%) as a yellow solid: $^1$H NMR (500 MHz, CDCl$_3$) δ 8.04 (d, J=2.1 Hz, 1H), 7.61 (d, J=2.1 Hz, 1H), 6.69 (bs, 2H), 2.40 (s, 3H), 2.26 (s, 3H); ESI m/z 312 [M+H]$^+$.

Step 2: To a solution of 30 (500 mg, 1.60 mmol) in toluene (50 mL) under nitrogen atmosphere was added 4-chlorobenzylamine (1.36 g, 9.62 mmol), cesium carbonate (1.04 g, 3.02 mmol), 2-dicyclohexylphosphino-2',4',6'-tri-i-propyl-1,1'-biphenyl (114 mg, 0.240 mmol), and tris(dibenzylideneacetone)dipalladium(0) (146 mg, 0.160 mmol). The reaction mixture was heated at 90° C. overnight, cooled to room temperature, and purified by chromatography (silica gel, 0-50% ethyl acetate in hexanes) to afford 31 (290 mg, 49%) as a red solid: ESI m/z 373 [M+H]$^+$.

Step 3: To a mixture of 31 (290 mg, 0.779 mmol) in 1,4-dioxane (10 mL) was added 1,1'-carbonyldiimidazole (630 mg, 3.89 mmol) and DMAP (a crystal). The reaction was heated in a sealed tube at 130° C. for 4 days. The mixture was concentrated and purified by chromatography (silica gel, 0-100% ethyl acetate in hexanes) to give Example Compound 91 (144 mg, 46%) as an orange solid: $^1$H NMR (500 MHz, CD$_3$OD) δ 7.80 (d, J=1.4 Hz, 1H), 7.40-7.35 (m, 4H), 7.24 (d, J=1.4 Hz, 1H), 5.15 (s, 2H), 2.32 (s, 3H), 2.15 (s, 3H); ESI m/z 399 [M+H]$^+$.

Step 4: To a solution of Example Compound 91 (70 mg, 0.18 mmol) in tetrahydrofuran (10 mL) was added sodium dithionite (183 mg, 1.05 mmol) in water (10 mL). The reaction mixture was stirred at room temperature overnight and concentrated under vacuum. To the residue was added 2N HCl and heated to reflux, cooled to room temperature, and concentrated in vacuum. The residue was dissolved in MeOH and basified by conc. NH$_4$OH, concentrated, and purified by chromatography (silica gel, 0-100% hexanes/ethyl acetate). It was further purified by reverse phase HPLC on a Polaris C$_{18}$ column eluting with 10-90% CH$_3$CN in H$_2$O to give Example Compound 90 (34 mg, 51%) as an off-white solid: $^1$H NMR (500 MHz, CD$_3$OD) δ 7.36-7.28 (m, 4H), 6.40 (d, J=1.4 Hz, 1H), 6.25 (d, J=1.4 Hz, 1H), 5.03 (s, 2H), 2.28 (s, 3H), 2.12 (s, 3H); ESI m/z 369 [M+H]$^+$.

General Procedure F:

Preparation of 4-(1-(cyclopropylmethyl)-2-methyl-4-nitro-1H-benzo[d]imidazol-6-yl)-3,5-dimethylisoxazole (Example Compound 14) and 1-(cyclopropylmethyl)-6-(3,5-dimethylisoxazol-4-yl)-2-methyl-1H-benzo[d]imidazol-4-amine (Example Compound 75)

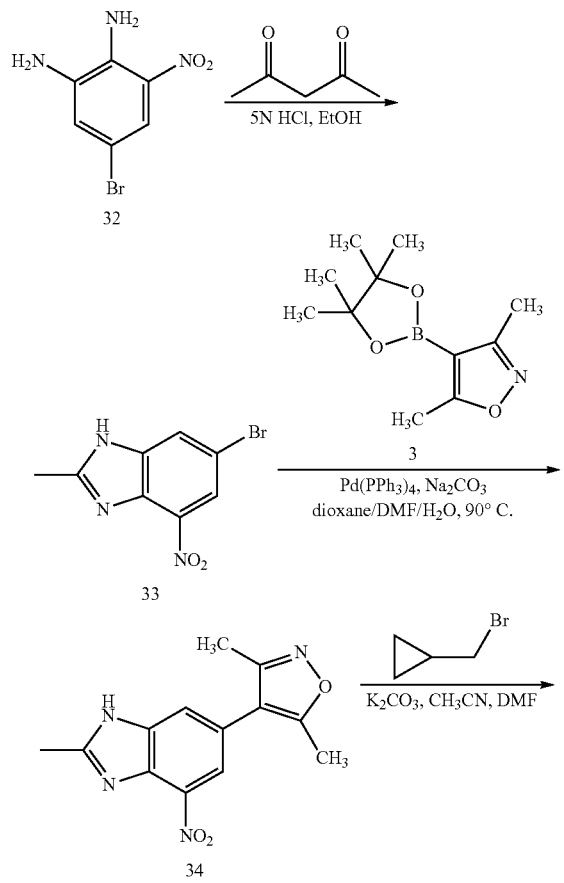

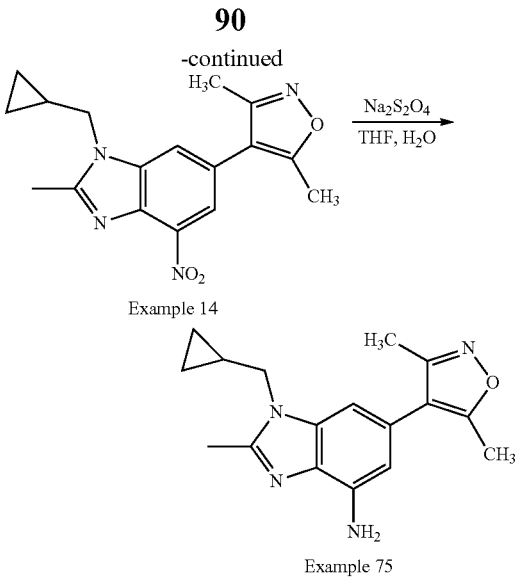

Step 1: A solution of 32 (488 mg, 2.10 mmol) and 2,4-pentanedione (421 mg, 4.21 mmol) in absolute ethanol (28 mL) and 5 N aq. HCl (7.8 mL) was heated to reflux for 3 h. The mixture was concentrated to dryness and ethyl acetate was added (200 mL). The solution was washed with saturated aq. NaHCO$_3$ (250 mL) and saturated aq. NaCl solution (250 mL), dried over Na$_2$SO$_4$, filtered and concentrated. The residue was purified by chromatography (silica gel, 0-40% hexanes/ethyl acetate) to afford 33 (495 mg, 92%) as a orange solid: $^1$H NMR (500 MHz, CDCl$_3$) δ 10.38 (br s, 1H), 8.24 (d, J=2.0 Hz, 1H), 8.12 (d, J=1.0 Hz, 1H), 2.73 (s, 3H).

Step 2: To a mixture of 33 (200 mg, 0.78 mmol) and 3 (262 mg, 1.17 mmol) in 1,4-dioxane (6 mL) and water (1.5 mL) was added potassium carbonate (216 mg, 1.56 mmol) and tetrakis(triphenylphosphine)palladium(0) (45 mg, 0.04 mmol). The reaction was stirred and heated at 90° C. for 17 h. The reaction mixture was diluted with methanol (20 mL) and silica gel (15 g) was added. The suspension was concentrated to dryness and the resulting powder was purified by chromatography (silica gel, 0-90% hexanes/ethyl acetate) to give 34 (187 mg, 88%) as a yellow solid: $^1$H NMR (500 MHz, CDCl$_3$) δ 8.00 (d, J=1.5 Hz, 1H), 7.89 (s, 1H), 2.76 (s, 3H), 2.45 (s, 3H), 2.30 (s, 3H).

Step 3: To a solution of 34 (217 mg, 0.797 mmol), potassium carbonate (220 mg, 1.59 mmol), acetonitrile (5 mL) and DMF (1 mL) was added bromomethylcyclopropane (129 mg, 0.956 mmol) and the reaction was heated at 60° C. for 17 h. The material was cooled to room temperature and poured into a saturated aq. NaCl solution (30 mL). Ethyl acetate (100 mL) was added and the layers were separated. The ethyl acetate layer was washed with saturated aq. NaCl solution (2×20 mL), dried over Na$_2$SO$_4$, filtered and concentrated. The residue was purified by chromatography (silica gel, 0-90% hexanes/ethyl acetate) to give Example 14 (178 mg, 68%) as an yellow solid: $^1$H NMR (500 MHz, CD$_3$OD) δ 8.03 (d, J=1.5 Hz, 1H), 7.93 (d, J=1.5 Hz, 1H), 4.27 (d, J=7.0 Hz, 2H), 2.75 (s, 3H), 2.46 (s, 3H), 2.30 (s, 3H), 1.38-1.28 (m, 1H), 0.65-0.60 (m, 2H), 0.51-0.46 (m, 2H). ESI m/z 327 [M+H]$^+$ Step 4: To a solution of Example Compound 14 (160 mg, 0.51 mmol) in THF (10 mL) was added a solution of sodium dithionite (446 mg, 2.56 mmol) in water (10 mL) dropwise over 5 min. The solution was stirred at room temperature for 16 h and the solvents were removed in vacuo. Methanol (20 mL) was added and the suspension stirred at room temperature for 3 h. The mixture was filtered and the filtrate was concentrated to dryness. A solution of 2N aq. HCl (10 mL) was added to the residue and was heated to reflux for 5 min. After concentration to dryness, methanol (20 mL) was added and the solution was adjusted to pH 8 using saturated aq. NaHCO$_3$ solution (10 mL). Silica gel was added (10 g) and the suspension was concentrated to dryness. The resulting powder was purified by chromatography (silica gel, 0-5% methanol/methylene chloride), the product was then purified by reverse phase HPLC on a Polaris C$_{18}$ column eluting with 10-90% CH$_3$CN in H$_2$O to give Example Compound 75 (131 mg, 99%) as a white solid: $^1$H NMR (500 MHz, CD$_3$OD) δ 6.70 (s, 1H), 6.44 (d, J=1.0 Hz, 1H), 4.08 (d, J=6.5 Hz, 2H), 2.61 (s, 3H), 2.40 (s, 3H), 2.25 (s, 3H), 1.30-1.19 (m, 1H), 0.62-0.53 (m, 2H), 0.45-0.40 (m, 2H). ESI m/z 297 [M+H]$^+$.

General Procedure G:

Preparation of 1-benzyl-6-(3,5-dimethylisoxazol-4-yl)-4-nitro-1H-benzo[d]imidazol-2(3H)-one (Example Compound 15) and 4-amino-1-benzyl-6-(3,5-dimethylisoxazol-4-yl)-1H-benzo[d]imidazol-2(3H)-one (Example Compound 16)

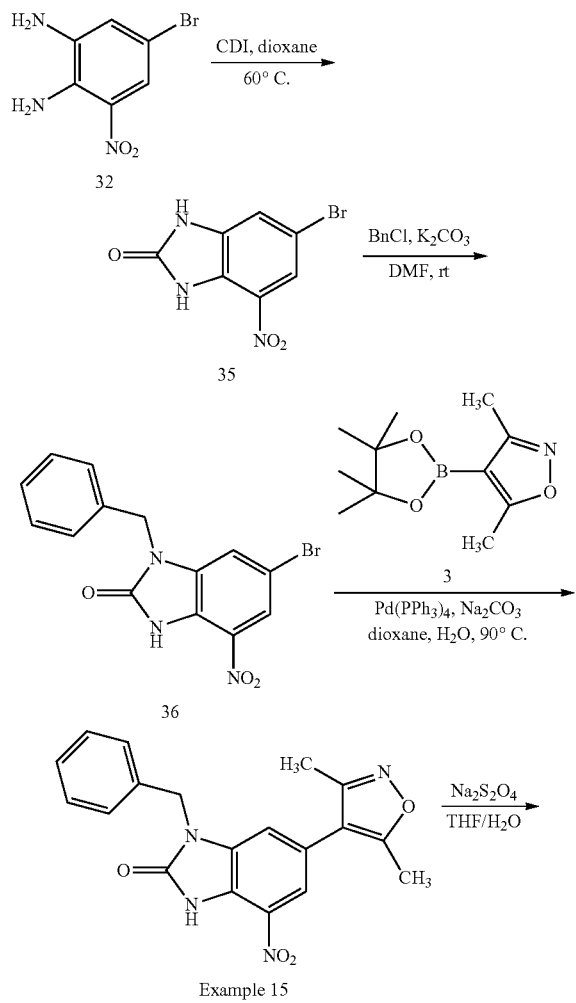

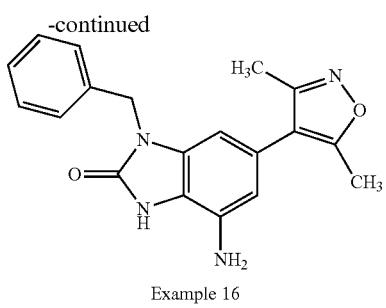

Example 16

Step 1: To a solution of 32 (232 mg, 1.0 mmol) in 1,4-dioxane (5 mL) was added CDI (194 mg, 1.2 mmol). The reaction was heated at 60° C. for 16 h. The solid was collected and dried to give 35 (202 mg, 78%) as a brown yellow solid: $^1$H NMR (300 MHz, DMSO-d$_6$) δ 11.83 (br s, 1H), 11.53 (br s, 1H), 7.86 (d, J=1.8 Hz, 1H), 7.43 (d, J=1.8 Hz, 1H).

Step 2: To a solution of 35 (200 mg, 0.78 mmol) in DMF (7 mL) was added potassium carbonate (118 mg, 0.85 mmol) and benzyl chloride (98 mg, 0.78 mmol). The reaction was stirred at rt for 16 h. The mixture was diluted with EtOAc (100 mL) and washed with brine (50 mL). The organic layer was dried over sodium sulfate, filtered and concentrated. Purification by chromatography (silica gel, 0-100% ethyl acetate/hexanes) afforded 36 (101 mg, 37%) as a yellow solid: $^1$H NMR (300 MHz, DMSO-d$_6$) δ 12.15 (s, 1H), 7.90 (d, J=0.9 Hz, 1H), 7.75 (d, J=1.2 Hz, 1H), 7.36-7.28 (m, 5H), 5.10 (s, 2H).

Step 3: To a solution of 36 (100 mg, 0.29 mmol) in 1,4-dioxane (7 mL) was added 3,5-dimethyl-4-(4,4,5,5-tetramethyl-1,3,2-dioxaborolan-2-yl)isoxazole (128 mg, 0.57 mmol), sodium carbonate (2.0 M in H$_2$O, 0.43 mL, 0.86 mmol) and tetrakis(triphenylphosphine)palladium(0) (34 mg, 0.03 mmol). The reaction mixture was purged with nitrogen and heated at 80° C. for 16 h. The mixture was diluted with methylene chloride (20 mL) and filtered. The filtrate was concentrated and purified by chromatography (silica gel, 10-50% ethyl acetate/hexanes) followed by trituration with ethyl acetate to afford Example Compound 15 (70 mg, 66%) as a yellow solid: $^1$H NMR (300 MHz, DMSO-d$_6$) δ 12.11 (s, 1H), 7.72 (d, J=1.5 Hz, 1H), 7.50 (d, J=1.5 Hz, 1H), 7.42-7.28 (m, 5H), 5.13 (s, 2H), 2.35 (s, 3H), 2.15 (s, 3H); ESI m/z 365 [M+H]$^+$.

Step 4: To a solution of Example Compound 15 (52 mg, 0.14 mmol) in THF (5 mL) and water (4 mL) was added Na$_2$S$_2$O$_4$ (149 mg, 0.86 mmol). The mixture was stirred at rt for 4 h, 2N HCl (1 mL) was added, the mixture was heated to reflux for 15 minutes then cooled to rt. Na$_2$CO$_3$ was added slowly to adjust to pH 9. The mixture was extracted with CH$_2$Cl$_2$ (100 mL), the organic layer was washed with brine (50 mL), filtered, concentrated and purified by chromatography (silica gel, 70-100% ethyl acetate/hexanes) to afford Example Compound 16 (30 mg, 63%) as an off-white solid: $^1$H NMR (500 MHz, DMSO-d$_6$) δ 10.44 (s, 1H), 7.36-7.25 (m, 5H), 6.28 (s, 2H), 5.04 (s, 2H), 4.95 (s, 2H), 2.28 (s, 3H), 2.10 (s, 3H); ESI m/z 335 [M+H]$^+$.

General Procedure H:

Preparation of 4-(1-benzyl-4-bromo-1H-benzo[d]imidazol-6-yl)-3,5-dimethylisoxazole (Example Compound 121)

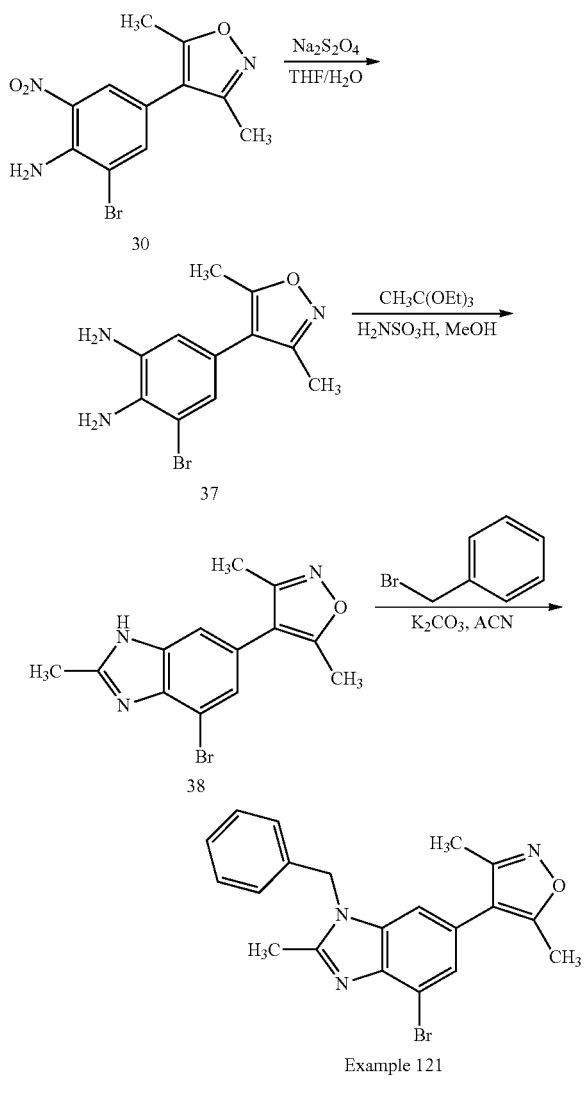

Step 1: To a solution of 30 (1.09 g, 3.49 mmol) in tetrahydrofuran (30 mL) was added sodium dithionite (4.86 g, 28.0 mmol) in water (15 mL). The reaction mixture was stirred at room temperature overnight and concentrated under vacuum. The residue was dissolved in MeOH/water (1:1, 150 mL) and the solid was precipitated by removing some MeOH under vacuum. The solid was filtered, washed with water and dried under vacuum to afford 37 (440 mg, 34%) as a yellow solid: $^1$H NMR (500 MHz, CDCl$_3$) δ 6.85 (d, J=1.8 Hz, 1H), 6.51 (d, J=1.8 Hz, 1H), 4.00-3.60 (bs, 2H), 3.60-3.30 (bs, 2H), 2.36 (s, 3H), 2.23 (s, 3H); ESI m/z 282 [M+H]$^+$.

Step 2: To a solution of 37 (4.01 g, 14.2 mmol) in methanol (87 mL) was added triethyl orthoacetate (3.45 g, 21.3 mmol) and sulfamic acid (69 mg, 0.71 mmol). The reaction was stirred at room temperature for 5 h. The reaction mixture was diluted with water (50 mL), basified with NaHCO$_3$ and filtered. The solid was dried to afford 38 (4.2 g, 96%) as a brown solid: $^1$H NMR (300 MHz, DMSO-d$_6$) δ 12.82 (br.s, 1H), 7.42 (d, J=1.5 Hz, 1H), 7.31 (d, J=1.5 Hz, 1H), 2.52 (s, 3H), 2.40 (s, 3H), 2.24 (s, 3H).

Step 3: The mixture of 38 (300 mg, 0.980 mmol), benzyl bromide (503 mg, 2.94 mmol), and potassium carbonate (676 mg, 4.90 mmol) in acetonitrile (50 mL) was heated in sealed tube at 75° C. overnight. The reaction mixture was cooled to room temperature, concentrated and purified by chromatography (silica gel, 0-100% ethyl acetate in hexanes) to give Example Compound 121 (276 mg, 71%) as an off-white solid: $^1$H NMR (500 MHz, CD$_3$OD) δ 7.40-7.25 (m, 5H), 7.15 (d, J=7.7 Hz, 2H), 5.51 (s, 2H), 2.64 (s, 3H), 2.32 (s, 3H), 2.15 (s, 3H); ESI m/z 396 [M+H]$^+$.

Preparation of 4-(1-benzyl-4-methoxy-2-methyl-1H-benzo[d]imidazol-6-yl)-3,5-dimethylisoxazole (Example Compound 66)

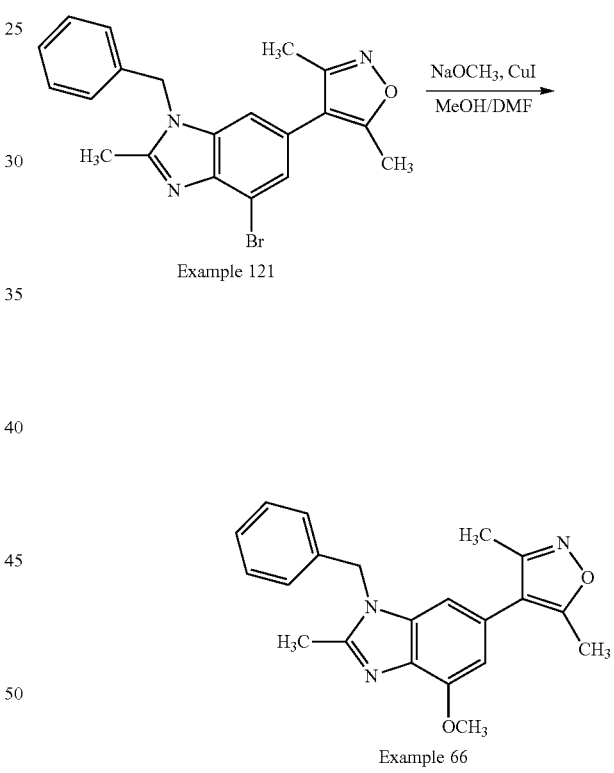

A mixture of Example 121 (80 mg, 0.20 mmol), NaOCH$_3$ (108 mg, 2.0 mmol) and CuI (57 mg, 0.30 mmol) in MeOH (1 mL) and DMF (3 mL) was purged with nitrogen and heated at 100° C. for 6 h. The mixture was diluted with ethyl acetate (100 mL) and washed with brine (50 mL). The organic layer was dried over Na$_2$SO$_4$, filtered and concentrated. The residue was purified by chromatography (silica gel, 40-100% EtOAc/hexanes) to afford Example Compound 66 (386 mg, 55%) as an off-white solid: $^1$H NMR (300 MHz, CDCl$_3$) δ 7.35-7.30 (m, 3H), 7.09-7.06 (m, 2H), 6.64 (d, J=1.2 Hz, 1H), 6.53 (s, 1H), 5.32 (s, 2H), 4.03 (s, 3H), 2.66 (s, 3H), 2.33 (s, 3H), 2.19 (s, 3H); ESI m/z 348 [M+H]$^+$.

General Procedure I:

Preparation of 1-benzyl-6-(3,5-dimethylisoxazol-4-yl)-N-ethyl-4-nitro-1H-benzo[d]imidazol-2-amine (Example Compound 18) and 1-benzyl-6-(3,5-dimethylisoxazol-4-yl)-$N^2$-ethyl-1H-benzo[d]imidazole-2,4-diamine (Example Compound 19)

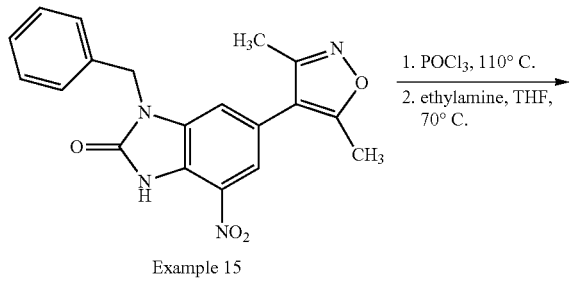

Example 15

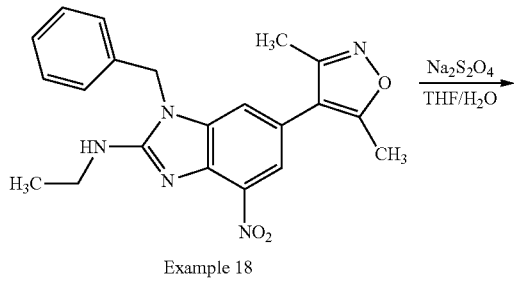

Example 18

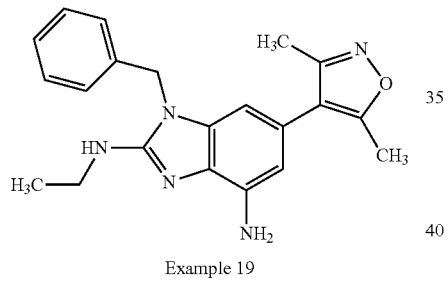

Example 19

Step 1: A mixture of Example Compound 15 (73 mg, 0.668 mmol) in POCl$_3$ (3 mL) was heated at 110° C. for 16 h. The reaction mixture was concentrated, the residue was dissolved in CH$_2$Cl$_2$ (100 mL), washed with saturated NaHCO$_3$ (2×50 mL) and brine (50 mL). The organic layer was dried over sodium sulfate, filtered and concentrated. The residue was dissolved in a solution of ethylamine in THF (2.0 M, 10 mL), and the mixture was heated at 70° C. for 3 h. The reaction mixture was concentrated, the residue was purified by chromatography (silica gel, 20-60% EtOAc/hexanes) to afford Example Compound 18 (113 mg, 43%) as an orange solid: $^1$H NMR (300 MHz, CDCl$_3$) δ 7.84 (d, J=1.5 Hz, 1H), 7.42-7.35 (m, 3H), 7.16-7.13 (m, 2H), 7.03 (d, J=1.5 Hz, 1H), 5.15 (s, 2H), 4.29 (t, J=5.4 Hz, 1H), 3.78-3.69 (m, 2H), 2.36 (s, 3H), 2.21 (s, 3H), 1.27 (t, J=7.5 Hz, 3H); ESI m/z 392 [M+H]$^+$.

Step 2: To a solution of Example Compound 18 (90 mg, 0.23 mmol) in THF (5 mL) and water (4 mL) was added Na$_2$S$_2$O$_4$ (240 mg, 1.38 mmol). The mixture was stirred at rt for 4 h, 2N HCl (1 mL) was added, the mixture was heated to reflux for 15 minutes then cooled to rt. Na$_2$CO$_3$ was added slowly to adjust to pH 9. The mixture was extracted with CH$_2$Cl$_2$ (100 mL), the organic layer was washed with brine (50 mL), dried over Na$_2$SO$_4$, filtered, concentrated and purified by chromatography (silica gel, 0-10% methanol/ethyl acetate) to afford Example Compound 19 (60 mg, 72%) as an off-white solid: $^1$H NMR (300 MHz, DMSO-d$_6$) δ 7.34-7.20 (m, 5H), 6.62 (t, J=5.4 Hz, 1H), 6.30 (d, J=1.5 Hz, 1H), 6.21 (d, J=1.5 Hz, 1H), 5.19 (s, 2H), 4.83 (s, 2H), 3.47-3.38 (m, 2H), 2.28 (s, 3H), 2.11 (s, 3H), 1.22 (t, J=7.2 Hz, 3H); ESI m/z 362 [M+H]$^+$.

General Procedure J:

Preparation of methyl 1-benzyl-6-(3,5-dimethylisoxazol-4-yl)-2-oxo-2,3-dihydro-1H-benzo[d]imidazole-4-carboxylate (Example Compound 20), 1-benzyl-6-(3,5-dimethylisoxazol-4-yl)-2-oxo-2,3-dihydro-1H-benzo[d]imidazole-4-carboxamide (Example Compound 21) and 4-(aminomethyl)-1-benzyl-6-(3,5-dimethylisoxazol-4-yl)-1H-benzo[d]imidazol-2(3H)-one (Example Compound 22)

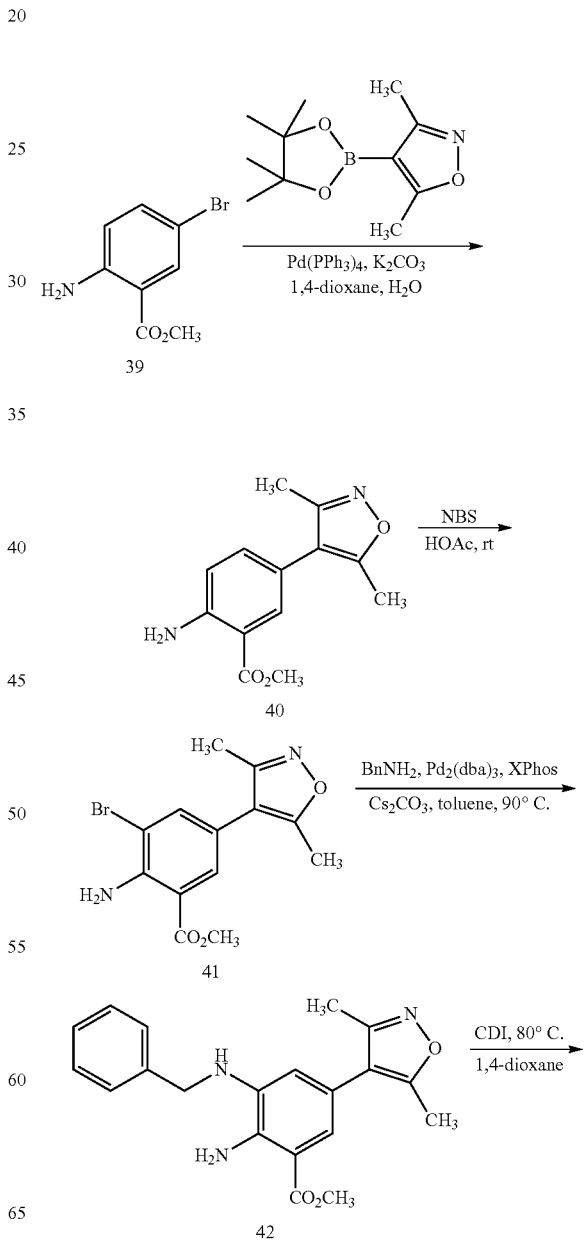

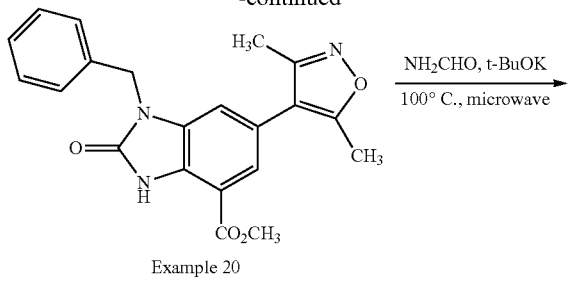

Example 20

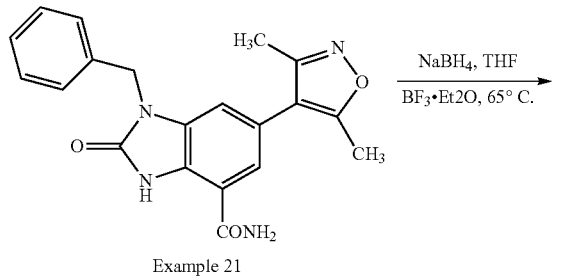

Example 21

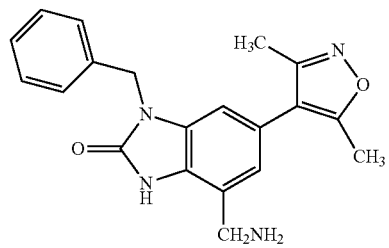

Example 22

Step 1: To a solution of 39 (2.00 g, 8.70 mmol) in 1,4-dioxane (80 mL) and water (8 mL) was added 3,5-dimethyl-4-(4,4,5,5-tetramethyl-1,3,2-dioxaborolan-2-yl) isoxazole (2.13 g, 9.57 mmol), potassium carbonate (2.40 g, 17.4 mmol) and tetrakis(triphenylphosphine)palladium(0) (502 mg, 0.435 mmol). The reaction mixture was purged with nitrogen and heated at 90° C. overnight. The reaction mixture was cooled to room temperature, concentrated and purified by chromatography (silica gel, 0-50% ethyl acetate in hexanes) to afford 40 (1.43 g, 63%) as an off-white solid: $^1$H NMR (500 MHz, CDCl$_3$) δ 7.74 (d, J=2.1 Hz, 1H), 7.15 (dd, J=2.1, 8.4 Hz, 1H), 6.73 (d, J=8.4 Hz, 1H), 5.81 (s, 2H), 3.88 (s, 3H), 2.37 (s, 3H), 2.23 (s, 3H); ESI m/z 247 [M+H]$^+$.

Step 2: To a mixture of 40 (1.34 g, 5.45 mmol) in acetic acid (40 mL) was added N-bromosuccinimide (1.07 g, 5.99 mmol). The mixture was stirred at room temperature for 30 min and concentrated. The residue was dissolved in MeOH and neutralized to pH 7 with 10% sodium bicarbonate. The mixture was diluted with water, filtered. The filter cake was washed with water, and dried under vacuum to afford 41 (1.65 g, 93%) as a yellow solid: $^1$H NMR (500 MHz, CDCl$_3$) δ 7.74 (d, J=2.1 Hz, 1H), 7.47 (d, J=2.1 Hz, 1H), 6.43 (bs, 2H), 3.90 (s, 3H), 2.37 (s, 3H), 2.23 (s, 3H).

Step 3: To a solution of 41 (500 mg, 1.54 mmol) in toluene (40 mL) under nitrogen atmosphere was added benzylamine (823 mg, 7.69 mmol), cesium carbonate (1.00 g, 2.08 mmol), 2-dicyclohexylphosphino-2',4',6'-triisopropyl-1,1'-biphenyl (110 mg, 0.231 mmol), and tris(dibenzylideneacetone)dipalladium(0) (141 mg, 0.154 mmol). The reaction mixture was heated at 90° C. overnight, cooled to room temperature and purified by chromatography (silica gel, 0-20% ethyl acetate in hexanes) to afford 42 (310 mg, 57%) as a light brown solid: $^1$H NMR (500 MHz, CDCl$_3$) δ 7.40-7.25 (m, 6H), 6.56 (d, J=1.8 Hz, 1H), 5.68 (s, 2H), 4.36 (d, J=4.4 Hz, 2H), 3.88 (s, 3H), 3.68 (s, 1H), 2.22 (s, 3H), 2.09 (s, 3H); ESI m/z 352 [M+H]$^+$.

Step 4: To a mixture of 42 (310 mg, 0.883 mmol) in 1,4-dioxane (10 mL) was added 1,1'-carbonyldiimidazole (244 mg, 2.12 mmol) and DMAP (one crystal). The reaction was heated in a sealed tube at 80° C. for 5 days. The mixture was concentrated and purified by chromatography (silica gel, 0-100% ethyl acetate in hexanes) to give Example Compound 20 (160 mg, 48%) as an off-white solid: $^1$H NMR (500 MHz, CD$_3$OD) δ 7.54 (d, J=1.5 Hz, 1H), 7.37-7.24 (m, 5H), 7.07 (d, J=1.5 Hz, 1H), 5.14 (s, 2H), 3.97 (s, 3H), 2.27 (s, 3H), 2.09 (s, 3H); HPLC >99%, t$_R$=15.0 min; ESI m/z 378 [M+H]$^+$.

Step 5: To a mixture of Example Compound 20 (50 mg, 0.13 mmol) in formamide (4 mL) was added potassium tert-butoxide (30 mg, 0.26 mmol). The mixture was heated in the microwave at 100° C. for 3 h, concentrated, and purified by chromatography (silica gel, 0-20% methanol in ethyl acetate) to afford Example Compound 21 (13 mg, 26%) as an off-white solid: 1H NMR (500 MHz, CD$_3$OD) δ7.41 (d, J=1.3 Hz, 1H), 7.37-7.24 (m, 5H), 7.00 (d, J=1.4 Hz, 1H), 5.13 (s, 2H), 2.28 (s, 3H), 2.11 (s, 3H); HPLC 98.3%, t$_R$=12.3 min; ESI m/z 363 [M+H]$^+$.

Step 6: To a solution of Example Compound 21 (40 mg, 0.11 mmol) in THF (10 mL) under nitrogen atmosphere was added sodium borohydride (38 mg, 0.99 mmol). The mixture was heated to 65° C. and boron trifluoride diethyl etherate (0.2 mL) was added. The mixture was heated at 65° C. for 2 h. After cooling to room temperature, hydrochloride acid (2N, 5 mL) was added and the mixture stirred for 2 h. The mixture was basified with NaOH (2N, 5 mL), concentrated, and purified by chromatography (silica gel, 0-100% CMA in methylene chloride) (CMA=chloroform:methanol:concentrated ammonium hydroxide=80:18:2). It was further purified by reverse phase HPLC on a Polaris column eluting with 10-90% CH$_3$CN in H$_2$O to give Example Compound 22 (16 mg, 42%) as an off-white solid: $^1$H NMR (500 MHz, CD$_3$OD) δ 7.37-7.23 (m, 5H), 6.99 (d, J=1.4 Hz, 1H), 6.77 (d, J=1.4 Hz, 1H), 5.10 (s, 2H), 3.93 (s, 2H), 2.27 (s, 3H), 2.10 (s, 3H); ESI m/z 340 [M+H]$^+$.

General Procedure K:

1-benzyl-6-(3,5-dimethylisoxazol-4-yl)-2-methyl-1H-benzo[d]imidazol-4-amine (Example Compound 55)

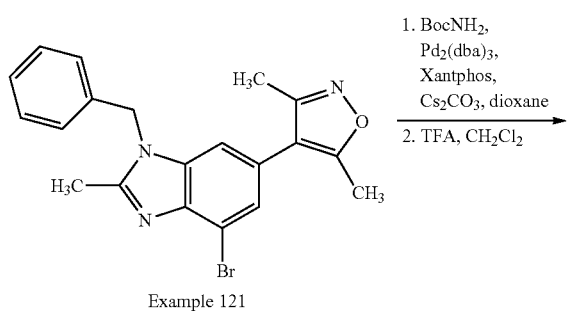

Example 121

-continued

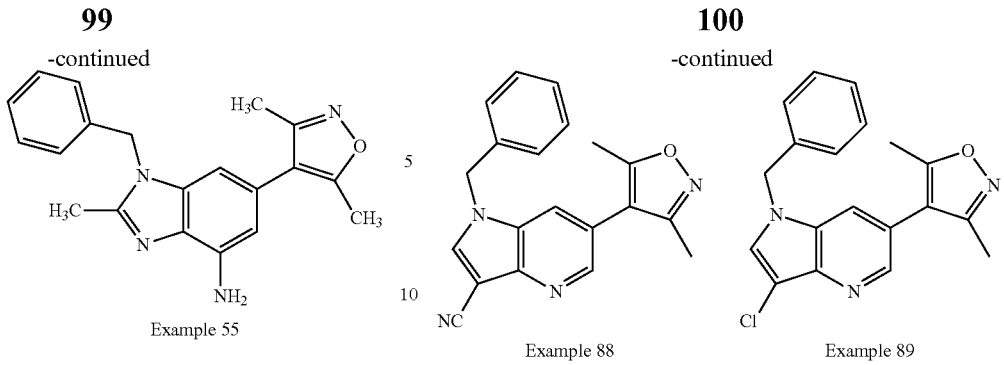

Example 55

Example 88

Example 89

A mixture of Example 121 (250 mg, 0.63 mmol), BocNH$_2$ (221 mg, 1.89 mmol), Xantphos (73 mg, 0.126 mmol), Pd$_2$(dba)$_3$ (58 mg, 0.063 mmol) and Cs$_2$CO$_3$ (720 mg, 2.21 mmol) in 1,4-dioxane (13 mL) was purged with nitrogen and heated at 100° C. for 18 h. The mixture was diluted with methylene chloride (200 mL) and filtered. The filtrate was concentrated and purified by chromatography (silica gel, 0-50% EtOAc/hexanes) to afford a light brown foam which was dissolved in CH$_2$Cl$_2$ (4 mL), TFA (2 mL) was added. The mixture was stirred at rt for 2 h, concentrated, the residue was dissolved in ethyl acetate (100 mL) and washed with saturated NaHCO$_3$ (50 mL×2). The organic layer was dried over sodium sulfate, filtered and concentrated. Purification by chromatography (silica gel, 0-10% MeOH/EtOAc) afforded Example Compound 55 (146 mg, 88%) as an off-white solid: $^1$H NMR (500 MHz, CDCl$_3$) δ 7.34-7.28 (m, 3H), 7.09-7.08 (m, 2H), 6.42 (d, J=1.5 Hz, 1H), 6.36 (d, J=1.5 Hz, 1H), 5.28 (s, 2H), 4.42 (br.s, 2H), 2.60 (s, 3H), 2.31 (s, 3H), 2.17 (s, 3H); ESI m/z 333 [M+H]$^+$.

Preparation of 1-benzyl-6-(3,5-dimethylisoxazol-4-yl)-1H-pyrrolo[3,2-b]pyridine-3-carbonitrile (Example Compound 88) and 4-(1-benzyl-3-chloro-1H-pyrrolo[3,2-b]pyridin-6-yl)-3,5-dimethylisoxazole (Example Compound 89)

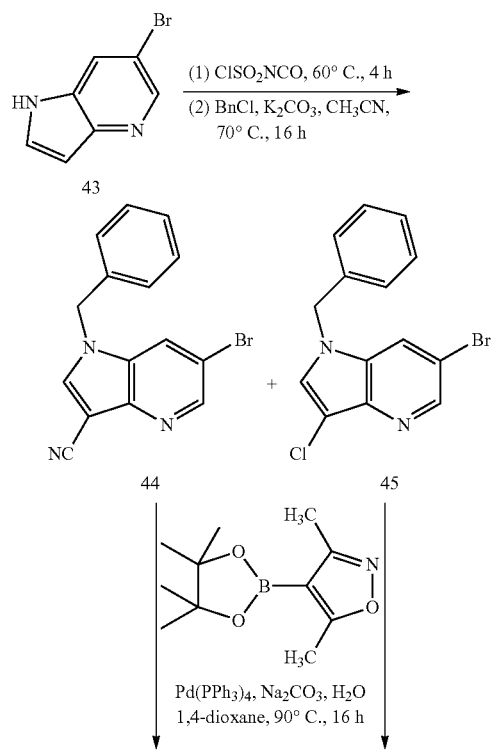

Step 1: To a suspension of 43 (200 mg, 1.0 mmol) in CH$_3$CN (6 mL) was added ClSO$_2$NCO (360 mg, 2.5 mmol). The reaction mixture was stirred at 60° C. for 4 h. After the mixture was cooled to rt, DMF (1 mL) was added. The mixture was stirred at rt for 1 h. The mixture was diluted with 30% i-PrOH in CHCl$_3$ (50 mL) and washed with brine (20 mL). The organic layer was dried over sodium sulfate, filtered and concentrated. The crude was dissolved in CH$_3$CN (4 mL), potassium carbonate (280 mg, 2.0 mmol) and benzyl chloride (128 mg, 1.0 mmol) were added. The reaction was stirred at 70° C. for 16 h. The reaction mixture was filtered through a layer of celite, concentrated. The residue was purified by chromatography (silica gel, 0-50% ethyl acetate/hexanes) to afford 44 (16 mg, 5%) as a yellow oil and 45 (12 mg, 4%) as an off-white solid; 44: ESI MS m/z 312 [M+H]$^+$; 45: ESI MS m/z 321 [M+H]$^+$.

Step 2: Using the similar procedure used for General Procedure C step 1 on compound 44 (16 mg, 0.051 mmol) afforded Example Compound 88 (6 mg, 36%) as an off-white solid: $^1$H NMR (300 MHz, CDCl$_3$) δ 8.55 (s, 1H), 7.98 (s, 1H), 7.50 (s, 1H), 7.41-7.40 (m, 3H), 7.20-7.15 (m, 2H), 5.42 (s, 2H), 2.34 (s, 3H), 2.16 (s, 3H); ESI MS m/z 329 [M+H]$^+$.

Using the similar procedure used for General Procedure C step 1 on compound 45 (12 mg, 0.037 mmol) afforded Example Compound 89 (8 mg, 64%) as a yellow solid: $^1$H NMR (300 MHz, CDCl$_3$) δ 8.49 (s, 1H), 7.55 (s, 1H), 7.50 (s, 1H), 7.38-7.36 (m, 3H), 7.18-7.16 (m, 2H), 5.36 (s, 2H), 2.34 (s, 3H), 2.16 (s, 3H); ESI MS m/z 338 [M+H]$^+$.

General Procedure M:

Preparation of 5-(3,5-dimethylisoxazol-4-yl)-N-phenyl-1H-pyrrolo[3,2-b]pyridin-3-amine (Example Compound 23)

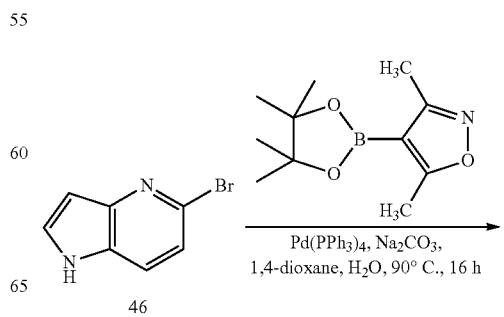

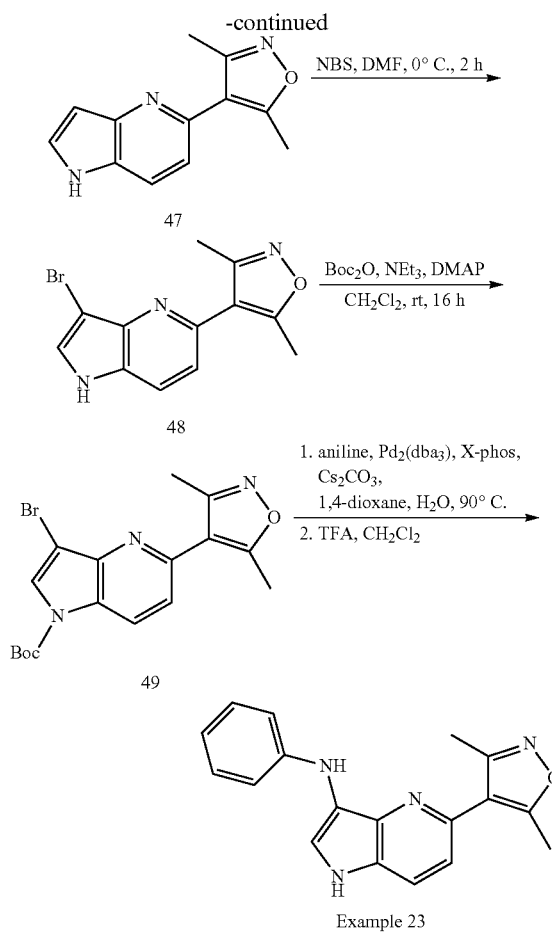

tography (silica gel, 0-30% ethyl acetate/hexanes) afforded 49 (210 mg, 70%) as an off-white solid: $^1$H NMR (300 MHz, CDCl$_3$) δ 8.43 (d, J=5.4 Hz, 1H), 7.93 (s, 1H), 7.34 (d, J=5.1 Hz, 1H), 2.64 (s, 3H), 2.50 (s, 3H), 1.69 (s, 9H).

Step 4: To a solution of 49 (100 mg, 0.26 mmol) in 1,4-dioxane (5 mL) under nitrogen atmosphere was added aniline (71 mg, 0.76 mmol), cesium carbonate (250 mg, 0.76 mmol), X-phos (24 mg, 0.05 mmol), and tris(dibenzylideneacetone)dipalladium(0) (23 mg, 0.03 mmol). The reaction mixture was heated at 90° C. for 16 h. The mixture was diluted with methylene chloride (10 mL) and filtered through a layer of Celite. The filtrate was concentrated. Purification by chromatography (silica gel, 0-50% ethyl acetate/hexanes) gave a red oil which was dissolved in methylene chloride (5 mL), TFA (2 mL) was added, the mixture was stirred at rt for 2 h. The mixture was concentrated, the residue was dissolved in methylene chloride (100 mL), washed with saturated NaHCO$_3$ (50 mL×2) and brine (50 mL). The organic layer was dried over sodium sulfate, filtered and concentrated. Purification by chromatography (silica gel, 0-50% ethyl acetate/dichloromethane) afforded Example Compound 23 (47 mg, 64%) as a yellow solid: $^1$H NMR (300 MHz, DMSO-d$_6$) δ 11.1 (d, J=1.8 Hz, 1H), 7.82 (d, J=8.4 Hz, 1H), 7.61 (d, J=2.7 Hz, 1H), 7.43 (s, 1H), 7.25 (d, J=8.4 Hz, 1H), 7.09 (d, J=8.4 Hz, 1H), 7.07 (d, J=7.2 Hz, 1H), 6.85 (d, J=7.5 Hz, 2H), 6.60 (t, J=7.2 Hz, 1H), 2.48 (s, 3H), 2.29 (s, 3H); ESI MS m/z 305 [M+H]$^+$.

General Procedure N:

Preparation of 6-(3,5-dimethylisoxazol-4-yl)-1-(4-fluorobenzyl)-3-methyl-1H-pyrazolo[4,3-b]pyridine-4-oxide (Example Compound 24) and 6-(3,5-dimethylisoxazol-4-yl)-1-(4-fluorobenzyl)-3-methyl-1H-pyrazolo[4,3-b]pyridin-5(4H)-one (Example Compound 25)

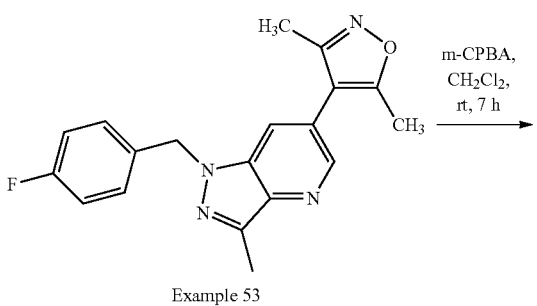

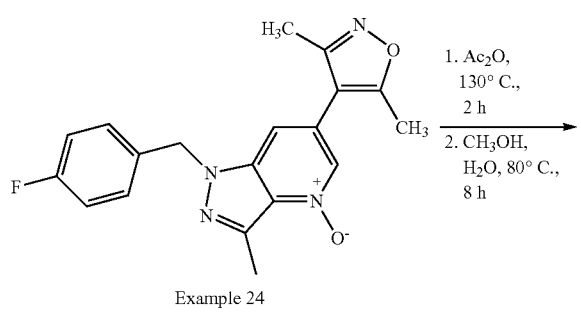

Step 1: To a solution of 46 (500 mg, 2.54 mmol) in 1,4-dioxane (10 mL) was added 3,5-dimethyl-4-(4,4,5,5-tetramethyl-1,3,2-dioxaborolan-2-yl)isoxazole (792 mg, 3.56 mmol), sodium carbonate (538 mg in 2 mL H$_2$O, 5.08 mmol) and tetrakis(triphenylphosphine)palladium(0) (294 mg, 0.25 mmol). The reaction mixture was purged with nitrogen and heated at 90° C. for 16 h. The mixture was filtered through a layer of Celite. The filtrate was concentrated. Purification by chromatography (silica gel, 0-50% ethyl acetate/dichloromethane) afforded 47 (700 mg, >100%) as a yellow oil: $^1$H NMR (300 MHz, DMSO-d$_6$) δ 11.4 (s, 1H), 7.85 (dd, J=8.1, 0.9 Hz, 1H), 7.68 (t, J=3.0 Hz, 1H), 7.23 (d, J=8.1 Hz, 1H), 6.58 (d, J=2.1 Hz, 1H), 2.49 (s, 3H), 2.37 (s, 3H).

Step 2: To a solution of 47 (700 mg, 2.54 mmol) in DMF (8 mL) at 0° C. was added NBS (497 mg, 2.79 mmol). The reaction mixture was stirred at 0° C. for 2 h. The mixture was diluted with methylene chloride (50 mL) and washed with brine (20 mL). The organic layer was dried over sodium sulfate, filtered and concentrated. Purification by chromatography (silica gel, 0-50% ethyl acetate/dichloromethane) afforded 48 (660 mg, 89%) as a brown solid: $^1$H NMR (300 MHz, DMSO-d$_6$) δ 11.8 (s, 1H), 7.92 (d, J=6.0 Hz, 1H), 7.90 (s, 1H), 7.36 (d, J=8.4 Hz, 1H), 2.49 (s, 3H), 2.37 (s, 3H); ESI m/z 292 [M+H]$^+$.

Step 3: To a solution of 48 (250 mg, 0.86 mmol) in CH$_2$Cl$_2$ (5 mL) was added NEt$_3$ (130 mg, 1.28 mmol), DMAP (12 mg, 0.1 mmol) and di-tert-butyl dicarbonate (224 mg, 1.03 mmol). The reaction was stirred at rt for 16 h. The reaction mixture was concentrated. Purification by chroma-

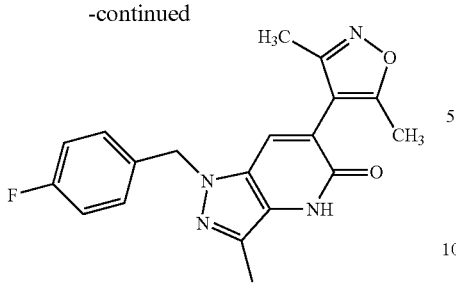

Example 25

Step 1: To a solution of Example Compound 53 (85 mg, 0.25 mmol) in CH$_2$Cl$_2$ (3 mL) was added m-CPBA (160 mg, 0.5 mmol). The reaction mixture was stirred at rt for 7 h. The mixture was diluted with methylene chloride (50 mL) and washed with 10% Na$_2$S$_2$O$_3$ solution (10 mL), 2N NaOH solution (10 mL) and brine (10 mL). The organic layer was dried over sodium sulfate, filtered and concentrated. Purification by chromatography (silica gel, 0-70% ethyl acetate/dichloromethane) afforded Example Compound 24 (60 mg, 67%) as an off-white solid: $^1$H NMR (300 MHz, DMSO-d$_6$) δ 8.21 (d, J=0.9 Hz, 1H), 7.83 (d, J=0.9 Hz, 1H), 7.40-7.35 (m, 2H), 7.20-7.14 (m, 2H), 5.59 (s, 2H), 2.69 (s, 3H), 2.45 (s, 3H), 2.27 (s, 3H); ESI MS m/z 353 [M+H]$^+$.

Step 2: A solution of Example Compound 24 (32 mg, 0.091 mmol) in Ac$_2$O (3 mL) was heated at 130° C. for 2 h. The mixture was concentrated. The residue was diluted with 1:1 CH$_3$OH/H$_2$O (10 mL) and stirred at 80° C. for 10 h. The reaction mixture was concentrated. Purification by chromatography (silica gel, 0-5% methanol/dichloromethane) afforded Example Compound 25 (20 mg, 63%) as an off-white solid: $^1$H NMR (300 MHz, DMSO-d$_6$) δ 12.0 (s, 1H), 8.07 (s, 1H), 7.36-7.31 (m, 2H), 7.19-7.13 (m, 2H), 5.45 (s, 2H), 2.30 (s, 6H), 2.14 (s, 3H); ESI MS m/z 353 [M+H]$^+$.

Preparation of 4-(3-benzyl-3H-imidazo[4,5-b]pyridin-5-yl)-3,5-dimethylisoxazole (Example Compound 26)

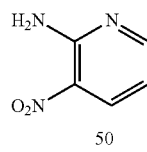

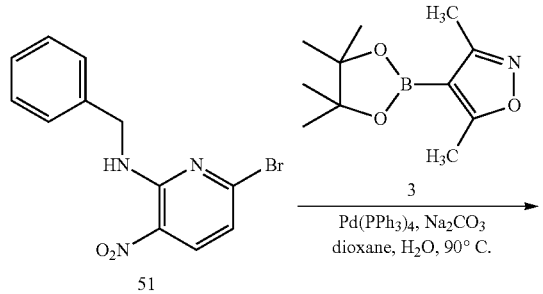

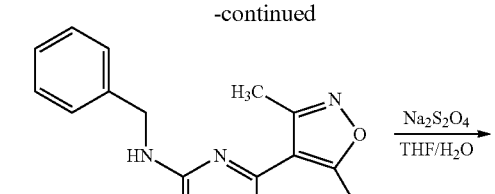

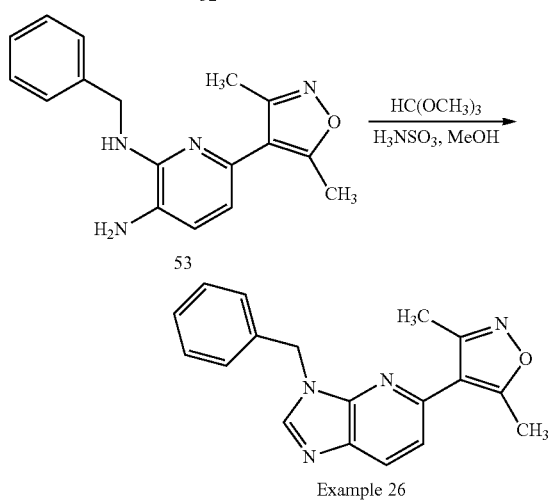

Example 26

Step 1: To a solution of 50 (560 mg, 2.57 mmol) in CH$_3$CN (15 mL) was added K$_2$CO$_3$ (887 mg, 6.43 mmol) and benzyl chloride (484 mg, 2.83 mmol). The reaction was heated at 60° C. for 16 h. The mixture was diluted with ethyl acetate (100 mL), filtered and concentrated to give 51 (790 mg, 100%) as a yellow solid: $^1$H NMR (300 MHz, CDCl$_3$) δ 8.58 (br s, 1H), 8.24 (d, J=8.4 Hz, 1H), 7.46-7.35 (m, 5H), 6.82 (d, J=8.7 Hz, 1H), 4.82 (d, J=5.7 Hz, 2H).

Step 2: To a solution of 51 (790 mg, 2.56 mmol) in 1,4-dioxane (25 mL) was added 3,5-dimethyl-4-(4,4,5,5-tetramethyl-1,3,2-dioxaborolan-2-yl)isoxazole (1.14 g, 5.12 mmol), sodium carbonate (2.0 M in H$_2$O, 3.84 mL, 7.68 mmol) and tetrakis(triphenylphosphine)palladium(0) (300 mg, 0.26 mmol). The reaction mixture was purged with nitrogen and heated at 90° C. for 8 h. The mixture was diluted with methylene chloride (200 mL) and filtered. The filtrate was concentrated and purified by chromatography (silica gel, 0-20% EtOAc/hexanes) to afford 52 (500 mg, 60%) as a yellow oil: $^1$H NMR (300 MHz, DMSO-d$_6$) δ 9.09 (t, J=6.0 Hz, 1H), 8.51 (d, J=8.4 Hz, 1H), 7.32-7.20 (m, 5H), 6.96 (d, J=8.7 Hz, 1H), 4.85 (d, J=6.3 Hz, 2H), 2.47 (s, 3H), 2.25 (s, 3H); ESI m/z 325 [M+H]$^+$.

Step 3: To a solution of 52 (500 mg, 1.54 mmol) in THF (15 mL) and water (12 mL) was added Na$_2$S$_2$O$_4$ (1.61 g, 9.24 mmol). The mixture was stirred at rt for 5 h; 2 N HCl (10 mL) was added, and the mixture was heated to reflux for 15 minutes then cooled to rt. Na$_2$CO$_3$ was added slowly to adjust to pH 9. The mixture was extracted with ethyl acetate (100 mL), the organic layer was washed with brine (50 mL), filtered and concentrated to give 53 (460 mg, 100%) as a brown oil: $^1$H NMR (300 MHz, DMSO-d$_6$) δ 7.33-7.18 (m, 5H), 6.78 (d, J=7.5 Hz, 1H), 6.52 (d, J=7.5 Hz, 1H), 6.29 (t, J=5.7 Hz, 1H), 4.94 (s, 2H), 4.60 (d, J=5.7 Hz, 2H), 2.36 (s, 3H), 2.17 (s, 3H); ESI m/z 295 [M+H]$^+$.

Step 4: A solution of 53 (150 mg, 0.51 mmol), trimethylorthoformate (81 mg, 0.765 mmol) and sulfamic acid (3 mg) in MeOH (5 mL) was heated to reflux for 4 h. The mixture was concentrated, the residue was purified by chromatography (silica gel, 30-100% ethyl acetate/hexanes) to afford Example Compound 26 (100 mg, 65%) as an off-white solid: $^1$H NMR (300 MHz, DMSO-d$_6$) δ 8.67 (s, 1H), 8.17 (d, J=8.1 Hz, 1H), 7.44 (d, J=8.1 Hz, 1H), 7.36-7.27 (m, 5H), 5.52 (s, 2H), 2.54 (s, 3H), 2.34 (s, 3H); ESI m/z 305 [M+H]$^+$.

Preparation of 6-(3,5-dimethylisoxazol-4-yl)-1-(4-fluorobenzyl)-1H-benzo[d]imidazol-4-amine (Example Compound 27), 6-(3,5-dimethylisoxazol-4-yl)-1-(4-fluorobenzyl)-N-methyl-1H-benzo[d]imidazol-4-amine (Example Compound 28) and 6-(3,5-dimethylisoxazol-4-yl)-1-(4-fluorobenzyl)-N,N-dimethyl-1H-benzo[d]imidazol-4-amine (Example Compound 29)

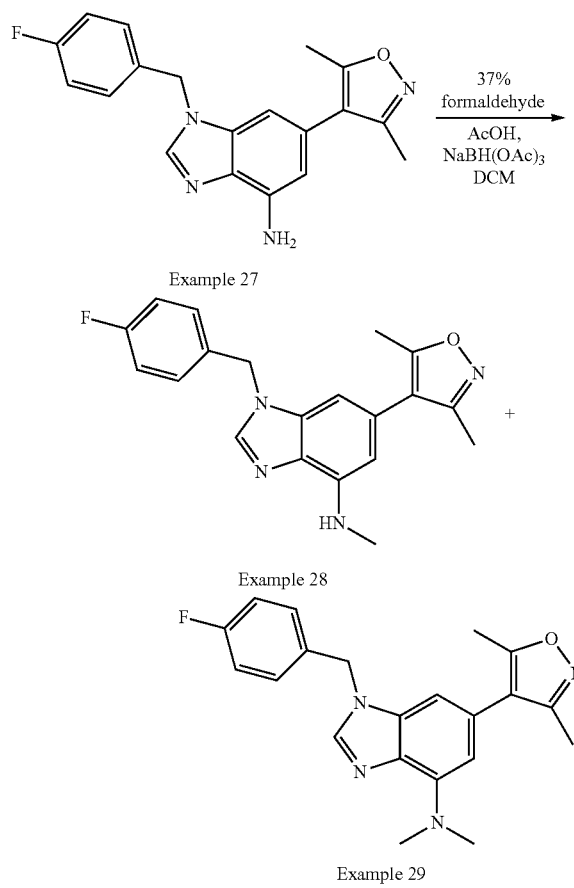

Example Compound 27 was made followed by the similar procedure described for Example 7: $^1$H NMR (300 MHz, DMSO-d$_6$) δ 8.23 (s, 1H), 7.42 (dd, J=8.0, 6.0 Hz, 2H), 7.17 (dd, J=9.0, 9.0 Hz, 2H), 6.62 (s, 1H), 6.32 (s, 1H), 5.40 (s, 4H), 2.33 (s, 3H), 2.16 (s, 3H); ESI m/z 337 [M+H]$^+$.

To a solution of Example Compound 27 (35 mg, 0.10 mmol) in methylene chloride (5 mL), was added a 37% solution of formaldehyde in water (8.5 μL) and acetic acid (1 drop). The solution was stirred for 45 min, sodium triacetoxyborohydride (66 mg, 0.31 mmol) was added and the mixture stirred for 16 h. The mixture was diluted with methylene chloride (20 mL) and neutralized with saturated sodium bicarbonate (5 mL). The organic layer was dried over anhydrous sodium sulfate and concentrated in vacuo. The residue was purified by chromatography (silica gel, 0-75% ethyl acetate/methylene chloride) to afford Example Compound 28 as a white solid (8 mg, 22%) and Example Compound 29 as a clear solid (7 mg, 18%). Example Compound 28: $^1$H NMR (500 MHz, DMSO-d$_6$) δ 8.22 (s, 1H), 7.43 (dd, J=8.8, 5.5 Hz, 2H), 7.16 (dd, J=8.8, 5.5 Hz, 2H), 6.65 (d, J=1.0 Hz, 1H), 6.09 (d, J=1.0 Hz, 1H), 5.85 (q, J=5.0 Hz, 1H), 5.41 (s, 2H), 2.83 (d, J=5.5 Hz, 3H), 2.35 (s, 3H), 2.17 (s, 3H); ESI m/z 351 [M+H]$^+$; Example 29: $^1$H NMR (500 MHz, DMSO-d$_6$) δ 8.28 (s, 1H), 7.41 (dd, J=8.5, 5.5 Hz, 2H), 7.17 (dd, J=9.0, 9.0 Hz, 2H), 6.85 (d, J=1.0 Hz, 1H), 6.25 (d, J=1.0 Hz, 1H), 5.43 (s, 2H), 3.18 (s, 6H), 2.35 (s, 3H), 2.18 (s, 3H); ESI m/z 365 [M+H]$^+$.

Preparation of 4-(1-benzyl-1H-imidazo[4,5-b]pyridin-6-yl)-3,5-dimethylisoxazole (Example Compound 30)

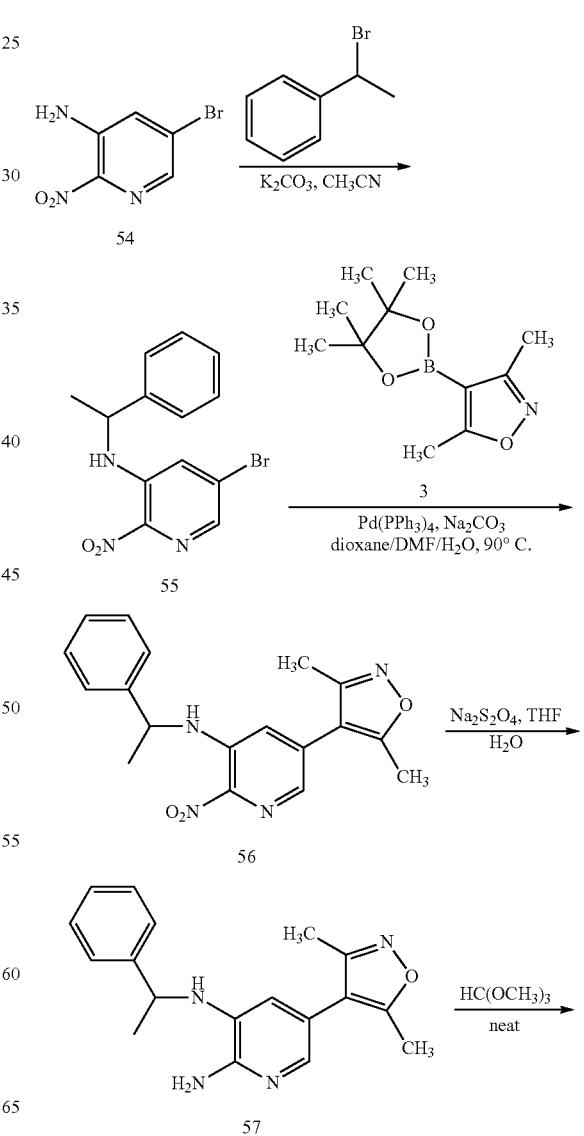

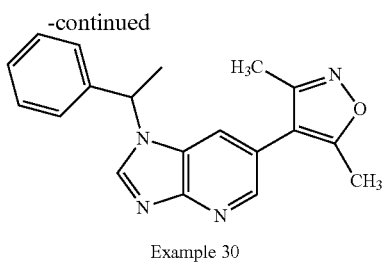

Example 30

Step 1: To a suspension of 3-amino-5-bromo-2-nitropyridine (54, 780 mg, 3.58 mmol) and potassium carbonate (2.28 g, 16.5 mmol) in dry acetonitrile (50 mL) was added 1-(bromoethyl)benzene (1.22 g, 6.60 mmol). The mixture was heated to 80° C. for 48 h then water (20 mL) and ethyl acetate (20 mL) were added. The layers were separated and the aqueous layer was extracted with ethyl acetate (2×20 mL). The combined ethyl acetate fractions were dried over $Na_2SO_4$, filtered and concentrated. The residue was purified by chromatography (silica gel, 0-40% ethyl acetate in hexanes) to afford 55 (219 mg, 19%) as a yellow solid: $^1$H NMR (500 MHz, $CDCl_3$) δ 8.14 (d, J=5.0 Hz, 1H), 7.84 (d, J=2.0 Hz, 1H), 7.40-7.29 (m, 6H), 4.64 (quint, J=6.5 Hz, 1H), 1.67 (d, J=7.0 Hz, 3H).

Step 2: To a mixture of 55 (261 mg, 0.81 mmol) and 3 (217 mg, 0.97 mmol) in 1,4-dioxane (7 mL) and water (1.5 mL) was added potassium carbonate (224 mg, 1.62 mmol) and tetrakis(triphenylphosphine)palladium(0) (47 mg, 0.04 mmol). The reaction was stirred and heated at 90° C. for 17 h. The reaction mixture was diluted with methanol (20 mL) and silica gel (15 g) was added. The suspension was concentrated to dryness and the resulting powder was loaded onto silica gel and eluted with 0-50% ethyl acetate in hexanes. The clean product was concentrated to give 56 (226 mg, 82%) as a yellow solid: $^1$H NMR (500 MHz, $CDCl_3$) δ 8.19 (d, J=4.5 Hz, 1H), 7.77 (d, J=2.0 Hz, 1H), 7.40-7.28 (m, 5H), 6.89 (d, J=2.0 Hz, 1H), 4.66 (quint, J=5.0 Hz, 1H), 2.10 (s, 3H), 1.94 (s, 3H), 1.71 (d, J=7.0 Hz, 3H).

Step 3: To a solution of 56 (226 mg, 0.67 mmol) in THF (20 ml) was added a solution of sodium dithionite (698 mg, 4.01 mmol) in water (20 mL) dropwise over 5 min. The solution was stirred at room temperature for 16 h and the solvents were removed in vacuo. Methanol (20 mL) was added and the suspension stirred at room temperature for 3 h. The mixture was filtered and the filtrate was concentrated to dryness. A solution of 2N aq. HCl was added to the residue and was heated to reflux for 5 min. After concentration to dryness, methanol was added (10 mL) and the solution was adjusted to pH 8 using saturated aq. $NaHCO_3$ solution (20 mL). Silica gel was added (10 g) and the suspension was concentrated to dryness. The resulting powder was loaded onto silica gel and eluted with 0-70% ethyl acetate in hexanes. The clean product was concentrated to give 57 (96 mg, 47%) as a beige solid: $^1$H NMR (500 MHz, $CDCl_3$) δ 7.42 (d, J=2.0 Hz, 1H), 7.33-7.30 (m, 4H), 7.25-7.22 (m, 1H), 6.34 (d, J=1.5 Hz, 1H), 4.44 (quint, J=5.0 Hz, 1H), 4.36 (br s, 2H), 3.70 (br s, 1H), 2.07 (s, 3H), 1.89 (s, 3H), 1.58 (d, J=6.5 Hz, 3H).

Step 4: A mixture of 57 (47 mg, 0.15 mmol), trimethylorthoformate (2 mL, 18.3 mmol) and sulfamic acid (1 mg) were heated in a sealed tube at 100° C. for 30 min. The mixture was cooled, concentrated and loaded onto silica gel and eluted with 0-20% ethyl acetate in hexanes. The resulting material was purified by reverse phase HPLC on a Polaris column eluting with 10-90% $CH_3CN$ in $H_2O$ to afford (Example Compound 30) (19 mg, 39%) as a white solid: $^1$H NMR (500 MHz, $CD_3OD$) δ 8.76 (s, 1H), 8.36 (d, J=2.0 Hz, 1H), 7.65 (d, J=2.5 Hz, 1H), 7.40-7.30 (m, 5H), 4.44 (q, J=7.0 Hz, 1H), 2.29 (s, 3H), 2.10 (s, 3H), 2.06 (d, J=7.0 Hz, 3H). ESI m/z 319 [M+H]$^+$.

Preparation of 4-(1-benzyl-1H-imidazo[4,5-c]pyridin-6-yl)-3,5-dimethylisoxazole (Example Compound 31), 1-benzyl-6-(3,5-dimethylisoxazol-4-yl)-1H-imidazo[4,5-c]pyridine 5-oxide (Example 32) and 1-benzyl-6-(3,5-dimethylisoxazol-4-yl)-1H-imidazo[4,5-c]pyridin-4-amine (Example Compound 33)

Example 31

Example 32

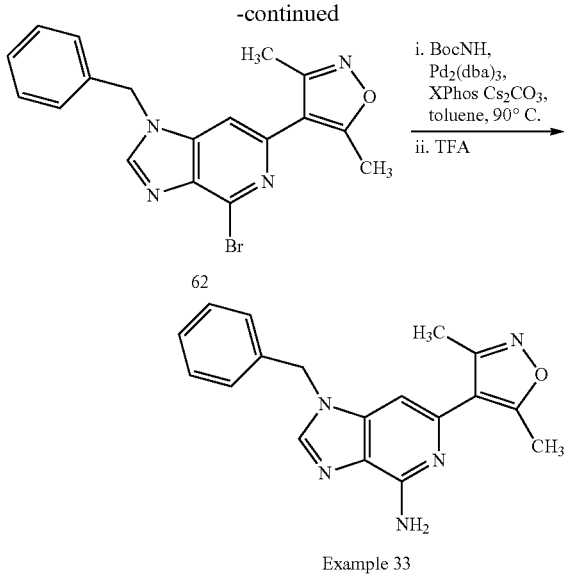

Example 33

Step 1: To a solution of 58 (1.00 g, 5.76 mmol) in 1,4-dioxane (40 mL) and water (4 mL) was added 3,5-dimethyl-4-(4,4,5,5-tetramethyl-1,3,2-dioxaborolan-2-yl)isoxazole (1.93 g, 8.64 mmol), potassium carbonate (1.59 g, 11.5 mmol), and tetrakis(triphenylphosphine)palladium(0) (333 mg, 0.288 mmol). The reaction mixture was purged with nitrogen and heated at 90° C. overnight. The reaction mixture was cooled to room temperature, concentrated and purified by chromatography (silica gel, 0-100% ethyl acetate in hexanes) to afford 59 (1.42 g, >99%) as a yellow solid: $^1$H NMR (300 MHz, CDCl$_3$) δ 9.26 (s, 1H), 6.67 (s, 1H), 6.90-6.00 (bs, 2H), 2.61 (s, 3H), 2.44 (s, 3H); ESI m/z 235 [M+H]$^+$.

Step 2: A mixture of 59 (710 mg, 3.03 mmol), benzyl bromide (778 mg, 4.55 mmol), and potassium carbonate (836 mg, 6.06 mmol) in acetonitrile (30 mL) was heated in sealed tube at 90° C. overnight. The reaction mixture was cooled to room temperature, concentrated and purified by chromatography (silica gel, 0-30% ethyl acetate in hexanes) to afford 60 (303 mg, 30%) as a brown solid: $^1$H NMR (500 MHz, CDCl$_3$) δ 9.26 (s, 1H), 8.68 (s, 1H), 7.50-7.10 (m, 5H), 6.50 (s, 1H), 4.65 (d, J=4.1 Hz, 2H), 2.39 (s, 3H), 2.19 (s, 3H); ESI m/z 325 [M+H]$^+$.

Step 3: To a solution of 60 (300 mg, 0.926 mmol) in tetrahydrofuran (10 mL) was added sodium dithionite (967 mg, 5.56 mmol) in water (10 mL). The reaction mixture was stirred at room temperature overnight and concentrated under vacuum. The residue was suspended in MeOH and the solid was filtered, washed with MeOH, and the filtrate concentrated under vacuum. To the residue was added 2N HCl and heated to just boiling, cooled to room temperature and concentrated under vacuum. The residue was dissolved in MeOH and basified with 10% NaHCO$_3$, concentrated and purified by chromatography (silica gel, 0-20% methanol in ethyl acetate) to afford 61 (150 mg, 55%) as a gray solid: $^1$H NMR (500 MHz, CDCl$_3$) δ 7.99 (s, 1H), 7.40-7.28 (m, 5H), 6.39 (s, 1H), 4.64 (s, 1H), 4.43 (d, J=5.4 Hz, 2H), 3.15 (s, 2H), 2.33 (s, 3H), 2.21 (s, 3H); ESI m/z 295 [M+H]$^+$.

Step 4: To a solution of 61 (150 mg, 0.51 mmol) in ethanol (5 mL) was added trimethylorthoformate (81 mg, 0.77 mmol) and sulfamic acid (1 mg, 0.01 mmol). The reaction was heated in a sealed tube at 90° C. overnight. The mixture was concentrated and purified by chromatography (silica gel, 0-100% ethyl acetate in hexanes) to give Example Compound 31 (143 mg, 92%) as a yellow solid: $^1$H NMR (500 MHz, CD$_3$OD) δ 9.00 (d, J=1.0 Hz, 1H), 8.05 (s, 1H), 7.48 (d, J=1.0 Hz, 1H), 7.40-7.30 (m, 5H), 5.58 (s, 2H), 2.40 (s, 3H), 2.25 (s, 3H); ESI m/z 305 [M+H]$^+$.

Step 5: To a mixture of Example Compound 31 (100 mg, 0.329 mmol) in dichloromethane (5 mL) was added 3-chloroperoxybenzoic acid (264 mg, 77% with water, 1.18 mmol). The mixture was stirred at room temperature overnight, concentrated and purified by chromatography (silica gel, 0-20% methanol in ethyl acetate) to afford Example Compound 32 (127 mg, >99%) as an off-white solid: $^1$H NMR (500 MHz, CD$_3$OD) δ 8.92 (s, 1H), 8.61 (s, 1H), 7.67 (s, 1H), 7.45-7.25 (m, 5H), 6.57 (s, 2H), 2.28 (s, 3H), 2.17 (s, 3H); ESI m/z 321 [M+H]$^+$.

Step 6: To a mixture of phosphorus oxybromide (268 mg, 0.938 mmol) in DMF (2 mL) was added Example 32 (100 mg, 0.313 mmol) in DMF (6 mL). The mixture was stirred at room temperature for 10 min and heated at 100° C. for 1 h. After cooling to room temperature, water and MeOH were added. The mixture was neutralized to pH 7 by addition of 10% sodium bicarbonate and concentrated. The residue was purified by chromatography (silica gel, 0-100% ethyl acetate in hexanes) to afford 62 (30 mg, 25%) as an off-white solid: $^1$H NMR (500 MHz, CDCl$_3$) δ 8.09 (s, 1H), 7.43-7.35 (m, 3H), 7.23-7.19 (m, 2H), 7.03 (s, 1H), 5.38 (s, 2H), 2.47 (s, 3H), 2.31 (s, 3H); ESI m/z 383 [M+H]$^+$.

Step 7: To a solution of 62 (30 mg, 0.078 mmol) in toluene (10 mL) under nitrogen atmosphere was added tert-butyl carbamate (27 mg, 0.23 mmol), cesium carbonate (51 mg, 0.16 mmol), 2-dicyclohexylphosphino-2',4',6'-triisopropyl-1,1'-biphenyl (6 mg, 0.01 mmol) and tris(dibenzylideneacetone)dipalladium(0) (7 mg, 0.008 mmol). The reaction mixture was heated at 90° C. overnight, cooled to room temperature, and purified by chromatography (silica gel, 0-20% methanol in ethyl acetate). It was further purified by reverse phase HPLC on a Polaris column eluting with 10-90% CH$_3$CN in H$_2$O to give Example Compound 33 (10 mg, 40%) as an off-white solid: $^1$H NMR (500 MHz, CD$_3$OD) δ 8.21 (s, 1H), 7.42-7.25 (m, 5H), 6.70 (s, 1H), 5.46 (s, 2H), 2.39 (s, 3H), 2.24 (s, 3H); HPLC 96.9%, $t_R$=10.1 min; ESI m/z 320 [M+H]$^+$.

Preparation of 4-(1-benzyl-3-bromo-1H-pyrrolo[3,2-b]pyridin-6-yl)-3,5-dimethylisoxazole. (Example Compound 34)

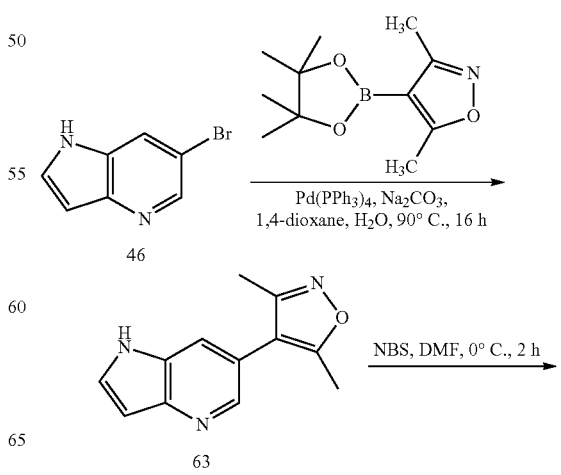

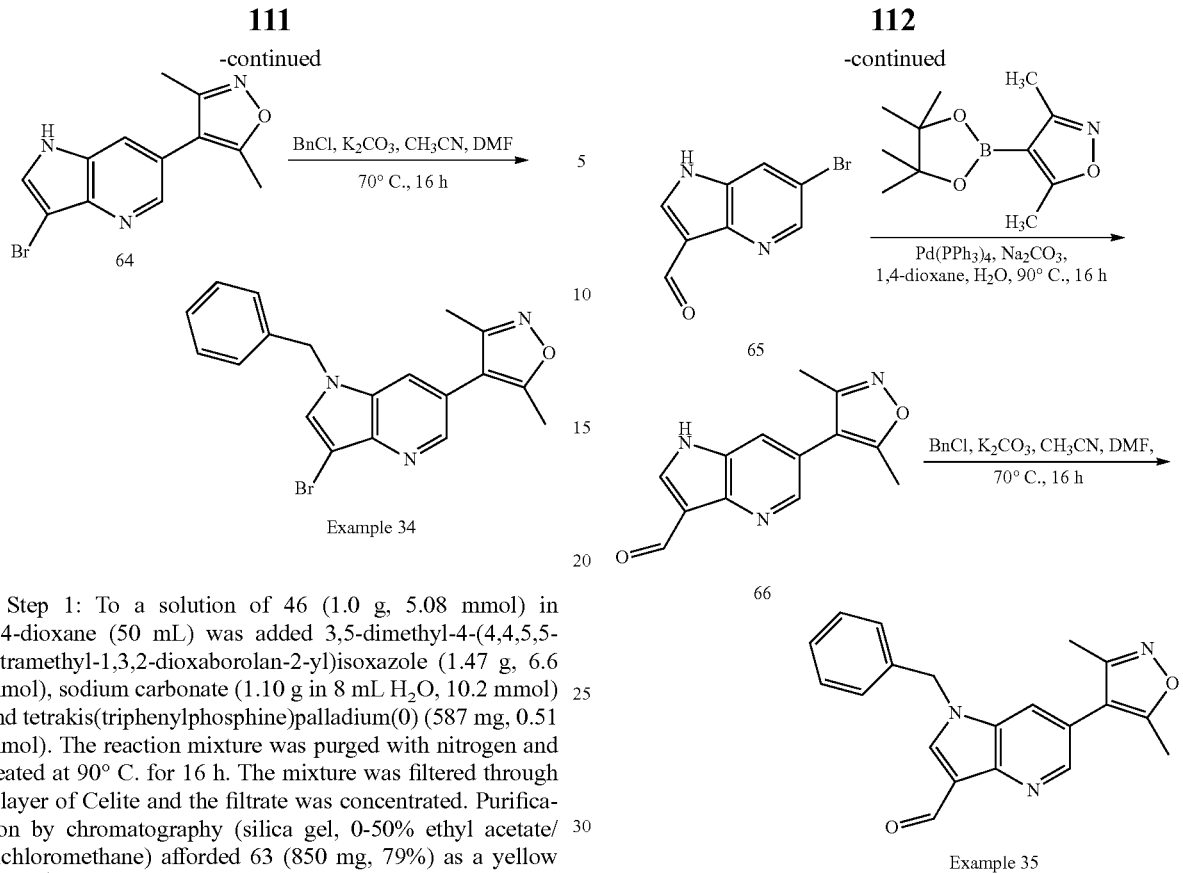

Example 34

Step 1: To a solution of 46 (1.0 g, 5.08 mmol) in 1,4-dioxane (50 mL) was added 3,5-dimethyl-4-(4,4,5,5-tetramethyl-1,3,2-dioxaborolan-2-yl)isoxazole (1.47 g, 6.6 mmol), sodium carbonate (1.10 g in 8 mL H₂O, 10.2 mmol) and tetrakis(triphenylphosphine)palladium(0) (587 mg, 0.51 mmol). The reaction mixture was purged with nitrogen and heated at 90° C. for 16 h. The mixture was filtered through a layer of Celite and the filtrate was concentrated. Purification by chromatography (silica gel, 0-50% ethyl acetate/dichloromethane) afforded 63 (850 mg, 79%) as a yellow solid: $^1$H NMR (300 MHz, DMSO-$d_6$) δ 11.4 (s, 1H), 8.30 (t, J=2.1 Hz, 1H), 7.75 (dd, J=1.8, 0.9 Hz, 1H), 7.70 (t, J=3.0 Hz, 1H), 6.61-6.59 (m, 1H), 2.42 (s, 3H), 2.24 (s, 3H).

Step 2/3: To a solution of 63 (500 mg, 2.35 mmol) in DMF (10 mL) at 0° C. was added NBS (500 mg, 2.82 mmol). The reaction mixture was stirred at 0° C. for 2 h. The mixture was diluted with methylene chloride (50 mL) and washed with brine (20 mL). The organic layer was dried over sodium sulfate, filtered and concentrated. The crude 64 was carried forward. To a solution of 64 (300 mg, 1.03 mmol) in DMF (1 mL) and CH₃CN (10 mL) was added potassium carbonate (283 mg, 2.06 mmol) and benzyl chloride (130 mg, 1.03 mmol). The reaction was stirred at 70° C. for 16 h. The mixture was filtered through a layer of Celite and the filtrate was concentrated. Purification by chromatography silica gel, 0-50% ethyl acetate/dichloromethane) afforded Example Compound 34 (200 mg, 51%) as an off-white solid: $^1$H NMR (500 MHz, CD₃OD) δ 8.33 (d, J=1.5 Hz, 1H), 7.86 (s, 1H), 7.80 (d, J=2.0 Hz, 1H), 7.34-7.24 (m, 5H), 5.48 (s, 2H), 2.35 (s, 3H), 2.17 (s, 3H); ESI MS m/z 382 [M+H]⁺.

Preparation of 1-benzyl-6-(3,5-dimethylisoxazol-4-yl)-1H-pyrrolo[3,2-b]pyridine-3-carbaldehyde (Example Compound 35)

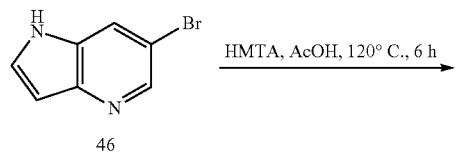

Step 1: To a mixture of 46 (300 mg, 1.5 mmol) and hexamethylenetetramine (0.32 g, 2.25 mmol) was added AcOH (2 mL). The reaction mixture was stirred at 120° C. for 6 h and was quenched with H₂O (5 mL). The precipitate was collected by filtration to afford 65 (190 mg, 56%) as a yellow solid: $^1$H NMR (300 MHz, DMSO-$d_6$) δ 12.4 (s, 1H), 10.1 (s, 1H), 8.58 (d, J=2.1 Hz, 1H), 8.47 (s, 1H), 8.18 (d, J=2.1 Hz, 1H).

Step 2: To a solution of 65 (190 mg, 0.84 mmol) in 1,4-dioxane (5 mL) was added 3,5-dimethyl-4-(4,4,5,5-tetramethyl-1,3,2-dioxaborolan-2-yl)isoxazole (245 mg, 1.09 mmol), sodium carbonate (178 mg in 1 mL H₂O, 1.68 mmol) and tetrakis(triphenylphosphine)palladium(0) (97 mg, 0.08 mmol). The reaction mixture was purged with nitrogen and heated at 90° C. for 16 h. The mixture was filtered through a layer of Celite and the filtrate was concentrated. Purification by chromatography (silica gel, 0-50% ethyl acetate/dichloromethane) afforded 66 (135 mg, 67%) as an off-white solid: $^1$H NMR (300 MHz, DMSO-$d_6$) δ 12.5 (s, 1H), 10.2 (s, 1H), 8.51 (d, J=1.8 Hz, 1H), 8.49 (d, J=3.0 Hz, 1H), 7.92 (d, J=1.8 Hz, 1H), 2.44 (s, 3H), 2.26 (s, 3H); ESI MS m/z 242 [M+H]⁺.

Step 3: To a solution of 66 (92 mg, 0.38 mmol) in DMF (0.5 mL) and CH₃CN (5 mL) was added potassium carbonate (105 mg, 0.76 mmol) and benzyl chloride (58 mg, 0.46 mmol). The reaction was stirred at 70° C. for 16 h. The reaction mixture was filtered through a layer of Celite and the filtrate was concentrated. Purification by chromatography (silica gel, 0-50% ethyl acetate/dichloromethane) afforded Example Compound 35 (72 mg, 57%) as an off-white solid: $^1$H NMR (300 MHz, DMSO-$d_6$) δ 10.2 (s, 1H), 8.73 (s, 1H), 8.53 (d, J=1.8 Hz, 1H), 8.11 (d, J=1.8 Hz, 1H), 7.44-7.30 (m, 5H), 5.59 (s, 2H), 2.40 (s, 3H), 2.21 (s, 3H); ESI MS m/z 332 [M+H]⁺.

Preparation of 1-(1-benzyl-6-(3,5-dimethylisoxazol-4-yl)-1H-pyrrolo[3,2-b]pyridin-3-yl)-N,N-dimethyl-methanamine (Example Compound 72)

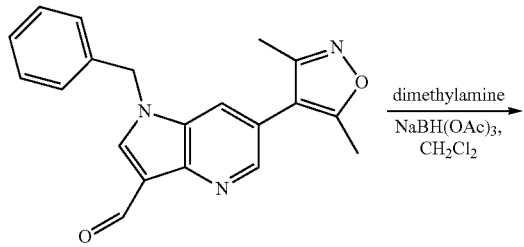

Example 35

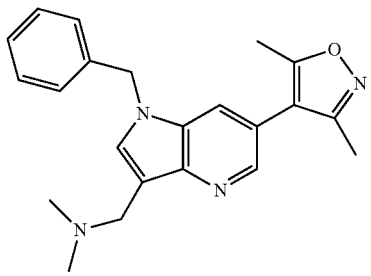

Example 72

A solution of Example Compound 35 (54 mg, 0.16 mmol), dimethylamine (0.25 mL, 2M in THF, 0.49 mmol) and NaBH(OAc)$_3$ (104 mg, 0.49 mmol) in CH$_2$Cl$_2$ (3 mL) was stirred at room temperature for 16 h. The reaction mixture was concentrated under reduced pressure. The crude reaction mixture was purified by chromatography (silica gel, 0-10% methanol/dichloromethane) to provide Example Compound 72 (42 mg, 71%) as an off-white solid: $^1$H NMR (300 MHz, CDCl$_3$) δ 8.34 (d, J=1.8 Hz, 1H), 8.30 (s, 1H), 7.36-7.32 (m, 4H), 7.21-7.18 (m, 2H), 5.39 (s, 2H), 4.50 (s, 2H), 2.86 (s, 6H), 2.32 (s, 3H), 2.16 (s, 3H); ESI MS m/z 361 [M+H]$^+$.

Preparation of 1-(1-benzyl-6-(3,5-dimethylisoxazol-4-yl)-1H-pyrrolo[3,2-b]pyridin-3-yl)ethanone (Example Compound 36)

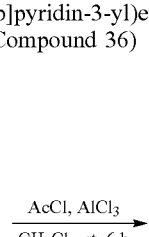

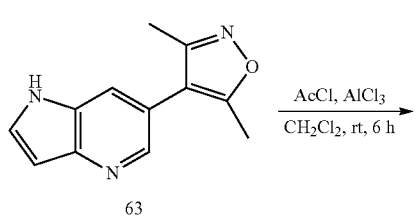

63

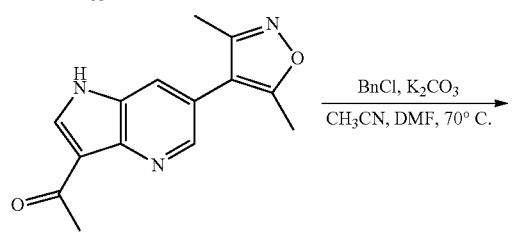

67

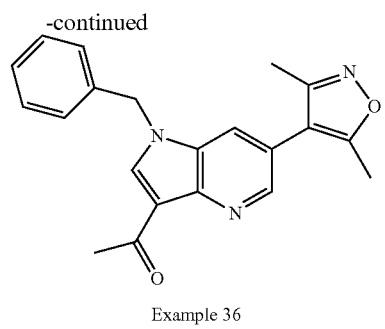

Example 36

Step 1: To a suspension of AlCl$_3$ (313 mg, 2.35 mmol) in CH$_2$Cl$_2$ (20 mL) was added 63 (100 mg, 0.47 mmol) and AcCl (184 mg, 2.35 mmol). The reaction mixture was stirred at rt for 6 h. The reaction was quenched with methanol (10 mL) carefully and the pH adjusted to neutral with solid Na$_2$CO$_3$. The mixture was filtered through a layer of Celite and the filtrate was concentrated. Purification by chromatography (silica gel, 0-10% methanol/dichloromethane) afforded 67 (82 mg, 68%) as an off-white solid: $^1$H NMR (300 MHz, DMSO-d$_6$) δ 12.8 (s, 1H), 8.67 (s, 1H), 8.57 (s, 1H), 8.21 (s, 1H), 2.71 (s, 3H), 2.45 (s, 3H), 2.26 (s, 3H); ESI MS m/z 256 [M+H]$^+$.

Step 2: To a solution of 67 (62 mg, 0.24 mmol) in DMF (0.5 mL) and CH$_3$CN (5 mL) was added potassium carbonate (67 mg, 0.48 mmol) and benzyl chloride (37 mg, 0.29 mmol). The reaction was stirred at 70° C. for 16 h. The reaction mixture was filtered through a layer of Celite and the filtrate was concentrated. Purification by chromatography (silica gel, 0-50% ethyl acetate/dichloromethane) afforded Example Compound 36 (30 mg, 36%) as an off-white solid: $^1$H NMR (300 MHz, CDCl$_3$) δ 8.59 (d, J=1.5 Hz, 1H), 8.22 (s, 1H), 7.45 (d, J=1.8 Hz, 1H), 7.40-7.36 (m, 3H), 7.21-7.18 (m, 2H), 5.40 (s, 2H), 2.89 (s, 3H), 2.34 (s, 3H), 2.17 (s, 3H); ESI MS m/z 346 [M+H]$^+$.

Preparation of 1-benzyl-6-(3,5-dimethylisoxazol-4-yl)-1H-pyrrolo[3,2-b]pyridin-5-yl formate (Example Compound 37)

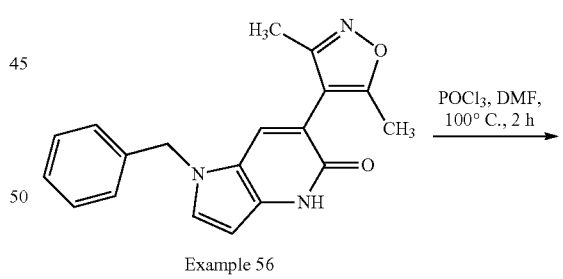

Example 56

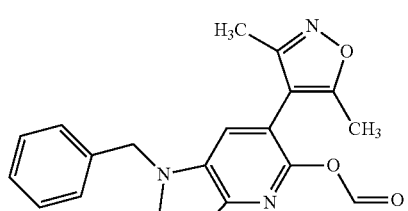

Example 37

Step 1: A solution of Example Compound 56 (165 mg, 0.52 mmol) in DMF (2 mL) was added POCl$_3$ (159 mg, 1.03 mmol). The reaction mixture was heated at 100° C. for 2 h and concentrated. The residue was dissolved in CH$_2$Cl$_2$ (100 mL), washed with saturated NaHCO$_3$ (2×20 mL) and brine (20 mL). The organic layer was dried over sodium sulfate, filtered and concentrated. Purification by chromatography (silica gel, 0-50% ethyl acetate/dichloromethane) afforded Example Compound 37 (81 mg, 45%) as a yellow solid: $^1$H NMR (300 MHz, CDCl$_3$) δ 9.90 (s, 1H), 7.62 (s, 1H), 7.43-7.41 (m, 3H), 7.28 (s, 1H), 7.22-7.18 (m, 3H), 5.31 (s, 2H), 2.22 (s, 3H), 2.10 (s, 3H); ESI MS m/z 348 [M+H]$^+$.

Preparation of 4-((6-(3,5-dimethylisoxazol-4-yl)-2-methyl-1H-imidazo[4,5-b]pyridin-1-yl)methyl)benzamide (Example Compound 38)

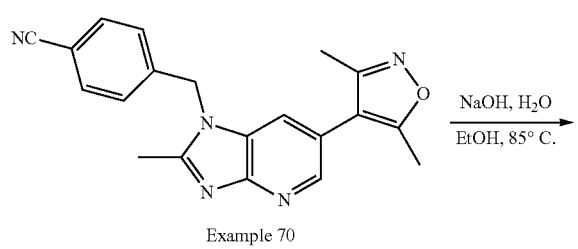

Example 70

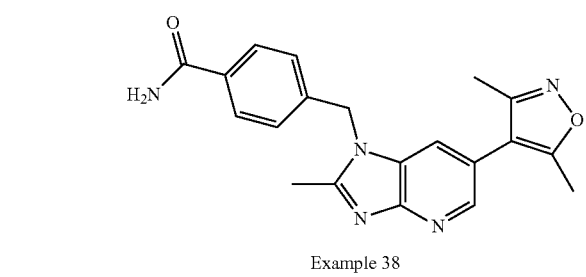

Example 38

To a solution of Example Compound 70 (100 mg, 0.29 mmol) in ethanol (3 mL) was added 2N sodium hydroxide in water (1.46 mL, 2.9 mmol). The mixture was heated to 85° C. for 20 min, then cooled to room temperature, and neutralized with 2 mL of acetic acid. The mixture was basified (pH 8) with solid sodium carbonate, diluted in methylene chloride (100 mL), washed with brine (20 mL), and dried over anhydrous sodium sulfate. After filtration, the filtrate was concentrated in vacuo and purified by chromatography (silica gel, 0-20% methanol/methylene chloride) to afford Example Compound 38 as a white solid (71 mg, 68%): $^1$H NMR (300 MHz, DMSO-d$_6$) δ 8.35 (d, J=1.8 Hz, 1H), 7.99 (d, J=2.1 Hz, 1H), 7.94 (br s, 1H), 7.83 (d, J=8.4 Hz, 2H), 7.37 (br s, 1H), 7.27 (d, J=8.4 Hz, 2H), 5.61 (s, 2H), 2.60 (s, 3H), 2.39 (s, 3H), 2.21 (s, 3H); ESI m/z 362 [M+H]$^+$.

Preparation of 4-(1-benzyl-3-nitro-1H-pyrrolo[3,2-b]pyridin-6-yl)-3,5-dimethylisoxazole (Example Compound 39)

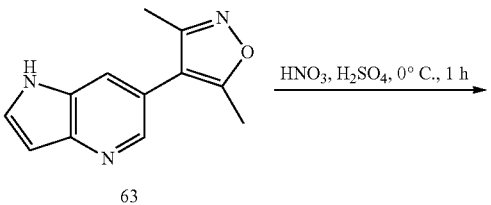

63

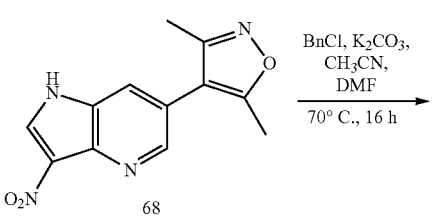

68

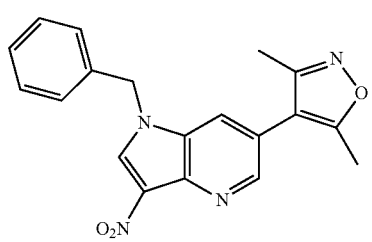

Example 39

Step 1: To a solution of 63 (100 mg, 0.47 mmol) in H$_2$SO$_4$ (0.5 mL) at 0° C. was added HNO$_3$ (35 mg, 0.47 mmol). The reaction mixture was stirred at 0° C. for 1 h. The reaction mixture was diluted with H$_2$O (10 mL) and adjusted to neutral pH with 6N NaOH solution. The solution was extracted with CH$_2$Cl$_2$ (30 mL). The organic layer was dried, filtered and concentrated. Purification by chromatography (silica gel, 0-10% methanol/dichloromethane) afforded 68 (82 mg, 68%) as a yellow solid: $^1$H NMR (300 MHz, DMSO-d$_6$) δ 12.9 (s, 1H), 8.85 (s, 1H), 8.58 (d, J=2.1 Hz, 1H), 7.95 (d, J=1.8 Hz, 1H), 2.45 (s, 3H), 2.26 (s, 3H); ESI MS m/z 259 [M+H]$^+$.

Step 2: To a solution of 68 (82 mg, 0.32 mmol) in DMF (0.5 mL) and CH$_3$CN (5 mL) was added potassium carbonate (88 mg, 0.64 mmol) and benzyl chloride (44 mg, 0.35 mmol). The reaction was stirred at 70° C. for 16 h. The reaction mixture was filtered through a layer of Celite and the filtrate was concentrated. Purification by chromatography (silica gel, 0-50% ethyl acetate/dichloromethane) afforded Example Compound 39 (68 mg, 61%) as an off-white solid: $^1$H NMR (300 MHz, CDCl$_3$) δ 8.74 (s, 1H), 8.47 (s, 1H), 7.56 (s, 1H), 7.45-7.42 (m, 3H), 7.27-7.26 (m, 2H), 5.47 (s, 2H), 2.35 (s, 3H), 2.17 (s, 3H); ESI MS m/z 349 [M+H]$^+$.

Preparation of 1-benzyl-6-(3,5-dimethylisoxazol-4-yl)-2-ethoxy-1H-benzo[d]imidazol-4-amine (Example Compound 17)

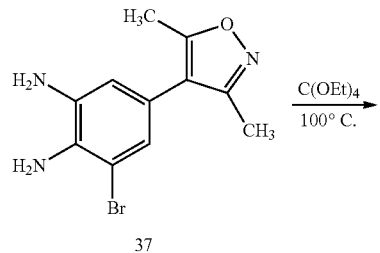

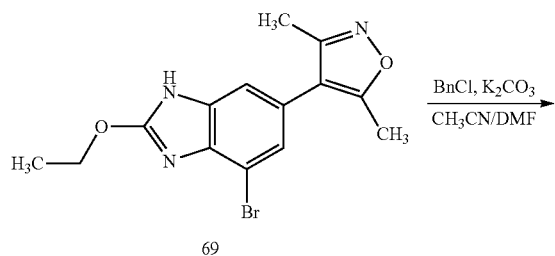

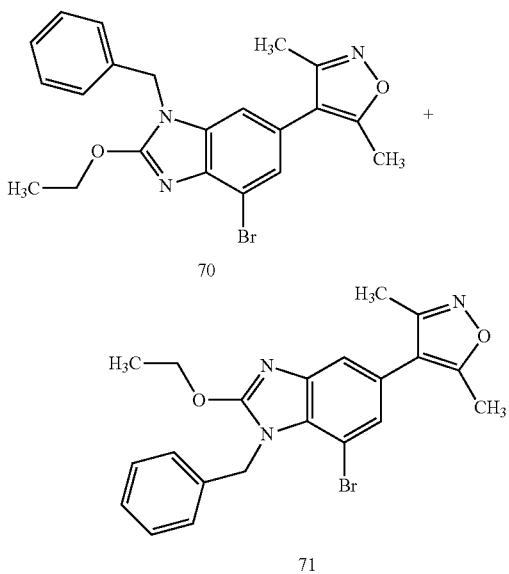

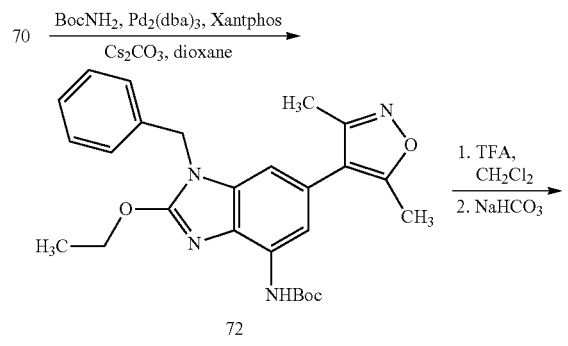

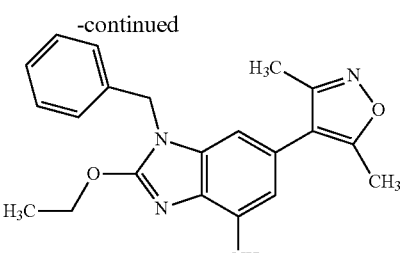

Example 17

Step 1: A mixture of 37 (200 mg, 0.709 mmol) in tetraethoxymethane (340 mg, 1.77 mmol) was heated at 100° C. for 4 h. The reaction mixture was cooled to room temperature, concentrated and purified by chromatography (silica gel, 0-50% ethyl acetate in hexanes) to afford 69 (177 mg, 74%) as a yellow solid: $^1$H NMR (500 MHz, CD$_3$OD) δ 7.30-7.15 (m, 2H), 4.57 (q, J=7.0 Hz, 2H), 2.39 (s, 3H), 2.23 (s, 3H), 1.47 (t, J=7.0 Hz, 3H); ESI m/z 336 [M+H]$^+$.

Step 2: To a solution of 69 (250 mg, 0.74 mmol) in CH$_3$CN (8 mL) and DMF (2 mL) was added K$_2$CO$_3$ (155 mg, 0.82 mmol) and benzyl chloride (104 mg, 0.82 mmol). The reaction was heated at 60° C. for 16 h. The mixture was diluted with ethyl acetate (100 mL), filtered and concentrated. The residue was purified by chromatography (silica gel, 0-30% EtOAc/hexanes) to afford 70 (200 mg, 63%) as an off-white solid and 71 (87 mg, 27%) as a colorless oil: 70: $^1$H NMR (300 MHz, CDCl$_3$) δ 7.34-7.29 (m, 3H), 7.21-7.18 (m, 3H), 6.77 (d, J=1.5 Hz, 1H), 5.16 (s, 2H), 4.75 (q, J=7.5 Hz, 2H), 2.29 (s, 3H), 2.14 (s, 3H), 1.50 (t, J=7.0 Hz, 3H); 71: $^1$H NMR (300 MHz, CDCl$_3$) δ 7.37 (d, J=1.5 Hz, 1H), 7.34-7.28 (m, 3H), 7.18 (d, J=7.5 Hz, 2H), 7.12 (d, J=1.5 Hz, 1H), 5.60 (s, 2H), 4.63 (q, J=7.0 Hz, 2H), 2.41 (s, 3H), 2.28 (s, 3H), 1.45 (t, J=7.0 Hz, 3H).

Step 3: A mixture of 70 (100 mg, 0.235 mmol), BocNH$_2$ (82 mg, 0.705 mmol), Xantphos (28 mg, 0.048 mmol), Pd$_2$(dba)$_3$ (22 mg, 0.024 mmol) and Cs$_2$CO$_3$ (268 mg, 0.823 mmol) in 1,4-dioxane (8 mL) was purged with nitrogen and heated at 100° C. for 18 h. The mixture was diluted with methylene chloride (200 mL) and filtered. The filtrate was concentrated and purified by chromatography (silica gel, 0-30% EtOAc/hexanes) to afford 72 (90 mg, 83%) as an off-white solid: $^1$H NMR (300 MHz, CDCl$_3$) δ 7.74 (br s, 1H), 7.41 (s, 1H), 7.32-7.29 (m, 3H), 7.22-7.19 (m, 2H), 6.51 (d, J=1.5 Hz, 1H), 5.14 (s, 2H), 4.64 (q, J=7.2 Hz, 2H), 2.32 (s, 3H), 2.17 (s, 3H), 1.49 (t, J=7.2 Hz, 3H), 1.46 (s, 9H).

Step 4: A solution of 72 (90 mg, 0.195 mmol) in TFA (1 mL) and CH$_2$Cl$_2$ (2 mL) was stirred at rt for 1 h. The mixture was concentrated, the residue was dissolved in ethyl acetate (100 mL) and washed with saturated NaHCO$_3$ (50 mL×2). The organic layer was dried over sodium sulfate, filtered and concentrated. Purification by chromatography (silica gel, 40-100% EtOAc/hexanes) afforded Example Compound 17 (51 mg, 72%) as an off-white solid: $^1$H NMR (300 MHz, CDCl$_3$) δ 7.35-7.20 (m, 5H), 6.33 (d, J=1.5 Hz, 1H), 6.30 (d, J=1.5 Hz, 1H), 5.13 (s, 2H), 4.68 (q, J=6.9 Hz, 2H), 4.30 (br s, 2H), 2.30 (s, 3H), 2.16 (s, 3H), 1.49 (t, J=7.2 Hz, 3H); ESI m/z 363 [M+H]$^+$.

Preparation of 4-(1-benzyl-2-ethoxy-1H-imidazo[4,5-b]pyridin-6-yl)-3,5-dimethylisoxazole (Example Compound 59)

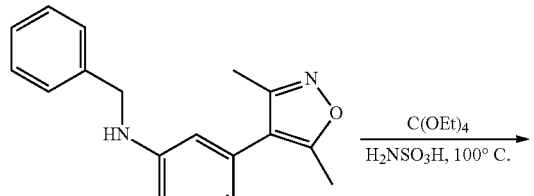

28

To a mixture of 28 (50 mg, 0.17 mmol) and tetraethyl orthocarbonate (131 mg, 0.68 mmol) was added sulfamic acid (3 mg, 0.034 mmol). The mixture was then heated to 100° C. for 8 h, then diluted with ethyl acetate (30 mL), washed with brine (15 mL), dried over anhydrous sodium sulfate, and concentrated in vacuo. The residue was purified by chromatography (silica gel, 0-10% methanol/methylene chloride) to afford Example Compound 59 (24 mg, 41%) as an off-white solid: $^1$H NMR (300 MHz, DMSO-$d_6$) δ 7.75 (d, J=1.2 Hz, 1H), 7.38-7.22 (m, 5H), 7.18 (d, J=1.5 Hz, 1H), 4.99 (s, 2H), 4.34 (q, J=7.2 Hz, 2H), 2.37 (s, 3H), 2.18 (s, 3H), 1.42 (t, J=7.2 Hz, 3H); ESI m/z 349 [M+H]$^+$.

Preparation of 1-benzyl-6-(3,5-dimethylisoxazol-4-yl)-2-methyl-1H-benzo[d]imidazole-4-carbonitrile (Example Compound 85)

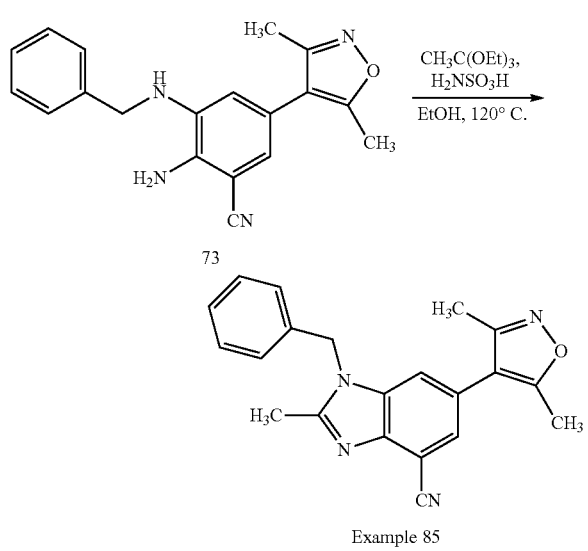

Compound 73 was prepared by following the method for General Procedure J steps 1 to 3 starting with 2-amino-5-bromobenzonitrile. Using the procedure used for General Procedure D step 3 on compound 73 (30 mg, 0.09 mmol) afforded Example Compound 85 (10 mg, 31%) as an off-white solid: $^1$H NMR (500 MHz, CD$_3$OD) δ 7.63 (d, J=1.5 Hz, 1H), 7.60 (d, J=1.5 Hz, 1H), 7.38-7.27 (m, 3H), 7.19-7.14 (m, 2H), 5.57 (s, 2H), 2.69 (s, 3H), 2.32 (s, 3H), 2.16 (s, 3H); ESI m/z 343 [M+H]$^+$.

General Procedure O:

Preparation of N-(1-benzyl-6-(3,5-dimethylisoxazol-4-yl)-2-oxo-2,3-dihydro-1H-benzo[d]imidazol-4-yl)acetamide (Example Compound 111)

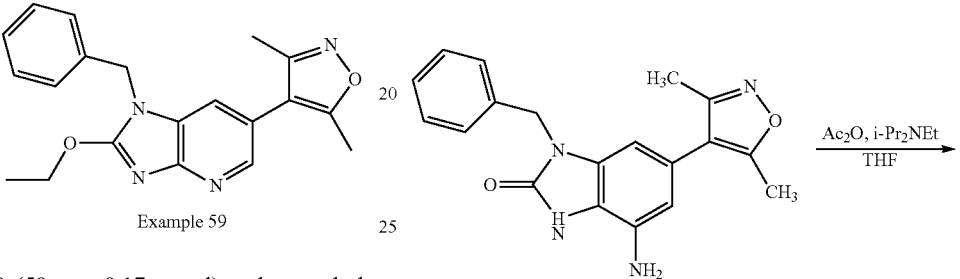

Example 16

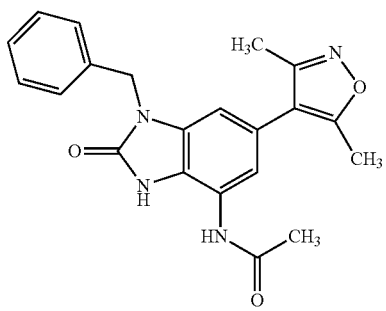

Example 111

A solution of Example Compound 16 (34 mg, 0.10 mmol), acetic anhydride (12 mg, 0.12 mmol) and i-Pr$_2$NEt (26 mg, 0.20 mmol) in THF (3 mL) was stirred at rt for 16 h. The mixture was concentrated, and the residue was purified by chromatography (silica gel, 0-5% methanol/EtOAc) to afford Example Compound 111 (28 mg, 74%) as a white solid: $^1$H NMR (300 MHz, DMSO-$d_6$) δ 10.78 (s, 1H), 9.85 (s, 1H), 7.60-7.46 (m, 5H), 7.28 (d, J=1.2 Hz, 1H), 7.06 (d, J=1.2 Hz, 1H), 5.22 (s, 2H), 2.51 (s, 3H), 2.33 (s, 3H), 2.27 (s, 3H); ESI m/z 377 [M+H]$^+$.

General Procedure P:

Preparation of 6-(3,5-dimethylisoxazol-4-yl)-4-nitro-1-(1-phenylethyl)-1H-benzo[d]imidazol-2(3H)-one (Example Compound 110) and 4-amino-6-(3,5-dimethylisoxazol-4-yl)-1-(1-phenylethyl)-1H-benzo[d]imidazol-2(3H)-one (Example Compound 115)

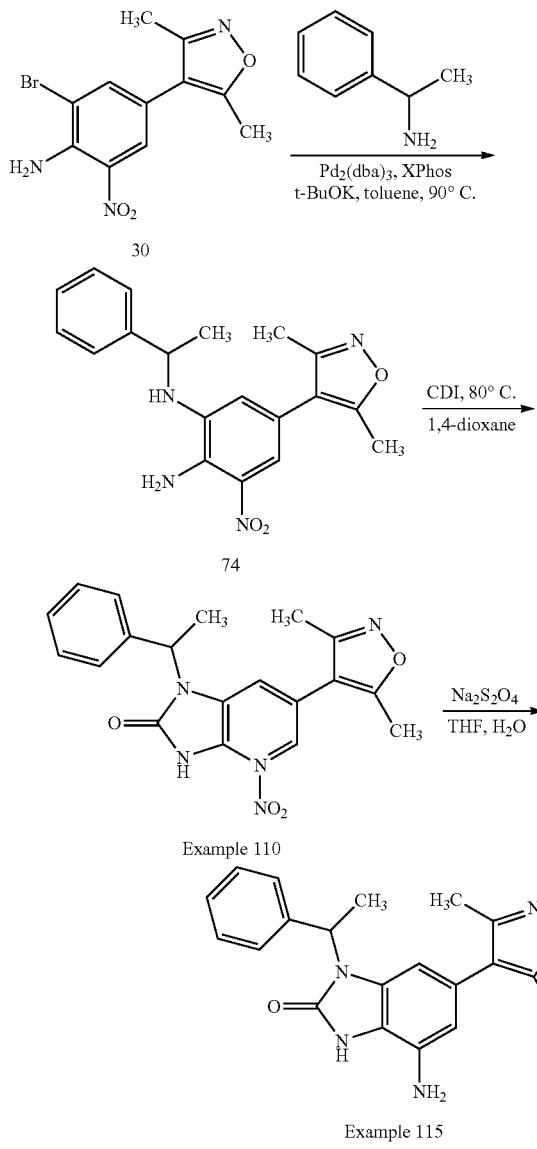

Step 1: To a solution of 30 (1.00 g, 3.21 mmol) in toluene (70 mL) under nitrogen atmosphere was added benzyl amine (1.94 g, 16.0 mmol), potassium tert-butoxide (539 mg, 4.82 mmol), 2-dicyclohexylphosphino-2',4',6'-tri-i-propyl-1,1'-biphenyl (229 mg, 0.482 mmol), and tris(dibenzylideneacetone)dipalladium(0) (293 mg, 0.321 mmol). The reaction mixture was heated at 90° C. overnight, cooled to room temperature, and purified by chromatography (silica gel, 0-50% ethyl acetate in hexanes) to afford 74 (700 mg, 62%) as a red-brown solid: $^1$H NMR (500 MHz, CDCl$_3$) δ 7.50 (d, J=1.8 Hz, 1H), 7.70-7.22 (m, 5H), 6.41 (d, J=1.6 Hz, 1H), 6.07 (s, 2H), 4.48 (q, J=3.5 Hz, 1H), 3.65 (s, 1H), 2.05 (s, 3H), 1.90 (s, 3H), 1.62 (d, J=6.6 Hz, 3H); ESI m/z 353 [M+H]$^+$.

Step 2: To a mixture of 74 (600 mg, 1.70 mmol) in 1,4-dioxane (40 mL) was added 1,1'-carbonyldiimidazole (2.76 mg, 17.0 mmol) and DMAP (a crystal). The reaction was heated in a sealed tube at 120° C. for 2 days. The mixture was concentrated and purified by chromatography (silica gel, 0-100% ethyl acetate in hexanes) to give Example Compound 110 (420 mg, 65%) as an orange solid: $^1$H NMR (500 MHz, CD$_3$OD) δ 7.75 (d, J=1.3 Hz, 1H), 7.44 (d, J=7.7 Hz, 2H), 7.38 (t, J=7.7 Hz, 2H), 7.31 (t, J=7.7 Hz, 1H), 6.88 (d, J=1.3 Hz, 1H), 5.88 (q, J=7.1 Hz, 1H), 2.20 (s, 3H), 2.02 (s, 3H), 1.91 (d, J=7.2 Hz, 3H); ESI m/z 377 [M+H]$^+$.

Step 3: To a solution of Example Compound 110 (100 mg, 0.265 mmol) in tetrahydrofuran (10 mL) was added sodium dithionite (276 mg, 1.59 mmol) in water (10 mL). The reaction mixture was stirred at room temperature overnight and concentrated under vacuum. The residue was added 2N HCl and heated to just boiling, cooled to room temperature, and concentrated in vacuum. The residue was dissolved in MeOH and basified by conc. NH$_4$OH, concentrated, and purified by chromatography (silica gel, 0-100% hexanes/ethyl acetate). It was further purified by reverse phase HPLC on a Polaris C$_{18}$ column eluted with 10-90% CH$_3$CN in H$_2$O to give Example Compound 115 (49 mg, 53%) as an off-white solid: $^1$H NMR (500 MHz, CD$_3$OD) δ 7.42-7.32 (m, 4H), 7.26 (t, J=6.9 Hz, 1H), 6.35 (s, 1H), 5.94 (s, 1H), 5.78 (q, J=7.2 Hz, 1H), 2.17 (s, 3H), 2.00 (s, 3H), 1.86 (d, J=7.2 Hz, 3H); ESI m/z 349 [M+H]$^+$.

General Procedure Q:

Preparation of 4-(1-benzyl-6-(3,5-dimethylisoxazol-4-yl)-1H-imidazo[4,5-b]pyridin-2-yl)morpholine (Example Compound 114)

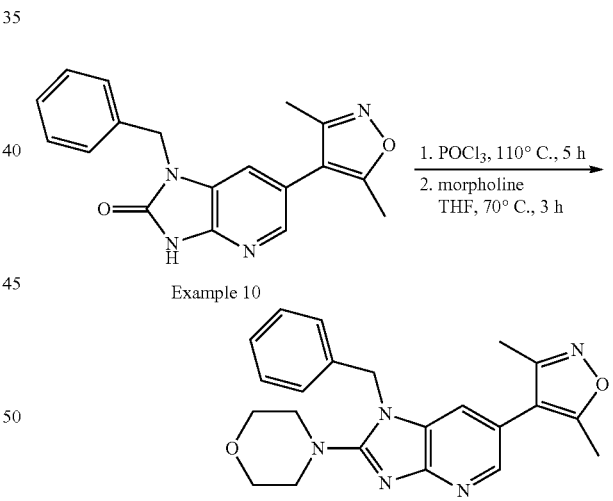

A mixture of Example Compound 10 (90 mg, 0.28 mmol) and phosphorus (V) oxychloride (1 mL) was heated to 110° C. for 5 h, then cooled to room temperature. The mixture was concentrated, dissolved with methylene chloride (75 mL), and washed with saturated sodium bicarbonate solution (20 mL). The organic layer was dried over sodium sulfate, filtered, and concentrated. The residue was dissolved in a 2.0 M solution of morpholine in tetrahydrofuran (5.6 mL, 11.2 mmol) and the mixture was heated to 75° C. for 3 h. The reaction mixture was concentrated, and the residue was purified by chromatography (silica gel, 0-5% methanol/ methylene chloride), and then triturated with ethyl acetate/ hexanes to afford Example Compound 114 (62 mg, 57%) as a white solid: $^1$H NMR (500 MHz, CDCl$_3$) δ 8.24 (d, J=2.0 Hz, 1H), 7.41-7.34 (m, 3H), 7.15 (d, J=6.5 Hz, 2H), 7.06 (d, J=1.0 Hz, 1H), 5.26 (s, 2H), 3.83 (t, J=4.5 Hz, 4H), 3.50 (t, J=4.5 Hz, 4H), 2.29 (s, 3H), 2.11 (s, 3H); ESI m/z 390 [M+H]$^+$.

General Procedure R:

Preparation of 1-(3,4-dichlorobenzyl)-6-(3,5-dimethylisoxazol-4-yl)-1H-imidazo[4,5-b]pyridin-2(3H)-one (Example Compound 101)

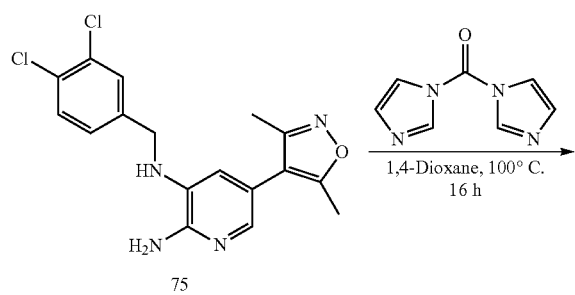

General Procedure S:

Preparation of (S)-3,5-dimethyl-4-(2-methyl-4-nitro-1-(1-phenylethyl)-1H-benzo[d]imidazol-6-yl)isoxazole (Example Compound 125) and (S)-6-(3,5-dimethylisoxazol-4-yl)-2-methyl-1-(1-phenylethyl)-1H-benzo[d]imidazol-4-amine (Example Compound 143)

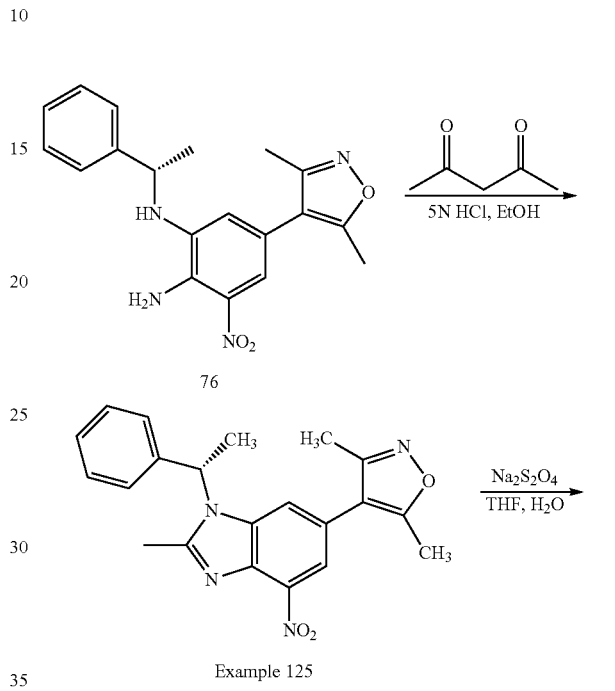

Compound 75 was prepared according to General Procedure D, steps 1-2.

To a solution of 75 (218 mg, 0.60 mmol) in 1,4-dioxane (5 mL) was added 1,1'-carbonyldiimidazole (117 mg, 0.72 mmol), and the mixture was heated to 100° C. for 16 h. The mixture was diluted with methylene chloride (70 mL), and washed with brine (20 mL). The organic layer was dried over sodium sulfate, filtered, and concentrated. The residue was purified by chromatography (silica gel, 0-10% methanol/methylene chloride) to afford Example Compound 101 (155 mg, 66%) as a white solid: $^1$H NMR (500 MHz, DMSO-d$_6$) δ 11.83 (s, 1H), 7.92 (d, J=1.5 Hz, 1H), 7.73 (d, J=2.0 Hz, 1H), 7.61 (d, J=8.0 Hz, 1H), 7.53 (d, J=2.0 Hz, 1H), 7.35 (dd, J=8.5, 2.0 Hz, 1H), 5.05 (s, 2H), 2.37 (s, 3H), 2.19 (s, 3H); ESI m/z 389 [M+H]$^+$.

Compound 76 was prepared by following the method of General Procedure P step 1 starting with (S)-1-phenylethanamine.

Step 1: Using the procedure used in General Procedure F step 1 starting with compound 76 (140 mg, 0.40 mmol) afforded Example Compound 125 (108 mg, 72%) as a yellow solid: $^1$H NMR (300 MHz, DMSO-d$_6$) δ 7.87 (d, J=1.5 Hz, 1H), 7.42-7.30 (m, 6H), 6.11 (q, J=7.2 Hz, 1H), 2.74 (s, 3H), 2.23 (s, 3H), 2.04 (s, 3H), 1.94 (d, J=6.9 Hz, 3H); ESI MS m/z 377 [M+H]$^+$.

Step 2: Using the procedure used in General Procedure P step 3 starting with compound Example Compound 125 (80 mg, 0.21 mmol) afforded Example Compound 143 (53 mg, 72%) as an off-white solid: $^1$H NMR (300 MHz, DMSO-d$_6$) δ 7.39-7.26 (m, 5H), 6.23 (d, J=1.5 Hz, 1H), 6.14 (d, J=1.2 Hz, 1H), 5.86 (q, J=7.2 Hz, 1H), 5.26 (s, 2H), 2.58 (s, 3H), 2.20 (s, 3H), 2.02 (s, 3H), 1.86 (d, J=6.9 Hz, 3H); ESI MS m/z 347 [M+H]$^+$.

General Procedure T:

Preparation of 4-(1-benzyl-2-(pyridin-3-yloxy)-1H-imidazo[4,5-b]pyridin-6-yl)-3,5-dimethylisoxazole (Example Compound 236)

Preparation of 6-(3,5-dimethylisoxazol-4-yl)-N-ethyl-4-nitro-1-(1-phenylethyl)-1H-benzo[d]imidazol-2-amine (Example Compound 127) and 6-(3,5-dimethylisoxazol-4-yl)-$N^2$-ethyl-1-(1-phenylethyl)-1H-benzo[d]imidazole-2,4-diamine (Example Compound 134)

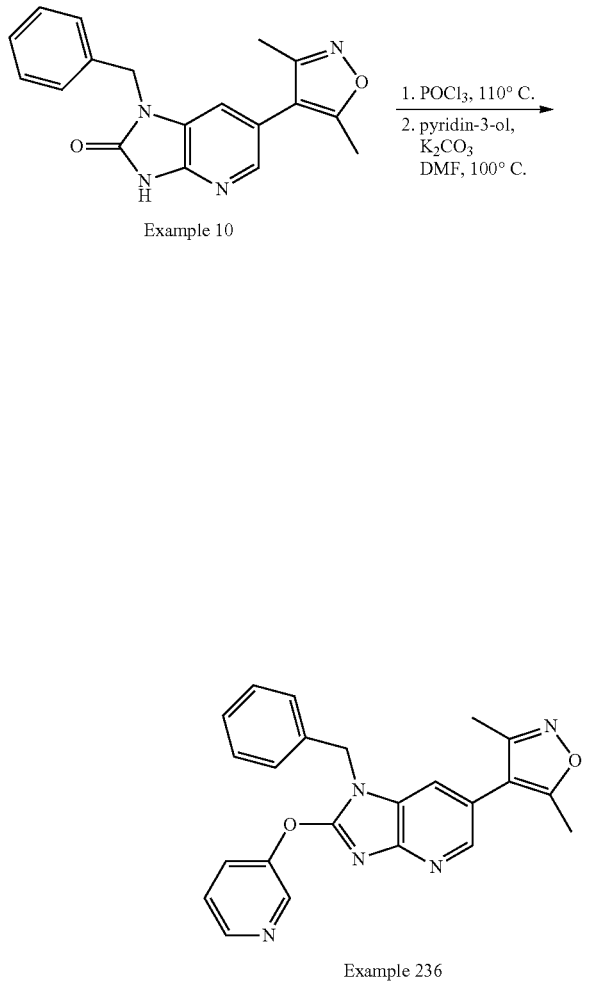

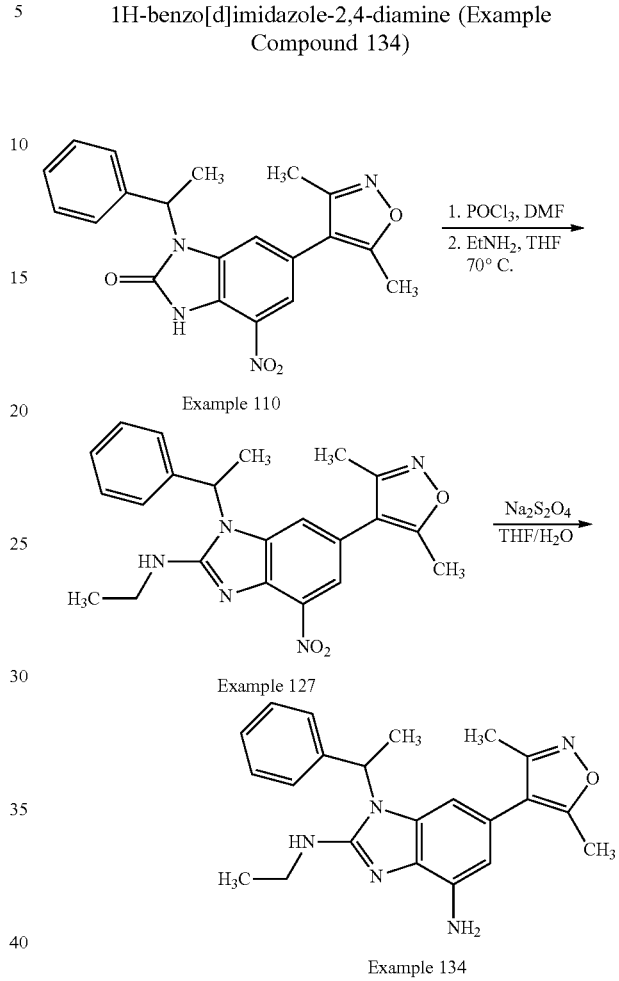

A mixture of Example Compound 10 (100 mg, 0.31 mmol) and phosphorus (V) oxychloride (1 mL) was heated to 110° C. for 5 h, then cooled to room temperature. The mixture was concentrated, dissolved with methylene chloride (75 mL), and washed with saturated sodium bicarbonate solution (20 mL). The organic layer was dried over sodium sulfate, filtered, and concentrated. The residue was dissolved in N,N-dimethylformamide (2.5 mL), 3-hydroxypyridine (109 mg, 1.15 mmol) and potassium carbonate (175 mg, 1.27 mmol) were added. The mixture was heated to 100° C. for 16 h, then diluted with ethyl acetate (75 mL), washed with brine (2×25 mL), dried over sodium sulfate, filtered and concentrated. The residue was purified by chromatography (silica gel, 0-10% methanol/methylene chloride) to afford Example Compound 236 (58 mg, 47%) as a light brown solid: $^1$H NMR (300 MHz, DMSO-$d_6$) δ 8.74 (d, J=2.7 Hz, 1H), 8.57 (dd, J=4.5, 0.9 Hz, 1H), 8.27 (d, J=1.8 Hz, 1H), 8.02-7.98 (m, 2H), 7.59 (dd, J=8.4, 4.5 Hz, 1H), 7.47 (d, J=6.9 Hz, 2H), 7.42-7.30 (m, 3H), 5.53 (s, 2H), 2.40 (s, 3H), 2.22 (s, 3H); ESI m/z 398 [M+H]$^+$.

Step 1: To Example Compound 110 (200 mg, 0.529 mmol) was added phosphorus(V) oxychloride (2 mL, 21.5 mmol) and N,N-dimethylformamide (one drop). The reaction was heated at 90° C. overnight. The mixture was concentrated, the residue was dissolved in tetrahydrofuran (5 mL), ethylamine (10 mL, 1M in tetrahydrofuran) was added. The reaction mixture was heated in a sealed tube at 70° C. for 2 days. The mixture was concentrated and purified by chromatography (silica gel, 0-100% ethyl acetate in hexanes) to give Example Compound 127 (40 mg, 19%) as a yellow solid: $^1$H NMR (500 MHz, CD$_3$OD) δ 7.70 (d, J=1.5 Hz, 1H), 7.45-7.30 (m, 5H), 6.72 (d, J=1.5 Hz, 1H), 5.86 (q, J=7.0 Hz, 1H), 3.72 (q, J=7.2 Hz, 2H), 2.17 (s, 3H), 1.98 (s, 3H), 1.90 (d, J=7.0 Hz, 3H), 1.36 (t, J=7.2 Hz, 3H); ESI m/z 406 [M+H]$^+$.

Step 2: To a solution of Example Compound 127 (35 mg, 0.086 mmol) in tetrahydrofuran (10 mL) was added sodium dithionite (90 mg, 0.52 mmol) in water (10 mL). The reaction mixture was stirred at room temperature overnight and concentrated under vacuum. The residue was added 2N HCl and heated to just boiling, cooled to room temperature, and concentrated in vacuum. The residue was dissolved in MeOH and basified by conc. NH$_4$OH, concentrated, and purified by chromatography (silica gel, 0-100% hexanes/ ethyl acetate). It was further purified by reverse phase HPLC on a Polaris $C_{18}$ column eluting with 10-90% $CH_3CN$ in $H_2O$ to give Example Compound 134 (15 mg, 47%) as an off-white solid: $^1H$ NMR (500 MHz, $CD_3OD$) δ 7.40-7.25 (m, 5H), 6.31 (d, J=1.5 Hz, 1H), 5.92 (d, J=1.5 Hz, 1H), 5.72 (q, J=6.9 Hz, 1H), 3.53 (q, J=7.2 Hz, 2H), 2.15 (s, 3H), 1.99 (s, 3H), 1.86 (d, J=7.0 Hz, 3H), 1.33 (t, J=7.2 Hz, 3H); ESI m/z 376 [M+H]$^+$.

Preparation of 1-benzyl-6-(3,5-dimethylisoxazol-4-yl)-3-methyl-4-nitro-1H-benzo[d]imidazol-2(3H)-one (Example Compound 150) and 4-amino-1-benzyl-6-(3,5-dimethylisoxazol-4-yl)-3-methyl-1H-benzo[d]imidazol-2(3H)-one (Example Compound 162)

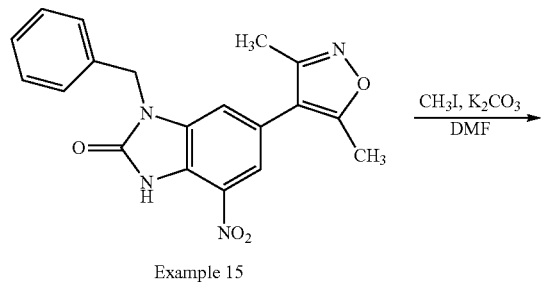

Example 15

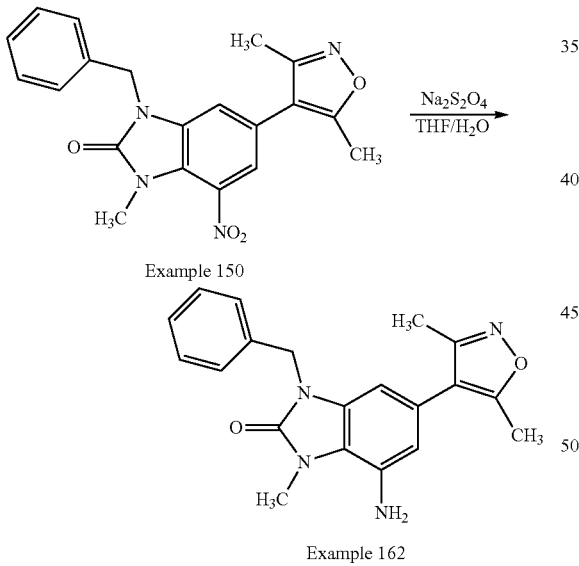

Example 150

Example 162

Step 1: A mixture of Example Compound 15 (73 mg, 0.20 mmol), $CH_3I$ (85 mg, 0.60 mmol) and $K_2CO_3$ (110 mg, 0.8 mmol) in DMF (3 mL) was stirred at rt for 16 h. The reaction mixture was diluted with EtOAc (100 mL) and washed with brine (3×50 mL). The organic layer was dried over sodium sulfate, filtered and concentrated. The residue was triturated with EtOAc/hexanes to afford Example Compound 150 (65 mg, 86%) as a yellow solid: $^1H$ NMR (300 MHz, $CDCl_3$) δ 7.48 (d, J=1.5 Hz, 1H), 7.35-7.30 (m, 5H), 6.84 (d, J=1.5 Hz, 1H), 5.15 (s, 2H), 3.65 (s, 3H), 2.26 (s, 3H), 2.09 (s, 3H); ESI m/z 379 [M+H]$^+$.

Step 2: To a solution of Example Compound 150 (57 mg, 0.15 mmol) in THF (5 mL) and water (4 mL) was added $Na_2S_2O_4$ (153 mg, 0.90 mmol). The mixture was stirred at rt for 4 h, 2N HCl (1 mL) was added, the mixture was heated to reflux for 15 minutes. After cooled to rt, $Na_2CO_3$ was added slowly to adjust to pH 9. The mixture was extracted with $CH_2Cl_2$ (100 mL), the organic layer was washed with brine (50 mL), filtered, concentrated and purified by chromatography (silica gel, 0-10% methanol/ethyl acetate) to afford Example Compound 162 (60 mg, 72%) as a white solid: $^1H$ NMR (300 MHz, DMSO-$d_6$) δ 7.36-7.24 (m, 5H), 6.40 (d, J=1.5 Hz, 1H), 6.39 (d, J=1.8 Hz, 1H), 5.08 (s, 2H), 4.99 (s, 2H), 3.62 (s, 3H), 2.29 (s, 3H), 2.12 (s, 3H); ESI m/z 349 [M+H]$^+$. HPLC >99%

Preparation of 4-(1-benzyl-2-methyl-4-(methylsulfonyl)-1H-benzo[d]imidazol-6-yl)-3,5-dimethylisoxazole (Example Compound 168)

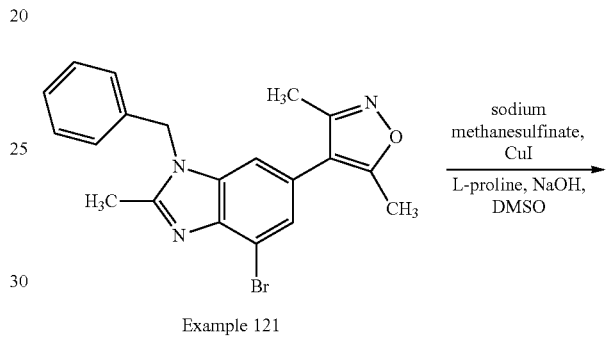

Example 121

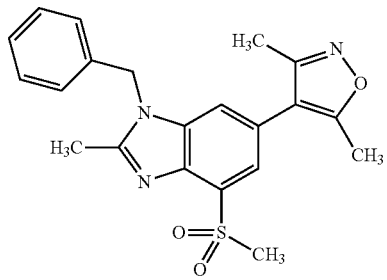

Example 168

A mixture of Example Compound 121 (100 mg, 0.25 mmol), sodium methanesulfinate (39 mg, 0.38 mmol), CuI (5 mg, 0.025 mmol), L-proline (6 mg, 0.05 mmol) and NaOH (2 mg, 0.05 mmol) in DMSO (3 mL) was heated at 150° C. in a microwave reactor for 2 h. The mixture was diluted with ethyl acetate (100 mL) and washed with brine (50 mL). The organic layer was dried over $Na_2SO_4$, filtered and concentrated. The residue was purified by chromatography (silica gel, 50-100% EtOAc/hexanes) to afford Example Compound 168 (13 mg, 13%) as an off-white solid: $^1H$ NMR (300 MHz, $CDCl_3$) δ 7.75 (d, J=1.5 Hz, 1H), 7.37-7.33 (m, 3H), 7.24 (d, J=1.5 Hz, 1H), 7.11-7.08 (m, 2H), 5.39 (s, 2H), 3.54 (s, 3H), 2.73 (s, 3H), 2.31 (s, 3H), 2.16 (s, 3H); ESI m/z 396 [M+H]$^+$. HPLC 92.3%.

Preparation of 4-(1-benzyl-2,7-dimethyl-1H-imidazo[4,5-b]pyridin-6-yl)-3,5-dimethylisoxazole (Example Compound 181)

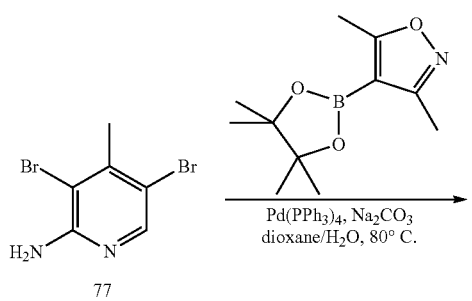

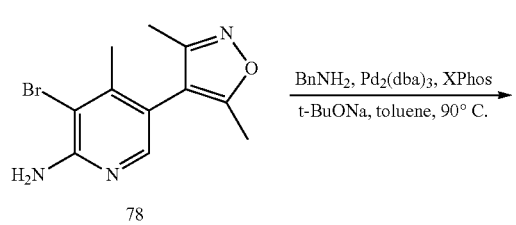

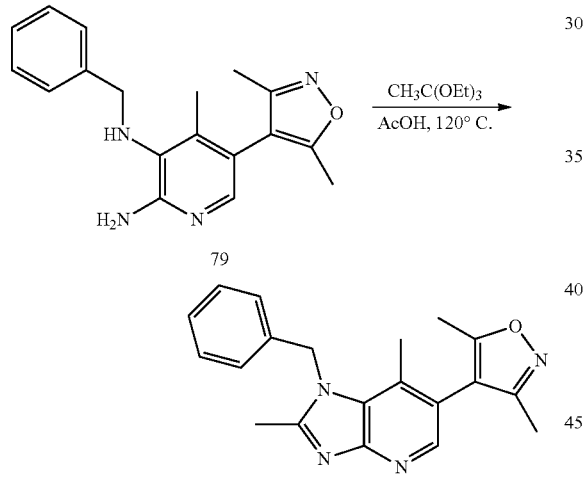

Step 1: To a solution of 77 (4.4 g, 16.5 mmol) in 1,4-dioxane (100 mL) was added 3,5-dimethyl-4-(4,4,5,5-tetramethyl-1,3,2-dioxaborolan-2-yl)isoxazole (4.4 g, 19.8 mmol), Na$_2$CO$_3$ (2.0 M in H$_2$O, 25 mL, 50.0 mmol) and tetrakis(triphenylphosphine)palladium(0) (959 mg, 0.83 mmol). The reaction mixture was purged with nitrogen and heated at 80° C. for 16 h. The mixture was diluted with EtOAc (100 mL) and washed with brine (50 mL). The organic layer was dried over Na$_2$SO$_4$, and filtered. The filtrate was concentrated and then purified by chromatography (silica gel, 0-60% ethyl acetate/hexanes) to afford 78 (2.64 g, 57%) as an off-white solid: $^1$H NMR (300 MHz, DMSO-d$_6$) δ 7.71 (s, 1H), 6.32 (s, 2H), 2.22 (s, 3H), 2.08 (s, 3H), 2.02 (s, 3H).

Step 2: A mixture of 78 (1.3 g, 4.61 mmol), benzylamine (2.51 mL, 23.05 mmol), X-phos (658 mg, 1.38 mmol), Pd$_2$(dba)$_3$ (632 mg, 0.69 mmol) and t-BuOK (774 mg, 6.92 mmol) in toluene (50 mL) was purged with nitrogen for 10 minutes and then heated at 90° C. for 18 h. The mixture was diluted with methylene chloride (200 mL) and filtered. The filtrate was concentrated and purified by chromatography (silica gel, 0-100% EtOAc/hexanes) to afford 79 (125 mg, 9%) as a brown gum: $^1$H NMR (300 MHz, DMSO-d$_6$) δ 7.38 (s, 1H), 7.31-7.22 (m, 5H), 5.68 (s, 2H), 4.28 (t, J=7.5 Hz, 1H), 4.01 (d, J=7.0 Hz, 2H), 2.14 (s, 3H), 1.93 (s, 3H), 1.74 (s, 3H).

Step 3: To a solution of 79 (80 mg, 0.26 mmol) in triethylorthoacetate (2 mL) was added AcOH (0.2 mL). The mixture was heated to 120° C. for 2 h. The mixture was concentrated, the residue was dissolved in EtOAc (100 mL) and washed with saturated NaHCO$_3$ (50 mL×2). The organic layer was dried over Na$_2$SO$_4$, filtered and concentrated. The residue was purified by chromatography (silica gel, 0-10% MeOH/ethyl acetate) to afford Example Compound 181 (39 mg, 45%) as an off-white solid: $^1$H NMR (300 MHz, CDCl$_3$) δ 8.23 (s, 1H), 7.37-7.31 (m, 3H), 6.95-6.92 (m, 2H), 5.58 (s, 2H), 2.64 (s, 3H), 2.23 (s, 3H), 2.22 (s, 3H), 2.06 (s, 3H); ESI m/z 333 [M+H]$^+$.

Preparation of 1-benzyl-6-(3,5-dimethylisoxazol-4-yl)-7-methyl-1H-imidazo[4,5-b]pyridin-2(3H)-one (Example Compound 180)

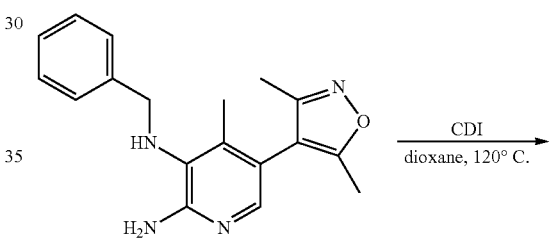

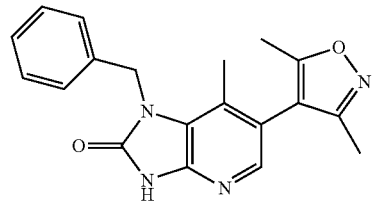

A mixture of 79 (31 mg, 0.10 mmol) and CDI (33 mg, 0.2 mmol) in dioxane (3 mL) was heated to 120° C. for 16 h. The mixture was concentrated, the residue was purified by chromatography (silica gel, 50-100% ethyl acetate/hexanes) to afford Example Compound 180 (10 mg, 30%) as an off-white solid: $^1$H NMR (300 MHz, DMSO-d$_6$) δ 11.89 (s, 1H), 7.74 (s, 1H), 7.38-7.24 (m, 3H), 7.17-7.14 (m, 2H), 5.26 (s, 2H), 2.16 (s, 3H), 2.01 (s, 3H), 1.99 (s, 3H); ESI m/z 335 [M+H]$^+$.

Preparation of 3,5-dimethyl-4-(2-methyl-1-(1-phenylethyl)-1H-imidazo[4,5-b]pyridin-6-yl)isoxazole (Example Compound 108)

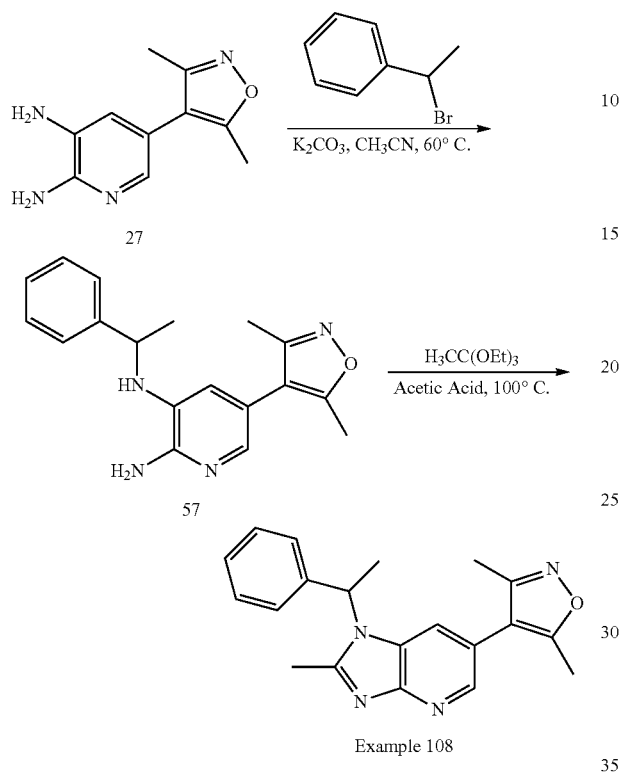

Preparation of 6-(3,5-dimethylisoxazol-4-yl)-1-(1-phenylethyl)-1H-imidazo[4,5-b]pyridin-2(3H)-one (Example Compound 112) and 6-(3,5-dimethylisoxazol-4-yl)-N-ethyl-1-(1-phenylethyl)-1H-imidazo[4,5-b]pyridin-2-amine (Example Compound 113)

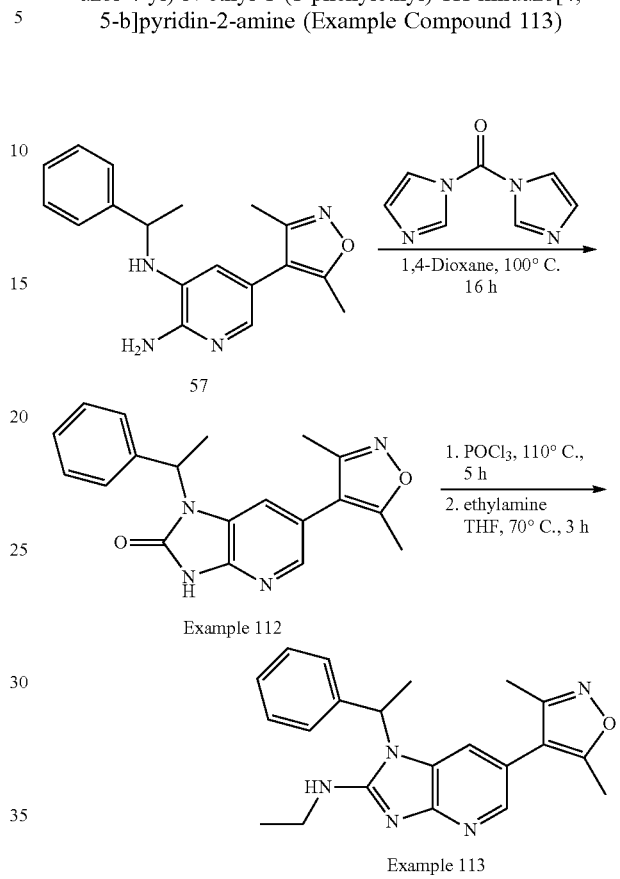

Step 1: To a suspension of 27 (660 mg, 3.23 mmol) in acetonitrile (33 mL) was added (1-bromoethyl)benzene (658 mg, 3.55 mmol) and potassium carbonate (893 mg, 6.46 mmol). The mixture was heated to 60° C. for 16 hours, then cooled, diluted with methylene chloride (120 mL) and washed with brine (40 mL). The organic layer was dried over sodium sulfate, filtered and concentrated. The residue was purified by chromatography (silica gel, 0-10% methanol/methylene chloride) to afford 57 (256 mg, 26%) as white solid: $^1$H NMR (500 MHz, DMSO-$d_6$) δ 7.36 (d, J=1.5 Hz, 2H), 7.30 (t, J=7.5 Hz, 2H), 7.20-7.17 (m, 2H), 6.15 (d, J=2.0 Hz, 1H), 5.82 (s, 2H), 5.40 (d, J=5.5 Hz, 1H), 4.51-4.45 (m, 1H), 2.05 (s, 3H), 1.84 (s, 3H), 1.48 (d, J=7.0 Hz, 3H).

Step 2: To a solution of 57 (41 mg, 0.13 mmol) in triethylorthoacetate (0.24 mL, 1.33 mmol) was added acetic acid (20 µL, 0.36 mmol). The mixture was heated to 100° C. for 1 h, then one drop of concentrated HCl was added. The mixture was heated to 100° C. for 10 min. The mixture was basified with saturated sodium bicarbonate, diluted with methylene chloride (45 mL) and washed with brine (20 mL). The organic layer was dried over sodium sulfate, filtered and concentrated. The residue was purified by chromatography (silica gel, 0-3% methanol/methylene chloride) followed by trituration with methylene chloride/hexanes to afford Example Compound 108 (11 mg, 28%) as white solid: $^1$H NMR (500 MHz, DMSO-$d_6$) δ 8.27 (d, J=2.0 Hz, 1H), 7.44 (d, J=2.0 Hz, 1H), 7.40-7.36 (m, 4H), 7.33-7.30 (m, 1H), 6.01 (q, J=7.0 Hz, 1H), 2.70 (s, 3H), 2.26 (s, 3H), 2.06 (s, 3H), 1.93 (d, J=7.0 Hz, 3H); ESI m/z 333 [M+H]$^+$.

Step 1: To a suspension of 57 (250 mg, 0.81 mmol) in 1,4-dioxane (6 mL), was added 1,1'-carbonyldiimidazole (158 mg, 0.97 mmol). The mixture was purged with nitrogen for 5 min, and then heated to 100° C. for 16 h. The mixture was diluted with methylene chloride (100 mL), filtered and concentrated. The residue was purified by chromatography (silica gel, 0-5% methanol/methylene chloride) then triturated with methylene chloride/hexanes to afford Example Compound 112 (258 mg, 95%) as off-white solid: $^1$H NMR (500 MHz, DMSO-$d_6$) δ 11.78 (s, 1H), 7.87 (d, J=2.0 Hz, 1H), 7.44 (d, J=7.5 Hz, 2H), 7.36 (t, J=7.5 Hz, 2H), 7.29 (t, J=7.5 Hz, 1H), 7.09 (d, J=2.0 Hz, 1H), 5.72 (q, J=7.0 Hz, 1H), 2.26 (s, 3H), 2.06 (s, 3H), 1.84 (d, J=7.0 Hz, 3H); ESI m/z 335 [M+H]$^+$.

Step 2: A mixture of Example Compound 112 (100 mg, 0.30 mmol) and phosphorus (V) oxychloride (1 mL) was heated to 110° C. for 5 h, and cooled to room temperature. The reaction mixture was concentrated, diluted with methylene chloride (75 mL), and washed with saturated sodium bicarbonate solution (20 mL). The organic layer was dried over sodium sulfate, filtered, and concentrated. The residue was dissolved in a 2.0 M solution of ethylamine in tetrahydrofuran (6.0 mL, 12.0 mmol) and the mixture was heated to 75° C. for 7 h. The reaction mixture was concentrated, and the residue was purified by chromatography (silica gel, 0-5% methanol/methylene chloride), then triturated with ethyl acetate/hexanes to afford Example Compound 113 (52 mg, 49%) as a white solid: $^1$H NMR (500 MHz, DMSO-$d_6$)

δ 7.90 (d, J=2.0 Hz, 1H), 7.40-7.28 (m, 6H), 6.81 (d, J=2.0 Hz, 1H), 5.84 (q, J=7.0 Hz, 1H), 3.54-3.48 (m, 2H), 2.20 (s, 3H), 1.99 (s, 3H), 1.83 (d, J=7.0 Hz, 3H), 1.27 (t, J=7.0 Hz, 3H); ESI m/z 362 [M+H]+.

Preparation of 6-(3,5-dimethylisoxazol-4-yl)-1-(1-phenylethyl)-1H-imidazo[4,5-b]pyridin-2(3H)-one (Enantiomer A) (Example Compound 218) and 6-(3,5-dimethylisoxazol-4-yl)-1-(1-phenylethyl)-1H-imidazo[4,5-b]pyridin-2(3H)-one (Enantiomer B) (Example Compound 219)

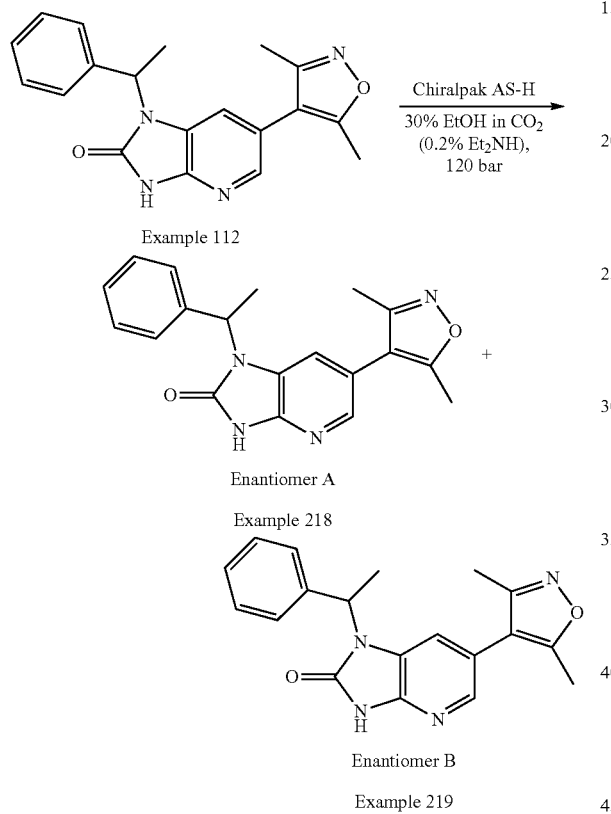

Example Compound 112 (87 mg) was separated by SFC chiral HPLC (Chiralpak AS-H, 30 mm×250 mm, mobile phase 30% EtOH in CO2 (0.2% Et2NH), 120 bar, flow rate 80 mL/min) to afford Example Compound 218 (Enantiomer A) (41 mg, 46%) and Example Compound 219 (Enantiomer B) (41 mg, 46%) as off-white solids.

Example Compound 218 (Enantiomer A):

1H NMR (500 MHz, DMSO-d6) δ 11.77 (s, 1H), 7.87 (d, J=2.0 Hz, 1H), 7.44 (d, J=7.5 Hz, 2H), 7.37 (t, J=7.5 Hz, 2H), 7.29 (t, J=7.5 Hz, 1H), 7.09 (d, J=2.0 Hz, 1H), 5.72 (q, J=7.5 Hz, 1H), 2.26 (s, 3H), 2.06 (s, 3H), 1.84 (d, J=7.5 Hz, 3H); ESI m/z 335 [M+H]+; HPLC (Chiralcel OD, 4.6 mm×250 mm, 10% EtOH in heptane, 1 mL/min) >99%, $t_R$=9.4 min.

Example Compound 219 (Enantiomer B):

1H NMR (500 MHz, DMSO-d6) δ 11.78 (s, 1H), 7.87 (d, J=1.5 Hz, 1H), 7.44 (d, J=7.5 Hz, 2H), 7.36 (t, J=7.5 Hz, 2H), 7.29 (t, J=7.5 Hz, 1H), 7.08 (d, J=2.0 Hz, 1H), 5.72 (q, J=7.5 Hz, 1H), 2.26 (s, 3H), 2.06 (s, 3H), 1.84 (d, J=7.5 Hz, 3H); ESI m/z 335 [M+H]+; HPLC (Chiralcel OD, 4.6 mm×250 mm, 10% EtOH in heptane, 1 mL/min) >99%, $t_R$=10.9 min.

Preparation of 3-benzyl-5-(3,5-dimethylisoxazol-4-yl)-1-ethyl-1H-benzo[d]imidazol-2(3H)-one (Example Compound 122)

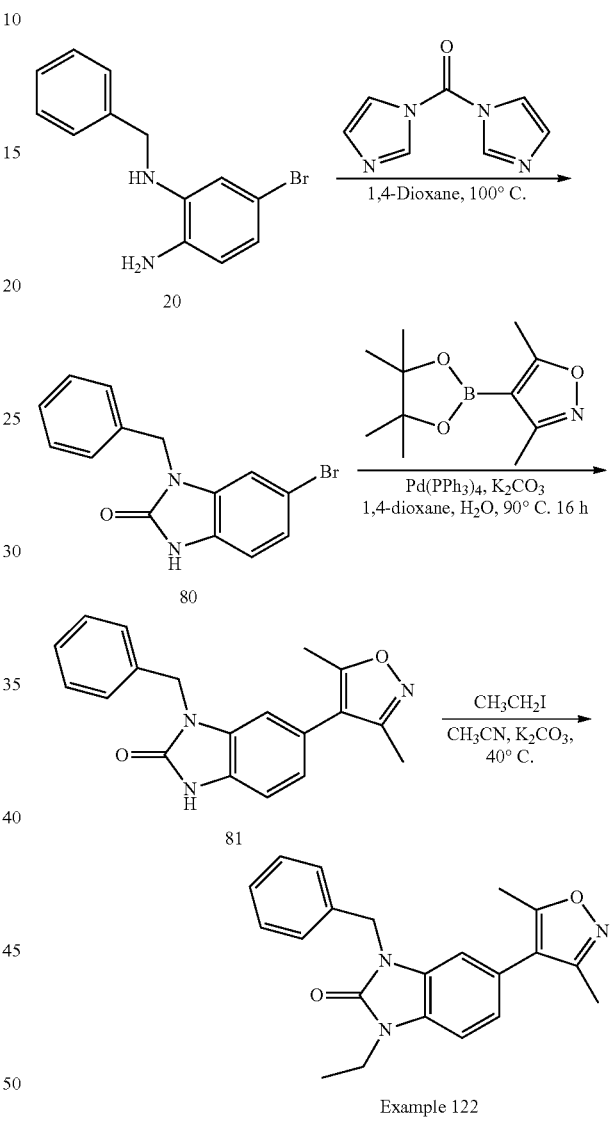

Step 1: To a solution of 20 (214 mg, 0.77 mmol) in 1,4-dioxane (5 mL) was added 1,1'-carbonyldiimidazole (150 mg, 0.93 mmol) and the mixture was heated to 100° C. for 15 h. The mixture was concentrated and purified by chromatography (silica gel, 0-20% ethyl acetate/hexanes) to afford 80 (142 mg, 61%) as a white solid; 1H NMR (500 MHz, DMSO-d6) δ 11.13 (s, 1H), 7.35-7.25 (m, 6H), 7.12 (dd, J=8.5, 2.0 Hz, 1H), 6.94 (d, J=8.0 Hz, 1H), 5.01 (s, 2H).

Step 2: To a solution of 80 (100 mg, 0.33 mmol) in 1,4-dioxane (5 mL) was added 3,5-dimethyl-4-(4,4,5,5-tetramethyl-1,3,2-dioxaborolan-2-yl)isoxazole (110 mg, 0.49 mmol), potassium carbonate (91 mg, 0.66 mmol), and water (1 mL). The mixture was purged with nitrogen for 10 min, tetrakis(triphenylphosphine)palladium(0) (19 mg, 0.016 mmol) was added, and the mixture was heated to 90° C. for 16 h. The mixture was diluted with methylene chloride (100 mL), and washed with brine (30 mL). The organic layer was dried over sodium sulfate, filtered, and concentrated. The residue was purified by chromatography (silica gel, 0-5% methanol/methylene chloride) then triturated with ethyl acetate/hexanes to afford 81 (55 mg, 52%) as a white solid: $^1$H NMR (300 MHz, DMSO-d$_6$) δ 11.07 (s, 1H), 7.40-7.23 (m, 5H), 7.06 (d, J=8.1 Hz, 1H), 7.02 (s, 1H), 6.95 (dd, J=7.8, 1.5 Hz, 1H), 5.03 (s, 2H), 2.30 (s, 3H), 2.13 (s, 3H); ESI m/z 320 [M+H]$^+$.

Step 3: To a solution of 81 (36 mg, 0.11 mmol) in acetonitrile (3 mL) was added potassium carbonate (109 mg, 0.79 mmol) and iodoethane (80 mg, 0.56 mmol), then the mixture was heated to 40° C. for 48 h. The mixture was diluted with methylene chloride (75 mL), and washed with brine (20 mL). The organic layer was dried over sodium sulfate, filtered, and concentrated. The residue was purified by chromatography (silica gel, 0-20% ethyl acetate/methylene chloride), then triturated with ethyl acetate/hexanes to afford Example Compound 122 (14 mg, 37%) as a yellow-white solid: $^1$H NMR (500 MHz, DMSO-d$_6$) δ 7.37 (d, J=7.5 Hz, 2H), 7.33 (t, J=7.0 Hz, 2H), 7.29 (d, J=8.0 Hz, 1H), 7.26 (t, J=7.0 Hz, 1H), 7.09 (d, J=1.5 Hz, 1H), 7.03 (dd, J=8.0, 1.5 Hz, 1H), 5.08 (s, 2H), 3.94 (q, J=7.0 Hz, 2H), 2.31 (s, 3H), 2.13 (s, 3H), 1.26 (t, J=7.0 Hz, 3H); ESI m/z 348 [M+H]$^+$.

Preparation of 1-benzyl-N$^6$-(3,5-dimethylisoxazol-4-yl)-2-methyl-1H-benzo[d]imidazole-4,6-diamine (Example Compound 142)

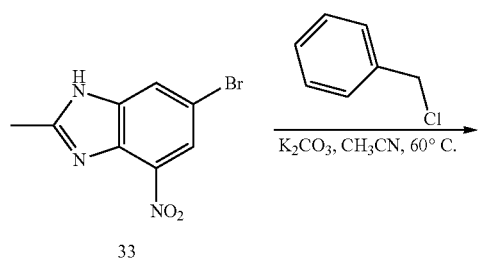

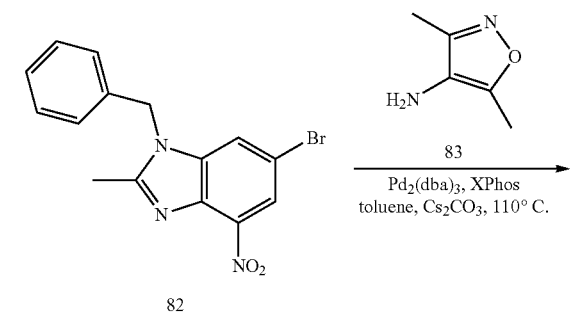

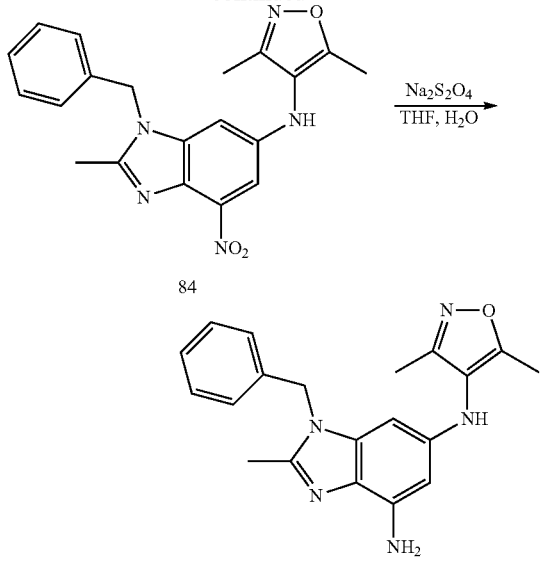

Example 142

Step 1: To a suspension of 33 (790 mg, 3.09 mmol) in acetonitrile (15 mL) was added benzyl chloride (703 mg, 5.55 mmol) and potassium carbonate (1.07 g, 7.71 mmol). The reaction mixture was heated to 60° C. for 16 h, then concentrated, and the residue was purified by chromatography (silica gel, 0-30% ethyl acetate/hexanes) to afford 82 (813 mg, 76%) as a yellow solid: $^1$H NMR (300 MHz, DMSO-d$_6$) δ 8.33 (d, J=1.8 Hz, 1H), 8.12 (d, J=1.8 Hz, 1H), 7.39-7.27 (m, 3H), 7.13 (d, J=6.6 Hz, 2H), 5.62 (s, 2H), 2.60 (s, 3H).

Step 2: To a solution of 82 (150 mg, 0.43 mmol) in toluene (5 mL) was added 83 (73 mg, 0.65 mmol), cesium carbonate (282 mg, 0.87 mmol) and XPhos (41 mg, 0.087 mmol). The solution was purged with nitrogen for 5 min, then tris(dibenzylideneacetone)dipalladium(0) (40 mg, 0.043 mmol) was added and heated to 110° C. for 16 h. The mixture was filtered through celite and concentrated, the residue was purified by chromatography (silica gel, 0-7% methanol/methylene chloride) to afford 84 (80 mg, 49%) as a brown oil: $^1$H NMR (500 MHz, DMSO-d$_6$) δ 7.59 (s, 1H), 7.34-7.28 (m, 4H), 7.06 (d, J=7.0 Hz, 2H), 6.76 (d, J=2.5 Hz, 1H), 5.44 (s, 2H), 2.54 (s, 3H), 2.13 (s, 3H), 1.91 (s, 3H).

Step 3: To a solution of 84 (78 mg, 0.21 mmol) in tetrahydrofuran (5 mL) was added a solution of sodium dithionite (215 mg, 1.24 mmol) in water (4 mL). The mixture was stirred at room temperature for 2 h, the 2N HCl (1 mL) was added, the mixture was heated to reflux for 15 min. The mixture was basified by sodium carbonate, and extracted with methylene chloride (50 mL). The organic layer was dried over sodium sulfate, filtered, and concentrated. The residue was purified by chromatography (silica gel, 0-10% methanol/methylene chloride) to afford Example Compound 142 (38 mg, 53%) as a red-brown solid: $^1$H NMR (500 MHz, DMSO-d$_6$) δ 7.31 (t, J=7.5 Hz, 2H), 7.25 (t, J=7.5 Hz, 1H), 7.04 (d, J=7.5 Hz, 2H), 6.69 (s, 1H), 5.73 (d, J=2.0 Hz, 1H), 5.60 (d, J=2.0 Hz, 1H), 5.18 (s, 2H), 5.05 (s, 2H), 2.38 (s, 3H), 2.13 (s, 3H), 1.92 (s, 3H); ESI m/z 348 [M+H]$^+$.

General Procedure U:

Preparation of 1-benzyl-2-methyl-6-(5-methylisoxazol-4-yl)-1H-benzo[d]imidazol-4-amine (Example Compound 201)

Preparation of N-(1-benzyl-2-methyl-1H-imidazo[4,5-b]pyridin-6-yl)-3,5-dimethylisoxazol-4-amine (Example Compound 155)

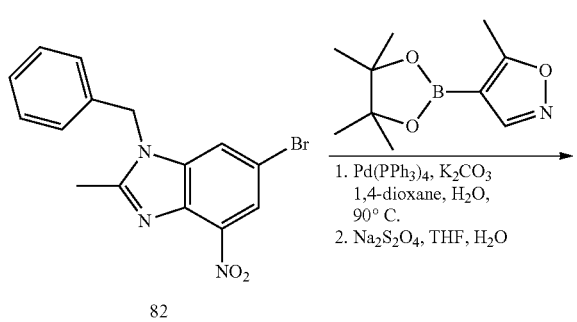

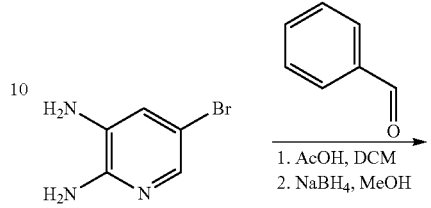

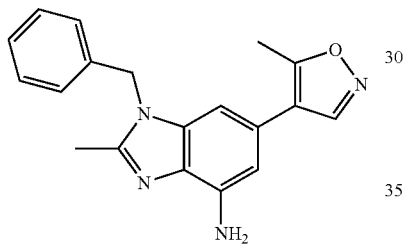

Example 201

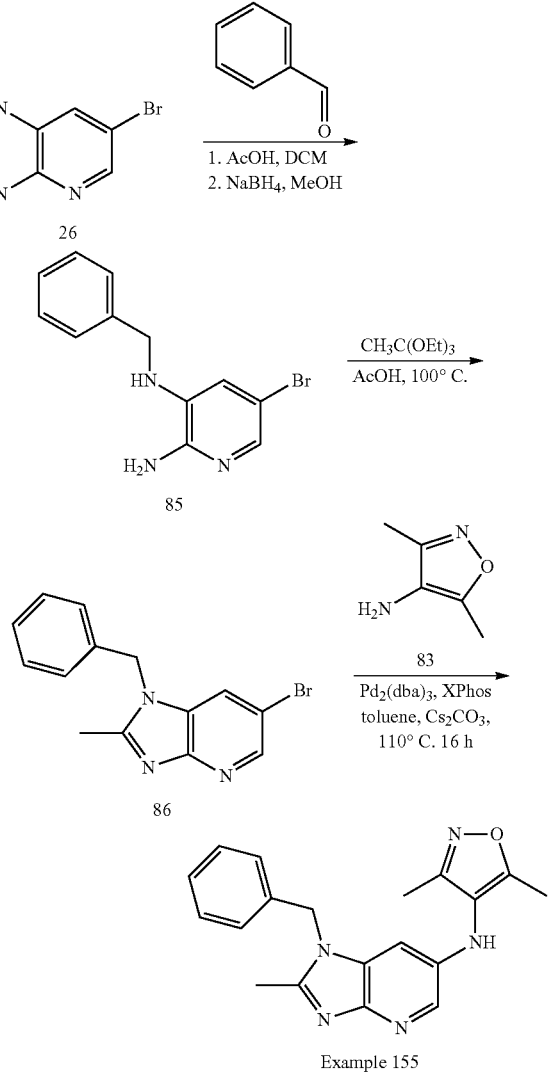

To a solution of 82 (100 mg, 0.29 mmol) in 1,4-dioxane (5 mL) was added 5-methylisoxazole-4-boronic acid pinacol ester (91 mg, 0.43 mmol), sodium carbonate (80 mg, 0.58 mmol), water (1 mL), and tetrakis(triphenylphosphine)palladium(0) (17 mg, 0.01 mmol). The reaction mixture was purged with nitrogen and heated at 90° C. for 5 h. The mixture was diluted with methylene chloride (70 mL), washed with brine (25 mL), dried over sodium sulfate, filtered and concentrated. The residue was purified by chromatography (silica gel, 0-5% ethyl acetate/methylene chloride) to a yellow solid which was dissolved in THF (4 mL), a solution of sodium dithionite (159 mg, 0.91 mmol) in water (2 mL) was added and the mixture was stirred at room temperature for 2 h. 2 N HCl (1 mL) was added to the mixture, and the mixture was heated to reflux for 15 min. The mixture was basified by saturated aqueous sodium bicarbonate solution, and extracted with methylene chloride (40 mL×2). The organic layer was dried over sodium sulfate, filtered, and concentrated. The residue was purified by chromatography (silica gel, 0-8% methanol/methylene chloride) and triturated with ethyl acetate/hexanes to afford Example Compound 201 (12 mg, 25%) as an off-white solid: $^1$H NMR (300 MHz, DMSO-$d_6$) δ 8.69 (d, J=0.6 Hz, 1H), 7.36-7.26 (m, 3H), 7.15 (d, J=6.9 Hz, 2H), 6.78 (d, J=1.5 Hz, 1H), 6.47 (d, J=1.5 Hz, 1H), 5.40 (s, 2H), 5.33 (s, 2H), 2.50 (s, 3H), 2.47 (s, 3H); ESI m/z 319 [M+H]$^+$.

Step 1: To a suspension of 2,3-diamino-5-bromopyridine 26 (1.5 g, 7.98 mmol) in methylene chloride (80 mL) was added benzaldehyde (931 mg, 8.78 mmol) and acetic acid (40 drops). The mixture was stirred at room temperature for 16 h, then washed with saturated sodium bicarbonate solution (40 mL). The organic layer was dried over sodium sulfate, filtered, and concentrated. The residue was dissolved in methanol (50 mL) and sodium borohydride (815 mg, 21.5 mmol) was slowly added. The mixture was stirred at room temperature for 1 h. The mixture was diluted with methylene chloride (100 mL), washed with saturated sodium bicarbonate (40 mL), dried over sodium sulfate, filtered, and concentrated. The residue was purified by chromatography (silica gel, 0-10% methanol/methylene chloride) to afford 85 (1.12 g, 51%) as an off-white solid: $^1$H NMR (500 MHz, DMSO-$d_6$) δ 7.35-7.34 (m, 4H), 7.28-7.23 (m, 2H), 6.54 (d, J=2.0 Hz, 1H), 5.78 (s, 2H), 5.73 (t, J=5.5 Hz, 1H), 4.30 (d, J=5.5 Hz, 2H).

Step 2: To a suspension of 85 (970 mg, 3.49 mmol) in triethylorthoacetate (5.66 g, 37.9 mmol) was added acetic acid (539 μL, 9.42 mmol). The mixture was heated to 100° C. for 40 min. The reaction mixture was basified with saturated sodium bicarbonate (8 mL), diluted with methylene chloride (50 mL), and washed with saturated sodium bicarbonate (30 mL). The organic layer was dried over sodium sulfate, filtered, and concentrated. The residue was purified by chromatography (silica gel, 0-8% methanol/methylene chloride) to afford 86 (305 mg, 30%) as a light brown solid: $^1$H NMR (500 MHz, DMSO-$d_6$) δ 8.41 (d, J=2.0 Hz, 1H), 8.29 (d, J=2.0 Hz, 1H), 7.35 (t, J=7.0 Hz, 2H), 7.30 (t, J=7.0 Hz, 1H), 7.15 (d, J=7.0 Hz, 2H), 5.52 (s, 2H), 2.55 (s, 3H).

Step 3: To a solution of 86 (80 mg, 0.26 mmol) in toluene (5 mL), was added 83 (44 mg, 0.40 mmol), cesium carbonate (173 mg, 0.53 mmol), and XPhos (25 mg, 0.053 mmol). The solution was purged with nitrogen for 5 min, then tris (dibenzylideneacetone)dipalladium(0) (24 mg, 0.026 mmol) was added. The mixture was heated to 110° C. for 16 h. The reaction mixture was diluted with methylene chloride (20 mL), filtered through celite, and concentrated. The residue was purified by chromatography (silica gel, 0-10% methanol/methylene chloride) then triturated with methylene chloride/hexanes to afford Example Compound 155 (40 mg, 45%) as a light-brown solid: $^1$H NMR (500 MHz, DMSO-$d_6$) δ 7.88 (d, J=2.5 Hz, 1H), 7.34-7.30 (m, 3H), 7.27 (t, J=7.0 Hz, 1H), 7.05 (d, J=7.0 Hz, 2H), 6.71 (d, J=2.5 Hz, 1H), 5.38 (s, 2H), 2.47 (s, 3H), 2.14 (s, 3H), 1.92 (s, 3H); ESI m/z 334 [M+H]$^+$.

Preparation of 1-benzyl-2-methyl-6-(1-methyl-1H-1,2,3-triazol-5-yl)-1H-imidazo[4,5-b]pyridine (Example Compound 206)

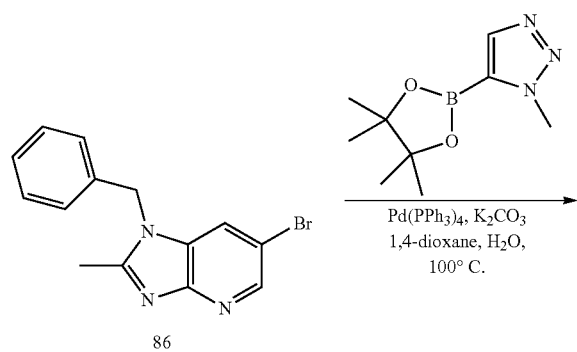

Example 206

To a solution of 86 (100 mg, 0.33 mmol) in 1,4-dioxane (5 mL) was added 1-methyl-5-(4,4,5,5-tetramethyl-1,3,2-dioxaborolan-2-yl)-1H-1,2,3-triazole (138 mg, 0.66 mmol), K$_2$CO$_3$ (137 mg, 0.99 mmol), water (1 mL), and tetrakis (triphenylphosphine)palladium(0) (19 mg, 0.02 mmol). The reaction mixture was purged with nitrogen and heated at 90° C. for 16 h. The mixture was diluted with ethyl acetate (70 mL), washed with brine (25 mL), dried over sodium sulfate, filtered and concentrated. The residue was purified by chromatography (silica gel, 0-8% methanol/methylene chloride) followed by trituration with methylene chloride/hexanes to afford Example Compound 206 (14 mg, 14%) as a white solid; $^1$H NMR (500 MHz, DMSO-$d_6$) δ 8.54 (d, J=2.5 Hz, 1H), 8.27 (d, J=2.0 Hz, 1H), 7.96 (s, 1H), 7.35 (t, J=7.0 Hz, 2H), 7.29 (t, J=7.0 Hz, 1H), 7.21 (d, J=7.0 Hz, 2H), 5.58 (s, 2H), 4.07 (s, 3H), 2.60 (s, 3H); ESI m/z 305 [M+H]$^+$.

Preparation of 1-benzyl-2-methyl-6-(1-methyl-1H-pyrazol-5-yl)-1H-imidazo[4,5-b]pyridine (Example Compound 154)

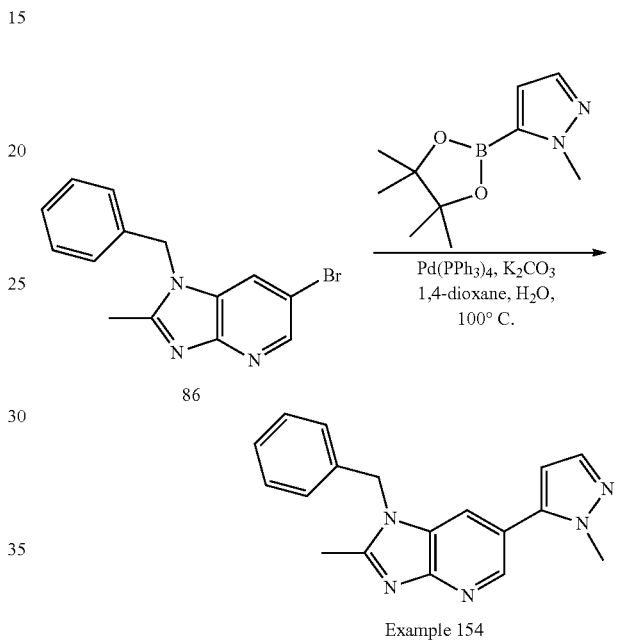

Example 154

1-Benzyl-2-methyl-6-(1-methyl-1H-pyrazol-5-yl)-1H-imidazo[4,5-b]pyridine (Example Compound 154) was prepared by following the similar method for the preparation of Example Compound 206 as an off-white solid: $^1$H NMR (500 MHz, DMSO-$d_6$) δ 8.48 (d, J=2.0 Hz, 1H), 8.14 (d, J=2.0 Hz, 1H), 7.50 (d, J=2.0 Hz, 1H), 7.35 (t, J=7.0 Hz, 2H), 7.29 (t, J=7.0 Hz, 1H), 7.21 (d, J=7.0 Hz, 2H), 6.46 (d, J=2.0 Hz, 1H), 5.57 (s, 2H), 3.83 (s, 3H), 2.60 (s, 3H); ESI m/z 304 [M+H]$^+$.

Preparation of 4-(1-benzyl-2-cyclopropyl-1H-imidazo[4,5-b]pyridin-6-yl)-3,5-dimethylisoxazole (Example Compound 138)

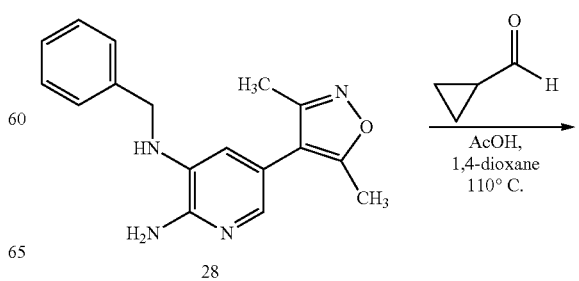

28

-continued

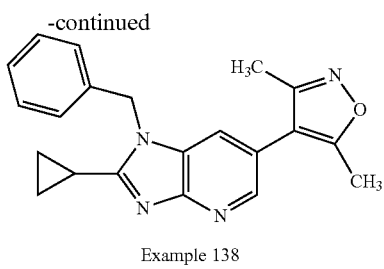

Example 138

To a solution of diamine 28 (100 mg, 0.340 mmol) in 1,4-dioxane (2 mL) was added cyclopropanecarboxaldehyde (29 mg, 0.408 mmol) and acetic acid (0.67 mL). The mixture was heated at 110° C. for 24 h. The mixture was then diluted with methylene chloride and washed with saturated sodium bicarbonate. The organic layer was then dried with sodium sulfate, filtered and concentrated. The residue was purified by chromatography (silica gel, 0-5% methanol/methylene chloride) to afford Example Compound 138 (68 mg, 58%) as an off-white solid: $^1$H NMR (500 MHz, DMSO-$d_6$) δ 8.29 (d, J=2.1 Hz, 1H), 7.95 (d, J=2.0 Hz, 1H), 7.37-7.33 (m, 2H), 7.30-7.28 (m, 3H), 5.67 (s, 2H), 2.38 (s, 3H), 2.37-2.35 (m, 1H), 2.20 (s, 3H), 1.13-1.11 (m, 4H); ESI m/z 345 [M+H]$^+$. HPLC >99%.

Preparation of 1-(cyclopropylmethyl)-6-(3,5-dimethylisoxazol-4-yl)-4-nitro-1H-benzo[d]imidazol-2(3H)-one (Example Compound 145), 1-(cyclopropylmethyl)-6-(3,5-dimethylisoxazol-4-yl)-N-ethyl-4-nitro-1H-benzo[d]imidazol-2-amine (Example Compound 159), 4-Amino-1-(cyclopropylmethyl)-6-(3,5-dimethylisoxazol-4-yl)-1H-benzo[d]imidazol-2(3H)-one (Example Compound 161) and 1-(cyclopropylmethyl)-6-(3,5-dimethylisoxazol-4-yl)-N$_2$-ethyl-1H-benzo[d]imidazole-2,4-diamine (Example Compound 160)

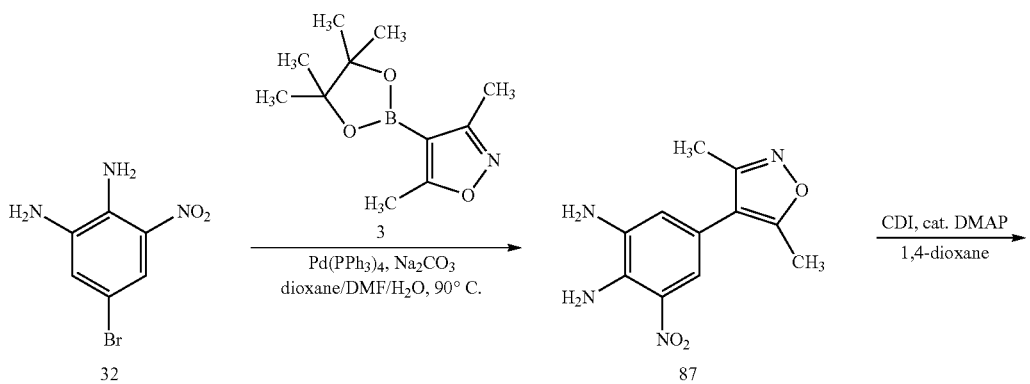

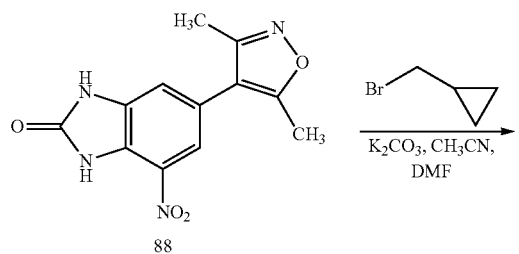

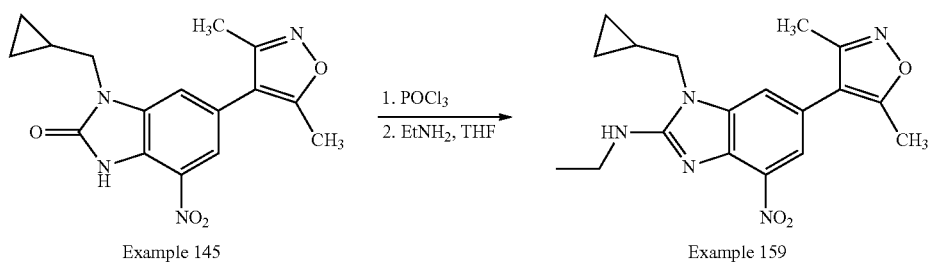

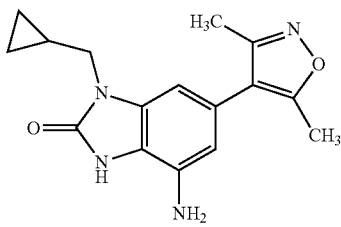

Example 161

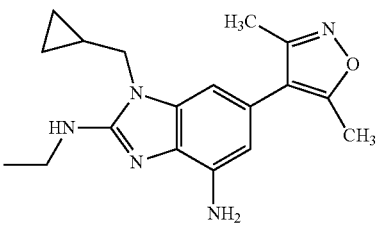

Example 160

Step 1: To a mixture of 32 (1.50 g, 6.46 mmol) and 3 (2.16 g, 9.70 mmol) in 1,4-dioxane (40 mL) and water (4 mL) was added potassium carbonate (1.79 g, 12.9 mmol) and tetrakis(triphenylphosphine)palladium(0) (373 mg, 0.32 mmol). The reaction was stirred and heated at 90° C. for 17 h. The reaction mixture was diluted with methanol (20 mL) and silica gel (20 g) was added. The suspension was concentrated to dryness and the resulting powder was loaded onto silica gel and eluted with 0-50% ethyl acetate in hexanes. The clean product was concentrated to give 87 (585 mg, 36%) as a brown solid: $^1$H NMR (500 MHz, CDCl$_3$) δ 7.62 (d, J=2.0 Hz, 1H), 6.81 (d, J=2.0 Hz, 1H), 6.01 (br s, 2H), 3.52 (br s, 2H), 2.39 (s, 3H), 2.25 (s, 3H).

Step 2: To a solution of 87 (250 mg, 1.01 mmol), a catalytic amount of DMAP and 1,4-dioxane (4 mL) in a pressure tube was added 1,1'-carbonyldiimidazole (327 mg, 2.01 mmol). The tube was sealed and heated to 80° C. for 17 h. The reaction mixture was diluted with methanol (20 mL) and silica gel (10 g) was added. The suspension was concentrated to dryness and the resulting powder was loaded onto silica gel (40 g) and eluted with 0-70% ethyl acetate in hexanes. The clean product was concentrated to give 88 (167 mg, 60%) as an orange solid: $^1$H NMR (500 MHz, CDCl$_3$) δ 7.74 (d, J=1.5 Hz, 1H), 7.17 (d, J=1.5 Hz, 1H), 2.43 (s, 3H), 2.28 (s, 3H).

Step 3: To a solution of 88 (309 mg, 1.13 mmol), potassium carbonate (312 mg, 2.25 mmol), acetonitrile (5 mL) and DMF (2 mL) in a pressure tube was added (bromomethyl)cyclopropane (183 mg, 1.35 mmol) and the reaction was sealed and heated at 80° C. for 17 h. The material was cooled to room temperature and poured into a saturated aq. NaCl solution (30 mL). Ethyl acetate (100 mL) was added and the layers were separated. The ethyl acetate layer was washed with saturated aq. NaCl solution (2×100 mL), dried over Na$_2$SO$_4$, filtered and the filtrate was concentrated. The resulting oil in CH$_2$Cl$_2$ (10 mL) was loaded onto silica gel (80 g) and eluted with 0-40% ethyl acetate in hexanes. The clean product was then purified by reverse phase HPLC on a Polaris column eluting with 10-90% CH$_3$CN in H$_2$O and the clean fractions were frozen and lyophilized to give Example Compound 145 (88 mg, 35%) as a yellow solid: $^1$H NMR (500 MHz, CD$_3$OD) δ 7.82 (d, J=1.5 Hz, 1H), 7.52 (d, J=1.0 Hz, 1H), 3.87 (d, J=7.0 Hz, 2H), 2.45 (s, 3H), 2.29 (s, 3H), 1.30-1.18 (m, 1H), 0.60-0.52 (m, 2H), 0.47-0.43 (m, 2H). ESI m/z 329 [M+H]$^+$. HPLC >99%.

Step 4: A solution of Example Compound 145 (171 mg, 0.521 mmol) in phosphorus(V) oxychloride (4 mL) was placed in a sealed tube and heated at 110° C. for 8 h. The solvent was removed in vacuo and a saturated aq. NaHCO$_3$ solution (5 mL) was added. The mixture was extracted with ethyl acetate (2×20 mL) and the combined extracts were dried over Na$_2$SO$_4$, filtered and the filtrate was concentrated. THF (5 mL) and 2.0M ethylamine solution in THF were then added and the reaction was heated at 70° C. for 12 h. The reaction was concentrated to dryness and the residue diluted with CH$_2$Cl$_2$ (5 mL). The resulting solution was loaded onto silica gel (40 g) and eluted with 0-80% ethyl acetate in hexanes. The clean product was then purified by reverse phase HPLC on a Polaris column eluting with 10-90% CH$_3$CN in H$_2$O and the clean fractions were frozen and lyophilized to give Example Compound 159 (105 mg, 57%) as a yellow solid: $^1$H NMR (500 MHz, CDCl$_3$) δ 7.78 (d, J=1.5 Hz, 1H), 7.44 (d, J=1.5 Hz, 1H), 4.03 (d, J=6.5 Hz, 2H), 3.67 (q, J=7.0 Hz, 2H), 2.44 (s, 3H), 2.29 (s, 3H), 1.33 (t, J=7.0 Hz, 3H), 1.30-1.18 (m, 1H), 0.60-0.52 (m, 2H), 0.47-0.41 (m, 2H). ESI m/z 356 [M+H]$^+$. HPLC >99%.

Step 5: A solution of Example Compound 145 (59 mg, 0.215 mmol) in THF (10 ml) was added a solution of sodium dithionite (225 mg, 1.29 mmol) in water (10 mL) dropwise over 5 min. The solution was stirred at room temperature for 16 h and the solvents were removed in vacuo. Methanol (20 mL) was added and the suspension stirred at room temperature for 3 h. The mixture was filtered and the filtrate was concentrated to dryness. A solution of 2N aq. HCl (10 mL) was added to the residue and heated to reflux for 5 min. After concentration to dryness, methanol was added (10 mL) and the solution was adjusted to pH 8 using saturated aq. NaHCO$_3$ solution (15 mL). Silica gel was added (10 g) and the suspension was concentrated to dryness. The resulting powder was loaded onto silica gel and eluted with 0-4% methanol in methylene chloride. The clean product was then purified by reverse phase HPLC on a Polaris C$_{18}$ column eluting with 10-90% CH$_3$CN in H$_2$O and the clean fractions were frozen and lyophilized to give Example Compound 161 (32 mg, 50%) as a white solid: $^1$H NMR (500 MHz, CD$_3$OD) δ 6.49 (d, J=1.5 Hz, 1H), 6.42 (d, J=1.5 Hz, 1H), 3.75 (d, J=6.5 Hz, 2H), 2.39 (s, 3H), 2.24 (s, 3H), 1.28-1.18 (m, 1H), 0.56-0.48 (m, 2H), 0.44-0.39 (m, 2H). ESI m/z 299 [M+H]$^+$. HPLC 97.4%.

Step 6: A solution of Example Compound 159 (90 mg, 0.253 mmol) in THF (10 ml) was added a solution of sodium dithionite (265 mg, 1.52 mmol) in water (10 mL) dropwise over 5 min. The solution was stirred at room temperature for 16 h and the solvents were removed in vacuo. Methanol (20 mL) was added and the suspension stirred at room temperature for 3 h. The mixture was filtered and the filtrate was concentrated to dryness. A solution of 2N aq. HCl (10 mL) was added to the residue and heated to reflux for 5 min. After concentration to dryness, methanol was added (10 mL) and the solution was adjusted to pH 8 using saturated aq. NaHCO$_3$ solution (15 mL). Silica gel was added (10 g) and the suspension was concentrated to dryness. The resulting powder was loaded onto silica gel and eluted with 0-4% methanol in methylene chloride. The clean product was then purified by reverse phase HPLC on a Polaris C$_{18}$ column eluting with 10-90% CH$_3$CN in H$_2$O and the clean fractions were frozen and lyophilized to give Example Compound 160 (61 mg, 74%) as a white solid: $^1$H NMR (500 MHz, CD$_3$OD) δ 6.49 (d, J=1.5 Hz, 1H), 6.37 (d, J=1.5 Hz, 1H), 3.88 (d, J=6.5 Hz, 2H), 3.48 (q, J=7.0 Hz, 2H), 2.39 (s, 3H), 2.24 (s, 3H), 1.28-1.18 (m, 1H), 0.53-0.48 (m, 2H), 0.40-0.35 (m, 2H). ESI m/z 326 [M+H]$^+$. HPLC >99%.

Preparation of 4-amino-6-(3,5-dimethylisoxazol-4-yl)-1-(4-hydroxybenzyl)-1H-benzo[d]imidazol-2(3H)-one (Example Compound 129)

To a solution of Example Compound 104 (54 mg, 0.15 mmol) in dichloromethane (5 mL) under nitrogen atmosphere was added boron tribromide (0.45 mL, 1M in dichloromethane, 0.45 mmol). The reaction mixture was stirred at room temperature overnight, treated with methanol, and concentrated in vacuum. The residue was dissolved in methanol, basified with ammonium hydroxide, concentrated in vacuum, and purified by chromatography (silica gel, 0-20% methanol in ethyl acetate). It was further purified by reverse phase HPLC on a Polaris C$_{18}$ column eluting with 10-90% CH$_3$CN in H$_2$O to give Example Compound 129 (31 mg, 59%) as an off-white solid: $^1$H NMR (500 MHz, CD$_3$OD) δ 7.17 (d, J=8.6 Hz, 2H), 6.72 (d, J=8.6 Hz, 2H), 6.39 (d, J=1.3 Hz, 1H), 6.26 (d, J=1.3 Hz, 1H), 4.94 (s, 2H), 2.28 (s, 3H), 2.12 (s, 3H); HPLC >99%, t$_R$=11.0 min; ESI m/z 351 [M+H]$^+$.

Preparation of 1-benzyl-6-(3,5-dimethylisoxazol-4-yl)-2-methyl-1H-benzo[d]imidazol-4-ol (Example Compound 173)

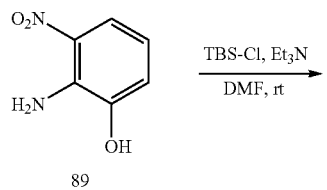

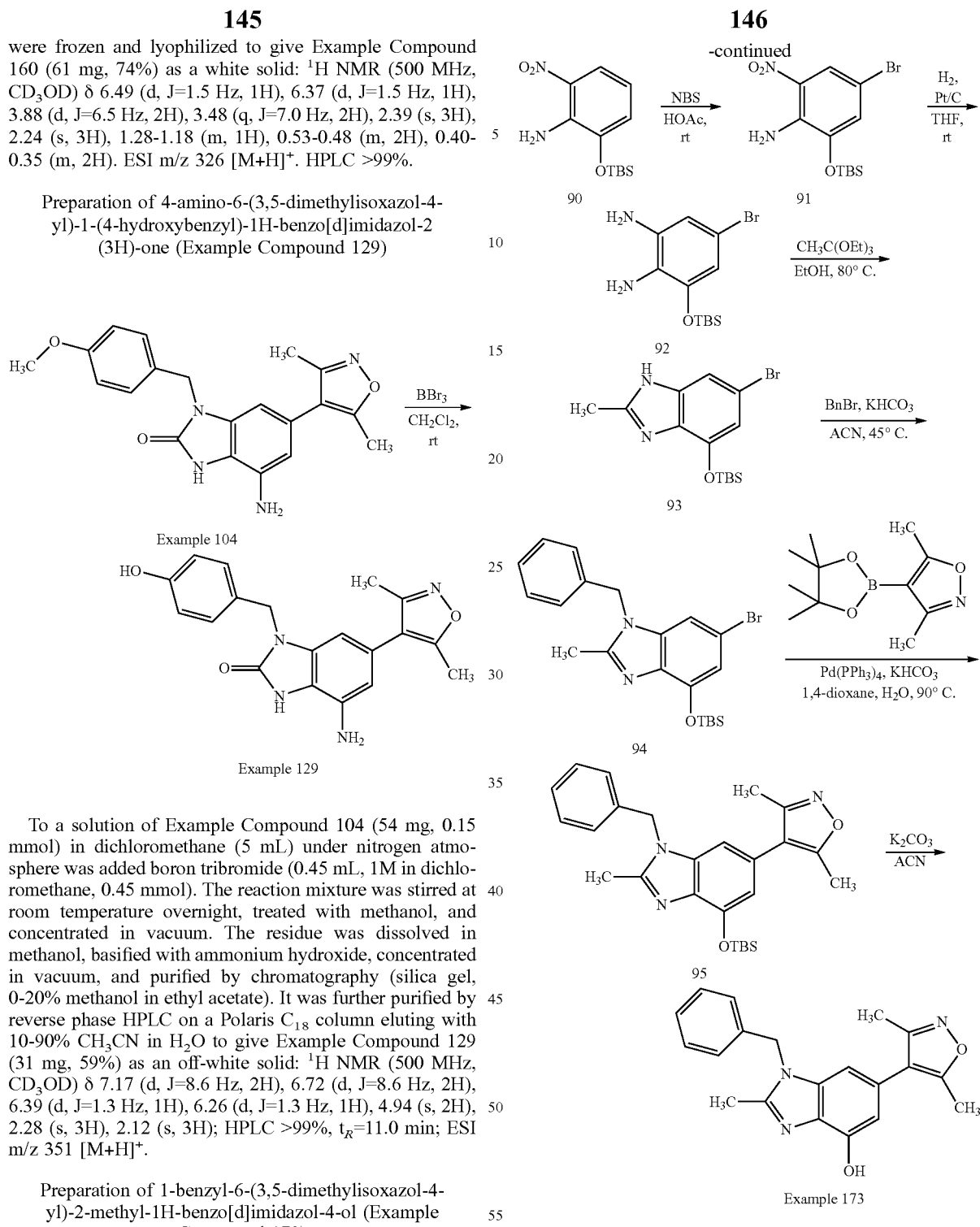

Step 1: To a solution of 89 (5.00 g, 32.5 mmol) and triethylamine (9.04 mL, 65.0 mmol) in N,N-dimethylformamide (150 mL) was added tert-butylchlorodimethylsilane (5.86 g, 39.0 mmol) at room temperature. The reaction mixture was stirred at room temperature for 1 h and diluted with ethyl acetate. The mixture was washed with water, brine, dried over sodium sulfate, and filtered. The filtrate was concentrated to afford 90 (8.59 g, 98%) as a brown oil: $^1$H NMR (300 MHz, CDCl$_3$) δ 7.75 (dd, J=1.3, 8.9 Hz, 1H), 6.89 (dd, J=1.2, 7.6 Hz, 1H), 6.53 (dd, J=8.8, 7.6 Hz, 1H), 6.45-6.15 (bs, 2H), 1.03 (s, 9H), 0.28 (s, 6H).

Step 2: To a solution of 90 (8.59 g, 32.1 mmol) in acetic acid (120 mL) was added N-bromosuccinimide (6.28 g, 35.3 mmol) at room temperature. The reaction mixture was stirred at room temperature for 30 min and then concentrated. The residue was dissolved in methanol and basified with 5% aqueous sodium bicarbonate. The precipitate formed was filtered, washed with water, and dried under vacuum to afford 91 (8.56 g, 76%) as an orange solid: $^1$H NMR (500 MHz, CDCl$_3$) δ 7.91 (d, J=2.1 Hz, 1H), 6.96 (d, J=2.1 Hz, 1H), 6.50-6.12 (bs, 2H), 1.03 (s, 9H), 0.30 (s, 6H).

Step 3: To a solution of 91 (5.00 g, 14.4 mmol) in tetrahydrofuran (60 mL) was added platinum on carbon (1.00 g, 5% Pt on carbon). The reaction mixture was stirred under hydrogen atmosphere at room temperature overnight. The mixture was filtered, washed with MeOH, and the filtrate was concentrated to afford 92 (5.65 g, >99%) as a dark brown oil: $^1$H NMR (500 MHz, CDCl$_3$) δ 6.51 (d, J=2.0 Hz, 1H), 6.46 (d, J=2.0 Hz, 1H), 3.50-2.50 (bs, 4H), 1.01 (s, 9H), 0.24 (s, 6H); ESI m/z 317 [M+H]$^+$.

Step 4: To a solution of 92 (2.00 g, 6.31 mmol) in ethanol (50 mL) was added triethylorthoacetate (3.07 g, 18.9 mmol) and sulfamic acid (1 mg, 0.01 mmol). The reaction was heated in a sealed tube at 80° C. overnight. The mixture was concentrated and purified by chromatography (silica gel, 0-100% ethyl acetate in hexanes) to afford 93 (2.07 g, 96%) as a light red solid: $^1$H NMR (500 MHz, CDCl$_3$) δ 8.75 (s, 1H), 7.45 (s, 1H), 6.78 (s, 1H), 3.61 (s, 3H), 1.03 (s, 9H), 0.28 (s, 6H); ESI m/z 341 [M+H]$^+$.

Step 5: A mixture of 93 (200 mg, 0.587 mmol), benzyl bromide (150 mg, 0.880 mmol), and potassium bicarbonate (113 mg, 0.822 mmol) in acetonitrile (20 mL) was heated at 45° C. for 2 days. The reaction mixture was cooled to room temperature, concentrated and purified by chromatography (silica gel, 0-30% ethyl acetate in hexanes) to afford 94 (303 mg, 30%) as a brown solid: $^1$H NMR (500 MHz, CDCl$_3$) δ 7.36-7.26 (m, 3H), 7.01 (d, J=8.2 Hz, 2H), 6.97 (d, J=1.6 Hz, 1H), 6.81 (d, J=1.6 Hz, 1H), 5.22 (s, 2H), 2.50 (s, 3H), 1.05 (s, 9H), 0.30 (s, 6H); ESI m/z 431 [M+H]$^+$.

Step 6: To a solution of 94 (75 mg, 0.17 mmol) in 1,4-dioxane (10 mL) and water (1 mL) was added 3,5-dimethyl-4-(4,4,5,5-tetramethyl-1,3,2-dioxaborolan-2-yl) isoxazole (58 mg, 0.26 mmol), potassium bicarbonate (70 mg, 0.70 mmol), and tetrakis(triphenylphosphine)palladium (0) (10 mg, 0.0087 mmol). The reaction mixture was purged with nitrogen and heated at 90° C. for 2 h. The reaction mixture was cooled to room temperature, concentrated and purified by chromatography (silica gel, 0-100% ethyl acetate in hexanes) to give 95 (53 mg, 70%) as an off-white solid: $^1$H NMR (500 MHz, CD$_3$OD) δ 7.33 (t, J=6.3 Hz, 2H), 7.27 (t, J=5.1 Hz, 1H), 7.14 (d, J=7.1 Hz, 2H), 6.89 (d, J=1.3 Hz, 1H), 6.58 (d, J=1.3 Hz, 1H), 5.45 (s, 2H), 2.59 (s, 3H), 2.32 (s, 3H), 2.16 (s, 3H), 1.05 (s, 9H), 0.30 (s, 6H); HPLC >99%, $t_R$=16.4 min; ESI m/z 448 [M+H]$^+$.

Step 7: A mixture of 95 (48 mg, 0.11 mmol) and potassium carbonate (30 mg, 0.22 mmol) in acetonitrile (10 mL) was heated in a sealed tube at 80° C. overnight. The reaction mixture was cooled to room temperature, concentrated and purified by chromatography (silica gel, 0-20% methanol in ethyl acetate). It was further purified by reverse phase HPLC on a Polaris C$_{18}$ column eluting with 10-90% CH$_3$CN in H$_2$O to give Example Compound 173 (32 mg, 87%) as an off-white solid: $^1$H NMR (500 MHz, DMSO-d$_6$) δ 9.84 (s, 1H), 7.33 (t, J=7.6 Hz, 2H), 7.26 (t, J=7.3 Hz, 1H), 7.18 (d, J=7.1 Hz, 2H), 6.86 (d, J=1.3 Hz, 1H), 6.47 (d, J=1.3 Hz, 1H), 5.42 (s, 2H), 2.52 (s, 3H), 2.33 (s, 3H), 2.15 (s, 3H); ESI m/z 334 [M+H]$^+$.

Preparation of 4-Amino-1-benzyl-6-(3,5-dimethyl-isoxazol-4-yl)-1H-benzo[d]imidazole-2(3H)-thione (Example Compound 177)

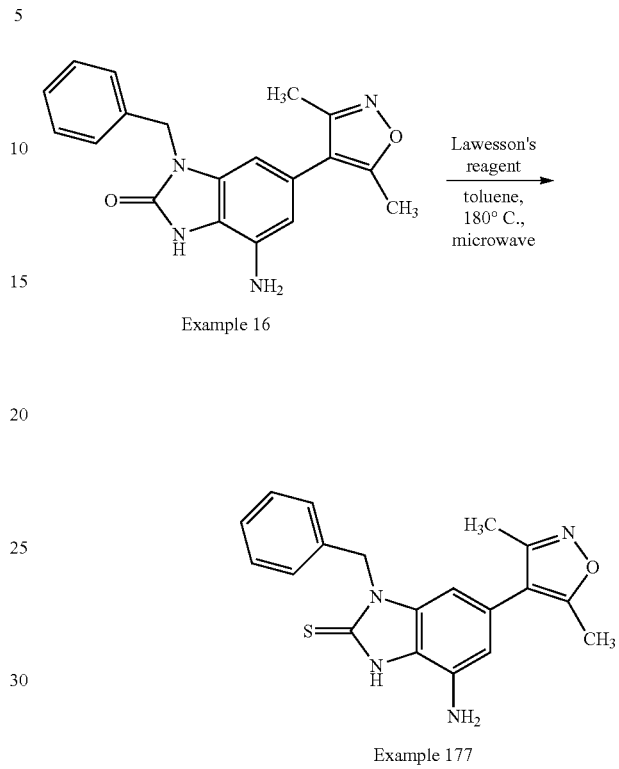

A mixture of Example Compound 16 (34 mg, 0.10 mmol) and Lawesson's reagent (202 mg, 0.5 mmol) was heated to 180° C. in microwave reactor for 2 h. The mixture was concentrated, the residue was purified by chromatography (silica gel, 0-40% EtOAc/hexanes) followed by chromatography (C$_{18}$, 10-70% CH$_3$CN/water) to give Example Compound 177 (13 mg, 37%) as an off-white solid: $^1$H NMR (300 MHz, DMSO-d$_6$) δ 12.56 (s, 1H), 7.45-7.42 (m, 2H), 7.34-7.25 (m, 3H), 6.44 (d, J=1.2 Hz, 1H), 6.39 (d, J=1.5 Hz, 1H), 5.44 (s, 4H), 2.29 (s, 3H), 2.11 (s, 3H); ESI m/z 351 [M+H]$^+$. HPLC 98.6%

Preparation of 1-benzyl-3-methyl-6-(1-methyl-1H-pyrazol-5-yl)-4-nitro-1H-benzo[d]imidazol-2(3H)-one (Example Compound 198) and 4-amino-1-benzyl-3-methyl-6-(1-methyl-1H-pyrazol-5-yl)-1H-benzo[d]imidazol-2(3H)-one (Example Compound 199)

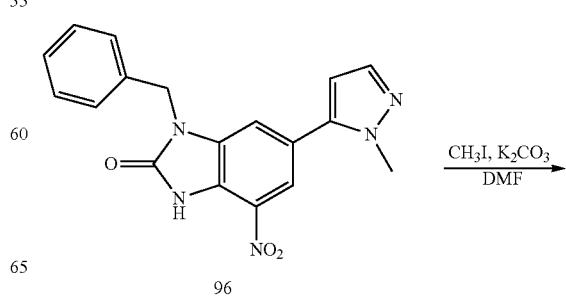

149

-continued

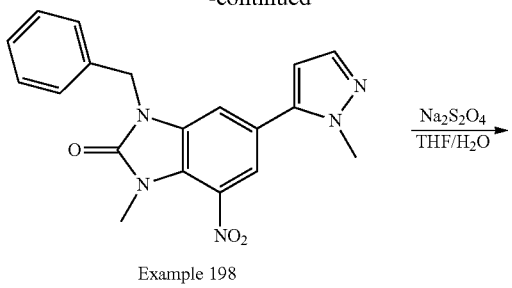

Example 198

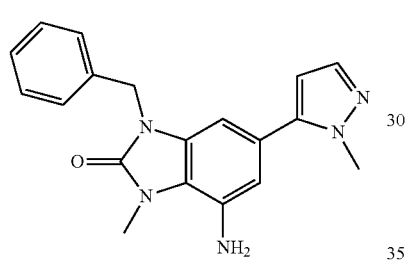

Example 199

Compound 96 was prepared by following the similar method for the preparation of Example Compound 15 using 1-methyl-5-(4,4,5,5-tetramethyl-1,3,2-dioxaborolan-2-yl)-1H-pyrazole.

Step 1: A mixture of 96 (70 mg, 0.20 mmol), CH₃I (85 mg, 0.60 mmol) and K₂CO₃ (110 mg, 0.8 mmol) in DMF (3 mL) was stirred at rt for 16 h. The reaction mixture was diluted with EtOAc (100 mL) and washed with brine (3×50 mL). The organic layer was dried over sodium sulfate, filtered and concentrated. The residue was purified by chromatography (silica gel, 20-70% ethyl acetate/hexanes) to afford Example Compound 198 (50 mg, 68%) as a yellow solid: ¹H NMR (300 MHz, CDCl₃) δ 7.66 (d, J=1.5 Hz, 1H), 7.50 (d, J=1.8 Hz, 1H), 7.36-7.30 (m, 5H), 7.02 (d, J=1.5 Hz, 1H), 6.27 (d, J=1.2 Hz, 1H), 5.16 (s, 2H), 3.69 (s, 3H), 3.65 (s, 3H); ESI m/z 364 [M+H]⁺.

Step 2: To a solution of Example Compound 198 (45 mg, 0.12 mmol) in THF (5 mL) and water (4 mL) was added Na₂S₂O₄ (129 mg, 0.74 mmol). The mixture was stirred at rt for 4 h, 2N HCl (1 mL) was added, the mixture was heated to reflux for 15 minutes then cooled to rt. Na₂CO₃ was added slowly to adjust to pH 9. The mixture was extracted with CH₂Cl₂ (100 mL), the organic layer was washed with brine (50 mL), filtered, concentrated and purified by chromatography (silica gel, 0-10% methanol/ethyl acetate) to afford Example Compound 199 (37 mg, 90%) as a white solid: ¹H NMR (300 MHz, DMSO-d₆) δ 7.39 (d, J=1.8 Hz, 1H), 7.35-7.24 (m, 5H), 6.56 (d, J=1.5 Hz, 1H), 6.54 (d, J=1.5 Hz, 1H), 6.20 (d, J=1.8 Hz, 1H), 5.15 (s, 2H), 5.01 (s, 2H), 3.72 (s, 3H), 3.63 (s, 3H); ESI m/z 334 [M+H]⁺.

150

Preparation of 4-(1-benzyl-2-(tetrahydro-2H-pyran-4-yl)-1H-imidazo[4,5-b]pyridin-6-yl)-3,5-dimethyl-isoxazole (Example Compound 220)

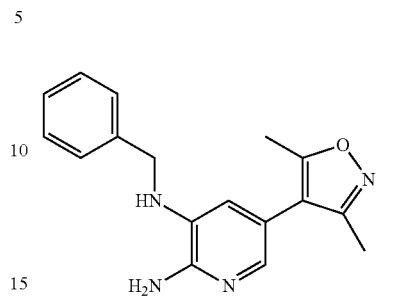

28

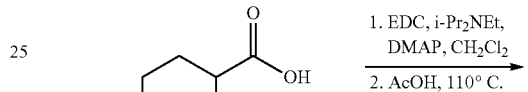

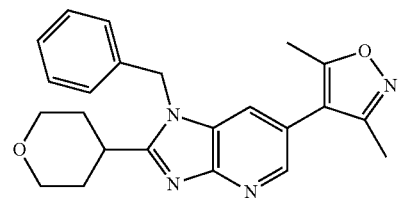

Example 220

To a solution of 28 (100 mg, 0.34 mmol) and tetrahydro-2H-pyran-4-carboxylic acid (65 mg, 0.51 mmol) in CH₂Cl₂ was added EDC (131 mg, 0.68 mmol), i-Pr₂NEt (132 mg, 1.02 mmol) and DMAP (10 mg). The reaction mixture was stirred at rt for 16 h. The mixture was diluted with EtOAc (100 mL), washed with brine (50 mL) and saturated NaHCO₃ (50 mL). The organic layer was dried over sodium sulfate, filtered and concentrated. The residue was dissolved in AcOH (2 mL) and heated to reflux for 5 h. The mixture was concentrated, the residue was dissolved in EtOAc (100 mL), washed with saturated NaHCO₃ (2×50 mL) and brine (50 mL). The organic layer was dried over sodium sulfate, filtered and concentrated. The residue was purified by chromatography (silica gel, 0-10% MeOH/EtOAc) to give Example Compound 220 (47 mg, 36%) as a light brown solid: ¹H NMR (300 MHz, CDCl₃) δ 8.41 (d, J=1.8 Hz, 1H), 7.38-7.32 (m, 3H), 7.24 (d, J=2.1 Hz, 1H), 7.08-7.05 (m, 2H), 5.42 (s, 2H), 4.12 (dd, J=11.7, 1.8 Hz, 2H), 3.52 (td, J=11.7, 1.8 Hz, 2H), 3.20-3.12 (m, 1H), 2.36-2.23 (m, 5H), 2.14 (s, 3H), 1.83-1.78 (m, 2H); ESI m/z 389 [M+H]⁺.

Preparation of 1-benzyl-6-(3,5-dimethylisoxazol-4-yl)-N-methyl-1H-imidazo[4,5-b]pyridine-2-carboxamide (Example Compound 221)

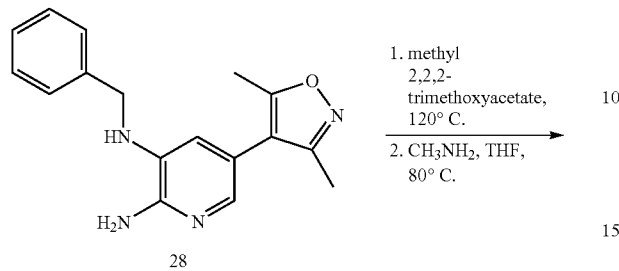

1. methyl 2,2,2-trimethoxyacetate, 120° C.
2. CH₃NH₂, THF, 80° C.

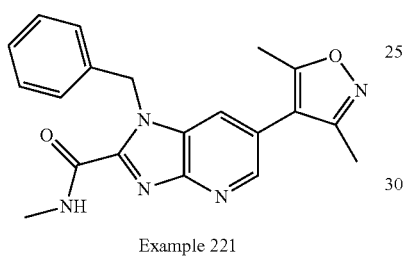

Example 221

A mixture of 28 (300 mg, 1.02 mmol) and methyl 2,2,2-trimethoxyacetate (1.5 mL) was heated to 120° C. for 16 h. The mixture was purified by chromatography (silica gel, 20-80% EtOAc/hexanes) to give a brown solid. The solid was dissolved in CH₃NH₂/THF (2 M) (3 mL) and heated 80° C. for 16 h. The mixture was concentrated, the residue was purified by chromatography (C$_{18}$, 10-70% CH$_3$CN/water) to give Example Compound 221 (45 mg, 12%) as an off-white solid: $^1$H NMR (300 MHz, DMSO-d$_6$) δ 8.31 (q, J=4.5 Hz, 1H), 8.27 (d, J=1.8 Hz, 1H), 7.54 (d, J=1.8 Hz, 1H), 7.36-7.24 (m, 5H), 5.54 (s, 2H), 3.00 (d, J=4.8 Hz, 3H), 2.21 (s, 3H), 2.00 (s, 3H); ESI m/z 362 [M+H].

Preparation of 1-benzyl-6-(1-methyl-1H-pyrazol-5-yl)-1H-imidazo[4,5-b]pyridin-2(3H)-one (Example Compound 171)

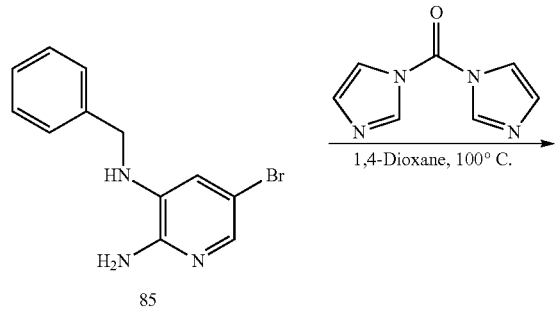

1,4-Dioxane, 100° C.

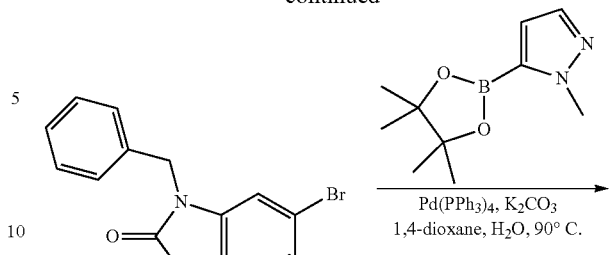

Pd(PPh₃)₄, K₂CO₃
1,4-dioxane, H₂O, 90° C.

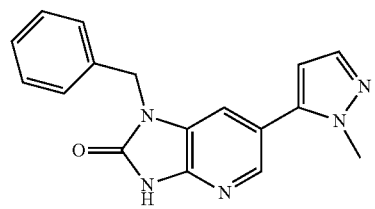

Example 171

Step 1: To a solution of 85 (1.14 g, 4.09 mmol) in 1,4-dioxane (41 mL) was added 1,1'-carbonyldiimidazole (796 mg, 4.91 mmol). The reaction mixture was heated at 110° C. for 16 h. The reaction mixture was concentrated. Purification by chromatography (silica gel, 0-100% ethyl acetate/hexanes) afforded 97 (1.03 g, 83%) as a white solid: $^1$H NMR (500 MHz, DMSO-d$_6$) δ 11.89 (s, 1H), 8.00 (d, J=2.0 Hz, 1H), 7.68 (d, J=2.0 Hz, 1H), 7.37-7.32 (m, 4H), 7.30-7.26 (m, 1H), 5.02 (s, 2H).

Step 2: To a solution of 97 (334 mg, 1.09 mmol) in 1,4-dioxane (11 mL) was added 1-methyl-1H-pyrazole-5-boronic acid pinacol ester (457 mg, 2.20 mmol), sodium carbonate (1.0 M in H₂O, 3.29 mL, 3.29 mmol) and tetrakis(triphenylphosphine)palladium(0) (127 mg, 0.1 mmol). The reaction mixture was purged with nitrogen and heated at 90° C. for 32 h. The mixture was diluted with methylene chloride (80 mL), washed with brine (40 mL), dried over sodium sulfate, filtered and concentrated. The residue was purified by chromatography (silica gel, 0-5% methanol/methylene chloride) followed by trituration with EtOAc to afford Example Compound 171 (173 mg, 52%) as a white solid: $^1$H NMR (500 MHz, DMSO-d$_6$) δ 11.87 (s, 1H), 8.04 (d, J=1.5 Hz, 1H), 7.57 (d, J=1.5, 1H), 7.46 (d, J=2.0 Hz, 1H), 7.38 (d, J=7.5 Hz, 2H), 7.34 (t, J=7.5 Hz, 2H), 7.27 (t, J=7.0 Hz, 1H), 6.37 (d, J=1.5 Hz, 1H), 5.06 (s, 2H), 3.77 (s, 3H); ESI m/z 306 [M+H]⁺.

Preparation of N-(1-benzyl-6-(3,5-dimethylisoxazol-4-yl)-1H-pyrrolo[3,2-b]pyridin-3-yl)acetamide (Example Compound 99)

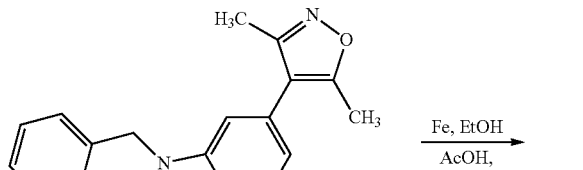

Example 39

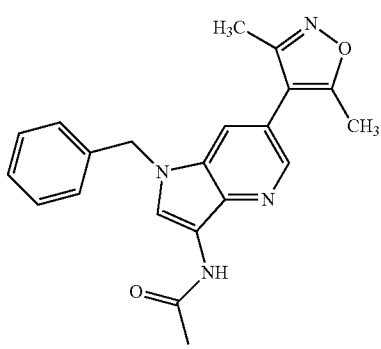

Example 99

A solution of Example Compound 39 (100 mg, 0.29 mmol) in EtOH (3 mL) and AcOH (1 mL) was added iron powder (162 mg, 2.9 mmol). The reaction mixture was heated at 80° C. for 1 h. It was filtered through a layer of Celite and the filtrate was concentrated. Purification by chromatography (silica gel, 0-5% methanol/dichloromethane) afforded Example Compound 99 (28 mg, 27%) as a red solid: $^1$H NMR (300 MHz, DMSO-$d_6$) δ 10.2 (s, 1H), 8.32 (d, J=1.8 Hz, 1H), 8.23 (s, 1H), 7.97 (d, J=1.8 Hz, 1H), 7.32-7.25 (m, 5H), 5.45 (s, 2H), 2.40 (s, 3H), 2.22 (s, 3H), 2.12 (s, 3H); ESI MS m/z 361 [M+H]$^+$.

Preparation of 1-benzyl-6-(3,5-dimethylisoxazol-4-yl)-1H-pyrrolo[3,2-b]pyridin-3-amine (Example Compound 100)

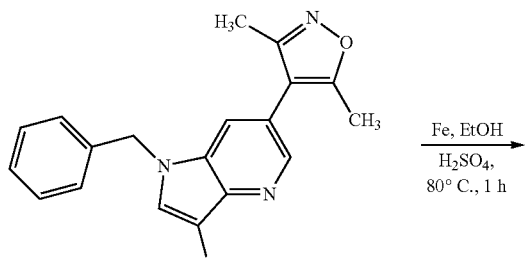

Example 39

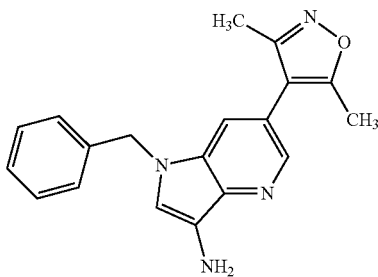

Example 100

To a solution of Example Compound 39 (100 mg, 0.29 mmol) in EtOH (3 mL) and $H_2SO_4$ (0.5 mL) was added iron powder (162 mg, 2.9 mmol). The reaction mixture was heated at 80° C. for 1 h. It was diluted with EtOH (20 mL), adjusted to pH 7 by 6 N aq. NaOH. The mixture was filtered through a layer of Celite and the filtrate was concentrated. Purification by chromatography (silica gel, 0-5% methanol/dichloromethane) afforded Example Compound 100 (12 mg, 13%) as a red solid: $^1$H NMR (300 MHz, DMSO-$d_6$) δ 8.18 (d, J=1.8 Hz, 1H), 7.82 (d, J=1.8 Hz, 1H), 7.33-7.21 (m, 5H), 7.06 (s, 1H), 5.30 (s, 2H), 4.26 (s, 2H), 2.37 (s, 3H), 2.21 (s, 3H); ESI MS m/z 319 [M+H]$^+$.

Preparation of 4-benzyl-6-(3,5-dimethylisoxazol-4-yl)-3,4-dihydroquinoxalin-2(1H)-one (Example Compound 156)

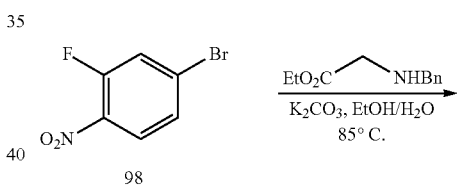

98

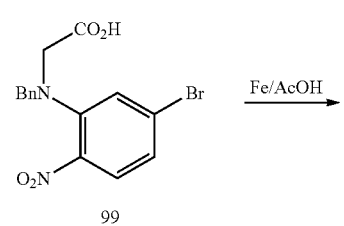

99

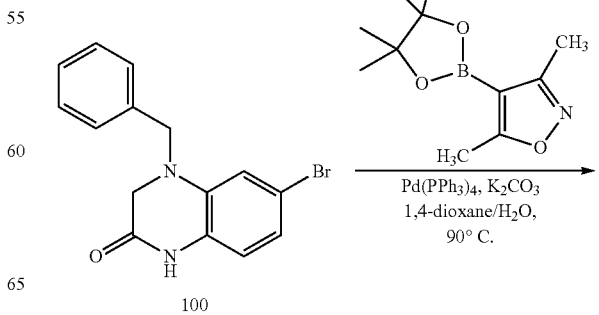

100

-continued

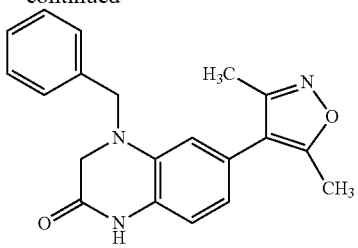

Example 156

Step 1: 4-Bromo-2-fluoro-1-nitrobenzene (1.00 g, 4.54 mmol), ethyl 2-(benzylamino)acetate (0.87 g, 4.5 mmol), and potassium carbonate (0.78 g, 5.7 mmol) in ethanol (15 mL) and water (11 mL) were heated at 85° C. for 10 h then stirred at rt for 8 h. The reaction mixture was diluted with water and brine then washed with methylene chloride. The resultant aqueous layer was filtered to afford 99 as an orange solid (1.28 g, 72%): $^1$H NMR (300 MHz, DMSO-$d_6$): δ 7.57 (d, J=8.6 Hz, 1H), 7.37-7.21 (m, 6H), 6.97 (dd, J=8.7, 2.0 Hz, 1H), 4.52 (s, 2H), 3.40 (s, 2H).

Step 2: To a solution of 99 (1.28 g, 3.51 mmol) in acetic acid (14 mL) at rt was added iron (470 mg, 8.4 mmol) and the resultant slurry was heated to 90° C. for 2.25 h. The mixture was cooled to rt and filtered through Celite, rinsing with methylene chloride. The filtrate was concentrated in vacuo and the resultant oil was partitioned between methylene chloride and saturated aqueous sodium bicarbonate. The aqueous layer was extracted with methylene chloride and the combined organic layers were dried with sodium sulfate, concentrated in vacuo, and purified by flash column chromatography (silica gel, 0-100% ethyl acetate/methylene chloride) to afford 100 as a white solid (430 mg, 39% yield): $^1$H NMR (300 MHz, CDCl$_3$) δ 8.74 (br s, 1H), 7.39-7.26 (m, 5H), 6.89-6.85 (m, 2H), 6.62 (d, J=8.0 Hz, 2H), 4.39 (s, 2H), 3.80 (s, 2H).

Step 3: Using the similar procedure used for Example Compound 7 step 1 on compound 100 afforded Example Compound 156 as a white solid: $^1$H NMR (500 MHz, DMSO-$d_6$) δ 10.58 (s, 1H), 7.38-7.34 (m, 4H), 7.30-7.23 (m, 1H), 6.87 (d, J=7.9 Hz, 1H), 6.65 (d, J=7.9 Hz, 1H), 6.51 (s, 1H), 4.46 (s, 2H), 3.86 (s, 2H), 2.15 (s, 3H), 1.97 (s, 3H); ESI m/z 334 [M+H]$^+$.

Preparation of 4-benzyl-6-(1-methyl-1H-pyrazol-5-yl)-3,4-dihydroquinoxalin-2(1H)-one (Example Compound 166)

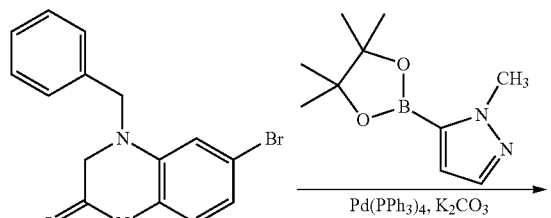

-continued

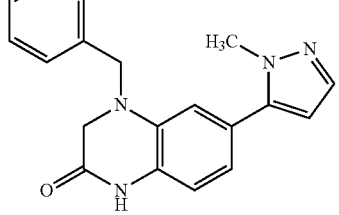

Example 166

Using the similar procedure used for Example Compound 7 step 1 on compound 100 afforded Example Compound 166 as a white solid: $^1$H NMR (500 MHz, DMSO-$d_6$) δ 10.62 (s, 1H), 7.37-7.33 (m, 5H), 7.29-7.25 (m, 1H), 6.90 (d, J=7.9 Hz, 1H), 6.80 (dd, J=7.9, 1.8 Hz, 1H), 6.70 (d, J=1.6 Hz, 1H), 6.18 (d, J=1.8 Hz, 1H), 4.49 (s, 2H), 3.83 (s, 2H), 3.58 (s, 3H); ESI m/z 319 [M+H]$^+$.

Preparation of (R)-4-benzyl-6-(3,5-dimethylisoxazol-4-yl)-3-methyl-3,4-dihydroquinoxalin-2(1H)-one (Example Compound 174)

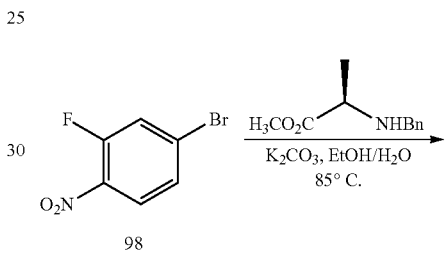

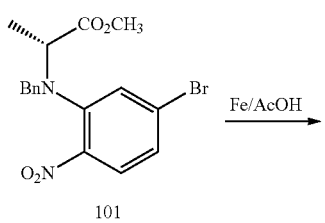

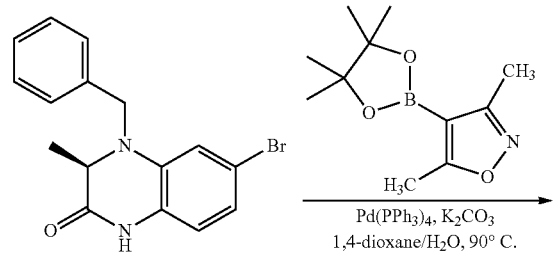

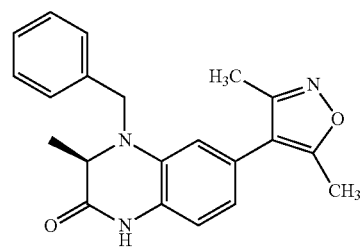

Example 174

Step 1: 4-Bromo-2-fluoro-1-nitrobenzene (0.50 g, 2.3 mmol), (R)-methyl 2-(benzylamino)propanoate (0.55 g, 2.3 mmol), and potassium carbonate (0.47 g, 3.4 mmol) in ethanol (8 mL) and water (6 mL) were heated at 85° C. for 10 h then stirred at rt for 8 h. The reaction mixture was diluted with water and filtered. The pH of the filtrate was adjusted to 4 with 6N aqueous HCl and the resultant slurry was re-filtered to afford 101 as a sticky orange solid (not weighed; used directly in the next step).

Step 2: Using the similar procedure used for Example Compound 156 step 2 on compound 101 afforded compound 102 as a white solid (430 mg, 39% yield): $^1$H NMR (500 MHz, DMSO-$d_6$) δ 10.57 (br s, 1H), 7.39-7.25 (m, 5H), 6.87-6.66 (m, 3H), 4.60 (d, J=15.5 Hz, 1H), 4.29 (d, J=15.2 Hz, 1H), 3.85 (q, J=6.9 Hz, 1H), 1.08 (d, J=6.7 Hz, 3H).

Step 3: Using the similar procedure used for Example Compound 156 step 3 on compound 102 afforded Example Compound 174 as an off-white solid: $^1$H NMR (500 MHz, DMSO-$d_6$) δ 10.53 (s, 1H), 7.37-7.32 (m, 4H), 7.26-7.23 (m, 1H), 6.88 (d, J=7.9 Hz, 1H), 6.66 (dd, J=7.9, 1.7 Hz, 1H), 6.42 (d, J=1.5 Hz, 1H), 4.54 (d, J=15.6 Hz, 1H), 4.37 (d, J=15.7 Hz, 1H), 3.98 (q, J=6.7 Hz, 1H), 2.11 (s, 3H), 1.93 (s, 3H), 1.12 (d, J=6.7 Hz, 3H); ESI m/z 348 [M+H]$^+$.

Preparation of 1-(cyclopropylmethyl)-6-(3,5-dimethylisoxazol-4-yl)-1H-imidazo[4,5-b]pyridin-2(3H)-one (Example Compound 118) and 1-(cyclopropylmethyl)-6-(3,5-dimethylisoxazol-4-yl)-N-ethyl-1H-imidazo[4,5-b]pyridin-2-amine (Example Compound 131)

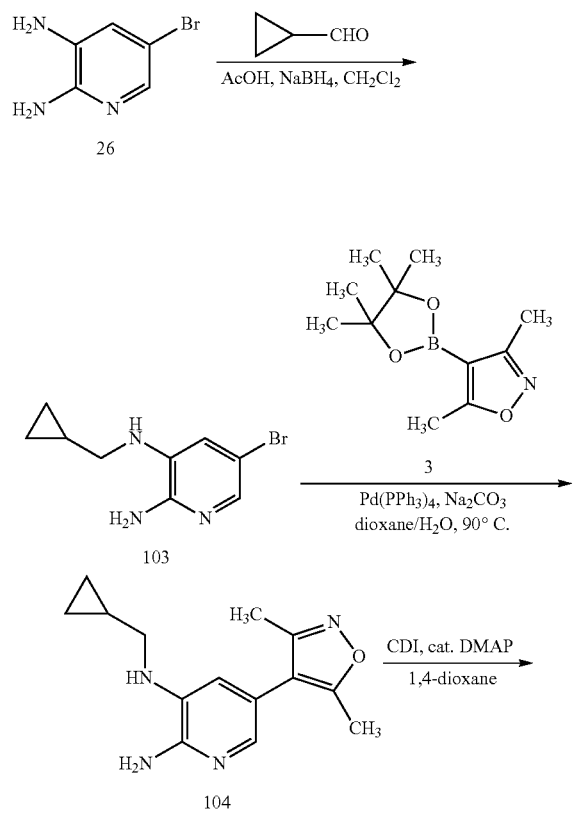

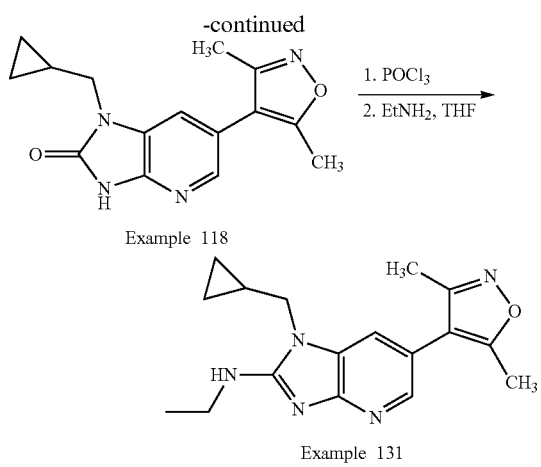

Example 118

Example 131

Step 1: To a stirred solution of 26 (2.00 g, 10.6 mmol) in dry CH$_2$Cl$_2$ (50 mL) was added glacial acetic acid (0.61 mL, 10.8 mmol) and cyclopropanecarboxaldehyde (0.81 mL, 12.3 mmol). The solution was stirred at room temperature for 1 h and was cooled to 0° C. Sodium borohydride (1.21 g, 31.8 mmol) was added carefully and the reaction was allowed to warm to room temperature. After stirring at ambient temperature for 15 h, saturated aq. NaHCO$_3$ (20 mL) was added to basify and then the mixture was extracted with CH$_2$Cl$_2$ (2×100 mL). The combined methylene chloride layers were dried over Na$_2$SO$_4$, filtered and the filtrate was concentrated to a brown residue. The residue was diluted with CH$_2$Cl$_2$ (20 mL), the solution was loaded onto silica gel (120 g) and eluted with 0-70% ethyl acetate in hexanes to afford 103 (330 mg, 13%) as a yellow solid: $^1$H NMR (500 MHz, CDCl$_3$) δ 7.62 (d, J=2.0 Hz, 1H), 6.83 (d, J=1.5 Hz, 1H), 4.17 (br s, 2H), 3.39 (br s, 1H), 2.90 (d, J=5.0 Hz, 1H), 2.89 (d, J=5.0 Hz, 1H), 1.19-1.07 (m, 1H), 0.63-0.56 (m, 2H), 0.27-0.22 (m, 2H).

Step 2: To a mixture of 103 (300 mg, 1.24 mmol) and 3 (415 mg, 1.86 mmol) in 1,4-dioxane (10 mL) and water (2.5 mL) was added potassium carbonate (343 mg, 2.48 mmol) and tetrakis(triphenylphosphine)palladium(0) (76 mg, 0.062 mmol). The reaction was stirred and heated at 90° C. for 17 h. The reaction was diluted with methanol (20 mL) and silica gel (10 g) was added. The suspension was concentrated to dryness and the resulting powder was loaded onto silica gel (80 g) and eluted with 0-80% ethyl acetate in hexanes. The clean product was concentrated to give 104 (312 mg, 97%) as a yellow solid: $^1$H NMR (500 MHz, CDCl$_3$) δ 7.48 (d, J=1.5 Hz, 1H), 6.61 (d, J=1.5 Hz, 1H), 4.27 (br s, 2H), 3.39 (br s, 1H), 2.92 (t, J=6.0 Hz, 2H), 2.38 (s, 3H), 2.24 (s, 3H), 1.18-1.09 (m, 1H), 0.63-0.56 (m, 2H), 0.28-0.22 (m, 2H).

Step 3: To a solution of 104 (310 mg, 1.20 mmol), a catalytic amount of DMAP and 1,4-dioxane (4 mL) in a pressure tube was added 1,1'-carbonyldiimidazole (390 mg, 2.40 mmol). The tube was sealed and heated to 80° C. for 2 h. The reaction mixture was diluted with methanol (20 mL) and silica gel (10 g) was added. The suspension was concentrated to dryness and the resulting powder was loaded onto silica gel (40 g) and eluted with 0-80% ethyl acetate in hexanes. The clean product was concentrated to give 1-(cyclopropylmethyl)-6-(3,5-dimethylisoxazol-4-yl)-1H-imidazo[4,5-b]pyridin-2(3H)-one (275 mg, 81%) as a yellow solid. A 50 mg sample was then purified by reverse phase HPLC on a Polaris C$_{18}$ column eluting with 10-90% CH$_3$CN in H$_2$O and the clean fractions were frozen and lyophilized to give Example Compound 118 (37 mg) as a white solid: $^1$H NMR (500 MHz, CD₃OD) δ 7.90 (d, J=1.5 Hz, 1H), 7.50 (d, J=1.5 Hz, 1H), 3.81 (d, J=7.0 Hz, 2H), 2.42 (s, 3H), 2.26 (s, 3H), 1.31-1.20 (m, 1H), 0.60-0.53 (m, 2H), 0.44-0.38 (m, 2H); ESI m/z 285 [M+H]⁺.

Step 4: A solution of Example Compound 118 (220 mg, 0.774 mmol) in phosphorus(V) oxychloride (3 mL) was placed in a sealed tube and heated at 110° C. for 6 h. The solvent was removed in vacuo and a saturated aq. NaHCO₃ solution (5 mL) was added. The mixture was extracted with ethyl acetate (2×20 mL) and the combined extracts were dried over Na₂SO₄, filtered and the filtrate was concentrated. THF (5 mL) and 2.0 M ethylamine solution in THF (6 mL, 12.0 mmol) were then added and the reaction was heated at 70° C. for 17 h. The reaction was concentrated to dryness and the residue diluted with CH₂Cl₂ (5 mL). The resulting solution was loaded onto silica gel (40 g) and eluted with 0-80% ethyl acetate in hexanes. The clean product was then purified by reverse phase HPLC on a Polaris column eluting with 10-90% CH₃CN in H₂O and the clean fractions were frozen and lyophilized to give Example Compound 131 (91 mg, 38%) as a white solid: ¹H NMR (500 MHz, CDCl₃) δ 7.93 (d, J=2.0 Hz, 1H), 7.48 (d, J=1.5 Hz, 1H), 3.98 (d, J=6.5 Hz, 2H), 3.57 (q, J=7.0 Hz, 2H), 2.42 (s, 3H), 2.26 (s, 3H), 1.30 (t, J=7.0 Hz, 3H), 1.29-1.19 (m, 1H), 0.59-0.52 (m, 2H), 0.45-0.39 (m, 2H); ESI m/z 312 [M+H]⁺.

Preparation of 4-(1-(cyclohexylmethyl)-2-methyl-1H-imidazo[4,5-b]pyridin-6-yl)-3,5-dimethylisoxazole (Example Compound 191), 4-(1-(cyclopentylmethyl)-2-methyl-1H-imidazo[4,5-b]pyridin-6-yl)-3,5-dimethylisoxazole (Example Compound 192) and 4-(1-(cyclobutylmethyl)-2-methyl-1H-imidazo[4,5-b]pyridin-6-yl)-3,5-dimethylisoxazole (Example Compound 193)

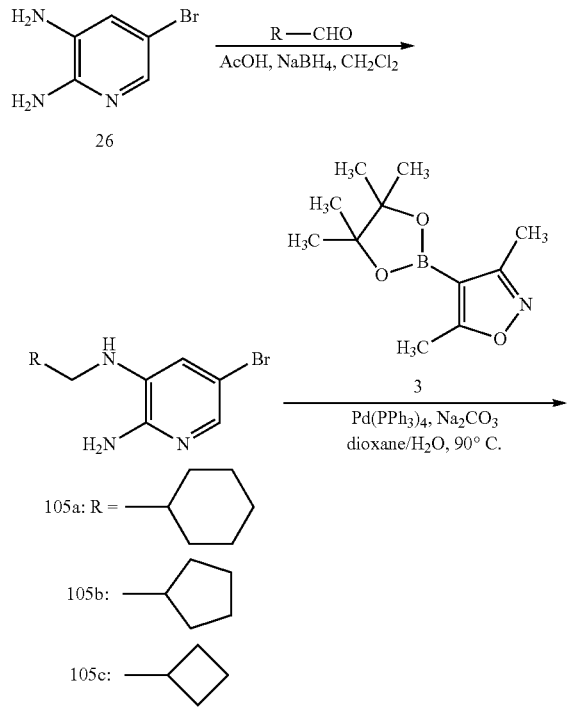

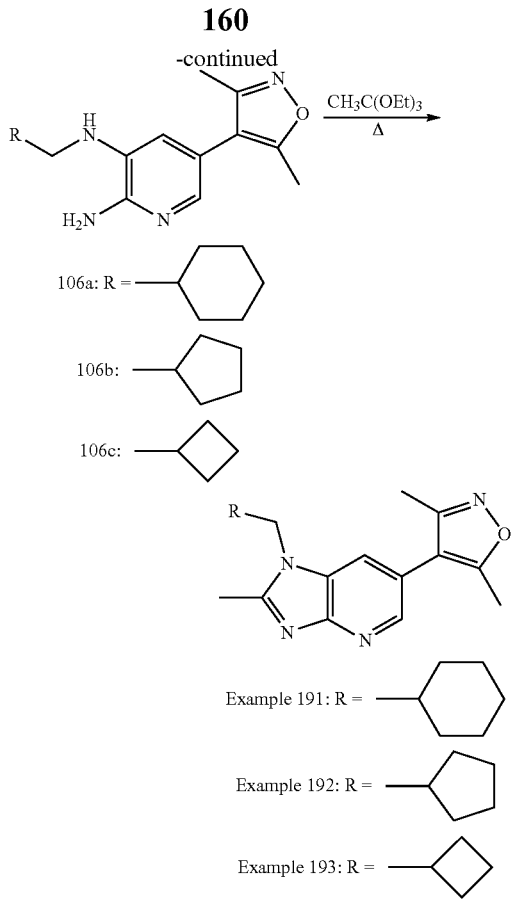

Step 1: A mixture of 2,3-diamino-5-bromopyridine (10.0 g, 0.053 mol), cyclohexanecarboxaldehyde (6.08 g, 0.054 mol) and glacial acetic acid (3.05 mL) in dry CH₂Cl₂ (250 mL) was stirred for 1.5 h at room temperature. Sodium borohydride (6.06 g, 0.159 mol) was added portionwise over 20 min and the mixture was stirred for 17 h at room temperature. Saturated aq. NaHCO₃ was added until the mixture reached pH 8 (70 mL) and the aqueous layer extracted with CH₂Cl₂ (100 mL). The combined CH₂Cl₂ layers were combined, washed with water (500 mL), dried over Na₂SO₄, filtered and concentrated. The brown solid was taken up in methanol (100 mL) and silica gel (40 g) was added. The suspension was concentrated to dryness and the material was purified by chromatography (silica gel, 0-50% EtOAc/hexane then 0-10% EtOAc/CH₂Cl₂) to afford 105a (1.30 g, 9%) as a brown-gray solid: ¹H NMR (500 MHz, CDCl₃) δ 7.60 (d, J=2.0 Hz, 1H), 6.85 (d, J=2.0 Hz, 1H), 4.11 (br s, 2H), 3.28 (br s, 1H), 2.88 (d, J=5.0 Hz, 2H), 1.88-1.64 (m, 4H), 1.70-1.52 (m, 1H), 1.38-1.15 (m, 4H), 1.10-0.96 (m, 2H).

105b was prepared starting with cyclopentanecarbaldehyde (14% yield; brown-gray solid): ¹H NMR (500 MHz, CDCl₃) δ 7.60 (d, J=2.0 Hz, 1H), 6.86 (d, J=2.0 Hz, 1H), 4.14 (br s, 2H), 3.28 (br s, 1H), 2.99-2.93 (m, 2H), 2.23-2.11 (m, 1H), 1.88-1.71 (m, 2H), 1.70-1.53 (m, 4H), 1.32-1.23 (m, 2H).

105c was prepared starting with cyclobutanecarbaldehyde (15% yield; brown-gray solid): ¹H NMR (500 MHz, CDCl₃) δ 7.61 (d, J=2.0 Hz, 1H), 6.86 (d, J=2.0 Hz, 1H), 4.12 (br s, 2H), 3.14 (br s, 1H), 3.09-3.02 (m, 2H), 2.67-2.52 (m, 1H), 2.18-2.11 (m, 2H), 2.07-1.86 (m, 2H), 1.80-1.71 (m, 2H).

Step 2: To a mixture of 105a (500 mg, 1.76 mmol), 3,5-dimethyl-4-(4,4,5,5-tetramethyl-1,3,2-dioxaborolan-2- yl)isoxazole (589 mg, 2.64 mmol), potassium carbonate (487 mg, 3.52 mmol), water (4 mL) and 1,4-dioxane (16 mL) was added tetrakis(triphenylphosphine)palladium (0) and the mixture was heated to 90° C. for 17 h. The two phase mixture was diluted with methanol (20 mL) and silica gel was added. After concentrating to dryness the material was purified by chromatography (silica gel, 0-80% EtOAc/hexane) to afford 106a (551 mg, 99%) as a brown solid: $^1$H NMR (500 MHz, CDCl$_3$) δ 7.47 (d, J=2.0 Hz, 1H), 6.62 (d, J=2.0 Hz, 1H), 4.25 (br s, 2H), 3.34 (br s, 1H), 2.92 (t, J=6.0 Hz, 2H), 2.38 (s, 3H), 2.25 (s, 3H), 1.88-1.67 (m, 4H), 1.67-1.56 (m, 1H), 1.33-1.19 (m, 4H), 1.10-0.96 (m, 2H).

106b was prepared starting with 105b (96% yield; brown-gray solid): $^1$H NMR (500 MHz, CDCl$_3$) δ 7.47 (d, J=1.5 Hz, 1H), 6.64 (d, J=1.5 Hz, 1H), 4.25 (br s, 2H), 3.28 (br s, 1H), 2.99 (t, J=6.0 Hz, 1H), 2.38 (s, 3H), 2.24 (s, 3H), 2.24-2.17 (m, 1H), 1.90-1.81 (m, 2H), 1.72-1.55 (m, 4H), 1.38-1.22 (m, 2H).

106c was prepared starting with 105c (95% yield; brown-gray solid): $^1$H NMR (500 MHz, CDCl$_3$) δ 7.65 (d, J=1.5 Hz, 1H), 6.64 (d, J=2.0 Hz, 1H), 4.26 (br s, 2H), 3.18 (br s, 1H), 3.09 (t, J=6.0 Hz, 1H), 2.67-2.58 (m, 1H), 2.20-2.12 (m, 2H), 2.02-1.86 (m, 2H), 1.82-1.72 (m, 2H).

Step 3: A solution of 106a (100 mg, 0.33 mmol), triethylorthoacetate (5 mL) and glacial acetic acid (0.10 mL) was heated in a sealed tube for 24 hours at 80° C. The mixture was evaporated to dryness and methanol (10 mL), saturated aq. NaHCO$_3$ (5 ml) and silica gel (10 g) were added. After concentrating to dryness the resulting powder was loaded onto silica gel and eluted with 0-5% methanol in methylene chloride. The clean product was then purified by reverse phase HPLC on a Polaris column eluting with 10-90% CH$_3$CN in H$_2$O and the clean fractions were frozen and lyophilized to give Example Compound 191 (56 mg, 52%) as a white solid: $^1$H NMR (500 MHz, CD$_3$OD) δ 8.30 (d, J=1.5 Hz, 1H), 7.96 (d, J=2.0 Hz, 1H), 4.14 (d, J=7.5 Hz, 2H), 2.69 (s, 3H), 2.44 (s, 3H), 2.28 (s, 3H), 1.95-1.82 (m, 1H), 1.76-1.50 (m, 5H), 1.29-1.07 (m, 5H); ESI m/z 325 [M+H]$^+$.

Starting with 106b, Example Compound 192 (31 mg, 29%) was prepared as a white solid: $^1$H NMR (500 MHz, CD$_3$OD) δ 8.30 (d, J=2.0 Hz, 1H), 7.98 (d, J=2.0 Hz, 1H), 4.26 (d, J=8.0 Hz, 2H), 2.71 (s, 3H), 2.49-2.38 (m, 1H), 2.44 (s, 3H), 2.28 (s, 3H), 1.80-1.68 (m, 4H), 1.66-1.57 (m, 2H), 1.40-1.27 (m, 2H); ESI m/z 311 [M+H]$^+$.

Starting with 106c, Example Compound 193 (33 mg, 30%) was prepared as a white solid: $^1$H NMR (500 MHz, CD$_3$OD) δ 8.30 (d, J=1.5 Hz, 1H), 8.00 (d, J=1.5 Hz, 1H), 4.33 (d, J=7.0 Hz, 2H), 2.92-2.80 (m, 1H), 2.70 (s, 3H), 2.45 (s, 3H), 2.28 (s, 3H), 2.10-1.98 (m, 2H), 1.96-1.81 (m, 4H); ESI m/z 297 [M+H]$^+$.

Preparation of 1-(cyclopentylmethyl)-6-(3,5-dimethylisoxazol-4-yl)-1H-imidazo[4,5-b]pyridin-2(3H)-one (Example Compound 202) and 1-(cyclobutylmethyl)-6-(3,5-dimethylisoxazol-4-yl)-1H-imidazo[4,5-b]pyridin-2(3H)-one (Example Compound 203)

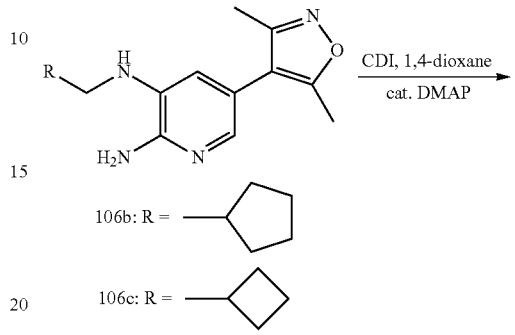

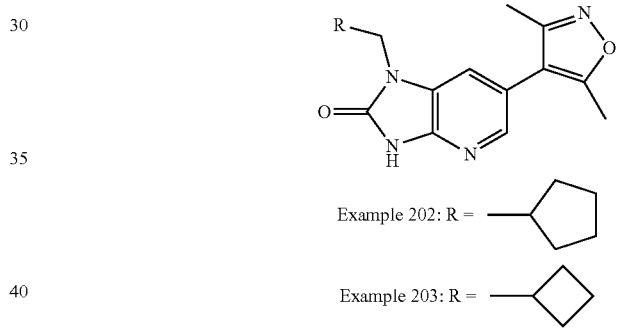

A solution of 106b (1.30 g, 4.54 mmol), 1,1'-carbonyldiimidazole (1.47 g) and N,N-dimethylaminopyridine (5 mg) in 1,4-dioxane (16 mL) was heated at 80° C. for 2 h and cooled to room temperature. To the mixture was added silica gel (10 g) and methanol (20 mL) and the suspension was concentrated to a dry powder. This material was loaded onto silica gel (80 g) and eluted with 0-90% ethyl acetate in hexanes to give 1.08 g (76%) of Example Compound 202 as a yellow solid. A 100 mg sample of the product was then purified by reverse phase HPLC on a Polaris column eluting with 10-90% CH$_3$CN in H$_2$O and the clean fractions were frozen and lyophilized to give Example Compound 202 as a white solid: $^1$H NMR (500 MHz, CD$_3$OD) δ 7.90 (d, J=1.5 Hz, 1H), 7.47 (d, J=2.0 Hz, 1H), 3.86 (d, J=7.5 Hz, 2H), 2.52-2.38 (m, 1H), 2.41 (s, 3H), 2.25 (s, 3H), 1.78-1.68 (m, 4H), 1.60-1.52 (m, 2H), 1.41-1.30 (m, 2H); ESI m/z 313 [M+H]$^+$.

Starting with 106c, Example Compound 203 (76% yield, white solid) was synthesized in a similar procedure as Example Compound 202: $^1$H NMR (500 MHz, CD$_3$OD) δ 7.89 (d, J=1.5 Hz, 1H), 7.46 (d, J=2.0 Hz, 1H), 3.94 (d, J=7.0 Hz, 2H), 2.86-2.77 (m, 1H), 2.41 (s, 3H), 2.25 (s, 3H), 2.08-1.98 (m, 2H), 1.94-1.80 (m, 4H); ESI m/z 299 [M+H]$^+$.

Preparation of 4-(1-(cyclopentylmethyl)-6-(3,5-dimethylisoxazol-4-yl)-1H-imidazo[4,5-b]pyridin-2-yl)morpholine (Example Compound 208) and 4-(2-(azetidin-1-yl)-1-(cyclopentylmethyl)-1H-imidazo[4,5-b]pyridin-6-yl)-3,5-dimethylisoxazole (Example Compound 209)

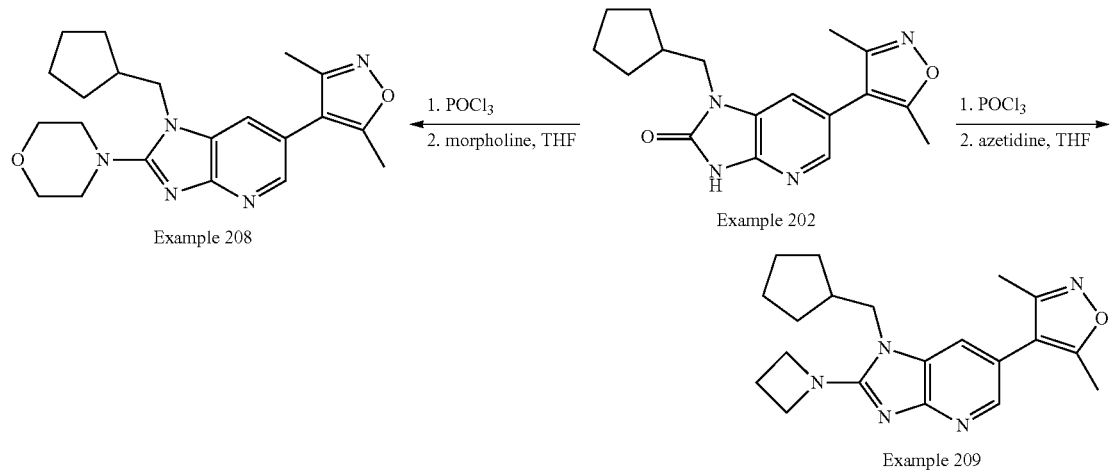

Example 208

Example 202

Example 209

A solution of Example Compound 202 (175 mg, 0.56 mmol) and phosphorus(V) oxychloride (4 mL) was heated to 110° C. for 17 h. The reaction was concentrated in vacuo and saturated aq. NaHCO$_3$ (5 mL) and ethyl acetate (20 mL) were added. The ethyl acetate layer was separated, dried over Na$_2$SO$_4$, filtered and the filtrate was concentrated to a dark yellow solid. The solid was dissolved in THF (5 mL) and morpholine (732 mg, 8.40 mmol) was added. The stirred solution was heated to 70° C. for 17 h. To the cooled mixture was added silica gel (5 g) and methanol (20 mL) and the suspension was concentrated to a dry powder. This material was loaded onto silica gel (40 g) and eluted with 0-3% methanol in methylene chloride to give 143 mg (67%) of product as an off-white solid. The product sample was then purified by reverse phase HPLC on a Polaris column eluting with 10-90% CH$_3$CN in H$_2$O and the clean fractions were frozen and lyophilized to give Example Compound 208 as a white solid: $^1$H NMR (500 MHz, CD$_3$OD) δ 8.17 (d, J=1.5 Hz, 1H), 7.81 (d, J=2.0 Hz, 1H), 4.14 (d, J=7.5 Hz, 2H), 3.87 (t, J=5.0 Hz, 4H), 3.41 (t, J=5.0 Hz, 4H), 2.58-2.49 (m, 1H), 2.43 (s, 3H), 2.27 (s, 3H), 1.75-1.66 (m, 2H), 1.62-1.50 (m, 4H), 1.30-1.19 (m, 2H). ESI m/z 382 [M+H]$^+$.

Example Compound 209 was synthesized using a similar procedure as was used for Example Compound 208; Example Compound 209 was collected as a white solid (166 mg, 84%): $^1$H NMR (500 MHz, CD$_3$OD) δ 8.00 (d, J=1.5 Hz, 1H), 7.59 (d, J=1.5 Hz, 1H), 4.42-4.37 (m, 4H), 4.01 (d, J=8.0 Hz, 2H), 2.57-2.44 (m, 2H), 2.50-2.41 (m, 1H), 2.41 (s, 3H), 2.25 (s, 3H), 1.76-1.51 (m, 6H), 1.32-1.22 (m, 2H). ESI m/z 352 [M+H]$^+$.-

Preparation of 4-(1-(cyclobutylmethyl)-6-(3,5-dimethylisoxazol-4-yl)-1H-imidazo[4,5-b]pyridin-2-yl)morpholine (Example 210) and 4-(2-(azetidin-1-yl)-1-(cyclobutylmethyl)-1H-imidazo[4,5-b]pyridin-6-yl)-3,5-dimethylisoxazole (Example 211)

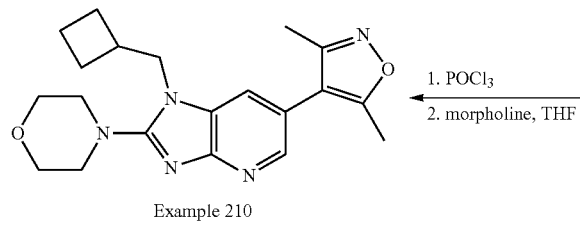

Example 210

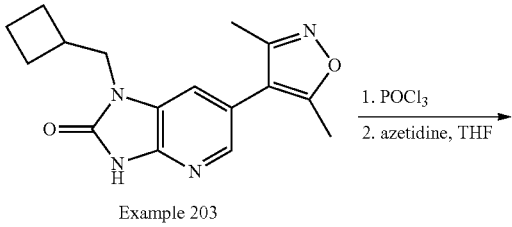

Example 203

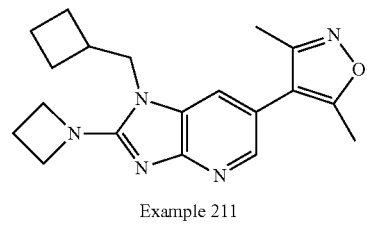

Example 211

Example 210 and Example 211 were synthesized using a similar procedure as was used for Example 208.

Example 210 collected as white solid (176 mg, 82% yield): $^1$H NMR (500 MHz, CD$_3$OD) δ 8.16 (d, J=1.5 Hz, 1H), 7.80 (d, J=2.0 Hz, 1H), 4.24 (d, J=7.0 Hz, 2H), 3.88 (t, J=5.0 Hz, 4H), 3.41 (t, J=5.0 Hz, 4H), 2.93-2.82 (m, 1H), 2.43 (s, 3H), 2.27 (s, 3H), 1.98-1.91 (m, 2H), 1.90-1.76 (m, 4H). ESI m/z 368 [M+H]$^+$.

Example 211 collected as white solid (180 mg, 91% yield): $^1$H NMR (500 MHz, CD$_3$OD) δ 7.99 (d, J=2.0 Hz, 1H), 7.61 (d, J=2.0 Hz, 1H), 4.38 (m, 4H), 4.10 (d, J=7.0 Hz, 2H), 2.88-2.79 (m, 1H), 2.57-2.48 (m, 2H), 2.41 (s, 3H), 2.25 (s, 3H), 2.04-1.95 (m, 2H), 1.95-1.78 (m, 4H). ESI m/z 338 [M+H]$^+$.

Preparation of 1-(cyclopentylmethyl)-6-(3,5-dimethylisoxazol-4-yl)-N-(tetrahydro-2H-pyran-4-yl)-1H-imidazo[4,5-b]pyridin-2-amine (Example 222)

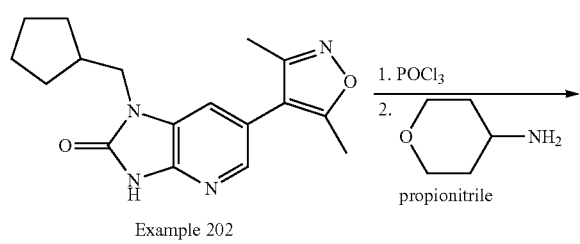

Example 202

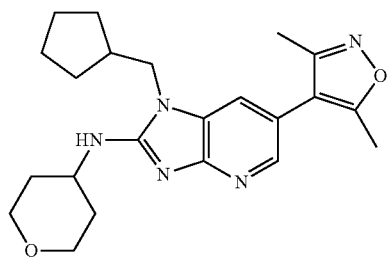

Example 222

A solution of Example 202 (175 mg, 0.56 mmol) and phosphorus (V) oxychloride (4 mL) was heated to 110° C. for 17 h. The reaction was concentrated in vacuo and saturated aq. NaHCO$_3$ (5 mL) and ethyl acetate (20 mL) were added. The ethyl acetate layer was separated, dried over Na$_2$SO$_4$, filtered and the filtrate was concentrated to a dark yellow solid. The solid was dissolved in propionitrile (5 mL) and 4-aminotetrahydropyran (283 mg, 28.0 mmol) was added. The stirred solution was heated to 180° C. in a microwave reactor for 6 h. To the cooled mixture was added silica gel (10 g) and methanol (20 mL) and the suspension was concentrated to a dry powder. This material was loaded onto silica gel (40 g) and eluted with 0-3% methanol in methylene chloride to give a yellow solid. The material was then purified by reverse phase HPLC on a Polaris column eluting with 10-90% CH$_3$CN in H$_2$O and the clean fractions were frozen and lyophilized to give Example 222 (70 mg, 31%) as a white solid: $^1$H NMR (500 MHz, CD$_3$OD) δ 7.94 (d, J=1.5 Hz, 1H), 7.50 (d, J=2.0 Hz, 1H), 4.17-4.05 (m, 1H), 4.05 (d, J=8.0 Hz, 2H), 4.02-3.97 (m, 2H), 3.57 (t, J=11.75 Hz, 2H), 2.44-2.36 (m, 1H), 2.41 (s, 3H), 2.25 (s, 3H), 2.08-2.00 (m, 2H), 1.78-1.64 (m, 6H), 1.62-1.54 (m, 2H), 1.38-1.25 (m, 2H). ESI m/z 396 [M+H]$^+$.

Preparation of 1-(cyclobutylmethyl)-6-(3,5-dimethyl isoxazol-4-yl)-N-(tetrahydro-2H-pyran-4-yl)-1H-imidazo[4,5-b]pyridin-2-amine (Example Compound 223)

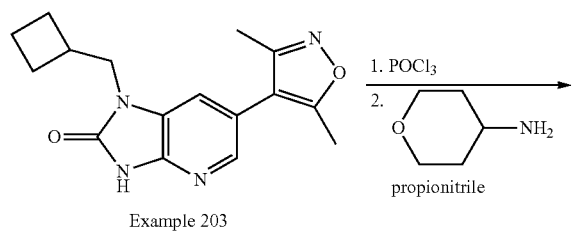

Example 203

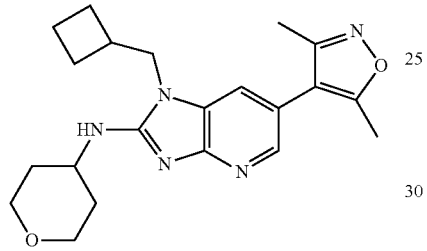

Example 223

Example Compound 223 was synthesized using a similar procedure as was used for Example Compound 222. Example Compound 223 collected as white solid (45 mg, 20% yield): $^1$H NMR (500 MHz, CD$_3$OD) δ 7.93 (d, J=2.0 Hz, 1H), 7.52 (d, J=2.0 Hz, 1H), 4.17-4.05 (m, 1H), 4.10 (d, J=7.5 Hz, 2H), 4.03-3.97 (m, 2H), 3.56 (t, J=11.75 Hz, 2H), 2.86-2.78 (m, 1H), 2.41 (s, 3H), 2.25 (s, 3H), 2.08-1.92 (m, 8H), 1.75-1.64 (m, 2H). ESI m/z 382 [M+H]$^+$.

Preparation of 4-(1-benzyl-7-methoxy-2-(trifluoromethyl)-1H-benzo[d]imidazol-6-yl)-3,5-dimethyl-isoxazole (Example Compound 241)

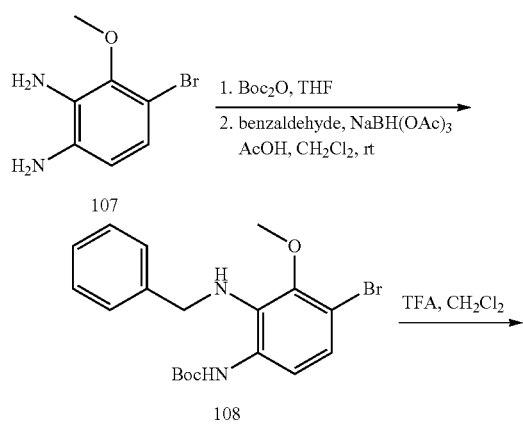

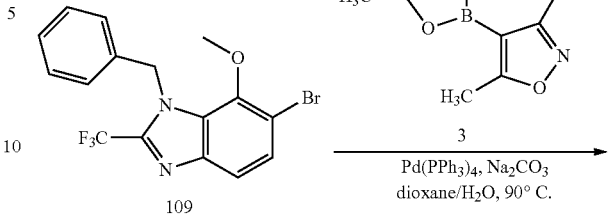

Example 241

Step 1: To a solution of 107 (136 mg, 0.627 mmol) in THF (6 mL) was added di-tert-butyl dicarbonate (137 mg, 0.627 mmol) and the reaction was stirred at rt for 16 h. The reaction was then concentrated and the residue was purified by chromatography (silica gel, 0-25% ethyl acetate/hexanes) to afford an off-white solid which was dissolved in CH$_2$Cl$_2$ (3 mL), benzaldehyde in CH$_2$Cl$_2$ (2 mL) was added followed by AcOH (2 drops). The reaction was stirred at rt for 1 h and NaBH(OAc)$_3$ (283 mg, 1.34 mmol) was added. The reaction was then stirred at rt for 16 h. The reaction was quenched with saturated NaHCO$_3$ and extracted with CH$_2$Cl$_2$ (2×50 mL). The combined organics were dried with Na$_2$SO$_4$, filtered and concentrated. The residue was purified by chromatography (silica gel, 0-30% ethyl acetate/hexanes) to afford 108 (97 mg, 38%) as an off-white solid: $^1$H NMR (500 MHz, DMSO-d$_6$) δ 8.43 (s, 1H), 7.32-7.26 (m, 4H), 7.23-7.00 (m, 1H), 6.95 (s, 2H), 4.87 (t, J=6.9 Hz, 1H), 4.31 (d, J=6.9 Hz, 2H), 3.64 (s, 3H), 1.42 (s, 9H).

Step 2: To a solution of 108 (135 mg, 0.332 mmol) in CH$_2$Cl$_2$ (5 mL) at 0° C. was added TFA (0.51 mL, 6.63 mmol) and the reaction was warmed to room temperature and stirred for 16 h. The reaction was then concentrated to afford 109 (114 mg, 90%): ESI m/z 385 [M+H]$^+$.

Step 3: Using the procedure used in General Procedure B step 1 starting with compound 109 (114 mg, 0.296 mmol) afforded Example Compound 241 (45 mg, 38%) as an off white solid: $^1$H NMR (300 MHz, DMSO-d$_6$) δ 7.72 (d, J=8.4 Hz, 1H), 7.36-7.26 (m, 4H), 7.03-7.00 (m, 2H), 5.81 (s, 2H), 3.13 (s, 3H), 2.27 (s, 3H), 2.09 (s, 3H); ESI m/z 402 [M+H]$^+$.

Preparation of 1-benzyl-6-(3,5-dimethylisoxazol-4-yl)-1H-benzo[d]imidazole-2-carboximidamide (Example Compound 243) and 1-benzyl-6-(3,5-dimethylisoxazol-4-yl)-1H-benzo[d]imidazole-2-carboxamide (Example Compound 244)

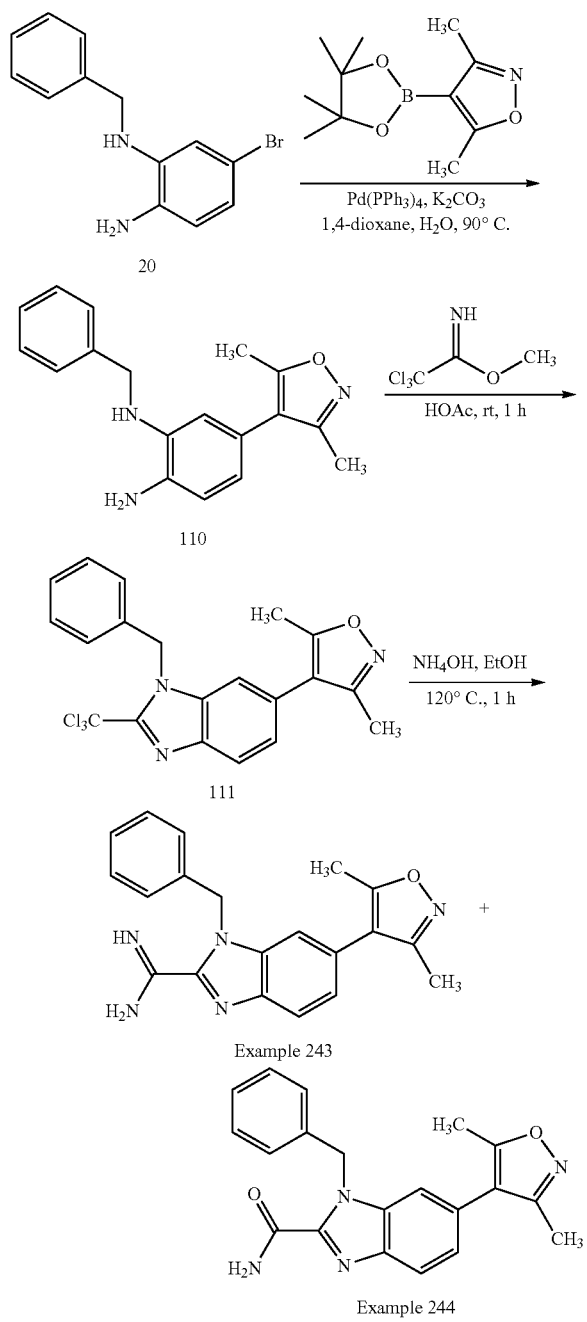

Step 1: To a solution of 20 (3.00 g, 10.8 mmol) in 1,4-dioxane (60 mL) and water (6 mL) was added 3,5-dimethyl-4-(4,4,5,5-tetramethyl-1,3,2-dioxaborolan-2-yl)isoxazole (2.90 g, 13.0 mmol), tetrakis(triphenylphosphine)palladium(0) (624 mg, 0.54 mmol) and potassium carbonate (2.98 g, 21.6 mmol). The reaction mixture was purged with nitrogen and heated at 90° C. for 18 h. The mixture was cooled to room temperature, concentrated and purified by chromatography (silica gel, 0-20% ethyl acetate in hexanes) to afford 110 (3.18 g, 99%) as a yellow solid: $^1$H NMR (500 MHz, CDCl$_3$) δ 7.38 (d, J=8.3 Hz, 2H), 7.34 (t, J=7.3 Hz, 2H), 7.28 (t, J=7.1 Hz, 1H), 6.78 (d, J=7.8 Hz, 1H), 6.55 (dd, J=1.8, 7.7 Hz, 1H), 6.43 (d, J=1.8 Hz, 1H), 4.35 (s, 2H), 3.88 (s, 1H), 3.42 (s, 2H), 2.23 (s, 3H), 2.11 (s, 3H); ESI m/z 294 [M+H]$^+$.

Step 1: To a solution of 110 (100 mg, 0.34 mmol) in acetic acid (2 mL) was added methyl 2,2,2-trichloroacetimidate (66 mg, 0.38 mmol) at room temperature. The reaction mixture was stirred at room temperature for 1 h and then water was added. The precipitate formed was collected by filtration, the filter cake was washed with water, and dried under vacuum at 40° C. to afford 111 (110 mg, 77%) as an off-white solid: $^1$H NMR (300 MHz, DMSO-d$_6$) δ 7.93 (dd, J=0.4, 8.4 Hz, 1H), 7.40-7.25 (m, 4H), 7.19-7.11 (m, 3H), 5.96 (s, 2H), 2.21 (s, 3H), 2.03 (s, 3H); ESI m/z 422 [M+H]$^+$.

Step 2: To a solution of 111 (100 mg, 0.238 mmol) in ethanol (1 mL) was added concentrated ammonium hydroxide (1 mL). The reaction mixture was heated at 120° C. for 1 h. The mixture was cooled to room temperature and concentrated. The residue was purified by chromatography (silica gel, 0-100% ethyl acetate in hexanes then to 20% methanol in ethyl acetate) followed by reverse phase HPLC on a Polaris C$_{18}$ column eluting with 10-90% CH$_3$CN in H$_2$O to afford Example Compound 243 (21 mg, 25%) and Example Compound 244 (29 mg, 35%) as an off-white solids. Example Compound 243: $^1$H NMR (500 MHz, DMSO-d$_6$) δ 7.77 (d, J=8.3 Hz, 1H), 7.49 (s, 1H), 7.36 (s, 1H), 7.33-7.19 (m, 6H), 6.58 (s, 2H), 6.27 (s, 2H), 2.32 (s, 3H), 2.15 (s, 3H); ESI m/z 346 [M+H]$^+$; Example Compound 244: $^1$H NMR (500 MHz, DMSO-d$_6$) δ 8.38 (s, 1H), 7.92 (s, 1H), 7.82 (d, J=8.5 Hz, 1H), 7.63 (d, J=1.0 Hz, 1H), 7.33-7.28 (m, 5H), 7.27-7.22 (m, 1H), 6.02 (s, 2H), 2.35 (s, 3H), 2.18 (s, 3H); ESI m/z 347 [M+H]$^+$.

Preparation of 1-benzyl-6-(3,5-dimethylisoxazol-4-yl)-N-(pyridin-3-yl)-1H-benzo[d]imidazol-2-amine (Example Compound 248)

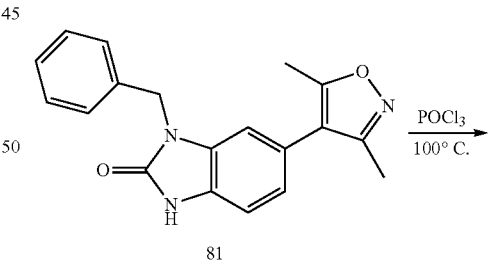

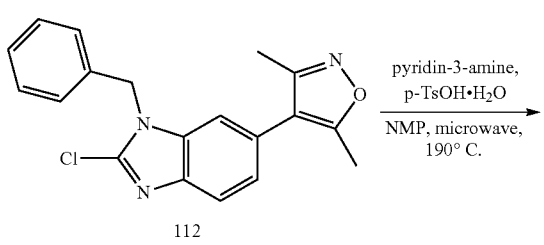

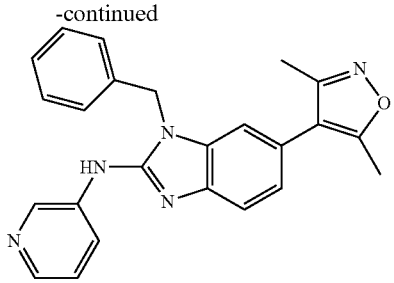

Example 248

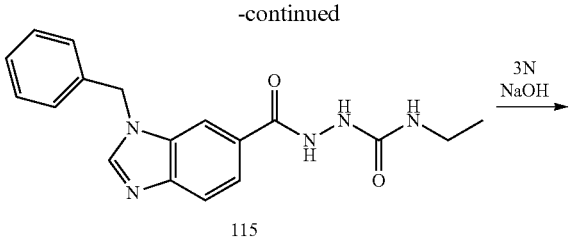

Step 1: A solution of 81 (500 mg, 1.57 mmol) and phosphorus(V) oxychloride (2 mL) was heated to 100° C. for 17 h. The reaction was concentrated in vacuo and saturated aq. NaHCO₃ (5 mL) and ethyl acetate (20 mL) were added. The ethyl acetate layer was separated, dried over Na₂SO₄, filtered and concentrated. The residue was purified by chromatography (silica gel, 0-30% ethyl acetate in hexanes) to afford 112 (415 mg, 78%) as a light brown oil: ESI m/z 338 [M+H]⁺.

Step 2: A mixture of 112 (20 mg, 0.06 mmol), pyridin-3-amine (28 mg, 0.30 mmol) and p-TsOH·H₂O (22 mg, 0.12 mmol) in NMP was heated at 190° C. in a microwave reactor for 2 h. The mixture was concentrated, and the residue was purified by chromatography (silica gel, 0-100% ethyl acetate in hexanes) to afford Example Compound 248 as an light brown oil: ESI m/z 396 [M+H]⁺.

Preparation of 3-(1-benzyl-1H-benzo[d]imidazol-6-yl)-4-ethyl-1H-1,2,4-triazol-5(4H)-one (Example Compound 249)

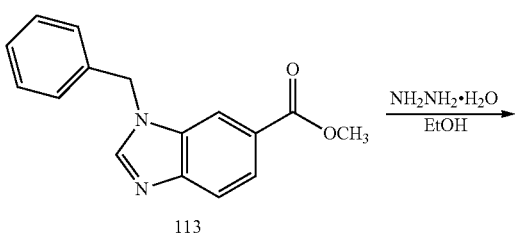

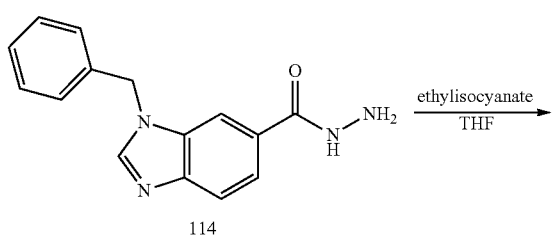

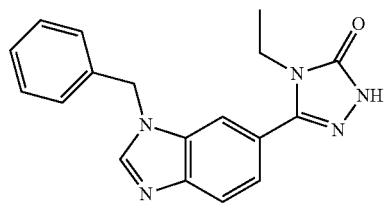

Example 249

Step 1: A solution of 113 (1.20 g, 4.51 mmol) and hydrazine monohydrate (3.27 mL, 67.65 mmol) in EtOH (20 mL) was heated to reflux for 16 h. The mixture was cooled to rt, the precipitate was collected by filtration, the filter cake was dried to afford 114 (1.02 g, 85%) as an off-white solid: ¹H NMR (300 MHz, DMSO-d₆) δ 9.74 (s, 1H), 8.54 (s, 1H), 8.07 (s, 1H), 7.73-7.67 (m, 2H), 7.38-7.26 (m, 5H), 5.54 (s, 2H), 4.47 (s, 2H).

Step 2: A suspension of 114 (500 mg, 1.88 mmol) and ethylisocyanate (160 mg, 2.26 mmol) in THF was stirred at rt for 5 h. The mixture was filtered, the filter cake was washed with ethyl acetate, and dried to afford 115 (610 mg, 96%) as a white solid: ¹H NMR (300 MHz, DMSO-d₆) δ 10.09 (s, 1H), 8.57 (s, 1H), 8.14 (s, 1H), 7.81-7.79 (m, 2H), 7.72 (d, J=8.4 Hz, 1H), 7.38-7.28 (m, 5H), 6.47 (t, J=5.4 Hz, 1H), 5.55 (s, 2H), 3.09-3.00 (m, 2H), 1.00 (t, J=7.2 Hz, 3H).

Step 3: A suspension of 115 (337 mg, 1.0 mmol) in 3 N NaOH (5 mL) was heated to reflux for 16 h. The mixture was adjusted to pH 8 by 2 N HCl, and then was extracted with CH₂Cl₂ (3×50 mL). The combined organic layers were dried over Na₂SO₄, filtered and concentrated. The residue was triturated with EtOAc/CH₂Cl₂ to afford Example Compound 249 as an off-white solid: ¹H NMR (300 MHz, DMSO-d₆) δ 11.85 (s, 1H), 8.59 (s, 1H), 7.81-7.76 (m, 2H), 7.43 (dd, J=8.1, 1.5 Hz, 1H), 7.35-7.28 (m, 5H), 5.58 (s, 2H), 3.63 (q, J=7.2, Hz 2H), 0.98 (t, J=7.2 Hz, 3H); ESI m/z 320 [M+H]⁺.

TABLE 2

Example Compounds

| Example Compound | Chemical Name | Structure | General procedure | Characterization | Purity HPLC (%) |
|---|---|---|---|---|---|
| 1 | 9-benzyl-2-(3,5-dimethyl-isoxazol-4-yl)-9H-purin-6-amine | 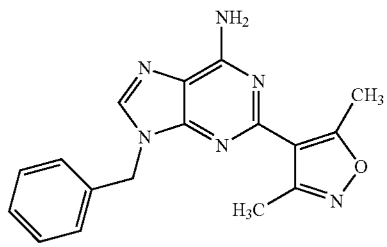 [SMILES: Cc1noc(C)c1-c1nc(N)c2ncn(Cc3ccccc3)c2n1] | A | $^1$H NMR (300 MHz, DMSO-d$_6$) δ 8.29 (s, 1H), 7.36-7.28 (m, 7H), 5.38 (s, 2H), 2.73 (s, 3H), 2.51 (s, 3H); ESI m/z 321 [M + H]$^+$. | 96.6 |
| 2 | 3-benzyl-5-(3,5-dimethyl-isoxazol-4-yl)-1H-imidazo[4,5-b]pyridin-2(3H)-one | 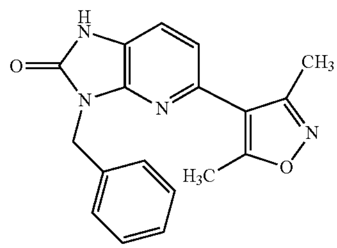 [SMILES: Cc1noc(C)c1-c1ccc2[nH]c(=O)n(Cc3ccccc3)c2n1] | No general procedure | $^1$H NMR (300 MHz, DMSO-d$_6$) δ 11.31 (s, 1H), 7.40 (d, J = 7.8 Hz, 1H), 7.34-7.25 (m, 5H), 7.15 (d, J = 7.8 Hz, 1H), 5.03 (s, 2H), 2.47 (s, 3H), 2.28 (s, 3H); ESI m/z 321 [M + H]$^+$. | >99 |
| 3 | 1-benzyl-5-(3,5-dimethyl-isoxazol-4-yl)-1H-imidazo[4,5-b]pyridin-2(3H)-one | 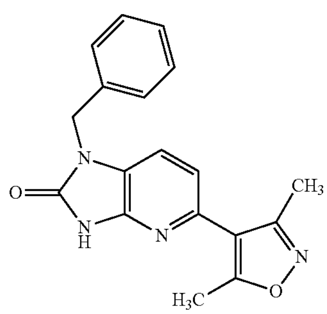 [SMILES: Cc1noc(C)c1-c1ccc2c(n1)[nH]c(=O)n2Cc1ccccc1] | No general procedure | $^1$H NMR (300 MHz, DMSO-d$_6$) δ 11.76 (s, 1H), 7.44 (d, J = 7.8 Hz, 1H), 7.36-7.28 (m, 5H), 7.11 (d, J = 7.8 Hz, 1H), 5.05 (s, 2H), 2.49 (s, 3H), 2.32 (s, 3H); ESI m/z 321 [M + H]$^+$. | >99 |
| 4 | 4-(3-benzyl-3H-imidazo[4,5-b]pyridin-6-yl)-3,5-dimethyl-isoxazole | 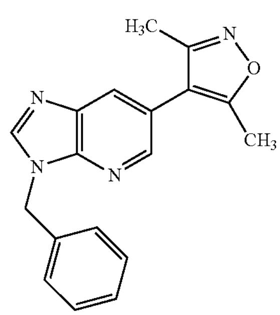 [SMILES: Cc1noc(C)c1-c1cnc2c(c1)ncn2Cc1ccccc1] | B | $^1$H NMR (300 MHz, CDCl$_3$) δ 8.62 (s, 1H), 8.36 (br s, 1H), 7.65 (s, 1H), 7.45 (s, 5H), 5.96 (s, 2H), 2.34 (s, 3H), 2.17 (s, 3H); ESI m/z 305 [M + H]$^+$. | >99 |
| 5 | 4-(1-benzyl-1H-imidazo[4,5-b]pyridin-6-yl)-3,5-dimethyl-isoxazole | 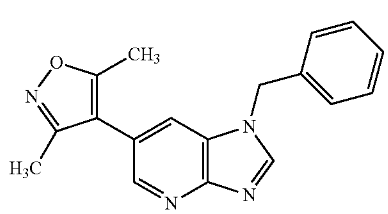 [SMILES: Cc1noc(C)c1-c1cnc2ncn(Cc3ccccc3)c2c1] | B | $^1$H NMR (300 MHz, CDCl$_3$) δ 8.62 (s, 1H), 8.36 (br s, 1H), 7.65 (s, 1H), 7.45 (s, 5H), 5.96 (s, 2H), 2.34 (s, 3H), 2.17 (s, 3H); ESI m/z 305 [M + H]$^+$. | >99 |

TABLE 2-continued

Example Compounds

| Example Compound | Chemical Name | Structure | General procedure | Characterization | Purity HPLC (%) |
|---|---|---|---|---|---|
| 6 | 3-benzyl-5-(3,5-dimethyl-isoxazol-4-yl)benzo[d]oxazol-2(3H)-one | 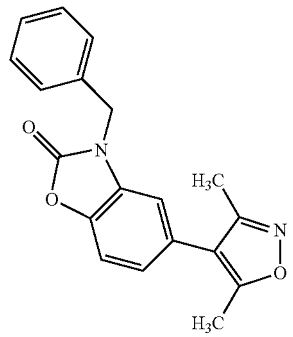 [SMILES: Cc1noc(C)c1-c1ccc2oc(=O)n(Cc3ccccc3)c2c1] | No general procedure | $^1$H NMR (500 MHz, DMSO-$d_6$) δ 7.47-7.42 (m, 3H), 7.40-7.34 (m, 2H), 7.34-7.28 (m, 1H), 7.23 (d, J = 1.6 Hz, 1H), 7.12 (dd, J = 8.2 Hz, 7.7 Hz, 1H), 5.07 (s, 2H), 2.33 (s, 3H), 2.15 (s, 3H); ESI m/z 321 [M + H]$^+$ | >99 |
| 7 | 1-benzyl-6-(3,5-dimethyl-isoxazol-4-yl)-1H-benzo[d]imidazol-4-amine | 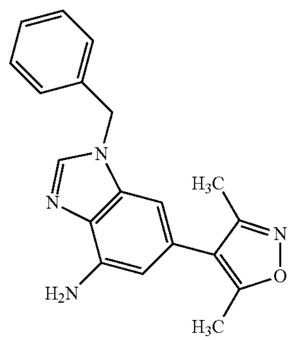 [SMILES: Cc1noc(C)c1-c1cc(N)c2ncn(Cc3ccccc3)c2c1] | C | $^1$H NMR (300 MHz, CDCl$_3$) δ 7.95 (s, 1H), 7.37-7.34 (m, 3H), 7.23-7.20 (m, 2H), 6.46 (d, J = 1.2 Hz, 1H), 6.40 (d, J = 1.2 Hz, 1H), 5.34 (s, 2H), 2.31 (s, 3H), 2.16 (s, 3H); ESI MS m/z 319 [M + H]$^+$ | >99 |
| 8 | 1-benzyl-5-(3,5-dimethyl-isoxazol-4-yl)-1H-benzo[d]imidazol-7-amine | 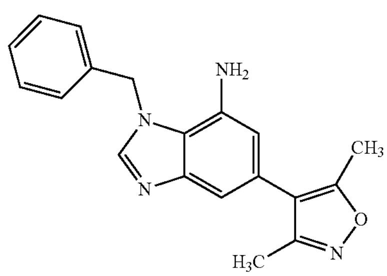 [SMILES: Cc1noc(C)c1-c1cc(N)c2c(c1)ncn2Cc1ccccc1] | C | $^1$H NMR (300 MHz, CDCl$_3$) δ 8.15 (s, 1H), 7.43-7.40 (m, 3H), 7.23 (d, J = 1.2 Hz, 1H), 7.20-7.17 (m, 2H), 6.39 (d, J = 1.2 Hz, 1H), 5.69 (s, 2H), 2.40 (s, 3H), 2.27 (s, 3H); ESI MS m/z 319 [M + H]$^+$ | 95.2 |
| 9 | N,1-dibenzyl-6-(3,5-dimethyl-isoxazol-4-yl)-1H-benzo[d]imidazol-4-amine | 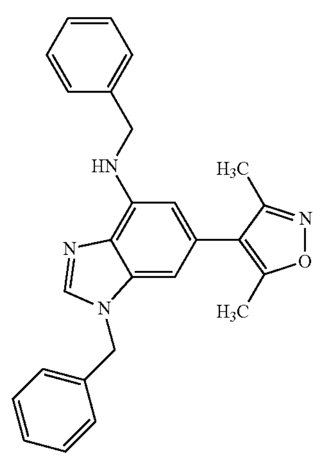 [SMILES: Cc1noc(C)c1-c1cc(NCc2ccccc2)c2ncn(Cc3ccccc3)c2c1] | C | $^1$H NMR (300 MHz, DMSO-$d_6$) δ 8.27 (s, 1H), 7.40-7.18 (m, 10H), 6.62 (d, J = 1.2 Hz, 1H), 6.57 (t, J = 6.0 Hz, 1H), 5.97 (d, J = 1.2 Hz, 1H), 5.41 (s, 2H), 4.48 (d, J = 6.0 Hz, 2H), 2.12 (s, 3H), 1.94 (s, 3H); ESI MS m/z 409 [M + H]$^+$. | >99 |

TABLE 2-continued

Example Compounds

| Example Compound | Chemical Name | Structure | General procedure | Characterization | Purity HPLC (%) |
|---|---|---|---|---|---|
| 10 | 1-benzyl-6-(3,5-dimethyl-isoxazol-4-yl)-1H-imidazo[4,5-b]pyridin-2(3H)-one | 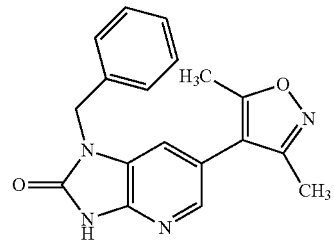 [SMILES: Cc1noc(C)c1-c1cnc2[nH]c(=O)n(Cc3ccccc3)c2c1] | No general procedure | $^1$H NMR (300 MHz, DMSO-d$_6$) δ 11.81 (s, 1H), 7.90 (d, J = 2.1 Hz, 1H), 7.44-7.25 (m, 6H), 5.05 (s, 2H), 2.34 (s, 3H), 2.16 (s, 3H); MM m/z 321 [M + H]$^+$. | >99 |
| 11 | 1-benzyl-7-(3,5-dimethyl-isoxazol-4-yl)quinoxalin-2(1H)-one | 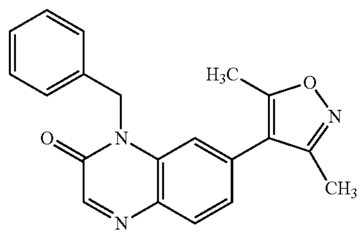 [SMILES: Cc1noc(C)c1-c1ccc2ncc(=O)n(Cc3ccccc3)c2c1] | No general procedure | $^1$H NMR (300 MHz, CDCl$_3$) δ 8.43 (s, 1H), 7.94 (d, J = 8.2 Hz, 1H), 7.35-7.32 (m, 2H), 7.29-7.27 (m, 1H), 7.21-7.18 (m, 3H), 7.04 (s, 1H), 5.51 (s, 2H), 2.16 (s, 3H), 2.02 (s, 3H); ESI m/z 332 [M + H]$^+$. | >99 |
| 12 | 1-benzyl-7-(3,5-dimethyl-isoxazol-4-yl)-3,4-dihydro-quinazolin-2(1H)-one | 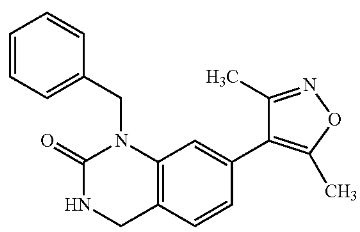 [SMILES: Cc1noc(C)c1-c1ccc2c(c1)N(Cc1ccccc1)C(=O)NC2] | No general procedure | $^1$H NMR (500 MHz, DMSO-d$_6$) δ 7.34-7.21 (m, 7H), 6.90 (dd, J = 7.5, 1.0 Hz, 1H), 6.58 (d, J = 1.0 Hz, 1H), 5.09 (s, 2H), 4.43 (s, 2H), 2.06 (s, 3H), 1.89 (s, 3H); MM m/z 334 [M + H]$^+$. | >99 |
| 13 | 4-(1-benzyl-2-methyl-1H-imidazo[4,5-b]pyridin-6-yl)-3,5-dimethylisoxazole | 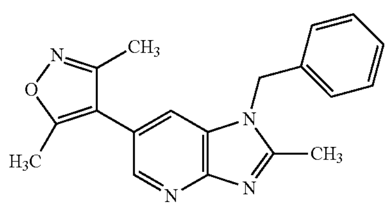 [SMILES: Cc1noc(C)c1-c1cnc2nc(C)n(Cc3ccccc3)c2c1] | D | $^1$H NMR (500 MHz, CD$_3$OD) δ 8.32 (d, J = 1.0 Hz, 1H), 7.78 (d, J = 1.0 Hz, 1H), 7.36-7.29 (m, 3H), 7.20-7.17 (m, 2H), 5.56 (s, 2H), 2.69 (s, 3H), 2.36 (s, 3H), 2.18 (s, 3H); ESI m/z 319 [M + H]$^+$. | >99 |
| 14 | 4-(1-(cyclopropyl-methyl)-2-methyl-4-nitro-1H-benzo[d]imidazol-6-yl)-3,5-dimethyl-isoxazole | 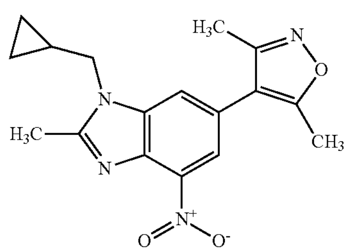 [SMILES: Cc1noc(C)c1-c1cc([N+](=O)[O-])c2nc(C)n(CC3CC3)c2c1] | F | $^1$H NMR (500 MHz, CD$_3$OD) δ 8.03 (d, J = 1.5 Hz, 1H), 7.93 (d, J = 1.5 Hz, 1H), 4.27 (d, J = 7.0 Hz, 2H), 2.75 (s, 3H), 2.46 (s, 3H), 2.30 (s, 3H), 1.38-1.28 (m, 1H), 0.65-0.60 (m, 2H), 0.51-0.46 (m, 2H). ESI m/z 327 [M + H]$^+$ | 97.3 |
| 15 | 1-benzyl-6-(3,5-dimethyl-isoxazol-4-yl)-4-nitro-1H-benzo[d]imidazol-2(3H)-one | 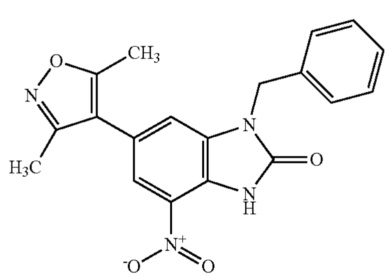 | G | $^1$H NMR (300 MHz, DMSO-d$_6$) δ 12.11 (s, 1H), 7.72 (d, J = 1.5 Hz, 1H), 7.50 (d, J = 1.5 Hz, 1H), 7.42-7.28 (m, 5H), 5.13 (s, 2H), 2.35 (s, 3H), 2.15 (s, 3H); ESI m/z 365 [M + H]$^+$. | 98.5 |

TABLE 2-continued

| Example Compound | Chemical Name | Structure | General procedure | Characterization | Purity HPLC (%) |
|---|---|---|---|---|---|
| 16 | 4-amino-1-benzyl-6-(3,5-dimethylisoxazol-4-yl)-1H-benzo[d]imidazol-2(3H)-one | 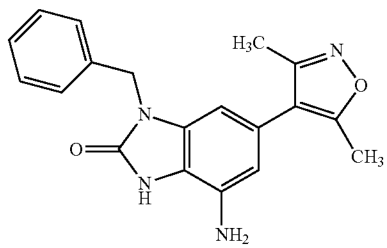 [SMILES: Cc1noc(C)c1-c1cc(N)c2[nH]c(=O)n(Cc3ccccc3)c2c1] | G | $^1$H NMR (500 MHz, DMSO-d$_6$) δ 10.44 (s, 1H), 7.36-7.25 (m, 5H), 6.28 (s, 2H), 5.04 (s, 2H), 4.95 (s, 2H), 2.28 (s, 3H), 2.10 (s, 3H); ESI m/z 335 [M + H]$^+$. | 98.6 |
| 17 | 1-benzyl-6-(3,5-dimethylisoxazol-4-yl)-2-ethoxy-1H-benzo[d]imidazol-4-amine | 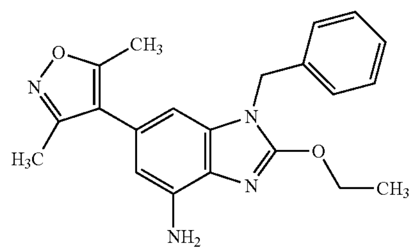 [SMILES: CCOc1nc2c(N)cc(-c3c(C)noc3C)cc2n1Cc1ccccc1] | No general procedure | $^1$H NMR (300 MHz, CDCl$_3$) δ 7.35-7.20 (m, 5H), 6.33 (d, J = 1.5 Hz, 1H), 6.30 (d, J = 1.5 Hz, 1H), 5.13 (s, 2H), 4.68 (q, J = 6.9 Hz, 2H), 4.30 (br.s, 2H), 2.30 (s, 3H), 2.16 (s, 3H), 1.49 (t, J = 7.2 Hz, 3H); ESI m/z 363 [M + H]$^+$. | 99 |
| 18 | 1-benzyl-6-(3,5-dimethylisoxazol-4-yl)-N-ethyl-4-nitro-1H-benzo[d]imidazol-2-amine | 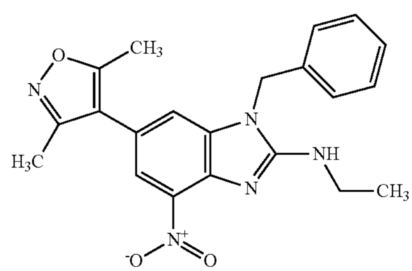 | I | $^1$H NMR (300 MHz, CDCl$_3$) δ 7.84 (d, J = 1.5 Hz, 1H), 7.42-7.35 (m, 3H), 7.16-7.13 (m, 2H), 7.03 (d, J = 1.5 Hz, 1H), 5.15 (s, 2H), 4.29 (t, J = 5.4 Hz, 1H), 3.78-3.69 (m, 2H), 2.36 (s, 3H), 2.21 (s, 3H), 1.27 (t, J = 7.5 Hz, 3H); ESI m/z 392 [M + H]$^+$. | 99 |
| 19 | 1-benzyl-6-(3,5-dimethylisoxazol-4-yl)-N2-ethyl-1H-benzo[d]imidazole-2,4-diamine | 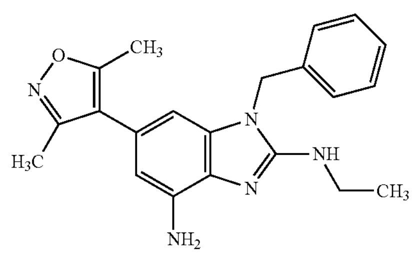 [SMILES: CCNc1nc2c(N)cc(-c3c(C)noc3C)cc2n1Cc1ccccc1] | I | $^1$H NMR (300 MHz, DMSO-d$_6$) δ 7.34-7.20 (m, 5H), 6.62 (t, J = 5.4 Hz, 1H), 6.30 (d, J = 1.5 Hz, 1H), 6.21 (d, J = 1.5 Hz, 1H), 5.19 (s, 2H), 4.83 (s, 2H), 3.47-3.38 (m, 2H), 2.28 (s, 3H), 2.11 (s, 3H), 1.22 (t, J = 7.2 Hz, 3H); ESI m/z 362 [M + H]$^+$. | 96.8 |
| 20 | methyl 1-benzyl-6-(3,5-dimethylisoxazol-4-yl)-2-oxo-2,3-dihydro-1H-benzo[d]imidazole-4-carboxylate | 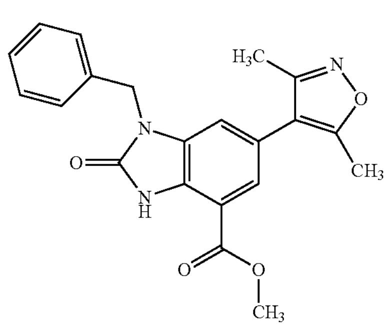 [SMILES: COC(=O)c1cc(-c2c(C)noc2C)cc2c1[nH]c(=O)n2Cc1ccccc1] | J | $^1$H NMR (500 MHz, CD$_3$OD) δ 7.54 (d, J = 1.5 Hz, 1H), 7.37-7.24 (m, 5H), 7.07 (d, J = 1.5 Hz, 1H), 5.14 (s, 2H), 3.97 (s, 3H), 2.27 (s, 3H), 2.09 (s, 3H); ESI m/z 378 [M + H]$^+$. | >99 |

TABLE 2-continued

Example Compounds

| Example Compound | Chemical Name | Structure | General procedure | Characterization | Purity HPLC (%) |
|---|---|---|---|---|---|
| 21 | 1-benzyl-6-(3,5-dimethylisoxazol-4-yl)-2-oxo-2,3-dihydro-1H-benzo[d]imidazole-4-carboxamide | 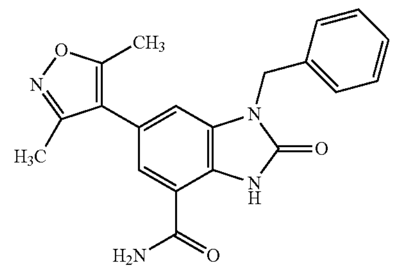 [SMILES: Cc1noc(C)c1-c1cc(C(N)=O)c2[nH]c(=O)n(Cc3ccccc3)c2c1] | J | $^1$H NMR (500 MHz, CD$_3$OD) δ 7.41 (d, J = 1.3 Hz, 1H), 7.37-7.24 (m, 5H), 7.00 (d, J = 1.4 Hz, 1H), 5.13 (s, 2H), 2.28 (s, 3H), 2.11 (s, 3H); ESI m/z 363 [M + H]$^+$. | 98.3 |
| 22 | 4-(aminomethyl)-1-benzyl-6-(3,5-dimethylisoxazol-4-yl)-1H-benzo[d]imidazol-2(3H)-one | 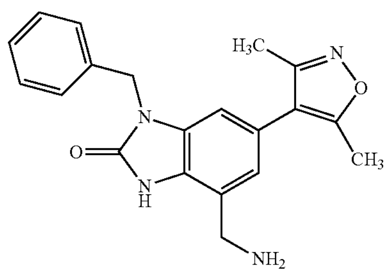 [SMILES: Cc1noc(C)c1-c1cc(CN)c2[nH]c(=O)n(Cc3ccccc3)c2c1] | J | $^1$H NMR (500 MHz, CD$_3$OD) δ 7.37-7.23 (m, 5H), 6.99 (d, J = 1.4 Hz, 1H), 6.77 (d, J = 1.4 Hz, 1H), 5.10 (s, 2H), 3.93 (s, 2H), 2.27 (s, 3H), 2.10 (s, 3H); ESI m/z 349 [M + H]$^+$. | 93.9 |
| 23 | 5-(3,5-dimethylisoxazol-4-yl)-N-phenyl-1H-pyrrolo[3,2-b]pyridin-3-amine | 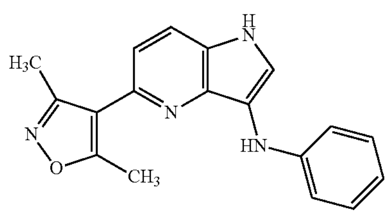 [SMILES: Cc1noc(C)c1-c1ccc2[nH]cc(Nc3ccccc3)c2n1] | M | $^1$H NMR (300 MHz, DMSO-d$_6$) δ 11.1 (d, J = 1.8 Hz, 1H), 7.82 (d, J = 8.4 Hz, 1H), 7.61 (d, J = 2.7 Hz, 1H), 7.43 (s, 1H), 7.25 (d, J = 8.4 Hz, 1H), 7.09 (d, J = 8.4 Hz, 1H), 7.07 (d, J = 7.2 Hz, 1H), 6.85 (d, J = 7.5 Hz, 2H), 6.60 (t, J = 7.2 Hz, 1H), 2.48 (s, 3H), 2.29 (s, 3H); ESI MS m/z 305 [M + H]$^+$. | >99 |
| 24 | 6-(3,5-dimethylisoxazol-4-yl)-1-(4-fluorobenzyl)-3-methyl-1H-pyrazolo[4,3-b]pyridine 4-oxide | 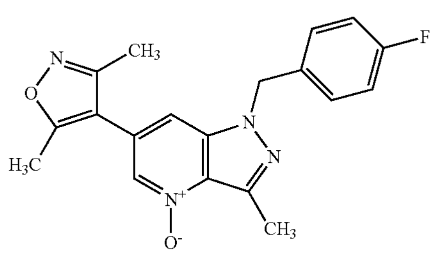 [SMILES: Cc1noc(C)c1-c1cc2c(c(C)nn2Cc2ccc(F)cc2)[n+]([O-])c1] | N | $^1$H NMR (300 MHz, DMSO-d$_6$) δ 8.21 (d, J = 0.9 Hz, 1H), 7.83 (d, J = 0.9 Hz, 1H), 7.40-7.35 (m, 2H), 7.20-7.14 (m, 2H), 5.59 (s, 2H), 2.69 (s, 3H), 2.45 (s, 3H), 2.27 (s, 3H); ESI MS m/z 353 [M + H]$^+$. | >99 |
| 25 | 6-(3,5-dimethylisoxazol-4-yl)-1-(4-fluorobenzyl)-3-methyl-1H-pyrazolo[4,3-b]pyridin-5(4H)-one | 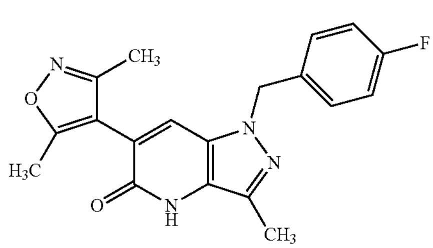 [SMILES: Cc1noc(C)c1-c1cc2c([nH]c1=O)c(C)nn2Cc1ccc(F)cc1] | N | $^1$H NMR (300 MHz, DMSO-d$_6$) δ 12.0 (s, 1H), 8.07 (s, 1H), 7.36-7.31 (m, 2H), 7.19-7.13 (m, 2H), 5.45 (s, 2H), 2.30 (s, 6H), 2.14 (s, 3H); ESI MS m/z 353 [M + H]$^+$. | 96.2 |

TABLE 2-continued

Example Compounds

| Example Compound | Chemical Name | Structure | General procedure | Characterization | Purity HPLC (%) |
|---|---|---|---|---|---|
| 26 | 4-(3-benzyl-3H-imidazo[4,5-b]pyridin-5-yl)-3,5-dimethyl-isoxazole | 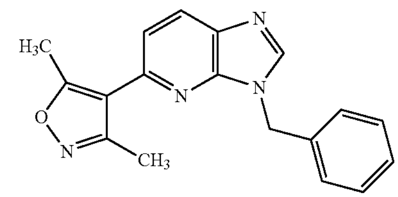 [SMILES: Cc1noc(C)c1-c1ccc2ncn(Cc3ccccc3)c2n1] | No general procedure | $^1$H-NMR (300 MHz, DMSO-$d_6$) δ 8.67 (s, 1H), 8.17 (d, J = 8.1 Hz, 1H), 7.44 (d, J = 8.1 Hz, 1H), 7.36-7.27 (m, 5H), 5.52 (s, 2H), 2.54 (s, 3H), 2.34 (s, 3H); ESI m/z 305 [M + H]$^+$. | 98 |
| 27 | 6-(3,5-dimethylisoxazol-4-yl)-1-(4-fluorobenzyl)-1H-benzo[d]imidazol-4-amine | 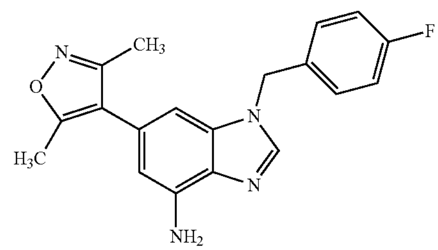 [SMILES: Cc1noc(C)c1-c1cc(N)c2ncn(Cc3ccc(F)cc3)c2c1] | C | $^1$H NMR (300 MHz, DMSO-$d_6$) δ 8.23 (s, 1H), 7.42 (dd, J = 8.0, 6.0 Hz, 2H), 7.17 (dd, J = 9.0, 9.0 Hz, 2H), 6.62 (s, 1H), 6.32 (s, 1H), 5.40 (s, 4H), 2.33 (s, 3H), 2.16 (s, 3H); ESI m/z 337 [M + H]$^+$. | >99 |
| 28 | 6-(3,5-dimethylisoxazol-4-yl)-1-(4-fluorobenzyl)-N-methyl-1H-benzo[d]imidazol-4-amine | 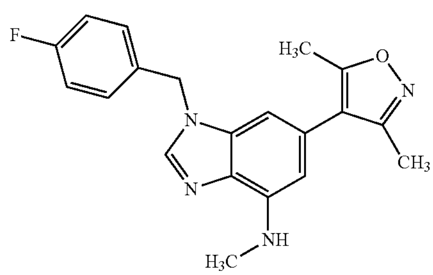 [SMILES: CNc1cc(-c2c(C)noc2C)cc2c1ncn2Cc1ccc(F)cc1] | No general procedure | $^1$H NMR (500 MHz, DMSO-$d_6$) δ 8.22 (s, 1H), 7.43 (dd, J = 8.8, 5.5 Hz, 2H), 7.16 (dd, J = 8.8, 5.5 Hz, 2H), 6.65 (d, J = 1.0 Hz, 1H), 6.09 (d, J = 1.0 Hz, 1H), 5.85 (q, J = 5.0 Hz, 1H), 5.41 (s, 2H), 2.83 (d, J = 5.5 Hz, 3H), 2.35 (s, 3H), 2.17 (s, 3H); ESI m/z 351 [M + H]$^+$ | >99 |
| 29 | 6-(3,5-dimethylisoxazol-4-yl)-1-(4-fluorobenzyl)-N,N-dimethyl-1H-benzo[d]imidazol-4-amine | 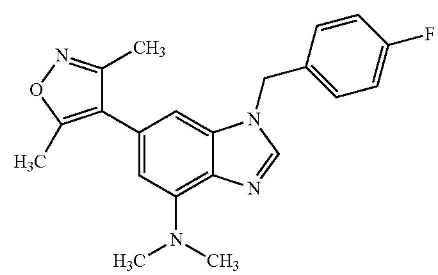 [SMILES: Cc1noc(C)c1-c1cc(N(C)C)c2ncn(Cc3ccc(F)cc3)c2c1] | No general procedure | $^1$H NMR (500 MHz, DMSO-$d_6$) δ 8.28 (s, 1H), 7.41 (dd, J = 8.5, 5.5 Hz, 2H), 7.17 (dd, J = 9.0, 9.0 Hz, 2H), 6.85 (d, J = 1.0 Hz, 1H), 6.25 (d, J = 1.0 Hz, 1H), 5.43 (s, 2H), 3.18 (s, 6H), 2.35 (s, 3H), 2.18 (s, 3H); ESI m/z 365 [M + H]$^+$. | 98.1 |
| 30 | 3,5-dimethyl-4-(1-(1-phenylethyl)-1H-imidazo[4,5-b]pyridin-6-yl)isoxazole | 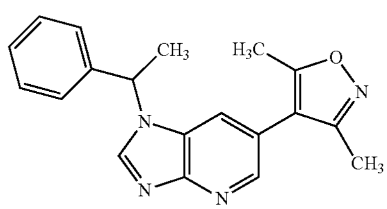 [SMILES: Cc1noc(C)c1-c1cnc2ncn(C(C)c3ccccc3)c2c1] | No general procedure | $^1$H NMR (500 MHz, CD$_3$OD) δ 8.76 (s, 1H), 8.36 (d, J = 2.0 Hz, 1H), 7.65 (d, J = 2.5 Hz, 1H), 7.40-7.30 (m, 5H), 4.44 (q, J = 7.0 Hz, 1H), 2.29 (s, 3H), 2.10 (s, 3H), 2.06 (d, J = 7.0 Hz, 3H). ESI m/z 319 [M + H]$^+$. | 98.6 |
| 31 | 4-(1-benzyl-1H-imidazo[4,5-c]pyridin-6-yl)-3,5-dimethyl-isoxazole | 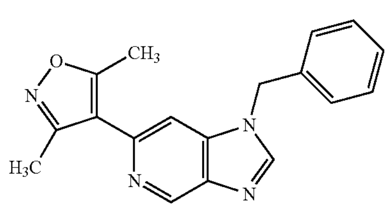 [SMILES: Cc1noc(C)c1-c1cc2c(cn1)ncn2Cc1ccccc1] | No general procedure | $^1$H NMR (500 MHz, CD$_3$OD) δ 9.00 (d, J = 1.0 Hz, 1H), 8.05 (s, 1H), 7.48 (d, J = 1.0 Hz, 1H), 7.40-7.30 (m, 5H), 5.58 (s, 2H), 2.40 (s, 3H), 2.25 (s, 3H); ESI m/z 305 [M + H]$^+$. | 98.6 |

TABLE 2-continued

Example Compounds

| Example Compound | Chemical Name | Structure | General procedure | Characterization | Purity HPLC (%) |
|---|---|---|---|---|---|
| 32 | 1-benzyl-6-(3,5-dimethylisoxazol-4-yl)-1H-imidazo[4,5-c]pyridine 5-oxide | 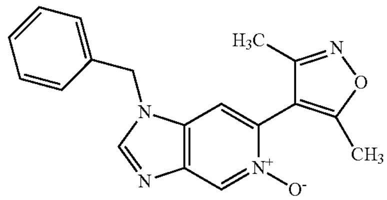 [SMILES: Cc1noc(C)c1-c1cc2c(c[n+]1[O-])ncn2Cc1ccccc1] | No general Procedure | $^1$H NMR (500 MHz, CD$_3$OD) δ 8.92 (s, 1H), 8.61 (s, 1H), 7.67 (s, 1H), 7.45-7.25 (m, 5H), 6.57 (s, 2H), 2.28 (s, 3H), 2.17 (s, 3H); ESI m/z 321 [M + H]$^+$. | 98.7 |
| 33 | 1-benzyl-6-(3,5-dimethylisoxazol-4-yl)-1H-imidazo[4,5-c]pyridin-4-amine | 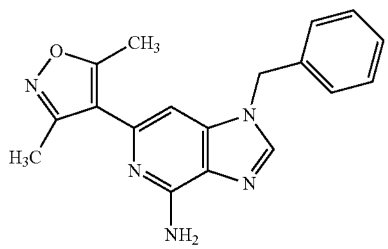 [SMILES: Cc1noc(C)c1-c1cc2c(ncn2Cc2ccccc2)c(N)n1] | No general procedure | $^1$H NMR (500 MHz, CD$_3$OD) δ 8.21 (s, 1H), 7.42-7.25 (m, 5H), 6.70 (s, 1H), 5.46 (s, 2H), 2.39 (s, 3H), 2.24 (s, 3H); ESI m/z 320 [M + H]$^+$. | 96.9 |
| 34 | 4-(1-benzyl-3-bromo-1H-pyrrolo[3,2-b]pyridin-6-yl)-3,5-dimethylisoxazole | 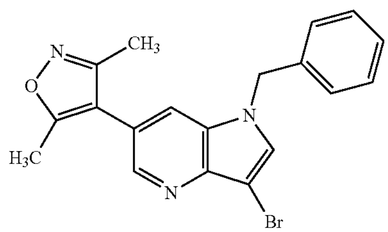 [SMILES: Cc1noc(C)c1-c1cnc2c(Br)cn(Cc3ccccc3)c2c1] | No general procedure | $^1$H NMR (500 MHz, CD$_3$OD) δ 8.33 (d, J = 1.5 Hz, 1H), 7.86 (s, 1H), 7.80 (d, J = 2.0 Hz, 1H), 7.34-7.24 (m, 5H), 5.48 (s, 2H), 2.35 (s, 3H), 2.17 (s, 3H); ESI MS m/z 382 [M + H]$^+$. | >99 |
| 35 | 1-benzyl-6-(3,5-dimethylisoxazol-4-yl)-1H-pyrrolo[3,2-b]pyridine-3-carbaldehyde | 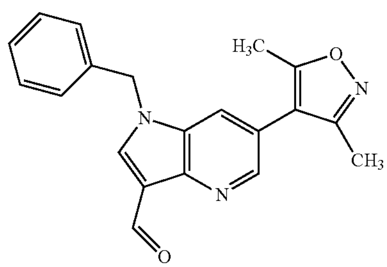 [SMILES: Cc1noc(C)c1-c1cnc2c(C=O)cn(Cc3ccccc3)c2c1] | No general procedure | $^1$H NMR (300 MHz, DMSO-d$_6$) δ 10.2 (s, 1H), 8.73 (s, 1H), 8.53 (d, J = 1.8 Hz, 1H), 8.11 (d, J = 1.8 Hz, 1H), 7.44-7.30 (m, 5H), 5.59 (s, 2H), 2.40 (s, 3H), 2.21 (s, 3H); ESI MS m/z 332 [M + H]$^+$ | >99 |
| 36 | 1-(1-benzyl-6-(3,5-dimethylisoxazol-4-yl)-1H-pyrrolo[3,2-b]pyridin-3-yl)ethanone | 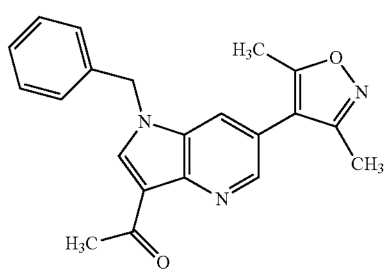 [SMILES: CC(=O)c1cn(Cc2ccccc2)c2cc(-c3c(C)noc3C)cnc12] | No general procedure | $^1$H NMR (300 MHz, CDCl$_3$) δ 8.59 (d, J = 1.5 Hz, 1H), 8.22 (s, 1H), 7.45 (d, J = 1.8 Hz, 1H), 7.40-7.36 (m, 3H), 7.21-7.18 (m, 2H), 5.40 (s, 2H), 2.89 (s, 3H), 2.34 (s, 3H), 2.17 (s, 3H); ESI MS m/z 346 [M + H]$^+$. | >99 |
| 37 | 1-benzyl-6-(3,5-dimethylisoxazol-4-yl)-1H-pyrrolo[3,2-b]pyridin-5-yl formate | 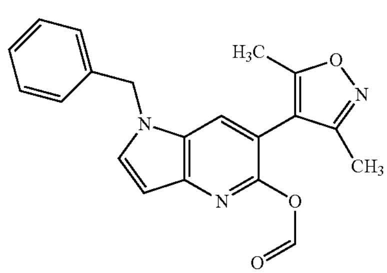 [SMILES: Cc1noc(C)c1-c1cc2c(ccn2Cc2ccccc2)nc1OC=O] | No general procedure | $^1$H NMR (300 MHz, CDCl$_3$) δ 9.90 (s, 1H), 7.62 (s, 1H), 7.43-7.41 (m, 3H), 7.28 (s, 1H), 7.22-7.18 (m, 3H), 5.31 (s, 2H), 2.22 (s, 3H), 2.10 (s, 3H); ESI MS m/z 348 [M + H]$^+$. | >99 |

TABLE 2-continued

Example Compounds

| Example Compound | Chemical Name | Structure | General procedure | Characterization | Purity HPLC (%) |
|---|---|---|---|---|---|
| 38 | 4-((6-(3,5-dimethylisoxazol-4-yl)-2-methyl-1H-imidazo[4,5-b]pyridin-1-yl)methyl)benzamide | 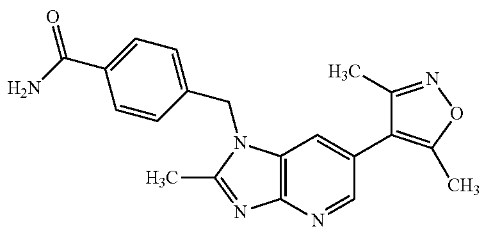 [SMILES: Cc1noc(C)c1-c1cnc2nc(C)n(Cc3ccc(C(N)=O)cc3)c2c1] | No general procedure | $^1$H NMR (300 MHz, DMSO-d$_6$) δ 8.35 (d, J = 1.8 Hz, 1H), 7.99 (d, J = 2.1 Hz, 1H), 7.94 (br.s, 1H), 7.83 (d, J = 8.4 Hz, 2H), 7.37 (br.s, 1H), 7.27 (d, J = 8.4 Hz, 2H), 5.61 (s, 2H), 2.60 (s, 3H), 2.39 (s, 3H), 2.21 (s, 3H); ESI m/z 362 [M + H]$^+$. | >99 |
| 39 | 4-(1-benzyl-3-nitro-1H-pyrrolo[3,2-b]pyridin-6-yl)-3,5-dimethylisoxazole | 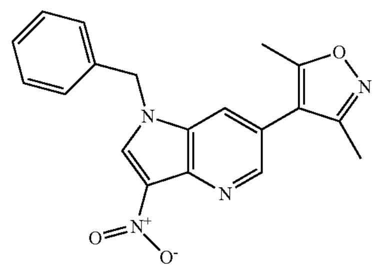 [SMILES: Cc1noc(C)c1-c1cnc2c([N+](=O)[O-])cn(Cc3ccccc3)c2c1] | No general procedure | $^1$H NMR (300 MHz, CDCl$_3$) δ 8.74 (s, 1H), 8.47 (s, 1H), 7.56 (s, 1H), 7.45-7.42 (m, 3H), 7.27-7.26 (m, 2H), 5.47 (s, 2H), 2.35 (s, 3H), 2.17 (s, 3H); ESI MS m/z 349 [M + H]$^+$. | >99 |
| 40 | 3,5-dimethyl-4-(3-(4-(trifluoromethyl)benzyl)-3H-imidazo[4,5-b]pyridin-6-yl)isoxazole | 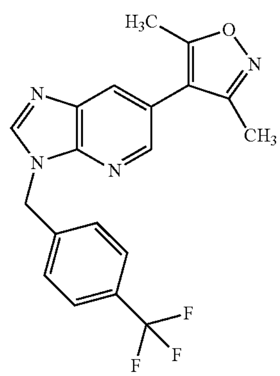 [SMILES: Cc1noc(C)c1-c1cnc2c(c1)ncn2Cc1ccc(C(F)(F)F)cc1] | B | $^1$H NMR (300 MHz, CDCl$_3$) δ 8.33 (d, J = 2.1 Hz, 1H), 8.15 (s, 1H), 8.00 (d, J = 2.1 Hz, 1H), 7.64 (d, J = 8.1 Hz, 2H), 7.45 (d, J = 8.1 Hz, 2H), 5.58 (s, 2H), 2.44 (s, 3H), 2.30 (s, 3H); MM m/z 373 [M + H]$^+$ | 98.3 |
| 41 | 3,5-dimethyl-4-(1-(4-(trifluoromethyl)benzyl)-1H-imidazo[4,5-b]pyridin-6-yl)isoxazole | 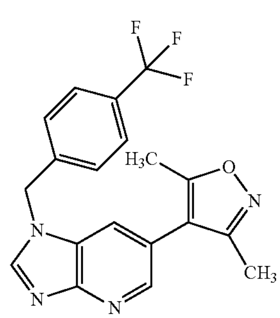 [SMILES: Cc1noc(C)c1-c1cnc2ncn(Cc3ccc(C(F)(F)F)cc3)c2c1] | B | $^1$H NMR (300 MHz, CDCl$_3$) δ 8.49 (d, J = 2.1 Hz, 1H), 8.29 (s, 1H), 7.66 (d, J = 8.1 Hz, 2H), 7.34-7.30 (m, 3H), 5.50 (s, 2H), 2.33 (s, 3H), 2.16 (s, 3H); MM m/z 373 [M + H]$^+$ | 98.9 |

TABLE 2-continued

Example Compounds

| Example Compound | Chemical Name | Structure | General procedure | Characterization | Purity HPLC (%) |
|---|---|---|---|---|---|
| 42 | 4-(3-(4-chlorobenzyl)-3H-imidazo[4,5-b]pyridin-6-yl)-3,5-dimethylisoxazole | 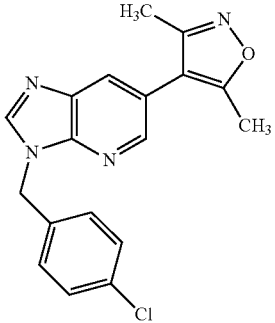 [SMILES: Cc1noc(C)c1-c1cnc2c(c1)ncn2Cc1ccc(Cl)cc1] | B | $^1$H NMR (300 MHz, CDCl$_3$) δ 8.32 (d, J = 2.1 Hz, 1H), 8.11 (s, 1H), 7.98 (d, J = 2.|1 Hz, 1H), 7.37-7.27 (m, 4H), 5.48 (s, 2H), 2.44 (s, 3H), 2.29 (s, 3H); MM m/z 339 [M + H]$^+$. | >99 |
| 43 | 4-(1-(4-chlorobenzyl)-1H-imidazo[4,5-b]pyridin-6-yl)-3,5-dimethylisoxazole | 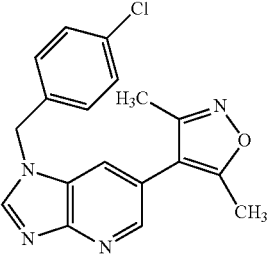 [SMILES: Cc1noc(C)c1-c1cnc2ncn(Cc3ccc(Cl)cc3)c2c1] | B | $^1$H NMR (300 MHz, CDCl$_3$) δ 8.47 (d, J = 2.1 Hz, 1H), 8.25 (s, 1H), 7.37 (d, J = 8.7 Hz, 2H), 7.32 (d, J = 2.1 Hz, 1H), 7.16 (d, J = 8.7 Hz, 2H), 5.39 (s, 2H), 2.35 (s, 3H), 2.18 (s, 3H); MM m/z 339 [M + H]$^+$ | >99 |
| 44 | 4-(3-(4-fluorobenzyl)-3H-imidazo[4,5-b]pyridin-6-yl)-3,5-dimethylisoxazole | 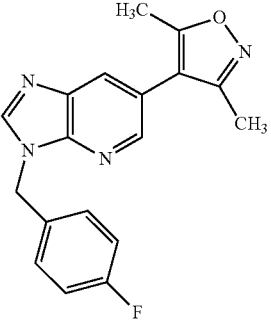 [SMILES: Cc1noc(C)c1-c1cnc2c(c1)ncn2Cc1ccc(F)cc1] | B | $^1$H NMR (300 MHz, CDCl$_3$) δ 8.33 (d, J = 2.1 Hz, 1H), 8.10 (s, 1H), 7.98 (d, J = 2.1 Hz, 1H), 7.38-7.33 (m, 2H), 7.09-7.03 (m, 2H), 5.48 (s, 2H), 2.44 (s, 3H), 2.30 (s, 3H); MM m/z 323 [M + H]+ | >99 |
| 45 | 4-(1-(4-fluorobenzyl)-1H-imidazo[4,5-b]pyridin-6-yl)-3,5-dimethylisoxazole | 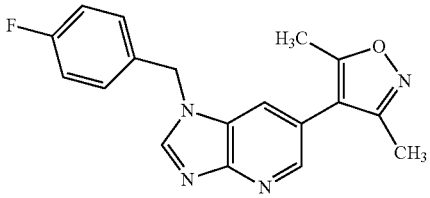 [SMILES: Cc1noc(C)c1-c1cnc2ncn(Cc3ccc(F)cc3)c2c1] | B | $^1$H NMR (300 MHz, CDCl$_3$) δ 8.47 (d, J = 2.1 Hz, 1H), 8.25 (s, 1H), 7.34 (d, J = 2.1 Hz, 1H), 7.24-7.19 (m, 2H), 7.09 (t, J = 8.7 Hz, 2H), 5.38 (s, 2H), 2.35 (s, 3H), 2.18 (s, 3H); MM m/z 323 [M + H]$^+$ | 98.4 |
| 46 | 3,5-dimethyl-4-(3-(pyridin-2-ylmethyl)-3H-imidazo[4,5-b]pyridin-6-yl)isoxazole | 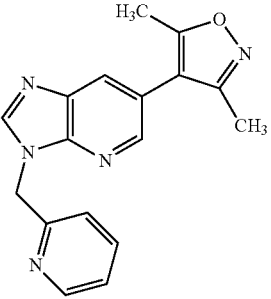 [SMILES: Cc1noc(C)c1-c1cnc2c(c1)ncn2Cc1ccccn1] | B | $^1$H NMR (300 MHz, CDCl$_3$) δ 8.62-8.59 (m, 1H), 8.33 (s, 1H), 8.31 (d, J = 2.1 Hz, 1H), 7.98 (d, J = 2.1 Hz, 1H), 7.71-7.65 (m, 1H), 7.33-7.23 (m, 2H), 5.63 (s, 2H), 2.43 (s, 3H), 2.29 (s, 3H); MM m/z 306 [M + H]$^+$ | 95.5 |

TABLE 2-continued

Example Compounds

| Example Compound | Chemical Name | Structure | General procedure | Characterization | Purity HPLC (%) |
|---|---|---|---|---|---|
| 47 | 3,5-dimethyl-4-(1-(pyridin-2-ylmethyl)-1H-imidazo[4,5-b]pyridin-6-yl)isoxazole | 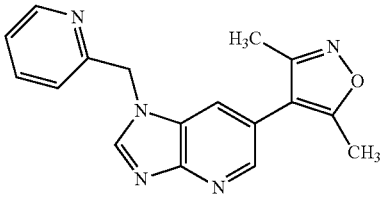 [SMILES: Cc1noc(C)c1-c1cnc2ncn(Cc3ccccn3)c2c1] | B | ¹H NMR (300 MHz, CDCl₃) δ 8.62-8.59 (m, 1H), 8.46 (d, J = 2.1 Hz, 1H), 8.34 (s, 1H), 7.72-7.66 (m, 1H), 7.59 (d, J = 2.1 Hz, 1H), 7.31-7.27 (m, 1H), 7.13 (d, J = 7.8 Hz, 1H), 5.51 (s, 2H), 2.38 (s, 3H), 2.22 (s, 3H); MM m/z 306 [M + H]⁺ | 98.3 |
| 48 | 4-(1-(4-fluorobenzyl)-1H-pyrrolo[3,2-b]pyridin-6-yl)-3,5-dimethylisoxazole | 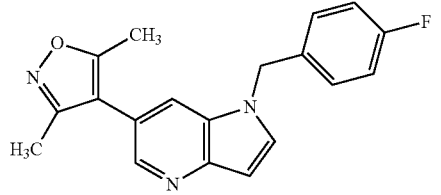 | A: using 6-bromo-1H-pyrrolo[3,2-b]pyridine as starting material | ¹H NMR (300 MHz, CD₃OD) δ 8.26 (d, J = 1.8 Hz, 1H), 7.78 (dd, J = 0.9, 1.8 Hz, 1H), 7.75 (d, J = 3.3 Hz, 1H), 7.29-7.24 (m, 2H), 7.08-7.02 (m, 2H), 6.70 (dd, J = 0.6, 3.3 Hz, 1H), 5.47 (s, 2H), 2.36 (s, 3H), 2.19 (s, 3H); ESI MS m/z 322 [M + H]⁺. | 97.6 |
| 49 | 4-(1-(4-fluorobenzyl)-1H-pyrrolo[2,3-b]pyridin-6-yl)-3,5-dimethylisoxazole | 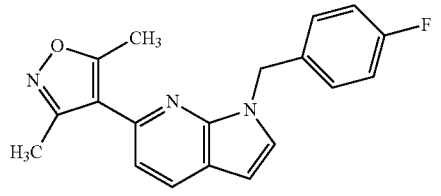 [SMILES: Cc1noc(C)c1-c1ccc2ccn(Cc3ccc(F)cc3)c2n1] | A: using 6-bromo-1H-pyrrolo[2,3-b]pyridine as starting material | ¹H NMR (300 MHz, CD₃OD) δ 8.04 (d, J = 8.1 Hz, 1H), 7.46 (d, J = 3.6 Hz, 1H), 7.26-7.21 (m, 3H), 7.04-6.98 (m, 2H), 6.55 (d, J = 3.6 Hz, 1H), 5.50 (s, 2H), 2.53 (s, 3H), 2.37 (s, 3H); ESI MS m/z 322 [M + H]⁺. | >99 |
| 50 | 4-(5-(4-fluorobenzyl)-5H-pyrrolo[2,3-b]pyrazin-3-yl)-3,5-dimethylisoxazole | 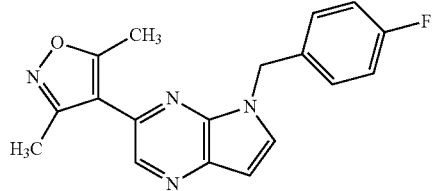 [SMILES: Cc1noc(C)c1-c1cnc2ccn(Cc3ccc(F)cc3)c2n1] | A: using 3-bromo-5H-pyrrolo[2,3-b]pyrazine as starting material | ¹H NMR (300 MHz, CD₃OD) δ 8.54 (s, 1H), 7.91 (d, J = 3.6 Hz, 1H), 7.35-7.30 (m, 2H), 7.08-7.02 (m, 2H), 6.72 (d, J = 3.6 Hz, 1H), 5.52 (s, 2H), 2.60 (s, 3H), 2.42 (s, 3H); ESI MS m/z 323 [M + H]⁺. | >99 |
| 51 | 4-(1-(4-fluorobenzyl)-1H-pyrazolo[4,3-b]pyridin-6-yl)-3,5-dimethylisoxazole | 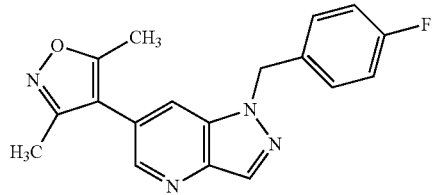 [SMILES: Cc1noc(C)c1-c1cnc2cnn(Cc3ccc(F)cc3)c2c1] | A: using 6-bromo-1H-pyrazolo[4,3-b]pyridine as starting material | ¹H NMR (300 MHz, CD₃OD) δ 8.50 (d, J = 1.8 Hz, 1H), 8.28 (d, J = 0.9 Hz, 1H), 8.05 (dd, J = 1.8, 1.2 Hz, 1H), 7.36-7.31 (m, 2H), 7.08-7.02 (m, 2H), 5.70 (s, 2H), 2.42 (s, 3H), 2.25 (s, 3H); ESI MS m/z 323 [M + H]⁺. | 98.5 |

TABLE 2-continued

Example Compounds

| Example Compound | Chemical Name | Structure | General procedure | Characterization | Purity HPLC (%) |
|---|---|---|---|---|---|
| 52 | 6-(3,5-dimethylisoxazol-4-yl)-1-(4-fluorobenzyl)-1H-pyrrolo[2,3-b]pyridin-4-amine | 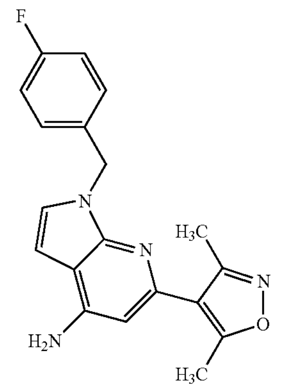 [SMILES: Cc1noc(C)c1-c1cc(N)c2ccn(Cc3ccc(F)cc3)c2n1] | A: using 6-bromo-1H-pyrrolo[2,3-b]pyridin-4-amine as starting material | $^1$H NMR (300 MHz, DMSO-$d_6$) d 7.29-7.24 (m, 3H), 7.15-7.09 (m, 2H), 6.55 (d, J = 3.6 Hz, 1H), 6.35 (s, 1H), 6.33 (s, 2H), 5.33 (s, 2H), 2.49 (s, 3H), 2.32 (s, 3H); ESI MS m/z 337 [M + H]$^+$. | >99 |
| 53 | 4-(1-(4-fluorobenzyl)-3-methyl-1H-pyrazolo[4,3-b]pyridin-6-yl)-3,5-dimethylisoxazole | 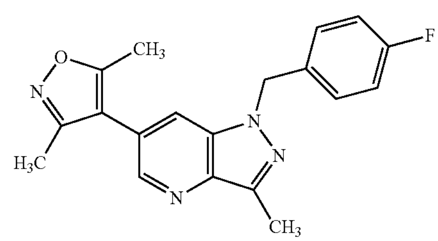 [SMILES: Cc1noc(C)c1-c1cnc2c(C)nn(Cc3ccc(F)cc3)c2c1] | A: using 6-bromo-3-methyl-1H-pyrazolo[4,3-b]pyridine as starting material | $^1$H NMR (300 MHz, CD$_3$OD) δ 8.45 (d, J = 1.8 Hz, 1H), 7.98 (d, J = 1.8 Hz, 1H), 7.34-7.29 (m, 2H), 7.08-7.02 (m, 2H), 5.61 (s, 2H), 2.65 (s, 3H), 2.42 (s, 3H), 2.25 (s, 3H); ESI MS m/z 337 [M + H]$^+$. | 96.7 |
| 54 | 1-benzyl-6-(3,5-dimethylisoxazol-4-yl)-1H-indazol-4-amine | 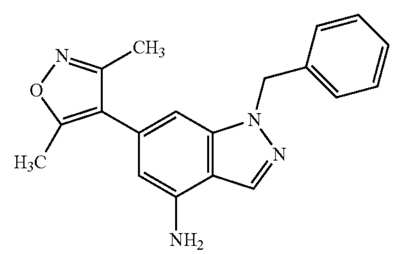 [SMILES: Cc1noc(C)c1-c1cc(N)c2cnn(Cc3ccccc3)c2c1] | B: using 6-bromo-1H-indazol-4-amine as starting material | $^1$H NMR (300 MHz, DMSO-$d_6$) δ 8.13 (d, J = 0.6 Hz, 1H), 7.32-7.23 (m, 5H), 6.70 (s, 1H), 6.11 (d, J = 1.2 Hz, 1H), 5.97 (s, 2H), 5.53 (s, 2H), 2.37 (s, 3H), 2.19 (s, 3H); ESI MS m/z 319 [M + H]$^+$. | >99 |
| 55 | 1-benzyl-6-(3,5-dimethylisoxazol-4-yl)-2-methyl-1H-benzo[d]imidazol-4-amine | 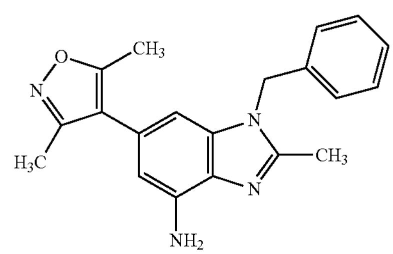 [SMILES: Cc1noc(C)c1-c1cc(N)c2nc(C)n(Cc3ccccc3)c2c1] | K | $^1$H NMR (500 MHz, CDCl$_3$) δ 7.34-7.28 (m, 3H), 7.09-7.08 (m, 2H), 6.42 (d, J = 1.5 Hz, 1H), 6.36 (d, J = 1.5 Hz, 1H), 5.28 (s, 2H), 4.42 (br.s, 2H), 2.60 (s, 3H), 2.31 (s, 3H), 2.17 (s, 3H); ESI m/z 333 [M + H]$^+$. | 99 |
| 56 | 1-benzyl-6-(3,5-dimethylisoxazol-4-yl)-1H-pyrrolo[3,2-b]pyridin-5(4H)-one | 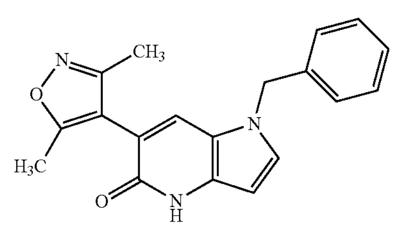 [SMILES: Cc1noc(C)c1-c1cc2c(ccn2Cc2ccccc2)[nH]c1=O] | N | $^1$H NMR (500 MHz, DMSO-$d_6$) δ 8.15 (d, J = 1.5 Hz, 1H), 7.83 (d, J = 3.5 Hz, 1H), 7.64 (s, 1H), 7.34-7.32 (m, 5H), 6.75 (d, J = 2.5 Hz, 1H), 5.50 (s, 2H), 2.39 (s, 3H), 2.20 (s, 3H); ESI MS m/z 320 [M + H]$^+$. | >99 |

TABLE 2-continued

Example Compounds

| Example Compound | Chemical Name | Structure | General procedure | Characterization | Purity HPLC (%) |
|---|---|---|---|---|---|
| 57 | 3-((5-(3,5-dimethylisoxazol-4-yl)-1H-pyrrolo[3,2-b]pyridin-3-yl)amino)benzonitrile | 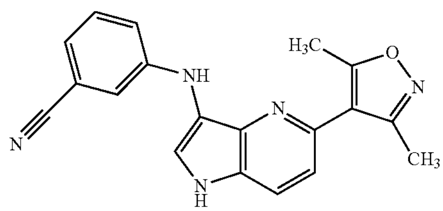 [SMILES: Cc1noc(C)c1-c1ccc2[nH]cc(Nc3cccc(C#N)c3)c2n1] | M | $^1$H NMR (300 MHz, DMSO-d$_6$) δ 11.5 (s, 1H), 7.98 (s, 2H), 7.78 (s, 1H), 7.36-7.25 (m, 2H), 7.11-7.07 (m, 1H), 7.01-6.99 (m, 2H), 2.46 (s, 3H), 2.26 (s, 3H); ESI MS m/z 330 [M + H]$^+$. | >99 |
| 58 | 4-(1-(4-fluorobenzyl)-2-methyl-1H-imidazo[4,5-b]pyridin-6-yl)-3,5-dimethylisoxazole | | D | $^1$H NMR (300 MHz, DMSO-d$_6$) δ 8.34 (d, J = 1.8 Hz, 1H), 7.99 (d, J = 2.1 Hz, 1H), 7.32-7.26 (m, 2H), 7.22-7.15 (m, 2H), 5.53 (s, 2H), 2.61 (s, 3H), 2.40 (s, 3H), 2.22 (s, 3H); ESI m/z 337 [M + H]$^+$. | 98.9 |
| 58 | 4-(1-benzyl-2-ethoxy-1H-imidazo[4,5-b]pyridin-6-yl)-3,5-dimethylisoxazole | | No general procedure | $^1$H NMR (300 MHz, DMSO-d$_6$) δ 7.75 (d, J = 1.2 Hz, 1H), 7.38-7.22 (m, 5H), 7.18 (d, J = 1.5 Hz, 1H), 4.99 (s, 2H), 4.34 (q, J = 7.2 Hz, 2H), 2.37 (s, 3H), 2.18 (s, 3H), 1.42 (t, J = 7.2 Hz, 3H); ESI m/z 349 [M + H]$^+$. | >99 |
| 60 | 4-((6-(3,5-dimethylisoxazol-4-yl)-2-methyl-1H-imidazo[4,5-b]pyridin-1-yl)methyl)-3,5-dimethylisoxazole | 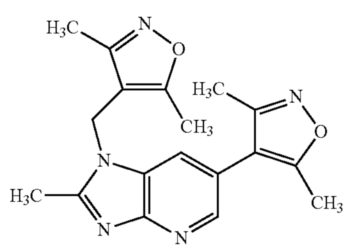 [SMILES: Cc1noc(C)c1Cn1c(C)nc2ncc(-c3c(C)noc3C)cc21] | D | $^1$H NMR (300 MHz, DMSO-d$_6$) δ 8.35 (d, J = 1.8 Hz, 1H), 7.93 (d, J = 2.1 Hz, 1H), 5.37 (s, 2H), 2.56 (s, 3H), 2.41 (s, 3H), 2.33 (s, 3H), 2.23 (s, 3H), 1.91 (s, 3H); ESI m/z 338 [M + H]$^+$. | >99 |
| 61 | 4-(1-(2,4-dichlorobenzyl)-2-methyl-1H-imidazo[4,5-b]pyridin-6-yl)-3,5-dimethylisoxazole | 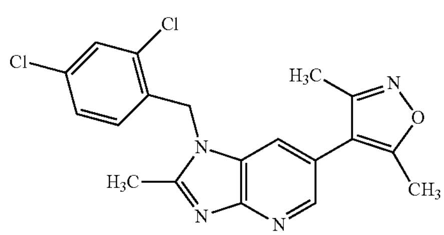 [SMILES: Cc1noc(C)c1-c1cnc2nc(C)n(Cc3ccc(Cl)cc3Cl)c2c1] | D | $^1$H NMR (300 MHz, DMSO-d$_6$) δ 8.36 (d, J = 2.1 Hz, 1H), 7.88 (d, J = 1.8 Hz, 1H), 7.74 (d, J = 2.1 Hz, 1H), 7.38 (dd, J = 8.4, 2.1 Hz, 1H), 6.77 (d, J = 8.4 Hz, 1H), 5.61 (s, 2H), 2.54 (s, 3H), 2.38 (s, 3H), 2.19 (s, 3H); ESI m/z 387 [M + H]$^+$. | >99 |
| 62 | 4-(1-(4-methoxybenzyl)-2-methyl-1H-imidazo[4,5-b]pyridin-6-yl)-3,5-dimethylisoxazole | 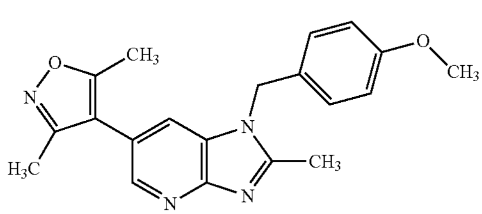 [SMILES: COc1ccc(Cn2c(C)nc3ncc(-c4c(C)noc4C)cc32)cc1] | D | $^1$H NMR (300 MHz, DMSO-d$_6$) δ 8.33 (d, J = 1.8 Hz, 1H), 7.98 (d, J = 2.1 Hz, 1H), 7.21 (d, J = 8.7 Hz, 2H), 6.90 (d, J = 8.7 Hz, 2H), 5.46 (s, 2H), 3.71 (s, 3H), 2.61 (s, 3H), 2.40 (s, 3H), 2.22 (s, 3H); ESI m/z 349 [M + H]$^+$. | >99 |

TABLE 2-continued

Example Compounds

| Example Compound | Chemical Name | Structure | General procedure | Characterization | Purity HPLC (%) |
|---|---|---|---|---|---|
| 63 | 4-(1-(cyclopropyl-methyl)-2-methyl-1H-imidazo[4,5-b]pyridin-6-yl)-3,5-dimethyl-isoxazole | 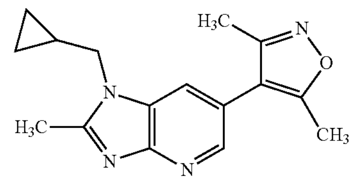 [SMILES: Cc1noc(C)c1-c1cnc2nc(C)n(CC3CC3)c2c1] | D | $^1$H NMR (300 MHz, DMSO-$d_6$) δ 8.31 (d, J = 2.1 Hz, 1H), 8.05 (d, J = 2.1 Hz, 1H), 4.17 (d, J = 7.2 Hz, 2H), 2.65 (s, 3H), 2.44 (s, 3H), 2.26 (s, 3H), 1.31-1.18 (m, 1H), 0.54-0.48 (m, 2H), 0.46-0.41 (m, 2H); ESI m/z 283 [M + H]$^+$. | 97.4 |
| 64 | N-(1-benzyl-6-(3,5-dimethylisoxazol-4-yl)-2-methyl-1H-benzo[d]imidazol-4-yl)acetamide | 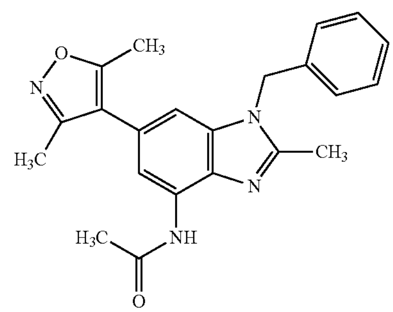 [SMILES: CC(=O)Nc1cc(-c2c(C)noc2C)cc2c1nc(C)n2Cc1ccccc1] | K | $^1$H NMR (300 MHz, CDCl$_3$) δ 8.59 (br.s, 1H), 8.20 (s, 1H), 7.38-7.31 (m, 3H), 7.09-7.06 (m, 2H), 6.76 (d, J = 1.2 Hz, 1H), 5.34 (s, 2H), 2.65 (s, 3H), 2.35 (s, 3H), 2.31 (s, 3H), 2.21 (s, 3H); ESI m/z 375 [M + H]$^+$. | 97.4 |
| 65 | N-(1-benzyl-6-(3,5-dimethylisoxazol-4-yl)-2-methyl-1H-benzo[d]imidazol-4-yl)ethane-sulfonamide | 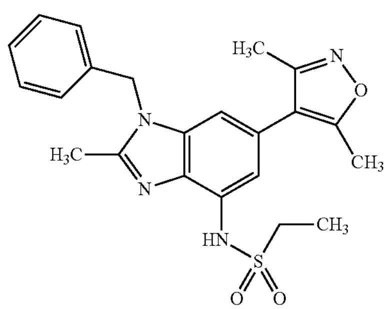 [SMILES: CCS(=O)(=O)Nc1cc(-c2c(C)noc2C)cc2c1nc(C)n2Cc1ccccc1] | K | $^1$H NMR (300 MHz, CDCl$_3$) δ 7.71 (br.s, 1H), 7.39-7.30 (m, 4H), 7.12-7.09 (m, 2H), 6.79 (d, J = 1.2 Hz, 1H), 5.33 (s, 2H), 3.21 (q, J = 7.5 Hz, 2H), 2.64 (s, 3H), 2.35 (s, 3H), 2.20 (s, 3H), 1.42 (t, J = 7.5 Hz, 3H); APCI m/z 425 [M + H]$^+$. | 95.7 |
| 66 | 4-(1-benzyl-4-methoxy-2-methyl-1H-benzo[d]imidazol-6-yl)-3,5-dimethylisoxazole | 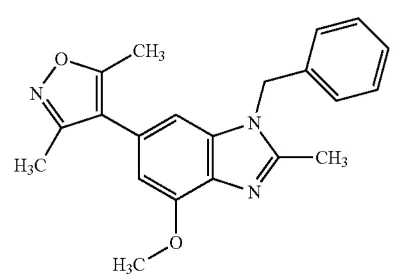 [SMILES: COc1cc(-c2c(C)noc2C)cc2c1nc(C)n2Cc1ccccc1] | No general procedure | $^1$H NMR (300 MHz, CDCl$_3$) δ 7.35-7.30 (m, 3H), 7.09-7.06 (m, 2H), 6.64 (d, J = 1.2 Hz, 1H), 6.53 (s, 1H), 5.32 (s, 2H), 4.03 (s, 3H), 2.66 (s, 3H), 2.33 (s, 3H), 2.19 (s, 3H); ESI m/z 348 [M + H]$^+$. | 93.7 |
| 67 | 7-amino-3-benzyl-5-(3,5-dimethylisoxazol-4-yl)benzo[d]oxazol-2(3H)-one | 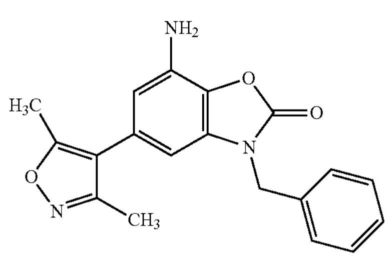 [SMILES: Cc1noc(C)c1-c1cc(N)c2oc(=O)n(Cc3ccccc3)c2c1] | G | $^1$H NMR (300 MHz, DMSO-$d_6$) δ 7.43-7.30 (m, 5H), 6.40 (d, J = 1.5 Hz, 1H), 6.39 (d, J = 1.5 Hz, 1H), 5.58 (s, 2H), 4.99 (s, 2H), 2.31 (s, 3H), 2.13 (s, 3H); ESI m/z 336 [M + H]$^+$. | 97.6 |

TABLE 2-continued

Example Compounds

| Example Compound | Chemical Name | Structure | General procedure | Characterization | Purity HPLC (%) |
|---|---|---|---|---|---|
| 68 | 3,5-dimethyl-4-(2-methyl-1-(pyridin-3-ylmethyl)-1H-imidazo[4,5-b]pyridin-6-yl)isoxazole | 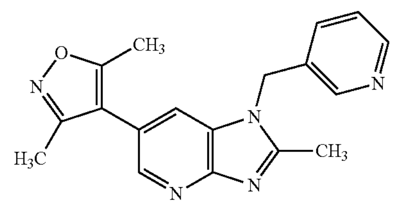 [SMILES: Cc1noc(C)c1-c1cnc2nc(C)n(Cc3cccnc3)c2c1] | D | $^1$H NMR (300 MHz, DMSO-$d_6$) δ 8.58 (d, J = 1.8 Hz, 1H), 8.51 (dd, J = 4.7, 1.8 Hz, 1H), 8.35 (d, J = 2.1 Hz, 1H), 8.03 (d, J = 2.1 Hz, 1H), 7.60 (dt, J = 8.1, 1.8 Hz, 1H), 7.37 (ddd, J = 7.8, 4.8, 0.6 Hz, 1H), 5.60 (s, 2H), 2.64 (s, 3H), 2.40 (s, 3H), 2.21 (s, 3H); ESI m/z 320 [M + H]$^+$ | 96.5 |
| 69 | 3,5-dimethyl-4-(2-methyl-1-(thiophen-2-ylmethyl)-1H-imidazo[4,5-b]pyridin-6-yl)isoxazole | 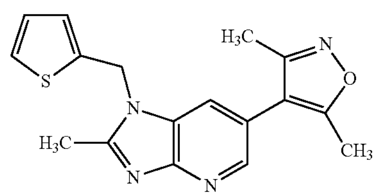 [SMILES: Cc1noc(C)c1-c1cnc2nc(C)n(Cc3cccs3)c2c1] | D | $^1$H NMR (300 MHz, DMSO-$d_6$) δ 8.34 (d, J = 2.1 Hz, 1H), 8.11 (d, J = 2.1 Hz, 1H), 7.48 (dd, J = 5.1, 1.2 Hz, 1H), 7.25 (dd, J = 3.1, 1.2 Hz, 1H), 7.00 (dd, J = 5.1, 3.3 Hz, 1H), 5.75 (s, 2H), 2.67 (s, 3H), 2.44 (s, 3H), 2.26 (s, 3H); ESI m/z 325 [M + H]$^+$. | >99 |
| 70 | 4-((6-(3,5-dimethylisoxazol-4-yl)-2-methyl-1H-imidazo[4,5-b]pyridin-1-yl)methyl)benzonitrile | 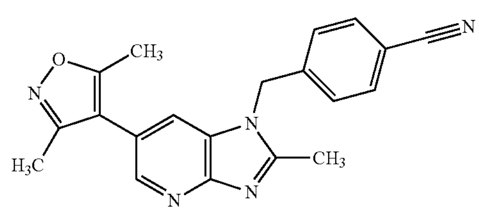 [SMILES: Cc1noc(C)c1-c1cnc2nc(C)n(Cc3ccc(C#N)cc3)c2c1] | D | $^1$H NMR (300 MHz, DMSO-$d_6$) δ 8.36 (d, J = 2.1 Hz, 1H), 7.98 (s, J = 2.1 Hz, 1H), 7.83 (d, J = 8.4 Hz, 2H), 7.36 (d, J = 8.4 Hz, 2H), 5.67 (s, 2H), 2.57 (s, 3H), 2.39 (s, 3H), 2.21 (s, 3H); ESI m/z 344 [M + H]$^+$. | 98.3 |
| 71 | 4-(1-benzyl-1H-pyrrolo[3,2-b]pyridin-6-yl)-3,5-dimethylisoxazole | 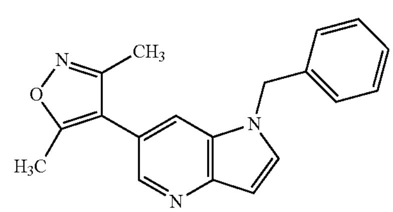 [SMILES: Cc1noc(C)c1-c1cnc2ccn(Cc3ccccc3)c2c1] | B: using 6-bromo-1H-pyrrolo[3,2-b]pyridine as starting material | $^1$H NMR (300 MHz, CDCl$_3$) δ 8.36 (d, J = 1.8 Hz, 1H), 7.54 (d, J = 2.7 Hz, 1H), 7.41 (s, 1H), 7.36-7.32 (m, 3H), 7.16-7.13 (m, 2H), 6.88 (s, 1H), 5.38 (s, 2H), 2.33 (s, 3H), 2.16 (s, 3H); ESI MS m/z 304 [M + H]$^+$. | >99 |
| 72 | 1-(1-benzyl-6-(3,5-dimethylisoxazol-4-yl)-1H-pyrrolo[3,2-b]pyridin-3-yl)-N,N-dimethyl-methanamine | 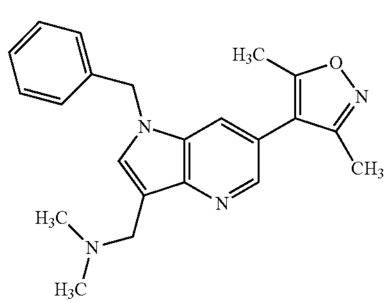 [SMILES: Cc1noc(C)c1-c1cnc2c(CN(C)C)cn(Cc3ccccc3)c2c1] | L | $^1$H NMR (300 MHz, CDCl$_3$) δ 8.34 (d, J = 1.8 Hz, 1H), 8.30 (s, 1H), 7.36-7.32 (m, 4H), 7.21-7.18 (m, 2H), 5.39 (s, 2H), 4.50 (s, 2H), 2.86 (s, 6H), 2.32 (s, 3H), 2.16 (s, 3H); ESI MS m/z 361 [M + H]$^+$. | 98.3 |

TABLE 2-continued

Example Compounds

| Example Compound | Chemical Name | Structure | General procedure | Characterization | Purity HPLC (%) |
|---|---|---|---|---|---|
| 73 | 1-benzyl-6-(3,5-dimethylisoxazol-4-yl)-1H-pyrrolo[2,3-b]pyridin-4-amine | 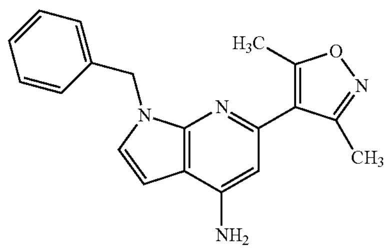 [SMILES: Cc1noc(C)c1-c1cc(N)c2ccn(Cc3ccccc3)c2n1] | B: using 6-bromo-1H-pyrrolo[2,3-b]pyridin-4-amine as starting material | $^1$H NMR (300 MHz, DMSO-$d_6$) δ 7.31-7.20 (m, 6H), 6.56 (d, J = 3.6 Hz, 1H), 6.35 (s, 1H), 6.32 (s, 2H), 5.35 (s, 2H), 2.49 (s, 3H), 2.32 (s, 3H); ESI MS m/z 319 [M + H]$^+$; | >99 |
| 74 | 3,5-dimethyl-4-(2-methyl-1-(pyridin-4-ylmethyl)-1H-imidazo[4,5-b]pyridin-6-yl)isoxazole | 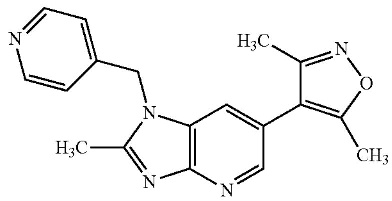 [SMILES: Cc1noc(C)c1-c1cnc2nc(C)n(Cc3ccncc3)c2c1] | D | $^1$H NMR (500 MHz, DMSO-$d_6$) δ 8.53 (dd, J = 3.0, 1.5 Hz, 2H), 8.36 (d, J = 2.0 Hz, 1H), 7.96 (d, J = 2.0 Hz, 1H), 7.12 (d, J = 6.0 Hz, 2H), 5.62 (s, 2H), 2.57 (s, 3H), 2.39 (s, 3H), 2.20 (s, 3H); ESI m/z 320 [M + H]$^+$. | 98.9 |
| 75 | 1-(cyclopropylmethyl)-6-(3,5-dimethylisoxazol-4-yl)-2-methyl-1H-benzo[d]imidazol-4-amine | 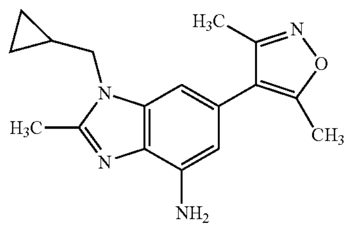 [SMILES: Cc1noc(C)c1-c1cc(N)c2nc(C)n(CC3CC3)c2c1] | F | $^1$H NMR (500 MHz, CD$_3$OD) δ 6.70 (s, 1H), 6.44 (d, J = 1.0 Hz, 1H), 4.08 (d, J = 6.5 Hz, 2H), 2.61 (s, 3H), 2.40 (s, 3H), 2.25 (s, 3H), 1.30-1.19 (m, 1H), 0.62-0.53 (m, 2H), 0.45-0.40 (m, 2H). ESI m/z 297 [M + H]$^+$. | >99 |
| 76 | 3,5-dimethyl-4-(2-methyl-1-((5-methylthiophen-2-yl)methyl)-1H-imidazo[4,5-b]pyridin-6-yl)isoxazole | 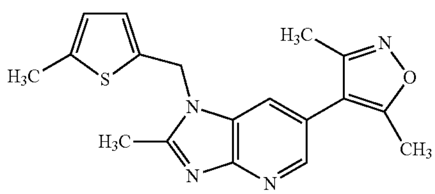 [SMILES: Cc1ccc(Cn2c(C)nc3ncc(-c4c(C)noc4C)cc32)s1] | D | $^1$H NMR (300 MHz, DMSO-$d_6$) δ 8.34 (d, J = 2.1 Hz, 1H), 8.09 (d, J = 2.1 Hz, 1H), 7.04 (d, J = 3.6 Hz, 1H), 6.66 (dd, J = 2.1, 1.2 Hz, 1H), 5.65 (s, 2H), 2.66 (s, 3H), 2.44 (s, 3H), 2.34 (d, J = 0.6 Hz, 3H), 2.27 (s, 3H); ESI m/z 339 [M + H]$^+$. | 98.1 |
| 77 | 4-(1-((5-chlorothiophen-2-yl)methyl)-2-methyl-1H-imidazo[4,5-b]pyridin-6-yl)-3,5-dimethylisoxazole | 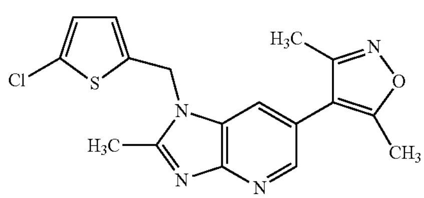 [SMILES: Cc1noc(C)c1-c1cnc2nc(C)n(Cc3ccc(Cl)s3)c2c1] | D | $^1$H NMR (300 MHz, DMSO-$d_6$) δ 8.35 (d, J = 2.1 Hz, 1H), 8.12 (d, J = 2.1 Hz, 1H), 7.13 (d, J = 3.6 Hz, 1H), 7.02 (d, J = 3.6 Hz, 1H), 5.70 (s, 2H), 2.66 (s, 3H), 2.44 (s, 3H), 2.27 (s, 3H); ESI m/z 359 [M + H]$^+$. | 96.3 |
| 78 | 5-((6-(3,5-dimethylisoxazol-4-yl)-2-methyl-1H-imidazo[4,5-b]pyridin-1-yl)methyl)thiophene-2-carbonitrile | 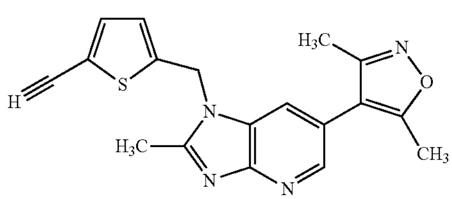 | D | $^1$H NMR (500 MHz, DMSO-$d_6$) δ 8.36 (d, J = 2.0 Hz, 1H), 8.11 (d, J = 2.0 Hz, 1H), 7.87 (d, J = 4.0 Hz, 1H), 7.31 (d, J = 4.0 Hz, 1H), 5.86 (s, 2H), 2.65 (s, 3H), 2.43 (s, 3H), 2.26 (s, 3H); ESI m/z 350 [M + H]$^+$. | >99 |

TABLE 2-continued

Example Compounds

| Example Compound | Chemical Name | Structure | General procedure | Characterization | Purity HPLC (%) |
|---|---|---|---|---|---|
| 79 | 6-(3,5-dimethylisoxazol-4-yl)-1-(4-fluorobenzyl)-1H-imidazo[4,5-b]pyridine 4-oxide | 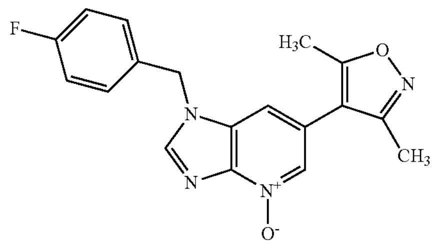 [SMILES: Cc1noc(C)c1-c1cc2c(ncn2Cc2ccc(F)cc2)[n+]([O-])c1] | N | $^1$H NMR (300 MHz, DMSO-d$_6$) δ 8.28 (s, 1H), 8.05 (s, 1H), 7.83 (s, 1H), 7.49-7.45 (m, 2H), 7.13-7.07 (m, 2H), 6.00 (s, 2H), 2.48 (s, 3H), 2.32 (s, 3H); ESI MS m/z 339 [M + H]$^+$ | >99 |
| 80 | 6-(3,5-dimethylisoxazol-4-yl)-1-(4-fluorobenzyl)-1H-imidazo[4,5-b]pyridin-5-yl acetate | 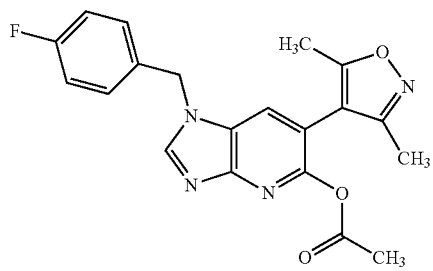 [SMILES: CC(=O)Oc1nc2ncn(Cc3ccc(F)cc3)c2cc1-c1c(C)noc1C] | N: using Example 59 as starting material | $^1$H NMR (300 MHz, CDCl$_3$) δ 8.34 (s, 1H), 8.07 (s, 1H), 7.43-7.38 (m, 2H), 7.12-7.06 (m, 2H), 5.46 (s, 2H), 2.31 (s, 3H), 2.19 (s, 3H), 2.16 (s, 3H); ESI MS m/z 381 [M + H]$^+$ | >99 |
| 81 | 1-benzyl-6-(1,4-dimethyl-1H-pyrazol-5-yl)-2-methyl-4-nitro-1H-benzo[d]imidazole | 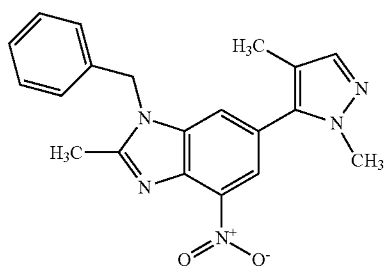 [SMILES: Cc1cnn(C)c1-c1cc([N+](=O)[O-])c2nc(C)n(Cc3ccccc3)c2c1] | F | $^1$H NMR (300 MHz, DMSO-d$_6$) δ 8.04 (d, J = 1.5 Hz, 1H), 7.95 (d, J = 1.5 Hz, 1H), 7.37-7.29 (m, 4H), 7.23-7.21 (m, 2H), 5.6 (s, 2H), 3.69 (s, 3H), 2.68 (s, 3H), 1.93 (s, 3H); ESI m/z 362 [M + H]$^+$. | 99 |
| 82 | 1-benzyl-6-(1,4-dimethyl-1H-pyrazol-5-yl)-2-methyl-1H-benzo[d]imidazol-4-amine | 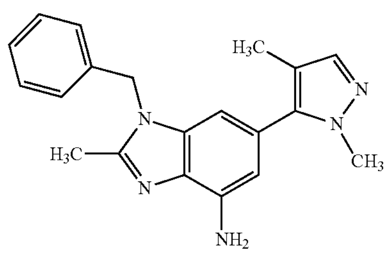 [SMILES: Cc1cnn(C)c1-c1cc(N)c2nc(C)n(Cc3ccccc3)c2c1] | F | $^1$H NMR (300 MHz, DMSO-d$_6$) δ 7.36-7.27 (m, 4H), 7.20-7.17 (m, 2H), 6.62 (d, J = 1.2 Hz, 1H), 6.30 (d, J = 1.2 Hz, 1H), 5.40 (s, 2H), 5.36 (s, 2H), 3.62 (s, 3H), 2.51 (s, 3H), 1.89 (s, 3H); ESI m/z 332 [M + H]$^+$. | 98.4 |
| 83 | 4-(1-(4-chlorobenzyl)-2-methyl-1H-imidazo[4,5-b]pyridin-6-yl)-3,5-dimethylisoxazole | 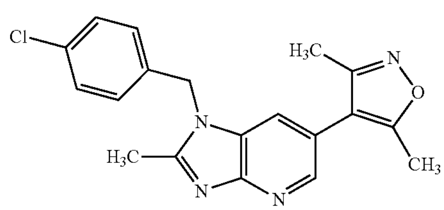 [SMILES: Cc1noc(C)c1-c1cnc2nc(C)n(Cc3ccc(Cl)cc3)c2c1] | D | $^1$H NMR (300 MHz, DMSO-d$_6$) δ 8.34 (d, J = 1.8 Hz, 1H), 7.98 (d, J = 1.8 Hz, 1H), 7.42 (d, J = 8.4 Hz, 2H), 7.24 (d, J = 8.4 Hz, 2H), 5.55 (s, 2H), 2.59 (s, 3H), 2.40 (s, 3H), 2.22 (s, 3H); ESI m/z 353 [M + H]$^+$. | >99 |
| 84 | 4-((6-(3,5-dimethylisoxazol-4-yl)-2-methyl-1H-imidazo[4,5-b]pyridin-1-yl)methyl)phenol | 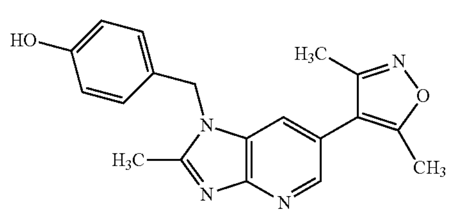 [SMILES: Cc1noc(C)c1-c1cnc2nc(C)n(Cc3ccc(O)cc3)c2c1] | D | $^1$H NMR (500 MHz, DMSO-d$_6$) δ 9.45 (s, 1H), 8.31 (d, J = 2.0 Hz, 1H), 7.95 (d, J = 2.0 Hz, 1H), 7.09 (d, J = 8.5 Hz, 2H), 6.71 (d, J = 8.5 Hz, 2H), 5.39 (s, 2H), 2.61 (s, 3H), 2.40 (s, 3H), 2.22 (s, 3H); ESI m/z 335 [M + H]$^+$. | >99 |

TABLE 2-continued

Example Compounds

| Example Compound | Chemical Name | Structure | General procedure | Characterization | Purity HPLC (%) |
|---|---|---|---|---|---|
| 85 | 1-benzyl-6-(3,5-dimethylisoxazol-4-yl)-2-methyl-1H-benzo[d]imidazole-4-carbonitrile | 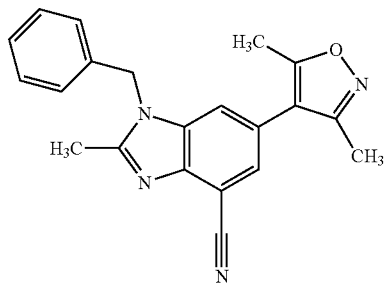 [SMILES: Cc1noc(C)c1-c1cc(C#N)c2nc(C)n(Cc3ccccc3)c2c1] | No general procedure | $^1$H NMR (500 MHz, CD$_3$OD) δ 7.63 (d, J = 1.5 Hz, 1H), 7.60 (d, J = 1.5 Hz, 1H), 7.38-7.27 (m, 3H), 7.19-7.14 (m, 2H), 5.57 (s, 2H), 2.69 (s, 3H), 2.32 (s, 3H), 2.16 (s, 3H); ESI m/z 343 [M + H]$^+$. | >99 |
| 86 | 1-benzyl-6-(3,5-dimethylisoxazol-4-yl)-2-oxo-2,3-dihydro-1H-benzo[d]imidazole-4-carbonitrile | 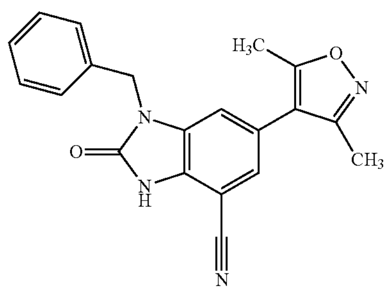 [SMILES: Cc1noc(C)c1-c1cc(C#N)c2[nH]c(=O)n(Cc3ccccc3)c2c1] | J: using 2-amino-5-bromobenzonitrile as starting material | $^1$H NMR (500 MHz, CD$_3$OD) δ 7.38-7.25 (m, 6H), 7.10 (d, J = 1.5 Hz, 1H), 5.13 (s, 2H), 2.27 (s, 3H), 2.09 (s, 3H); ESI m/z 345 [M + H]$^+$. | >99 |
| 87 | 1-benzyl-6-(3,5-dimethylisoxazol-4-yl)-2-morpholino-1H-benzo[d]imidazol-4-amine | 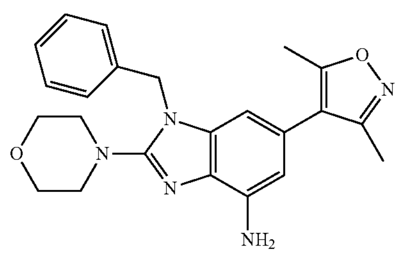 [SMILES: Cc1noc(C)c1-c1cc(N)c2nc(N3CCOCC3)n(Cc3ccccc3)c2c1] | I | $^1$H NMR (300 MHz, CDCl3) δ 7.35-7.27 (m, 3H), 7.18-7.15 (m, 2H), 6.36 (s, 1H), 6.23 (d, J = 0.9 Hz, 1H), 5.22 (s, 2H), 4.29 (br.s, 2H), 3.83 (t, J = 4.5 Hz, 4H), 3.25 (br.s, 4H), 2.27 (s, 3H), 2.13 (s, 3H); ESI m/z 404 [M + H]+. | >99 |
| 88 | 1-benzyl-6-(3,5-dimethylisoxazol-4-yl)-1H-pyrrolo[3,2-b]pyridine-3-carbonitrile | 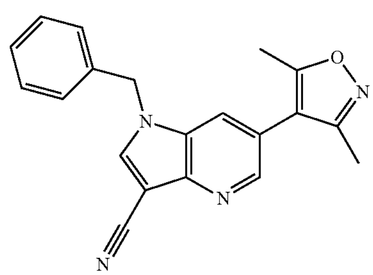 [SMILES: Cc1noc(C)c1-c1cnc2c(C#N)cn(Cc3ccccc3)c2c1] | No general procedure | $^1$H NMR (300 MHz, CDCl3) d 8.55 (s, 1H), 7.98 (s, 1H), 7.50 (s, 1H), 7.41-7.40 (m, 3H), 7.20-7.15 (m, 2H), 5.42 (s, 2H), 2.34 (s, 3H), 2.16 (s, 3H); ESI MS m/z 329 [M + H]+. | >99 |
| 89 | 4-(1-benzyl-3-chloro-1H-pyrrolo[3,2-b]pyridin-6-yl)-3,5-dimethylisoxazole | 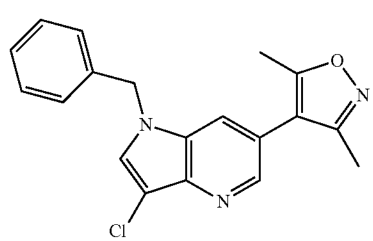 [SMILES: Cc1noc(C)c1-c1cnc2c(Cl)cn(Cc3ccccc3)c2c1] | No general procedure | $^1$H NMR (300 MHz, CDCl3) d 8.49 (s, 1H), 7.55 (s, 1H), 7.50 (s, 1H), 7.38-7.36 (m, 3H), 7.18-7.16 (m, 2H), 5.36 (s, 2H), 2.34 (s, 3H), 2.16 (s, 3H); ESI MS m/z 338 [M + H]+. | >99 |

TABLE 2-continued

Example Compounds

| Example Compound | Chemical Name | Structure | General procedure | Characterization | Purity HPLC (%) |
|---|---|---|---|---|---|
| 90 | 4-amino-1-(4-chlorobenzyl)-6-(3,5-dimethylisoxazol-4-yl)-1H-benzo[d]imidazol-2(3H)-one | 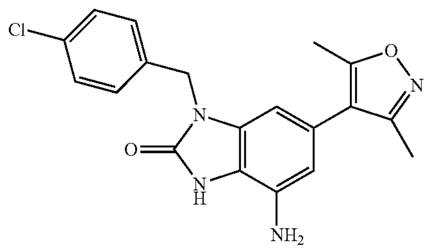 [SMILES: Cc1noc(C)c1-c1cc(N)c2[nH]c(=O)n(Cc3ccc(Cl)cc3)c2c1] | E | $^1$H NMR (500 MHz, CD$_3$OD) δ 7.36-7.28 (m, 4H), 6.40 (d, J = 1.4 Hz, 1H), 6.25 (d, J = 1.4 Hz, 1H), 5.03 (s, 2H), 2.28 (s, 3H), 2.12 (s, 3H); HPLC >99%, tR = 13.4 min; ESI m/z 369 [M + H]+. | >99 |
| 91 | 1-(4-chlorobenzyl)-6-(3,5-dimethylisoxazol-4-yl)-4-nitro-1H-benzo[d]imidazol-2(3H)-one | 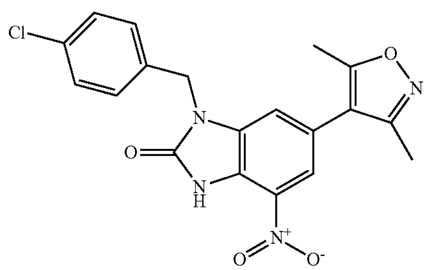 [SMILES: Cc1noc(C)c1-c1cc([N+](=O)[O-])c2[nH]c(=O)n(Cc3ccc(Cl)cc3)c2c1] | E | $^1$H NMR (500 MHz, CD3OD) δ 7.80 (d, J = 1.4 Hz, 1H), 7.40-7.35 (m, 4H), 7.24 (d, J = 1.4 Hz, 1H), 5.15 (s, 2H), 2.32 (s, 3H), 2.15 (s, 3H); HPLC 98.7%, tR = 16.5 min; ESI m/z 399 [M + H]+. | 98.7 |
| 92 | 4-(1-benzyl-1H-pyrazolo[4,3-b]pyridin-6-yl)-3,5-dimethylisoxazole | 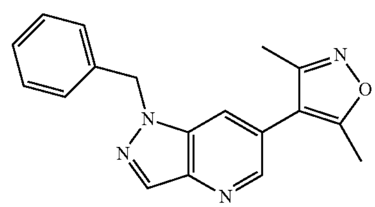 [SMILES: Cc1noc(C)c1-c1cnc2cnn(Cc3ccccc3)c2c1] | A | $^1$H NMR (500 MHz, DMSO-d6) δ 8.55 (d, J = 1.8 Hz, 1H), 8.38 (d, J = 0.9 Hz, 1H), 8.27 (dd, J = 1.8 Hz, 1.0 Hz, 1H), 7.32-7.26 (m, 5H), 5.72 (s, 2H), 2.45 (s, 3H), 2.27 (s, 3H); ESI m/z 305 [M + H]+. | 98.7 |
| 93 | 4-(1-(4-chlorobenzyl)-1H-pyrazolo[4,3-b]pyridin-6-yl)-3,5-dimethylisoxazole | 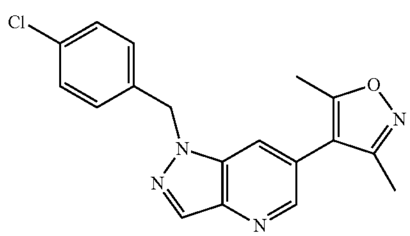 | A | $^1$H NMR (500 MHz, CDCl3) δ 8.48 (d, J = 1.0 Hz, 1H), 8.34 (s, 1H), 7.41 (s, 1H), 7.33-7.30 (m, 2H), 7.19-7.16 (m, 2H), 5.60 (s, 2H), 2.38 (s, 3H), 2.22 (s, 3H); ESI m/z 374 [M + H]+. | 98.8 |
| 94 | 1-benzyl-2-methyl-6-(1-methyl-1H-pyrazol-5-yl)-1H-benzo[d]imidazol-4-amine | 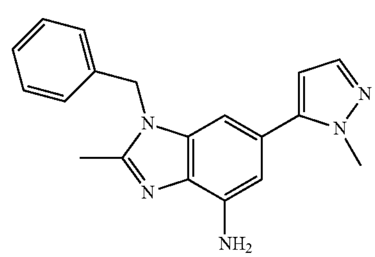 [SMILES: Cc1nc2c(N)cc(-c3ccnn3C)cc2n1Cc1ccccc1] | U | $^1$H NMR (500 MHz, DMSO-d$_6$) δ 7.39 (d, J = 1.5 Hz, 1H), 7.33 (t, J = 7.0 Hz, 2H), 7.26 (t, J = 7.0 Hz, 1H), 7.16 (d, J = 7.0 Hz, 2H), 6.76 (d, J = 1.5 Hz, 1H), 6.44 (d, J = 1.5 Hz, 1H), 6.22 (d, J = 2.0 Hz, 1H), 5.41 (s, 2H), 5.36 (s, 2H), 3.76 (s, 3H), 3.31 (s, 3H); ESI m/z 318 [M + H]+. | >99 |

TABLE 2-continued

Example Compounds

| Example Compound | Chemical Name | Structure | General procedure | Characterization | Purity HPLC (%) |
|---|---|---|---|---|---|
| 95 | 4-(1-(3,4-dichlorobenzyl)-2-methyl-1H-imidazo[4,5-b]pyridin-6-yl)-3,5-dimethylisoxazole | 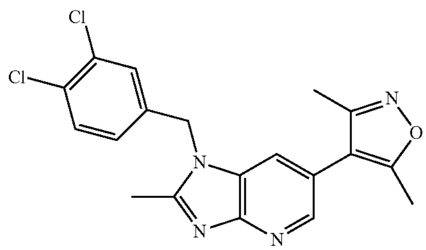 [SMILES: Cc1noc(C)c1-c1cnc2nc(C)n(Cc3ccc(Cl)c(Cl)c3)c2c1] | D | $^1$H NMR (500 MHz, DMSO-d6) δ 8.35 (d, J = 2.0 Hz, 1H), 8.00 (d, J = 2.0 Hz, 1H), 7.61-7.59 (m, 2H), 7.13 (dd, J = 8.5, 2.0 Hz, 1H), 5.56 (s, 2H), 2.61 (s, 3H), 2.40 (s, 3H), 2.22 (s, 3H); ESI m/z 387 [M + H]+. | >99 |
| 96 | 6-(3,5-dimethylisoxazol-4-yl)-2-methyl-1-(1-phenylethyl)-1H-benzo[d]imidazol-4-amine | 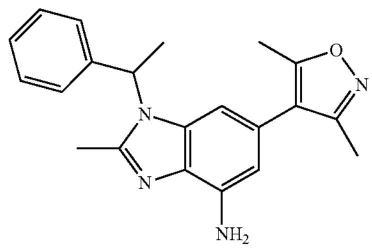 [SMILES: Cc1noc(C)c1-c1cc(N)c2nc(C)n(C(C)c3ccccc3)c2c1] | K | $^1$H NMR (300 MHz, DMSO-d$_6$) δ 7.39-7.28 (m, 5H), 6.24 (s, 1H), 6.15 (s, 1H), 5.86 (q, J = 6.9 Hz, 1H), 5.26 (s, 2H), 2.58 (s, 3H), 2.20 (s, 3H), 2.02 (s, 3H), 1.86 (d, J = 6.9 Hz, 3H); ESI m/z 347 [M + H]+. | >99 |
| 97 | 2-(azetidin-1-yl)-1-benzyl-6-(3,5-dimethylisoxazol-4-yl)-1H-benzo[d]imidazol-4-amine | 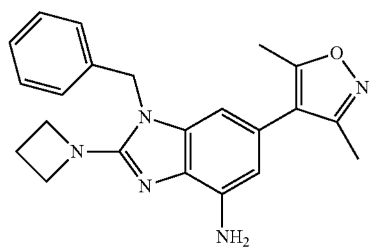 [SMILES: Cc1noc(C)c1-c1cc(N)c2nc(N3CCC3)n(Cc3ccccc3)c2c1] | I | $^1$H NMR (300 MHz, DMSO-d6) δ 7.34-7.17 (m, 5H), 6.38 (d, J = 1.5 Hz, 1H), 6.27 (d, J = 1.5 Hz, 1H), 5.16 (s, 2H), 5.02 (s, 2H), 4.08 (t, J = 7.5 Hz, 4H), 2.34-2.24 (m, 5H), 2.12 (s, 3H); ESI m/z 374 [M + H]+. | 98.8 |
| 98 | 3,5-dimethyl-4-(1-(thiophen-3-ylmethyl)-1H-pyrazolo[4,3-b]pyridin-6-yl)isoxazole | 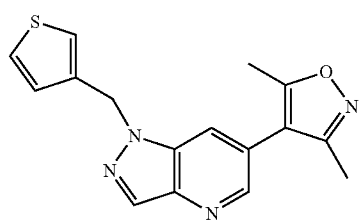 [SMILES: Cc1noc(C)c1-c1cnc2cnn(Cc3ccsc3)c2c1] | A | $^1$H NMR (500 MHz, CDCl3) δ 8.48 (d, J = 1.7 Hz, 1H), 8.39 (s, 1H), 7.47 (s, 1H), 7.34-7.32 (m, 1H), 7.23-7.21 (m, 1H), 6.97 (dd, J = 5.0 Hz, 1.3 Hz, 1H), 5.67 (s, 2H), 2.39 (s, 3H), 2.23 (s, 3H); ESI m/z 311 [M + H]+. | >99 |
| 99 | N-(1-benzyl-6-(3,5-dimethylisoxazol-4-yl)-1H-pyrrolo[3,2-b]pyridin-3-yl)acetamide | 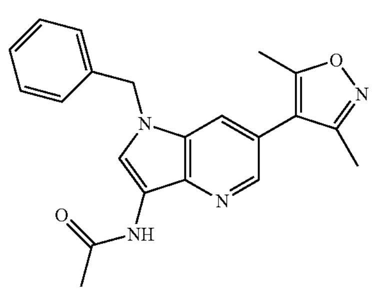 [SMILES: CC(=O)Nc1cn(Cc2ccccc2)c2cc(-c3c(C)noc3C)cnc12] | No general procedure | $^1$H NMR (300 MHz, DMSO-d6) d 10.2 (s, 1H), 8.32 (d, J = 1.8 Hz, 1H), 8.23 (s, 1H), 7.97 (d, J = 1.8 Hz, 1H), 7.32-7.25 (m, 5H), 5.45 (s, 2H), 2.40 (s, 3H), 2.22 (s, 3H), 2.12 (s, 3H); ESI MS m/z 361 [M + H]+. | 96.7 |
| 100 | 1-benzyl-6-(3,5-dimethylisoxazol-4-y)-1H-pyrrolo[3,2-b]pyridin-3-amine | 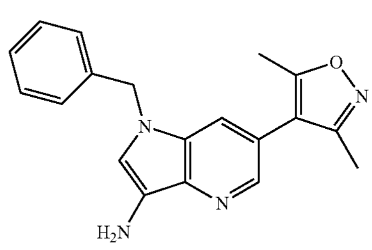 [SMILES: Cc1noc(C)c1-c1cnc2c(N)cn(Cc3ccccc3)c2c1] | No general procedure | $^1$H NMR (300 MHz, DMSO-d6) d 8.18 (d, J = 1.8 Hz, 1H), 7.82 (d, J = 1.8 Hz, 1H), 7.33-7.21 (m, 5H), 7.06 (s, 1H), 5.30 (s, 2H), 4.26 (s, 2H), 2.37 (s, 3H), 2.21 (s, 3H); ESI MS m/z 319 [M + H]+. | 84.2 |

TABLE 2-continued

Example Compounds

| Example Compound | Chemical Name | Structure | General procedure | Characterization | Purity HPLC (%) |
|---|---|---|---|---|---|
| 101 | 1-(3,4-dichlorobenzyl)-6-(3,5-dimethylisaxazol-4-yl)-1H-imidazo[4,5-b]pyridin-2(3H)-one | 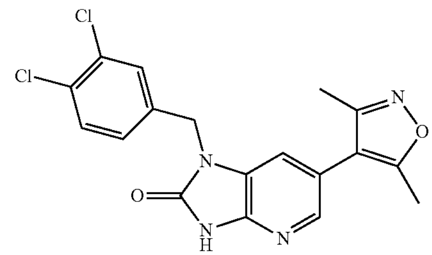 [SMILES: Cc1noc(C)c1-c1cnc2[nH]c(=O)n(Cc3ccc(Cl)c(Cl)c3)c2c1] | R | $^1$H NMR (500 MHz, DMSO-d6) δ 11.83 (s, 1H), 7.92 (d, J = 1.5 Hz, 1H), 7.73 (d, J = 2.0 Hz, 1H), 7.61 (d, J = 8.0 Hz, 1H), 7.53 (d, J = 2.0 Hz, 1H), 7.35 (dd, J = 8.5, 2.0 Hz, 1H), 5.05 (s, 2H), 2.37 (s, 3H), 2.19 (s, 3H); ESI m/z 389 [M + H]+. | >99 |
| 102 | 1-(4-chlorobenzyl)-6-(3,5-dimethylisoxazol-4-yl)-1H-indazol-4-amine | 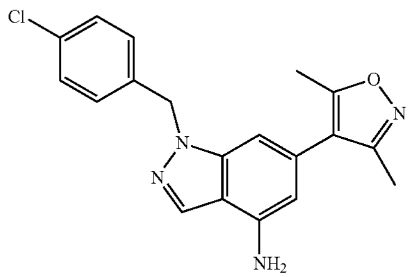 [SMILES: Cc1noc(C)c1-c1cc(N)c2cnn(Cc3ccc(Cl)cc3)c2c1] | C | $^1$H NMR (500 MHz, DMSO-d6) δ 8.14 (d, J = 0.8 Hz, 1H), 7.38-7.34 (m, 2H), 7.28-7.24 (m, 2H), 6.69 (s, 1H), 6.12 (d, J = 1.1 Hz, 1H), 5.94 (s, 2H), 5.53 (s, 2H), 2.37 (s, 3H), 2.20 (s, 3H); ESI m/z 353 [M + H]+. | >99 |
| 103 | 6-(3,5-dimethylisoxazol-4-yl)-1-(4-methoxybenzyl)-4-nitro-1H-benzo[d]imidazol-2(3H)-one | 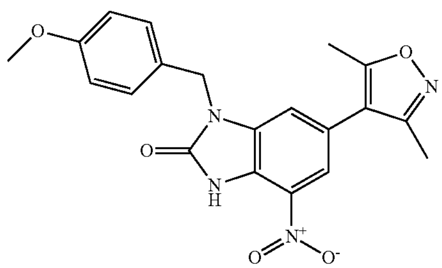 [SMILES: COc1ccc(Cn2c(=O)[nH]c3c([N+](=O)[O-])cc(-c4c(C)noc4C)cc32)cc1] | E | $^1$H NMR (500 MHz, CD3OD) δ 7.78 (d, J = 1.5 Hz, 1H), 7.31 (d, J = 8.7 Hz, 2H), 7.23 (d, J = 1.5 Hz, 1H), 6.90 (d, J = 8.7 Hz, 2H), 5.09 (s, 2H), 3.75 (s, 3H), 2.32 (s, 3H), 2.14 (s, 3H); ESI m/z 395 [M + H]+. | >99 |
| 104 | 4-amino-6-(3,5-dimethylisoxazol-4-yl)-1-(4-methoxybenzyl)-1H-benzo[d]imidazol-2(3H)-one | 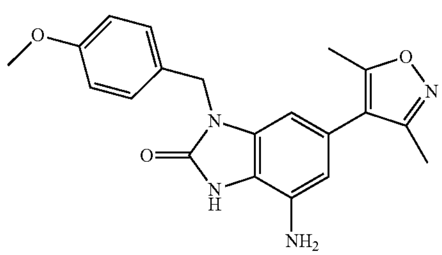 [SMILES: COc1ccc(Cn2c(=O)[nH]c3c(N)cc(-c4c(C)noc4C)cc32)cc1] | E | $^1$H NMR (500 MHz, CD3OD) δ 7.26 (d, J = 8.6 Hz, 2H), 6.87 (d, J = 8.6 Hz, 2H), 6.39 (d, J = 1.4 Hz, 1H), 6.26 (d, J = 1.4 Hz, 1H), 4.97 (s, 2H), 3.74 (s, 3H), 2.28 (s, 3H), 2.12 (s, 3H); HPLC 93.0%, tR = 12.2 min; ESI m/z 365 [M + H]+. | 93.0 |
| 105 | 1-(4-chlorobenzyl)-6-(3,5-dimethylisoxazol-4-yl)-1H-imidazo[4,5-b]pyridin-2(3H)-one | 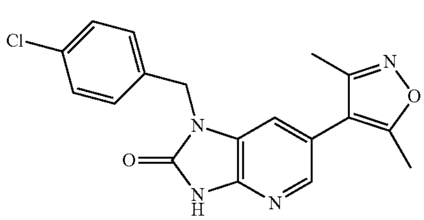 [SMILES: Cc1noc(C)c1-c1cnc2[nH]c(=O)n(Cc3ccc(Cl)cc3)c2c1] | R | $^1$H NMR (500 MHz, DMSO-d6) δ 11.81 (s, 1H), 7.91 (d, J = 1.5 Hz, 1H), 7.45 (d, J = 2.0 Hz, 1H), 7.43-7.39 (m, 4H), 5.04 (s, 2H), 2.35 (s, 3H), 2.17 (s, 3H); ESI m/z 355 [M + H]+. | >99 |

TABLE 2-continued

Example Compounds

| Example Compound | Chemical Name | Structure | General procedure | Characterization | Purity HPLC (%) |
|---|---|---|---|---|---|
| 106 | 6-(3,5-dimethylisoxazol-4-yl)-1-(thiophen-2-ylmethyl)-1H-imidazo[4,5-b]pyridin-2(3H)-one | 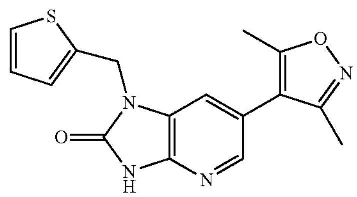 [SMILES: Cc1noc(C)c1-c1cnc2[nH]c(=O)n(Cc3cccs3)c2c1] | R | $^1$H NMR (500 MHz, DMSO-d6) δ 11.77 (s, 1H), 7.91 (d, J = 2.0 Hz, 1H), 7.57 (d, J = 2.0 Hz, 1H), 7.44 (dd, J = 5.0, 1.0 Hz, 1H), 7.26 (dd, J = 3.5, 1.0 Hz, 1H), 6.97 (dd, J = 5.0, 3.5 Hz, 1H), 5.24 (s, 2H), 2.39 (s, 3H), 2.21 (s, 3H); ESI m/z 327 [M + H]+. | 98.6 |
| 107 | 1-benzyl-6-(3,5-dimethylisoxazol-4-yl)-N-ethyl-1H-imidazo[4,5-b]pyridin-2-amisne | 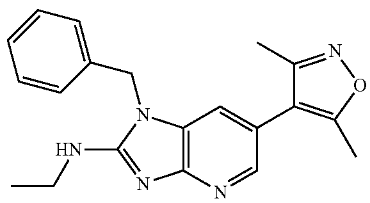 [SMILES: CCNc1nc2ncc(-c3c(C)noc3C)cc2n1Cc1ccccc1] | Q | $^1$H NMR (500 MHz, DMSO-d6) δ 7.95 (d, J = 1.5 Hz, 1H), 7.37-7.31 (m, 4H), 7.28-7.23 (m, 3H), 5.30 (s, 2H), 3.51-4.53 (m, 2H), 2.33 (s, 3H), 2.14 (s, 3H), 1.23 (t, J = 7.0 Hz, 3H); ESI m/z 348 [M + H]+. | >99 |
| 108 | 3,5-dimethyl-4-(2-methyl-1-(1-phenylethyl)-1H-imidazo[4,5-b]pyridin-6-yl)isoxazole | 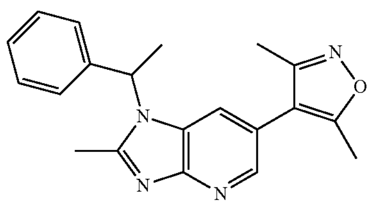 [SMILES: Cc1noc(C)c1-c1cnc2nc(C)n(C(C)c3ccccc3)c2c1] | No general procedure | $^1$H NMR (500 MHz, DMSO-d6) δ 8.27 (d, J = 2.0 Hz, 1H), 7.44 (d, J = 2.0 Hz, 1H), 7.40-7.36 (m, 4H), 7.33-7.30 (m, 1H), 6.01 (q, J = 7.0 Hz, 1H), 2.70 (s, 3H), 2.26 (s, 3H), 2.06 (s, 3H), 1.93 (d, J = 7.0 Hz, 3H); ESI m/z 333 [M + H]+. | 97.7 |
| 109 | 1-benzyl-6-(3,5-dimethylisoxazol-4-yl)-N2-(tetrahydro-2H-pyran-4-yl)-1H-benzo[d]imidazole-2,4-diamine | 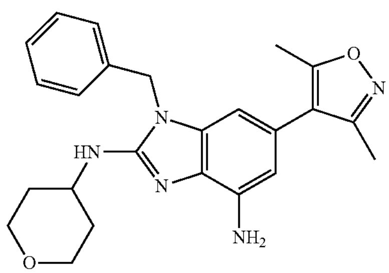 [SMILES: Cc1noc(C)c1-c1cc(N)c2nc(NC3CCOCC3)n(Cc3ccccc3)c2c1] | I | $^1$H NMR (300 MHz, DMSO-d6) δ 7.34-7.21 (m, 5H), 6.48 (d, J = 7.8 Hz, 1H), 6.29 (d, J = 1.5 Hz, 1H), 6.21 (d, J = 1.5 Hz, 1H), 5.23 (s, 2H), 4.83 (s, 2H), 4.04-3.96 (m, 1H), 3.89 (dd, J = 11.4, 2.7 Hz, 2H), 3.42 (td, J = 11.4, 2.7 Hz, 2H), 2.28 (s, 3H), 2.11 (s, 3H); 1.98 (dd, J = 12.3, 2.7 Hz, 2H), 1.62-1.49 (m, 2H), ESI m/z 418 [M + H]+. | >99 |
| 110 | 6-(3,5-dimethylisoxazol-4-yl)-4-nitro-1-(1-phenylethyl)-1H-benzo[d]imidazol-2(3H)-one | 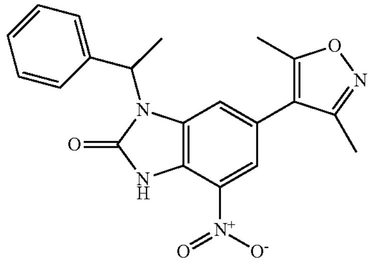 [SMILES: Cc1noc(C)c1-c1cc([N+](=O)[O-])c2[nH]c(=O)n(C(C)c3ccccc3)c2c1] | P | $^1$H NMR (500 MHz, CD3OD) δ 7.75 (d, J = 1.3 Hz, 1H), 7.44 (d, J = 7.7 Hz, 2H), 7.38 (t, J = 7.7 Hz, 2H), 7.31 (t, J = 7.7 Hz, 1H), 6.88 (d, J = 1.3 Hz, 1H), 5.88 (q, J = 7.1 Hz, 1H), 2.20 (s, 3H), 2.02 (s, 3H), 1.91 (d, J = 7.2 Hz, 3H); ESI m/z 377 [M − H]+. | >99 |

TABLE 2-continued

Example Compounds

| Example Compound | Chemical Name | Structure | General procedure | Characterization | Purity HPLC (%) |
|---|---|---|---|---|---|
| 111 | N-(1-benzyl-6-(3,5-dimethylisoxazol-4-yl)-2-oxo-2,3-dihydro-1H-benzo[d]imidazol-4-yl)acetamide | 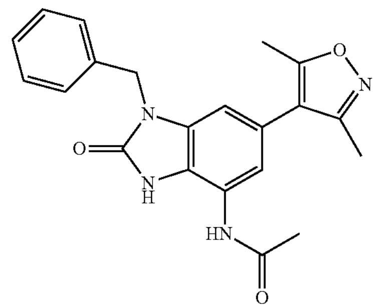 [SMILES: CC(=O)Nc1cc(-c2c(C)noc2C)cc2c1[nH]c(=O)n2Cc1ccccc1] | O | ¹H NMR (300 MHz, DMSO-d6) δ 10.78 (s, 1H), 9.85 (s, 1H), 7.60-7.46 (m, 5H), 7.28 (d, J = 1.2 Hz, 1H), 7.06 (d, J = 1.2 Hz, 1H), 5.22 (s, 2H), 2.51 (s, 3H), 2.33 (s, 3H), 2.27 (s, 3H); ESI m/z 377 [M + H]+. | 98.8 |
| 112 | 6-(3,5-dimethylisoxazol-4-yl)-1-(1-phenylethyl)-1H-imidazo[4,5-b]pyridin-2(3H)-one | 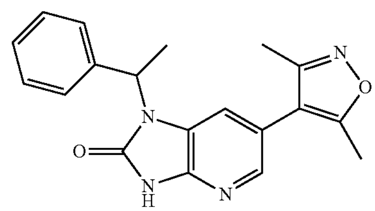 [SMILES: Cc1noc(C)c1-c1cnc2[nH]c(=O)n(C(C)c3ccccc3)c2c1] | No general procedure | ¹H NMR (500 MHz, DMSO-d6) δ 11.78 (s, 1H), 7.87 (d, J = 2.0 Hz, 1H), 7.44 (d, J = 7.5 Hz, 2H), 7.36 (t, J = 7.5 Hz, 2H), 7.29 (t, J = 7.5 Hz, 1H), 7.09 (d, J = 2.0 Hz, 1H), 5.72 (q, J = 7.0 Hz, 1H), 2.26 (s, 3H), 2.06 (s, 3H), 1.84 (d, J = 7.0 Hz, 3H); ESI m/z 335 [M + H]+. | >99 |
| 113 | 6-(3,5-dimethylisoxazol-4-yl)-N-ethyl-1-(1-phenylethyl)-1H-imidazo[4,5-b]pyridin-2-amine | 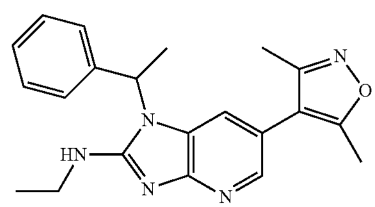 [SMILES: CCNc1nc2ncc(-c3c(C)noc3C)cc2n1C(C)c1ccccc1] | No general procedure | ¹H NMR (500 MHz, DMSO-d6) δ 7.90 (d, J = 2.0 Hz, 1H), 7.40-7.28 (m, 6H), 6.81 (d, J = 2.0 Hz, 1H), 5.84 (q, J = 7.0 Hz, 1H), 3.54-3.48 (m, 2H), 2.20 (s, 3H), 1.99 (s, 3H), 1.83 (d, J = 7.0 Hz, 3H), 1.27 (t, J = 7.0 Hz, 3H); ESI m/z 362 [M + H]+. | >99 |
| 114 | 4-(1-benzyl-6-(3,5-dimethylisoxazol-4-yl)-1H-imidazo[4,5-b]pyridin-2-yl)morpholine | 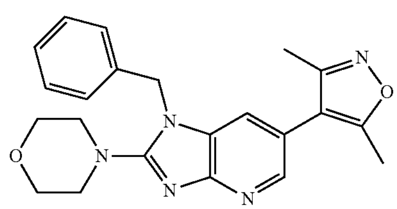 [SMILES: Cc1noc(C)c1-c1cnc2nc(N3CCOCC3)n(Cc3ccccc3)c2c1] | Q | ¹H NMR (300 MHz, CDCl3) δ 8.24 (d, J = 2.0 Hz, 1H), 7.41-7.34 (m, 3H), 7.15 (d, J = 6.5 Hz, 2H), 7.06 (d, J = 1.0 Hz, 1H), 5.26 (s, 2H), 3.83 (t, J = 4.5 Hz, 4H), 3.50 (t, J = 4.5 Hz, 4H), 2.29 (s, 3H), 2.11 (s, 3H); ESI m/z 390 [M + H]+. | >99 |
| 115 | 4-amino-6-(3,5-dimethylisoxazol-4-yl)-1-(1-phenylethyl)-1H-benzo[d]imidazol-2(3H)-one | 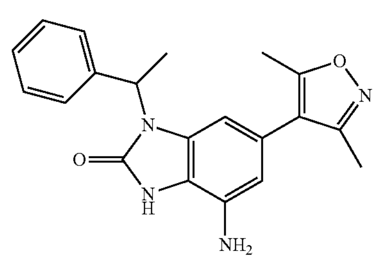 | P | ¹H NMR (500 MHz, CD3OD) δ 7.42-7.32 (m, 4H), 7.26 (t, J = 6.9 Hz, 1H), 6.35 (s, 1H), 5.94 (s, 1H), 5.78 (q, J = 7.2 Hz, 1H), 2.17 (s, 3H), 2.00 (s, 3H), 1.86 (d, J = 7.2 Hz, 3H); ESI m/z 349 [M + H]+. | >99 |

TABLE 2-continued

Example Compounds

| Example Compound | Chemical Name | Structure | General procedure | Characterization | Purity HPLC (%) |
|---|---|---|---|---|---|
| 116 | 4-(1-(cyclobutyl-methyl)-2-methyl-4-nitro-1H-benzo[d]imidazol-6-yl)-3,5-dimethyl-isoxazole | 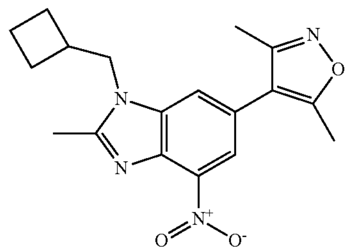 [SMILES: Cc1noc(C)c1-c1cc([N+](=O)[O-])c2nc(C)n(CC3CCC3)c2c1] | F | ¹H NMR (500 MHz, DMSO-d6) δ 8.09 (d, J = 1.5 Hz, 1H), 7.91 (d, J = 1.5 Hz, 1H), 4.37 (d, J = 7.0 Hz, 2H), 2.80-2.75 (m, 1H), 2.67 (s, 3H), 2.45 (s, 3H), 1.94 (s, 3H), 1.95-1.90 (m, 2H), 1.86-1.77 (m, 4H); ESI m/z 341 [M + H]+. | >99 |
| 117 | 4-(1-(cyclopentyl-methyl)-2-methyl-4-nitro-1H-benzo[d]imidazol-6-yl)-3,5-dimethyl-isoxazole | 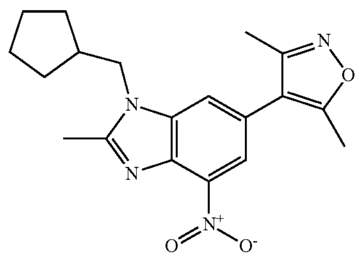 [SMILES: Cc1noc(C)c1-c1cc([N+](=O)[O-])c2nc(C)n(CC3CCCC3)c2c1] | F | ¹H NMR (500 MHz, DMSO-d6) δ 8.06 (d, J = 1.5 Hz, 1H), 7.91 (d, J = 1.5 Hz, 1H), 4.29 (d, J = 7.5 Hz, 2H), 2.68 (s, 3H), 2.45 (s, 3H), 2.37 (m, 1H), 2.27 (s, 3H), 1.71-1.58 (m, 4H), 1.57-1.47 (m, 2H), 1.33-1.27 (m, 2H); ESI m/z 355 [M + H]+. | >99 |
| 118 | 1-(cyclopropyl-methyl)-6-(3,5-dimethyl-isoxazol-4-yl)-1H-imidazo[4,5-b]pyridin-2(3H)-one | 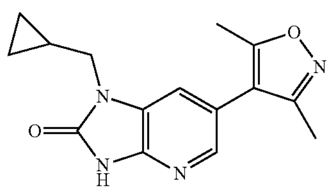 [SMILES: Cc1noc(C)c1-c1cnc2[nH]c(=O)n(CC3CC3)c2c1] | No general procedure | ¹H NMR (500 MHz, CD3OD) δ 7.90 (d, J = 1.5 Hz, 1H), 7.50 (d, J = 1.5 Hz, 1H), 3.81 (d, J = 7.0 Hz, 2H), 2.42 (s, 3H), 2.26 (s, 3H), 1.31-1.20 (m, 1H), 0.60-0.53 (m, 2H), 0.44-0.38 (m, 2H). ESI m/z 285 [M + H]+. | >99 |
| 119 | N-(1-benzyl-6-(3,5-dimethyl-isoxazol-4-yl)-2-(ethylamino)-1H-benzo[d]imidazol-4-yl)acetamide | 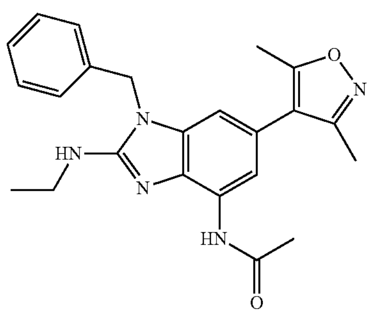 | O | ¹H NMR (300 MHz, DMSO-d6) δ 9.37 (s, 1H), 7.60 (s, 1H), 7.35-7.20 (m, 5H), 6.93 (t, J = 5.4 Hz, 1H), 6.80 (s, 1H), 5.29 (s, 2H), 3.57-3.48 (m, 2H), 2.31 (s, 3H), 2.15 (s, 3H), 2.13 (s, 3H), 1.23 (t, J = 7.2 Hz, 3H); ESI m/z 404 [M + H]+. | 99.0 |
| 120 | N-(1-benzyl-6-(3,5-dimethyl-isoxazol-4-yl)-2-ethoxy-1H-benzo[d]imidazol-4-yl)acetamide | 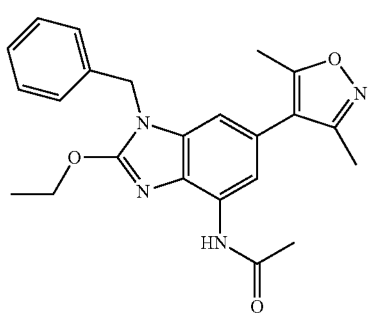 [SMILES: CCOc1nc2c(NC(C)=O)cc(-c3c(C)noc3C)cc2n1Cc1ccccc1] | O | ¹H NMR (300 MHz, DMSO-d6) δ 9.64 (s, 1H), 7.73 (s, 1H), 7.37-7.27 (m, 5H), 7.11 (s, 1H), 5.25 (s, 2H), 4.65 (q, J = 7.2 Hz, 2H), 2.35 (s, 3H), 2.18 (s, 3H), 2.16 (s, 3H), 1.43 (t, J = 7.2 Hz, 3H); ESI m/z 405 [M + H]+. | >99 |

TABLE 2-continued

Example Compounds

| Example Compound | Chemical Name | Structure | General procedure | Characterization | Purity HPLC (%) |
|---|---|---|---|---|---|
| 121 | 4-(1-benzyl-4-bromo-2-methyl-1H-benzo[d]imidazol-6-yl)-3,5-dimethyl-isoxazole | 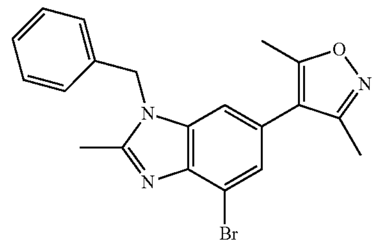 | H | ¹H NMR (500 MHz, CD3OD) δ 7.40-7.25 (m, 5H), 7.15 (d, J = 7.7 Hz, 2H), 5.51 (s, 2H), 2.64 (s, 3H), 2.32 (s, 3H), 2.15 (s, 3H); ESI m/z 396 [M + H]+. | >99 |
| 122 | 3-benzyl-5-(3,5-dimethyl-isoxazol-4-yl)-1-ethyl-1H-benzo[d]imidazol-2(3H)-one | 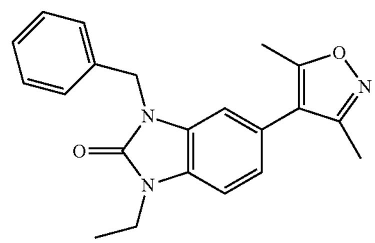 [SMILES: CCn1c(=O)n(Cc2ccccc2)c2cc(-c3c(C)noc3C)ccc21] | No general procedure | ¹H NMR (500 MHz, DMSO-d6) δ 7.37 (d, J = 7.5 Hz, 2H), 7.33 (t, J = 7.0 Hz, 2H), 7.29 (d, J = 8.0 Hz, 1H), 7.26 (t, J = 7.0 Hz, 1H), 7.09 (d, J = 1.5 Hz, 1H), 7.03 (dd, J = 8.0, 1.5 Hz, 1H), 5.08 (s, 2H), 3.94 (q, J = 7.0 Hz, 2H), 2.31 (s, 3H), 2.13 (s, 3H), 1.26 (t, J = 7.0 Hz, 3H); ESI m/z 348 [M + H]+. | 94.6 |
| 123 | 4-(2-(azetidin-1-yl)-1-benzyl-1H-imidazo[4,5-b]pyridin-6-yl)-3,5-dimethyl-isoxazole | 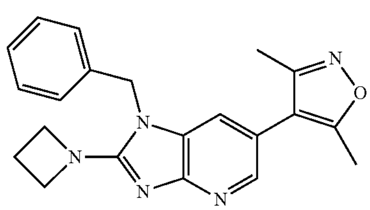 [SMILES: Cc1noc(C)c1-c1cnc2nc(N3CCC3)n(Cc3ccccc3)c2c1] | Q | ¹H NMR (500 MHz, CDCl3) δ 8.07 (s, 1H), 7.43-7.37 (m, 3H), 7.13 (d, J = 6.5 Hz, 2H), 7.05 (s, 1H), 5.23 (s, 2H), 4.49 (t, J = 7.0 Hz, 4H), 2.54 (quin, J = 7.5 Hz, 2H), 2.30 (s, 3H), 2.10 (s, 3H); ESI m/z 360 [M + H]+. | >99 |
| 124 | 1-((5-chlorothiophen-2-yl)methyl)-6-(3,5-dimethylisoxazol-4-yl)-1H-imidazo[4,5-b]pyridin-2(3H)-one | 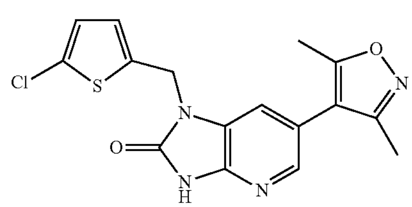 [SMILES: Cc1noc(C)c1-c1cnc2[nH]c(=O)n(Cc3ccc(Cl)s3)c2c1] | R | ¹H NMR (500 MHz, DMSO-d6) δ 11.81 (s, 1H), 7.92 (d, J = 2.0 Hz, 1H), 7.63 (d, J = 1.5 Hz, 1H), 7.15 (d, J = 4.0 Hz, 1H), 6.99 (s, J = 4.0 Hz, 1H), 5.17 (s, 2H), 2.40 (s, 3H), 2.22 (s, 3H); ESI m/z 361 [M + H]+. | >99 |
| 125 | (S)-3,5-dimethyl-4-(2-methyl-4-nitro-1-(1-phenylethyl)-1H-benzo[d]imidazol-6-yl)isoxazole | 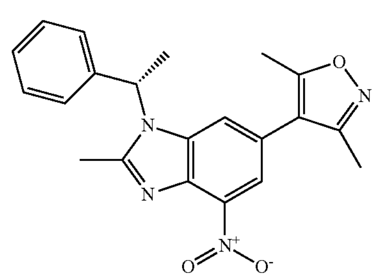 [SMILES: Cc1noc(C)c1-c1cc([N+](=O)[O-])c2nc(C)n([C@@H](C)c3ccccc3)c2c1] | S | ¹H NMR (300 MHz, DMSO-d6) d 7.87 (d, J = 1.5 Hz, 1H), 7.42-7.30 (m, 6H), 6.11 (q, J = 7.2 Hz, 1H), 2.74 (s, 3H), 2.23 (s, 3H), 2.04 (s, 3H), 1.94 (d, J = 6.9 Hz, 3H); ESI MS m/z 377 [M + H]+. | >99 |

TABLE 2-continued

Example Compounds

| Example Compound | Chemical Name | Structure | General procedure | Characterization | Purity HPLC (%) |
|---|---|---|---|---|---|
| 126 | (R)-3,5-dimethyl-4-(2-methyl-4-nitro-1-(1-phenylethyl)-1H-benzo[d]imidazol-6-yl)isoxazole | 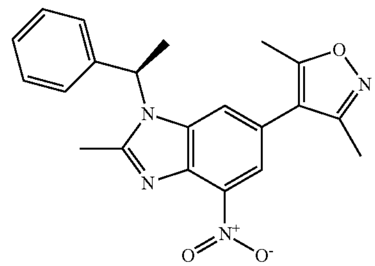 [SMILES: Cc1noc(C)c1-c1cc([N+](=O)[O-])c2nc(C)n([C@H](C)c3ccccc3)c2c1] | S | $^1$H NMR (300 MHz, DMSO-d6) d 7.87 (d, J = 1.5 Hz, 1H), 7.42-7.30 (m, 6H), 6.11 (q, J = 7.2 Hz, 1H), 2.74 (s, 3H), 2.23 (s, 3H), 2.04 (s, 3H), 1.94 (d, J = 6.9 Hz, 3H); ESI MS m/z 377 [M + H]+. | 98.3 |
| 127 | 6-(3,5-dimethyl-isoxazol-4-yl)-N-ethyl-4-nitro-1-(1-phenylethyl)-1H-benzo[d]imidazol-2-amine | 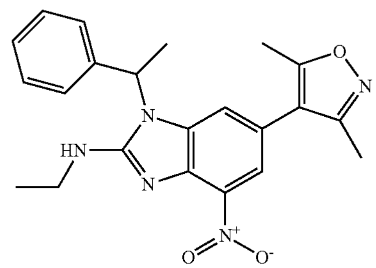 [SMILES: CCNc1nc2c([N+](=O)[O-])cc(-c3c(C)noc3C)cc2n1C(C)c1ccccc1] | No general procedure | $^1$H NMR (500 MHz, CD3OD) δ 7.70 (d, J = 1.5 Hz, 1H), 7.45-7.30 (m, 5H), 6.72 (d, J = 1.5 Hz, 1H), 5.86 (q, J = 7.0 Hz, 1H), 3.72 (q, J = 7.2 Hz, 2H), 2.17 (s, 3H), 1.98 (s, 3H), 1.90 (d, J = 7.0 Hz, 3H), 1.36 (t, J = 7.2 Hz, 3H); ESI m/z 406 [M + H]+. | 96.3 |
| 128 | 4-(1-benzyl-2-ethyl-1H-imidazo[4,5-b]pyridin-6-yl)-3,5-dimethyl-isoxazole | 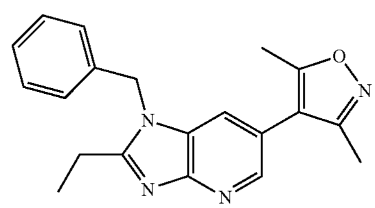 [SMILES: CCc1nc2ncc(-c3c(C)noc3C)cc2n1Cc1ccccc1] | D | $^1$H NMR (500 MHz, CDCl3) δ 8.42 (d, J = 1.7 Hz, 1H), 7.39-7.33 (m, 3H), 7.30 (d, J = 1.6 Hz, 1H), 7.10-7.09 (m, 2H), 5.41 (s, 2H), 3.08 (q, J = 7.5 Hz, 2H), 2.32 (s, 3H), 2.15 (s, 3H), 1.51 (t, J = 7.5 Hz, 3H); ESI m/z 333 [M + H]+. | >99 |
| 129 | 4-amino-6-(3,5-dimethylisoxazol-4-yl)-1-(4-hydroxybenzyl)-1H-benzo[d]imidazol-2(3H)-one | 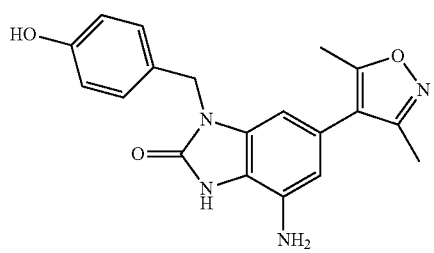 [SMILES: Cc1noc(C)c1-c1cc(N)c2[nH]c(=O)n(Cc3ccc(O)cc3)c2c1] | No general procedure | $^1$H NMR (500 MHz, CD3OD) δ 7.17 (d, J = 8.6 Hz, 2H), 6.72 (d, J = 8.6 Hz, 2H), 6.39 (d, J = 1.3 Hz, 1H), 6.26 (d, J = 1.3 Hz, 1H), 4.94 (s, 2H), 2.28 (s, 3H), 2.12 (s, 3H); ESI m/z 351 [M + H]+. | >99 |
| 130 | N-(2-(azetidin-1-yl)-1-benzyl-6-(3,5-dimethyl-isoxazol-4-yl)-1H-benzo[d]imidazol-4-yl)acetamide | 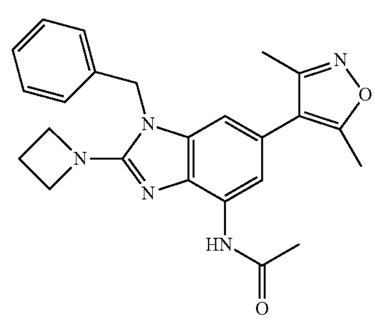 [SMILES: CC(=O)Nc1cc(-c2c(C)noc2C)cc2c1nc(N1CCC1)n2Cc1ccccc1] | O | $^1$H NMR (300 MHz, DMSO-d6) δ 7.69 (s, 1H), 7.36-7.16 (m, 6H), 6.92 (s, 1H), 5.26 (s, 2H), 4.18 (t, J = 7.5 Hz, 4H), 2.35-2.27 (m, 5H), 2.15 (s, 3H), 2.14 (s, 3H); ESI m/z 416 [M + H]+. | 98.2 |

TABLE 2-continued

Example Compounds

| Example Compound | Chemical Name | Structure | General procedure | Characterization | Purity HPLC (%) |
|---|---|---|---|---|---|
| 131 | 1-(cyclopropyl-methyl)-6-(3,5-dimethyl-isoxazol-4-yl)-N-ethyl-1H-imidazo[4,5-b]pyridine-2-amine | 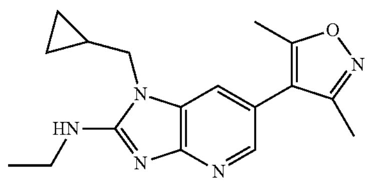 [SMILES: CCNc1nc2ncc(-c3c(C)noc3C)cc2n1CC1CC1] | No general procedure | $^1$H NMR (500 MHz, CDCl3) δ 7.93 (d, J = 2.0 Hz, 1H), 7.48 (d, J = 1.5 Hz, 1H), 3.98 (d, J = 6.5 Hz, 2H), 3.57 (q, J = 7.0 Hz, 2H), 2.42 (s, 3H), 2.26 (s, 3H), 1.30 (t, J = 7.0 Hz, 3H), 1.29-1.19 (m, 1H), 0.59-0.52 (m, 2H), 0.45-0.39 (m, 2H). ESI m/z 312 [M + H]+. | >99 |
| 132 | 1-(cyclobutyl-methyl)-6-(3,5-dimethyl-isoxazol-4-yl)-2-methyl-1H-benzo[d]imidazol-4-amine | 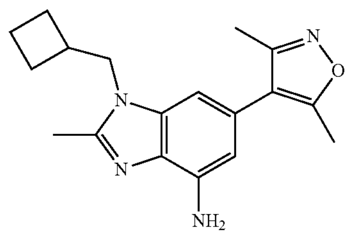 [SMILES: Cc1noc(C)c1-c1cc(N)c2nc(C)n(CC3CCC3)c2c1] | F | $^1$H NMR (500 MHz, CD3OD) δ 6.70 (d, J = 1.5 Hz, 1H), 6.43 (d, J = 1.5 Hz, 1H), 4.18 (d, J = 7.0 Hz, 2H), 2.85-2.79 (m, 1H), 2.60 (s, 3H), 2.40 (s, 3H), 2.25 (s, 3H), 2.06-1.98 (m, 2H), 1.94-1.82 (m, 4H); ESI m/z 311 [M + H]+. | 98.5 |
| 133 | 1-(cyclopentyl-methyl)-6-(3,5-dimethyl-isoxazol-4-yl)-2-methyl-1H-benzo[d]imidazol-4-amine | 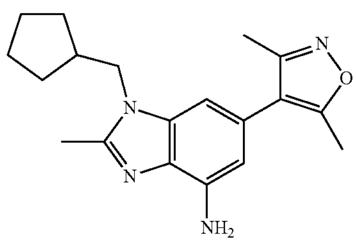 [SMILES: Cc1noc(C)c1-c1cc(N)c2nc(C)n(CC3CCCC3)c2c1] | F | $^1$H NMR (500 MHz, CD3OD) δ 6.69 (d, J = 1.5 Hz, 1H), 6.44 (d, J = 1.5 Hz, 1H), 4.10 (d, J = 7.5 Hz, 2H), 2.61 (s, 3H), 2.50-2.40 (m, 1H), 2.40 (s, 3H), 2.25 (s, 3H), 1.80-1.65 (m, 4H), 1.64-1.55 (m, 2H), 1.42-1.28 (m, 2H); ESI m/z 325 [M + H]+. | >99 |
| 134 | 6-(3,5-dimethylisoxazol-4-yl)-N2-ethyl-1-(1-phenylethyl)-1H-benzo[d]imidazole-2,4-diamine | 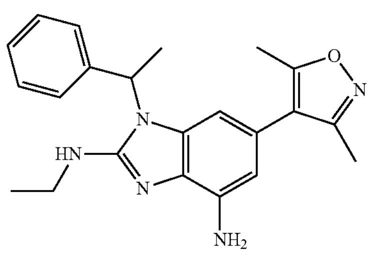 [SMILES: CCNc1nc2c(N)cc(-c3c(C)noc3C)cc2n1C(C)c1ccccc1] | No general procedure | $^1$H NMR (500 MHz, CD3OD) δ 7.40-7.25 (m, 5H), 6.31 (d, J = 1.5 Hz, 1H), 5.92 (d, J = 1.5 Hz, 1H), 5.72 (q, J = 6.9 Hz, 1H), 3.53 (q, J = 7.2 Hz, 2H), 2.15 (s, 3H), 1.99 (s, 3H), 1.86 (d, J = 7.0 Hz, 3H), 1.33 (t, J = 7.2 Hz, 3H); ESI m/z 376 [M + H]+. | >99 |
| 135 | 4-(1-benzyl-4-nitro-2-(pyrrolidin-1-yl)-1H-benzo[d]imidazol-6-yl)-3,5-dimethylisoxazole | 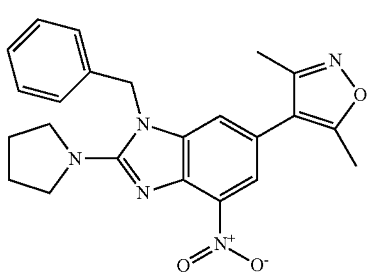 [SMILES: Cc1noc(C)c1-c1cc([N+](=O)[O-])c2nc(N3CCCC3)n(Cc3ccccc3)c2c1] | I | $^1$H NMR (300 MHz, DMSO-d6) δ 7.74 (d, J = 1.5 Hz, 1H), 7.55 (d, J = 1.5 Hz, 1H), 7.37-7.24 (m, 3H), 7.15-7.12 (m, 2H), 5.60 (s, 2H), 3.69 (t, J = 6.9 Hz, 4H), 2.34 (s, 3H), 2.16 (s, 3H), 1.92-1.88 (m, 4H); ESI m/z 418 [M + H]+. | 96.8 |

TABLE 2-continued

Example Compounds

| Example Compound | Chemical Name | Structure | General procedure | Characterization | Purity HPLC (%) |
|---|---|---|---|---|---|
| 136 | 4-(1-benzyl-2-(4-methylpiperazin-1-yl)-4-nitro-1H-benzo[d]imidazol-6-yl)-3,5-dimethylisoxazole | 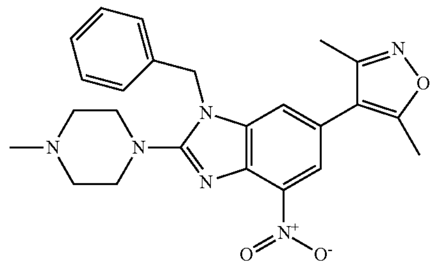 [SMILES: Cc1noc(C)c1-c1cc([N+](=O)[O-])c2nc(N3CCN(C)CC3)n(Cc3ccccc3)c2c1] | I | ¹H NMR (300 MHz, DMSO-d6) δ 7.82 (d, J = 1.5 Hz, 1H), 7.59 (d, J = 1.5 Hz, 1H), 7.37-7.28 (m, 3H), 7.22-7.19 (m, 2H), 5.45 (s, 2H), 3.40 (t, J = 4.8 Hz, 4H), 2.45 (t, J = 4.5 Hz, 4H), 2.33 (s, 3H), 2.21 (s, 3H), 2.13 (s, 3H); ESI m/z 447 [M + H]+. | 98.5 |
| 137 | 1-benzyl-6-(3,5-dimethyl-isoxazol-4-yl)-N-(2-methoxyethyl)-4-nitro-1H-benzo[d]imidazol-2-amine | 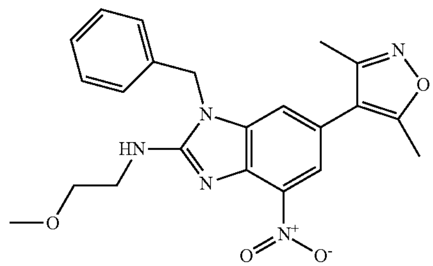 [SMILES: COCCNc1nc2c([N+](=O)[O-])cc(-c3c(C)noc3C)cc2n1Cc1ccccc1] | I | ¹H NMR (300 MHz, DMSO-d6) δ 7.84 (t, J = 5.1 Hz, 1H), 7.67 (d, J = 1.5 Hz, 1H), 7.44 (d, J = 1.5 Hz, 1H), 7.36-7.25 (m, 5H), 5.41 (s, 2H), 3.73-3.67 (m, 2H), 3.61-3.57 (m, 2H), 3.27 (s, 3H), 2.33 (s, 3H), 2.15 (s, 3H); ESI m/z 422 [M + H]+. | 97.4 |
| 138 | 4-(1-benzyl-2-cyclopropyl-1H-imidazo[4,5-b]pyridin-6-yl)-3,5-dimethylisoxazole | 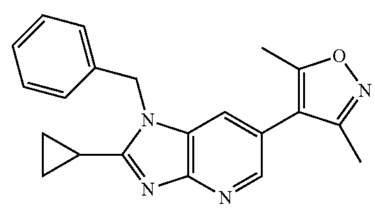 [SMILES: Cc1noc(C)c1-c1cnc2nc(C3CC3)n(Cc3ccccc3)c2c1] | No general procedure | ¹H NMR (500 MHz, DMSO-d6) δ 8.29 (d, J = 2.1 Hz, 1H), 7.95 (d, J = 2.0 Hz, 1H), 7.37-7.33 (m, 2H), 7.30-7.28 (m, 3H), 5.67 (s, 2H), 2.38 (s, 3H), 2.37-2.35 (m, 1H), 2.20 (s, 3H), 1.13-1.11 (m, 4H); ESI m/z 345 [M + H]+. | >99 |
| 139 | 1-benzyl-6-(3,5-dimethylisoxazol-4-yl)-N2-(2-methoxyethyl)-1H-benzo[d]imidazole-2,4-diamine | 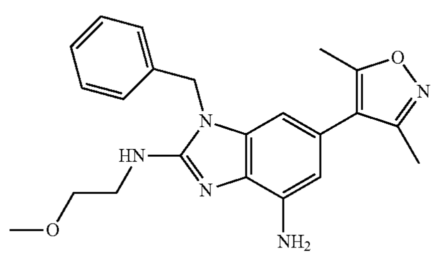 [SMILES: COCCNc1nc2c(N)cc(-c3c(C)noc3C)cc2n1Cc1ccccc1] | I | ¹H NMR (300 MHz, DMSO-d6) δ 7.33-7.20 (m, 5H), 6.76 (t, J = 5.1 Hz, 1H), 6.32 (d, J = 1.2 Hz, 1H), 6.21 (d, J = 1.5 Hz, 1H), 5.21 (s, 2H), 4.84 (s, 2H), 3.56 (s, 4H), 3.28 (s, 3H), 2.29 (s, 3H), 2.11 (s, 3H); ESI m/z 392 [M + H]+. | 97.5 |
| 140 | 1-benzyl-6-(3,5-dimethyl-isoxazol-4-yl)-2-(pyrrolidin-1-yl)-1H-benzo[d]imidazol-4-amine | 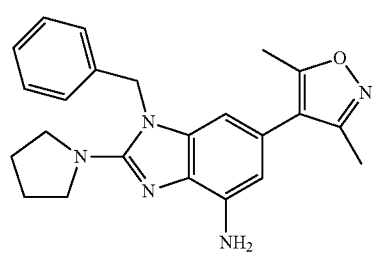 [SMILES: Cc1noc(C)c1-c1cc(N)c2nc(N3CCCC3)n(Cc3ccccc3)c2c1] | I | ¹H NMR (300 MHz, DMSO-d6) δ 7.34-7.24 (m, 3H), 7.18-7.15 (m, 2H), 6.35 (d, J = 1.5 Hz, 1H), 6.28 (d, J = 1.2 Hz, 1H), 5.42 (s, 2H), 4.98 (s, 2H), 3.47 (t, J = 6.9 Hz, 4H), 2.29 (s, 3H), 2.12 (s, 3H), 1.88-1.84 (m, 4H); ESI m/z 388 [M + H]+. | >99 |

TABLE 2-continued

Example Compounds

| Example Compound | Chemical Name | Structure | General procedure | Characterization | Purity HPLC (%) |
|---|---|---|---|---|---|
| 141 | 1-benzyl-6-(3,5-dimethyl-isoxazol-4-yl)-2-(4-methylpiperazin-1-yl)-1H-benzo[d]imidazol-4-amine | 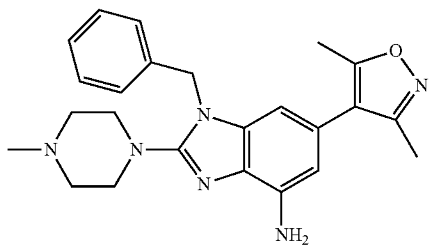 [SMILES: Cc1noc(C)c1-c1cc(N)c2nc(N3CCN(C)CC3)n(Cc3ccccc3)c2c1] | I | $^1$H NMR (300 MHz, DMSO-d6) δ 7.34-7.20 (m, 5H), 6.35 (d, J = 1.5 Hz, 1H), 6.29 (d, J = 1.2 Hz, 1H), 5.22 (s, 2H), 5.16 (s, 2H), 3.14 (t, J = 4.8 Hz, 4H), 2.50 (t, J = 4.5 Hz, 4H), 2.27 (s, 3H), 2.23 (s, 3H), 2.10 (s, 3H); ESI m/z 417 [M + H]+. | 97.8 |
| 142 | 1-benzyl-N6-(3,5-dimethyl-isoxazol-4-yl)-2-methyl-1H-benzo[d]imidazole-4,6-diamine | 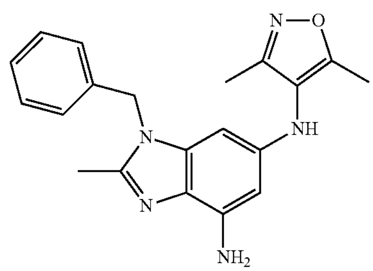 [SMILES: Cc1noc(C)c1Nc1cc(N)c2nc(C)n(Cc3ccccc3)c2c1] | No general procedure | $^1$H NMR (500 MHz, DMSO-d6) δ 7.31 (t, J = 7.5 Hz, 2H), 7.25 (t, J = 7.5 Hz, 1H), 7.04 (d, J = 7.5 Hz, 2H), 6.69 (s, 1H), 5.73 (d, J = 2.0 Hz, 1H), 5.60 (d, J = 2.0 Hz, 1H), 5.18 (s, 2H), 5.05 (s, 2H), 2.38 (s, 3H), 2.13 (s, 3H), 1.92 (s, 3H); ESI m/z 348 [M + H]+. | >99 |
| 143 | (S)-6-(3,5-dimethylisoxazol-4-yl)-2-methyl-1-(1-phenylethyl)-1H-benzo[d]imidazol-4-amine | 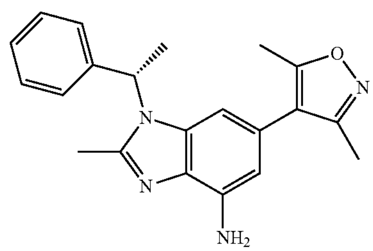 [SMILES: Cc1noc(C)c1-c1cc(N)c2nc(C)n([C@@H](C)c3ccccc3)c2c1] | S | $^1$H NMR (300 MHz, DMSO-d6) d 7.39-7.26 (m, 5H), 6.23 (d, J = 1.5 Hz, 1H), 6.14 (d, J = 1.2 Hz, 1H), 5.86 (q, J = 7.2 Hz, 1H), 5.26 (s, 2H), 2.58 (s, 3H), 2.20 (s, 3H), 2.02 (s, 3H), 1.86 (d, J = 6.9 Hz, 3H); ESI MS m/z 347 [M + H]+. | >99 |
| 144 | (R)-6-(3,5-dimethyl-isoxazol-4-yl)-2-methyl-1-(1-phenylethyl)-1H-benzo[d]imidazol-4-amine | 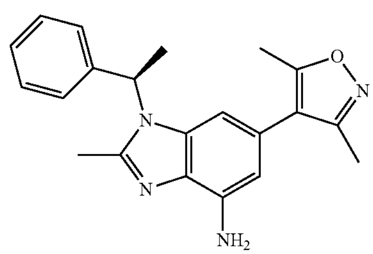 [SMILES: Cc1noc(C)c1-c1cc(N)c2nc(C)n([C@H](C)c3ccccc3)c2c1] | S | $^1$H NMR (300 MHz, DMSO-d6) d 7.39-7.26 (m, 5H), 6.23 (d, J = 1.5 Hz, 1H), 6.14 (d, J = 1.2 Hz, 1H), 5.86 (q, J = 7.2 Hz, 1H), 5.26 (s, 2H), 2.58 (s, 3H), 2.20 (s, 3H), 2.02 (s, 3H), 1.86 (d, J = 6.9 Hz, 3H); ESI MS m/z 347 [M + H]+. | >99 |
| 145 | 1-(cyclopropyl-methyl)-6-(3,5-dimethylisoxazol-4-yl)-4-nitro-1H-benzo[d]imidazol-2(3H)-one | 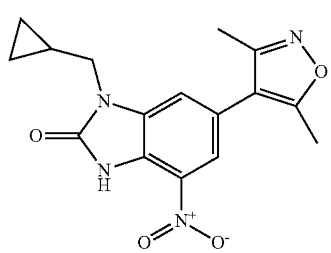 [SMILES: Cc1noc(C)c1-c1cc([N+](=O)[O-])c2[nH]c(=O)n(CC3CC3)c2c1] | No general procedure | $^1$H NMR (500 MHz, CD3OD) δ 7.82 (d, J = 1.5 Hz, 1H), 7.52 (d, J = 1.0 Hz, 1H), 3.87 (d, J = 7.0 Hz, 2H), 2.45 (s, 3H), 2.29 (s, 3H), 1.30-1.18 (m, 1H), 0.60-0.52 (m, 2H), 0.47-0.43 (m, 2H). ESI m/z 329 [M + H]+. | >99 |

TABLE 2-continued

Example Compounds

| Example Compound | Chemical Name | Structure | General procedure | Characterization | Purity HPLC (%) |
|---|---|---|---|---|---|
| 146 | 1-benzyl-6-(3,5-dimethyl-isoxazol-4-yl)-N-methyl-1H-imidazo[4,5-b]pyridin-2-amine | 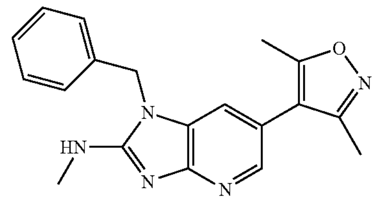 [SMILES: CNc1nc2ncc(-c3c(C)noc3C)cc2n1Cc1ccccc1] | Q | $^1$H NMR (500 MHz, DMSO-d6) δ 7.96 (d, J = 2.0 Hz, 1H), 7.42 (d, J = 1.0 Hz, 1H), 7.40-7.36 (br s, 1H), 7.35-7.31 (m, 2H), 7.28-7.23 (m, 3H), 5.29 (s, 2H), 3.00 (d, J = 4.6 Hz, 3H), 2.34 (s, 3H), 2.15 (s, 3H); ESI m/z 334 [M + H]+. | >99 |
| 147 | N,1-dibenzyl-6-(3,5-dimethyl-isoxazol-4-yl)-4-nitro-1H-benzo[d]imidazol-2-amine | 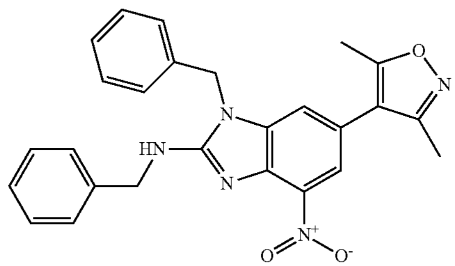 [SMILES: Cc1noc(C)c1-c1cc([N+](=O)[O-])c2nc(NCc3ccccc3)n(Cc3ccccc3)c2c1] | I | $^1$H NMR (300 MHz, DMSO-d6) δ 8.25 (t, J = 5.4 Hz, 1H), 7.69 (s, 1H), 7.50 (s, 1H), 7.39-7.22 (m, 10H), 5.44 (s, 2H), 4.77 (d, J = 5.7 Hz, 2H), 2.35 (s, 3H), 2.16 (s, 3H); ESI m/z 454 [M + H]+. | 97.9 |
| 148 | 1-benzyl-6-(3,5-dimethyl-isoxazol-4-yl)-4-nitro-N-(pyridin-3-ylmethyl)-1H-benzo[d]imidazol-2-amine | 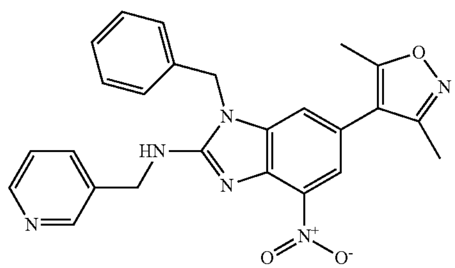 [SMILES: Cc1noc(C)c1-c1cc([N+](=O)[O-])c2nc(NCc3cccnc3)n(Cc3ccccc3)c2c1] | I | $^1$H NMR (300 MHz, DMSO-d6) δ 8.65 (d, J = 1.5 Hz, 1H), 8.47 (dd, J = 4.8, 1.5 Hz, 1H), 8.30 (t, J = 6.0 Hz, 1H), 7.81 (dt, J = 7.8, 1.8 Hz, 1H), 7.70 (d, J = 1.5 Hz, 1H), 7.51 (d, J = 1.5 Hz, 1H), 7.38-7.21 (m, 6H), 5.42 (s, 2H), 4.76 (d, J = 5.7 Hz, 2H), 2.34 (s, 3H), 2.16 (s, 3H); ESI m/z 455 [M + H]+. | 98.5 |
| 149 | 1-benzyl-6-(3,5-dimethyl-isoxazol-4-yl)-N-methyl-4-nitro-1H-benzo[d]imidazol-2-amine | 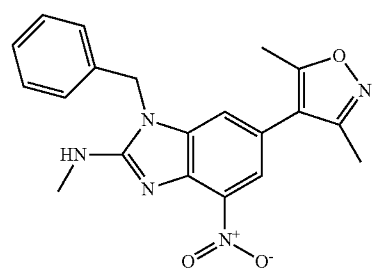 [SMILES: CNc1nc2c([N+](=O)[O-])cc(-c3c(C)noc3C)cc2n1Cc1ccccc1] | I | $^1$H NMR (300 MHz, DMSO-d6) δ 7.68-7.66 (m, 2H), 7.45 (d, J = 1.5 Hz, 1H), 7.37-7.22 (m, 5H), 5.37 (s, 2H), 3.06 (d, J = 4.8 Hz, 3H), 2.34 (s, 3H), 2.16 (s, 3H); ESI m/z 378 [M + H]+. | >99 |
| 150 | 1-benzyl-6-(3,5-dimethyl-isoxazol-4-yl)-3-methyl-4-nitro-1H-benzo[d]imidazol-2(3H)-one | 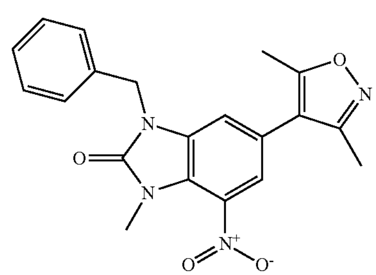 [SMILES: Cc1noc(C)c1-c1cc([N+](=O)[O-])c2c(c1)n(Cc1ccccc1)c(=O)n2C] | No general procedure | $^1$H NMR (300 MHz, CDCl3) δ 7.48 (d, J = 1.5 Hz, 1H), 7.35-7.30 (m, 5H), 6.84 (d, J = 1.5 Hz, 1H), 5.15 (s, 2H), 3.65 (s, 3H), 2.26 (s, 3H), 2.09 (s, 3H); ESI m/z 379 [M + H]+. | >99 |

TABLE 2-continued

Example Compounds

| Example Compound | Chemical Name | Structure | General procedure | Characterization | Purity HPLC (%) |
|---|---|---|---|---|---|
| 151 | 1-benzyl-6-(3,5-dimethyl-isoxazol-4-yl)-N2-methyl-1H-benzo[d]imidazole-2,4-diamine | 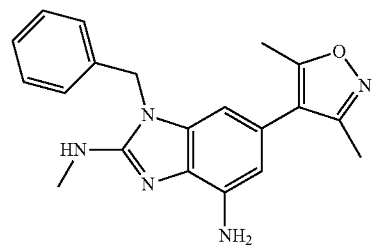 [SMILES: CNc1nc2c(N)cc(-c3c(C)noc3C)cc2n1Cc1ccccc1] | I | ¹H NMR (300 MHz, DMSO-d6) δ 7.33-7.20 (m, 5H), 6.63 (br.s, 1H), 6.32 (s, 1H), 6.23 (s, 1H), 5.17 (s, 2H), 4.86 (s, 2H), 2.94 (d, J = 4.5 Hz, 3H), 2.29 (s, 3H), 2.12 (s, 3H); ESI m/z 348 [M + H]+. | >99 |
| 152 | N2,1-dibenzyl-6-(3,5-dimethyl-isoxazol-4-yl)-1H-benzo[d]imidazole-2,4-diamine | 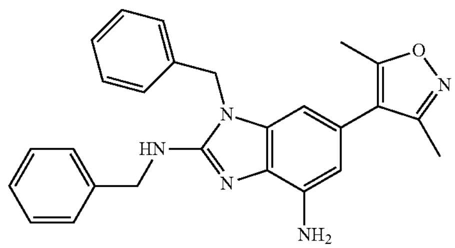 [SMILES: Cc1noc(C)c1-c1cc(N)c2nc(NCc3ccccc3)n(Cc3ccccc3)c2c1] | I | ¹H NMR (300 MHz, DMSO-d6) δ 7.37-7.22 (m, 11H), 6.35 (s, 1H), 6.22 (s, 1H), 5.26 (s, 2H), 4.83 (s, 2H), 4.65 (d, J = 5.7 Hz, 2H), 2.29 (s, 3H), 2.12 (s, 3H); ESI m/z 424 [M + H]+. | >99 |
| 153 | N,1-dibenzyl-6-(3,5-dimethyl-isoxazol-4-yl)-1H-imidazo[4,5-b]pyridin-2-amine | 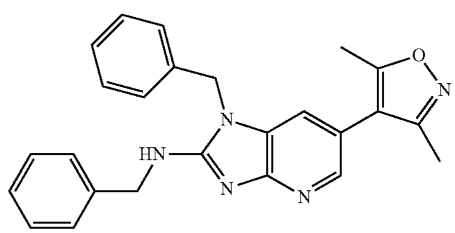 [SMILES: Cc1noc(C)c1-c1cnc2nc(NCc3ccccc3)n(Cc3ccccc3)c2c1] | Q | ¹H NMR (500 MHz, DMSO-d6) δ 7.98-7.95 (m, 2H), 7.44 (d, J = 2.0 Hz, 1H), 736-7.24 (m, 10H), 5.37 (s, 2H), 4.68 (d, J = 5.9 Hz, 2H), 2.34 (s, 3H), 2.15 (s, 3H); ESI m/z 410 [M + H]+. | >99 |
| 154 | 1-benzyl-2-methyl-6-(1-methyl-1H-pyrazol-5-yl)-1H-imidazo[4,5-b]pyridine | 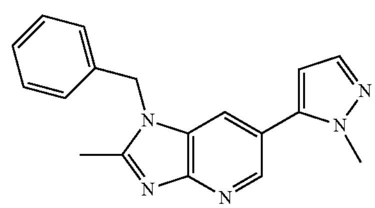 [SMILES: Cc1nc2ncc(-c3ccnn3C)cc2n1Cc1ccccc1] | No general procedure | ¹H NMR (500 MHz, DMSO-d6) δ 8.48 (d, J = 2.0 Hz, 1H), 8.14 (d, J = 2.0 Hz, 1H), 7.50 (d, J = 2.0 Hz, 1H), 7.35 (t, J = 7.0 Hz, 2H), 7.29 (t, J = 7.0 Hz, 1H), 7.21 (d, J = 7.0 Hz, 2H), 6.46 (d, J = 2.0 Hz, 1H), 5.57 (s, 2H), 3.83 (s, 3H), 2.60 (s, 3H); ESI m/z 304 [M + H]+. | 99.0 |
| 155 | N-(1-benzyl-2-methyl-1H-imidazo[4,5-b]pyridin-6-yl)-3,5-dimethyl-isoxazol-4-amine | 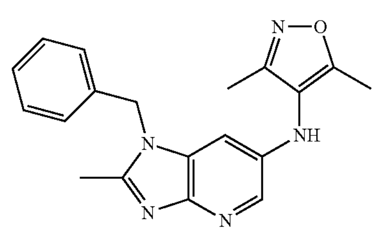 [SMILES: Cc1noc(C)c1Nc1cnc2nc(C)n(Cc3ccccc3)c2c1] | No general procedure | ¹H NMR (500 MHz, DMSO-d6) δ 7.88 (d, J = 2.5 Hz, 1H), 7.34-7.30 (m, 3H), 7.27 (t, J = 7.0 Hz, 1H), 7.05 (d, J = 7.0 Hz, 2H), 6.71 (d, J = 2.5 Hz, 1H), 5.38 (s, 2H), 2.47 (s, 3H), 2.14 (s, 3H), 1.92 (s, 3H); ESI m/z 334 [M + H]+. | >99 |
| 156 | 4-benzyl-6-(3,5-dimethyl-isoxazol-4-yl)-3,4-dihydro-quinoxalin-2(1H)-one | 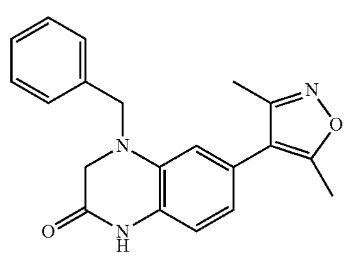 [SMILES: Cc1noc(C)c1-c1ccc2c(c1)N(Cc1ccccc1)CC(=O)N2] | No general procedure | ¹H NMR (500 MHz, DMSO-d6) δ 10.58 (s, 1H), 7.38-7.34 (m, 4H), 7.30-7.23 (m, 1H), 6.87 (d, J = 7.9 Hz, 1H), 6.65 (d, J = 7.9 Hz, 1H), 6.51 (s,1H), 4.46 (s, 2H), 3.86 (s, 2H), 2.15 (s, 3H), 1.97 (s, 3H); ESI m/z 334 [M + H]+. | >99 |

TABLE 2-continued

Example Compounds

| Example Compound | Chemical Name | Structure | General procedure | Characterization | Purity HPLC (%) |
|---|---|---|---|---|---|
| 157 | 1-benzyl-6-(3,5-dimethyl-isoxazol-4-yl)-N2-(pyridin-3-ylmethyl)-1H-benzo[d]imidazole-2,4-diamine | 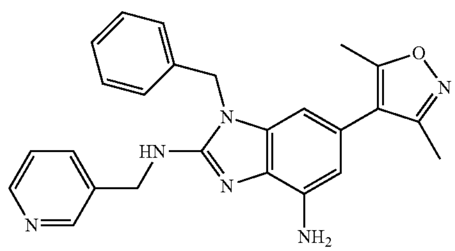 [SMILES: Cc1noc(C)c1-c1cc(N)c2nc(NCc3cccnc3)n(Cc3ccccc3)c2c1] | I | $^1$H NMR (300 MHz, DMSO-d6) δ 8.62 (d, J = 1.5 Hz, 1H), 8.44 (dd, J = 4.8, 1.5 Hz, 1H), 7.78 (dt, J = 7.8, 1.8 Hz, 1H), 7.35-7.20 (m, 7H), 6.35 (d, J = 1.5 Hz, 1H), 6.22 (d, J = 1.5 Hz, 1H), 5.24 (s, 2H), 4.87 (s, 2H), 4.64 (d, J = 5.7 Hz, 2H), 2.29 (s, 3H), 2.12 (s, 3H); ESI m/z 425 [M + H]+. | 97.9 |
| 158 | 4-(1-benzyl-4-fluoro-2-methyl-1H-benzo[d]imidazol-6-yl)-3,5-dimethylisoxazole | 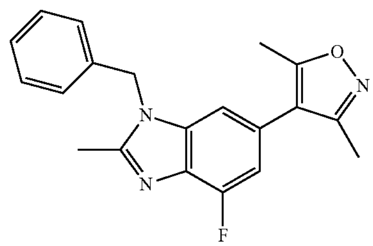 [SMILES: Cc1noc(C)c1-c1cc(F)c2nc(C)n(Cc3ccccc3)c2c1] | S | $^1$H NMR (300 MHz, DMSO-d6) d 7.38-7.26 (m, 4H), 7.22-7.19 (m, 2H), 7.03 (dd, J = 11.7, 1.2 Hz, 1H), 5.53 (s, 2H), 2.57 (s, 3H), 2.36 (s, 3H), 2.19 (s, 3H); ESI MS m/z 336 [M + H]+. | >99 |
| 159 | 1-(cyclopropyl-methyl)-6-(3,5-dimethyl-isoxazol-4-yl)-N-ethyl-4-nitro-1H-benzo[d]imidazol-2-amine | 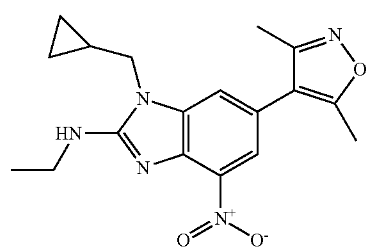 [SMILES: CCNc1nc2c([N+](=O)[O-])cc(-c3c(C)noc3C)cc2n1CC1CC1] | No general procedure | $^1$H NMR (500 MHz, CDCl3) δ 7.78 (d, J = 1.5 Hz, 1H), 7.44 (d, J = 1.5 Hz, 1H), 4.03 (d, J = 6.5 Hz, 2H), 3.67 (q, J = 7.0 Hz, 2H), 2.44 (s, 3H), 2.29 (s, 3H), 1.33 (t, J = 7.0 Hz, 3H), 1.30-1.18 (m, 1H), 0.60-0.52 (m, 2H), 0.47-0.41 (m, 2H). ESI m/z 356 [M + H]+. | >99 |
| 160 | 1-(cyclopropyl-methyl)-6-(3,5-dimethyl-isoxazol-4-yl)-N2-ethyl-1H-benzo[d]imidazole-2,4-diamine | 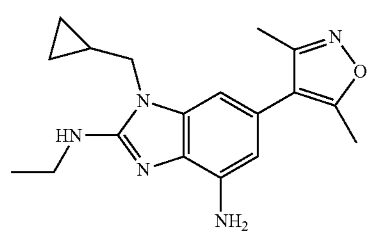 [SMILES: CCNc1nc2c(N)cc(-c3c(C)noc3C)cc2n1CC1CC1] | No general procedure | $^1$H NMR (500 MHz, CD3OD) δ 6.49 (d, J = 1.5 Hz, 1H), 6.37 (d, J = 1.5 Hz, 1H), 3.88 (d, J = 6.5 Hz, 2H), 3.48 (q, J = 7.0 Hz, 2H), 2.39 (s, 3H), 2.24 (s, 3H), 1.30 (t, J = 7.5 Hz, 3H), 1.28-1.18 (m, 1H), 0.53-0.48 (m, 2H), 0.40-0.35 (m, 2H). ESI m/z 326 [M + H]+. | >99 |
| 161 | 4-amino-1-(cyclopropyl-methyl)-6-(3,5-dimethyl-isoxazol-4-yl)-1H-benzo[d]imidazol-2(3H)-one | 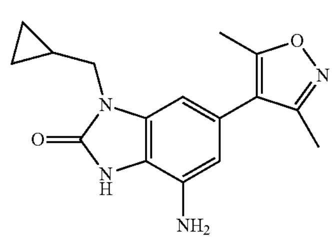 [SMILES: Cc1noc(C)c1-c1cc(N)c2[nH]c(=O)n(CC3CC3)c2c1] | No general procedure | $^1$H NMR (500 MHz, CD3OD) δ 6.49 (d, J = 1.5 Hz, 1H), 6.42 (d, J = 1.5 Hz, 1H), 3.75 (d, J = 6.5 Hz, 2H), 2.39 (s, 3H), 2.24 (s, 3H), 1.28-1.18 (m, 1H), 0.56-0.48 (m, 2H), 0.44-0.39 (m, 2H). ESI m/z 299 [M + H]+. | 97.4 |

TABLE 2-continued

Example Compounds

| Example Compound | Chemical Name | Structure | General procedure | Characterization | Purity HPLC (%) |
|---|---|---|---|---|---|
| 162 | 4-amino-1-benzyl-6-(3,5-dimethyl-isoxazol-4-yl)-3-methyl-1H-benzo[d]imidazol-2(3H)-one | 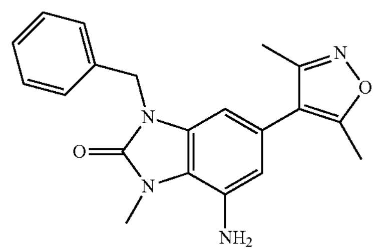 [SMILES: Cc1noc(C)c1-c1cc(N)c2c(c1)n(Cc1ccccc1)c(=O)n2C] | No general procedure | $^1$H NMR (300 MHz, DMSO-d6) δ 7.36-7.24 (m, 5H), 6.40 (d, J = 1.5 Hz, 1H), 6.39 (d, J = 1.8 Hz, 1H), 5.08 (s, 2H), 4.99 (s, 2H), 3.62 (s, 3H), 2.29 (s, 3H), 2.12 (s, 3H); ESI m/z 349 [M + H]+. | >99 |
| 163 | 1-benzyl-6-(3,5-dimethyl-isoxazol-4-yl)-4-fluoro-1H-benzo[d]imidazol-2(3H)-one | 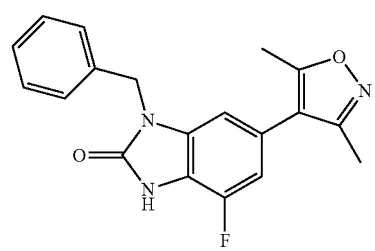 [SMILES: Cc1noc(C)c1-c1cc(F)c2[nH]c(=O)n(Cc3ccccc3)c2c1] | J | $^1$H NMR (300 MHz, DMSO-d6) d 11.7 (s, 1H), 7.39-7.27 (m, 5H), 6.96 (d, J = 1.2 Hz, 1H), 6.92 (s, 1H), 5.04 (s, 2H), 2.32 (s, 3H), 2.14 (s, 3H); ESI MS m/z 338 [M + H]+. | 90.3 |
| 164 | N-(1-benzyl-6-(3,5-dimethyl-isoxazol-4-yl)-3-methyl-2-oxo-2,3-dihydro-1H-benzo[d]imidazol-4-yl)acetamide | 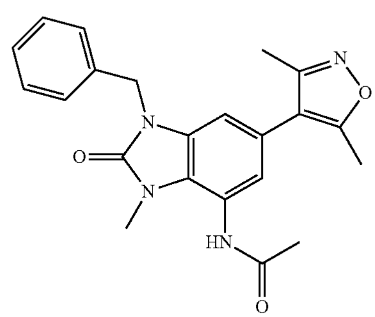 [SMILES: CC(=O)Nc1cc(-c2c(C)noc2C)cc2c1n(C)c(=O)n2Cc1ccccc1] | O | $^1$H NMR (300 MHz, DMSO-d6) δ 9.77 (s, 1H), 7.41-7.24 (m, 5H), 7.03 (d, J = 1.5 Hz, 1H), 6.77 (d, J = 1.5 Hz, 1H), 5.08 (s, 2H), 3.46 (s, 3H), 2.31 (s, 3H), 2.14 (s, 3H), 2.08 (s, 3H); ESI m/z 391 [M + H]+. | >99 |
| 165 | 4-(1-benzyl-2-(4-methyl-piperazin-1-yl)-1H-imidazo[4,5-b]pyridin-6-yl)-3,5-dimethylisoxazole | 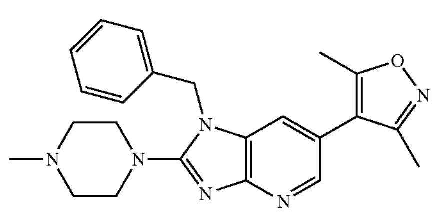 [SMILES: Cc1noc(C)c1-c1cnc2nc(N3CCN(C)CC3)n(Cc3ccccc3)c2c1] | Q | $^1$H NMR (500 MHz, DMSO-d6) δ 8.17 (d, J = 2.1 Hz, 1H), 7.57 (d, J = 2.1 Hz, 1H), 7.36-7.31 (m, 2H), 7.29-7.25 (m, 1H), 7.22-7.19 (m, 2H), 5.36 (s, 2H), 3.35-3.32 (m, 4H), 2.46-2.44 (m, 4H), 2.32 (s, 3H), 2.22 (s, 3H), 2.14 (s, 3H); ESI m/z 403 [M + H]+. | >99 |
| 166 | 4-benzyl-6-(1-methyl-1H-pyrazol-5-yl)-3,4-dihydroquinoxalin-2(1H)-one | 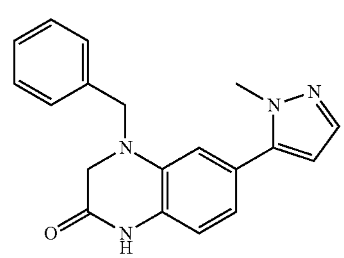 [SMILES: Cn1nccc1-c1ccc2c(c1)N(Cc1ccccc1)CC(=O)N2] | No general procedure | $^1$H NMR (500 MHz, DMSO-d6) δ 10.62 (s, 1H), 7.37-7.33 (m, 5H), 7.29-7.25 (m, 1H), 6.90 (d, J = 7.9 Hz, 1H), 6.80 (dd, J = 7.9, 1.8 Hz, 1H), 6.70 (d, J = 1.6 Hz, 1H), 6.18 (d, J = 1.8 Hz, 1H), 4.49 (s, 2H), 3.83 (s, 2H), 3.58 (s, 3H); ESI m/z 319 [M + H]+. | >99 |

TABLE 2-continued

Example Compounds

| Example Compound | Chemical Name | Structure | General procedure | Characterization | Purity HPLC (%) |
|---|---|---|---|---|---|
| 167 | 1-benzyl-6-(3,5-dimethylisoxazol-4-yl)-N-(2-methoxyethyl)-1H-imidazo[4,5-b]pyridin-2-amine | 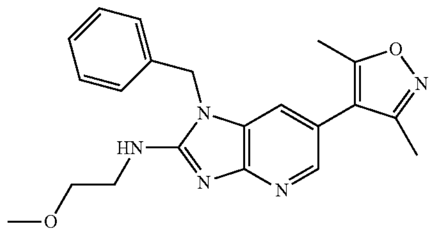 [SMILES: COCCNc1nc2ncc(-c3c(C)noc3C)cc2n1Cc1ccccc1] | Q | $^1$H NMR (500 MHz, DMSO-d6) δ 7.95 (d, J = 2.0 Hz, 1H), 7.54-7.50 (m, 1H), 7.40 (d, J = 2.0 Hz, 1H), 7.34-7.30 (m, 2H), 7.28-7.23 (m, 3H), 5.32 (s, 2H), 3.64-3.59 (m, 2H), 3.58-3.55 (m, 2H), 3.29 (s, 3H), 2.33 (s, 3H), 2.15 (s, 3H); ESI m/z 378 [M + H]+. | >99 |
| 168 | 4-(1-benzyl-2-methyl-4-(methylsulfonyl)-1H-benzo[d]imidazol-6-yl)-3,5-dimethyl-isoxazole | 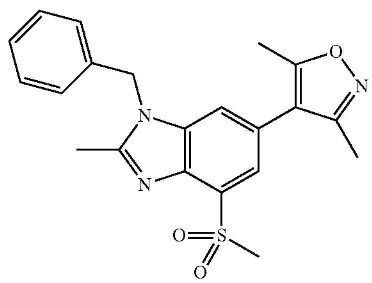 [SMILES: Cc1noc(C)c1-c1cc(S(C)(=O)=O)c2nc(C)n(Cc3ccccc3)c2c1] | No general procedure | $^1$H NMR (500 MHz, CDCl3) δ 7.75 (d, J = 1.5 Hz, 1H), 7.37-7.33 (m, 3H), 7.24 (d, J = 1.5 Hz, 1H), 7.11-7.08 (m, 2H), 5.39 (s, 2H), 3.54 (s, 3H), 2.73 (s, 3H), 2.31 (s, 3H), 2.16 (s, 3H); ESI m/z 396 [M + H]+. | 92.3 |
| 169 | 1-benzyl-6-(3,5-dimethyl-isoxazol-4-yl)-N-(pyridin-4-ylmethyl)-1H-imidazo[4,5-b]pyridin-2-amine | 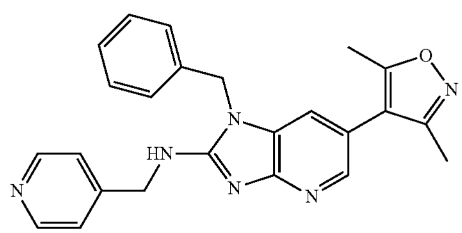 [SMILES: Cc1noc(C)c1-c1cnc2nc(NCc3ccncc3)n(Cc3ccccc3)c2c1] | Q | $^1$H NMR (300 MHz, DMSO-d6) δ 8.50-8.46 (m, 2H), 8.08 (t, J = 5.9 Hz, 1H), 7.97 (d, J = 2.0 Hz, 1H), 7.51 (d, J = 2.0 Hz, 1H), 7.40-7.25 (m, 7H), 5.40 (s, 2H), 4.69 (d, J = 5.9 Hz, 2H), 2.34 (s, 3H), 2.16 (s, 3H); ESI m/z 411 [M + H]+. | 98.0 |
| 170 | 1-benzyl-6-(3,5-dimethyl-isoxazol-4-yl)-N-(tetrahydro-2H-pyran-4-yl)-1H-imidazo[4,5-b]pyridin-2-amine | 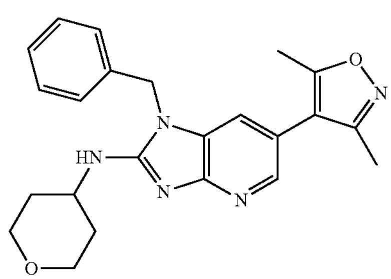 [SMILES: Cc1noc(C)c1-c1cnc2nc(NC3CCOCC3)n(Cc3ccccc3)c2c1] | Q | $^1$H NMR (300 MHz, DMSO-d6) δ 7.96 (d, J = 2.0 Hz, 1H), 7.39 (d, J = 2.0 Hz, 1H), 7.37-7.22 (m, 6H), 5.35 (s, 2H), 4.14-3.98 (m, 1H), 3.95-3.86 (m, 2H), 3.50-3.38 (m, 2H), 2.33 (s, 3H), 2.14 (s, 3H), 2.00-1.91 (m, 2H), 1.68-1.50 (m, 2H); ESI m/z 404 [M + H]+. | >99 |
| 171 | 1-benzyl-6-(1-methyl-1H-pyrazol-5-yl)-1H-imidazo[4,5-b]pyridin-2(3H)-one | 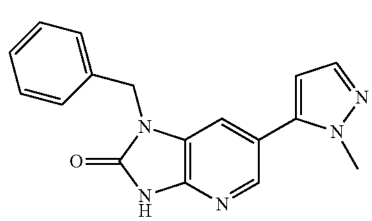 [SMILES: Cn1nccc1-c1cnc2[nH]c(=O)n(Cc3ccccc3)c2c1] | No general procedure | $^1$H NMR (500 MHz, DMSO-d6) δ 11.87 (s, 1H), 8.04 (d, J = 1.5 Hz, 1H), 7.57 (d, J = 1.5,1H), 7.46 (d, J = 2.0 Hz, 1H), 7.38 (d, J = 7.5 Hz, 2H), 7.34 (t, J = 7.5 Hz, 2H), 7.27 (t, J = 7.0 Hz, 1H), 6.37 (d, J = 1.5 Hz, 1H), 5.06 (s, 2H), 3.77 (s, 3H); ESI m/z 306 [M + H]+. | >99 |

TABLE 2-continued

Example Compounds

| Example Compound | Chemical Name | Structure | General procedure | Characterization | Purity HPLC (%) |
|---|---|---|---|---|---|
| 172 | (S)-6-(3,5-dimethyl-isoxazol-4-yl)-4-nitro-1-(1-phenylethyl)-1H-benzo[d]imidazol-2(3H)-one | 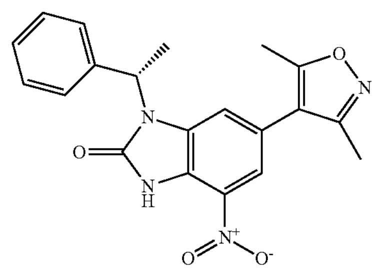 [SMILES: Cc1noc(C)c1-c1cc([N+](=O)[O-])c2[nH]c(=O)n([C@@H](C)c3ccccc3)c2c1] | P | $^1$H NMR (300 MHz, DMSO-d6) d 12.1 (s, 1H), 7.68 (d, J = 1.5 Hz, 1H), 7.45-7.29 (m, 5H), 7.13 (d, J = 1.2 Hz, 1H), 5.79 (q, J = 7.2 Hz, 1H), 2.25 (s, 3H), 2.04 (s, 3H), 1.88 (d, J = 7.2 Hz, 3H); ESI MS m/z 379 [M + H]+. | >99 |
| 173 | 1-benzyl-6-(3,5-dimethyl-isoxazol-4-yl)-2-methyl-1H-benzo[d]imidazol-4-ol | 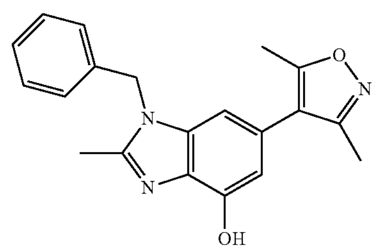 [SMILES: Cc1noc(C)c1-c1cc(O)c2nc(C)n(Cc3ccccc3)c2c1] | No general procedure | $^1$H NMR (500 MHz, DMSO-d6) δ 9.84 (s, 1H), 7.33 (t, J = 7.6 Hz, 2H), 7.26 (t, J = 7.3 Hz, 1H), 7.18 (d, J = 7.1 Hz, 2H), 6.86 (d, J = 1.3 Hz, 1H), 6.47 (d, J = 1.3 Hz, 1H), 5.42 (s, 2H), 2.52 (s, 3H), 2.33 (s, 3H), 2.15 (s, 3H); ESI m/z 334 [M + H]+. | >99 |
| 174 | (R)-4-benzyl-6-(3,5-dimethyl-isoxazol-4-yl)-3-methyl-3,4-dihydro-quinoxalin-2(1H)-one | 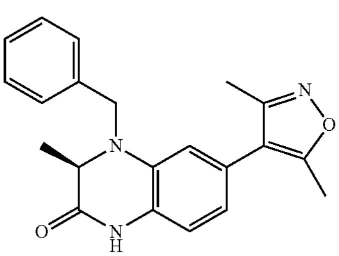 [SMILES: Cc1noc(C)c1-c1ccc2c(c1)N(Cc1ccccc1)[C@H](C)C(=O)N2] | No general procedure | $^1$H NMR (500 MHz, DMSO-d6) δ 10.53 (s, 1H), 7.37-7.32 (m, 4H), 7.26-7.23 (m, 1H), 6.88 (d, J = 7.9 Hz, 1H), 6.66 (dd, J = 7.9, 1.7 Hz, 1H), 6.42 (d, J = 1.5 Hz, 1H), 4.54 (d, J = 15.6 Hz, 1H), 4.37 (d, J = 15.7 Hz, 1H), 3.98 (q, J = 6.7 Hz, 1H), 2.11 (s, 3H), 1.93 (s, 3H), 1.12 (d, J = 6.7 Hz, 3H); ESI m/z 348 [M + H]+. | 98.7 |
| 175 | 4-(1-benzyl-6-(1-methyl-1H-pyrazol-5-yl)-1H-imidazo[4,5-b]pyridin-2-yl)morpholine | 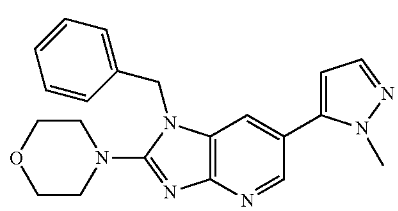 [SMILES: Cn1nccc1-c1cnc2nc(N3CCOCC3)n(Cc3ccccc3)c2c1] | Q | $^1$H NMR (500 MHz, DMSO-d6) δ 8.33 (d, J = 1.5 Hz, 1H), 7.74 (d, J = 1.5 Hz, 1H), 7.46 (d, J = 1.5 Hz, 1H), 7.34 (t, J = 7.5 Hz, 2H), 7.27 (t, J = 7.5 Hz, 1H), 7.20 (d, J = 7.0 Hz, 2H), 6.38 (d, J = 1.5 Hz, 1H), 5.42 (s, 2H), 3.76 (s, 3H), 3.72 (t, J = 4.5 Hz, 4H), 3.34 (t, J = 4.5 Hz, 4H); ESI m/z 375 [M + H]+. | 95.6 |

TABLE 2-continued

Example Compounds

| Example Compound | Chemical Name | Structure | General procedure | Characterization | Purity HPLC (%) |
|---|---|---|---|---|---|
| 176 | 1-benzyl-6-(1-methyl-1H-pyrazol-5-yl)-N-(tetrahydro-2H-pyran-4-yl)-1H-imidazo[4,5-b]pyridin-2-amine | 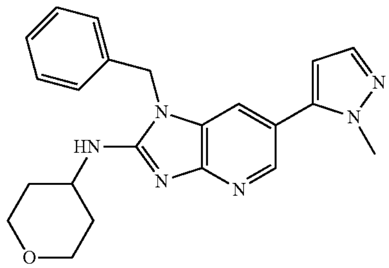 [SMILES: Cn1nccc1-c1cnc2nc(NC3CCOCC3)n(Cc3ccccc3)c2c1] | Q | $^1$H NMR (500 MHz, DMSO-d6) δ 8.10 (d, J = 2.0 Hz, 1H), 7.53 (d, J = 2.0 Hz, 1H), 7.43 (d, J = 2.0 Hz, 1H), 7.33 (t, J = 7.0 Hz, 2H), 7.28-7.21 (m, 4H), 6.32 (d, J = 1.5 Hz, 1H), 5.37 (s, 2H), 4.11-4.04 (m, 1H), 3.91 (dd, J = 10.0, 2.0 Hz, 2H), 3.75 (s, 3H), 3.44 (td, J = 12.0, 2.0 Hz, 2H), 1.96 (dd, J = 12.5, 2.0 Hz, 2H), 1.60 (qd, J = 12.0, 4.0 Hz, 2H); ESI m/z 389 [M + H]+. | >99 |
| 177 | 4-amino-1-benzyl-6-(3,5-dimethyl-isoxazol-4-yl)-1H-benzo[d]imidazole-2(3H)-thione | 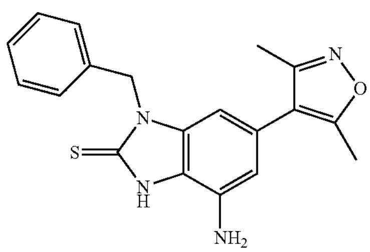 [SMILES: Cc1noc(C)c1-c1cc(N)c2[nH]c(=S)n(Cc3ccccc3)c2c1] | No general procedure | $^1$H NMR (300 MHz, DMSO-d6) δ 12.56 (s, 1H), 7.45-7.42 (m, 2H), 7.34-7.25 (m, 3H), 6.44 (d, J = 1.2 Hz, 1H), 6.39 (d, J = 1.5 Hz, 1H), 5.44 (s, 4H), 2.29 (s, 3H), 2.11 (s, 3H); ESI m/z 351 [M + H]+. | 98.6 |
| 178 | (S)-4-amino-6-(3,5-dimethyl-isoxazol-4-yl)-1-(1-phenylethyl)-1H-benzo[d]imidazol-2(3H)-one | 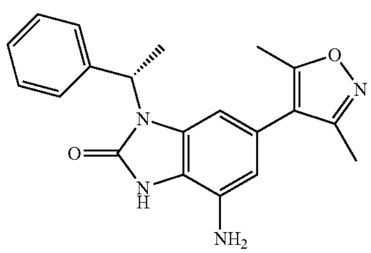 [SMILES: Cc1noc(C)c1-c1cc(N)c2[nH]c(=O)n([C@@H](C)c3ccccc3)c2c1] | P | $^1$H NMR (300 MHz, DMSO-d6) d 10.5 (s, 1H), 7.41-7.26 (m, 5H), 6.24 (d, J = 1.5 Hz, 1H), 5.97 (d, J = 1.2 Hz, 1H), 5.65 (q, J = 7.2 Hz, 1H), 5.04 (s, 2H), 2.19 (s, 3H), 2.01 (s, 3H), 1.79 (d, J = 7.2 Hz, 3H); ESI MS m/z 349 [M + H]+. | >99 |
| 179 | (R)-4-amino-6-(3,5-dimethyl-isoxazol-4-yl)-1-(1-phenylethyl)-1H-benzo[d]imidazol-2(3H)-one | 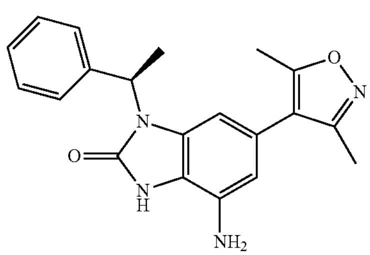 [SMILES: Cc1noc(C)c1-c1cc(N)c2[nH]c(=O)n([C@H](C)c3ccccc3)c2c1] | P | $^1$H NMR (300 MHz, DMSO-d6) d 10.5 (s, 1H), 7.41-7.26 (m, 5H), 6.24 (d, J = 1.5 Hz, 1H), 5.97 (d, J = 1.2 Hz, 1H), 5.65 (q, J = 7.2 Hz, 1H), 5.04 (s, 2H), 2.19 (s, 3H), 2.01 (s, 3H), 1.79 (d, J = 7.2 Hz, 3H); ESI MS m/z 349 [M + H]+. | >99 |
| 180 | 1-benzyl-6-(3,5-dimethyl-isoxazol-4-yl)-7-methyl-1H-imidazo[4,5-b]pyridin-2(3H)-one | 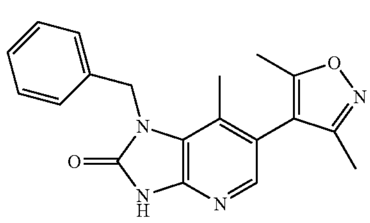 [SMILES: Cc1noc(C)c1-c1cnc2[nH]c(=O)n(Cc3ccccc3)c2c1C] | No general procedure | $^1$H NMR (300 MHz, DMSO-d6) δ 11.89 (s, 1H), 7.74 (s, 1H), 7.38-7.24 (m, 3H), 7.17-7.14 (m, 2H), 5.26 (s, 2H), 2.16 (s, 3H), 2.01 (s, 3H), 1.99 (s, 3H); ESI m/z 335 [M + H]+. | 94.3 |

TABLE 2-continued

Example Compounds

| Example Compound | Chemical Name | Structure | General procedure | Characterization | Purity HPLC (%) |
|---|---|---|---|---|---|
| 181 | 4-(1-benzyl-2,7-dimethyl-1H-imidazo[4,5-b]pyridin-6-yl)-3,5-dimethyl-isoxazole | 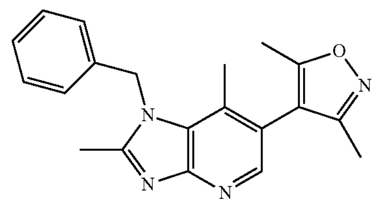 [SMILES: Cc1noc(C)c1-c1cnc2nc(C)n(Cc3ccccc3)c2c1C] | No general procedure | $^1$H NMR (300 MHz, CDCl3) δ 8.23 (s, 1H), 7.37-7.31 (m, 3H), 6.95-6.92 (m, 2H), 5.58 (s, 2H), 2.64 (s, 3H), 2.23 (s, 3H), 2.22 (s, 3H), 2.06 (s, 3H); ESI m/z 333 [M + H]+. | 98.7 |
| 182 | 4-(1-benzyl-6-(3,5-dimethyl-isoxazol-4-yl)-2-methyl-1H-benzo[d]imidazol-4-yl)morpholine | 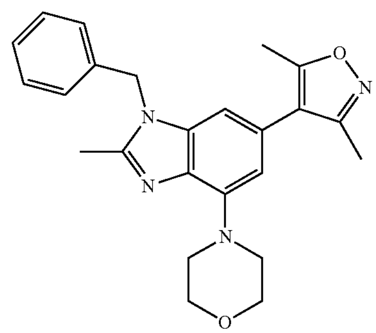 [SMILES: Cc1noc(C)c1-c1cc(N2CCOCC2)c2nc(C)n(Cc3ccccc3)c2c1] | K | $^1$H NMR (300 MHz, CDCl3) δ 7.31-7.29 (m, 3H), 7.07-7.04 (m, 2H), 6.61 (d, J = 1.2 Hz, 1H), 6.42 (d, J = 1.2 Hz, 1H), 5.30 (s, 2H), 4.00 (t, J = 4.5 Hz, 4H), 3.58 (t, J = 4.5 Hz, 4H), 2.58 (s, 3H), 2.32 (s, 3H), 2.18 (s, 3H); ESI m/z 403 [M + H]+. | >99 |
| 183 | 1-(1-benzyl-6-(3,5-dimethyl-isoxazol-4-yl)-2-methyl-1H-benzo[d]imidazol-4-yl)azetidin-2-one | 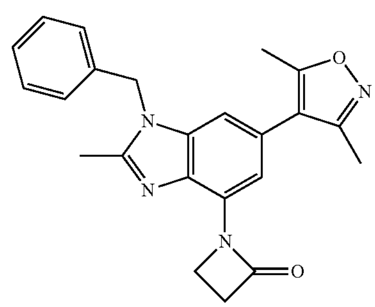 [SMILES: Cc1noc(C)c1-c1cc(N2CCC2=O)c2nc(C)n(Cc3ccccc3)c2c1] | K | $^1$H NMR (300 MHz, CDCl3) δ 7.75 (d, J = 1.2 Hz, 1H), 7.35-7.29 (m, 3H), 7.07-7.05 (m, 2H), 6.72 (d, J = 1.5 Hz, 1H), 5.31 (s, 2H), 4.32 (t, J = 4.5 Hz, 2H), 3.22 (t, J = 4.5 Hz, 2H), 2.60 (s, 3H), 2.33 (s, 3H), 2.19 (s, 3H); ESI m/z 387 [M + H]+. | >99 |
| 184 | 1-benzyl-2-methyl-6-(1,3,5-trimethyl-1H-pyrazol-4-yl)-1H-benzo[d]imidazol-4-amine | 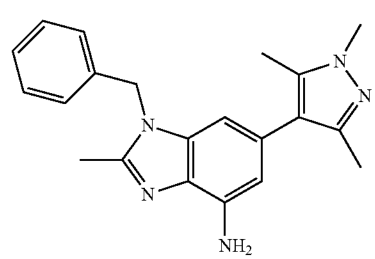 [SMILES: Cc1nn(C)c(C)c1-c1cc(N)c2nc(C)n(Cc3ccccc3)c2c1] | U | $^1$H NMR (300 MHz, DMSO-d6) δ 7.35-7.16 (m, 5H), 6.40 (d, J = 1.2 Hz, 1H), 6.23 (d, J = 1.2 Hz, 1H), 5.35 (s, 2H), 5.18 (s, 2H), 3.66 (s, 3H), 2.50 (s, 3H), 2.13 (s, 3H), 2.04 (s, 3H); ESI MS m/z 346 [M + H]+. | >99 |
| 185 | 1-benzyl-6-(3,5-dimethyl-isoxazol-4-yl)-N-(pyridin-3-ylmethyl)-1H-imidazo[4,5-b]pyridin-2-amine | 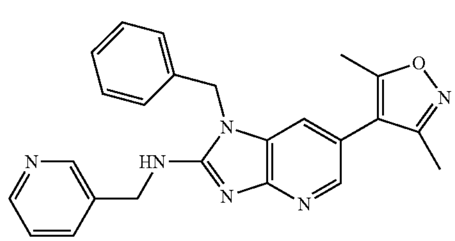 [SMILES: Cc1noc(C)c1-c1cnc2nc(NCc3cccnc3)n(Cc3ccccc3)c2c1] | Q | $^1$H NMR (300 MHz, DMSO-d6) δ 8.60 (d, J = 1.6 Hz, 1H), 8.46 (dd, J = 4.7, 1.6 Hz, 1H), 8.08-8.01 (m, 1H), 7.97 (d, J = 2.0 Hz, 1H), 7.77-7.72 (m, 1H), 7.48 (d, J = 2.0 Hz, 1H), 7.38-7.20 (m, 6H), 5.36 (s, 2H), 4.69 (d, J = 5.8 Hz, 2H), 2.34 (s, 3H), 2.16 (s, 3H); ESI m/z 411 [M + H]+. | >99 |

TABLE 2-continued

Example Compounds

| Example Compound | Chemical Name | Structure | General procedure | Characterization | Purity HPLC (%) |
|---|---|---|---|---|---|
| 186 | 4-(4-bromo-2-methyl-1-phenethyl-1H-benzo[d]imidazol-6-yl)-3,5-dimethyl-isoxazole | 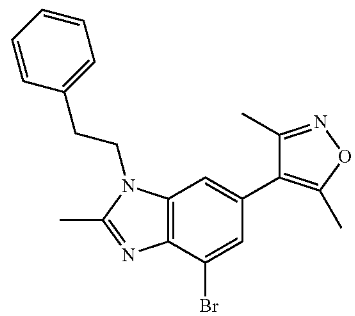 [SMILES: Cc1noc(C)c1-c1cc(Br)c2nc(C)n(CCc3ccccc3)c2c1] | H | ¹H NMR (500 MHz, DMSO-d6) δ 7.51 (s, 1H), 7.33 (s, 1H), 7.25-7.17 (m, 3H), 7.10 (d, J = 7.0 Hz, 2H), 4.45 (t, J = 7.0 Hz, 2H), 3.03 (t, J = 7.0 Hz, 2H), 2.40 (s, 3H), 2.29 (s, 3H), 2.23 (s, 3H); ESI m/z 410 [M + H]+. | >99 |
| 187 | 4-(4-bromo-2-methyl-1-(3-phenylpropyl)-1H-benzo[d]imidazol-6-yl)-3,5-dimethyl-isoxazole | 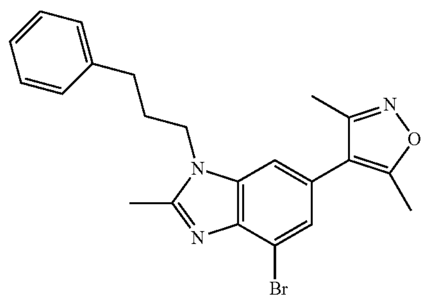 [SMILES: Cc1noc(C)c1-c1cc(Br)c2nc(C)n(CCCc3ccccc3)c2c1] | H | ¹H NMR (500 MHz, DMSO-d6) δ 7.49 (d, J = 1.5 Hz, 1H), 7.35 (d, J = 1.5 Hz, 1H), 7.26 (t, J = 7.5 Hz, 2H), 7.20 (d, J = 7.0 Hz, 2H), 7.17 (t, J = 7.0 Hz, 1H), 4.25 (t, J = 7.5 Hz, 2H), 2.65 (t, J = 7.5 Hz, 2H), 2.55 (s, 3H), 2.41 (s, 3H), 2.23 (s, 3H), 2.06-2.00 (m, 2H); ESI m/z 424 [M + H]+. | 98.6 |
| 188 | 4-(7-bromo-2-methyl-1-(3-phenylpropyl)-1H-benzo[d]imidazol-5-yl)-3,5-dimethyl-isoxazole | 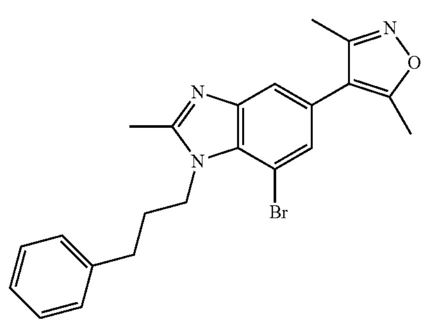 [SMILES: Cc1noc(C)c1-c1cc(Br)c2c(c1)nc(C)n2CCCc1ccccc1] | H | ¹H NMR (500 MHz, DMSO-d6) δ 7.53 (d, J = 1.0 Hz, 1H), 7.34 (d, J = 1.5 Hz, 1H), 7.32-7.23 (m, 4H), 7.20 (t, J = 7.0 Hz, 1H), 4.43 (t, J = 8.0 Hz, 2H), 2.76 (t, J = 8.0 Hz, 2H), 2.53 (s, 3H), 2.39 (s, 3H), 2.21 (s, 3H), 2.11-2.04 (m, 2H); ESI m/z 424 [M + H]+. | 99.0 |
| 189 | 4-(4-bromo-2-methyl-1-(2-phenoxyethyl)-1H-benzo[d]imidazol-6-yl)-3,5-dimethyl-isoxazole | 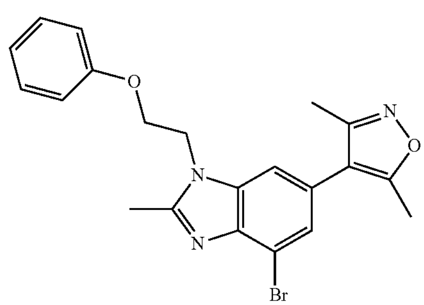 [SMILES: Cc1noc(C)c1-c1cc(Br)c2nc(C)n(CCOc3ccccc3)c2c1] | H | ¹H NMR (500 MHz, DMSO-d6) δ 7.63 (d, J = 1.0 Hz, 1H), 7.36 (d, J = 1.5 Hz, 1H), 7.24 (td, J = 7.0, 2.0 Hz, 2H), 6.90 (t, J = 7.0 Hz, 1H), 6.84 (d, J = 8.0 Hz, 2H), 4.66 (t, J = 5.0 Hz, 2H), 4.30 (t, J = 5.0 Hz, 2H), 2.67 (s, 3H), 2.41 (s, 3H), 2.24 (s, 3H); ESI m/z 426 [M + H]+. | >99 |

TABLE 2-continued

Example Compounds

| Example Compound | Chemical Name | Structure | General procedure | Characterization | Purity HPLC (%) |
|---|---|---|---|---|---|
| 190 | 4-(7-bromo-2-methyl-1-(2-phenoxyethyl)-1H-benzo[d]imidazol-5-yl)-3,5-dimethylisoxazole | 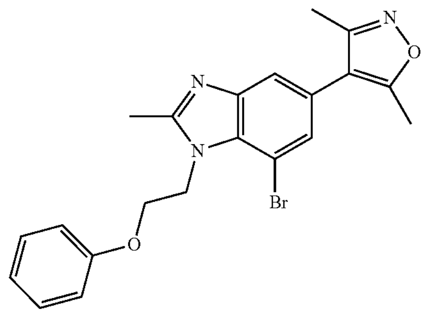 [SMILES: Cc1noc(C)c1-c1cc(Br)c2c(c1)nc(C)n2CCOc1ccccc1] | H | $^1$H NMR (500 MHz, DMSO-d6) δ 7.55 (d, J = 1.5 Hz, 1H), 7.39 (d, J = 1.0 Hz, 1H), 7.26 (t, J = 8.0 Hz, 2H), 6.94-6.89 (m, 3H), 4.89 (t, J = 5.0 Hz, 2H), 4.40 (t, J = 5.0 Hz, 2H), 2.67 (s, 3H), 2.39 (s, 3H), 2.21 (s, 3H); ESI m/z 426 [M + H]+. | >99 |
| 191 | 4-(1-(cyclohexylmethyl)-2-methyl-1H-imidazo[4,5-b]pyridin-6-yl)-3,5-dimethylisoxazole | 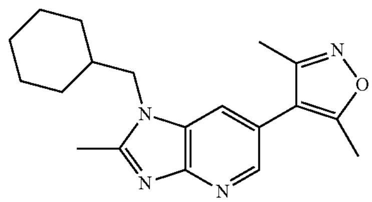 [SMILES: Cc1noc(C)c1-c1cnc2nc(C)n(CC3CCCCC3)c2c1] | No general procedure | $^1$H NMR (500 MHz, CD3OD) δ 8.30 (d, J = 1.5 Hz, 1H), 7.96 (d, J = 2.0 Hz, 1H), 4.14 (d, J = 7.5 Hz, 2H), 2.69 (s, 3H), 2.44 (s, 3H), 2.28 (s, 3H), 1.95-1.82 (m, 1H), 1.76-1.50 (m, 5H), 1.29-1.07 (m, 5H). ESI m/z 325 [M + H]+. | >99 |
| 192 | 4-(1-(cyclopentylmethyl)-2-methyl-1H-imidazo[4,5-b]pyridin-6-yl)-3,5-dimethylisoxazole | 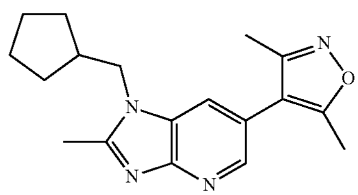 [SMILES: Cc1noc(C)c1-c1cnc2nc(C)n(CC3CCCC3)c2c1] | No general procedure | $^1$H NMR (500 MHz, CD3OD) δ 8.30 (d, J = 2.0 Hz, 1H), 7.98 (d, J = 2.0 Hz, 1H), 4.26 (d, J = 8.0 Hz, 2H), 2.71 (s, 3H), 2.49-2.38 (m, 1H), 2.44 (s, 3H), 2.28 (s, 3H), 1.80-1.68 (m, 4H), 1.66-1.57 (m, 2H), 1.40-1.27 (m, 2H). ESI m/z 311 [M + H]+. HPLC 98.5%. | 98.5 |
| 193 | 4-(1-(cyclobutylmethyl)-2-methyl-1H-imidazo[4,5-b]pyridin-6-yl)-3,5-dimethylisoxazole | 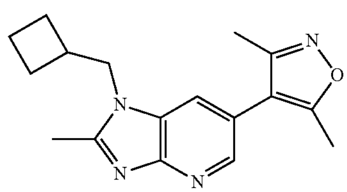 [SMILES: Cc1noc(C)c1-c1cnc2nc(C)n(CC3CCC3)c2c1] | No general procedure | $^1$H NMR (500 MHz, CD3OD) δ 8.30 (d, J = 1.5 Hz, 1H), 8.00 (d, J = 1.5 Hz, 1H), 4.33 (d, J = 7.0 Hz, 2H), 2.92-2.80 (m, 1H), 2.70 (s, 3H), 2.45 (s, 3H), 2.28 (s, 3H), 2.10-1.98 (m, 2H), 1.96-1.81 (m, 4H). ESI m/z 297 [M + H]+. | 97.9 |
| 194 | 1-benzyl-6-(3,5-dimethylisoxazol-4-yl)-N-(pyridin-2-ylmethyl)-1H-imidazo[4,5-b]pyridin-2-amine | 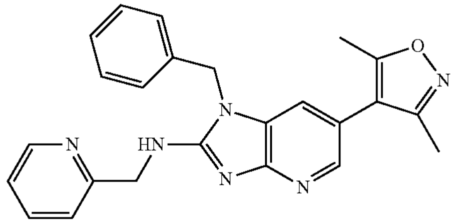 [SMILES: Cc1noc(C)c1-c1cnc2nc(NCc3ccccn3)n(Cc3ccccc3)c2c1] | Q | $^1$H NMR (300 MHz, DMSO-d6) δ 8.56-8.51 (m, 1H), 8.11 (t, J = 6.2 Hz, 1H), 7.95 (d, J = 2.0 Hz, 1H), 7.72 (td, J = 7.7 Hz, 1.8 Hz, 1H), 7.47 (d, J = 2.0 Hz, 1H), 7.38-7.25 (m, 7H), 5.40 (s, 2H), 4.75 (d, J = 5.9 Hz, 2H), 2.34 (s, 3H), 2.16 (s, 3H); ESI m/z 411 [M + H]+. | >99 |

TABLE 2-continued

Example Compounds

| Example Compound | Chemical Name | Structure | General procedure | Characterization | Purity HPLC (%) |
|---|---|---|---|---|---|
| 195 | 4-(1-benzyl-2-(pyrrolidin-1-yl)-1H-imidazo[4,5-b]pyridin-6-yl)-3,5-dimethylisoxazole | 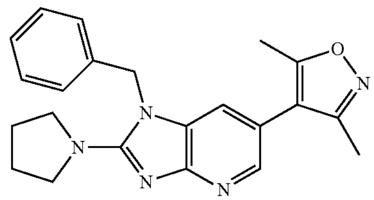 [SMILES: Cc1noc(C)c1-c1cnc2nc(N3CCCC3)n(Cc3ccccc3)c2c1] | Q | $^1$H NMR (300 MHz, DMSO-d6) δ 8.04 (d, J = 2.0 Hz, 1H), 7.53 (d, J = 2.0 Hz, 1H), 7.37-7.22 (m, 3H), 7.16-7.09 (m, 2H), 5.51 (s, 2H), 3.61 (m, 4H), 2.35 (s, 3H), 2.17 (s, 3H), 1.91-1.86 (m, 4H); ESI m/z 374 [M + H]+. | >99 |
| 196 | 2-((1-benzyl-6-(3,5-dimethyl-isoxazol-4-yl)-1H-imidazo[4,5-b]pyridin-2-yl)amino)ethanol | 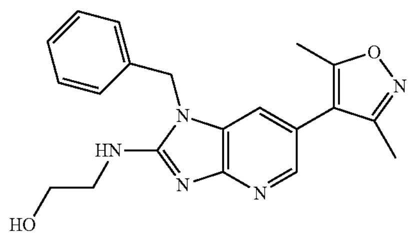 [SMILES: Cc1noc(C)c1-c1cnc2nc(NCCO)n(Cc3ccccc3)c2c1] | Q | $^1$H NMR (300 MHz, DMSO-d6) δ 7.95 (d, J = 2.0 Hz, 1H), 7.48 (t, J = 5.5 Hz, 1H), 7.38 (d, J = 2.0 Hz, 1H), 7.36-7.22 (m, 5H), 5.32 (s, 2H), 4.87 (t, J = 5.4 Hz, 1H), 3.66-3.60 (m, 2H), 3.54-3.48 (m, 2H), 2.33 (s, 3H), 2.14 (s, 3H); ESI m/z 364 [M + H]+. | >99 |
| 197 | 1-(1-benzyl-6-(3,5-dimethyl-isoxazol-4-yl)-2-methyl-1H-benzo[d]imidazol-4-yl)azetidin-3-ol | 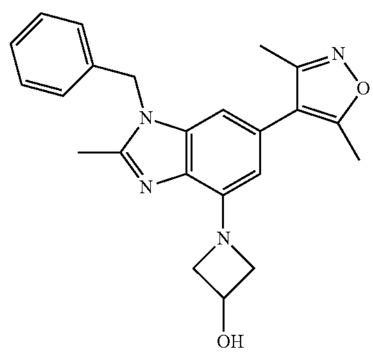 [SMILES: Cc1noc(C)c1-c1cc(N2CC(O)C2)c2nc(C)n(Cc3ccccc3)c2c1] | K | $^1$H NMR (300 MHz, CDCl3) δ 7.36-7.24 (m, 3H), 7.18-7.15 (m, 2H), 6.73 (d, J = 1.5 Hz, 1H), 5.95 (d, J = 1.5 Hz, 1H), 5.54 (d, J = 6.6 Hz, 1H), 5.40 (s, 2H), 4.58-4.53 (m, 1H), 4.37 (dd, J = 8.7, 6.3 Hz, 2H), 3.78 (dd, J = 8.7, 5.4 Hz, 2H), 2.50 (s, 3H), 2.33 (s, 3H), 2.16 (s, 3H); ESI m/z 389 [M + H]+. | 94.1 |
| 198 | 1-benzyl-3-methyl-6-(1-methyl-1H-pyrazol-5-yl)-4-nitro-1H-benzo[d]imidazol-2(3H)-one | 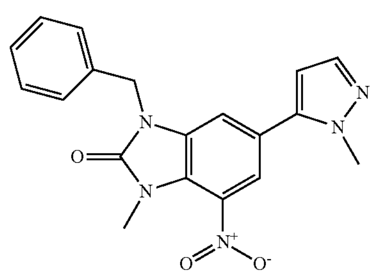 [SMILES: Cn1nccc1-c1cc([N+](=O)[O-])c2c(c1)n(Cc1ccccc1)c(=O)n2C] | No general procedure | $^1$H NMR (300 MHz, CDCl3) δ 7.66 (d, J = 1.5 Hz, 1H), 7.50 (d, J = 1.8 Hz, 1H), 7.36-7.30 (m, 5H), 7.02 (d, J = 1.5 Hz, 1H), 6.27 (d, J = 1.2 Hz, 1H), 5.16 (s, 2H), 3.69 (s, 3H), 3.65 (s, 3H); ESI m/z 364 [M + H]+. | >99 |
| 199 | 4-amino-1-benzyl-3-methyl-6-(1-methyl-1H-pyrazol-5-yl)-1H-benzo[d]imidazol-2(3H)-one | 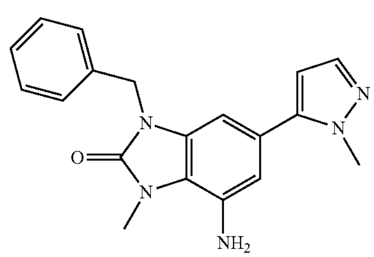 [SMILES: Cn1nccc1-c1cc(N)c2c(c1)n(Cc1ccccc1)c(=O)n2C] | No general procedure | $^1$H NMR (300 MHz, DMSO-d6) δ 7.39 (d, J = 1.8 Hz, 1H), 7.35-7.24 (m, 5H), 6.56 (d, J = 1.5 Hz, 1H), 6.54 (d, J = 1.5 Hz, 1H), 6.20 (d, J = 1.8 Hz, 1H), 5.15 (s, 2H), 5.01 (s, 2H), 3.72 (s, 3H), 3.63 (s, 3H); ESI m/z 334 [M + H]+. | >99 |

TABLE 2-continued

Example Compounds

| Example Compound | Chemical Name | Structure | General procedure | Characterization | Purity HPLC (%) |
|---|---|---|---|---|---|
| 200 | (4-bromo-6-(3,5-dimethylisoxazol-4-yl)-2-methyl-1H-benzo[d]imidazol-1-yl)(phenyl)methanone | 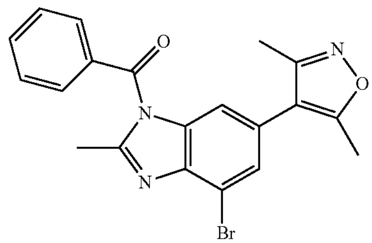 [SMILES: Cc1noc(C)c1-c1cc(Br)c2nc(C)n(C(=O)c3ccccc3)c2c1] | H | $^1$H NMR (500 MHz, DMSO-d6) δ 7.83 (dd, J = 8.0, 1.5 Hz, 2H), 7.78 (t, J = 7.5 Hz, 1H), 7.62 (t, J = 7.5 Hz, 2H), 7.53 (d, J = 1.5 Hz, 1H), 6.63 (d, J = 1.5 Hz, 1H), 2.64 (s, 3H), 2.22 (s, 3H), 2.03 (s, 3H); ESI m/z 410 [M + H]+. | 96.1 |
| 201 | 1-benzyl-2-methyl-6-(5-methylisoxazol-4-yl)-1H-benzo[d]imidazol-4-amine | 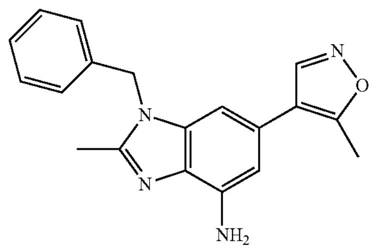 [SMILES: Cc1oncc1-c1cc(N)c2nc(C)n(Cc3ccccc3)c2c1] | U | $^1$H NMR (300 MHz, DMSO-d6) δ 8.69 (d, J = 0.6 Hz, 1H), 7.36-7.26 (m, 3H), 7.15 (d, J = 6.9 Hz, 2H), 6.78 (d, J = 1.5 Hz, 1H), 6.47 (d, J = 1.5 Hz, 1H), 5.40 (s, 2H), 5.33 (s, 2H), 2.50 (s, 3H), 2.47 (s, 3H); ESI m/z 319 [M + H]+. | 99.0 |
| 202 | 1-(cyclopentylmethyl)-6-(3,5-dimethylisoxazol-4-yl)-1H-imidazo[4,5-b]pyridin-2(3H)-one | 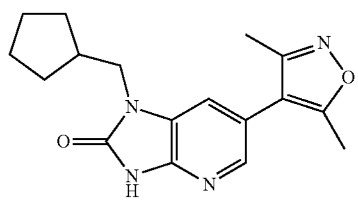 [SMILES: Cc1noc(C)c1-c1cnc2[nH]c(=O)n(CC3CCCC3)c2c1] | No general procedure | $^1$H NMR (500 MHz, CD3OD) δ 7.90 (d, J = 1.5 Hz, 1H), 7.47 (d, J = 2.0 Hz, 1H), 3.86 (d, J = 7.5 Hz, 2H), 2.52-2.38 (m, 1H), 2.41 (s, 3H), 2.25 (s, 3H), 1.78-1.68 (m, 4H), 1.60-1.52 (m, 2H), 1.41-1.30 (m, 2H). ESI m/z 313 [M + H]+. | >99 |
| 203 | 1-(cyclobutylmethyl)-6-(3,5-dimethyl-isoxazol-4-yl)-1H-imidazo[4,5-b]pyridin-2(3H)-one | 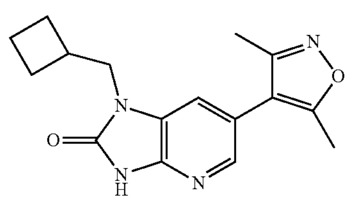 [SMILES: Cc1noc(C)c1-c1cnc2[nH]c(=O)n(CC3CCC3)c2c1] | No general procedure | $^1$H NMR (500 MHz, CD3OD) δ 7.89 (d, J = 1.5 Hz, 1H), 7.46 (d, J = 2.0 Hz, 1H), 3.94 (d, J = 7.0 Hz, 2H), 2.86-2.77 (m, 1H), 2.41 (s, 3H), 2.25 (s, 3H), 2.08-1.98 (m, 2H), 1.94-1.80 (m, 4H). ESI m/z 299 [M + H]+. | >99 |
| 204 | N-(1-benzyl-3-methyl-6-(1-methyl-1H-pyrazol-5-yl)-2-oxo-2,3-dihydro-1H-benzo[d]imidazol-4-yl)acetamide | 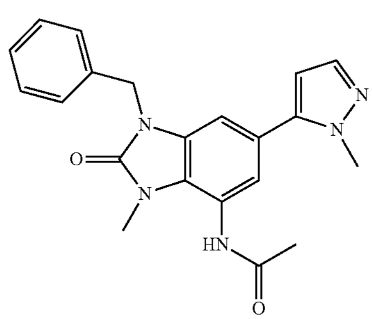 [SMILES: CC(=O)Nc1cc(-c2ccnn2C)cc2c1n(C)c(=O)n2Cc1ccccc1] | P | $^1$H NMR (300 MHz, DMSO-d6) δ 9.81 (s, 1H), 7.43 (d, J = 1.8 Hz, 1H), 7.40-7.26 (m, 5H), 7.20 (d, J = 1.5 Hz, 1H), 6.92 (d, J = 1.5 Hz, 1H), 6.29 (d, J = 1.8 Hz, 1H), 5.10 (s, 2H), 3.75 (s, 3H), 3.47 (s, 3H), 2.08 (s, 3H); ESI m/z 376 [M + H]+. | >99 |

TABLE 2-continued

Example Compounds

| Example Compound | Chemical Name | Structure | General procedure | Characterization | Purity HPLC (%) |
|---|---|---|---|---|---|
| 205 | 1-benzyl-6-(3,5-dimethylisoxazol-4-yl)-N-(4-methoxybenzyl)-1H-imidazo[4,5-b]pyridin-2-amine | 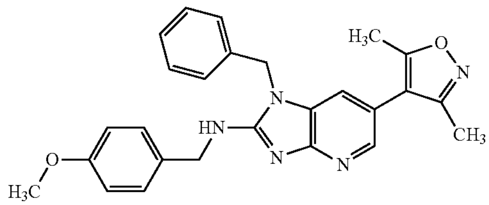 [SMILES: COc1ccc(CNc2nc3ncc(-c4c(C)noc4C)cc3n2Cc2ccccc2)cc1] | Q | $^1$H NMR (300 MHz, DMSO-d6) δ 7.95 (d, J = 2.0 Hz, 1H), 7.94-7.88 (m, 1H), 7.43 (d, J = 2.0 Hz, 1H), 7.35-7.22 (m, 7H), 6.89-6.86 (m, 2H), 5.35 (s, 2H), 4.60 (d, J = 5.7 Hz, 2H), 3.72 (s, 3H), 2.34 (s, 3H), 2.15 (s, 3H); ESI m/z 440 [M + H]+. | >99 |
| 206 | 1-benzyl-2-methyl-6-(1-methyl-1H-1,2,3-triazol-5-yl)-1H-imidazo[4,5-b]pyridine | 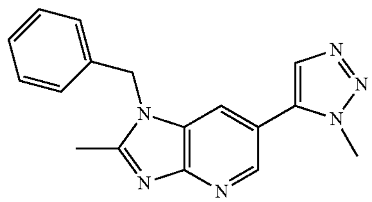 [SMILES: Cc1nc2ncc(-c3cnnn3C)cc2n1Cc1ccccc1] | No general procedure | $^1$H NMR (500 MHz, DMSO-d6) δ 8.54 (d, J = 2.5 Hz, 1H), 8.27 (d, J = 2.0 Hz, 1H), 7.96 (s, 1H), 7.35 (t, J = 7.0 Hz, 2H), 7.29 (t, J = 7.0 Hz, 1H), 7.21 (d, J = 7.0 Hz, 2H), 5.58 (s, 2H), 4.07 (s, 3H), 2.60 (s, 3H); ESI m/z 305 [M + H]+. | 98.6 |
| 207 | 4-((1-benzyl-6-(3,5-dimethylisoxazol-4-yl)-1H-imidazo[4,5-b]pyridin-2-yl)amino)cyclohexanol | 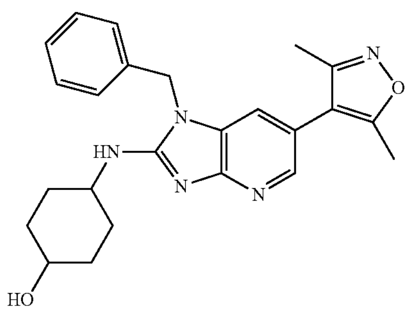 [SMILES: Cc1noc(C)c1-c1cnc2nc(NC3CCC(O)CC3)n(Cc3ccccc3)c2c1] | Q | $^1$H NMR (500 MHz, DMSO-d6) δ 7.94 (d, J = 2.0 Hz, 1H), 7.35-7.30 (m, 3H), 7.27-7.21 (m, 3H), 7.08 (d, J = 8.0 Hz, 1H), 5.32 (s, 2H), 4.57 (d, J = 4.0 Hz, 1H), 3.83-3.75 (m, 1H), 3.47-3.40 (m, 1H), 2.32 (s, 3H), 2.14 (s, 3H), 2.01 (br.d, 11.0 Hz, 2H), 1.88 (br.d, 11.5 Hz, 2H), 1.44-1.35 (m, 2H), 1.34-1.26 (m, 2H); ESI m/z 418 [M + H]+. | >99 |
| 208 | 4-(1-(cyclopentylmethyl)-6-(3,5-dimethylisoxazol-4-yl)-1H-imidazo[4,5-b]pyridin-2-yl)morpholine | 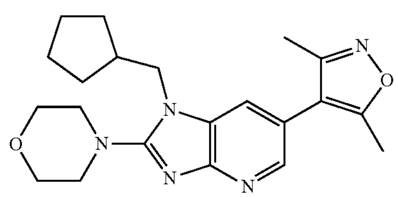 [SMILES: Cc1noc(C)c1-c1cnc2nc(N3CCOCC3)n(CC3CCCC3)c2c1] | No general procedure | $^1$H NMR (500 MHz, CD3OD) δ 8.17 (d, J = 1.5 Hz, 1H), 7.81 (d, J = 2.0 Hz, 1H), 4.14 (d, J = 7.5 Hz, 2H), 3.87 (t, J = 5.0 Hz, 4H), 3.41 (t, J = 5.0 Hz, 4H), 2.58-2.49 (m, 1H), 2.43 (s, 3H), 2.27 (s, 3H), 1.75-1.66 (m, 2H), 1.62-1.50 (m, 4H), 1.30-1.19 (m, 2H). ESI m/z 382 [M + H]+. | 98.5 |
| 209 | 4-(2-(azetidin-1-yl)-1-(cyclopentylmethyl)-1H-imidazo[4,5-b]pyridin-6-yl)-3,5-dimethylisoxazole | 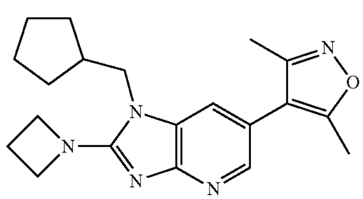 [SMILES: Cc1noc(C)c1-c1cnc2nc(N3CCC3)n(CC3CCCC3)c2c1] | No general procedure | $^1$H NMR (500 MHz, CD3OD) δ 8.00 (d, J = 1.5 Hz, 1H), 7.59 (d, J = 1.5 Hz, 1H), 4.42-4.37 (m, 4H), 4.01 (d, J = 8.0 Hz, 2H), 2.57-2.44 (m, 2H), 2.50-2.41 (m, 1H), 2.41 (s, 3H), 2.25 (s, 3H), 1.76-1.51 (m, 6H), 1.32-1.22 (m, 2H). ESI m/z 352 [M + H]+. | >99 |

TABLE 2-continued

Example Compounds

| Example Compound | Chemical Name | Structure | General procedure | Characterization | Purity HPLC (%) |
|---|---|---|---|---|---|
| 210 | 4-(1-(cyclobutyl-methyl)-6-(3,5-dimethylisoxazol-4-yl)-1H-imidazo[4,5-b]pyridin-2-yl)morpholine | 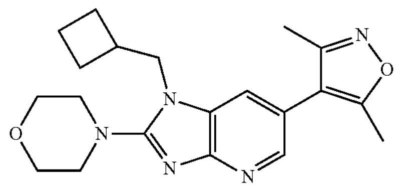 [SMILES: Cc1noc(C)c1-c1cnc2nc(N3CCOCC3)n(CC3CCC3)c2c1] | No general procedure | $^1$H NMR (500 MHz, CD3OD) δ 8.16 (d, J = 1.5 Hz, 1H), 7.80 (d, J = 2.0 Hz, 1H), 4.24 (d, J = 7.0 Hz, 2H), 3.88 (t, J = 5.0 Hz, 4H), 3.41 (t, J = 5.0 Hz, 4H), 2.93-2.82 (m, 1H), 2.43 (s, 3H), 2.27 (s, 3H), 1.98-1.91 (m, 2H), 1.90-1.76 (m, 4H). ESI m/z 368 [M + H]+. | >99 |
| 211 | 4-(2-(azetidin-1-yl)-1-(cyclobutyl-methyl)-1H-imidazo[4,5-b]pyridin-6-yl)-3,5-dimethylisoxazole | 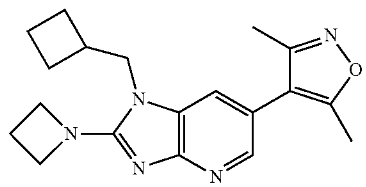 [SMILES: Cc1noc(C)c1-c1cnc2nc(N3CCC3)n(CC3CCC3)c2c1] | No general procedure | $^1$H NMR (500 MHz, CD3OD) δ 7.99 (d, J = 2.0 Hz, 1H), 7.61 (d, J = 2.0 Hz, 1H), 4.38 (m, 4H), 4.10 (d, J = 7.0 Hz, 2H), 2.88-2.79 (m, 1H), 2.57-2.48 (m, 2H), 2.41 (s, 3H), 2.25 (s, 3H), 2.04-1.95 (m, 2H), 1.95-1.78 (m, 4H). ESI m/z 338 [M + H]+. | >99 |
| 212 | N1-(1-benzyl-6-(3,5-dimethylisoxazol-4-yl)-1H-imidazo[4,5-b]pyridin-2-yl)-N2,N2-dimethylethane-1,2-diamine | 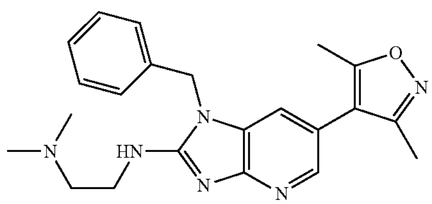 [SMILES: Cc1noc(C)c1-c1cnc2nc(NCCN(C)C)n(Cc3ccccc3)c2c1] | Q | $^1$H NMR (500 MHz, CD3OD) δ 7.95 (d, J = 1.9 Hz, 1H), 7.34 (d, J = 7.6 Hz, 2H), 7.31-7.26 (m, 2H), 7.22 (d, J = 7.1 Hz, 2H), 5.31 (s, 2H), 3.69 (t, J = 6.0 Hz, 2H), 2.71 (bs, 2H), 2.35 (s, 6H), 2.32 (s, 3H), 2.14 (s, 3H); ESI m/z 391 [M + H]+. | >99 |
| 213 | 4-(1-benzyl-2-(piperazin-1-yl)-1H-imidazo[4,5-b]pyridin-6-yl)-3,5-dimethylisoxazole | 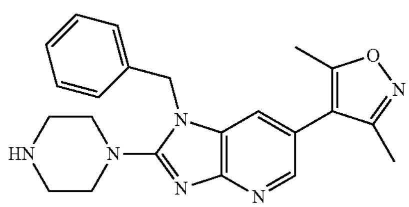 [SMILES: Cc1noc(C)c1-c1cnc2nc(N3CCNCC3)n(Cc3ccccc3)c2c1] | Q | $^1$H NMR (300 MHz, CDCl3) δ 8.24 (d, J = 1.8 Hz, 1H), 7.37-7.33 (m, 3H), 7.18-7.15 (m, 2H), 7.00 (d, J = 2.0 Hz, 1H), 5.23 (s, 2H), 3.51-3.48 (m, 4H), 3.14-3.11 (m, 4H), 2.30 (s, 3H), 2.12 (s, 3H), 2.08 (br. s, 1H); ESI m/z 389 [M + H]+. | 97.1 |
| 214 | 1-benzyl-N-cyclopentyl-6-(3,5-dimethylisoxazol-4-yl)-1H-imidazo[4,5-b]pyridin-2-amine | 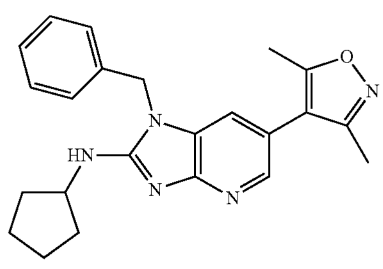 [SMILES: Cc1noc(C)c1-c1cnc2nc(NC3CCCC3)n(Cc3ccccc3)c2c1] | Q | $^1$H NMR (500 MHz, CD3OD) δ 7.93 (d, J = 1.9 Hz, 1H), 7.34 (t, J = 7.0 Hz, 2H), 7.28 (t, J = 7.3 Hz, 1H), 7.23 (d, J = 1.9 Hz, 1H), 7.18 (d, J = 7.0 Hz, 2H), 5.36 (s, 2H), 4.39 (pentet, J = 6.5 Hz, 1H), 2.31 (s, 3H), 2.13 (s, 3H), 2.15-2.00 (m, 2H), 1.95-1.30 (m, 6H); ESI m/z 388 [M + H]+. | >99 |

TABLE 2-continued

Example Compounds

| Example Compound | Chemical Name | Structure | General procedure | Characterization | Purity HPLC (%) |
|---|---|---|---|---|---|
| 215 | 1-benzyl-6-(3,5-dimethylisoxazol-4-yl)-N-(2-morpholinoethyl)-1H-imidazo[4,5-b]pyridin-2-amine | 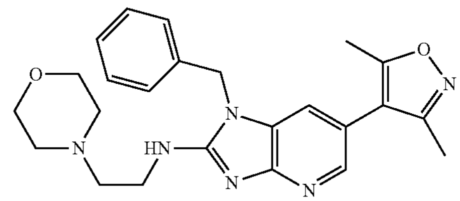 [SMILES: Cc1noc(C)c1-c1cnc2nc(NCCN3CCOCC3)n(Cc3ccccc3)c2c1] | Q | $^1$H NMR (500 MHz, CD3OD) δ 7.95 (d, J = 1.9 Hz, 1H), 7.38-7.32 (m, 3H), 7.29 (t, J = 7.2 Hz, 1H), 7.23 (d, J = 7.0 Hz, 2H), 5.32 (s, 2H), 3.68 (t, J = 6.3 Hz, 2H), 3.63 (t, J = 4.6 Hz, 4H), 2.66 (t, J = 6.3 Hz, 2H), 2.50 (t, J = 4.2 Hz, 4H), 2.33 (s, 3H), 2.15 (s, 3H); ESI m/z 433 [M + H]+. | >99 |
| 216 | 1-benzyl-6-(3,5-dimethylisoxazol-4-yl)-1H-imidazo[4,5-b]pyridin-2-amine | 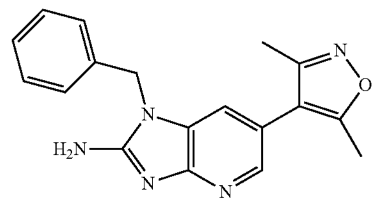 [SMILES: Cc1noc(C)c1-c1cnc2nc(N)n(Cc3ccccc3)c2c1] | Q | $^1$H NMR (500 MHz, DMSO-d6) δ 7.93 (d, J = 2.0 Hz, 1H), 7.38 (d, J = 2.0 Hz, 1H), 7.33 (t, J = 7.0 Hz, 2H), 7.28-7.24 (m, 3H), 7.16 (s, 2H), 5.30 (s, 2H), 2.33 (s, 3H), 2.15 (s, 3H); ESI m/z 320 [M + H]+. | 98.6 |
| 217 | 3-(((1-benzyl-6-(3,5-dimethylisoxazol-4-yl)-1H-imidazo[4,5-b]pyridin-2-yl)amino)methyl)benzonitrile | 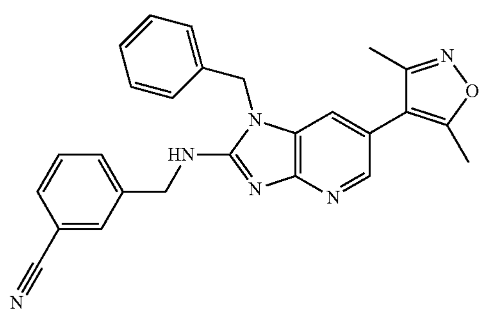 [SMILES: Cc1noc(C)c1-c1cnc2nc(NCc3cccc(C#N)c3)n(Cc3ccccc3)c2c1] | Q | $^1$H NMR (500 MHz, DMSO-d6) δ 8.03 (t, J = 6.0 Hz, 1H), 7.97 (d, J = 1.5 Hz, 1H), 7.74 (s, 1H), 7.75 (d, J = 7.5 Hz, 1H), 7.69 (d, J = 8.0 Hz, 1H), 7.54 (t, J = 8.0 Hz, 1H), 7.50 (d, J = 2.0 Hz, 1H), 7.34 (td, J = 7.0, 1.5 Hz, 2H), 7.28 (tt, J = 7.5, 1.5 Hz, 1H), 7.24 (d, J = 7.0 Hz, 2H), 5.38 (s, 2H), 4.72 (d, J = 6.0 Hz, 2H), 2.34 (s, 3H), 2.16 (s, 3H); ESI m/z 435 [M + H]+. | >99 |
| 218 | (R)-6-(3,5-dimethylisoxazol-4-yl)-1-(1-phenylethyl)-1H-imidazo[4,5-b]pyridin-2(3H)-one | 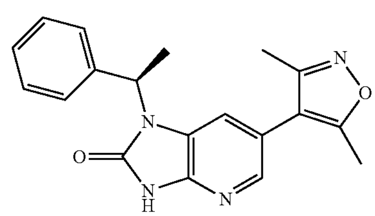 [SMILES: Cc1noc(C)c1-c1cnc2[nH]c(=O)n([C@H](C)c3ccccc3)c2c1] | No general procedure | $^1$H NMR (500 MHz, DMSO-d6) δ 11.77 (s, 1H), 7.87 (d, J = 2.0 Hz, 1H), 7.44 (d, J = 7.5 Hz, 2H), 7.37 (t, J = 7.5 Hz, 2H), 7.29 (t, J = 7.5 Hz, 1H), 7.09 (d, J = 2.0 Hz, 1H), 5.72 (q, J = 7.5 Hz, 1H), 2.26 (s, 3H), 2.06 (s, 3H), 1.84 (d, J = 7.5 Hz, 3H); ESI m/z 335 [M + H]+; HPLC (Chiralcel OD, 4.6 mm × 250 mm, 10% EtOH in heptane, 1 mL/min) >99%, tR = 9.4 min. | 99.0 |

TABLE 2-continued

Example Compounds

| Example Compound | Chemical Name | Structure | General procedure | Characterization | Purity HPLC (%) |
|---|---|---|---|---|---|
| 219 | (S)-6-(3,5-dimethylisoxazol-4-yl)-1-(1-phenylethyl)-1H-imidazo[4,5-b]pyridin-2(3H)-one | 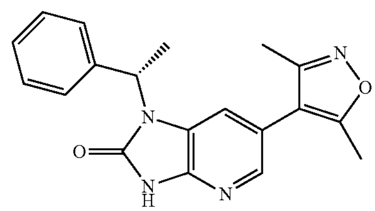 [SMILES: Cc1noc(C)c1-c1cnc2[nH]c(=O)n([C@@H](C)c3ccccc3)c2c1] | No general procedure | $^1$H NMR (500 MHz, DMSO-d6) δ 11.78 (s, 1H), 7.87 (d, J = 1.5 Hz, 1H), 7.44 (d, J = 7.5 Hz, 2H), 7.36 (t, J = 7.5 Hz, 2H), 7.29 (t, J = 7.5 Hz, 1H), 7.08 (d, J = 2.0 Hz, 1H), 5.72 (q, J = 7.5 Hz, 1H), 2.26 (s, 3H), 2.06 (s, 3H), 1.84 (d, J = 7.5 Hz, 3H); ESI m/z 335 [M + H]+; HPLC (Chiralcel OD, 4.6 mm × 250 mm, 10% EtOH in heptane, 1 mL/min) >99%, tR = 10.9 min. | >99 |
| 220 | 4-(1-benzyl-2-(tetrahydro-2H-pyran-4-yl)-1H-imidazo[4,5-b]pyridin-6-yl)-3,5-dimethylisoxazole | 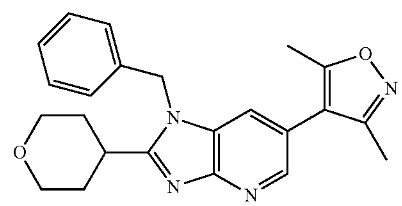 [SMILES: Cc1noc(C)c1-c1cnc2nc(C3CCOCC3)n(Cc3ccccc3)c2c1] | No general procedure | $^1$H NMR (300 MHz, CDCl3) δ 8.41 (d, J = 1.8 Hz, 1H), 7.38-7.32 (m, 3H), 7.24 (d, J = 2.1 Hz, 1H), 7.08-7.05 (m, 2H), 5.42 (s, 2H), 4.12 (dd, J = 11.7, 1.8 Hz, 2H), 3.52 (td, J = 11.7, 1.8 Hz, 2H), 3.20-3.12 (m, 1H), 2.36-2.23 (m, 5H), 2.14 (s, 3H), 1.83-1.78 (m, 2H); ESI m/z 389 [M + H]+. | 95.8 |
| 221 | 1-benzyl-6-(3,5-dimethylisoxazol-4-yl)-N-methyl-1H-imidazo[4,5-b]pyridine-2-carboxamide | 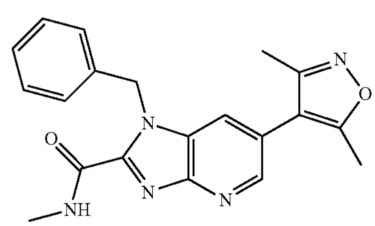 [SMILES: CNC(=O)c1nc2ncc(-c3c(C)noc3C)cc2n1Cc1ccccc1] | No general procedure | $^1$H NMR (300 MHz, DMSO-d6) δ 8.31 (q, J = 4.5 Hz, 1H), 8.27 (d, J = 1.8 Hz, 1H), 7.54 (d, J = 1.8 Hz, 1H), 7.36-7.24 (m, 5H), 5.54 (s, 2H), 3.00 (d, J = 4.8 Hz, 3H), 2.21 (s, 3H), 2.00 (s, 3H); ESI m/z 362 [M + H]+. | >99 |
| 222 | 1-(cyclopentylmethyl)-6-(3,5-dimethylisoxazol-4-yl)-N-(tetrahydro-2H-pyran-4-yl)-1H-imidazo[4,5-b]pyridin-2-amine | 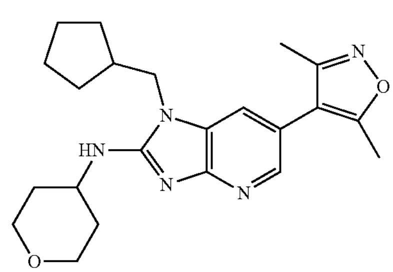 [SMILES: Cc1noc(C)c1-c1cnc2nc(NC3CCOCC3)n(CC3CCCC3)c2c1] | No general procedure | $^1$H NMR (500 MHz, CD3OD) δ 7.94 (d, J = 1.5 Hz, 1H), 7.50 (d, J = 2.0 Hz, 1H), 4.17-4.05 (m, 1H), 4.05 (d, J = 8.0 Hz, 2H), 4.02-3.97 (m, 2H), 3.57 (t, J = 11.75 Hz, 2H), 2.44-2.36 (m, 1H), 2.41 (s, 3H), 2.25 (s, 3H), 2.08-2.00 (m, 2H), 1.78-1.64 (m, 6H), 1.62-1.54 (m, 2H), 1.38-1.25 (m, 2H). ESI m/z 396 [M + H]+. | 98.0 |

TABLE 2-continued

Example Compounds

| Example Compound | Chemical Name | Structure | General procedure | Characterization | Purity HPLC (%) |
|---|---|---|---|---|---|
| 223 | 1-(cyclobutyl-methyl)-6-(3,5-dimethylisoxazol-4-yl)-N-(tetrahydro-2H-pyran-4-yl)-1H-imidazo[4,5-b]pyridin-2-amine | 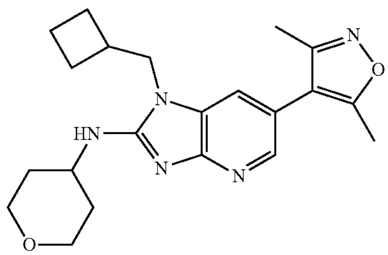 [SMILES: Cc1noc(C)c1-c1cnc2nc(NC3CCOCC3)n(CC3CCC3)c2c1] | No general procedure | $^1$H NMR (500 MHz, CD3OD) δ 7.93 (d, J = 2.0 Hz, 1H), 7.52 (d, J = 2.0 Hz, 1H), 4.17-4.05 (m, 1H), 4.10 (d, J = 7.5 Hz, 2H), 4.03-3.97 (m, 2H), 3.56 (t, J = 11.75 Hz, 2H), 2.86-2.78 (m, 1H), 2.41 (s, 3H), 2.25 (s, 3H), 2.08-1.92 (m, 8H), 1.75-1.64 (m, 2H). ESI m/z 382 [M + H]+. | 96.4 |
| 224 | N1-(1-benzyl-6-(3,5-dimethylisoxazol-4-yl)-1H-imidazo[4,5-b]pyridin-2-yl)cyclohexane-1,4-diamine | 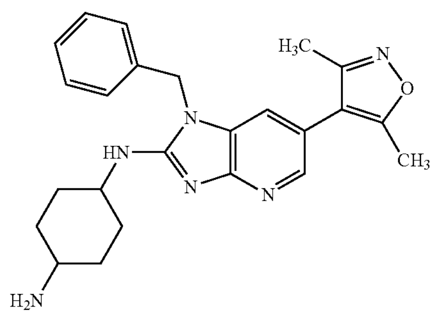 [SMILES: Cc1noc(C)c1-c1cnc2nc(NC3CCC(N)CC3)n(Cc3ccccc3)c2c1] | Q | $^1$H NMR (500 MHz, CD3OD) δ 7.95 (d, J = 2.0 Hz, 1H), 7.38-7.32 (m, 2H), 7.31-7.28 (m, 2H), 7.21-7.19 (m, 2H), 5.37 (s, 2H), 4.10-4.00 (m, 1H), 3.02-2.97 (m, 1H), 2.32 (s, 3H), 2.14 (s, 3H), 1.93-1.71 (m, 6H), 1.60-1.49 (m, 2H); ESI m/z 417 [M + H]+. | 95.7 |
| 225 | 1-benzyl-N-(cyclohexyl-methyl)-6-(3,5-dimethylisoxazol-4-yl)-1H-imidazo[4,5-b]pyridin-2-amine | 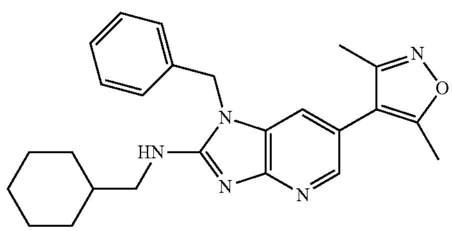 [SMILES: Cc1noc(C)c1-c1cnc2nc(NCC3CCCCC3)n(Cc3ccccc3)c2c1] | Q | $^1$H NMR (500 MHz, CD3OD) δ 7.95 (d, J = 2.0 Hz, 1H), 7.38-7.22 (m, 4H), 7.21-7.18 (m, 2H), 5.32 (s, 2H), 3.41-3.32 (m, 2H), 2.33 (s, 3H), 2.15 (s, 3H), 1.79-1.60 (m, 6H), 1.30-1.10 (m, 3H), 0.99-0.89 (m, 2H); ESI m/z 416 [M + H]+. | >99 |
| 226 | 1-benzyl-6-(3,5-dimethylisoxazol-4-yl)-N-(3-methoxypropyl)-1H-imidazo[4,5-b]pyridin-2-amine | 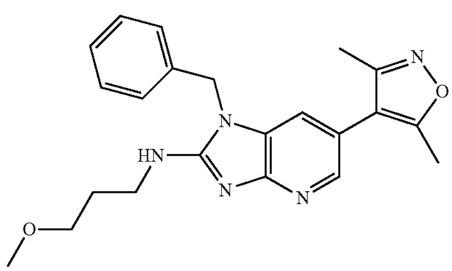 [SMILES: COCCCNc1nc2ncc(-c3c(C)noc3C)cc2n1Cc1ccccc1] | Q | $^1$H NMR (500 MHz, CD3OD) δ 7.94 (d, J = 2.0 Hz, 1H), 7.38-7.22 (m, 4H), 7.21-7.18 (m, 2H), 5.30 (s, 2H), 3.60 (t, J = 7.0 Hz, 2H), 3.45 (t, J = 6.0 Hz, 2H), 3.28 (s, 3H), 2.33 (s, 3H), 2.15 (s, 3H), 1.94 (quin, J = 6.5 Hz, 2H); ESI m/z 392 [M + H]+. | >99 |
| 227 | 1-benzyl-6-(3,5-dimethylisoxazol-4-yl)-N-(oxetan-3-yl)-1H-imidazo[4,5-b]pyridin-2-amine | 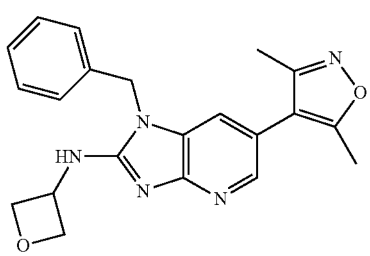 [SMILES: Cc1noc(C)c1-c1cnc2nc(NC3COC3)n(Cc3ccccc3)c2c1] | Q | $^1$H NMR (500 MHz, CD3OD) δ 7.97 (d, J = 2.0 Hz, 1H), 7.38-7.24 (m, 4H), 7.21-7.18 (m, 2H), 5.39 (s, 2H), 5.24-5.17 (m, 1H), 5.03 (t, J = 7.0 Hz, 2H), 4.71 (t, J = 7.0 Hz, 2H), 2.30 (s, 3H), 2.12 (s, 3H); ESI m/z 376 [M + H]+. | >99 |

TABLE 2-continued

Example Compounds

| Example Compound | Chemical Name | Structure | General procedure | Characterization | Purity HPLC (%) |
|---|---|---|---|---|---|
| 228 | 6-(3,5-dimethylisoxazol-4-yl)-1-(4-fluorobenzyl)-1H-imidazo[4,5-b]pyridin-2(3H)-one | 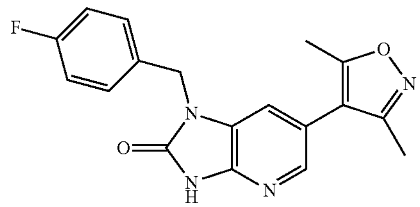 [SMILES: Cc1noc(C)c1-c1cnc2[nH]c(=O)n(Cc3ccc(F)cc3)c2c1] | R | $^1$H NMR (300 MHz, DMSO-d6) δ 11.82 (s, 1H), 7.91 (d, J = 1.8 Hz, 1H), 7.48 (d, J = 1.8 Hz, 1H), 7.46-7.43 (m, 2H), 7.20-7.14 (m, 2H), 5.03 (s, 2H), 2.36 (s, 3H), 2.17 (s, 3H); ESI m/z 339 [M + H]+. | >99 |
| 229 | 1-benzyl-6-(3,5-dimethylisoxazol-4-yl)-N-(pyrazin-2-ylmethyl)-1H-imidazo[4,5-b]pyridin-2-amine | 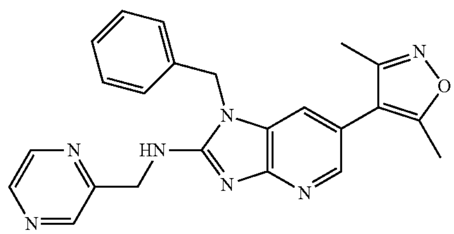 [SMILES: Cc1noc(C)c1-c1cnc2nc(NCc3cnccn3)n(Cc3ccccc3)c2c1] | Q | $^1$H NMR (500 MHz, DMSO-d6) δ 9.13 (d, J = 1.5 Hz, 1H), 8.70 (d, J = 5.5, 1H), 8.16 (t, J = 6.0 Hz, 1H), 7.96 (d, J = 2.0 Hz, 1H), 7.49 (d, J = 2.0 Hz, 1H), 7.39-7.27 (m, 6H), 5.42 (s, 2H), 4.74 (d, J = 6.0 Hz, 2H), 2.33 (s, 3H), 2.15 (s, 3H); ESI m/z 412 [M + H]+. | >99 |
| 230 | 1-benzyl-6-(3,5-dimethylisoxazol-4-yl)-N-((tetrahydro-2H-pyran-4-yl)methyl)-1H-imidazo[4,5-b]pyridin-2-amine | 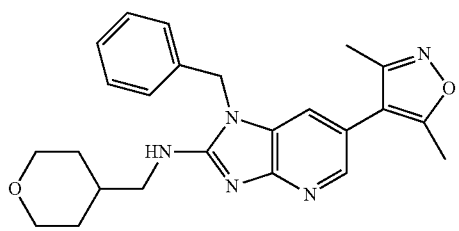 [SMILES: Cc1noc(C)c1-c1cnc2nc(NCC3CCOCC3)n(Cc3ccccc3)c2c1] | Q | $^1$H NMR (500 MHz, DMSO-d6) δ 7.95 (d, J = 2.0 Hz, 1H), 7.42-7.39 (m, 2H), 7.32 (t, J = 7.0 Hz, 2H), 7.27-7.21 (m, 3H), 5.32 (s, 2H), 3.84 (dd, J = 11.0, 2.5 Hz, 2H), 3.34 (t, J = 6.5 Hz, 2H), 3.25 (td, J = 11.0, 2.0 Hz, 2H), 2.33 (s, 3H), 2.15 (s, 3H), 1.97-1.90 (m, 1H), 1.57 (d, J = 12.0 Hz, 2H), 1.20 (qd, J = 12.0, 4.0 Hz, 2H); ESI m/z 418 [M + H]+. | >99 |
| 231 | 1-benzyl-6-(3,5-dimethylisoxazol-4-yl)-N-(2-(4-methylpiperazin-1-yl)ethyl)-1H-imidazo[4,5-b]pyridin-2-amine | 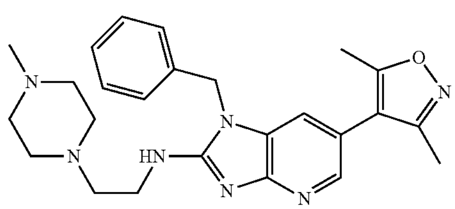 [SMILES: Cc1noc(C)c1-c1cnc2nc(NCCN3CCN(C)CC3)n(Cc3ccccc3)c2c1] | Q | $^1$H NMR (500 MHz, CD3OD) δ 7.95 (d, J = 1.9 Hz, 1H), 7.38-7.26 (m, 4H), 7.22 (d, J = 7.1 Hz, 2H), 5.31 (s, 2H), 3.67 (t, J = 6.3 Hz, 2H), 2.68 (t, J = 6.3 Hz, 2H), 2.80-2.20 (broad peak, 8H), 2.33 (s, 3H), 2.26 (s, 3H), 2.15 (s, 3H); ESI m/z 446 [M + H]+. | >99 |
| 232 | 6-(3,5-dimethylisoxazol-4-yl)-1-(4-fluorobenzyl)-N-methyl-1H-imidazo[4,5-b]pyridin-2-amine | 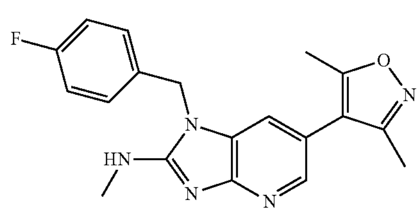 [SMILES: CNc1nc2ncc(-c3c(C)noc3C)cc2n1Cc1ccc(F)cc1] | Q | $^1$H NMR (300 MHz, DMSO-d6) δ 7.96 (d, J = 1.8 Hz, 1H), 7.46 (d, J = 1.8 Hz, 1H), 7.37-7.28 (m, 3H), 7.20-7.14 (m, 2H), 5.27 (s, 2H), 2.99 (d, J = 4.5 Hz, 3H), 2.35 (s, 3H), 2.17 (s, 3H); ESI m/z 352 [M + H]+. | >99 |

TABLE 2-continued

Example Compounds

| Example Compound | Chemical Name | Structure | General procedure | Characterization | Purity HPLC (%) |
|---|---|---|---|---|---|
| 233 | 1-(4-chlorobenzyl)-6-(3,5-dimethylisoxazol-4-yl)-N-methyl-1H-imidazo[4,5-b]pyridin-2-amine | 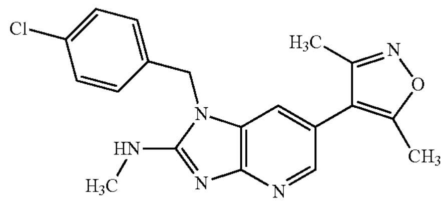 [SMILES: CNc1nc2ncc(-c3c(C)noc3C)cc2n1Cc1ccc(Cl)cc1] | Q | $^1$H NMR (300 MHz, DMSO-d6) δ 7.97 (d, J = 2.1 Hz, 1H), 7.44 (d, J = 1.8 Hz, 1H), 7.40 (d, J = 8.4 Hz, 2H), 7.33 (q, J = 4.2 Hz, 1H), 7.25 (d, J = 8.7 Hz, 2H), 5.28 (s, 2H), 2.99 (d, J = 4.8 Hz, 3H), 2.35 (s, 3H), 2.17 (s, 3H); ESI m/z 368 [M + H]+. | >99 |
| 234 | 1-benzyl-N-cyclohexyl-6-(3,5-dimethylisoxazol-4-yl)-1H-imidazo[4,5-b]pyridin-2-amine | 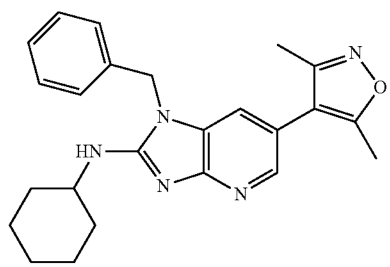 [SMILES: Cc1noc(C)c1-c1cnc2nc(NC3CCCCC3)n(Cc3ccccc3)c2c1] | Q | $^1$H NMR (300 MHz, DMSO-d6) δ 7.94 (d, J = 2.1 Hz, 1H), 7.35-7.30 (m, 3H), 7.27-7.22 (m, 3H), 7.10 (d, J = 7.5 Hz, 1H), 5.33 (s, 2H), 3.90-3.75 (m, 1H), 2.32 (s, 3H), 2.14 (s, 3H), 2.00 (d, J = 7.2 Hz, 2H), 1.81-1.71 (m, 2H), 1.64 (d, J = 11.7 Hz, 1H), 1.42-1.30 (m, 4H), 1.23-1.14 (m, 1H); ESI m/z 402 [M + H]+. | >99 |
| 235 | 1-benzyl-6-(3,5-dimethylisoxazol-4-yl)-N-(1-methylpiperidin-4-yl)-1H-imidazo[4,5-b]pyridin-2-amine | 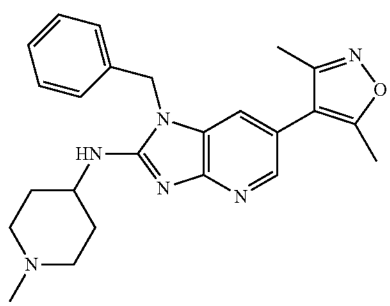 [SMILES: Cc1noc(C)c1-c1cnc2nc(NC3CCN(C)CC3)n(Cc3ccccc3)c2c1] | Q | $^1$H NMR (300 MHz, DMSO-d6) δ 7.95 (d, J = 1.8 Hz, 1H), 7.38 (d, J = 2.1 Hz, 1H), 7.36-7.30 (m, 2H), 7.28-7.22 (m, 3H), 7.16 (d, J = 7.5 Hz, 1H), 5.34 (s, 2H), 3.85-3.73 (m, 1H), 2.78 (d, J = 10.5 Hz, 2H), 2.33 (s, 3H), 2.18 (s, 3H), 2.14 (s, 3H), 2.04-1.93 (m, 4H), 1.67-1.54 (m, 2H); ESI m/z 417 [M + H]+. | 97.0 |
| 236 | 4-(1-benzyl-2-(pyridin-3-yloxy)-1H-imidazo[4,5-b]pyridin-6-yl)-3,5-dimethylisoxazole | 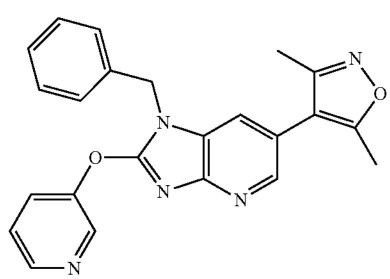 [SMILES: Cc1noc(C)c1-c1cnc2nc(Oc3cccnc3)n(Cc3ccccc3)c2c1] | T | $^1$H NMR (300 MHz, DMSO-d6) δ 8.74 (d, J = 2.7 Hz, 1H), 8.57 (dd, J = 4.5, 0.9 Hz, 1H), 8.27 (d, J = 1.8 Hz, 1H), 8.02-7.98 (m, 2H), 7.59 (dd, J = 8.4, 4.5 Hz, 1H), 7.47 (d, J = 6.9 Hz, 2H), 7.42-7.30 (m, 3H), 5.53 (s, 2H), 2.40 (s, 3H), 2.22 (s, 3H); ESI m/z 398 [M + H]+. | 98.0 |
| 237 | 1-((1-benzyl-6-(3,5-dimethylisoxazol-4-yl)-1H-imidazo[4,5-b]pyridin-2-yl)amino)-2-methylpropan-2-ol | 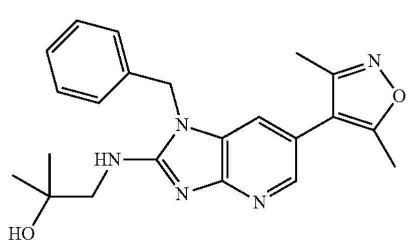 [SMILES: Cc1noc(C)c1-c1cnc2nc(NCC(C)(C)O)n(Cc3ccccc3)c2c1] | Q | $^1$H NMR (500 MHz, CD3OD) δ 7.94 (d, J = 2.0 Hz, 1H), 7.38-7.28 (m, 4H), 7.27-7.21 (m, 2H), 5.35 (s, 2H), 3.55 (s, 2H), 2.33 (s, 3H), 2.15 (s, 3H), 1.20 (s, 6H); ESI m/z 392 [M + H]+. | >99 |

TABLE 2-continued

Example Compounds

| Example Compound | Chemical Name | Structure | General procedure | Characterization | Purity HPLC (%) |
|---|---|---|---|---|---|
| 238 | 1-benzyl-6-(3,5-dimethylisoxazol-4-yl)-N-(2-(pyrrolidin-1-yl)ethyl)-1H-imidazo[4,5-b]pyridin-2-amine | 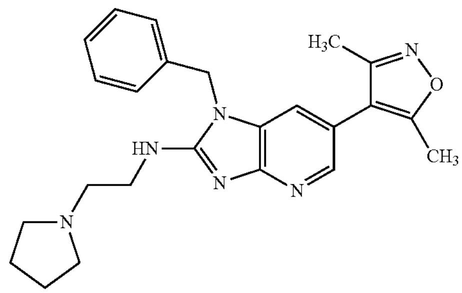 [SMILES: Cc1noc(C)c1-c1cnc2nc(NCCN3CCCC3)n(Cc3ccccc3)c2c1] | Q | $^1$H NMR (500 MHz, CD3OD) δ 7.94 (d, J = 2.0 Hz, 1H), 7.38-7.28 (m, 4H), 7.27-7.21 (m, 2H), 5.31 (s, 2H), 3.70 (t, J = 6.5 Hz, 2H), 2.81 (t, J = 6.5 Hz, 2H), 2.70-2.55 (m, 4H), 2.32 (s, 3H), 2.14 (s, 3H), 1.89-1.76 (m, 4H); ESI m/z 417 [M + H]+. | 98.1 |
| 239 | 1-benzyl-6-(3,5-dimethylisoxazol-4-yl)-N-(2-(piperidin-1-yl)ethyl)-1H-imidazo[4,5-b)pyridin-2-amine | 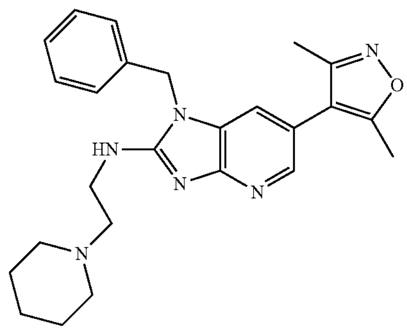 [SMILES: Cc1noc(C)c1-c1cnc2nc(NCCN3CCCCC3)n(Cc3ccccc3)c2c1] | Q | $^1$H NMR (500 MHz, CD3OD) δ 7.95 (d, J = 1.5 Hz, 1H), 7.38-7.28 (m, 4H), 7.27-7.21 (m, 2H), 5.31 (s, 2H), 3.69 (t, J = 6.5 Hz, 2H), 2.66 (t, J = 6.5 Hz, 2H), 2.60-2.40 (m, 4H), 2.33 (s, 3H), 2.15 (s, 3H), 1.66-1.57 (m, 4H), 1.52-1.42 (m, 2H); ESI m/z 431 [M + H]+. | >99 |
| 240 | (R)-6-(3,5-dimethylisoxazol-4-yl)-4-nitrophenylethyl)-1H-benzo[d]imidazol-2(3H)-one | 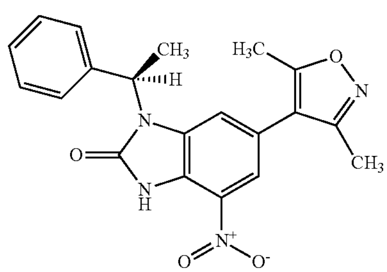 [SMILES: Cc1noc(C)c1-c1cc([N+](=O)[O-])c2[nH]c(=O)n([C@H](C)c3ccccc3)c2c1] | P | $^1$H NMR (300 MHz, DMSO-d6) δ 12.1 (s, 1H), 7.68 (d, J = 1.5 Hz, 1H), 7.45-7.29 (m, 5H), 7.13 (d, J = 1.2 Hz, 1H), 5.79 (q, J = 7.2 Hz, 1H), 2.25 (s, 3H), 2.04 (s, 3H), 1.88 (d, J = 7.2 Hz, 3H); ESI MS m/z 379 [M + H]+. | 98.1 |
| 241 | 4-(1-benzyl-7-methoxy-2-(trifluoromethyl)-1H-benzo[d]imidazol-6-yl)-3,5-dimethylisoxazole | 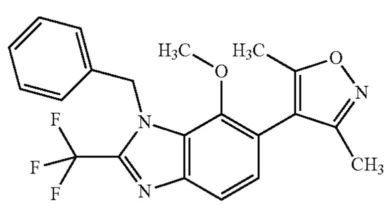 [SMILES: COc1c(-c2c(C)noc2C)ccc2nc(C(F)(F)F)n(Cc3ccccc3)c12] | No general procedure | $^1$H NMR (300 MHz, DMSO-d6) δ 7.72 (d, J = 8.4 Hz, 1H), 7.36-7.26 (m, 4H), 7.03-7.00 (m, 2H), 5.81 (s, 2H), 3.13 (s, 3H), 2.27 (s, 3H), 2.09 (s, 3H); ESI m/z 402 [M + H]+. | 95.6 |
| 242 | 1-benzyl-6-(3,5-dimethylisoxazol-4-yl)-N-(thiazol-2-ylmethyl)-1H-imidazo[4,5-b]pyridin-2-amine | 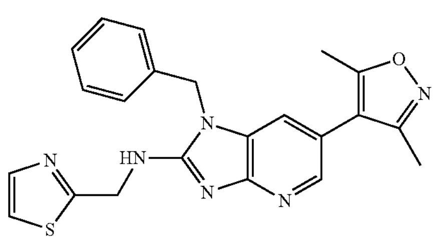 [SMILES: Cc1noc(C)c1-c1cnc2nc(NCc3nccs3)n(Cc3ccccc3)c2c1] | Q | $^1$H NMR (500 MHz, CD3OD) δ 7.98 (d, J = 1.9 Hz, 1H), 7.73 (d, J = 3.3 Hz, 1H), 7.49 (d, J = 3.3 Hz, 1H), 7.38-7.22 (m, 6H), 5.37 (s, 2H), 5.07 (s, 2H), 2.32 (s, 3H), 2.14 (s, 3H); ESI m/z 417 [M + H]+. | >99 |

TABLE 2-continued

Example Compounds

| Example Compound | Chemical Name | Structure | General procedure | Characterization | Purity HPLC (%) |
|---|---|---|---|---|---|
| 243 | 1-benzyl-6-(3,5-dimethylisoxazol-4-yl)-1H-benzo[d]imidazole-2-carboximidamide | 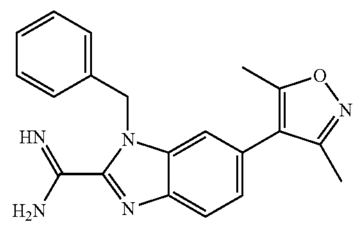 [SMILES: Cc1noc(C)c1-c1ccc2nc(C(=N)N)n(Cc3ccccc3)c2c1] | No general procedure | ¹H NMR (500 MHz, DMSO-d₆) δ 7.77 (d, J = 8.3 Hz, 1H), 7.49 (s, 1H), 7.36 (s, 1H), 7.33-7.19 (m, 6H), 6.58 (s, 2H), 6.27 (s, 2H), 2.32 (s, 3H), 2.15 (s, 3H); ESI m/z 346 [M + H]+. | >99 |
| 244 | 1-benzyl-6-(3,5-dimethylisoxazol-4-yl)-1H-benzo[d]imidazole-2-carboxamide | 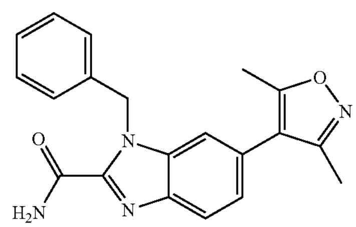 [SMILES: Cc1noc(C)c1-c1ccc2nc(C(N)=O)n(Cc3ccccc3)c2c1] | No general procedure | ¹H NMR (500 MHz, DMSO-d₆) δ 8.38 (s, 1H), 7.92 (s, 1H), 7.82 (d, J = 8.5 Hz, 1H), 7.63 (d, J = 1.0 Hz, 1H), 7.33-7.28 (m, 5H), 7.27-7.22 (m, 1H), 6.02 (s, 2H), 2.35 (s, 3H), 2.18 (s, 3H); ESI m/z 347 [M + H]+. | >99 |
| 245 | 1-benzyl-6-(3,5-dimethylisoxazol-4-yl)-N-((1-methylpiperidin-4-yl)methyl)-1H-imidazo[4,5-b]pyridin-2-amine | 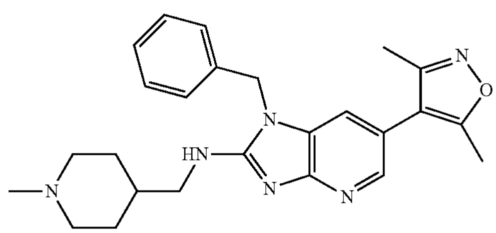 [SMILES: Cc1noc(C)c1-c1cnc2nc(NCC3CCN(C)CC3)n(Cc3ccccc3)c2c1] | Q | ¹H NMR (500 MHz, DMSO-d₆) δ 7.94 (d, J = 2.0 Hz, 1H), 7.34-7.37 (m, 2H), 7.32 (t, J = 7.0 Hz, 2H), 7.27-7.21 (m, 3H), 5.31 (s, 2H), 3.32 (t, J = 6.0 Hz, 2H), 2.84-2.72 (m, 2H), 2.33 (s, 3H), 2.16 (br.s, 3H), 2.15 (s, 3H), 1.98-1.71 (m, 2H), 1.69-1.61 (m, 3H), 1.23-1.15 (m, 2H); ESI m/z 431 [M + H]+. | >99 |
| 246 | 1-(1-benzyl-6-(3,5-dimethylisoxazol-4-yl)-1H-imidazo[4,5-b]pyridin-2-yl)azetidin-3-ol | 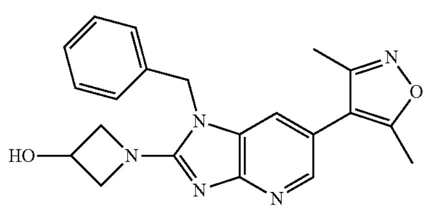 [SMILES: Cc1noc(C)c1-c1cnc2nc(N3CC(O)C3)n(Cc3ccccc3)c2c1] | Q | ¹H NMR (300 MHz, DMSO-d₆) δ 7.74 (s, 1H), 7.41 (d, J = 6.6 Hz, 2H), 7.36-7.23 (m, 3H), 7.18 (s, 1H), 5.20 (d, J = 3.3 Hz, 1H), 5.04 (s, 2H), 4.12 (d, J = 3.3 Hz, 1H), 3.89 (qd, J = 12.0, 3.3 Hz, 2H), 3.45 (qd, J = 14.4, 3.3 Hz, 2H), 2.33 (s, 3H), 2.14 (s, 3H); ESI m/z 376 [M + H]+. | >99 |
| 247 | 4-(1-benzyl-2-(pyridin-4-yloxy)-1H-imiazo[4,5-b]pyidin-6-yl)-3,5-dimethylisoxazole | 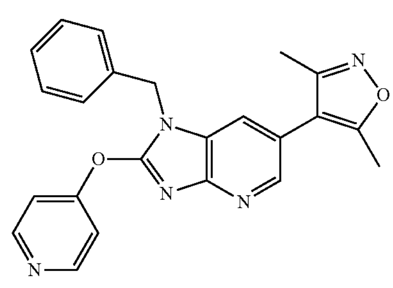 [SMILES: Cc1noc(C)c1-c1cnc2nc(Oc3ccncc3)n(Cc3ccccc3)c2c1] | T | ¹H NMR (500 MHz, DMSO-d₆) δ 8.54 (d, J = 2.0 Hz, 1H), 8.20 (d, J = 2.0 Hz, 1H), 8.00 (dd, J = 6.0, 2.0 Hz, 2H), 7.32-7.27 (m, 3H), 7.12 (dd, J = 8.0, 1.0 Hz, 2H), 6.26 (dd, J = 6.0, 2.0 Hz, 2H), 5.57 (s, 2H), 2.41 (s, 3H), 2.23 (s, 3H); ESI m/z 398 [M + H]+. | >99 |

TABLE 2-continued

Example Compounds

| Example Compound | Chemical Name | Structure | General procedure | Characterization | Purity HPLC (%) |
|---|---|---|---|---|---|
| 248 | 1-benzyl-6-(3,5-dimethylisoxazol-4-yl)-N-(pyridin-3-yl)-1H-benzo[d]imidazol-2-amine | 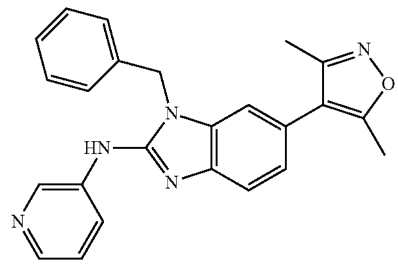 [SMILES: Cc1noc(C)c1-c1ccc2nc(Nc3cccnc3)n(Cc3ccccc3)c2c1] | No general procedure | ESI m/z 396 [M + H]+. | — |
| 249 | 3-(1-benzyl-1H-benzo[d]imidazol-6-yl)-4-ethyl-1H-1,2,4-triazol-5(4H)-one | 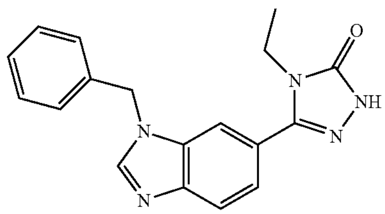 [SMILES: CCn1c(-c2ccc3ncn(Cc4ccccc4)c3c2)n[nH]c1=O] | No general procedure | $^1$H NMR (300 MHz, DMSO-d$_6$) δ 11.85 (s, 1H), 8.59 (s, 1H), 7.81-7.76 (m, 2H), 7.43 (dd, J = 8.1, 1.5 Hz, 1H), 7.35-7.28 (m, 5H), 5.58 (s, 2H), 3.63 (q, J = 7.2, Hz 2H), 0.98 (t, J = 7.2 Hz, 3H); ESI m/z 320 [M + H]+. | — |

Example 1:

Inhibition of Tetra-Acetylated Histone H4 Binding Individual BET Bromodomains

Proteins were cloned and overexpressed with a N-terminal 6xHis tag, then purified by nickel affinity followed by size exclusion chromatography. Briefly, *E. coli* BL21(DE3) cells were transformed with a recombinant expression vector encoding N-terminally Nickel affinity tagged bromodomains from Brd2, Brd3, Brd4. Cell cultures were incubated at 37° C. with shaking to the appropriate density and induced overnight with IPTG. The supernatant of lysed cells was loaded onto Ni-IDA column for purification. Eluted protein was pooled, concentrated and further purified by size exclusion chromatography. Fractions representing monomeric protein were pooled, concentrated, aliquoted, and frozen at −80° C. for use in subsequent experiments.

Binding of tetra-acetylated histone H4 and BET bromodomains was confirmed by a Time Resolved Fluorescence Resonance Energy Transfer (TR-FRET) method. N-terminally His-tagged bromodomains (200 nM) and biotinylated tetra-acetylated histone H4 peptide (25-50 nM, Millipore) were incubated in the presence of Europium Cryptate-labeled streptavidin (Cisbio Cat. #610SAKLB) and XL665-labeled monoclonal anti-His antibody (Cisbio Cat. #61HISXLB) in a white 96 well microtiter plate (Greiner). For inhibition assays, serially diluted test compound was added to these reactions in a 0.2% final concentration of DMSO. Final buffer concentrations were 30 mM HEPES pH 7.4, 30 mM NaCl, 0.3 mM CHAPS, 20 mM phosphate pH 7.0, 320 mM KF, 0.08% BSA). After a 2-h incubation at room temperature, the fluorescence by FRET was measured at 665 and 620 nm by a SynergyH4 plate reader (Biotek). Illustrative results with the first bromodomain of Brd4 are shown below. The binding inhibitory activity was shown by a decrease in 665 nm fluorescence relative to 620 nm. IC$_{50}$ values were determined from a dose response curve.

Compounds with an IC$_{50}$ value less than or equal to 0.3 μM were deemed to be highly active (+++); compounds with an IC$_{50}$ value between 0.3 and 3 μM were deemed to be very active (++); compounds with an IC$_{50}$ value between 3 and 30 μM were deemed to be active (+).

TABLE 3

Inhibition of Tetra-acetylated Histone H4 Binding to Brd4 bromodomain 1 (BRD4(1)) as Measured by FRET

| Example Compound | FRET activity BRD4(1) | Example Compound | FRET activity BRD4(1) | Example Compound | FRET activity BRD4(1) | Example Compound | FRET activity BRD4(1) |
|---|---|---|---|---|---|---|---|
| 1 | ++ | 2 | +++ | 3 | ++ | 4 | ++ |
| 5 | +++ | 6 | ++ | 7 | +++ | 8 | +++ |
| 9 | + | 10 | +++ | 11 | +++ | 12 | +++ |
| 13 | +++ | 14 | +++ | 15 | +++ | 16 | +++ |
| 17 | +++ | 18 | +++ | 19 | +++ | 20 | +++ |
| 21 | +++ | 22 | ++ | 23 | ++ | 24 | +++ |
| 25 | + | 26 | ++ | 27 | +++ | 28 | +++ |
| 29 | +++ | 30 | +++ | 31 | ++ | 32 | Not active |

TABLE 3-continued

Inhibition of Tetra-acetylated Histone H4 Binding to Brd4 bromodomain 1 (BRD4(1) as Measured by FRET

| Example Compound | FRET activity BRD4(1) | Example Compound | FRET activity BRD4(1) | Example Compound | FRET activity BRD4(1) | Example Compound | FRET activity BRD4(1) |
|---|---|---|---|---|---|---|---|
| 33 | +++ | 34 | +++ | 35 | +++ | 36 | +++ |
| 37 | ++ | 38 | +++ | 39 | +++ | 40 | ++ |
| 41 | +++ | 42 | ++ | 43 | +++ | 44 | ++ |
| 45 | +++ | 46 | ++ | 47 | + | 48 | +++ |
| 49 | + | 50 | +++ | 51 | +++ | 52 | ++ |
| 53 | +++ | 54 | +++ | 55 | +++ | 56 | ++ |
| 57 | + | 58 | +++ | 59 | ++ | 60 | ++ |
| 61 | +++ | 62 | +++ | 63 | ++ | 64 | +++ |
| 65 | +++ | 66 | +++ | 67 | +++ | 68 | +++ |
| 69 | +++ | 70 | +++ | 71 | +++ | 72 | ++ |
| 73 | ++ | 74 | ++ | 75 | +++ | 76 | ++ |
| 77 | +++ | 78 | +++ | 79 | Not active | 80 | ++ |
| 81 | ++ | 82 | ++ | 83 | +++ | 84 | +++ |
| 85 | +++ | 86 | +++ | 87 | +++ | 88 | +++ |
| 89 | +++ | 90 | +++ | 91 | +++ | 92 | +++ |
| 93 | +++ | 94 | +++ | 95 | +++ | 96 | +++ |
| 97 | +++ | 98 | ++ | 99 | +++ | 100 | +++ |
| 101 | ++ | 102 | +++ | 103 | +++ | 104 | +++ |
| 105 | +++ | 106 | +++ | 107 | +++ | 108 | +++ |
| 109 | +++ | 110 | +++ | 111 | +++ | 112 | +++ |
| 113 | +++ | 114 | +++ | 115 | +++ | 116 | +++ |
| 117 | +++ | 118 | +++ | 119 | +++ | 120 | +++ |
| 121 | +++ | 122 | +++ | 123 | +++ | 124 | +++ |
| 125 | +++ | 126 | +++ | 127 | +++ | 128 | +++ |
| 129 | +++ | 130 | +++ | 131 | +++ | 132 | +++ |
| 133 | +++ | 134 | +++ | 135 | +++ | 136 | +++ |
| 137 | +++ | 138 | +++ | 139 | +++ | 140 | +++ |
| 141 | +++ | 142 | ++ | 143 | +++ | 144 | +++ |
| 145 | +++ | 146 | +++ | 147 | +++ | 148 | +++ |
| 149 | +++ | 150 | +++ | 151 | +++ | 152 | +++ |
| 153 | +++ | 154 | +++ | 155 | +++ | 156 | +++ |
| 157 | +++ | 158 | +++ | 159 | +++ | 160 | +++ |
| 161 | +++ | 162 | +++ | 163 | +++ | 164 | +++ |
| 165 | +++ | 166 | ++ | 167 | +++ | 168 | +++ |
| 169 | +++ | 170 | +++ | 171 | ++ | 172 | +++ |
| 173 | +++ | 174 | +++ | 175 | ++ | 176 | ++ |
| 177 | ++ | 178 | +++ | 179 | +++ | 180 | +++ |
| 181 | +++ | 182 | +++ | 183 | +++ | 184 | + |
| 185 | +++ | 186 | +++ | 187 | ++ | 188 | + |
| 189 | ++ | 190 | ++ | 191 | +++ | 192 | +++ |
| 193 | +++ | 194 | +++ | 195 | +++ | 196 | +++ |
| 197 | +++ | 198 | +++ | 199 | +++ | 200 | ++ |
| 201 | +++ | 202 | +++ | 203 | +++ | 204 | ++ |
| 205 | +++ | 206 | +++ | 207 | +++ | 208 | +++ |
| 209 | +++ | 210 | +++ | 211 | +++ | 212 | +++ |
| 213 | +++ | 214 | +++ | 215 | +++ | 216 | +++ |
| 217 | +++ | 218 | +++ | 219 | ++ | 220 | +++ |
| 221 | +++ | 222 | +++ | 223 | +++ | 224 | +++ |
| 225 | +++ | 226 | +++ | 227 | +++ | 228 | +++ |
| 229 | +++ | 230 | +++ | 231 | +++ | 232 | +++ |
| 233 | +++ | 234 | +++ | 235 | +++ | 236 | +++ |
| 237 | +++ | 238 | +++ | 239 | +++ | 240 | +++ |
| 241 | ++ | — | — | — | — | — | — |

Example 2:

Inhibition of c-Myc Expression in Cancer Cell Lines

MV4-11 cells (CRL-9591) were plated at a density of $2.5 \times 10^4$ cells per well in 96 well U-bottom plates and treated with increasing concentrations of test compound or DMSO (0.1%) in IMDM media containing 10% FBS and penicillin/streptomycin, and incubated for 3 h at 37° C. Triplicate wells were used for each concentration. Cells were pelleted by centrifugation and harvested using the mRNA Catcher PLUS kit according to manufacturer's instructions. The eluted mRNA isolated was then used in a one-step quantitative real-time PCR reaction, using components of the RNA UltraSense™ One-Step Kit (Life Technologies) together with Applied Biosystems TaqMan® primer-probes for cMYC and Cyclophilin. Real-time PCR plates were run on a VIa™7 real time PCR machine (Applied Biosystems), data was analyzed, normalizing the Ct values for cMYC to an internal control, prior to determining the fold expression of each sample, relative to the control.

Compounds with an $IC_{50}$ value less than or equal to 0.3 μM were deemed to be highly active (+++); compounds with an $IC_{50}$ value between 0.3 and 3 μM were deemed to be very active (++); compounds with an $IC_{50}$ value between 3 and 30 μM were deemed to be active (+).

TABLE 4

Inhibition of c-myc Activity in Human AML MV4-11 cells

| Example Compound | c-myc activity | Example Compound | c-myc activity | Example Compound | c-myc activity | Example Compound | c-myc activity |
|---|---|---|---|---|---|---|---|
| 1 | Not active | 2 | + | 3 | + | 4 | ++ |
| 5 | ++ | 6 | ++ | 7 | ++ | 8 | ++ |
| 9 | + | 10 | ++ | 11 | Not active | 12 | ++ |
| 13 | ++ | 14 | ++ | 15 | ++ | 16 | +++ |
| 17 | +++ | 18 | +++ | 19 | +++ | 20 | Not active |
| 22 | ++ | 23 | Not active | 24 | + | 26 | + |
| 27 | ++ | 28 | ++ | 29 | ++ | 30 | ++ |
| 31 | Not active | 33 | ++ | 34 | ++ | 35 | ++ |
| 36 | ++ | 37 | + | 38 | + | 39 | ++ |
| 40 | Not active | 41 | Not active | 42 | + | 43 | Not active |
| 44 | + | 45 | ++ | 46 | + | 47 | Not active |
| 48 | ++ | 49 | + | 50 | + | 51 | ++ |
| 52 | + | 53 | Not active | 54 | ++ | 55 | +++ |
| 56 | Not active | 58 | ++ | 60 | + | 61 | ++ |
| 62 | ++ | 63 | + | 64 | +++ | 65 | ++ |
| 66 | ++ | 67 | +++ | 68 | ++ | 69 | ++ |
| 70 | Not active | 71 | ++ | 72 | + | 73 | + |
| 74 | + | 75 | ++ | 76 | ++ | 77 | ++ |
| 78 | + | 79 | Not active | 80 | Not active | 81 | + |
| 82 | ++ | 83 | ++ | 84 | ++ | 85 | +++ |
| 86 | ++ | 87 | +++ | 88 | ++ | 89 | ++ |
| 90 | +++ | 91 | ++ | 92 | ++ | 93 | + |
| 94 | ++ | 95 | ++ | 96 | +++ | 97 | +++ |
| 98 | ++ | 99 | ++ | 100 | ++ | 102 | +++ |
| 103 | ++ | 104 | ++ | 105 | ++ | 106 | ++ |
| 108 | ++ | 109 | +++ | 110 | ++ | 111 | +++ |
| 112 | +++ | 113 | +++ | 114 | ++ | 115 | +++ |
| 116 | +++ | 117 | +++ | 118 | ++ | 119 | +++ |
| 120 | ++ | 121 | +++ | 122 | ++ | 123 | +++ |
| 124 | ++ | 125 | +++ | 126 | +++ | 127 | +++ |
| 128 | ++ | 129 | +++ | 130 | ++ | 131 | ++ |
| 132 | ++ | 133 | +++ | 134 | +++ | 138 | +++ |
| 139 | +++ | 140 | +++ | 141 | +++ | 142 | ++ |
| 143 | +++ | 144 | +++ | 145 | + | 146 | +++ |
| 148 | ++ | 149 | +++ | 150 | Not active | 151 | +++ |
| 152 | +++ | 153 | +++ | 154 | Not active | 155 | + |
| 156 | ++ | 157 | +++ | 158 | ++ | 159 | +++ |
| 160 | ++ | 161 | Not active | 163 | ++ | 165 | ++ |
| 167 | +++ | 168 | ++ | 169 | +++ | 170 | +++ |
| 171 | ++ | 172 | +++ | 173 | +++ | 174 | ++ |
| 176 | ++ | 177 | +++ | 178 | +++ | 179 | +++ |
| 180 | ++ | 181 | +++ | 182 | ++ | 183 | ++ |
| 185 | +++ | 186 | + | 191 | +++ | 192 | ++ |
| 193 | ++ | 194 | +++ | 195 | +++ | 196 | +++ |
| 197 | +++ | 198 | + | 199 | ++ | 200 | Not active |
| 201 | ++ | 202 | ++ | 203 | + | 205 | ++ |
| 206 | Not active | 208 | +++ | 209 | ++ | 210 | ++ |
| 211 | ++ | 212 | ++ | 213 | ++ | 214 | +++ |
| 215 | +++ | 216 | ++ | 217 | +++ | 218 | ++ |
| 219 | ++ | 220 | + | 221 | ++ | 222 | +++ |
| 223 | +++ | — | — | — | — | — | — |

Example 3:

Inhibition of Cell Proliferation in Cancer Cell Lines

MV4-11 cells: 96-well plates were seeded with 5×10$^4$ cells per well of exponentially growing human AML MV-4-11 (CRL-9591) cells and immediately treated with two-fold dilutions of test compounds, ranging from 30 μM to 0.2 μM. Triplicate wells were used for each concentration, as well as a media only and three DMSO control wells. The cells and compounds were incubated at 37° C., 5% CO$_2$ for 72 h before adding 20 μL of the CellTiter Aqueous One Solution (Promega) to each well and incubating at 37° C., 5% CO$_2$ for an additional 3-4 h. The absorbance was taken at 490 nm in a spectrophotometer and the percentage of proliferation relative to DMSO-treated cells was calculated after correction from the blank well. IC$_{50}$ were calculated using the GraphPad Prism software.

Compounds with an IC$_{50}$ value less than or equal to 0.3 μM were deemed to be highly active (+++); compounds with an IC$_{50}$ value between 0.3 and 3 μM were deemed to be very active (++); compounds with an IC$_{50}$ value between 3 and 30 μM were deemed to be active (+).

TABLE 5

Inhibition of Cell Proliferation in Human AML MV-4-11 cells

| Example Compound | Cell Proliferation activity | Example Compound | Cell Proliferation activity | Example Compound | Cell Proliferation activity | Example Compound | Cell Proliferation activity |
|---|---|---|---|---|---|---|---|
| 1 | Not active | 2 | ++ | 3 | + | 4 | + |
| 5 | ++ | 6 | ++ | 7 | +++ | 8 | ++ |
| 9 | + | 10 | ++ | 11 | Not active | 12 | ++ |
| 13 | ++ | 14 | + | 15 | ++ | 16 | +++ |
| 17 | ++ | 18 | +++ | 19 | +++ | 20 | Not active |
| 21 | ++ | 22 | ++ | 23 | + | 24 | Not active |
| 25 | Not active | 26 | ++ | 27 | ++ | 28 | ++ |
| 29 | ++ | 30 | ++ | 31 | + | 33 | + |
| 34 | ++ | 35 | ++ | 36 | ++ | 37 | Not active |
| 38 | Not active | 39 | ++ | 40 | Not active | 41 | ++ |
| 42 | + | 43 | ++ | 44 | + | 45 | ++ |
| 46 | + | 47 | Not active | 48 | + | 49 | + |
| 50 | + | 51 | ++ | 52 | ++ | 53 | Not active |
| 54 | ++ | 55 | +++ | 57 | + | 58 | ++ |
| 59 | Not active | 60 | Not active | 61 | + | 62 | ++ |
| 64 | ++ | 65 | ++ | 66 | ++ | 67 | ++ |
| 68 | + | 69 | ++ | 70 | + | 71 | ++ |
| 72 | + | 73 | + | 74 | + | 75 | ++ |
| 76 | + | 77 | ++ | 78 | + | 79 | Not active |
| 80 | Not active | 81 | + | 82 | + | 83 | ++ |
| 84 | ++ | 86 | + | 87 | +++ | 88 | ++ |
| 89 | ++ | 90 | ++ | 91 | + | 92 | ++ |
| 93 | + | 94 | ++ | 95 | ++ | 96 | +++ |
| 97 | +++ | 98 | ++ | 99 | ++ | 100 | ++ |
| 102 | ++ | 103 | ++ | 104 | ++ | 105 | ++ |
| 106 | ++ | 107 | ++ | 108 | ++ | 109 | +++ |
| 110 | ++ | 111 | +++ | 112 | ++ | 113 | +++ |
| 114 | ++ | 115 | +++ | 116 | +++ | 117 | +++ |
| 118 | ++ | 119 | +++ | 120 | ++ | 121 | +++ |
| 122 | +++ | 123 | ++ | 124 | ++ | 125 | ++ |
| 126 | ++ | 127 | +++ | 128 | ++ | 129 | ++ |
| 130 | ++ | 131 | ++ | 132 | ++ | 133 | ++ |
| 134 | +++ | 135 | ++ | 136 | ++ | 137 | +++ |
| 138 | ++ | 139 | +++ | 140 | +++ | 141 | +++ |
| 142 | + | 143 | +++ | 144 | +++ | 145 | + |
| 146 | +++ | 148 | ++ | 149 | ++ | 150 | Not active |
| 151 | +++ | 152 | ++ | 153 | +++ | 154 | + |
| 155 | Not active | 156 | ++ | 157 | +++ | 158 | ++ |
| 159 | ++ | 160 | ++ | 161 | ++ | 162 | +++ |
| 163 | ++ | 165 | ++ | 167 | +++ | 168 | ++ |
| 169 | +++ | 170 | +++ | 171 | ++ | 172 | ++ |
| 173 | ++ | 174 | ++ | 176 | ++ | 177 | +++ |
| 178 | ++ | 179 | +++ | 180 | ++ | 181 | ++ |
| 182 | ++ | 183 | + | 185 | +++ | 186 | Not active |
| 191 | ++ | 192 | ++ | 193 | ++ | 194 | +++ |
| 195 | +++ | 196 | ++ | 197 | +++ | 198 | + |
| 199 | ++ | 200 | Not active | 201 | ++ | 202 | ++ |
| 203 | + | 205 | ++ | 206 | + | 207 | +++ |
| 208 | ++ | 209 | +++ | 210 | ++ | 211 | +++ |
| 212 | ++ | 213 | ++ | 214 | +++ | 215 | ++ |
| 216 | +++ | 217 | ++ | 218 | + | 219 | ++ |
| 220 | ++ | 221 | ++ | 222 | +++ | 223 | ++ |

Example 4:

Inhibition of hIL-6 mRNA Transcription

In this example, hIL-6 mRNA in tissue culture cells was quantitated to measure the transcriptional inhibition of hIL-6 when treated with a compound of the invention.

In this example, hIL-6 mRNA in tissue culture cells was quantitated to measure the transcriptional inhibition of hIL-6 when treated with a compound of the invention.

Human leukemic monocyte lymphoma U937 cells (CRL-1593.2) were plated at a density of 3.2×104 cells per well in a 96-well plate in 100 µL RPMI-1640 containing 10% FBS and penicillin/streptomycin, and differentiated into macrophages for 3 days in 60 ng/mL PMA (phorbol-13-myristate-12-acetate) at 37° C. in 5% CO2 prior to the addition of compound. The cells were pretreated for 1 h with increasing concentrations of test compound in 0.1% DMSO prior to stimulation with 1 ug/mL lipopolysaccharide from *Escherichia coli*. Triplicate wells were used for each concentration. The cells were incubated at 37° C., 5% CO2 for 3 h before the cells were harvested. At time of harvest, media was removed and cells were rinsed in 200 µL PBS. Cells were harvested using the mRNA Catcher PLUS kit according to manufacturer's instructions. The eluted mRNA was then used in a one-step quantitative real-time PCR reaction using components of the RNA UltraSense™ One-Step Kit (Life Technologies) together with Applied Biosystems TaqMan® primer-probes for hIL-6 and Cyclophilin. Real-time PCR plates were run on a VIa™7 real time PCR machine (Applied Biosystems), data was analyzed, normalizing the Ct values for hIL-6 to an internal control, prior to determining the fold expression of each sample, relative to the control.

Compounds with an IC$_{50}$ value less than or equal to 0.3 µM were deemed to be highly active (+++); compounds with an IC$_{50}$ value between 0.3 and 3 µM were deemed to be very active (++); compounds with an IC$_{50}$ value between 3 and 30 µM were deemed to be active (+).

TABLE 6

Inhibition of hIL-6 mRNA Transcription

| Example Compound | IL-6 activity | Example Compound | IL-6 activity | Example Compound | IL-6 activity | Example Compound | IL-6 activity |
|---|---|---|---|---|---|---|---|
| 1 | ++ | 2 | ++ | 3 | + | 4 | ++ |
| 5 | ++ | 6 | ++ | 7 | +++ | 8 | ++ |
| 9 | + | 10 | +++ | 11 | ++ | 12 | ++ |
| 13 | +++ | 14 | ++ | 15 | ++ | 16 | +++ |
| 17 | ++ | 18 | ++ | 19 | +++ | 20 | Not active |
| 21 | +++ | 22 | ++ | 23 | ++ | 24 | ++ |
| 25 | Not active | 26 | ++ | 27 | ++ | 28 | ++ |
| 29 | ++ | 30 | ++ | 31 | ++ | 33 | ++ |
| 34 | ++ | 35 | ++ | 36 | ++ | 37 | + |
| 38 | + | 39 | ++ | 40 | + | 41 | + |
| 42 | + | 43 | ++ | 44 | ++ | 45 | ++ |
| 46 | + | 47 | Not active | 48 | ++ | 49 | + |
| 50 | ++ | 51 | ++ | 52 | ++ | 53 | ++ |
| 54 | ++ | 55 | +++ | 56 | + | 58 | ++ |
| 59 | Not active | 60 | ++ | 61 | ++ | 62 | ++ |
| 63 | ++ | 64 | +++ | 65 | ++ | 66 | ++ |
| 67 | +++ | 68 | ++ | 69 | ++ | 70 | ++ |
| 71 | ++ | 72 | + | 73 | ++ | 74 | ++ |
| 75 | ++ | 76 | ++ | 77 | ++ | 78 | ++ |
| 79 | Not active | 80 | Not active | 81 | ++ | 82 | ++ |
| 83 | ++ | 84 | ++ | 85 | ++ | 86 | ++ |
| 87 | +++ | 88 | +++ | 89 | ++ | 91 | ++ |
| 92 | ++ | 93 | ++ | 94 | ++ | 95 | ++ |
| 96 | +++ | 97 | +++ | 98 | ++ | 99 | ++ |
| 100 | ++ | 102 | +++ | 103 | ++ | 105 | ++ |
| 106 | ++ | 108 | +++ | 109 | +++ | 111 | +++ |
| 112 | ++ | 113 | +++ | 114 | ++ | 115 | +++ |
| 116 | ++ | 117 | +++ | 118 | ++ | 119 | +++ |
| 121 | ++ | 122 | ++ | 123 | +++ | 127 | +++ |
| 129 | +++ | 131 | ++ | 132 | +++ | 133 | +++ |
| 135 | +++ | 136 | ++ | 137 | +++ | 140 | +++ |
| 141 | +++ | 143 | +++ | 144 | +++ | 146 | +++ |
| 148 | +++ | 149 | +++ | 150 | ++ | 151 | +++ |
| 152 | +++ | 153 | +++ | 154 | + | 155 | ++ |
| 156 | ++ | 157 | +++ | 158 | ++ | 162 | +++ |
| 164 | +++ | 207 | +++ | 208 | +++ | 209 | +++ |
| 211 | +++ | 214 | +++ | 215 | +++ | 216 | +++ |
| 217 | +++ | 218 | ++ | 220 | ++ | 221 | ++ |
| 223 | ++ | — | — | — | — | — | — |

Example 5:

Inhibition of IL-17 mRNA Transcription

In this example, hIL-17 mRNA in human peripheral blood mononuclear cells was quantitated to measure the transcriptional inhibition of hIL-17 when treated with a compound of the invention.

Human peripheral blood mononuclear cells were plated (2.0×10$^5$ cells per well) in a 96-well plate in 45 µL OpTimizer T Cell expansion media containing 20 ng/ml IL-2 and penicillin/streptomycin. The cells were treated with the test compound (45 µL at 2× concentration), and then the cells were incubated at 37° C. for 1 h before addition of 10× stock OKT3 antibody at 10 µg/ml in media. Cells were incubated at 37° C. for 6 h before the cells were harvested. At time of harvest, cells were centrifuged (800 rpm, 5 min). Spent media was removed and cell lysis solution (70 µL) was added to the cells in each well and incubated for 5-10 min at room temperature, to allow for complete cell lysis and detachment. mRNA was then prepared using the "mRNA Catcher PLUS plate" (Invitrogen), according to the protocol supplied. After the last wash, as much wash buffer as possible was aspirated without allowing the wells to dry. Elution buffer (E3, 70 µL) was then added to each well. mRNA was then eluted by incubating the mRNA Catcher PLUS plate with Elution Buffer for 5 min at 68° C. and then immediately placing the plate on ice.

The eluted mRNA isolated was then used in a one-step quantitative RT-PCR reaction, using components of the Ultra Sense Kit together with Applied Biosystems primer-probe mixes. Real-time PCR data was analyzed, normalizing the Ct values for hIL-17 to an internal control, prior to determining the fold induction of each unknown sample, relative to the control.

Compounds with an IC$_{50}$ value less than or equal to 0.3 µM were deemed to be highly active (+++); compounds with an IC$_{50}$ value between 0.3 and 3 µM were deemed to be very active (++); compounds with an IC$_{50}$ value between 3 and 30 µM were deemed to be active (+).

TABLE 7

Inhibition of hIL-17 mRNA Transcription

| Example Compound | IL-17 activity | Example Compound | IL-17 activity | Example Compound | IL-17 activity | Example Compound | IL-17 activity |
|---|---|---|---|---|---|---|---|
| 5 | ++ | 7 | +++ | 8 | ++ | 10 | +++ |
| 13 | ++ | 16 | ++ | 18 | ++ | 19 | +++ |
| 30 | ++ | 45 | ++ | 51 | ++ | 53 | + |
| 55 | +++ | 64 | +++ | 105 | ++ | 106 | ++ |
| 112 | +++ | – | – | – | – | – | – |

Example 6:

Inhibition of hVCAM mRNA Transcription

In this example, hVCAMmRNA in tissue culture cells is quantitated to measure the transcriptional inhibition of hVCAM when treated with a compound of the present disclosure.

Human umbilical vein endothelial cells (HUVECs) are plated in a 96-well plate ($4.0 \times 10^3$ cells/well) in 100 µL EGM media and incubated for 24 h prior to the addition of the compound of interest. The cells are pretreated for 1 h with the test compound prior to stimulation with tumor necrosis factor-α. The cells are incubated for an additional 24 h before the cells are harvested. At time of harvest, the spent media is removed from the HUVECs and rinsed in 200 µL PBS. Cell lysis solution (70 µL) is then added the cells in each well and incubated for ~5-10 min at room temperature, to allow for complete cell lysis and detachment. mRNA is then prepared using the "mRNA Catcher PLUS plate" (Invitrogen), according to the protocol supplied. After the last wash, as much wash buffer as possible is aspirated without allowing the wells to dry. Elution buffer (E3, 70 µL) is then added to each well. mRNA is then eluted by incubating the mRNA Catcher PLUS plate with elution buffer for 5 min at 68° C. and then immediately placing the plate on ice.

The eluted mRNA so isolated is then used in a one-step quantitative real-time PCR reaction, using components of the Ultra Sense Kit together with Applied Biosystems primer-probe mixes. Real-time PCR data is analyzed, normalizing the Ct values for hVCAM to an internal control, prior to determining the fold induction of each unknown sample, relative to the control.

Example 7:

Inhibition of hMCP-1 mRNA Transcription

In this example, hMCP-1 mRNA in human peripheral blood mononuclear cells is quantitated to measure the transcriptional inhibition of hMCP-1 when treated with a compound of the present disclosure.

Human Peripheral Blood Mononuclear Cells are plated ($1.0 \times 10^5$ cells per well) in a 96-well plate in 45 µL RPMI-1640 containing 10% FBS and penicillin/streptomycin. The cells are treated with the test compound (45 µL at 2× concentration), and then the cells are incubated at 37° C. for 3 h before the cells are harvested. At time of harvest, cells are transferred to V-bottom plates and centrifuged (800 rpm, 5 min). Spent media is removed and cell lysis solution (70 µL) is added to the cells in each well and incubated for 5-10 min at room temperature, to allow for complete cell lysis and detachment. mRNA is then prepared using the "mRNA Catcher PLUS plate" (Invitrogen), according to the protocol supplied. After the last wash, as much wash buffer as possible is aspirated without allowing the wells to dry. Elution buffer (E3, 70 µL) is then added to each well. mRNA is then eluted by incubating the mRNA Catcher PLUS plate with Elution Buffer for 5 min at 68° C. and then immediately placing the plate on ice.

The eluted mRNA isolated is then used in a one-step quantitative real-time PCR reaction, using components of the Ultra Sense Kit together with Applied Biosystems primer-probe mixes. Real-time PCR data is analyzed, normalizing the Ct values for hMCP-1 to an internal control, prior to determining the fold induction of each unknown sample, relative to the control.

Example 8:

Up-Regulation of hApoA-1 mRNA Transcription

In this example, ApoA-I mRNA in tissue culture cells was quantitated to measure the transcriptional up-regulation of ApoA-I when treated with a compound of the invention.

Huh7 cells ($2.5 \times 10^5$ per well) were plated in a 96-well plate using 100 µL DMEM per well, (Gibco DMEM supplemented with penicillin/streptomycin and 10% FBS), 24 h before the addition of the compound of interest. After 48 h treatment, the spent media was removed from the Huh-7 cells and placed on ice (for immediate use) or at −80° C. (for future use) with the "LDH cytotoxicity assay Kit II" from Abcam. The cells remaining in the plate were rinsed with 100 µL PBS.

Then 85 µL of cell lysis solution was added to each well and incubated for 5-10 min at room temperature, to allow for complete cell lysis and detachment. mRNA was then prepared using the "mRNA Catcher PLUS plate" from Life Technologies, according to the protocol supplied. After the last wash, as much wash buffer as possible was aspirated without allowing the wells to dry. Elution Buffer (E3, 80 µL) was then added to each well. mRNA was then eluted by incubating the mRNA Catcher PLUS plate with Elution Buffer for 5 min at 68° C., and then 1 min at 4° C. Catcher plates with mRNA eluted were kept on ice for use or stored at −80° C.

The eluted mRNA isolated was then used in a one-step real-time PCR reaction, using components of the Ultra Sense Kit together with Life Technologies primer-probe mixes. Real-time PCR data was analyzed, using the Ct values, to determine the fold induction of each unknown sample, relative to the control (that is, relative to the control for each independent DMSO concentration).

Compounds with an $EC_{170}$ value less than or equal to 0.3 µM were deemed to be highly active (+++); compounds with an $EC_{170}$ value between 0.3 and 3 µM were deemed to be very active (++); compounds with an $EC_{170}$ value between 3 and 30 µM were deemed to be active (+).

TABLE 8

Up-regulation of hApoA-1 mRNA Transcription.

| Example Compound | ApoA-1 activity |
|---|---|
| 7 | +++ |

Example 9:

In Vivo Efficacy in Athymic Nude Mouse Strain of an Acute Myeloid Leukemia Xenograft Model Using MV4-11 Cells MV4-11 cells (ATCC) are grown under standard cell culture conditions and (NCr) nu/nu fisol strain of female mice age 6-7 weeks are injected with $5 \times 10^6$ cells/animal in 100 μL PBS+100 μL Matrigel in the lower left abdominal flank. By approximately day 18 after MV4-11 cells injection, mice are randomized based on tumor volume (L×W×H)/2) of average ~120 mm$^3$. Mice are dosed orally with compound at 75 mg/kg b.i.d and 120 mg/kg b.i.d in EA006 formulation at 10 mL/kg body weight dose volume. Tumor measurements are taken with electronic micro calipers and body weights measured on alternate days beginning from dosing period. The average tumor volumes, percent Tumor Growth Inhibition (TGI) and % change in body weights are compared relative to Vehicle control animals. The means, statistical analysis and the comparison between groups are calculated using Student's t-test in Excel.

TABLE 9

In vivo efficacy in athymic nude mouse strain of an acute myeloid leukemia xenograft model

| Example Compound | In vivo activity |
|---|---|
| Example 7 | Active |

Example 10:

In Vivo Efficacy in Athymic Nude Mouse Strain of an Acute Myeloid Leukemia Xenograft Model Using OCI-3 AML Cells OCI-3 AML cells (DMSZ) were grown under standard cell culture conditions and (NCr) nu/nu fisol strain of female mice age 6-7 weeks were injected with $10 \times 10^6$ cells/animal in 100 μL PBS+100 μL Matrigel in the lower left abdominal flank. By approximately day 18-21 after OCI-3 AML cells injection, mice were randomized based on tumor volume (L×W ×H)/2) of average ~100-300 mm$^3$. Mice were dosed orally with compound at 30 mg/kg b.i.d on a continuous dosing schedule and at 2.5 to 45 mg/kg q.d. on a 5 day on and 2 day off dosing schedule in EA006 formulation at 10 mL/kg body weight dose volume. Tumor measurements were taken with electronic micro calipers and body weights measured on alternate days beginning from dosing period. The average tumor volumes, percent Tumor Growth Inhibition (TGI) and % change in body weights were compared relative to Vehicle control animals. The means, statistical analysis and the comparison between groups were calculated using Student's t-test in Excel.

Example 11:

Evaluation of Target Engagement

MV4-11 cells (ATCC) are grown under standard cell culture conditions and (NCr) nu/nu fisol strain of female mice age 6-7 weeks are injected with $5 \times 10^6$ cells/animal in 100 μL PBS+100 μL Matrigel in the lower left abdominal flank. By approximately day 28 after MV4-11 cells injection, mice are randomized based on tumor volume (L x Wx H)/2) of average ~500 mm$^3$. Mice are dosed orally with compound in EA006 formulation at 10 mL/kg body weight dose volume and tumors harvested 6 hrs post dose for Bcl2 and c-myc gene expression analysis as PD biomarkers.

Example 12:

In Vivo Efficacy in Mouse Endotoxemia Model Assay

Sub lethal doses of Endotoxin (*E. Coli* bacterial lipopolysaccharide) are administered to animals to produce a generalized inflammatory response which is monitored by increases in secreted cytokines. Compounds are administered to C57/Bl6 mice at T=4 hours orally at 75 mg/kg dose to evaluate inhibition in IL-6 and IL-17 and MCP-1 cytokines post 3-h challenge with lipopolysaccharide (LPS) at T=0 hours at 0.5 mg/kg dose intraperitoneally.

Example 13:

In Vivo Efficacy in Rat Collagen-Induced Arthritis

Rat collagen-induced arthritis is an experimental model of polyarthritis that has been widely used for preclinical testing of numerous anti-arthritic agents. Following administration of collagen, this model establishes a measurable polyarticular inflammation, marked cartilage destruction in association with pannus formation and mild to moderate bone resorption and periosteal bone proliferation. In this model, collagen is administered to female Lewis strain of rats on Day 1 and 7 of study and dosed with compounds from Day 11 to Day 17. Test compounds are evaluated to assess the potential to inhibit the inflammation (including paw swelling), cartilage destruction and bone resorption in arthritic rats, using a model in which the treatment is administered after the disease has been established.

Example 14:

In Vivo Efficacy in Experimental Autoimmune Encephalomyelitis (EAE) Model of MS Experimental autoimmune encephalomyelitis (EAE) is a T-cell-mediated autoimmune disease of the CNS which shares many clinical and histopathological features with human multiple sclerosis (MS). EAE is the most commonly used animal model of MS. T cells of both Th1 and Th17 lineage have been shown to induce EAE. Cytokines IL-23, IL-6 and IL-17, which are either critical for Th1 and Th17 differentiation or produced by these T cells, play a critical and non-redundant role in EAE development. Therefore, drugs targeting production of these cytokines are likely to have therapeutic potential in treatment of MS.

Compounds of Formula I or Ia were administered at 50 to 125 mg/kg b.i.d. from time of immunization to EAE mice to assess anti-inflammatory activity. In this model, EAE is induced by $MOG_{35-55}$/CFA immunization and pertussis toxin injection in female C57Bl/6 mice.

TABLE 10

In Vivo Efficacy in Experimental autoimmune encephalomyelitis (EAE) Model of MS

| Example Compound | In vivo activity |
| --- | --- |
| Example 7 | Active |

Example 15:

Ex Vivo Effects on T Cell Function from Splenocyte and Lymphocyte Cultures Stimulated with External MOG Stimulation Mice were immunized with MOG/CFA and simultaneously treated with the compound for 11 days on a b.i.d regimen. Inguinal Lymph node and spleen were harvested, cultures were set up for lymphocytes and splenocytes and stimulated with external antigen (MOG) for 72 hours. Supernatants from these cultures were analyzed for TH1, Th2 and Th17 cytokines using a Cytometric Bead Array assay.

Example 16:

In Vivo Efficacy in Athymic Nude Mouse Strain of Multiple Myeloma Xenograft Model Using MM1.s Cells MM1.s cells (ATCC) are grown under standard cell culture conditions and (NCr) nu/nu fisol strain of female mice age 6-7 weeks are injected with $10 \times 10^6$ cells/animal in 100 μL PBS+100 μL Matrigel in the lower left abdominal flank. By approximately day 21 after MM1.s cells injection, mice are randomized based on tumor volume (L ×W×H)/2) of average ~120 mm$^3$. Mice are dosed orally with compound at 75 mg/kg b.i.d in EA006 formulation at 10 mL/kg body weight dose volume. Tumor measurements are taken with electronic micro calipers and body weights measured on alternate days beginning from dosing period. The average tumor volumes, percent Tumor Growth Inhibition (TGI) and % change in body weights are compared relative to Vehicle control animals. The means, statistical analysis and the comparison between groups are calculated using Student's t-test in Excel.

Other embodiments of the present disclosure will be apparent to those skilled in the art from consideration of the specification and practice of the present disclosure disclosed herein. It is intended that the specification and examples be considered as exemplary only, with a true scope and spirit of the present disclosure being indicated by the following claims.

What is claimed is:

1. A method for treating a disease or disorder selected from an autoimmune disease or disorder, an inflammatory disease or disorder, cancer, a benign proliferative or fibrotic disorder, a cardiovascular disease or disorder, a metabolic disease or disorder, HIV, and a neurological disease or disorder, comprising administering a therapeutically effective amount of a compound of Formula IIb' or Formula IId':

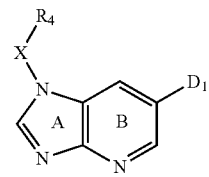

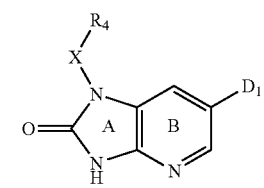

or a stereoisomer, tautomer, pharmaceutically acceptable salt, or hydrate thereof, wherein:

Rings A and B may be optionally substituted with groups independently selected from hydrogen, deuterium, —NH$_2$, amino, heterocycle(C$_4$-C$_6$), carbocycle(C$_4$-C$_6$), halogen, —CN, —OH, —CF$_3$, alkyl (C$_1$-C$_6$), thioalkyl(C$_1$-C$_6$), alkenyl(C$_1$-C$_6$), and alkoxy(C$_1$-C$_6$);

X is selected from —NH—, —CH$_2$—, —CH$_2$CH$_2$—, —CH$_2$CH$_2$CH$_2$—, —CH$_2$CH$_2$O—, —CH$_2$CH$_2$NH—, —CH$_2$CH$_2$S—, —C(O)—, —C(O)CH$_2$—, —C(O)CH$_2$CH$_2$—, —CH$_2$C(O)—, —CH$_2$CH$_2$C(O)—, —C(O)NH—, —C(O)O—, —C(O)S—, —C(O)NHCH$_2$—, —C(O)OCH$_2$—, and —C(O)SCH$_2$—, wherein one or more hydrogen may independently be replaced with deuterium, hydroxy, methyl, halogen, —CF$_3$, or ketone, and wherein S may be oxidized to sulfoxide or sulfone;

R$_4$ is selected from optionally substituted 3-7 membered carbocycles and heterocycles; and D$_1$ is selected from the following 5-membered monocyclic heterocycles:

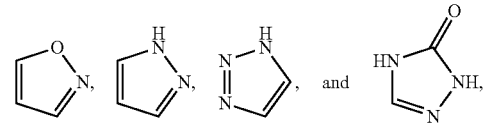

which are optionally substituted with hydrogen, deuterium, alkyl(C$_1$-C$_4$), alkoxy(C$_1$-C$_4$), amino, halogen, amide, —CF$_3$, CN, —N$_3$, ketone (C$_1$-C$_4$), —S(O)Alkyl (C$_1$-C$_4$), —SO$_2$alkyl(C$_1$-C$_4$), -thioalkyl(C$_1$-C$_4$), —COOH, and/or ester, each of which may be optionally substituted with hydrogen, F, Cl, Br, —OH, —NH$_2$, —NHMe, —OMe, —SMe, oxo, and/or thiooxo.

2. The method according to claim 1, wherein the compound of Formula IIb' is selected from a compound of Formula IIb'':

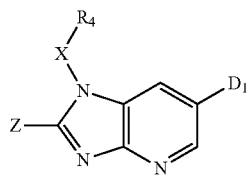

or a stereoisomer, tautomer, pharmaceutically acceptable salt, or hydrate thereof, wherein:

Z is selected from hydrogen, deuterium, —$NH_2$, amino, alkyl($C_1$-$C_6$), thioalkyl($C_1$-$C_6$), alkenyl($C_1$-$C_6$), and alkoxy($C_1$-$C_6$).

3. The method according to claim 1, wherein $R_4$ is selected from 3-7 membered optionally substituted carbocycles.

4. The method according to claim 3, wherein $R_4$ is selected from 5-6 membered optionally substituted carbocycles.

5. The method according to claim 3, wherein $R_4$ is selected from cycloalkyl($C_3$-$C_6$) and a phenyl ring optionally substituted with one or more groups independently selected from deuterium, alkyl($C_1$-$C_4$), alkoxy($C_1$-$C_4$), halogen, —$CF_3$, CN, and -thioalkyl($C_1$-$C_4$), wherein each alkyl, alkoxy, and thioalkyl may be optionally substituted with F, Cl, or Br.

6. The method according to claim 3, wherein $R_4$ is a phenyl ring optionally substituted with groups independently selected from hydrogen, deuterium, alkyl($C_1$-$C_4$), alkoxy($C_1$-$C_4$), amino, halogen, amide, —$CF_3$, CN, —$N_3$, ketone ($C_1$-$C_4$), —S(O)Alkyl($C_1$-$C_4$), —$SO_2$alkyl($C_1$-$C_4$), -thioalkyl($C_1$-$C_4$), carboxyl, and ester, each of which may be optionally substituted with hydrogen, F, Cl, Br, —OH, —$NH_2$, —NHMe, —OMe, —SMe, oxo, and/or thio-oxo.

7. The method according to claim 1, wherein $R_4$ is selected from 5- or 6-membered heterocycles containing 1 or 2 nitrogens, optionally substituted with groups independently selected from hydrogen, deuterium, alkyl($C_1$-$C_4$), alkoxy($C_1$-$C_4$), amino, halogen, amide, —$CF_3$, CN, —$N_3$, ketone ($C_1$-$C_4$), —S(O)Alkyl($C_1$-$C_4$), —$SO_2$alkyl($C_1$-$C_4$), -thioalkyl($C_1$-$C_4$), carboxyl, and ester, each of which may be optionally substituted with hydrogen, F, Cl, Br, —OH, —$NH_2$, —NHMe, —OMe, —SMe, oxo, and/or thio-oxo.

8. The method according to claim 7, wherein $R_4$ is selected from pyrimidyl, pyridyl, isoxazole, and pyrazole, optionally substituted with groups independently selected from hydrogen, deuterium, alkyl($C_1$-$C_4$), alkoxy($C_1$-$C_4$), amino, halogen, amide, —$CF_3$, CN, —$N_3$, ketone ($C_1$-$C_4$), —S(O)Alkyl($C_1$-$C_4$), —$SO_2$alkyl($C_1$-$C_4$), -thioalkyl($C_1$-$C_4$), carboxyl, and ester, each of which may be optionally substituted with hydrogen, F, Cl, Br, —OH, —$NH_2$, —NHMe, —OMe, —SMe, oxo, and/or thio-oxo.

9. The method according to claim 1, wherein $D_1$ is isoxazole optionally substituted with hydrogen, deuterium, alkyl($C_1$-$C_4$), alkoxy($C_1$-$C_4$), amino, halogen, amide, —$CF_3$, CN, —$N_3$, ketone ($C_1$-$C_4$), —S(O)Alkyl($C_1$-$C_4$), —$SO_2$alkyl($C_1$-$C_4$), -thioalkyl($C_1$-$C_4$), —COOH, and/or ester, each of which may be optionally substituted with hydrogen, F, Cl, Br, —OH, —$NH_2$, —NHMe, —OMe, —SMe, oxo, and/or thio-oxo.

10. The method according to claim 1, wherein $D_1$ is selected from

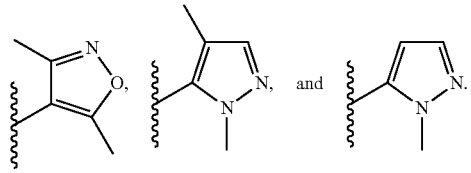

11. The method according to claim 1, wherein $D_1$ is

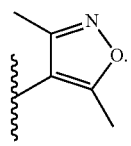

12. The method according to claim 1, wherein X is selected from —$CH_2$—, —CH($CH_3$)—, —CH(OH)—, —NH—, and —$CH_2CH_2$—, and wherein one or more hydrogen may independently be replaced with deuterium or halogen.

13. The method according to claim 12, wherein X is selected from —$CH_2$—, CH($CH_3$)—, and —NH—, and wherein one or more hydrogen may independently be replaced with deuterium or halogen.

14. The method according to claim 13, wherein X is selected from —$CH_2$— and —CH($CH_3$)—, and wherein one or more hydrogen may independently be replaced with deuterium or halogen.

15. The method according to claim 6, wherein X is —$CH_2$—.

16. The method according to claim 1, wherein the compound of Formula IIb' is selected from a compound of Formula IIb":

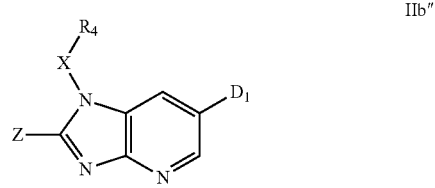

or a stereoisomer, tautomer, pharmaceutically acceptable salt, or hydrate thereof, wherein:

Z is selected from hydrogen, deuterium, —$NH_2$, amino, alkyl($C_1$-$C_6$), thioalkyl($C_1$-$C_6$), alkenyl($C_1$-$C_6$), and alkoxy($C_1$-$C_6$);

$D_1$ is

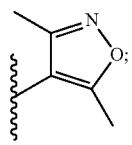 [SMILES: *c1c(C)noc1C]

X is selected from —CH$_2$— and —CH(CH$_3$)—; and

R$_4$ is a phenyl ring optionally substituted with one or more groups independently selected from deuterium, alkyl(C$_1$-C$_4$), alkoxy(C$_1$-C$_4$), halogen, —CF$_3$, CN, and -thioalkyl(C$_1$-C$_4$), wherein each alkyl, alkoxy, and thioalkyl may be optionally substituted with F, Cl, and/or Br.

17. The method according to claim 16, wherein Z is amino.

18. The method according to claim 1, wherein the autoimmune disease or disorder is selected from Acute Disseminated Encephalomyelitis, Agammaglobulinemia, Allergic Disease, Ankylosing spondylitis, Anti-GBM/Anti-TBM nephritis, Anti-phospholipid syndrome, Autoimmune aplastic anemia, Autoimmune hepatitis, Autoimmune inner ear disease, Autoimmune myocarditis, Autoimmune pancreatitis, Autoimmune retinopathy, Autoimmune thrombocytopenic purpura, Behcet's Disease, Bullous pemphigoid, Castleman's Disease, Celiac Disease, Churg-Strauss syndrome, Crohn's Disease, Cogan's syndrome, Dry eye syndrome, Essential mixed cryoglobulinemia, Dermatomyositis, Devic's Disease, Encephalitis, Eosinophlic esophagitis, Eosinophilic fasciitis, Erythema nodosum, Giant cell arteritis, Glomerulonephritis, Goodpasture's syndrome, Granulomatosis with Polyangiitis (Wegener's), Graves' Disease, Guillain-Barre syndrome, Hashimoto's thyroiditis, Hemolytic anemia, Henoch-Schonlein purpura, IgA nephropathy, Inclusion body myositis, Type I diabetes, Interstitial cystitis, Kawasaki's Disease, Leukocytoclastic vasculitis, Lichen planus, Systemic lupus erythematosus (SLE), Microscopic polyangitis, Multiple sclerosis, Myasthenia gravis, myositis, Optic neuritis, Pemphigus, POEMS syndrome, Polyarteritis nodosa, Primary biliary cirrhosis, Psoriasis, Psoriatic arthritis, Pyoderma gangrenosum, Relapsing polychondritis, Rheumatoid arthritis, Sarcoidosis, Scleroderma, Sjogren's syndrome, Takayasu's arteritis, Transverse myelitis, Ulcerative colitis, Uveitis, and Vitiligo.

19. The method of claim 1, wherein the inflammatory disease or disorder is selected from sinusitis, pneumonitis, osteomyelitis, gastritis, enteritis, gingivitis, appendicitis, irritable bowel syndrome, tissue graft rejection, chronic obstructive pulmonary disease (COPD), septic shock, toxic shock syndrome, SIRS, bacterial sepsis, osteoarthritis, acute gout, acute lung injury, acute renal failure, burns, Herxheimer reaction, and SIRS associated with viral infections.

20. The method of claim 1, wherein the disease or disorder is cancer.

21. The method of claim 20, wherein the cancer is selected from B-acute lymphocytic leukemia, Burkitt's lymphoma, diffuse large cell lymphoma, multiple myeloma, primary plasma cell leukemia, atypical carcinoid lung cancer, bladder cancer, breast cancer, cervix cancer, colon cancer, gastric cancer, glioblastoma, hepatocellular carcinoma, large cell neuroendocrine carcinoma, medulloblastoma, melanoma, neuroblastoma, esophageal squamous cell carcinoma, osteosarcoma, ovarian cancer, prostate cancer, renal clear cell carcinoma, retinoblastoma, rhabdomyosarcoma, small cell lung carcinoma, NUT midline carcinoma, non-small cell lung cancer, head and neck squamous cell carcinoma, chronic lymphocytic leukemia, follicular lymphoma, diffuse large B cell lymphoma with germinal center phenotype, Hodgkin's lymphoma, activated anaplastic large cell lymphoma, primary neuroectodermal tumor, pancreatic cancer, adenoid cystic carcinoma, T-cell prolymphocytic leukemia, malignant glioma, thyroid cancer, Barret's adenocarcinoma, pro-myelocytic leukemia, and mantle celllymphoma.

22. The method of claim 20, wherein the cancer:
(a) exhibits overexpression, translocation, amplification, or rearrangement of a myc family oncoprotein;
(b) results from aberrant regulation of BET proteins;
(c) relies on pTEFb (Cdk9/cyclin T) and BET proteins to regulate oncogenes;
(d) is associated with upregulation of BET responsive genes CDK6, Bcl2, TYRO3, MYB and/or hTERT; and/or
(e) is associated with a viral infection.

23. The method of claim 22, wherein:
(a) the cancer exhibiting overexpression, translocation, amplification, or rearrangement of a myc family oncoprotein is selected from B-acute lymphocytic leukemia, Burkitt's lymphoma, Diffuse large cell lymphoma, Multiple myeloma, Primary plasma cell leukemia, Atypical carcinoid lung cancer, Bladder cancer, Breast cancer, Cervix cancer, Colon cancer, Gastric cancer, Glioblastoma, Hepatocellular carcinoma, Large cell neuroendocrine carcinoma, Medulloblastoma, Nodular melamona, Superficial spreading melanoma, Neuroblastoma, esophageal squamous cell carcinoma, Osteosarcoma, Ovarian cancer, Prostate cancer, Renal clear cell carcinoma, Retinoblastoma, Rhabdomyosarcoma, and Small cell lung carcinoma;
(b) the cancer resulting from aberrant regulation of BET proteins is selected from NUT midline carcinoma, B-cell lymphoma, non-small cell lung cancer, esophageal cancer, head and neck squamous cell carcinoma, and colon cancer;
(c) the cancer relying on pTEFb (Cdk9/cyclin T) and BET proteins to regulate oncogenes is selected from chronic lymphocytic leukemia, multiple myeloma, follicular lymphoma, diffuse large B cell lymphoma with germinal center phenotype, Burkitt's lymphoma, Hodgkin's lymphoma, anaplastic large cell lymphoma, neuroblastoma, primary neuroectodermal tumor, rhabdomyosarcoma, prostate cancer, and breast cancer;
(d) the cancer associated with upregulation of BET responsive genes CDK6, Bcl2, TYRO3, MYB, and/or hTERT is selected from pancreatic cancer, breast cancer, colon cancer, glioblastoma, adenoid cystic carcinoma, T-cell prolymphocytic leukemia, malignant glioma, bladder cancer, medulloblastoma, thyroid cancer, melanoma, multiple myeloma, Barret's adenocarcinoma, hepatoma, prostate cancer, pro-myelocytic leukemia, chronic lymphocytic leukemia, mantle cell lymphoma, diffuse large B-cell lymphoma, small cell lung cancer, and renal carcinoma; and/or
(e) the viral infection is selected from Epstein-Barr Virus, hepatitis B virus, hepatitis C virus, Kaposi's sarcoma associated virus, human papilloma virus, Merkel cell polyomavirus, and human cytomegalovirus.

24. The method of claim 20, wherein the compound of Formula IIb' or Formula IId' is administered in combination with another anticancer agent.

25. The method of claim 24, wherein the anticancer agent is selected from ABT-737, Azacitidine (Vidaza), AZD1152 (Barasertib), AZD2281 (Olaparib), AZD6244 (Selumetinib), BEZ235, Bleomycin Sulfate, Bortezomib (Velcade), Busulfan (Myleran), Camptothecin, Cisplatin, Cyclophosphamide (Clafen), CYT387, Cytarabine (Ara-C), Dacarbazine, DAPT (GSI-IX), Decitabine, Dexamethasone, Doxorubicin (Adriamycin), Etoposide, Everolimus (RAD001), Flavopiridol (Alvocidib), Ganetespib (STA-9090), Gefitinib (Iressa), Idarubicin, Ifosfamide (Mitoxana), IFNa2a (Roferon A), Melphalan (Alkeran), Methazolastone (temozolomide), Metformin, Mitoxantrone (Novantrone), Paclitaxel, Phenformin, PKC412 (Midostaurin), PLX4032 (Vemurafenib), Pomalidomide (CC-4047), Prednisone (Deltasone), Rapamycin, Revlimid (Lenalidomide), Ruxolitinib (INCB018424), Sorafenib (Nexavar), SU11248 (Sunitinib), SU11274, Vinblastine, Vincristine (Oncovin), Vinorelbine (Navelbine), Vorinostat (SAHA), and WP1130 (Degrasyn).

26. A method for treating a disease or disorder selected from an autoimmune disease or disorder, an inflammatory disease or disorder, cancer, a benign proliferative or fibrotic disorder, a cardiovascular disease or disorder, a metabolic disease or disorder, HIV, and a neurological disease or disorder, comprising administering a therapeutically effective amount of a compound of Formula IIa''' or Formula IIc''':

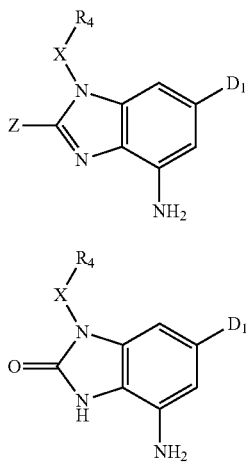

or a stereoisomer, tautomer, pharmaceutically acceptable salt, or hydrate thereof,
wherein:
Z if present, is selected from hydrogen, deuterium, —$NH_2$, amino, alkyl($C_1$-$C_6$), thioalkyl($C_1$-$C_6$), alkenyl($C_1$-$C_6$), alkoxy($C_1$-$C_6$), and carboxyl;
$D_1$ is

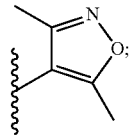 [SMILES: *c1c(C)noc1C]

X is selected from —$CH_2$— and —CH($CH_3$)—; and
$R_4$ is a phenyl ring optionally substituted with one or more groups independently selected from deuterium, alkyl($C_1$-$C_4$), alkoxy($C_1$-$C_4$), halogen, —$CF_3$, CN, and -thioalkyl($C_1$-$C_4$), wherein each alkyl, alkoxy, and thioalkyl may be optionally substituted with F, Cl, and/or Br.

27. The method according to claim 26, wherein the $R_4$ phenyl ring is substituted with one or more of the following groups:
alkyl($C_1$-$C_4$) selected from methyl, ethyl, propyl, isopropyl, and butyl;
alkoxy($C_1$-$C_4$), selected from methoxy, ethoxy, and isopropoxy;
halogen selected from F and Cl; and
thioalkyl($C_1$-$C_4$) selected from —SMe, —SEt, —SPr, and —Sbu.

28. A method for treating a disease or disorder selected from an autoimmune disease or disorder, an inflammatory disease or disorder, cancer, a benign proliferative or fibrotic disorder, a cardiovascular disease or disorder, a metabolic disease or disorder, HIV, and a neurological disease or disorder, comprising administering a therapeutically effective amount of a compound of Formula IIb'':

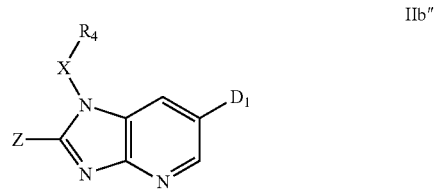

or a stereoisomer, tautomer, pharmaceutically acceptable salt, or hydrate thereof, wherein:
X is selected from —NH—, —$CH_2$—, —$CH_2CH_2$—, —$CH_2CH_2CH_2$—, —$CH_2CH_2O$—, —$CH_2CH_2NH$—, —$CH_2CH_2S$—, —C(O)—, —C(O)$CH_2$—, —C(O)$CH_2CH_2$—, —$CH_2$C(O)—, —$CH_2CH_2$C(O)—, —C(O)NH—, —C(O)O—, —C(O)S—, —C(O)NH$CH_2$—, —C(O)O$CH_2$—, and —C(O)S$CH_2$—, wherein one or more hydrogen may independently be replaced with deuterium, hydroxy, methyl, halogen, —$CF_3$, or ketone, and wherein S may be oxidized to sulfoxide or sulfone;
$R_4$ is selected from optionally substituted 3-7 membered carbocycles and heterocycles;
$D_1$ is selected from the following 5-membered monocyclic heterocycles:

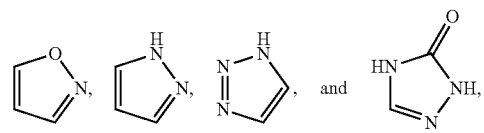

which are optionally substituted with hydrogen, deuterium, alkyl($C_1$-$C_4$), alkoxy($C_1$-$C_4$), amino, halogen, amide, —$CF_3$, CN, —$N_3$, ketone ($C_1$-$C_4$), —S(O)Alkyl($C_1$-$C_4$), —$SO_2$alkyl($C_1$-$C_4$), -thioalkyl($C_1$-$C_4$), —COOH, and/or ester, each of which may be optionally substituted with hydrogen, F, Cl, Br, —OH, —$NH_2$, —NHMe, —OMe, —SMe, oxo, and/or thio-oxo; and
Z is selected from:
-Me, —$CF_3$, -Et, $CH_3CH_2O$—, $CF_3CH_2$—, —SMe, —SOMe, —$SO_2$Me, —CN,

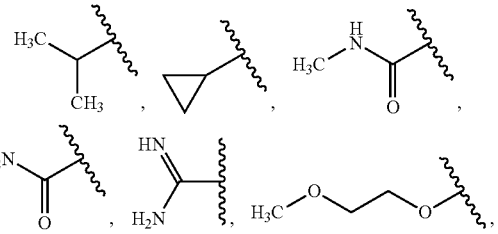

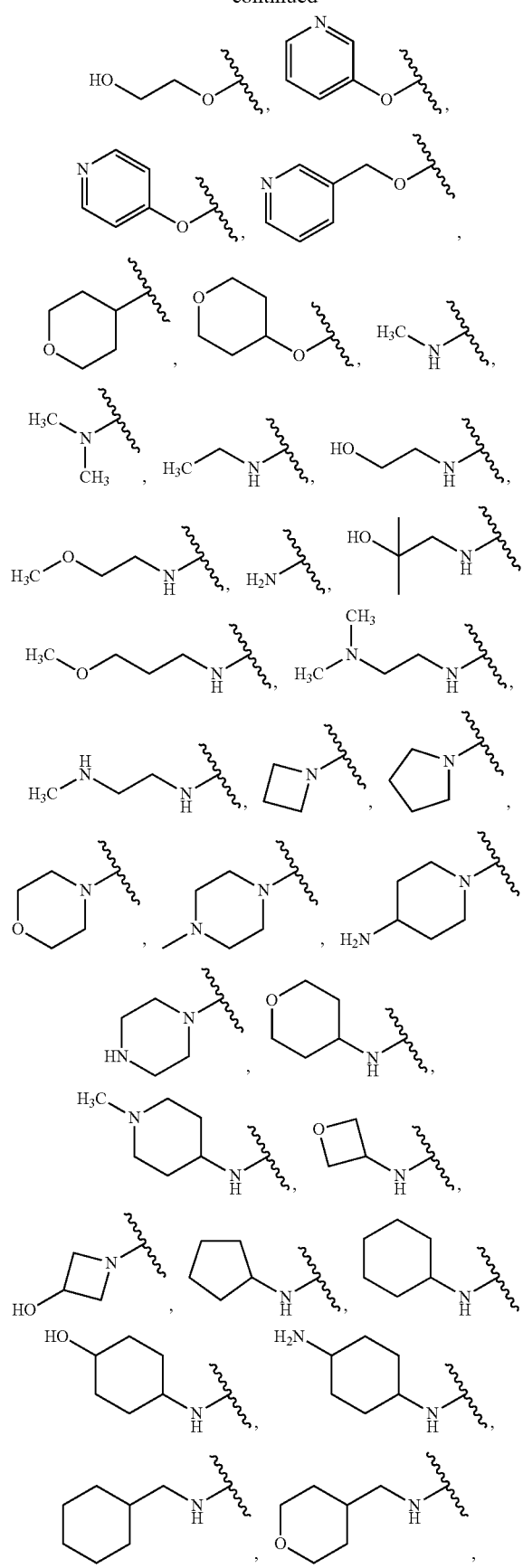
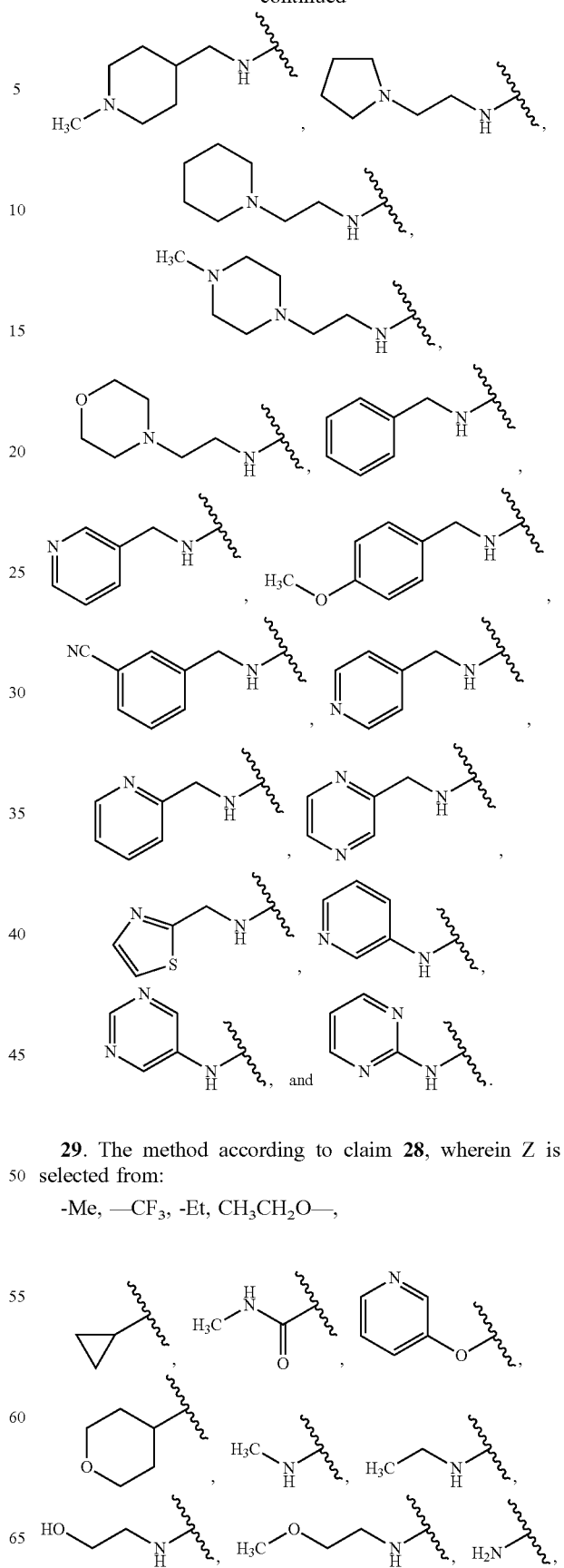
29. The method according to claim 28, wherein Z is selected from:
-Me, —CF$_3$, -Et, CH$_3$CH$_2$O—,

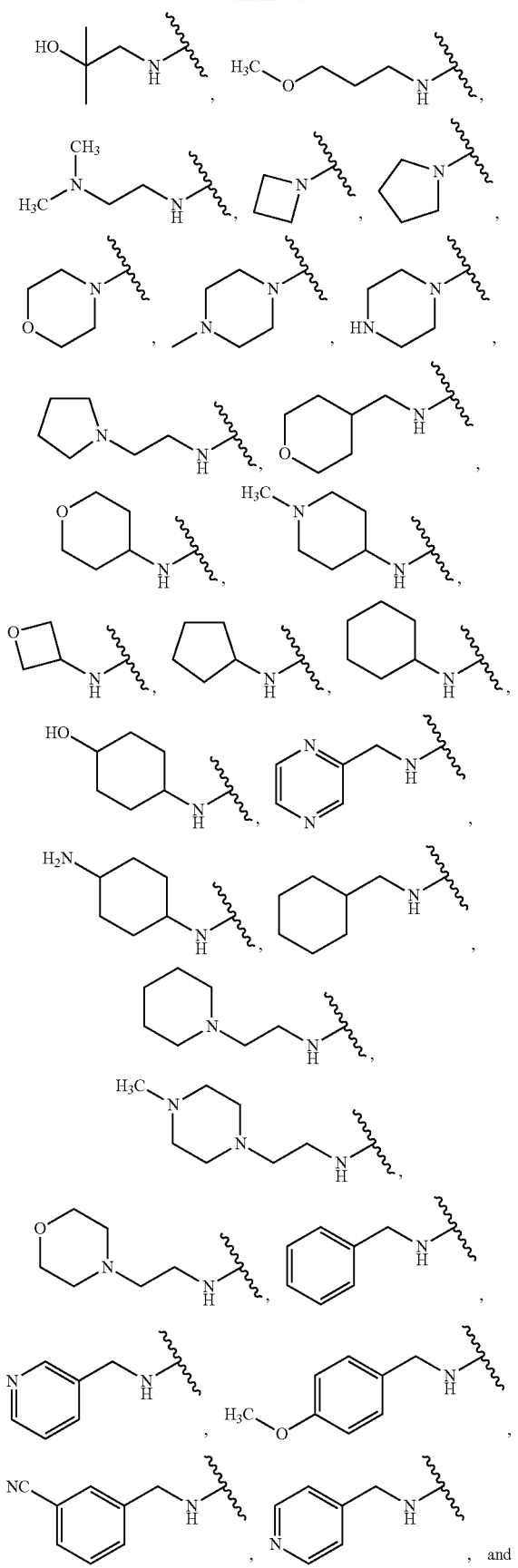

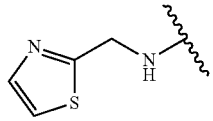

30. A method for treating a disease or disorder selected from an autoimmune disease or disorder, an inflammatory disease or disorder, cancer, a benign proliferative or fibrotic disorder, a cardiovascular disease or disorder, a metabolic disease or disorder, HIV, and a neurological disease or disorder, comprising administering a therapeutically effective amount of a compound selected from:

4-(3-benzyl-3H-imidazo[4, 5-b]pyridin-6-yl)-3,5-dimethylisoxazole;
4-(1-benzyl-1H-imidazo[4,5-b]pyridin-6-yl)-3,5-dimethylisoxazole;
1-benzyl-6-(3,5-dimethylisoxazol-4-yl)-1H-benzo[d]imidazol-4-amine;
N,1-dibenzyl-6-(3,5-dimethylisoxazol-4-yl)-1H-benzo[d]imidazol-4-amine;
1-benzyl-6-(3,5-dimethylisoxazol-4-yl)-1H-imidazo[4,5-b]pyridin-2(3H)-one;
4-(1-benzyl-2-methyl-1H-imidazo[4,5-b]pyridin-6-yl)-3,5-dimethylisoxazole;
4-(1-(cyclopropylmethyl)-2-methyl-4-nitro-1H-benzo[d]imidazol-6-yl)-3,5-dimethylisoxazole;
1-benzyl-6-(3, 5-dimethylisoxazol-4-yl)-4-nitro-1H-benzo[d]imidazol-2(3H)-one;
4-amino-1-benzyl-6-(3,5-dimethylisoxazol-4-yl)-1H-benzo[d]imidazol-2(3H)-one;
1-benzyl-6-(3,5-dimethylisoxazol-4-yl)-2-ethoxy-1H-benzo[d]imidazol-4-amine;
1-benzyl-6-(3, 5-dimethylisoxazol-4-yl)-N-ethyl-4-nitro-1H-benzo[d]imidazol-2-amine;
1-benzyl-6-(3,5-dimethylisoxazol-4-yl)-N2-ethyl-1H-benzo[d]imidazole-2,4-diamine;
methyl 1-benzyl-6-(3,5-dimethylisoxazol-4-yl)-2-oxo-2,3-dihydro-1H-benzo[d]imidazole-4-carboxylate;
1-benzyl-6-(3,5-dimethylisoxazol-4-yl)-2-oxo-2,3-dihydro-1H-benzo[d]imidazole-4-carboxamide;
4-(aminomethyl)-1-benzyl-6-(3,5-dimethylisoxazol-4-yl)-1H-benzo[d]imidazol-2(3H)-one;
6-(3,5-dimethylisoxazol-4-yl)-1-(4-fluorobenzyl)-1H-benzo[d]imidazol-4-amine;
6-(3,5-dimethylisoxazol-4-yl)-1-(4-fluorobenzyl)-N-methyl-1H-benzo[d]imidazol-4-amine;
6-(3,5-dimethylisoxazol-4-yl)-1-(4-fluorobenzyl)-N,N-dimethyl-1H-benzo[d]imidazol-4-amine;
3,5-dimethyl-4-(1-(1-phenylethyl)-1H-imidazo[4,5-b]pyridin-6-yl)isoxazole;
4-((6-(3,5-dimethylisoxazol-4-yl)-2-methyl-1H-imidazo[4,5-b]pyridin-1-yl)methyl)benzamide;
3,5-dimethyl-4-(1-(4-(trifluoromethyl)benzyl)-1H-imidazo[4,5-b]pyridin-6-yl)isoxazole;
4-(1-(4-chlorobenzyl)-1H-imidazo[4,5-b]pyridin-6-yl)-3,5-dimethylisoxazole;
4-(1-(4-fluorobenzyl)-1H-imidazo[4,5-b]pyridin-6-yl)-3,5-dimethylisoxazole;
3,5-dimethyl-4-(1-(pyridin-2-ylmethyl)-1H-imidazo[4,5-b]pyridin-6-yl)isoxazole;
1-benzyl-6-(3,5-dimethylisoxazol-4-yl)-2-methyl-1H-benzo[d]imidazol-4-amine;
4-(1-(4-fluorobenzyl)-2-methyl-1H-imidazo[4,5-b]pyridin-6-yl)-3,5-dimethylisoxazole;

4-(1-benzyl-2-ethoxy-1H-imidazo[4,5-b]pyridin-6-yl)-3,5-dimethylisoxazole;
4-((6-(3,5-dimethylisoxazol-4-yl)-2-methyl-1H-imidazo[4,5-b]pyridin-1-yl)methyl)-3,5-dimethylisoxazole;
4-(1-(2,4-dichlorobenzyl)-2-methyl-1H-imidazo[4,5-b]pyridin-6-yl)-3,5-dimethylisoxazole;
4-(1-(4-methoxybenzyl)-2-methyl-1H-imidazo[4,5-b]pyridin-6-yl)-3,5-dimethylisoxazole;
4-(1-(cyclopropylmethyl)-2-methyl-1H-imidazo[4,5-b]pyridin-6-yl)-3,5-dimethylisoxazole;
N-(1-benzyl-6-(3,5-dimethylisoxazol-4-yl)-2-methyl-1H-benzo[d]imidazol-4-yl)acetamide;
N-(1-benzyl-6-(3,5-dimethylisoxazol-4-yl)-2-methyl-1H-benzo[d]imidazol-4-yl)ethanesulfonamide;
4-(1-benzyl-4-methoxy-2-methyl-1H-benzo[d]imidazol-6-yl)-3,5-dimethylisoxazole;
3,5-dimethyl-4-(2-methyl-1-(pyridin-3-ylmethyl)-1H-imidazo[4,5-b]pyridin-6-yl)isoxazole;
3,5-dimethyl-4-(2-methyl-1-(thiophen-2-ylmethyl)-1H-imidazo[4,5-b]pyridin-6-yl)isoxazole;
4-((6-(3,5-dimethylisoxazol-4-yl)-2-methyl-1H-imidazo[4,5-b]pyridin-1-yl)methyl)benzonitrile;
3,5-dimethyl-4-(2-methyl-1-(pyridin-4-ylmethyl)-1H-imidazo[4,5-b]pyridin-6-yl)isoxazole;
1-(cyclopropylmethyl)-6-(3,5-dimethylisoxazol-4-yl)-2-methyl-1H-benzo[d]imidazol-4-amine;
3,5-dimethyl-4-(2-methyl-1-((5-methylthiophen-2-yl)methyl)-1H-imidazo[4,5-b]pyridin-6-yl)isoxazole;
4-(1-((5-chlorothiophen-2-yl)methyl)-2-methyl-1H-imidazo[4,5-b]pyridin-6-yl)-3,5-dimethylisoxazole;
5-((6-(3,5-dimethylisoxazol-4-yl)-2-methyl-1H-imidazo[4,5-b]pyridin-1-yl)methyl)thiophene-2-carbonitrile;
6-(3,5-dimethylisoxazol-4-yl)-1-(4-fluorobenzyl)-1H-imidazo[4,5-b]pyridine 4-oxide;
6-(3,5-dimethylisoxazol-4-yl)-1-(4-fluorobenzyl)-1H-imidazo[4,5-b]pyridin-5-yl acetate;
1-benzyl-6-(1,4-dimethyl-1H-pyrazol-5-yl)-2-methyl-4-nitro-1H-benzo[d]imidazole;
1-benzyl-6-(1,4-dimethyl-1H-pyrazol-5-yl)-2-methyl-1H-benzo[d]imidazol-4-amine;
4-(1-(4-chlorobenzyl)-2-methyl-1H-imidazo[4,5-b]pyridin-6-yl)-3,5-dimethylisoxazole;
4-((6-(3,5-dimethylisoxazol-4-yl)-2-methyl-1H-imidazo[4,5-b]pyridin-1-yl)methyl)phenol;
1-benzyl-6-(3,5-dimethylisoxazol-4-yl)-2-methyl-1H-benzo[d]imidazole-4-carbonitrile;
1-benzyl-6-(3,5-dimethylisoxazol-4-yl)-2-oxo-2,3-dihydro-1H-benzo[d]imidazole-4-carbonitrile;
1-benzyl-6-(3,5-dimethylisoxazol-4-yl)-2-morpholino-1H-benzo[d]imidazol-4-amine;
4-amino-1-(4-chlorobenzyl)-6-(3, 5-dimethylisoxazol-4-yl)-1H-benzo[d]imidazol-2(3H)-one;
1-(4-chlorobenzyl)-6-(3,5-dimethylisoxazol-4-yl)-4-nitro-1H-benzo[d]imidazol-2(3H)-one;
1-benzyl-2-methyl-6-(1-methyl-1H-pyrazol-5-yl)-1H-benzo[d]imidazol-4-amine;
4-(1-(3,4-dichlorobenzyl)-2-methyl-1H-imidazo[4,5-b]pyridin-6-yl)-3,5-dimethylisoxazole;
6-(3,5-dimethylisoxazol-4-yl)-2-methyl-1-(1-phenylethyl)-1H-benzo[d]imidazol-4-amine;
2-(azetidin-1-yl)-1-benzyl-6-(3,5-dimethylisoxazol-4-yl)-1H-benzo[d]imidazol-4-amine;
1-(3,4-dichlorobenzyl)-6-(3,5-dimethylisoxazol-4-yl)-1H-imidazo[4,5-b]pyridin-2(3H)-one;
6-(3,5-dimethylisoxazol-4-yl)-1-(4-methoxybenzyl)-4-nitro-1H-benzo[d]imidazol-2(3H)-one;
4-amino-6-(3,5-dimethylisoxazol-4-yl)-1-(4-methoxybenzyl)-1H-benzo[d]imidazol-2(3H)-one;
1-(4-chlorobenzyl)-6-(3,5-dimethylisoxazol-4-yl)-1H-imidazo[4,5-b]pyridin-2(3H)-one;
6-(3,5-dimethylisoxazol-4-yl)-1-(thiophen-2-ylmethyl)-1H-imidazo[4,5-b]pyridin-2(3H)-one;
1-benzyl-6-(3,5-dimethylisoxazol-4-yl)-N-ethyl-1H-imidazo[4,5-b]pyridin-2-amine;
3,5-dimethyl-4-(2-methyl-1-(1-phenylethyl)-1H-imidazo[4,5-b]pyridin-6-yl)isoxazole;
1-benzyl-6-(3,5-dimethylisoxazol-4-yl)-N2-(tetrahydro-2H-pyran-4-yl)-1H-benzo[d]imidazole-2,4-diamine;
6-(3,5-dimethylisoxazol-4-yl)-4-nitro-1-(1-phenylethyl)-1H-benzo[d]imidazol-2(3H)-one;
N-(1-benzyl-6-(3,5-dimethylisoxazol-4-yl)-2-oxo-2,3-dihydro-1H-benzo[d]imidazol-4-yl)acetamide;
6-(3,5-dimethylisoxazol-4-yl)-1-(1-phenylethyl)-1H-imidazo[4,5-b]pyridin-2(3H)-one;
6-(3,5-dimethylisoxazol-4-yl)-N-ethyl-1-(1-phenylethyl)-1H-imidazo[4,5-b]pyridin-2-amine;
4-(1-benzyl-6-(3,5-dimethylisoxazol-4-yl)-1H-imidazo[4,5-b]pyridin-2-yl)morpholine;
4-amino-6-(3,5-dimethylisoxazol-4-yl)-1-(1-phenylethyl)-1H-benzo[d]imidazol-2(3H)-one;
4-(1-(cyclobutylmethyl)-2-methyl-4-nitro-1H-benzo[d]imidazol-6-yl)-3,5-dimethylisoxazole;
4-(1-(cyclopentylmethyl)-2-methyl-4-nitro-1H-benzo[d]imidazol-6-yl)-3,5-dimethylisoxazole;
1-(cyclopropylmethyl)-6-(3,5-dimethylisoxazol-4-yl)-1H-imidazo[4,5-b]pyridin-2(3H)-one;
N-(1-benzyl-6-(3,5-dimethylisoxazol-4-yl)-2-(ethylamino)-1H-benzo[d]imidazol-4-yl)acetamide;
N-(1-benzyl-6-(3,5-dimethylisoxazol-4-yl)-2-ethoxy-1H-benzo[d]imidazol-4-yl)acetamide;
4-(1-benzyl-4-bromo-2-methyl-1H-benzo[d]imidazol-6-yl)-3,5-dimethylisoxazole;
3-benzyl-5-(3,5-dimethylisoxazol-4-yl)-1-ethyl-1H-benzo[d]imidazol-2(3H)-one;
4-(2-(azetidin-1-yl)-1-benzyl-1H-imidazo[4,5-b]pyridin-6-yl)-3,5-dimethylisoxazole;
1-((5-chlorothiophen-2-yl)methyl)-6-(3,5-dimethylisoxazol-4-yl)-1H-imidazo[4,5-b]pyridin-2(3H)-one;
(S)-3,5-dimethyl-4-(2-methyl-4-nitro-1-(1-phenylethyl)-1H-benzo[d]imidazol-6-yl)isoxazole;
(R)-3,5-dimethyl-4-(2-methyl-4-nitro-1-(1-phenylethyl)-1H-benzo[d]imidazol-6-yl)isoxazole;
6-(3,5-dimethylisoxazol-4-yl)-N-ethyl-4-nitro-1-(1-phenylethyl)-1H-benzo[d]imidazol-2-amine;
4-(1-benzyl-2-ethyl-1H-imidazo[4,5-b]pyridin-6-yl)-3,5-dimethylisoxazole;
4-amino-6-(3,5-dimethylisoxazol-4-yl)-1-(4-hydroxybenzyl)-1H-benzo[d]imidazol-2(3H)-one;
N-(2-(azetidin-1-yl)-1-benzyl-6-(3,5-dimethylisoxazol-4-yl)-1H-benzo[d]imidazol-4-yl)acetamide;
1-(cyclopropylmethyl)-6-(3,5-dimethylisoxazol-4-yl)-N-ethyl-1H-imidazo[4,5-b]pyridin-2-amine;
1-(cyclobutylmethyl)-6-(3,5-dimethylisoxazol-4-yl)-2-methyl-1H-benzo[d]imidazol-4-amine;
1-(cyclopentylmethyl)-6-(3,5-dimethylisoxazol-4-yl)-2-methyl-1H-benzo[d]imidazol-4-amine;
6-(3,5-dimethylisoxazol-4-yl)-N2-ethyl-1-(1-phenylethyl)-1H-benzo[d]imidazole-2,4-diamine;
4-(1-benzyl-4-nitro-2-(pyrrolidin-1-yl)-1H-benzo[d]imidazol-6-yl)-3,5-dimethylisoxazole;
4-(1-benzyl-2-(4-m ethylpiperazin-1-yl)-4-nitro-1H-benzo[d]imidazol-6-yl)-3,5-dimethylisoxazole;

1-benzyl-6-(3, 5-dimethylisoxazol-4-yl)-N-(2-methoxyethyl)-4-nitro-1H-benzo[d]imidazol-2-amine;
4-(1-benzyl-2-cyclopropyl-1H-imidazo[4,5-b]pyridin-6-yl)-3,5-dimethylisoxazole;
1-benzyl-6-(3,5-dimethylisoxazol-4-yl)-N2-(2-methoxyethyl)-1H-benzo[d]imidazole-2,4-diamine;
1-benzyl-6-(3,5-dimethylisoxazol-4-yl)-2-(pyrrolidin-1-yl)-1H-benzo[d]imidazol-4-amine;
1-benzyl-6-(3,5-dimethylisoxazol-4-yl)-2-(4-methylpiperazin-1-yl)-1H-benzo[d]imidazol-4-amine;
1-benzyl-N6-(3,5-dimethylisoxazol-4-yl)-2-methyl-1H-benzo[d]imidazole-4,6-diamine;
(S)-6-(3,5-dimethyl isoxazol-4-yl)-2-methyl-1-(1-phenylethyl)-1H-benzo[d]imidazol-4-amine;
(R)-6-(3,5-dimethylisoxazol-4-yl)-2-methyl-1-(1-phenylethyl)-1H-benzo[d]imidazol-4-amine;
1-(cyclopropylmethyl)-6-(3,5-dimethylisoxazol-4-yl)-4-nitro-1H-benzo[d]imidazol-2(3H)-one;
1-benzyl-6-(3,5-dimethylisoxazol-4-yl)-N-methyl-1H-imidazo[4,5-b]pyridin-2-amine;
N, 1-dibenzyl-6-(3, 5-dimethylisoxazol-4-yl)-4-nitro-1H-benzo[d]imidazol-2-amine;
1-benzyl-6-(3,5-dimethylisoxazol-4-yl)-4-nitro-N-(pyridin-3-ylmethyl)-1H-benzo[d]imidazol-2-amine;
1-benzyl-6-(3, 5-dimethylisoxazol-4-yl)-N-methyl-4-nitro-1H-benzo[d]imidazol-2-amine;
1-benzyl-6-(3, 5-dimethylisoxazol-4-yl)-3-methyl-4-nitro-1H-benzo[d]imidazol-2(3H)-one;
1-benzyl-6-(3,5-dimethylisoxazol-4-yl)-N2-methyl-1H-benzo[d]imidazole-2,4-diamine;
N2,1-dibenzyl-6-(3,5-dimethylisoxazol-4-yl)-1H-benzo[d]imidazole-2,4-diamine;
N,1-dibenzyl-6-(3,5-dimethylisoxazol-4-yl)-1H-imidazo[4,5-b]pyridin-2-amine;
1-benzyl-2-methyl-6-(1-methyl-1H-pyrazol-5-yl)-1H-imidazo[4,5-b]pyridine;
1-benzyl-6-(3,5-dimethylisoxazol-4-yl)-N2-(pyridin-3-ylmethyl)-1H-benzo[d]imidazole-2,4-diamine;
4-(1-benzyl-4-fluoro-2-methyl-1H-benzo[d]imidazol-6-yl)-3,5-dimethylisoxazole;
1-(cyclopropylmethyl)-6-(3,5-dimethylisoxazol-4-yl)-N-ethyl-4-nitro-1H-benzo[d]imidazol-2-amine;
1-(cyclopropylmethyl)-6-(3,5-dimethylisoxazol-4-yl)-N2-ethyl-1H-benzo[d]imidazole-2,4-diamine;
4-amino-1-(cyclopropylmethyl)-6-(3,5-dimethylisoxazol-4-yl)-1H-benzo[d]imidazol-2(3H)-one;
4-amino-1-benzyl-6-(3,5-dimethylisoxazol-4-yl)-3-methyl-1H-benzo[d]imidazol-2(3H)-one;
1-benzyl-6-(3,5-dimethylisoxazol-4-yl)-4-fluoro-1H-benzo[d]imidazol-2(3H)-one;
N-(1-benzyl-6-(3,5-dimethylisoxazol-4-yl)-3-methyl-2-oxo-2,3-dihydro-1H-benzo[d]imidazol-4-yl)acetamide;
4-(1-benzyl-2-(4-methylpiperazin-1-yl)-1H-imidazo[4,5-b]pyridin-6-yl)-3,5-dimethylisoxazole;
1-benzyl-6-(3,5-dimethylisoxazol-4-yl)-N-(2-methoxyethyl)-1H-imidazo[4,5-b]pyridin-2-amine;
4-(1-benzyl-2-methyl-4-(methylsulfonyl)-1H-benzo[d]imidazol-6-yl)-3,5-dimethylisoxazole;
1-benzyl-6-(3,5-dimethylisoxazol-4-yl)-N-(pyridin-4-ylmethyl)-1H-imidazo[4,5-b]pyridin-2-amine;
1-benzyl-6-(3,5-dimethylisoxazol-4-yl)-N-(tetrahydro-2H-pyran-4-yl)-1H-imidazo[4, 5-b]pyridin-2-amine;
1-benzyl-6-(1-methyl-1H-pyrazol-5-yl)-1H-imidazo[4,5-b]pyridin-2(3H)-one;
(S)-6-(3,5-dimethyl isoxazol-4-yl)-4-nitro-1-(1-phenylethyl)-1H-benzo[d]imidazol-2(3H)-one;
1-benzyl-6-(3,5-dimethylisoxazol-4-yl)-2-methyl-1H-benzo[d]imidazol-4-ol;
4-(1-benzyl-6-(1-methyl-1H-pyrazol-5-yl)-1H-imidazo[4,5-b]pyridin-2-yl)morpholine;
1-benzyl-6-(1-methyl-1H-pyrazol-5-yl)-N-(tetrahydro-2H-pyran-4-yl)-1H-imidazo[4, 5-b]pyridin-2-amine;
4-amino-1-benzyl-6-(3, 5-dimethylisoxazol-4-yl)-1H-benzo[d]imidazole-2(3H)-thione;
(S)-4-amino-6-(3,5-dimethylisoxazol-4-yl)-1-(1-phenylethyl)-1H-benzo[d]imidazol-2(3H)-one;
(R)-4-amino-6-(3,5-dimethylisoxazol-4-yl)-1-(1-phenylethyl)-1H-benzo[d]imidazol-2(3H)-one;
1-benzyl-6-(3,5-dimethylisoxazol-4-yl)-7-methyl-1H-imidazo[4,5-b]pyridin-2(3H)-one;
4-(1-benzyl-2,7-dimethyl-1H-imidazo[4,5-b]pyridin-6-yl)-3,5-dimethylisoxazole;
4-(1-benzyl-6-(3,5-dimethylisoxazol-4-yl)-2-methyl-1H-benzo[d]imidazol-4-yl)morpholine;
1-(1-benzyl-6-(3,5-dimethylisoxazol-4-yl)-2-methyl-1H-benzo[d]imidazol-4-yl)azetidin-2-one;
1-benzyl-2-methyl-6-(1,3,5-trimethyl-1H-pyrazol-4-yl)-1H-benzo[d]imidazol-4-amine;
1-benzyl-6-(3,5-dimethylisoxazol-4-yl)-N-(pyridin-3-ylmethyl)-1H-imidazo[4,5-b]pyridin-2-amine;
4-(4-bromo-2-methyl-1-phenethyl-1H-benzo[d]imidazol-6-yl)-3,5-dimethylisoxazole;
4-(4-bromo-2-methyl-1-(3-phenylpropyl)-1H-benzo[d]imidazol-6-yl)-3,5-dimethylisoxazole;
4-(4-bromo-2-methyl-1-(2-phenoxyethyl)-1H-benzo[d]imidazol-6-yl)-3,5-dimethylisoxazole;
4-(1-(cyclohexylmethyl)-2-methyl-1H-imidazo[4,5-b]pyridin-6-yl)-3,5-dimethylisoxazole;
4-(1-(cyclopentylmethyl)-2-methyl-1H-imidazo[4,5-b]pyridin-6-yl)-3,5-dimethylisoxazole;
4-(1-(cyclobutylmethyl)-2-methyl-1H-imidazo[4,5-b]pyridin-6-yl)-3,5-dimethylisoxazole;
1-benzyl-6-(3,5-dimethylisoxazol-4-yl)-N-(pyridin-2-ylmethyl)-1H-imidazo[4,5-b]pyridin-2-amine;
4-(1-benzyl-2-(pyrrolidin-1-yl)-1H-imidazo[4,5-b]pyridin-6-yl)-3,5-dimethylisoxazole;
2-((1-benzyl-6-(3,5-dimethylisoxazol-4-yl)-1H-imidazo[4,5-b]pyridin-2-yl)amino)ethanol;
1-(1-benzyl-6-(3,5-dimethylisoxazol-4-yl)-2-methyl-1H-benzo[d]imidazol-4-yl)azetidin-3-ol;
1-benzyl-3-methyl-6-(1-methyl-1H-pyrazol-5-yl)-4-nitro-1H-benzo[d]imidazol-2(3H)-one;
4-amino-1-benzyl-3-methyl-6-(1-methyl-1H-pyrazol-5-yl)-1H-benzo[d]imidazol-2(3H)-one;
(4-bromo-6-(3,5-dimethylisoxazol-4-yl)-2-methyl-1H-benzo[d]imidazol-1-yl)(phenyl)methanone;
1-benzyl-2-methyl-6-(5-methylisoxazol-4-yl)-1H-benzo[d]imidazol-4-amine;
1-(cyclopentylmethyl)-6-(3,5-dimethylisoxazol-4-yl)-1H-imidazo[4,5-b]pyridin-2(3H)-one;
1-(cyclobutylmethyl)-6-(3,5-dimethylisoxazol-4-yl)-1H-imidazo[4,5-b]pyridin-2(3H)-one;
N-(1-benzyl-3-methyl-6-(1-methyl-1H-pyrazol-5-yl)-2-oxo-2,3-dihydro-1H-benzo[d]imidazol-4-yl)acetamide;
1-benzyl-6-(3,5-dimethylisoxazol-4-yl)-N-(4-methoxybenzyl)-1H-imidazo[4,5-b]pyridin-2-amine;
1-benzyl-2-methyl-6-(1-methyl-1H-1,2,3-triazol-5-yl)-1H-imidazo[4,5-b]pyridine;
4-((1-benzyl-6-(3,5-dimethylisoxazol-4-yl)-1H-imidazo[4,5-b]pyridin-2-yl)amino)cyclohexanol;
4-(1-cyclopentylmethyl)-6-(3,5-dimethylisoxazol-4-yl)-1H-imidazo[4,5-b]pyridin-2-yl)morpholine;

4-(2-(azetidin-1-yl)-1-(cyclopentylmethyl)-1H-imidazo [4, 5-b]pyridin-6-yl)-3,5-dimethylisoxazole;
4-(1-(cyclobutylmethyl)-6-(3,5-dimethylisoxazol-4-yl)-1H-imidazo[4,5-b]pyridin-2-yl)morpholine;
4-(2-(azetidin-1-yl)-1-(cyclobutylmethyl)-1H-imidazo[4, 5-b]pyridin-6-yl)-3,5-dimethylisoxazole;
N1-(1-benzyl-6-(3,5-dimethylisoxazol-4-yl)-1H-imidazo [4,5-b]pyridin-2-yl)-N2,N2-dimethylethane-1,2-diamine;
4-(1-benzyl-2-(piperazin-1-yl)-1H-imidazo[4,5-b]pyridin-6-yl)-3,5-dimethylisoxazole;
1-benzyl-N-cyclopentyl-6-(3,5-dimethylisoxazol-4-yl)-1H-imidazo[4,5-b]pyridin-2-amine;
1-benzyl-6-(3,5-dimethylisoxazol-4-yl)-N-(2-morpholinoethyl)-1H-imidazo[4,5-b]pyridin-2-amine;
1-benzyl-6-(3,5-dimethylisoxazol-4-yl)-1H-imidazo[4,5-b]pyridin-2-amine;
3-(((1-benzyl-6-(3,5-dimethylisoxazol-4-yl)-1H-imidazo [4,5-b]pyridin-2-yl)amino)methyl)benzonitrile;
(R)-6-(3,5-dimethylisoxazol-4-yl)-1-(1-phenylethyl)-1H-imidazo[4,5-b]pyridin-2(3H)-one;
(S)-6-(3,5-dimethyl isoxazol-4-yl)-1-(1-phenylethyl)-1H-imidazo[4,5-b]pyridin-2(3H)-one;
4-(1-benzyl-2-(tetrahydro-2H-pyran-4-yl)-1H-imidazo[4, 5-b]pyridin-6-yl)-3,5-dimethylisoxazole;
1-benzyl-6-(3,5-dimethylisoxazol-4-yl)-N-methyl-1H-imidazo[4,5-b]pyridine-2-carboxamide;
1-(cyclopentylmethyl)-6-(3,5-dimethyl isoxazol-4-yl)-N-(tetrahydro-2H-pyran-4-yl)-1H-imidazo[4,5-b]pyridin-2-amine;
1-(cyclobutylmethyl)-6-(3, 5-dimethylisoxazol-4-yl)-N-(tetrahydro-2H-pyran-4-yl)-1H-imidazo[4,5-b]pyridin-2-amine
N1-(1-benzyl-6-(3,5-dimethylisoxazol-4-yl)-1H-imidazo [4,5-b]pyridin-2-yl)cyclohexane-1,4-diamine;
1-benzyl-N-(cyclohexylmethyl)-6-(3,5-dimethylisoxazol-4-yl)-1H-imidazo[4,5-b]pyridin-2-amine;
1-benzyl-6-(3,5-dimethylisoxazol-4-yl)-N-(3-methoxypropyl)-1H-imidazo[4,5-b]pyridin-2-amine;
1-benzyl-6-(3,5-dimethylisoxazol-4-yl)-N-(oxetan-3-yl)-1H-imidazo[4,5-b]pyridin-2-amine;
6-(3,5-dimethylisoxazol-4-yl)-1-(4-fluorobenzyl)-1H-imidazo[4,5-b]pyridin-2(3H)-one;
1-benzyl-6-(3,5-dimethylisoxazol-4-yl)-N-(pyrazin-2-ylmethyl)-1H-imidazo[4,5-b]pyridin-2-amine;
1-benzyl-6-(3,5-dimethylisoxazol-4-yl)-N-((tetrahydro-2H-pyran-4-yl)methyl)-1H-imidazo[4, 5-b]pyridin-2-amine;
1-benzyl-6-(3,5-dimethylisoxazol-4-yl)-N-(2-(4-methylpiperazin-1-yl)ethyl)-1H-imidazo[4, 5-b]pyridin-2-amine;
6-(3,5-dimethylisoxazol-4-yl)-1-(4-fluorobenzyl)-N-methyl-1H-imidazo[4,5-b]pyridin-2-amine;
1-(4-chlorobenzyl)-6-(3,5-dimethylisoxazol-4-yl)-N-methyl-1H-imidazo[4,5-b]pyridin-2-amine;
1-benzyl-N-cyclohexyl-6-(3,5-dimethylisoxazol-4-yl)-1H-imidazo[4,5-b]pyridin-2-amine;
1-benzyl-6-(3,5-dimethylisoxazol-4-yl)-N-(1-methylpiperidin-4-yl)-1H-imidazo[4,5-b]pyridin-2-amine;
4-(1-benzyl-2-(pyridin-3-yloxy)-1H-imidazo[4,5-b]pyridin-6-yl)-3,5-dimethylisoxazole;
1-((1-benzyl-6-(3,5-dimethylisoxazol-4-yl)-1H-imidazo [4,5-b]pyridin-2-yl)amino)-2-methylpropan-2-ol;
1-benzyl-6-(3,5-dimethylisoxazol-4-yl)-N-(2-(pyrrolidin-1-yl)ethyl)-1H-imidazo[4,5-b]pyridin-2-amine;
1-benzyl-6-(3,5-dimethylisoxazol-4-yl)-N-(2-(piperidin-1-yl)ethyl)-1H-imidazo[4,5-b]pyridin-2-amine;
(R)-6-(3,5-dimethylisoxazol-4-yl)-4-nitro-1-(1-phenylethyl)-1H-benzo[d]imidazol-2(3H)-one;
4-(1-benzyl-7-methoxy-2-(trifluoromethyl)-1H-benzo[d] imidazol-6-yl)-3,5-dimethylisoxazole;
1-benzyl-6-(3,5-dimethylisoxazol-4-yl)-N-(thiazol-2-ylmethyl)-1H-imidazo[4,5-b]pyridin-2-amine;
1-benzyl-6-(3,5-dimethylisoxazol-4-yl)-1H-benzo[d]imidazole-2-carboximidamide;
1-benzyl-6-(3, 5-dimethylisoxazol-4-yl)-1H-benzo[d] imidazole-2-carboxamide;
1-benzyl-6-(3,5-dimethylisoxazol-4-yl)-N-((1-methylpiperidin-4-yl)methyl)-1H-imidazo[4, 5-b]pyridin-2-amine;
1-(1-benzyl-6-(3,5-dimethylisoxazol-4-yl)-1H-imidazo [4, 5-b]pyridin-2-yl)azetidin-3-ol;
4-(1-benzyl-2-(pyridin-4-yloxy)-1H-imidazo[4,5-b]pyridin-6-yl)-3,5-dimethylisoxazole;
1-benzyl-6-(3,5-dimethylisoxazol-4-yl)-N-(pyridin-3-yl)-1H-benzo[d]imidazol-2-amine;
3-(1-benzyl-1H-benzo[d]imidazol-6-yl)-4-ethyl-1H-1,2, 4-triazol-5(4H)-one; and
stereoisomers, tautomers, pharmaceutically acceptable salts, and hydrates thereof.

31. The method according to claim 26, wherein the autoimmune disease or disorder is selected from Acute Disseminated Encephalomyelitis, Agammaglobulinemia, Allergic Disease, Ankylosing spondylitis, Anti-GBM/Anti-TBM nephritis, Anti-phospholipid syndrome, Autoimmune aplastic anemia, Autoimmune hepatitis, Autoimmune inner ear disease, Autoimmune myocarditis, Autoimmune pancreatitis, Autoimmune retinopathy, Autoimmune thrombocytopenic purpura, Behcet's Disease, Bullous pemphigoid, Castleman's Disease, Celiac Disease, Churg-Strauss syndrome, Crohn's Disease, Cogan's syndrome, Dry eye syndrome, Essential mixed cryoglobulinemia, Dermatomyositis, Devic's Disease, Encephalitis, Eosinophlic esophagitis, Eosinophilic fasciitis, Erythema nodosum, Giant cell arteritis, Glomerulonephritis, Goodpasture's syndrome, Granulomatosis with Polyangiitis (Wegener's), Graves' Disease, Guillain-Barre syndrome, Hashimoto's thyroiditis, Hemolytic anemia, Henoch-Schonlein purpura, IgA nephropathy, Inclusion body myositis, Type I diabetes, Interstitial cystitis, Kawasaki's Disease, Leukocytoclastic vasculitis, Lichen planus, Systemic lupus erythematosus (SLE), Microscopic polyangitis, Multiple sclerosis, Myasthenia gravis, myositis, Optic neuritis, Pemphigus, POEMS syndrome, Polyarteritis nodosa, Primary biliary cirrhosis, Psoriasis, Psoriatic arthritis. Pyoderma gangrenosum, Relapsing polychondritis, Rheumatoid arthritis, Sarcoidosis, Scleroderma, Sjogren's syndrome, Takayasu's arteritis, Transverse myelitis, Ulcerative colitis, Uveitis, and Vitiligo.

32. The method of claim 26, wherein the inflammatory disease or disorder is selected from sinusitis, pneumonitis, osteomyelitis, gastritis, enteritis, gingivitis, appendicitis, irritable bowel syndrome, tissue graft rejection, chronic obstructive pulmonary disease (COPD), septic shock, toxic shock syndrome, SIRS, bacterial sepsis, osteoarthritis, acute gout, acute lung injury, acute renal failure, burns, Herxheimer reaction, and SIRS associated with viral infections.

33. The method of claim 26, wherein the disease or disorder is cancer.

34. The method of claim 33, wherein the cancer is selected from B-acute lymphocytic leukemia, Burkitt's lymphoma, diffuse large cell lymphoma, multiple myeloma, primary plasma cell leukemia, atypical carcinoid lung cancer, bladder cancer, breast cancer, cervix cancer, colon cancer, gastric cancer, glioblastoma, hepatocellular carcinoma, large cell neuroendocrine carcinoma, medulloblastoma, melanoma, neuroblastoma, esophageal squamous cell carcinoma, osteosarcoma, ovarian cancer, prostate cancer, renal clear cell carcinoma, retinoblastoma, rhabdomyosarcoma, small cell lung carcinoma, NUT midline carcinoma, non-small cell lung cancer, head and neck squamous cell carcinoma, chronic lymphocytic leukemia, follicular lymphoma, diffuse large B cell lymphoma with germinal center phenotype, Hodgkin's lymphoma, activated anaplastic large cell lymphoma, primary neuroectodermal tumor, pancreatic cancer, adenoid cystic carcinoma, T-cell prolymphocytic leukemia, malignant glioma, thyroid cancer, Barret's adenocarcinoma, pro-myelocytic leukemia, and mantle cell lymphoma.

35. The method of claim 33, wherein the cancer:
   (a) exhibits overexpression, translocation, amplification, or rearrangement of a myc family oncoprotein;
   (b) results from aberrant regulation of BET proteins;
   (c) relies on pTEFb (Cdk9/cyclin T) and BET proteins to regulate oncogenes;
   (d) is associated with upregulation of BET responsive genes CDK6, Bcl2, TYRO3, MYB and/or hTERT; and/or
   (e) is associated with a viral infection.

36. The method of claim 35, wherein:
   (a) the cancer exhibiting overexpression, translocation, amplification, or rearrangement of a myc family oncoprotein is selected from B-acute lymphocytic leukemia, Burkitt's lymphoma, Diffuse large cell lymphoma, Multiple myeloma, Primary plasma cell leukemia, Atypical carcinoid lung cancer, Bladder cancer, Breast cancer, Cervix cancer, Colon cancer, Gastric cancer, Glioblastoma, Hepatocellular carcinoma, Large cell neuroendocrine carcinoma, Medulloblastoma, Nodular melanoma, Superficial spreading melanoma, Neuroblastoma, Esophageal squamous cell carcinoma, Osteosarcoma, Ovarian cancer, Prostate cancer, Renal clear cell carcinoma, Retinoblastoma, Rhabdomyosarcoma, and Small cell lung carcinoma;
   (b) the cancer resulting from aberrant regulation of BET proteins is selected from NUT midline carcinoma, B-cell lymphoma, non-small cell lung cancer, esophageal cancer, head and neck squamous cell carcinoma, and colon cancer;
   (c) the cancer relying on pTEFb (Cdk9/cyclin T) and BET proteins to regulate oncogenes is selected from chronic lymphocytic leukemia, multiple myeloma, follicular lymphoma, diffuse large B cell lymphoma with germinal center phenotype, Burkitt's lymphoma, Hodgkin's lymphoma, anaplastic large cell lymphoma, neuroblastoma, primary neuroectodermal tumor, rhabdomyosarcoma, prostate cancer, and breast cancer;
   (d) the cancer associated with upregulation of BET responsive genes CDK6, Bcl2, TYRO3, MYB, and/or hTERT is selected from pancreatic cancer, breast cancer, colon cancer, glioblastoma, adenoid cystic carcinoma, T-cell prolymphocytic leukemia, malignant glioma, bladder cancer, medulloblastoma, thyroid cancer, melanoma, multiple myeloma, Barret's adenocarcinoma, hepatoma, prostate cancer, pro-myelocytic leukemia, chronic lymphocytic leukemia, mantle cell lymphoma, diffuse large B-cell lymphoma, small cell lung cancer, and renal carcinoma; and/or
   (e) the viral infection is selected from Epstein-Barr Virus, hepatitis B virus, hepatitis C virus, Kaposi's sarcoma associated virus, human papilloma virus, Merkel cell polyomavirus, and human cytomegalovirus.

37. The method of claim 33, wherein the compound of Formula IIa''' or Formula IIc''' is administered in combination with another anticancer agent.

38. The method of claim 37, wherein the anticancer agent is selected from ABT-737, Azacitidine (Vidaza), AZD1152 (Barasertib), AZD2281 (Olaparib), AZD6244 (Selumetinib), BEZ235, Bleomycin Sulfate, Bortezomib (Velcade), Busulfan (Myleran), Camptothecin, Cisplatin, Cyclophosphamide (Clafen), CYT387, Cytarabine (Ara-C), Dacarbazine, DAPT (GSI-IX), Decitabine, Dexamethasone, Doxorubicin (Adriamycin), Etoposide, Everolimus (RAD001), Flavopiridol (Alvocidib), Ganetespib (STA-9090), Gefitinib (lressa), Idarubicin, Ifosfamide (Mitoxana), IFNa2a (Roferon A), Melphalan (Alkeran), Methazolastone (temozolomide), Metformin, Mitoxantrone (Novantrone), Paclitaxel, Phenformin, PKC412 (Midostaurin), PLX4032 (Vemurafenib), Pomalidomide (CC-4047), Prednisone (Deltasone), Rapamycin, Revlimid (Lenalidomide), Ruxolitinib (INCB018424), Sorafenib (Nexavar), SU11248 (Sunitinib), SU11274, Vinblastine, Vincristine (Oncovin), Vinorelbine (Navelbine), Vorinostat (SAHA), and WP1130 (Degrasyn).

39. The method according to claim 28, wherein the autoimmune disease or disorder is selected from Acute Disseminated Encephalomyelitis, Agammaglobulinemia, Allergic Disease, Ankylosing spondylitis, Anti-GBM/Anti-TBM nephritis, Antiphospholipid syndrome, Autoimmune aplastic anemia, Autoimmune hepatitis, Autoimmune inner ear disease, Autoimmune myocarditis, Autoimmune pancreatitis, Autoimmune retinopathy, Autoimmune thrombocytopenic purpura, Behcet's Disease, Bullous pemphigoid, Castleman's Disease, Celiac Disease, Churg-Strauss syndrome, Crohn's Disease, Cogan's syndrome, Dry eye syndrome, Essential mixed cryoglobulinemia, Dermatomyositis, Devic's Disease, Encephalitis, Eosinophlic esophagitis, Eosinophilic fasciitis, Erythema nodosum, Giant cell arteritis, Glomerulonephritis, Goodpasture's syndrome, Granulomatosis with Polyangiitis (Wegener's), Graves' Disease, Guillain-Barre syndrome, Hashimoto's thyroiditis, Hemolytic anemia, Henoch-Schonlein purpura, IgA nephropathy, Inclusion body myositis, Type I diabetes, Interstitial cystitis, Kawasaki's Disease, Leukocytoclastic vasculitis, Lichen planus, Systemic lupus erythematosus (SLE), Microscopic polyangitis, Multiple sclerosis, Myasthenia gravis, myositis, Optic neuritis, Pemphigus, POEMS syndrome, Polyarteritis nodosa, Primary biliary cirrhosis, Psoriasis, Psoriatic arthritis, Pyoderma gangrenosum, Relapsing polychondritis, Rheumatoid arthritis, Sarcoidosis, Scleroderma, Sjogren's syndrome, Takayasu's arteritis, Transverse myelitis, Ulcerative colitis, Uveitis, and Vitiligo.

40. The method of claim 28, wherein the inflammatory disease or disorder is selected from sinusitis, pneumonitis, osteomyelitis, gastritis, enteritis, gingivitis, appendicitis, irritable bowel syndrome, tissue graft rejection, chronic obstructive pulmonary disease (COPD), septic shock, toxic shock syndrome, SIRS, bacterial sepsis, osteoarthritis, acute gout, acute lung injury, acute renal failure, burns, Herxheimer reaction, and SIRS associated with viral infections.

41. The method of claim 28, wherein the disease or disorder is cancer.

42. The method of claim 41, wherein the cancer is selected from B-acute lymphocytic leukemia, Burkitt's lymphoma, diffuse large cell lymphoma, multiple myeloma, primary plasma cell leukemia, atypical carcinoid lung cancer, bladder cancer, breast cancer, cervix cancer, colon cancer, gastric cancer, glioblastoma, hepatocellular carcinoma, large cell neuroendocrine Carcinoma, medulloblastoma, melanoma, neuroblastoma, esophageal squamous cell carcinoma, osteosarcoma, ovarian cancer, prostate cancer, renal clear cell carcinoma, retinoblastoma, rhabdomyosarcoma, small cell lung carcinoma, NUT midline carcinoma, non-small cell lung cancer, head and neck squamous cell carcinoma, chronic lymphocytic leukemia, follicular lymphoma, diffuse large B cell lymphoma with germinal center phenotype, Hodgkin's lymphoma, activated anaplastic large cell lymphoma, primary neuroectodermal tumor, pancreatic cancer, adenoid cystic carcinoma, T-cell prolymphocytic leukemia, malignant glioma, thyroid cancer, Barret's adenocarcinoma, pro-myelocytic leukemia, and mantle cell lymphoma.

43. The method of claim 41, wherein the cancer:
(a) exhibits overexpression, translocation, amplification, or rearrangement of a myc family oncoprotein;
(b) results from aberrant regulation of BET proteins;
(c) relies on pTEFb (Cdk9/cyclin T) and BET proteins to regulate oncogenes;
(d) is associated with upregulation of BET responsive genes CDK6, Bcl2, TYRO3, MYB and/or hTERT; and/or
(e) is associated with a viral infection.

44. The method of claim 43, wherein:
(a) the cancer exhibiting overexpression, translocation, amplification, or rearrangement of a myc family oncoprotein is selected from B-acute lymphocytic leukemia, Burkitt's lymphoma, Diffuse large cell lymphoma, Multiple myeloma, Primary plasma cell leukemia, Atypical carcinoid lung cancer, Bladder cancer, Breast cancer, Cervix cancer, Colon cancer, Gastric cancer, Glioblastoma, Hepatocellular carcinoma, Large cell neuroendocrine carcinoma, Medulloblastoma, Nodular melanoma, Superficial spreading melanoma, Neuroblastoma, Esophageal squamous cell carcinoma, Osteosarcoma, Ovarian cancer, Prostate cancer, Renal clear cell carcinoma, Retinoblastoma, Rhabdomyosarcoma, and Small cell lung carcinoma;
(b) the cancer resulting from aberrant regulation of BET proteins is selected from NUT midline carcinoma, B-cell lymphoma, non-small cell lung cancer, esophageal cancer, head and neck squamous cell carcinoma, and colon cancer;
(c) the cancer relying on pTEFb (Cdk9/cyclin T) and BET proteins to regulate oncogenes is selected from chronic lymphocytic leukemia, multiple myeloma, follicular lymphoma, diffuse large B cell lymphoma with germinal center phenotype, Burkitt's lymphoma, Hodgkin's lymphoma, anaplastic large cell lymphoma, neuroblastoma, primary neuroectodermal tumor, rhabdomyosarcoma, prostate cancer, and breast cancer;
(d) the cancer associated with upregulation of BET responsive genes CDK6, Bcl2, TYRO3, MYB, and/or hTERT is selected from pancreatic cancer, breast cancer, colon cancer, glioblastoma, adenoid cystic carcinoma, T-cell prolymphocytic leukemia, malignant glioma, bladder cancer, medulloblastoma, thyroid cancer, melanoma, multiple myeloma, Barret's adenocarcinoma, hepatoma, prostate cancer, pro-myelocytic leukemia, chronic lymphocytic leukemia, mantle cell lymphoma, diffuse large B-cell lymphoma, small cell lung cancer, and renal carcinoma; and/or
(e) the viral infection is selected from Epstein-Barr Virus, hepatitis B virus, hepatitis C virus, Kaposi's sarcoma associated virus, human papilloma virus, Merkel cell polyomavirus, and human cytomegalovirus.

45. The method of claim 41, wherein the compound of Formula IIb" is administered in combination with another anticancer agent.

46. The method of claim 45, wherein the anticancer agent is selected from ABT-737, Azacitidine (Vidaza), AZD1152 (Barasertib), AZD2281 (Olaparib), AZD6244 (Selumetinib), BEZ235, Bleomycin Sulfate, Bortezomib (Velcade), Busulfan (Myleran), Camptothecin, Cisplatin, Cyclophosphamide (Clafen), CYT387, Cytarabine (Ara-C), Dacarbazine, DAPT (GSI-IX), Decitabine, Dexamethasone, Doxorubicin (Adriamycin), Etoposide, Everolimus (RAD001). Flavopiridol (Alvocidib), Ganetespib (STA-9090). Gefitinib (Iressa), Idarubicin, Ifosfamide (Mitoxana), IFNa2a (Roferon A), Melphalan (Alkeran), Methazolastone (temozolomide), Metformin, Mitoxantrone (Novantrone), Paclitaxel, Phenformin, PKC412 (Midostaurin), PLX4032 (Vemurafenib), Pomalidomide (CC-4047), Prednisone (Deltasone), Rapamycin, Revlimid (Lenalidomide), Ruxolitinib (INCB018424), Sorafenib (Nexavar), SU11248 (Sunitinib), SU11274, Vinblastine, Vincristine (Oncovin), Vinorelbine (Navelbine), Vorinostat (SAHA), and WP1130 (Degrasyn).

47. The method according to claim 30, wherein the autoimmune disease or disorder is selected from Acute Disseminated Encephalomyelitis, Agammaglobulinemia, Allergic Disease, Ankylosing spondylitis, Anti-GBM/Anti-TBM nephritis, Anti-phospholipid syndrome, Autoimmune aplastic anemia, Autoimmune hepatitis, Autoimmune inner ear disease, Autoimmune myocarditis, Autoimmune pancreatitis, Autoimmune retinopathy, Autoimmune thrombocytopenic purpura, Behcet's Disease, Bullous pemphigoid, Castleman's Disease, Celiac Disease, Churg-Strauss syndrome, Crohn's Disease, Cogan's syndrome, Dry eye syndrome, Essential mixed cryoglobulinemia, Dermatomyositis, Devic's Disease, Encephalitis, Eosinophlic esophagitis, Eosinophilic fasciitis, Erythema nodosum, Giant cell arteritis, Glomerulonephritis, Goodpasture's syndrome, Granulomatosis with Polyangiitis (Wegener's), Graves' Disease, Guillain-Barre syndrome, Hashimoto's thyroiditis, Hemolytic anemia, Henoch-Schonlein purpura, IgA nephropathy, Inclusion body myositis, Type I diabetes, Interstitial cystitis, Kawasaki's Disease, Leukocytoclastic vasculitis, Lichen planus, Systemic lupus erythematosus (SLE), Microscopic polyangitis, Multiple sclerosis, Myasthenia gravis, myositis, Optic neuritis, Pemphigus, POEMS syndrome, Polyarteritis nodosa, Primary biliary cirrhosis, Psoriasis, Psoriatic arthritis, Pyoderma gangrenosum, Relapsing polychondritis, Rheumatoid arthritis, Sarcoidosis, Scleroderma, Sjogren's syndrome, Takayasu's arteritis, Transverse myelitis, Ulcerative colitis, Uveitis, and Vitiligo.

48. The method of claim 30, wherein the inflammatory disease or disorder is selected from sinusitis, pneumonitis, osteomyelitis, gastritis, enteritis, gingivitis, appendicitis, irritable bowel syndrome, tissue graft rejection, chronic obstructive pulmonary disease (COPD), septic shock, toxic shock syndrome, SIRS, bacterial sepsis, osteoarthritis, acute gout, acute lung injury, acute renal failure, burns, Herxheimer reaction, and SIRS associated with viral infections.

49. The method of claim 30, wherein the disease or disorder is cancer.

50. The method of claim 49, wherein the cancer is selected from B-acute lymphocytic leukemia, Burkitt's lymphoma, diffuse large cell lymphoma, multiple myeloma, primary plasma cell leukemia, atypical carcinoid lung cancer, bladder cancer, breast cancer, cervix cancer, colon cancer, gastric cancer, glioblastoma, hepatocellular carcinoma, large cell neuroendocrine carcinoma, medulloblastoma, melanoma, neuroblastoma, esophageal squamous cell carcinoma, osteosarcoma, ovarian cancer, prostate cancer, renal clear cell carcinoma, retinoblastoma, rhabdomyosarcoma, small cell lung carcinoma, NUT midline carcinoma, non-small cell lung cancer, head and neck squamous cell carcinoma, chronic lymphocytic leukemia, follicular lymphoma, diffuse large B cell lymphoma with germinal center phenotype, Hodgkin's lymphoma, activated anaplastic large cell lymphoma, primary neuroectodermal tumor, pancreatic cancer, adenoid cystic carcinoma, T-cell prolymphocytic leukemia, malignant glioma, thyroid cancer, Barret's adenocarcinoma, pro-myelocytic leukemia, and mantle cell lymphoma.

51. The method of claim 49, wherein the cancer:
(a) exhibits overexpression, translocation, amplification, or rearrangement of a myc family oncoprotein;
(b) results from aberrant regulation of BET proteins;
(c) relies on pTEFb (Cdk9/cyclin T) and BET proteins to regulate oncogenes;
(d) is associated with upregulation of BET responsive genes CDK6, Bcl2, TYRO3, MYB and/or hTERT; and/or
(e) is associated with a viral infection.

52. The method of claim 51, wherein:
(a) the cancer exhibiting overexpression, translocation, amplification, or rearrangement of a myc family oncoprotein is selected from B-acute lymphocytic leukemia, Burkitt's lymphoma, Diffuse large cell lymphoma, Multiple myeloma, Primary plasma cell leukemia, Atypical carcinoid lung cancer, Bladder cancer, Breast cancer, Cervix cancer, Colon cancer, Gastric cancer, Glioblastoma, Hepatocellular carcinoma, Large cell neuroendocrine carcinoma, Medulloblastoma, Nodular melanoma, Superficial spreading melanoma, Neuroblastoma, Esophageal squamous cell carcinoma, Osteosarcoma, Ovarian cancer, Prostate cancer, Renal clear cell carcinoma, Retinoblastoma, Rhabdomyosarcoma, and Small cell lung carcinoma;
(b) the cancer resulting from aberrant regulation of BET proteins is selected from NUT midline carcinoma, B-cell lymphoma, non-small cell lung cancer, esophageal cancer, head and neck squamous cell carcinoma, and colon cancer;
(c) the cancer relying on pTEFb (Cdk9/cyclin T) and BET proteins to regulate oncogenes is selected from chronic lymphocytic leukemia, multiple myeloma, follicular lymphoma, diffuse large B cell lymphoma with germinal center phenotype, Burkitts lymphoma, Hodgkin's lymphoma, anaplastic large cell lymphoma, neuroblastoma, primary neuroectodermal tumor, rhabdomyosarcoma, prostate cancer, and breast cancer;
(d) the cancer associated with upregulation of BET responsive genes CDK6, Bcl2, TYRO3, MYB, and/or hTERT is selected from pancreatic cancer, breast cancer, colon cancer, glioblastoma, adenoid cystic carcinoma, T-cell prolymphocytic leukemia, malignant glioma, bladder cancer, medulloblastoma, thyroid cancer, melanoma, multiple myeloma, Barret's adenocarcinoma, hepatoma, prostate cancer, pro-myelocytic leukemia, chronic lymphocytic leukemia, mantle cell lymphoma, diffuse large B-cell lymphoma, small cell lung cancer, and renal carcinoma; and/or
(e) the viral infection is selected from Epstein-Barr Virus, hepatitis B virus, hepatitis C virus, Kaposi's sarcoma associated virus, human papilloma virus, Merkel cell polyomavirus, and human cytomegalovirus.

53. The method of claim 49, wherein said compound is administered in combination with another anticancer agent.

54. The method of claim 53, wherein the anticancer agent is selected from ABT-737, Azacitidine (Vidaza), AZD1152 (Barasertib), AZD2281 (Olaparib), AZD6244 (Selumetinib), BEZ235, Bleomycin Sulfate, Bortezomib (Velcade), Busulfan (Myleran), Camptothecin, Cisplatin, Cyclophosphamide (Clafen), CYT387, Cytarabine (Ara-C), Dacarbazine, DAPT (GSI-IX), Decitabine, Dexamethasone, Doxorubicin (Adriamycin), Etoposide, Everolimus (RAD001), Flavopiridol (Alvocidib), Ganetespib (STA-9090), Gefitinib (Iressa), Idarubicin, Ifosfamide (Mitoxana), IFNa2a (Roferon A), Melphalan (Alkeran), Methazolastone (temozolomide), Metformin, Mitoxantrone (Novantrone), Paclitaxel, Phenformin, PKC412 (Midostaurin), PLX4032 (Vemurafenib), Pomalidomide (CC-4047), Prednisone (Deltasone), Rapamycin, Revlimid (Lenalidomide), Ruxolitinib (INCB018424), Sorafenib (Nexava), SU11248 (Sunitinib), SU11274, Vinblastine, Vincristine (Oncovin), Vinorelbine (Navelbine), Vorinostat (SAHA), and WP1130 (Degrasyn).

* * * * *

UNITED STATES PATENT AND TRADEMARK OFFICE
CERTIFICATE OF CORRECTION

PATENT NO. : 10,010,556 B2
APPLICATION NO. : 15/486256
DATED : July 3, 2018
INVENTOR(S) : John Frederick Quinn et al.

It is certified that error appears in the above-identified patent and that said Letters Patent is hereby corrected as shown below:

Claim 23, Column 290, Line 21, "melamona" should read --melanoma--.

Claim 30, Column 298, Line 66, "4-(1-benzyl-2-(4-m ethylpiperazin-1-yl)-4-nitro-1H-" should read --4-(1-benzyl-2-(4-methylpiperazin-1-yl)-4-nitro-1H- --.

Claim 30, Column 299, Line 13 and Line 66, "dimethyl isoxazol" should read --dimethylisoxazol--.

Claim 30, Column 301, Line 22, "dimethyl isoxazol" should read --dimethylisoxazol--.

Claim 38, Column 304, Line 12, "Gefitnib (lressa)" should read --Gefitinib (Iressa)--.

Claim 42, Column 304, Line 66, "neuroendocrine Carcinoma" should read --neuroendocrine carcinoma--.

Claim 46, Column 306, Line 11, "Everolimus (RAD001)." should read --Everolimus (RAD001),--.

Claim 36, Column 306, Line 12, "Ganetespib (STA-9090)." should read --Ganetespib (STA-9090),--.

Claim 52, Column 308, Line 3, "Burkitts" should read --Burkitt's--.

Claim 54, Column 308, Line 41, "(Nexava)" should read --(Nexavar)--.

Signed and Sealed this
Eighteenth Day of September, 2018

Andrei Iancu
*Director of the United States Patent and Trademark Office*